US012660820B2

(12) United States Patent
Dota et al.

(10) Patent No.: US 12,660,820 B2
(45) Date of Patent: Jun. 23, 2026

(54) HETEROCYCLIC COMPOUND AND HARMFUL ARTHROPOD-CONTROLLING COMPOSITION INCLUDING SAME

(71) Applicant: SUMITOMO CHEMICAL COMPANY, LIMITED, Chuo-ku (JP)

(72) Inventors: Koichiro Dota, Takarazuka (JP); Takayuki Shioda, Takarazuka (JP); Ryota Maehata, Takarazuka (JP); Yasumasa Saito, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 519 days.

(21) Appl. No.: 18/247,390

(22) PCT Filed: Sep. 29, 2021

(86) PCT No.: PCT/JP2021/035952
§ 371 (c)(1),
(2) Date: Mar. 30, 2023

(87) PCT Pub. No.: WO2022/071428
PCT Pub. Date: Apr. 7, 2022

(65) Prior Publication Data

US 2024/0008488 A1 Jan. 11, 2024

(30) Foreign Application Priority Data

Sep. 30, 2020 (JP) ................................ 2020-165683

(51) Int. Cl.
*A01N 43/50* (2006.01)
*A01N 43/58* (2006.01)
(Continued)

(52) U.S. Cl.
CPC ............ *A01N 43/50* (2013.01); *A01N 43/58* (2013.01); *A01P 7/04* (2021.08); *C07D 471/04* (2013.01); *C07D 519/00* (2013.01)

(58) Field of Classification Search
None
See application file for complete search history.

(56) References Cited

U.S. PATENT DOCUMENTS

2018/0022760 A1 1/2018 Kudo et al.
2022/0095620 A1 3/2022 Tashiro et al.
(Continued)

FOREIGN PATENT DOCUMENTS

DE 41 20 108 A1 12/1992
JP 2018-177759 A 11/2018
(Continued)

OTHER PUBLICATIONS

JP-2022081650-A machine english translation from espacenet, May 2022, no pagination.*
(Continued)

*Primary Examiner* — Erin E Hirt
(74) *Attorney, Agent, or Firm* — Oblon, McClelland, Maier & Neustadt, L.L.P.

(57) ABSTRACT

A compound of formula (I) or its N-oxide, (I)

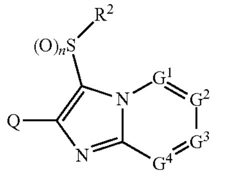

where Q is Q1;

Q1

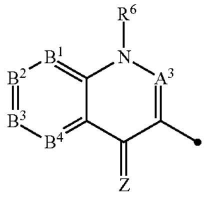

● represents the binding site to the rest of molecule; Z represents an oxygen atom; $A^3$ represents $CR^{4b}$; $B^1$ represents $CR^1$; $B^2$ represents $CR^{6b}$; $B^3$ represents $CR^{6c}$; $B^4$ represents $CR^{6d}$; $R^6$ represents a C1-C6 chain hydrocarbon group; $G^1$ represents a nitrogen atom or $CR^{3a}$; $G^2$ represents a nitrogen atom or $CR^{3b}$; $G^3$ represents a nitrogen atom or $CR^{3c}$; $G^4$ represents a nitrogen atom or $CR^{3d}$; $R^1$ represents a C1-C6 chain hydrocarbon group optionally substituted with one or more substituent(s) selected from the group consisting of a cyano group and a halogen atom; $R^2$ represents a C1-C6 alkyl group; $R^{3a}$, $R^{3b}$, $R^{3c}$, $R^{3d}$, $R^{4b}$, $R^{6b}$, $R^{6c}$, and $R^{6d}$ are identical to or different from each other, and each represent a C1-C6 alkyl group optionally substituted with one or more halogen atom(s); and n represents 0, 1, or 2.

10 Claims, No Drawings

(51) Int. Cl.

| | |
|---|---|
| ***A01P 7/04*** | (2006.01) |
| ***C07D 471/04*** | (2006.01) |
| ***C07D 519/00*** | (2006.01) |

(56) References Cited

U.S. PATENT DOCUMENTS

| | | | |
|---|---|---|---|
| 2022/0217979 | A1 | 7/2022 | Tsuruda et al. |
| 2023/0115523 | A1 | 4/2023 | Maehata et al. |

FOREIGN PATENT DOCUMENTS

| | | | | |
|---|---|---|---|---|
| JP | 2022081650 | A | * | 5/2022 |
| WO | WO 2016/129684 | A1 | | 8/2016 |
| WO | WO 2020/158889 | A1 | | 8/2020 |
| WO | WO 2020/203763 | A1 | | 10/2020 |
| WO | WO 2021/033141 | A1 | | 2/2021 |
| WO | WO 2021/141106 | A1 | | 7/2021 |

OTHER PUBLICATIONS

International Search Report issued Nov. 22, 2021, in PCT/JP2021/035952 (with English Translation), 5 pages.

International Preliminary Report on Patentability and Written Opinion issued Mar. 28, 2023, in PCT/JP2021/035952, 4 pages.

Ann-Maree Duncan et al., "Assessment of novel inhibitors of Helicoverpa aminopeptidases as anti-insect agents", Pest Management Science, 2006, 62 (11), pp. 1098-1108.

* cited by examiner

HETEROCYCLIC COMPOUND AND HARMFUL ARTHROPOD-CONTROLLING COMPOSITION INCLUDING SAME

CROSS-REFERENCE TO RELATED APPLICATIONS

The present application is a 35 U.S.C. § 371 national stage patent application of International patent application PCT/JP2021/035952, filed on Sep. 29, 2021, which is based on and claims the benefits of priority to Japanese Application No. 2020-165683, filed on Sep. 30, 2020. The entire contents of these applications are incorporated herein by reference.

TECHNICAL FIELD

This application claims the priority to and the benefit of Japanese Patent Application No. 2020-165683 filed on Sep. 30, 2020, the entire contents of which are incorporated herein by reference.

The present invention relates to heterocyclic compounds and compositions for controlling harmful arthropods comprising the same.

BACKGROUND ART

To date, various compounds have been studied in order to control harmful arthropods. For example, Patent Document 1 discloses that certain kinds of compounds have control effects on pests.

CITATION LIST

Patent Document

Patent Document 1: WO 2016/129684 pamphlet

SUMMARY OF THE INVENTION

Problems to be Solved by Invention

An object of the present invention is to provide compounds having excellent control efficacy against harmful arthropods.

Means to Solve Problems

The present invention provides the followings.

[1] A compound represented by formula (I)

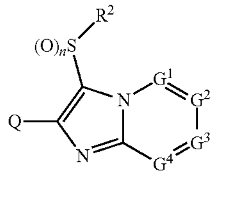

(I)

[wherein:

$R^2$ represents a C1-C6 alkyl group optionally substituted with one or more halogen atom(s), a cyclopropyl group, or a cyclopropylmethyl group;

n represents 0, 1, or 2;

$G^1$ represents a nitrogen atom or $CR^{3a}$;

$G^2$ represents a nitrogen atom or $CR^{3b}$;

$G^3$ represents a nitrogen atom or $CR^{3c}$;

$G^4$ represents a nitrogen atom or $CR^{3d}$;

$R^{3a}$, $R^{3b}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_mR^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with one or more halogen atom(s), a halogen atom, $OR^{35}$, $NR^{36}R^{37}$, or a hydrogen atom;

$R^{35}$ represents a C1-C6 chain hydrocarbon group optionally substituted with one or more halogen atom(s);

$R^{17}$ represents a C1-C6 chain hydrocarbon group optionally substituted with one or more halogen atom(s), a phenyl group optionally substituted with one or more substituent(s) selected from Group D, or a hydrogen atom;

$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom;

$R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$;

$R^{23}$ represents a C1-C6 chain hydrocarbon group optionally substituted with one or more halogen atom(s), or a phenyl group optionally substituted with one or more substituent(s) selected from Group D;

$R^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group {wherein the phenyl moiety in said phenyl C1-C3 alkyl group is optionally substituted with one or more substituent(s) selected from Group D};

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

Q represents a group represented by Q1, a group represented by Q2, a group represented by Q3, a group represented by Q4, or a group represented by Q5;

Q1

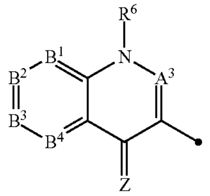

Q2

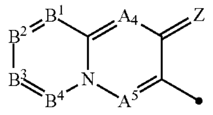

Q3

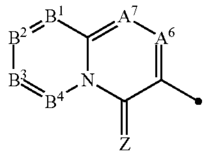

Q4

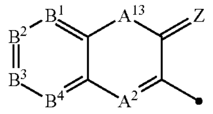

Q5

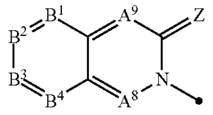

● represents the binding site to the rest of molecule;

Z represents an oxygen atom or a sulfur atom;

$A^2$ represents a nitrogen atom or $CR^{4a}$;

$A^3$ represents a nitrogen atom or $CR^{4b}$;

$A^4$ represents a nitrogen atom or $CR^{4c}$;

$A^5$ represents a nitrogen atom or $CR^{4d}$;

$A^6$ represents a nitrogen atom or $CR^{4e}$;

$A^7$ represents a nitrogen atom or $CR^{4f}$;

$A^8$ represents a nitrogen atom or $CR^{4g}$;

$A^9$ represents a nitrogen atom or $CR^{4h}$;

$A^{13}$ represents an oxygen atom, a sulfur atom, or $NR^6$;

the combination of $B^1$, $B^2$, $B^3$, and $B^4$ represents:

a combination wherein $B^1$ represents $CR^1$, $B^2$ represents a nitrogen atom or $CR^{6b}$, $B^3$ represents a nitrogen atom or $CR^{6c}$, and $B^4$ represents a nitrogen atom or $CR^{6d}$;

a combination wherein $B^1$ represents a nitrogen atom or $CR^{6a}$, $B^2$ represents $CR^1$, $B^3$ represents a nitrogen atom or $CR^{6c}$, and $B^4$ represents a nitrogen atom or $CR^{6d}$ (provided that a combination wherein $B^1$, $B^2$, $B^3$, and $B^4$ all represent CH is excluded);

a combination wherein $B^1$ represents a nitrogen atom or $CR^{6a}$, $B^2$ represents a nitrogen atom or $CR^{6b}$, $B^3$ represents $CR^1$, and $B^4$ represents a nitrogen atom or $CR^{6d}$ (provided that a combination wherein $B^1$, $B^2$, $B^3$, and $B^4$ all represent CH is excluded);

a combination wherein $B^1$ represents a nitrogen atom or $CR^{6a}$, $B^2$ represents a nitrogen atom or $CR^{6b}$, $B^2$ represents $CR^{6c}$, and $B^4$ represents $CR^1$ (provided that a combination wherein $B^1$, $B^2$, $B^3$, and $B^4$ all represent CH is excluded); or a combination wherein $B^1$ represents a nitrogen atom or $CR^{6a}$, $B^2$ represents $CR^{6b}$, $B^2$ represents a nitrogen atom, and $B^4$ represents $CR^1$;

$R^1$ represents a C1-C6 chain hydrocarbon group optionally substituted with one or more substituent(s) selected from the group consisting of a cyano group and a halogen atom, a C3-C4 cycloalkyl group optionally substituted with one or more substituent(s) selected from the group consisting of a cyano group and a halogen atom, $S(O)_kR^8$, $OR^8$, a halogen atom, $OS(O)_2R^8$, or a hydrogen atom;

$R^8$ represents a C1-C6 chain hydrocarbon group optionally substituted with one or more substituent(s) selected from the group consisting of a cyano group and a halogen atom; or a C3-C4 cycloalkyl group optionally substituted with one or more substituent(s) selected from the group consisting of a cyano group and a halogen atom;

k represents 0, 1, or 2;

$R^{4a}$, $R^{4b}$, $R^{4c}$, $R^{4d}$, $R^{4f}$, $R^{4g}$, and $R^{4h}$ are identical to or different from each other, and each represent a C1-C6 chain hydrocarbon group optionally substituted with one or more halogen atom(s), a nitro group, $OR^{18}$, $NR^{18}R^{19}$, a cyano group, an amino group, a halogen atom, or a hydrogen atom;

$R^{4e}$ represents a C1-C6 chain hydrocarbon group optionally substituted with one or more halogen atom(s), a nitro group, $OR^{18}$, $NR^{18}R^{19}$, a cyano group, an amino group, a halogen atom, a hydroxy group, or a hydrogen atom;

$R^{6a}$, $R^{6b}$, $R^{6c}$, and $R^{6d}$ are identical to or different from each other, and each represent a C1-C6 chain hydrocarbon group optionally substituted with one or more halogen atom(s), a C3-C7 cycloalkyl group optionally substituted with one or more halogen atom(s), a C1-C6 alkoxy group optionally substituted with one or more halogen atom(s), a halogen atom, or a hydrogen atom;

$R^{18}$ represents a C1-C6 chain hydrocarbon group optionally substituted with one or more halogen atom(s);

$R^{19}$ represents a C1-C6 chain hydrocarbon group optionally substituted with one or more halogen atom(s), or a hydrogen atom; and $R^6$ represents a C1-C6 chain hydrocarbon group optionally substituted with one or more substituent(s) selected from Group F, a C3-C6 cycloalkyl group optionally substituted with one or more substituent(s) selected from Group J, a phenyl group optionally substituted with one or more substituent(s) selected from Group H, a 5 or 6 membered aromatic heterocyclic group optionally substituted with one or more substituent(s) selected from Group H, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s), or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group]

(hereinafter referred to as "Present compound N" or "Compound N of the present invention") or an N-oxide thereof (hereinafter the compound represented by formula (I) or an N-oxide thereof is referred to as "Present compound" or "Compound of the present invention").

[2] The compound or an N-oxide thereof according to [1], wherein $R^2$ represents a C1-C6 alkyl group optionally substituted with one or more halogen atom(s);

$G^1$ represents $CR^{3a}$;

$G^2$ represents $CR^{3b}$;

$G^3$ represents $CR^{3c}$;

$G^4$ represents $CR^{3d}$;

$R^{3a}$, $R^{3b}$, $R^{3c}$, and $R^{3d}$ are identical to or different from each other, and each represent a C1-C6 chain hydrocarbon group optionally substituted with one or more halogen atom(s), a C3-C7 cycloalkyl group (wherein said C3-C7 cycloalkyl group is optionally substituted with one or more substituent(s) selected from the group consisting of a halogen atom and a cyano group), a hydrogen atom, or a halogen atom;

Q represents the group represented by Q2, the group represented by Q3, the group represented by Q4, or the group represented by Q5;

Z represents an oxygen atom;

$A^4$ represents a nitrogen atom;

$A^5$ represents CH;

$A^6$ represents CH;

$A^7$ represents a nitrogen atom;

$A^8$ represents $CR^{4g}$;

the combination of $B^1$, $B^2$, $B^3$, and $B^4$ represents:

a combination wherein $B^1$ represents a nitrogen atom or $CR^{6a}$, $B^2$ represents $CR^1$, $B^3$ represents a nitrogen atom or $CR^{6c}$, and $B^4$ represents $CR^{6d}$; or a combination wherein $B^1$ represents $CR^{6a}$, $B^2$ represents $CR^{6b}$, $B^3$ represents $CR^1$, and $B^4$ represents $CR^{6d}$;

$R^1$ represents a C1-C6 chain hydrocarbon group optionally substituted with one or more halogen atom(s), a C3-C4 cycloalkyl group optionally substituted with one or more halogen atom(s), or a halogen atom; and $R^{6a}$, $R^{6b}$, $R^{6c}$, and $R^{6d}$ each represent a hydrogen atom.

[3] The compound or an N-oxide thereof according to [2], wherein Q represents the group represented by Q2 or the group represented by Q3;

the combination of $B^1$, $B^2$, $B^3$, and $B^4$ represents:

a combination wherein $B^1$ represents $CR^{6a}$, $B^2$ represents $CR^1$, $B^3$ represents $CR^{6c}$, and $B^4$ represents $CR^{6d}$; or a combination wherein $B^1$ represents $CR^{6a}$, $B^2$ represents $CR^{6b}$, $B^3$ represents $CR^1$, and $B^4$ represents $CR^{6d}$; and $R^1$ represents a C1-C6 chain hydrocarbon group optionally substituted with one or more halogen atom(s), or a halogen atom.

[4] The compound or an N-oxide thereof according to [2] or [3], wherein $R^{3a}$, $R^{3b}$, $R^{3c}$ and $R^{3d}$ are identical to or different from each other, and each represent a C1-C6 chain hydrocarbon group optionally substituted with one or more halogen atom(s), a hydrogen atom, or a halogen atom.

[5] A composition for controlling a harmful arthropod comprising the compound or an N-oxide thereof according to any one of [1] to [4].

[6] A composition comprising one or more ingredient(s) selected from the group consisting of Group (a), Group (b), Group (c), and Group (d), and the compound or an N-oxide thereof according to any one of [1] to [4]:

Group (a): a group consisting of insecticidal active ingredients, miticidal active ingredients, and nematicidal active ingredients;

Group (b): fungicidal active ingredients;

Group (c): plant growth regulatory ingredients;

Group (d): repellent ingredients.

[7] A method for controlling a harmful arthropod which comprises applying an effective amount of the compound or an N-oxide thereof according to any one of [1] to [4] or an effective amount of the composition according to [6] to a harmful arthropod or a habitat where a harmful arthropod lives.

[8] A seed or a vegetative reproductive organ holding an effective amount of the compound or an N-oxide thereof according to any one of [1] to [4] or an effective amount of the composition according to [6].

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent is substituted with two or more halogen atoms or substituents, these halogen atoms or substituents may be identical to or different from each other.

The expression of "CX-CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a 1-ethylpropyl group, a butyl group, a sec-butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1-ethyl-2-propenyl group, a 3-butenyl group, a 4-pentenyl group, and a 5-hexenyl group.

Examples of the term of "alkynyl group" include an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, and a 5-hexynyl group.

Examples of the term of "alkoxy group" include a methoxy group, an ethoxy group, a propoxy group, an isopropoxy group, a butoxy group, a tert-butoxy group, a pentyloxy group, and a hexyloxy group.

Examples of the term of "alkenyloxy group" include a 2-propenyloxy group, a 2-butenyloxy group, and a 5-hexenyloxy group.

Examples of the term of "alkynyloxy group" include a 2-propynyloxy group, a 2-butynyloxy group, and a 5-hexynyloxy group.

Examples of the term of "cycloalkyl group" include a cyclopropyl group, a cyclobutyl group, a cyclopentyl group, a cyclohexyl group, and a cycloheptyl group.

Examples of the term of "cycloalkenyl group" include a cyclopropenyl group, a cyclobutenyl group, a cyclopentenyl group, a cyclohexenyl group, and a cycloheptenyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring.

Examples of the term of "3-7 membered nonaromatic heterocyclic group optionally substituted with one or more substituent(s) selected from Group E" include the following groups.

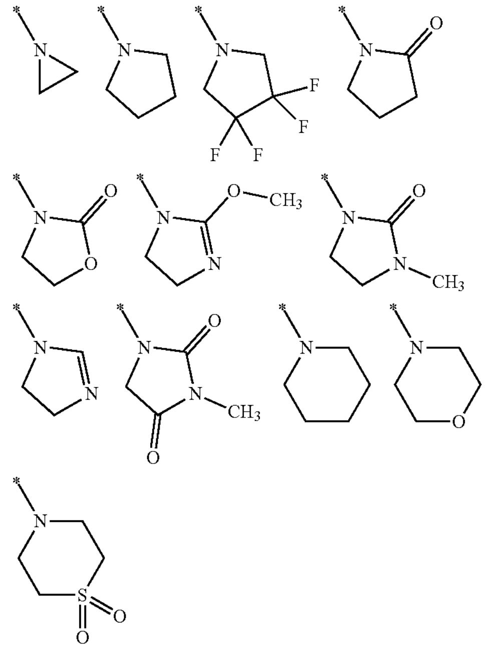

The term of "5 or 6 membered aromatic heterocyclic group" represents a 5 membered aromatic heterocyclic group or a 6 membered aromatic heterocyclic group. The term of "5 membered aromatic heterocyclic group" represents a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "6 membered aromatic heterocyclic group" represents a pyridyl group, a pyridazinyl group, a pyrimidinyl group, a pyrazinyl group, a triazinyl group, or a tetrazinyl group.

Examples of the term of "(C3-C6 cycloalkyl) C1-C3 alkyl group optionally substituted with one or more halogen atom(s)" include a cyclopropylmethyl group, a (2-fluorocyclopropyl)methyl group, a cyclopropyl(fluoro)methyl group, and a (2-fluorocyclopropyl) (fluoro)methyl group.

Examples of the term of "phenyl C1-C3 alkyl group {wherein the phenyl moiety in said phenyl C1-C3 alkyl group is optionally substituted with one or more substituent(s) selected from Group D}" include a benzyl group, a 2-fluorobenzyl group, a 4-chlorobenzyl group, a 4-(trifluoromethyl)benzyl group, and a 2-[4-(trifluoromethyl)phenyl]ethyl group.

Examples of the term of "alkylsulfanyl group" include a methylsulfanyl group, an ethylsulfanyl group, a propylsulfanyl group, and an isopropylsulfanyl group.

Examples of the term of "alkylsulfinyl group" include a methylsulfinyl group, an ethylsulfinyl group, a propylsulfinyl group, and an isopropylsulfinyl group.

Examples of the term of "alkylsulfonyl group" include a methylsulfonyl group, an ethylsulfonyl group, a propylsulfonyl group, and an isopropylsulfonyl group.

Examples of the N-oxide of the compound represented by formula (I) include the compounds represented by the following formulae.

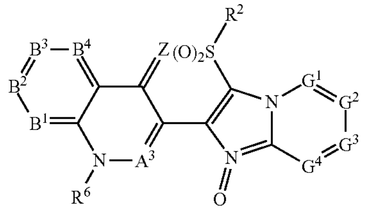

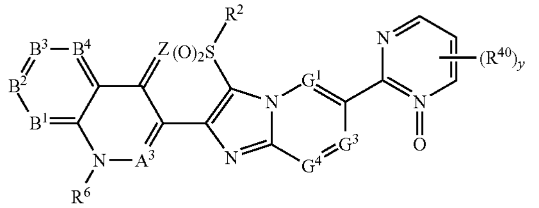

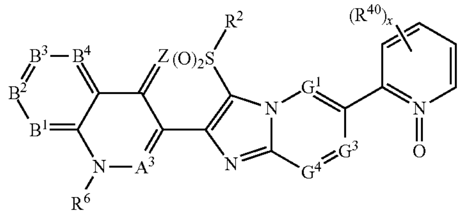

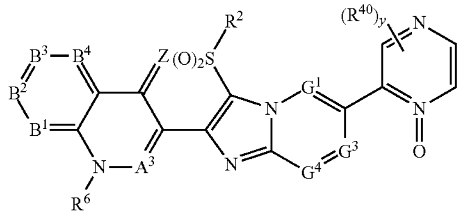

[wherein $R^{40}$ represents any one substituent selected from Group H; x represents 0, 1, 2, 3, or 4; y represents 0, 1, 2, or 3; and the other symbols are the same as defined above.]

The Present compound may optionally have one or more stereoisomer(s). Examples of the stereoisomer(s) include enantiomers, diastereomers, and geometric isomers. The Present compound encompasses each stereoisomer and mixtures of stereoisomers at any ratio.

The Present compound may optionally form an acid addition salt. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. Such acid addition salt may be prepared by mixing the Present compound with an acid.

Aspects of the Present compound N include the following compounds.

[Aspect 1] The Present compound N, wherein;
$G^1$ represents $CR^{3a}$;
$G^2$ represents $CR^{3b}$;
$G^3$ represents $CR^{3c}$;
$G^4$ represents $CR^{3d}$; and
$R^{3a}$, $R^{3b}$, $R^{3c}$, and $R^{3d}$ are identical to or different from each other, and each represent a C1-C6 chain hydrocarbon group optionally substituted with one or more halogen atom(s), a C3-C7 cycloalkyl group {wherein said C3-C7 cycloalkyl group is optionally substituted with one or more substituent(s) selected from the group consisting of a halogen atom and a cyano group}, a halogen atom, or a hydrogen atom.

[Aspect 2] The Present compound N, wherein
$G^1$ represents $CR^{3a}$;
$G^2$ represents $CR^{3b}$;
$G^3$ represents $CR^{3c}$;
$G^4$ represents $CR^{3d}$; and
$R^{3a}$, $R^{3b}$, $R^{3c}$, and $R^{3d}$ are identical to or different from each other, and each represent a C1-C6 chain hydrocarbon group optionally substituted with one or more halogen atom(s), a halogen atom, or a hydrogen atom.

[Aspect 3] The Present compound N, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 chain hydrocarbon group optionally substituted with one or more halogen atom (s), a halogen atom, or a hydrogen atom.

[Aspect 4] The Present compound N, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a trifluoromethyl group or a hydrogen atom.

[Aspect 5] The Present compound N, wherein $R^2$ represents a C1-C6 alkyl group.

[Aspect 6] The Present compound N, wherein $R^2$ represents an ethyl group.

[Aspect 7] The compound according to the Aspect 1, wherein $R^2$ represents a C1-C6 alkyl group.

[Aspect 8] The compound according to the Aspect 2, wherein $R^2$ represents a C1-C6 alkyl group.

[Aspect 9] The compound according to the Aspect 3, wherein $R^2$ represents a C1-C6 alkyl group.

[Aspect 10] The compound according to the Aspect 4, wherein $R^2$ represents a C1-C6 alkyl group.

[Aspect 11] The compound according to the Aspect 1, wherein $R^2$ represents an ethyl group.

[Aspect 12] The compound according to the Aspect 2, wherein $R^2$ represents an ethyl group.

[Aspect 13] The compound according to the Aspect 3, wherein $R^2$ represents an ethyl group.

[Aspect 14] The compound according to the Aspect 4, wherein $R^2$ represents an ethyl group.

[Aspect 15] The Present compound N, wherein n represents 2.

[Aspect 16] The compound according to the Aspect 1, wherein n represents 2.

[Aspect 17] The compound according to the Aspect 2, wherein n represents 2.

[Aspect 18] The compound according to the Aspect 3, wherein n represents 2.

[Aspect 19] The compound according to the Aspect 4, wherein n represents 2.

[Aspect 20] The compound according to the Aspect 5, wherein n represents 2.

[Aspect 21] The compound according to the Aspect 6, wherein n represents 2.

[Aspect 22] The compound according to the Aspect 7, wherein n represents 2.

[Aspect 23] The compound according to the Aspect 8, wherein n represents 2.

[Aspect 24] The compound according to the Aspect 9, wherein n represents 2.

[Aspect 25] The compound according to the Aspect 10, wherein n represents 2.

[Aspect 26] The compound according to the Aspect 11, wherein n represents 2.

[Aspect 27] The compound according to the Aspect 12, wherein n represents 2.

[Aspect 28] The compound according to the Aspect 13, wherein n represents 2.

[Aspect 29] The compound according to the Aspect 14, wherein n represents 2.

[Aspect 30] The compound according to any one of the Aspects 1 to 29 or the Present compound N, wherein Q represents the group represented by Q2, the group represented by Q3, the group represented by Q4, or the group represented by Q5;

Z represents an oxygen atom;

$A^4$ represents a nitrogen atom;

$A^5$ represents CH;

$A^6$ represents CH;

$A^7$ represents a nitrogen atom;

$A^8$ represents $CR^{4g}$;

$B^1$ represents $CR^{6a}$;

$B^4$ represents $CR^{6d}$; and the combination of $B^2$ and $B^3$ represents:

a combination wherein $B^2$ represents $CR^1$ and $B^3$ represents $CR^{6c}$; or a combination wherein $B^2$ represents $CR^{6b}$ and $B^3$ represents $CR^1$.

[Aspect 31] The compound according to any one of the Aspects 1 to 29 or the Present compound N, wherein Q represents the group represented by Q2, the group represented by Q3, or the group represented by Q4;

Z represents an oxygen atom;

$A^2$ represents $CR^{4a}$;

$A^4$ represents a nitrogen atom;

$A^5$ represents CH;

$A^6$ represents CH;

$A^7$ represents a nitrogen atom;

$A^{13}$ represents an oxygen atom;

$B^1$ represents $CR^{6a}$;

$B^4$ represents $CR^{6d}$; and the combination of $B^2$ and $B^3$ represents:

a combination wherein $B^2$ represents $CR^1$ and $B^3$ represents $CR^{6c}$; or a combination wherein $B^2$ represents $CR^{6b}$ and $B^3$ represents $CR^1$.

[Aspect 32] The compound according to any one of the Aspects 1 to 29 or the Present compound N, wherein Q represents the group represented by Q2, the group represented by Q3, or the group represented by Q4;

Z represents an oxygen atom;

$A^2$ represents CH;

$A^4$ represents a nitrogen atom;

$A^5$ represents CH;

$A^6$ represents CH;

$A^7$ represents a nitrogen atom;

$A^{13}$ represents an oxygen atom;

$B^1$ represents $CR^{6a}$;

$B^4$ represents $CR^{6d}$; and the combination of $B^2$ and $B^3$ represents:

a combination wherein $B^2$ represents $CR^1$ and $B^3$ represents $CR^{6c}$; or a combination wherein $B^2$ represents $CR^6$b and $B^3$ represents $CR^1$.

[Aspect 33] The compound according to any one of the Aspects 1 to 29 or the Present compound N, wherein Q represents the group represented by Q2;

Z represents an oxygen atom;

$A^4$ represents a nitrogen atom;

$A^5$ represents CH;

$B^1$ represents $CR^{6a}$;

$B^4$ represents $CR^{6a}$; and the combination of $B^2$ and $B^3$ represents:

a combination wherein $B^2$ represents $CR^1$ and $B^3$ represents $CR^{6c}$; or a combination wherein $B^2$ represents $CR^{6b}$ and $B^3$ represents $CR^1$.

[Aspect 34] The compound according to any one of the Aspects 1 to 29 or the Present compound N, wherein Q represents the group represented by Q3;

Z represents an oxygen atom;

$A^6$ represents CH;

$A^7$ represents a nitrogen atom;

$B^1$ represents $CR^6$S;

$B^4$ represents $CR^{6d}$; and the combination of $B^2$ and $B^3$ represents:

a combination wherein $B^2$ represents $CR^1$ and $B^3$ represents $CR^{6c}$; or a combination wherein $B^2$ represents $CR^{6b}$ and $B^3$ represents $CR^1$.

[Aspect 35] The Present compound N, wherein $B^1$ represents $CR^{6a}$;

$B^4$ represents $CR^{6d}$; and the combination of $B^2$ and $B^3$ represents:

a combination wherein $B^2$ represents $CR^1$ and $B^3$ represents $CR^{6c}$; or a combination wherein $B^2$ represents $CR^6$b and $B^3$ represents $CR^1$.

[Aspect 36] The Present compound N, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 37] The Present compound N, wherein $R^1$ represents a C1-C6 chain hydrocarbon group optionally substituted with one or more halogen atom(s), or a halogen atom.

[Aspect 38] The Present compound N, wherein $R^1$ represents a trifluoromethyl group or a halogen atom.

[Aspect 39] The compound according to the Aspect 30, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 40] The compound according to the Aspect 31, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 41] The compound according to the Aspect 32, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 42] The compound according to the Aspect 33, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 43] The compound according to the Aspect 34, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 44] The compound according to the Aspect 35, wherein $R^1$ represents a C1-C6 chain hydrocarbon group optionally substituted with one or more halogen atom(s), a C3-C4 cycloalkyl group optionally substituted with one or more halogen atom(s), or a halogen atom.

[Aspect 45] The compound according to the Aspect 30, wherein $R^1$ represents a C1-C6 chain hydrocarbon group optionally substituted with one or more halogen atom(s), or a halogen atom.

[Aspect 46] The compound according to the Aspect 31, wherein $R^1$ represents a C1-C6 chain hydrocarbon group optionally substituted with one or more halogen atom(s), or a halogen atom.

[Aspect 47] The compound according to the Aspect 32, wherein $R^1$ represents a C1-C6 chain hydrocarbon group optionally substituted with one or more halogen atom(s), or a halogen atom.

[Aspect 48] The compound according to the Aspect 33, wherein $R^1$ represents a C1-C6 chain hydrocarbon group optionally substituted with one or more halogen atom(s), or a halogen atom.

[Aspect 49] The compound according to the Aspect 34, wherein $R^1$ represents a C1-C6 chain hydrocarbon group optionally substituted with one or more halogen atom(s), or a halogen atom.

[Aspect 50] The compound according to the Aspect 35, wherein $R^1$ represents a C1-C6 chain hydrocarbon group optionally substituted with one or more halogen atom(s), or a halogen atom.

[Aspect 51] The compound according to the Aspect 30, wherein $R^1$ represents a trifluoromethyl group or a halogen atom.

[Aspect 52] The compound according to the Aspect 31, wherein $R^1$ represents a trifluoromethyl group or a halogen atom.

[Aspect 53] The compound according to the Aspect 32, wherein $R^1$ represents a trifluoromethyl group or a halogen atom.

[Aspect 54] The compound according to the Aspect 33, wherein $R^1$ represents a trifluoromethyl group or a halogen atom.

[Aspect 55] The compound according to the Aspect 34, wherein $R^1$ represents a trifluoromethyl group or a halogen atom.

[Aspect 56] The compound according to the Aspect 35, wherein $R^1$ represents a trifluoromethyl group or a halogen atom.

[Aspect 57] The compound according to the Aspect 36, wherein $R^{6a}$, $R^{6b}$, $R^{6c}$, and $R^{6d}$ each represent a hydrogen atom.

[Aspect 58] The compound according to the Aspect 37, wherein $R^{6a}$, $R^{6b}$, $R^{6c}$, and $R^{6d}$ each represent a hydrogen atom.

[Aspect 59] The compound according to the Aspect 38, wherein $R^{6a}$, $R^{6b}$, $R^{6c}$, and $R^{6d}$ each represent a hydrogen atom.

[Aspect 60] The compound according to the Aspect 39, wherein $R^{6a}$, $R^{6b}$, $R^{6c}$, and $R^{6d}$ each represent a hydrogen atom.

[Aspect 61] The compound according to the Aspect 40, wherein $R^{6a}$, $R^{6b}$, $R^{6c}$, and $R^{6d}$ each represent a hydrogen atom.

[Aspect 62] The compound according to the Aspect 41, wherein $R^{6a}$, $R^{6b}$, $R^{6c}$, and $R^{6d}$ each represent a hydrogen atom.

[Aspect 63] The compound according to the Aspect 42, wherein $R^{6a}$, $R^{6b}$, $R^{6c}$, and $R^{6d}$ each represent a hydrogen atom.

[Aspect 64] The compound according to the Aspect 43, wherein $R^{6a}$, $R^{6b}$, $R^{6c}$, and $R^{6d}$ each represent a hydrogen atom.

[Aspect 65] The compound according to the Aspect 44, wherein $R^{6a}$, $R^{6b}$, $R^{6c}$, and $R^{6d}$ each represent a hydrogen atom.

[Aspect 66] The compound according to the Aspect 45, wherein $R^{6a}$, $R^{6b}$, $R^{6c}$, and $R^{6d}$ each represent a hydrogen atom.

[Aspect 67] The compound according to the Aspect 46, wherein $R^{6a}$, $R^{6b}$, $R^{6c}$, and $R^{6d}$ each represent a hydrogen atom.

[Aspect 68] The compound according to the Aspect 47, wherein $R^{6a}$, $R^{6b}$, $R^{6c}$, and $R^{6d}$ each represent a hydrogen atom.

[Aspect 69] The compound according to the Aspect 48, wherein $R^{6a}$, $R^{6b}$, $R^{6c}$, and $R^{6d}$ each represent a hydrogen atom.

[Aspect 70] The compound according to the Aspect 49, wherein $R^{6a}$, $R^{6b}$, $R^{6c}$, and $R^{6d}$ each represent a hydrogen atom.

[Aspect 71] The compound according to the Aspect 50, wherein $R^{6a}$, $R^{6b}$, $R^{6c}$, and $R^{6d}$ each represent a hydrogen atom.

[Aspect 72] The compound according to the Aspect 51, wherein $R^{6a}$, $R^{6b}$, $R^{6c}$, and $R^{6d}$ each represent a hydrogen atom.

[Aspect 73] The compound according to the Aspect 52, wherein $R^{6a}$, $R^{6b}$, $R^{6c}$, and $R^{6d}$ each represent a hydrogen atom.

[Aspect 74] The compound according to the Aspect 53, wherein $R^{6a}$, $R^{6b}$, $R^{6c}$, and $R^{6d}$ each represent a hydrogen atom.

[Aspect 75] The compound according to the Aspect 54, wherein $R^{6a}$, $R^{6b}$, $R^{6c}$, and $R^{6d}$ each represent a hydrogen atom.

[Aspect 76] The compound according to the Aspect 55, wherein $R^{6a}$, $R^{6b}$, $R^{6c}$, and $R^{6d}$ each represent a hydrogen atom.

[Aspect 77] The compound according to the Aspect 56, wherein $R^{6a}$, $R^{6b}$, $R^{6c}$, and $R^{6d}$ each represent a hydrogen atom.

[Aspect 78] The Present compound N, wherein $G^1$ represents CH;
$G^2$ represents $CR^{3b}$;
$G^3$ represents $CR^{3c}$;
$G^4$ represents CH;
$R^{3b}$ and $R^{3c}$ are identical to or different from each other, and each represent a trifluoromethyl group, a halogen atom, or a hydrogen atom;
$R^2$ represents an ethyl group;
n represents 2;
Q represents the group represented by Q2, the group represented by Q3, or the group represented by Q4;
Z represents an oxygen atom;
$A^2$ represents CH;
$A^4$ represents a nitrogen atom;
$A^5$ represents CH;
$A^6$ represents CH;
$A^7$ represents a nitrogen atom;
$A^{13}$ represents an oxygen atom;
$B^1$ represents CH;
$B^4$ represents CH;
the combination of $B^2$ and $B^3$ represents:
a combination wherein $B^2$ represents $CR^1$ and $B^3$ represents CH; or
a combination wherein $B^2$ represents CH and $B^3$ represents $CR^1$; and
$R^1$ represents a trifluoromethyl group or a halogen atom.

[Aspect 79] The Present compound N, wherein $G^1$ represents CH;
$G^2$ represents $CR^{3b}$;
$G^3$ represents $CR^{3c}$;
$G^4$ represents CH;
$R^{3b}$ and $R^{3c}$ are identical to or different from each other, and each represent a trifluoromethyl group or a hydrogen atom;
$R^2$ represents an ethyl group;
n represents 2;
Q represents the group represented by Q2, the group represented by Q3, or the group represented by Q4;
Z represents an oxygen atom;
$A^2$ represents CH;
$A^4$ represents a nitrogen atom;
$A^5$ represents CH;
$A^6$ represents CH;
$A^7$ represents a nitrogen atom;
$A^{13}$ represents an oxygen atom;
$B^1$ represents CH;
$B^4$ represents CH;
the combination of $B^2$ and $B^3$ represents:
a combination wherein $B^2$ represents $CR^1$ and $B^3$ represents CH; or
a combination wherein $B^2$ represents CH and $B^3$ represents $CR^1$; and
$R^1$ represents a trifluoromethyl group or a halogen atom.

Next, production methods of the Present compounds are described.

Production Method 1

A compound represented by formula (I-b) (hereinafter referred to as "Compound (I-b)") or a compound represented by formula (I-c) (hereinafter referred to as "Compound (I-c)") may be prepared by reacting a compound represented by formula (I-a) (hereinafter referred to as "Compound (I-a)") with an oxidizing agent.

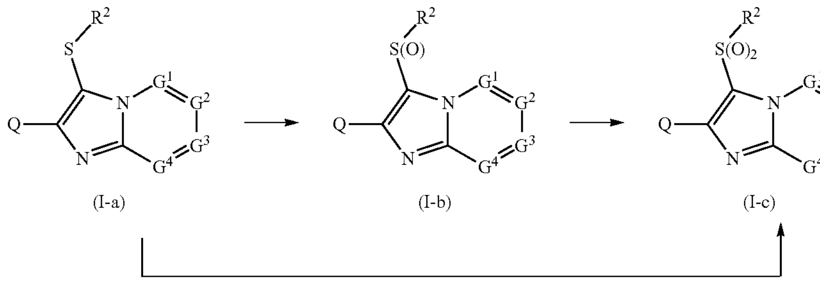

(I-a) (I-b) (I-c)

[wherein the symbols are the same as defined above.]

First, a method for producing the Compound (I-b) from the Compound (I-a) is described.

The reaction is usually carried out in a solvent. Examples of the solvent include ethers such as tetrahydrofuran, 1,4-dioxane, 1,2-dimethoxyethane, methyl tert-butyl ether, and diethyl ether (hereinafter collectively referred to as "ethers"); halogenated hydrocarbons such as dichloromethane and chloroform (hereinafter collectively referred to as "halogenated hydrocarbons"); nitriles such as acetonitrile (hereinafter collectively referred to as "nitriles"); acetic acid; water; and mixtures of two or more of them.

Examples of the oxidizing agent include sodium periodate, m-chloroperbenzoic acid (hereinafter referred to as "mCPBA"), and hydrogen peroxide.

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-a).

Examples of the catalyst include tungstic acid and sodium tungstate. When a catalyst is used in the reaction, the catalyst is usually used at a ratio of 0.01 to 0.5 mol relative to 1 mol of the Compound (I-a).

In the reaction, the oxidizing agent is usually used at a ratio of 1 to 1.2 mol relative to 1 mol of the Compound (I-a).

The reaction temperature is usually within the range of −20 to 80° C. The reaction time is usually within the range of 0.1 to 12 hour(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer may be dried and/or concentrated to give the Compound (I-b).

Next, a method for producing the Compound (I-c) from the Compound (I-b) is described.

The reaction is usually carried out in a solvent. Examples of the solvent include halogenated hydrocarbons; nitriles; alcohols such as methanol and ethanol (hereinafter collectively referred to as "alcohols"); acetic acid; water; and mixtures of two or more of them.

Examples of the oxidizing agent include mCPBA and hydrogen peroxide.

In the reaction, the oxidizing agent is usually used at a ratio of 1 to 2 mol relative to 1 mol of the Compound (I-b).

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-b).

Examples of the catalyst include sodium tungstate. When a catalyst is used in the reaction, the catalyst is usually used at a ratio of 0.01 to 0.5 mol relative to 1 mol of the Compound (I-b).

The reaction temperature is usually within the range of −20 to 120° C. The reaction time is usually within the range of 0.1 to 12 hour(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer may be dried and/or concentrated to give the Compound (I-c).

Also, the Compound (I-c) may be prepared in one step reaction (one-pot) by reacting the Compound (I-a) with an oxidizing agent.

The reaction may be carried out according to the method for producing the Compound (I-c) from the Compound (I-b) by usually using the oxidizing agent at a ratio of 2 to 5 mol relative to 1 mol of the Compound (I-a).

Production Method 2

A compound represented by formula (I-Q1-2) (hereinafter referred to as "Compound (I-Q1-2)") may be prepared by reacting a compound represented by formula (I-Q1-1) (hereinafter referred to as "Compound (I-Q1-1)") with a sulfating agent.

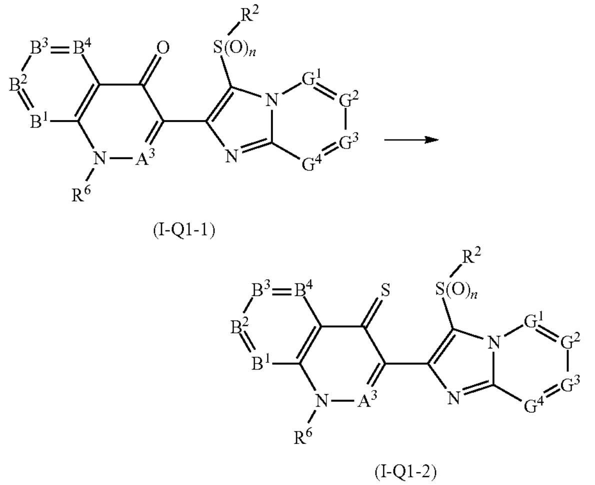

(I-Q1-1)

(I-Q1-2)

[wherein the symbols are the same as defined above.]

The reaction is carried out in a solvent or in the absence of a solvent. Examples of the solvent include ethers, halogenated hydrocarbons; aromatic hydrocarbons such as toluene and xylene (hereinafter collectively referred to as "aromatic hydrocarbons"); nitriles; and mixtures of two or more of them.

Examples of the sulfating agent include phosphorus pentasulfide and Lawesson's reagent (2,4-bis(4-methoxyphenyl)-1,3-dithia-2,4-diphosphetane-2,4-disulfide).

In the reaction, the sulfating agent is usually used at a ratio of 1 to 3 mol relative to 1 mol of the Compound (I-Q1-1).

The reaction temperature is usually within the range of 0 to 200° C. The reaction time is usually within the range of 1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-Q1-2).

Production Method 3

A compound represented by formula (I-Q2-2) (hereinafter referred to as "Compound (I-Q2-2)") may be prepared by reacting a compound represented by formula (I-Q2-1) (hereinafter referred to as "Compound (I-Q2-1)") with a sulfating agent.

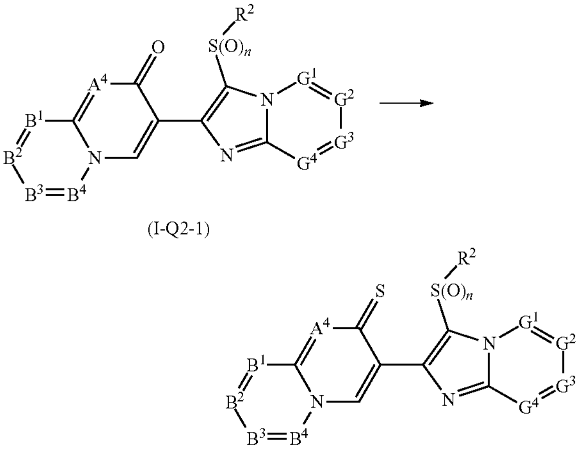

(I-Q2-1)

(I-Q2-2)

[wherein the symbols are the same as defined above.]

The reaction may be carried out according to the Production method 2.

Production Method 4

A compound represented by formula (I-Q3-2) (hereinafter referred to as "Compound (I-Q3-2)") may be prepared by reacting a compound represented by formula (I-Q3-1) (hereinafter referred to as "Compound (I-Q3-1)") with a sulfating agent.

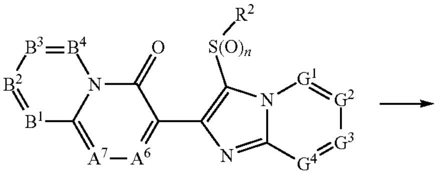

(I-Q3-1)

-continued

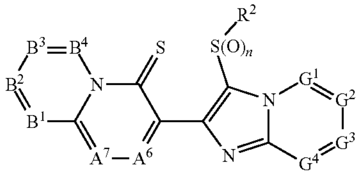

(I-Q3-2)

[wherein the symbols are the same as defined above.]

The reaction may be carried out according to the Production method 2.

Production Method 5

A compound represented by formula (I-Q4-2) (hereinafter referred to as "Compound (I-Q4-2)") may be prepared by reacting a compound represented by formula (I-Q4-1) (hereinafter referred to as "Compound (I-Q4-1)") with a sulfating agent.

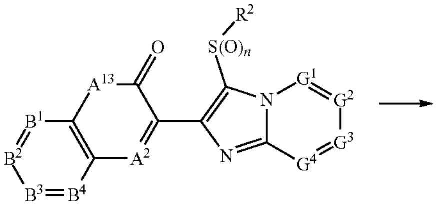

(I-Q4-1)

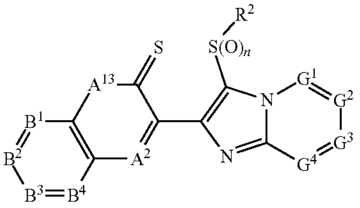

(I-Q4-2)

[wherein the symbols are the same as defined above.]

The reaction may be carried out according to the Production method 2.

Production Method 6

A compound represented by formula (I-Q5-2) (hereinafter referred to as "Compound (I-Q5-2)") may be prepared by reacting a compound represented by formula (I-Q5-1) (hereinafter referred to as "Compound (I-Q5-1)") with a sulfating agent.

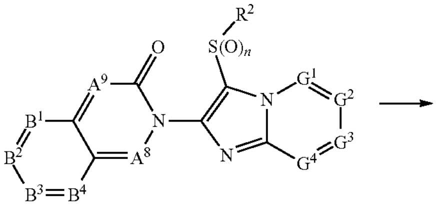

(I-Q5-1)

-continued

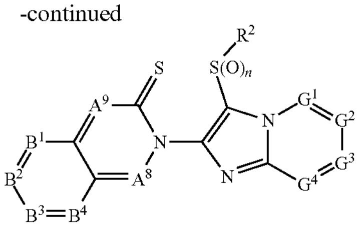

(I-Q5-2)

[wherein the symbols are the same as defined above.]

The reaction may be carried out according to the Production method 2.

Production Method 7

A compound represented by formula (II-Q3-1) (hereinafter referred to as "Compound (II-Q3-1)") may be prepared by reacting a compound represented by formula (M-Q3-1) (hereinafter referred to as "Compound (M-Q3-1)") with a compound represented by formula (R-1) (hereinafter referred to as "Compound (R-1)").

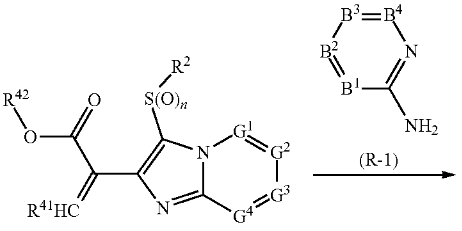

(M-Q3-1)

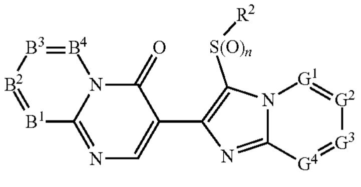

(II-Q3-1)

[wherein $R^{41}$ represents a methoxy group, an ethoxy group, a dimethylamino group, or a hydroxy group; $R^{42}$ represents a methyl group or an ethyl group; and the other symbols are the same as defined above.]

The reaction is usually carried out in a solvent. Examples of the solvent to be used in the reaction include aprotic polar solvents such as N-methylpyrrolidone (hereinafter referred to as "NMP"), N,N-dimethylformamide (hereinafter referred to as "DMF"), and dimethyl sulfoxide (hereinafter referred to as "DMSO") (hereinafter collectively referred to as "aprotic polar solvents"); alcohols; ethers; halogenated hydrocarbons; aromatic hydrocarbons; nitriles; water; and mixtures of two or more of them.

In the reaction, a base may be used as needed. Examples of the base to be used in the reaction include organic bases such as triethylamine, diisopropylethylamine, pyridine, and 4-(dimethylamino)pyridine (hereinafter collectively referred to as "organic bases"); and alkali metal carbonates such as sodium carbonate and potassium carbonate (hereinafter collectively referred to as "alkali metal carbonates"). When a base is used in the reaction, the base is usually used at a ratio of 0.1 to 5 mol relative to 1 mol of the Compound (M-Q3-1).

In the reaction, the Compound (R-1) is usually used at a ratio of 1 to 10 mol relative to 1 mol of the Compound (M-Q3-1).

The reaction temperature is usually within the range of −20° C. to 200° C. The reaction time is usually within the range of 0.1 to 48 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-Q3-1).

The Compound (R-1) is a commercially available compound or may be prepared by using known method(s).

Production Method 8

A compound represented by formula (II-Q2-1) (hereinafter referred to as "Compound (II-Q2-1)") may be prepared by cyclizing a compound represented by formula (M-Q2-1) (hereinafter referred to as "Compound (M-Q2-1)").

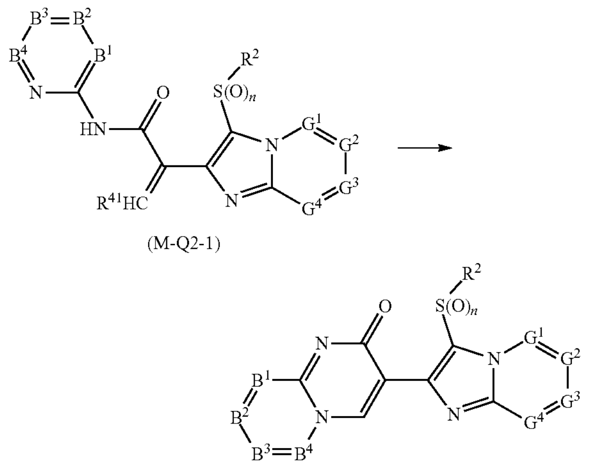

(M-Q2-1)

(II-Q2-1)

[wherein the symbols are the same as defined above.]

The reaction is usually carried out in a solvent. Examples of the solvent to be used in the reaction include ethers, aromatic hydrocarbons, nitriles, halogenated hydrocarbons, aprotic polar solvents, alcohols, water, and mixtures of two or more of them.

In the reaction, an acid may be used as needed. Examples of the acid to be used in the reaction include organic acids such as formic acid, acetic acid, propionic acid, trifluoroacetic acid, p-toluenesulfonic acid, and trifluoromethanesulfonic acid (hereinafter collectively referred to as "organic acids"); and inorganic acids such as hydrochloric acid and sulfuric acid (hereinafter collectively referred to as "inorganic acids"). When an acid is used in the reaction, the acid is usually used at a ratio of 0.1 to 5 mol relative to 1 mol of the Compound (M-Q2-1).

When an acid is used, the reaction temperature is usually within the range of −20° C. to 150° C., and the reaction time is usually within the range of 0.1 to 48 hour(s). When an acid is not used, the reaction temperature is within the range of 20 to 150° C., and the reaction time is usually within the range of 0.5 to 48 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-Q2-1).

Production Method 9

A compound represented by formula (I-Qa) (hereinafter referred to as "Compound (I-Qa)") may be prepared according to the following scheme.

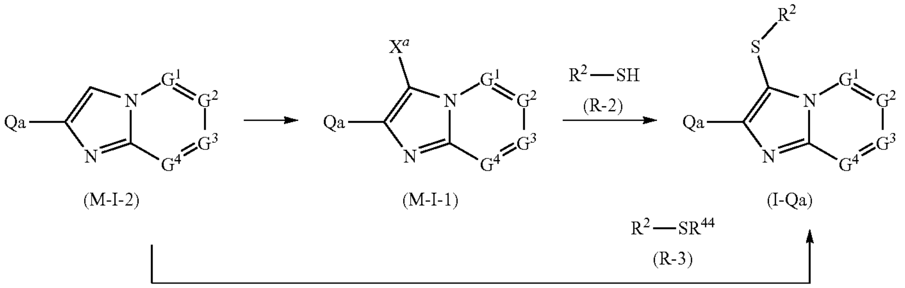

(M-I-2)

(M-I-1)

(I-Qa)

Qa=

Q1a

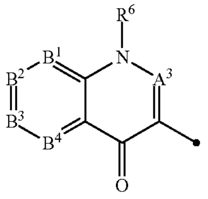

Q2a

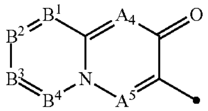

Q3a

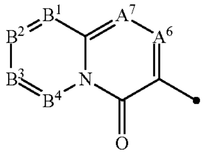

Q4a

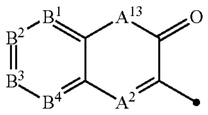

Q5a

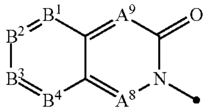

[wherein $X^a$ represents a chlorine atom, a bromine atom, or an iodine atom; $R^{44}$ represents $SR^2$ or a hydrogen atom; Qa represents a group represented by Q1a, a group represented by Q2a, a group represented by Q3a, a group represented by Q4a, or a group represented by Q5a; and the other symbols are the same as defined above.]

First, a step to produce a compound represented by formula (M-I-1) (hereinafter referred to as "Compound (M-I-1)") from a compound represented by formula (M-I-2) (hereinafter referred to as "Compound (M-I-2)") is described.

The Compound (M-I-1) may be prepared by reacting the Compound (M-I-2) with a halogenating agent.

The reaction is usually carried out in a solvent. Examples of the solvent to be used in the reaction include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide (hereinafter referred to as "NIS").

In the reaction, the halogenating agent is usually used at a ratio of 1 to 20 mol relative to 1 mol of the Compound (M-I-2).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-I-1).

Next, a step to produce the Compound (I-Qa) from the Compound (M-I-1) is described.

The Compound (I-Qa) may be prepared by reacting the Compound (M-I-1) with a compound represented by formula (R-2) (hereinafter referred to as "Compound (R-2)") in the presence of a metal catalyst and a base.

The reaction is usually carried out in a solvent. Examples of the solvent to be used in the reaction include alcohols, nitriles, ethers, aromatic hydrocarbons, aprotic polar solvents, water, and mixtures of two or more of them.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetone)dipalladium(0) (hereinafter referred to as "$Pd_2$ $(dba)_3$"), and palladium(II) acetate; nickel catalysts such as bis(cyclooctadiene)nickel(0) and nickel(II) chloride; and copper catalysts such as copper(I) iodide and copper(I) chloride.

Examples of the base to be used in the reaction include alkali metal hydrides such as sodium hydride (hereinafter collectively referred to as "alkali metal hydrides"); alkali metal carbonates; and organic bases.

In the reaction, a ligand may be used. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When a ligand is used in the reaction, the ligand is usually used at a ratio of 0.01 to 1 mol relative to 1 mol of the Compound (M-I-1).

In the reaction, the Compound (R-2) is usually used at a ratio of 1 to 20 mol, the metal catalyst is usually used at a ratio of 0.01 to 0.5 mol, and the base is usually used at a ratio of 0.1 to 5 mol, relative to 1 mol of the Compound (M-I-1).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-Qa).

Next, a step to produce the Compound (I-Qa) from the Compound (M-I-2) is described.

The Compound (I-Qa) may also be prepared by reacting the Compound (M-I-2) with a compound represented by formula (R-3) (hereinafter referred to as "Compound (R-3)") in the presence of a halogenating agent.

The reaction is usually carried out in a solvent. Examples of the solvent to be used in the reaction include alcohols, nitriles, ethers, aromatic hydrocarbons, aprotic polar solvents, water, and mixtures of two or more of them.

Examples of the halogenating agent include bromine, iodine, sodium bromide, potassium bromide, sodium iodide, and potassium iodide.

In the reaction, an oxidizing agent may be used as needed. Examples of the oxidizing agent include hydrogen peroxide, tert-butyl hydroperoxide, and DMSO. When an oxidizing agent is used in the reaction, the oxidizing agent is usually used at a ratio of 1 to 20 mol relative to 1 mol of the Compound (M-I-2).

In the reaction, the Compound (R-3) is usually used at a ratio of 0.5 to 10 mol, and the halogenating agent is usually used at a ratio of 0.05 to 10 mol, relative to 1 mol of the Compound (M-I-2).

The reaction temperature is usually within the range of 0° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-Qa).

The Compound (R-2) and the Compound (R-3) are known or may be prepared according to known method(s).

Production Method 10

The Compound (I-Q5-1) may be prepared by reacting a compound represented by formula (M-Q5-1) (hereinafter referred to as "Compound (M-Q5-1)") with a compound represented by formula (M-Q5-2) (hereinafter referred to as "Compound (M-Q5-2)") in the presence of a base.

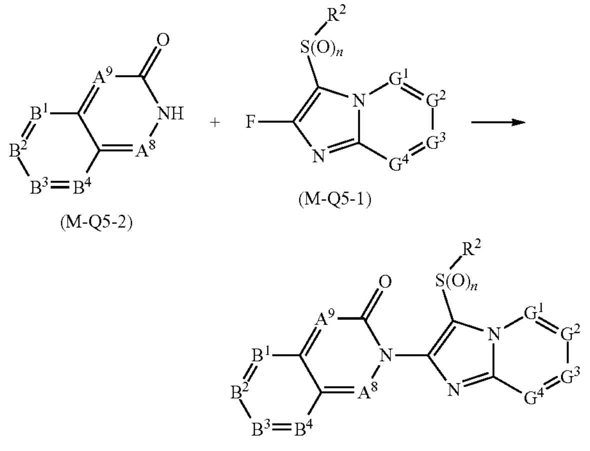

(M-Q5-2) (M-Q5-1) (I-Q5-1)

[wherein the symbols are the same as defined above.]

The reaction is usually carried out in a solvent. Examples of the solvent to be used in the reaction include ethers, aromatic hydrocarbons, nitriles, aprotic polar solvents, halogenated hydrocarbons, alcohols, and mixtures of two or more of them.

Examples of the base to be used in the reaction include alkali metal carbonates and alkali metal hydrides.

In the reaction, the Compound (M-Q5-2) is usually used at a ratio of 1 to 2 mol, and the base is usually used at a ratio of 1 to 10 mol, relative to 1 mol of the Compound (M-Q5-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-Q5-1).

The Compound (M-Q5-2) is known or may be prepared according to known method(s) (for example, a method disclosed in Org. Biomol. Chem., 2018, 16, 7050, Org. Lett., 2004, 6, 2433, or Science of Synthesis 2005, 15, 947.).

Production Method 11

A compound represented by formula (II-Q4-1) (hereinafter referred to as "Compound (II-Q4-1)") may be prepared by reacting a compound represented by formula (M-Q4-1) (hereinafter referred to as "Compound (M-Q4-1)") with a compound represented by formula (R-4) (hereinafter referred to as "Compound (R-4)") in the presence of an acid or a base.

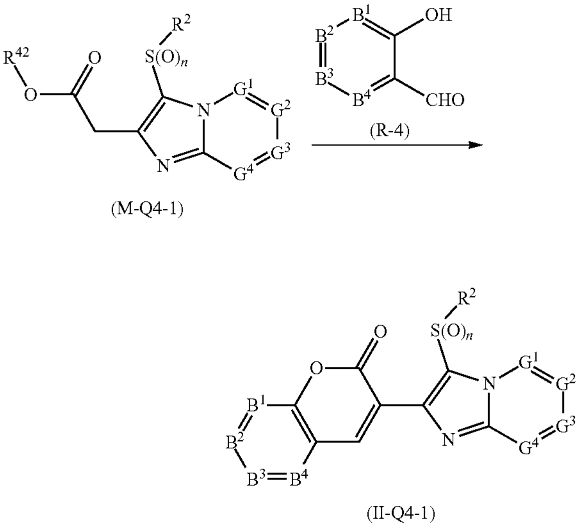

(M-Q4-1) (R-4) (II-Q4-1)

[wherein the symbols are the same as defined above.]

The reaction is usually carried out in a solvent. Examples of the solvent to be used in the reaction include ethers, aromatic hydrocarbons, nitriles, aprotic polar solvents, halogenated hydrocarbons, and mixtures of two or more of them.

Examples of the base to be used in the reaction include organic bases, alkali metal carbonates, and alkali metal hydrides.

Examples of the acid to be used in the reaction include organic acids and inorganic acids.

In the reaction, the Compound (R-4) is usually used at a ratio of 1 to 10 mol, and the base or the acid is usually used at a ratio of 1 to 10 mol, relative to 1 mol of the Compound (M-Q4-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-Q4-1).

Production Method 12

An N-oxide of the compound represented by formula (I) may be prepared by reacting the compound represented by formula (I) with an oxidizing agent. The reaction may be carried out according to the method disclosed in, for example, the Production method 1, US Patent Application Publication No. 2018/0009778, or WO 2016/121970 pamphlet.

Hereinafter, production methods of the production intermediate compounds are described.

Reference Production Method 1

The Compound (M-Q2-1) may be prepared from a compound represented by formula (M-Q2-2) (hereinafter referred to as "Compound (M-Q2-2)").

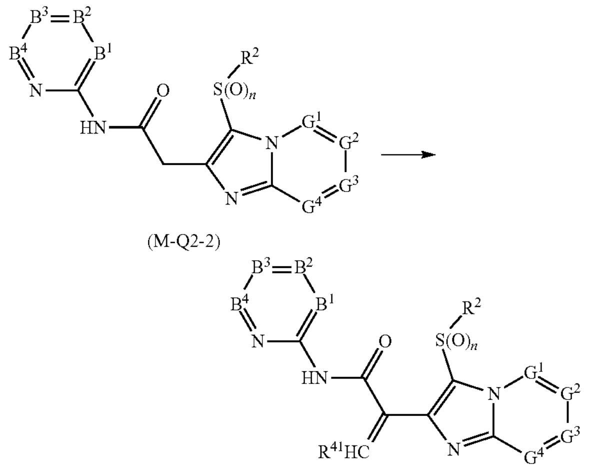

(M-Q2-2)

(M-Q2-1)

[wherein the symbols are the same as defined above.]

The reaction may be carried out according to the method disclosed in, for example, Chem. Med. Chem., 2018, 13, 988, Org. Lett., 2016, 18, 6344, or Tetrahedron, 2017, 73, 3939.

Reference Production Method 2

The Compound (M-Q2-2) may be prepared by reacting a compound represented by formula (M-Q2-3) (hereinafter referred to as "Compound (M-Q2-3)") with the Compound (R-1).

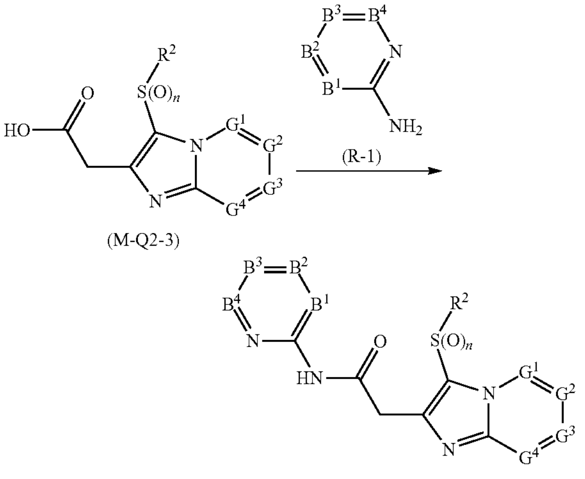

(M-Q2-3)

(M-Q2-2)

[wherein the symbols are the same as defined above.]

The reaction may be carried out according to the method disclosed in, for example, Bioorganic & Medicinal Chemistry Letters, 2015, 25, 4793, European Journal of Medicinal Chemistry, 2016, 122, 178, or Tetrahedron Lett. 1975, 16, 1219.

The Compound (M-Q2-3) is known or may be prepared according to known method(s) (for example, a method disclosed in Journal of Medicinal Chemistry, 2019, 62, 2798. or WO 2019/178129 pamphlet).

Reference Production Method 3

The Compound (M-Q3-1) may be prepared from the Compound (M-Q4-1).

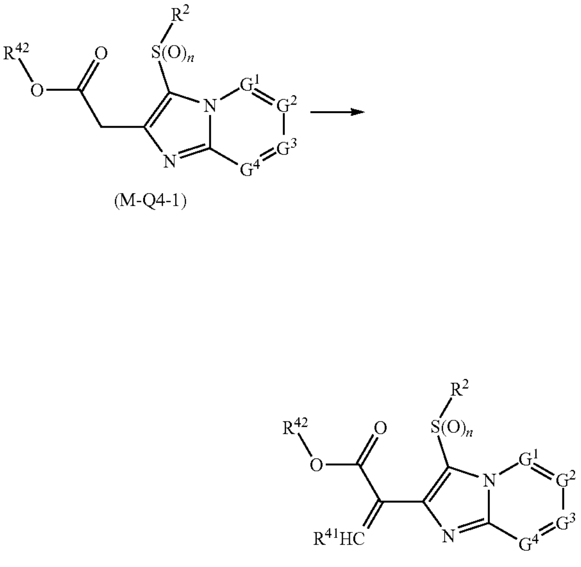

(M-Q4-1)

(M-Q3-1)

[wherein the symbols are the same as defined above.]

The reaction may be carried out according to the Reference Production method 1.

Reference Production Method 4

A compound represented by formula (M-Q4-1b) and a compound represented by formula (M-Q4-1c) may be prepared by reacting a compound represented by formula (M-Q4-1a) (hereinafter referred to as "Compound (M-Q4-1a)") with an oxidizing agent. A compound represented by formula (M-Q4-1c) may also be prepared by reacting a compound represented by formula (M-Q4-1b) with an oxidizing agent.

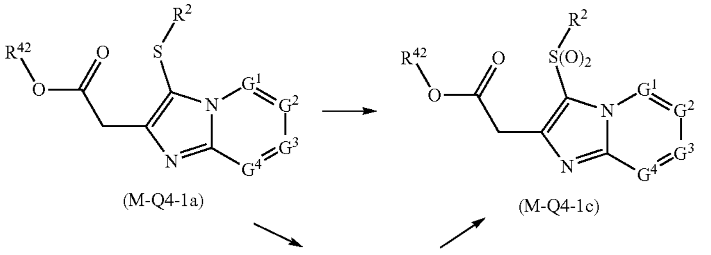

(M-Q4-1a)

(M-Q4-1c)

-continued

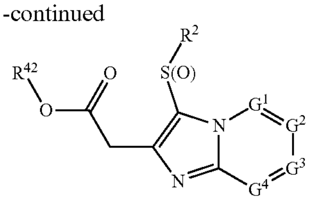

(M-Q4-1b)

[wherein the symbols are the same as defined above.]

These reactions may be carried out according to the Production method 1.

Reference Production Method 5

The Compound (M-Q4-1a) may be prepared according to the following scheme.

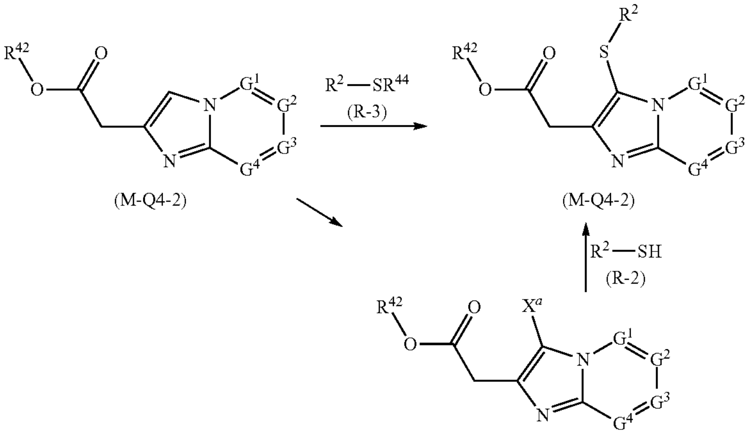

(M-Q4-2) (M-Q4-2) (M-Q4-3)

[wherein the symbols are the same as defined above.]

These reactions may be carried out according to the Production method 9.

A compound represented by formula (M-Q4-2) is known or may be prepared according to known method(s) (for example, a method disclosed in Bioorganic & Medicinal Chemistry, 2008, 16(6), 3125.).

Reference Production Method 6

A compound represented by formula (M2-Q5-1) and a compound represented by formula (M2-Q5-2) may be prepared by reacting a compound represented by formula (M2-Q5-3) with an oxidizing agent. A compound represented by formula (M2-Q5-1) may also be prepared by reacting a compound represented by formula (M2-Q5-2) with an oxidizing agent.

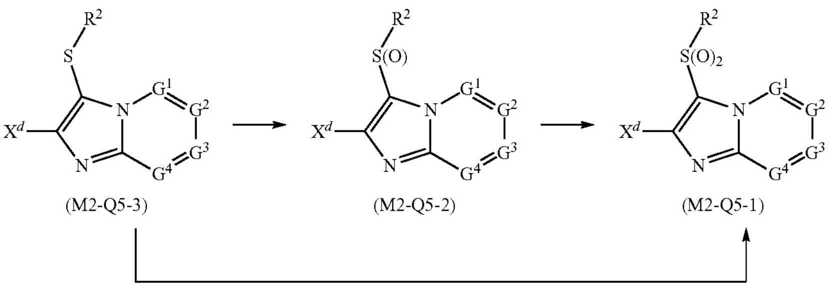

(M2-Q5-3) (M2-Q5-2) (M2-Q5-1)

[wherein $X^d$ represents a fluorine atom or a chlorine atom; and the other symbols are the same as defined above.]

These reactions may be carried out according to the Production method 1.

Reference Production Method 7

A compound represented by formula (M2-Q5-4) (hereinafter referred to as "Compound (M2-Q5-4)") may be prepared according to the following scheme.

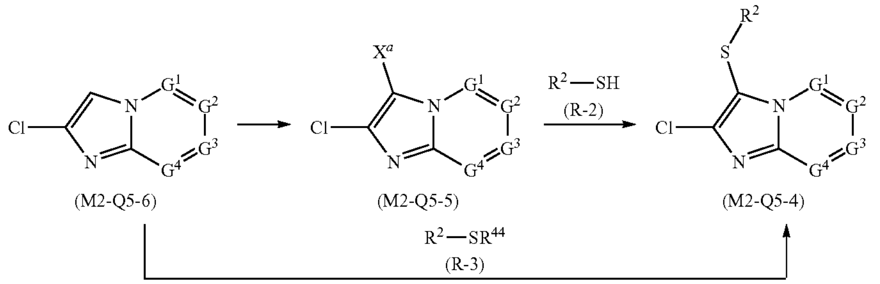

(M2-Q5-6) (M2-Q5-5) (M2-Q5-4)

[wherein the symbols are the same as defined above.]

These reactions may be carried out according to the Production method 9.

Reference Production Method 8

A compound represented by formula (M2-Q5-6) (hereinafter referred to as "Compound (M2-Q5-6)") may be prepared according to the following scheme.

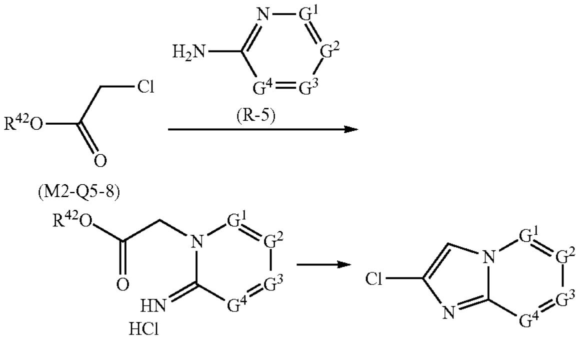

(M2-Q5-8) (M2-Q5-7) (M2-Q5-6)

[wherein the symbols are the same as defined above.]

A compound represented by formula (M2-Q5-7) (hereinafter referred to as "Compound (M2-Q5-7)") may be prepared by reacting a compound represented by formula (R-5) (hereinafter referred to as "Compound (R-5)") with a compound represented by formula (M2-Q5-8) (hereinafter referred to as "Compound (M2-Q5-8)").

The reaction is usually carried out in a solvent. Examples of the solvent include ethers, halogenated hydrocarbons, aromatic hydrocarbons, aprotic polar solvents, alcohols, nitriles, and mixtures of two or more of them.

In the reaction, the Compound (R-5) is usually used at a ratio of 1 to 10 mol relative to 1 mol of the Compound (M2-Q5-8).

The reaction temperature is usually within the range of 0° C. to 200° C. The reaction time is usually within the range of 0.1 to 48 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M2-Q5-7).

The Compound (R-5) and the Compound (M2-Q5-8) are commercially available compounds or may be prepared by using known method(s).

The Compound (M2-Q5-6) may be prepared by reacting the Compound (M2-Q5-7) with phosphorus oxychloride.

The reaction is usually carried out in a solvent. Examples of the solvent include aromatic hydrocarbons, nitriles, and mixtures of two or more of them.

In the reaction, phosphorus oxychloride is usually used at a ratio of 1 to 10 mol relative to 1 mol of the Compound (M2-Q5-7).

The reaction temperature is usually within the range of 60° C. to 120° C. The reaction time is usually within the range of 0.1 to 48 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M2-Q5-6).

Reference Production Method 9

The Compound (M-Q5-1) may be prepared by reacting a compound represented by formula (M-Q5-3) (hereinafter referred to as "Compound (M-Q5-3)") with cesium fluoride.

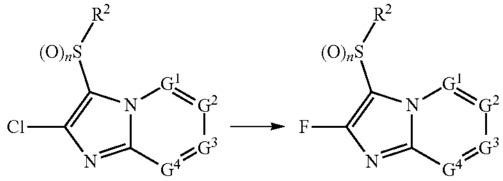

(M-Q5-3) (M-Q5-1)

[wherein the symbols are the same as defined above.]

The reaction may be carried out according to the method disclosed in, for example, Tetrahedron Lett., 2015, 56, 6043.

Reference Production Method 10

A compound represented by formula (M2-Q5-9) (hereinafter referred to as "Compound (M2-Q5-9)") may be prepared by reacting the Compound (M2-Q5-6) with cesium fluoride.

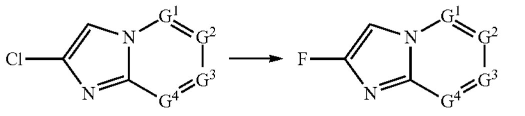

(M2-Q5-6) (M2-Q5-9)

[wherein the symbols are the same as defined above.]

The reaction may be carried out according to the Reference Production method 9.

Reference Production Method 11

A compound represented by formula (M2-Q5-10) (hereinafter referred to as "Compound (M2-Q5-10)") may be prepared by reacting the Compound (M2-Q5-9) with the Compound (M-Q5-2) in the presence of a base.

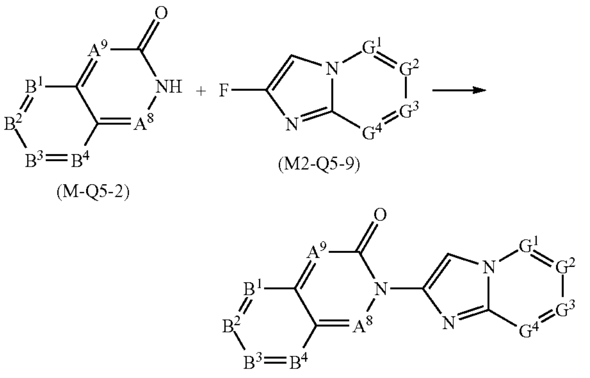

(M-Q5-2) (M2-Q5-9) (M2-Q5-10)

[wherein the symbols are the same as defined above.]

The reaction may be carried out according to the Production method 10.

Reference Production Method 12

The Compound (M-I-2) may be prepared by reacting a compound represented by formula (M-I-3) (hereinafter referred to as "Compound (M-I-3)") with the Compound (R-5).

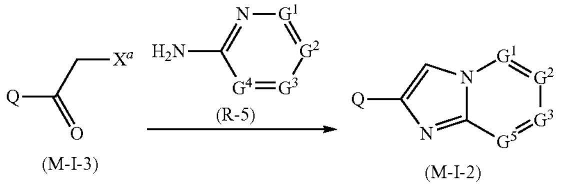

(M-I-3) (R-5) (M-I-2)

[wherein the symbols are the same as defined above.]

The reaction is usually carried out in a solvent. Examples of the solvent to be used in the reaction include ethers, aromatic hydrocarbons, aprotic polar solvents, halogenated hydrocarbons, alcohols, nitriles, water, and mixtures of two or more of them.

In the reaction, a base may be used as needed. Examples of the base to be used in the reaction include organic bases and alkali metal carbonates. When a base is used in the reaction, the base is usually used at a ratio of 0.1 to 5 mol relative to 1 mol of the Compound (M-I-3).

In the reaction, the Compound (R-5) is usually used at a ratio of 1 to 10 mol relative to 1 mol of the Compound (M-I-3).

The reaction temperature is usually within the range of −20° C. to 200° C. The reaction time is usually within the range of 0.1 to 48 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-I-2).

Reference Production Method 13

A compound represented by formula (M-Q1-1) (hereinafter referred to as "Compound (M-Q1-1)") may be prepared according to the following scheme.

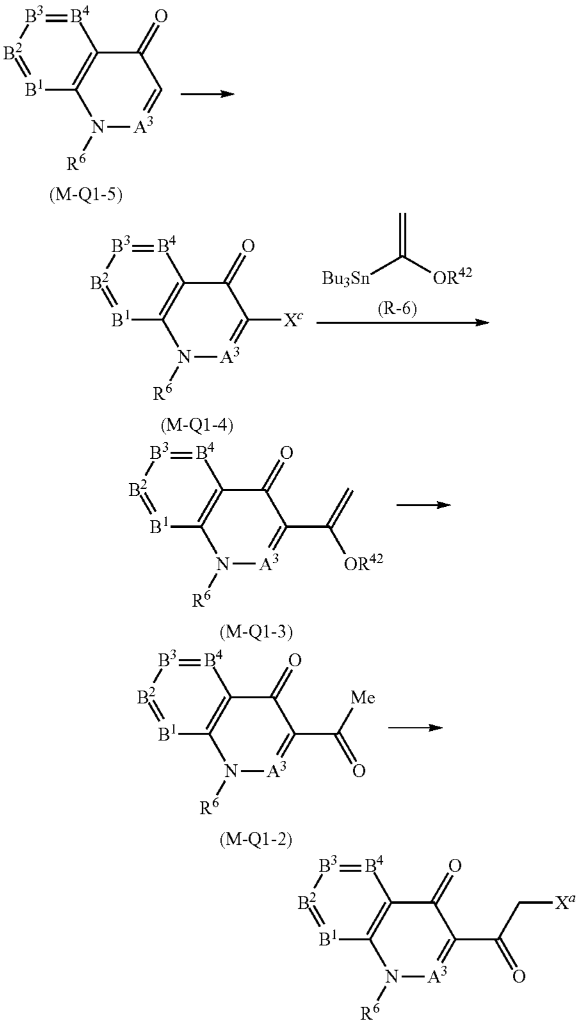

(M-Q1-5) (M-Q1-4) (R-6) (M-Q1-3) (M-Q1-2) (M-Q1-1)

[wherein $X^c$ represents a bromine atom or an iodine atom; and the other symbols are the same as defined above.]

A compound represented by formula (M-Q1-4) (hereinafter referred to as "Compound (M-Q1-4)") may be prepared by reacting a compound represented by formula (M-Q1-5) (hereinafter referred to as "Compound (M-Q1-5)") with a halogenating agent. The reaction may be carried out according to the method disclosed in, for example, WO 2012/020780 pamphlet or Chem. Commun., 2015, 51, 17744.

The Compound (M-Q1-5) is known or may be prepared according to known method(s) (for example, a method disclosed in Molecules 2020, 25, 268, or Tetrahedron Letters, 2016, 572488-2491).

A compound represented by formula (M-Q1-3) (hereinafter referred to as "Compound (M-Q1-3)") may be prepared by reacting the Compound (M-Q1-4) with a compound represented by formula (R-6) (hereinafter referred to as "Compound (R-6)"). The reaction may be carried out according to the method disclosed in, for example, WO 2016/123253 pamphlet.

The Compound (R-6) is known or may be prepared according to known method(s).

A compound represented by formula (M-Q1-2) (hereinafter referred to as "Compound (M-Q1-2)") may be prepared by reacting the Compound (M-Q1-3) with an acid. The reaction may be carried out according to the method disclosed in, for example, WO 2016/123253 pamphlet.

The Compound (M-Q1-1) may be prepared by reacting the Compound (M-Q1-2) with a halogenating agent. The reaction may be carried out according to the method disclosed in WO 2013/191113 pamphlet.

Reference Production Method 14

A compound represented by formula (M2-Q2-1) may be prepared according to the following scheme.

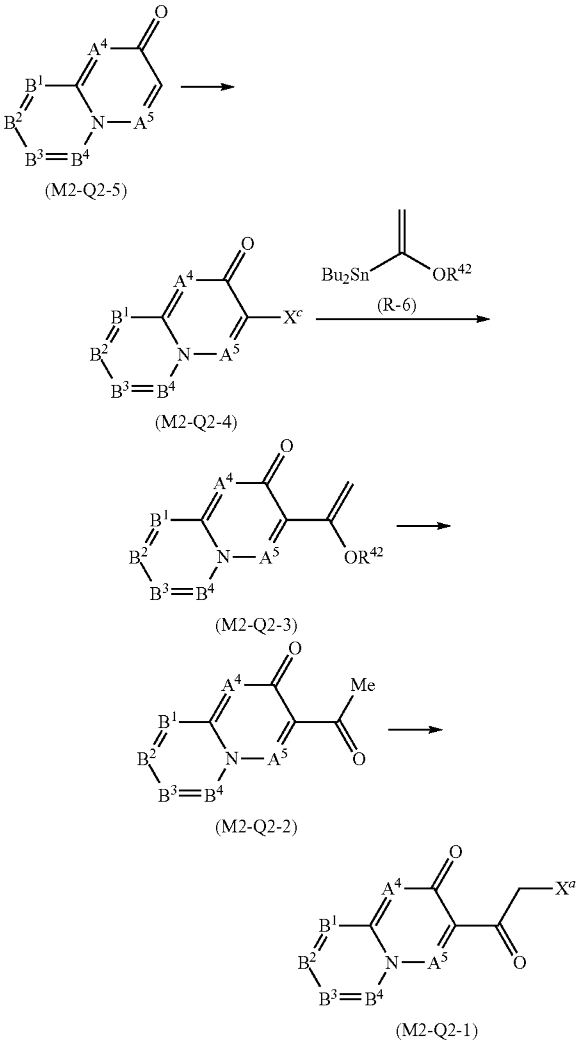

(M2-Q2-5) (M2-Q2-4) (M2-Q2-3) (M2-Q2-2) (M2-Q2-1)

[wherein the symbols are the same as defined above.]

These reactions may be carried out according to the Reference Production method 13.

A compound represented by formula (M2-Q2-5) is known or may be prepared according to known method(s) (for example, a method disclosed in Synthetic Communications 2018, 48, 375, Journal of Medicinal Chemistry 2016, 59, 6070, or Tetrahedron Letters 2014, 55, 1715.).

Reference Production Method 15

A compound represented by formula (M2-Q3-1) may be prepared according to the following scheme.

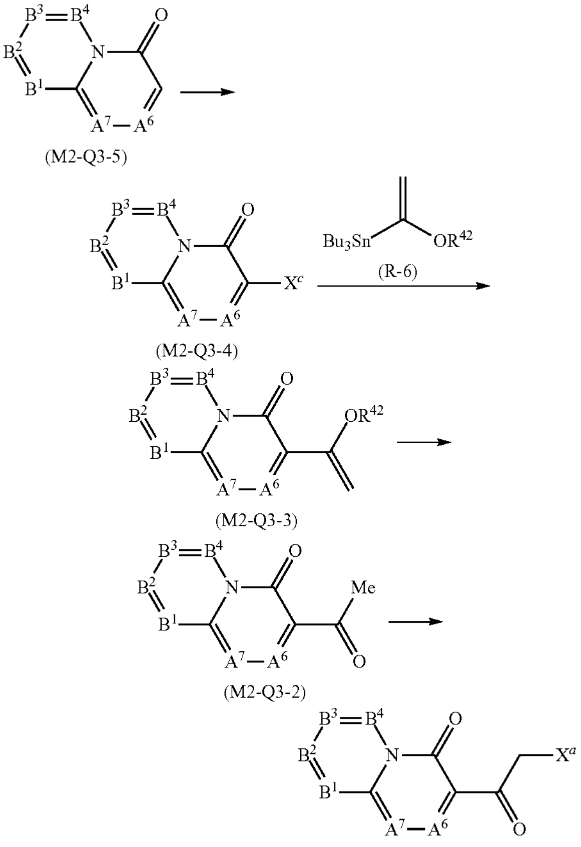

(M2-Q3-5) (M2-Q3-4) (M2-Q3-3) (M2-Q3-2) (M2-Q3-1)

[wherein the symbols are the same as defined above.]

These reactions may be carried out according to the Reference Production method 13.

A compound represented by formula (M2-Q3-5) is known or may be prepared according to known method(s) (for example, a method disclosed in Science of Synthesis, 2006, 23, 391.).

Reference Production Method 16

A compound represented by formula (M2-Q4-1) may be prepared according to the following scheme.

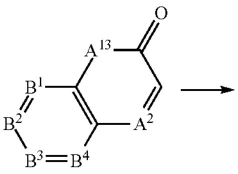
(M2-Q4-5)

-continued

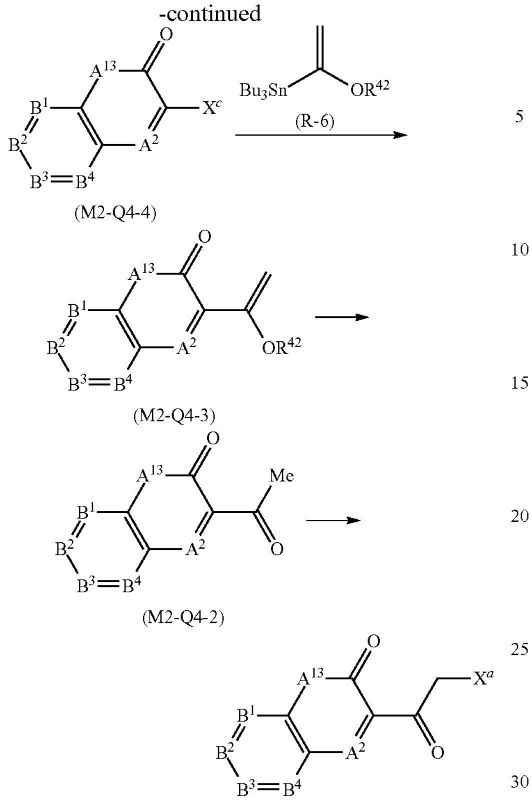

(M2-Q4-4)

(M2-Q4-3)

(M2-Q4-2)

(M2-Q4-1)

[wherein the symbols are the same as defined above.]

These reactions may be carried out according to the Reference Production method 8.

A compound represented by formula (M2-Q4-5) is known or may be prepared according to known method(s) (for example, a method disclosed in Journal of Heterocyclic Chemistry, 2013, 50, 1146, or Chemical Science, 2019, 10, 4328.).

The Present compound may be mixed with or used in combination with one or more ingredient(s) selected from the group consisting of the following Group (a), Group (b), Group (c), and Group (d) (hereinafter referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations or contained in one formulation.

One aspect of the present invention provides a composition comprising one or more ingredient(s) selected from the group consisting of Group (a), Group (b), Group (c), and Group (d), and the Present compound (hereinafter referred to as "Composition A").

Group (a) is a group consisting of acetylcholinesterase inhibitors (for example, carbamate insecticides and organophosphate insecticides), GABA-gated chloride channel blockers (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamate-gated chloride channel allosteric modulators (for example, macrolide insecticides), juvenile hormone mimics, multisite inhibitors, chordotonal organ TRPV channel modulators, mite growth inhibitors, microbial disruptors of insect midgut membranes, inhibitors of mitochondrial ATP synthase, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, mitochondrial complexes I, II, III, and IV electron transport inhibitors, voltage-dependent sodium channel blockers, inhibitors of acetyl CoA carboxylase, ryanodine receptor modulators (for example, diamide insecticides), chordotonal organ modulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acids synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acids synthesis and protein synthesis inhibitors (for example, anilino-pyrimidine fungicides), signal transduction inhibitors, lipid synthesis and membrane synthesis inhibitors, sterol biosynthesis inhibitors (for example, DMI fungicides such as triazole fungicides), cell wall biosynthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of repellent ingredients.

Hereinafter, examples of the combination of the Present ingredient and the Present compound are described. For example, "alanycarb+SX" indicates a combination of alanycarb and SX.

The abbreviation of "SX" indicates any one of the Present compound selected from the Compound groups SX1 to SX28 described in Examples. Also, all of the following Present ingredient are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combinations of the Present ingredient in the above Group (a) and the Present compound:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+

SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cyclaniliprole+SX, cyclobutrifluram+SX, cycloprothrin+SX, cycloxaprid+SX, cyenopyrafen+SX, cyetpyrafen+SX, cyflumetofen+SX, cyfluthrin+SX, cyhalodiamide+SX, cyhalothrin+SX, cyhexatin+SX, cypermethrin+SX, cyphenothrin+SX, cyproflanilide+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC(2-methyl-4,6-dinitrophenol)+SX, doramectin+SX, dried leaves of Dryopteris filix-mas+SX, emamectin-benzoate+SX, empenthrin+SX, endosulfan+SX, EPN(O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Azadirachta indica*+SX, extract of *Cassia nigricans*+SX, extract of clitoria ternatea+SX, extract of *Symphytum officinale*+SX, extract or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenmezoditiaz+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, fluchlordiniliprole+SX, flucycloxuron+SX, flucythrinate+SX, fluensulfone+SX, flufenoprox+SX, flufenoxuron+SX, flufiprole+SX, flumethrin+SX, flupentiofenox+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indazapyroxamet+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, nicofluprole+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spidoxamat+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near ambrosioides+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, 2-({2-fluoro-4-methyl-5-[(2,2,2-trifluoroethyl) sulfinyl]phenyl}imino)-3-(2,2,2-trifluoroethyl)-1,3-thiazolidin-4-one (1445683-71-5)+SX, (2Z)-2-({2-fluoro-4-methyl-5-[(R)-(2,2,2-trifluoroethyl)sulfinyl] phenyl}imino)-3-(2,2,2-trifluoroethyl)-1,3-thiazolidin-4-one (2377084-09-6)+SX, N-{4-chloro-3-[(1-cyanocyclopropyl)carbamoyl]phenyl}-1-methyl-4-(methanesulfonyl)-3-(1,1,2,2,2-pentafluoroethyl)-1H-pyrazole-3-carboxamide (1400768-21-9)+SX, N-[3-chloro-1-(pyridin-3-yl)-1H-pyrazol-4-yl]-2-(methanesulfonyl)propanamide (2396747-83-2)+SX, 1,4-dimethyl-2-[2-(pyridin-3-yl)-2H-indazol-5-yl]-1,2,4-triazolidine-3,5-dione (2171099-09-3)+SX, 2-isopropyl-5-[(3,4,4-trifluoro-3-buten-1-yl)sulfonyl]-1,3,4-thiadiazole (2058052-95-0)+SX, N-({2-fluoro-4-[(2S,3S)-2-hydroxy-3-(3,4,5-trichlorophenyl)-3-(trifluoromethyl)pyrrolidin-1-yl]phenyl}methyl) cyclopropanecarboxamide+SX, 7-fluoro-N-[1-

(methylsulfanyl)-2-methylpropan-2-yl]-2-(pyridin-3-yl)-2H-indazole-4-carboxamide+SX, 7-fluoro-N-[1-(methanesulfinyl)-2-methylpropan-2-yl]-2-(pyridin-3-yl)-2H-indazole-4-carboxamide+SX, 7-fluoro-N-[1-(methanesulfonyl)-2-methylpropan-2-yl]-2-(pyridin-3-yl)-2H-indazole-4-carboxamide+SX, N-(1-methylcyclopropyl)-2-(pyridin-3-yl)-2H-indazole-4-carboxamide+SX, 2,9-dihydro-9-(methoxymethyl)-2-(pyridin-3-yl)-10H-pyrazolo[3,4-f]pyrido[2,3-b][1,4]oxazepin-10-one (2607927-97-7)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein mCry3A+SX, BT crop protein Cry3Ab+SX, BT crop protein Cry3Bb+SX, BT crop protein Cry34Ab1/Cry35Ab1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, *Cryptophlebia leucotreta* GV+SX, *Dendrolimus punctatus* cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* strain GB-126+SX, *Bacillus firmus* strain I-1582+SX, *Bacillus firmus* strain NCIM2637+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362 serotype H5a5b+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR-371+SX, *Bacillus thuringiensis* subsp. *aizawai* strain ABTS-1857+SX, *Bacillus thuringiensis* subsp. *aizawai* strain AM65-52+SX, *Bacillus thuringiensis* subsp. *aizawai* strain GC-91+SX, *Bacillus thuringiensis* subsp. *aizawai* strain NB200+SX, *Bacillus thuringiensis* subsp. *aizawai* Serotype strain H-7+SX, *Bacillus thuringiensis* subsp. *kurstaki* strain ABTS351+SX, *Bacillus thuringiensis* subsp. *kurstaki* strain BMP123+SX, *Bacillus thuringiensis* subsp. *kurstaki* strain CCT1306)+SX, *Bacillus thuringiensis* subsp. *kurstaki* strain EG2348+SX, *Bacillus thuringiensis* subsp. *kurstaki* strain EG7841+SX, *Bacillus thuringiensis* subsp. *kurstaki* strain EVB113-19+SX, *Bacillus thuringiensis* subsp. *kurstaki* strain F810+SX, *Bacillus thuringiensis* subsp. *kurstaki* strain HD-1+SX, *Bacillus thuringiensis* subsp. *kurstaki* strain PB54+SX, *Bacillus thuringiensis* subsp. *kurstaki* strain SA-11+SX, *Bacillus thuringiensis* subsp. *kurstaki* strain SA-12+SX, *Bacillus thuringiensis* subsp. *tenebriosis* strain NB176+SX, *Bacillus thuringiensis* subsp. *thuringiensis* strain MPPL002+SX, *Bacillus thuringiensis* subsp. *morrisoni*+SX, *Bacillus thuringiensis* var. *colmeri*+SX, *Bacillus thuringiensis* var. *darmstadiensis* strain 24-91+SX, *Bacillus thuringiensis* var. *dendrolimus*+SX, *Bacillus thuringiensis* var. *galleriae*+SX, *Bacillus thuringiensis* var. *israelensis* strain BMP144+SX, *Bacillus thuringiensis* var. *israelensis* serotype strain H-14+SX, *Bacillus thuringiensis* var. *japonensis* strain buibui+SX, *Bacillus thuringiensis* var. *san diego* strain M-7+SX, *Bacillus thuringiensis* var. 7216+SX, *Bacillus thuringiensis* var. *aegypti*+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia rinojensis* strain A396+SX, *Chromobacterium subtsugae* strain PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* strain KV01+SX, *Lecanicillium lecanii* conidia of strain DAOM198499+SX, *Lecanicillium lecanii* conidia of strain DAOM216596+SX, *Lecanicillium muscarium* strain Ve6+SX, *Metarhizium anisopliae* strain F52+SX, *Metarhizium anisopliae* var. *acridum*+SX, *Metarhizium anisopliae* var. *anisopliae* BIPESCO 5/F52+SX, *Metarhizium flavoviride*+SX, *Monacrosporium phymatopagum*+SX, *Paecilomyces fumosoroseus* Apopka strain 97+SX, *Paecilomyces lilacinus* strain 251+SX, *Paecilomyces tenuipes* strain T1+SX, *Paenibacillus popilliae*+SX, *Pasteuria nishizawae* strain Pn1+SX, *Pasteuria penetrans*+SX, *Pasteuria usgae*+SX, *Pasteuria thornei*+SX, *Serratia entomophila*+SX, *Verticillium chlamydosporium*+SX, *Verticillium lecani* strain NCIM1312+SX, *Wolbachia pipientis*+SX.

Combination of the Present ingredient in the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroinconazide+SX, chloroneb+SX, chlorothalonil+SX, chlozolinate+SX, colletochlorin B+SX, copper(II) acetate+SX, copper (II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract of *Melaleuca alternifolia*+SX, extract of *Reynoutria sachalinensis*+SX, extract of the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, flubeneteram+SX, fludioxonil+SX, flufenoxadiazam+SX, flufenoxystrobin+SX, fluindapyr+SX, flumetylsulforim+SX, flumorph+SX, fluopicolide+SX, fluopyram+SX, fluopimomide+SX, fluoroimide+SX, fluoxapiprolin+SX, fluoxastrobin+SX, fluoxytioconazole+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metarylpicoxamid+SX, metconazole+SX, methasulfocarb+SX, metiram+SX, metominostrobin+SX, metrafenone+SX, metyltetraprole+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja* extract+SX, quinconazole+SX, quinofumelin+SX, quinoxyfen+SX, quintozene+SX, Saponins of *Chenopodium quinoa*+SX, seboctylamine+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, N'-{4-[(4,5-dichlorothiazol-2-yl)oxy]-2,5-dimethylphenyl}-N-ethyl-N-methylmethanimidamide (929908-57-6)+SX, N'-(2,5-dimethyl-4-phenoxyphenyl)-N-ethyl-N-methylmethanimidamide (1052688-31-9)+SX, N'-[5-chloro-4-(2-fluorophenoxy)-2-methylphenyl]-N-ethyl-N-methylmethanimidamide (2055589-28-9)+SX, N'-[2-choro-4-(2-fluorophenoxy)-5-methylphenyl]-N-ethyl-N-methylmethanimidamide (2055756-21-1)+SX, N'-(2-choro-4-phenoxy-5-methylphenyl)-N-ethyl-N-methylmethanimidamide (2062599-39-5)+SX, N'-[4-(1-hydroxy-1-phenyl-2,2,2-trifluoroethyl)-2-methyl-5-methoxyphenyl]-N-isopropyl-N-methylmethanimidamide (2101814-55-3)+SX, N'-[5-bromo-6-(1-methyl-2-propoxyethoxy)-2-methylpyridin-3-yl]-N-ethyl-N-methylmethanimidamide (1817828-69-5)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9)+SX, N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl] phenyl}methyl)isoxazolidin-3-one (2098918-25-1)+SX, 5,5-dimethyl-2-({4-[5-(trifluoromethyl)-1,2,4-oxadiazol-3-yl]phenyl}methyl)isoxazolidin-3-one (2098918-26-2)+SX, N-ethyl-2-methyl-N-({4-[5-(trifluoromethyl)-1,2,4-oxadiazol-3-yl]phenyl}methyl) propanamide+SX, N,2-dimethoxy-N-({4-[5-(trifluoromethyl)-1,2,4-oxadiazol-3-yl]phenyl}methyl) propanamide+SX, N-methoxy-N-({4-[5-(trifluoromethyl)-1,2,4-oxadiazol-3-yl]phenyl}methyl) cyclopropanecarboxamide+SX, N-methoxy-N'-methyl-N-({4-[5-(trifluoromethyl)-1,2,4-oxadiazol-3-yl]phenyl}methyl)urea+SX, N'-ethyl-N-methoxy-N-({4-[5-(trifluoromethyl)-1,2,4-oxadiazol-3-yl] phenyl}methyl)urea+SX, N,N'-dimethoxy-N-({4-[5-(trifluoromethyl)-1,2,4-oxadiazol-3-yl]phenyl}methyl) urea+SX, N-acetyl-2-(ethanesulfonyl)-N-[2-(methoxycarbonyl)-4-(trifluoromethoxy)phenyl]-4-(trifluoromethyl)benzamide (2043675-28-9)+SX, 3-(4-bromo-7-fluoroindol-1-yl)butan-2-yl N-[(3-hydroxy-4-methoxypyridin-2-yl)carbonyl]-L-alaninate+SX, 3-(7-bromoindol-1-yl)butan-2-yl N-[(3-hydroxy-4-methoxypyridin-2-yl)carbonyl]-L-alaninate+SX, 3-(7-bromo-4-fluoroindol-1-yl)butan-2-yl N-[(3-hydroxy-4-methoxypyridin-2-yl)carbonyl]-L-alaninate+SX, 3-(3,5-dichloropyridin-2-yl)butan-2-yl N-[(3-hydroxy-4-methoxypyridin-2-yl)carbonyl]-L-alaninate+SX, 3-(3,5-dichloropyridin-2-yl)butan-2-yl N-{[3-(acetoxymethoxy)-4-methoxypyridin-2-yl]carbonyl}-L-alaninate+SX, (1S)-1-[1-(naphthalen-1-yl) cyclopropyl]ethyl N-[(3-hydroxy-4-methoxypyridin-2-yl)carbonyl]-L-alaninate+SX, (1S)-1-[1-(naphthalen-1-yl)cyclopropyl]ethyl N-[(3-acetoxy-4-methoxypyridin-2-yl)carbonyl]-L-alaninate+SX, (1S)-1-[1-(naphthalen-1-yl)cyclopropyl]ethyl N-{[3-(acetoxymethoxy)-4-methoxypyridin-2-yl]carbonyl}-L-alaninate+SX, *Agrobacterium* radiobactor strain K1026+SX, *Agrobacterium* radiobactor strain K84+SX, *Bacillus amyloliquefaciens* strain PTA-4838 (Aveo (registered trademark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma asperellum* strain ICC012+SX, *Trichoderma asperellum* SKT-1+SX, *Trichoderma asperellum* strain T25+SX, *Trichoderma asperellum* strain T34+SX, *Trichoderma asperellum* strain TV1+SX, *Trichoderma atroviride* strain CNCM 1-1237+SX, *Trichoderma atroviride* strain LC52+SX, *Trichoderma atroviride* strain IMI 206040+SX, *Trichoderma atroviride* strain SC1+SX, *Trichoderma atroviride* strain SKT-1+SX, *Trichoderma atroviride* strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain M01+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *Trichoderma stromaticum*+SX, *Trichoderma virens* strain G-41+SX, *Trichoderma*

*virens* strain GL-21+SX, *Trichoderma viride*+SX, *Variovorax paradoxus* strain CGF4526+SX, Harpin protein+SX.

Combination of the Present ingredient in the above Group (c) and the Present compound:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, anisiflupurin+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, paclobutrazol+SX, pendimethalin+SX, prohexadione-calcium+SX, prohydrojasmon+SX, pyraflufen-ethyl+SX, sintofen+SX, sodium 1-naphthaleneacetate+SX, sodium cyanate+SX, thidiazuron+SX, triapenthenol+SX, tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]propan-1-ol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, Delftia *acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combination of the Present ingredient in the above Group (d) and the Present compound:

anthraquinone+SX, deet+SX, icaridin+SX.

The ratio of the Present compound to the Present ingredient includes, but not limited thereto, as a ratio by weight (the Present compound the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:50, and the others.

The Present compound has control effect on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*; from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and *Amrasca biguttula* biguttula;

from the family Aphrophoridae, for example, European spittlebug (*Philaenus spumarius*);

from the family Cercopidae, for example, *Mahanarva posticata* and *Mahanarva fimbriolata;* from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and English grain aphid (*Sitobion avenae*); from the family Phylloxeridae, for example, grapevine phylloxera (*Daktulosphaira vitifoliae*), Pecan phylloxera (*Phylloxera devastatrix*), Pecan leaf phylloxera (*Phylloxera notabilis*), and Southern pecan leaf phylloxera (*Phylloxera russelae*);

from the family Adelgidae, for example, hemlock woolly aphid (*Adelges tsugae*), balsam woolly aphid (*Adelges piceae*), and *Aphrastasia pectinatae;* from the family Pentatomidae, for example, black rice bug (*Scotinophara lurida*), black paddy bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), brown stink bug (*Euschistus heros*), red banded stink bug (*Piezodo-

*rus guildinii*), *Oebalus pugnax*, and *Dichelops melacanthus*; from the family Cydnidae, for example, *Scaptocoris castanea;* from the family Alydidae, for example, bean bug (*Riptortus clavatus*), corbett rice bug (*Leptocorisa chinensis*), and rice bug (*Leptocorisa acuta*);

from the family Coreidae, for example, *Cletus punctiger* and Australian leaf-footed bug (*Leptoglossus australis*);

from the family Lygaeidae, for example, oriental chinch bug (*Cavelerius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae;* from the family Diaspididae, for example, *Abgrallaspis cyanophylli*, red scale (*Aonidiella aurantii*), San Joss scale (*Diaspidiotus perniciosus*), white peach scale (*Pseudaulacaspis pentagona*), arrowhead scale (*Unaspis yanonensis*), and citrus snow scale (*Unaspis citri*); from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*) and tropical bed bug (*Cimex hemipterus*);

from the family Cicadidae, for example, *Quesada gigas;* from the family Reduviidae, for example, *Triatoma infestans*, large kissing bug (*Triatoma rubrofasciata*), *Triatoma dimidiata*, and *Rhodonius prolixus;* and the others.

Lepidoptera:

from the family Crambidae, for example, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Parapediasia teterrellus*), rice case-worm (*Nymphula depunctalis*), Sugarcane borer (*Diatraea saccharalis*), and eggplant fruit borer (*Leucinodes orbonalis*);

from the family Pyralidae, for example, lesser cornstalk borer (*Elasmopalpus lignosellus*), mealworm moth (*Plodia interpunctella*), persimmon bark borer (*Euzophera batangensis*), and fig moth (*Cadra cautella*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), semitropical armyworm (*Spodoptera eridania*), black cutworm (*Agrotis ipsilon*), beet worm (*Autographa nigrisigna*), rice looper (*Plusia festucae*), Soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), velvet-bean caterpillar (*Anticarsia gemmatalis*), cotton leafworm (*Alabama argillacea*), and hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*) smaller tea tortrix (*Adoxophyes honmai*), Japanese tea tortrix (*Homona magnanima*), apple *tortrix* (*Archips fuscocupreanus*), codling moth (*Cydia pomonella*), sugarcane shoot borer (*Tetramoera schistaceana*), bean shoot borer (*Epinotia aporema*), citrus fruit borer (*Citripestis sagittiferella*), and European grapevine moth (*Lobesia botrana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, coffee leaf miner (*Leucoptera coffeella*), peach leaf miner (*Lyonetia clerkella*), and *Lyonetia prunifoliella;* from the family Lymantriidae, for example, *Lymantria* spp. (such as gypsy moth (*Lymantria dispar*)) and *Euproctis* spp. (such as tea lymantriid (*Euproctis pseudoconspersa*)); from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*);

from the family Castniidae, for example, giant sugarcane borer (*Telchin licus*);

from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis*; from the family Hesperiidae, for example, rice skipper (*Parnara guttata*);

from the family Tineidae, for example, casemaking clothes moth (*Tinea translucens*), common clothes moth (*Tineola bisselliella*);

and the others.

Thysanoptera:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice *thrips* (*Stenchaetothrips biformis*), *Echinothrips americanus*, and avocado thrips (*Scirtothrips perseae*);

from the family Phlaeothripidae, for example, aculeated rice thrips (*Haplothrips aculeatus*);

and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*), and common fruit fly (*Drosophila melanogaster*);

from the family Phoridae, for example, *Megaselia spiracularis;* from the family Psychodidae, for example, *Clogmia albipunctata;* from the family Sciaridae, for example, *Bradysia difformis;* from the family Cecidomyiidae, for example, hessian fly (*Mayetiola destructor*) and paddy gall fly (*Orseolia oryzae*);

from the family Diopsidae, for example, *Diopsis macrophthalma;* from the family Glossinidae, for example, *Glossina palpalis* and *Glossina morsitans;* from the family Simuliidae, for example, *Simulium japonicum* and *Simulium damnosum;* from the subfamily Phlebotominae;

from the family Tipulidae, for example, rice crane fly (*Tipula aino*), common cranefly (*Tipula oleracea*), and European cranefly (*Tipula paludosa*);

from the family Culicidae, for example, southern house mosquito (*Culex pipiens pallens*), *Culex tritaeniorhynchus, Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae, Anopheles stephensi, Anopheles coluzzii, Anopheles albimanus, Anopheles sundaicus, Anopheles arabiensis, Anopheles funestus, Anopheles darlingi, Anopheles farauti*, and *Anopheles minimus;* from the family Simulidae, for example, *Prosimulium yezoensis* and *Simulium ornatum;* from the family Tabanidae, for example, *Tabanus trigonus;* from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, *Chironomus plumosus, Chironomus yoshimatsui*, and *Glyptotendipes tokunagai;* from the family Fannidae;

and the others.

Coleoptera:

from the family Chrysomelidae, for example, *Diabrotica* spp. (such as western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), cucurbit beetle (*Diabrotica speciosa*)), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), cabbage flea beetle (*Phyllotreta cruciferae*), western black flea beetle (*Phyllotreta pusilla*), cabbage stem flea beetle (*Psylliodes chrysocephala*), hop flea beetle (*Psylliodes punctulata*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweetpotato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, and tobacco flea beetle (*Epitrix hirtipennis*);

from the family Carabidae, for example, Seedcorn beetle (*Stenolophus lecontei*) and slender seed-corn ground beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Anthribidae, for example, coffee bean weevil (*Araecerus coffeae*);

from the family Aponidae, for example, sweet-potato weevil (*Cylas formicarius*);

from the family Bruchidae, for example, Mexican bean weevil (*Zabrotes subfasciatus*);

from the family Scolytidae, for example, pine beetle (*Tomicus piniperda*) and coffee berry borer (*Hypothenemus hampei*);

from the family Curculionidae, for example, West Indian sweet-potato weevil (*Euscepes postfasciatus*), alfalfa weevil (*Hypera postica*), maize wevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineaticollis*, boll weevil (*Anthonomus grandis*), nunting billbug (*Sphenophorus venatus*), southern corn billbug (*Sphenophorus callosus*), soybean stalk weevil (*Sternechus subsignatus*), sugarcane weevil (*Sphenophorus levis*), rusty gourd-shaped weevil (*Scepticus griseus*), brown gourd-shaped weevil (*Scepticus uniformis*), *Aracanthus* spp. (such as *Aracanthus mourei*), and cotton root borer (*Eutinobothrus brasiliensis*);

from the family Tenebrionidae, for example, red meal beetle (Tribolium castaneum), mason beetle (*Tribolium confusum*), and lesser mealworm (*Alphitobius diaperinus*);

from the family Coccinellidae, for example, twenty-eight-spotted ladybird (*Epilachna vigintioctopunctata*); from the family Bostrychidae, for example, common powder-post beetle (*Lyctus brunneus*), and lesser grain borer (*Rhizopertha dominica*);

from the family Ptinidae;

from the family Cerambycidae, for example, citrus long-horned beetle (*Anoplophora malasiaca*), *Migdolus fryanus*, and peach borer (*Aromia bungii*);

from the family Elateridae, for example, *Melanotus okinawensis*, barley wireworm (*Agriotes fuscicollis*), *Melanotus legatus, Anchastus* spp., *Conoderus* spp., *Ctenicera* spp., *Limonius* spp., and *Aeolus* spp.;

from the family Staphylinidae, for example, *Paederus fuscipes;* from the family Dermestidae, for example, varied carpet beetle (*Anthrenus verbasci*), hide beetle (*Dermestes maculates*), and khapra beetle (*Trogoderma granarium*);

from the family Anobiidae, for example, tobacco beetle (*Lasioderma serricorne*), and biscuit beetle (*Stegobium paniceum*);

from the family Laemophloeidae, for example, flat grain beetle (*Cryptolestes ferrugineus*);

from the family Silvanidae, for example, saw-toothed grain beetle (*Oryzaephilus surinamensis*);

from the family Nitidulidae, for example, blossom beetle (*Brassicogethes aeneus*);

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), two-striped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), Yellow-winged locust (*Gastrimargus musicus*), spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*), and emma field cricket (*Teleogryllus emma*);

from the family Tettigoniidae, for example, mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*), tropical fire ant (*Solenopsis geminata*)), *Atta* spp. (such as brown leaf-cutting ant (*Atta capiguara*), *Acromyrmex* spp., *Paraponera clavata*, black house ant (*Ochetellus glaber*), little red ant (*Monomorium pharaonis*), Argentine ant (*Linepithema humile*), *Formica japonica, Pristomyrmex punctutus, Pheidole noda*, big-headed ant (*Pheidole megacephala*), *Camponotus* spp. (such as *Camponotus japonicus, Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia, Vespa simillima, Vespa analis*, Asian hornet (*Vespa velutina*), and *Polistes jokahamae;* from the family Siricidae, for example, pine wood wasp (*Urocerus gigas*);

from the family Bethylidae;

and the others.

Blattodea:

from the family Ectobiidae, for example, German cockroach (*Blattella germanica*);

from the family Blattidae, for example, smoky-brown cockroach (*Periplaneta fuliginosa*), American cockroach (*Periplaneta americana*), Australian cockroach (*Periplaneta australasiae*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans;* and the others.

Siphonaptera:

from the family Pulicidae, for example, human flea (*Pulex irritans*), cat flea (*Ctenocephalides felis*), dog flea (*Ctenocephalides canis*), oriental rat flea (*Xenopsylla cheopis*), and chicken flea (*Echidnophaga gallinacea*);

from the family Pulicidae, for example, chigoe flea (*Tunga penetrans*);

from the family Ceratophyllidae, for example, European rat flea (*Nosopsyllus fasciatus*);

and the others.

Psocodae:

from the family Pediculidae, for example, head louse (*Pediculus humanus* capitis);

from the family Pthiridae, for example, crab louse (*Pthirus pubis*);

from the family Haematopinidae, for example, short-nosed cattle louse (*Haematopinus eurysternus*) and pig louse (*Haematopinus suis*);

from the family Linognathidae, for example, blue cattle louse (*Linognathus vituli*), sheep face louse (*Linognathus ovillus*), and capillate louse (*Solenopotes capillatus*);

from the family Bovicoliidae, for example, cattle biting louse (*Bovicola bovis*), sheep biting louse (*Bovicola ovis*), *Bovicola breviceps, Damalinia forficula*, and *Werneckiella* spp.;

from the family Trichodectidae, for example, dog biting louse (*Trichodectes canis*) and cat louse (*Felicola subrostratus*);

from the family Menoponidae, for example, common chicken louse (*Menopon gallinae*), chicken body louse (*Menacanthus stramineus*), and *Trinoton* spp.;

from the family Trimenoponidae, for example, *Cummingsia* spp.;

from the family Trogiidae, for example, death watch (*Trogium pulsatorium*);

from the family Liposcelidae or Liposcelididae, for example, book louse (*Liposcelis corrodens*), *Liposcelis bostrychophila, Liposcelis pearmani*, and *Liposcelis entomophila;* and the other.

Thysanura:

from the family Lepismatidae, for example, oriental silverfish (*Ctenolepisma villosa*) and moth fish (*Lepisma saccharina*);

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.; from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri, Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis;* from the family Tuckerellidae;

from the family Ixodidae, for example, *Haemaphysalis longicornis, Haemaphysalis flava, Haemaphysalis japonica, Haemaphysalis campanulata*, American dog tick (*Dermacentor variabilis*), *Dermacentor taiwanensis*, Rocky Mountain wood tick (*Dermacentor andersoni*), netted tick (*Dermacentor reticulatus*), *Ixodes ovatus, Ixodes persulcatus*, black-legged tick (*Ixodes scapularis*), *Ixodes pacificus, Ixodes holocyclus, Ixodes ricinus*, lone star tick (*Amblyomma americanum*), gulf coast tick (*Amblyomma maculatum*), *Rhipicephalus microplus*, cattle tick (*Rhipicephalus annulatus*), brown dog tick (*Rhipicephalus sanguineus*), *Rhipicephalus appendiculatus*, and *Rhipicephalus decoloratus;* from the family Argasidae, for example, fowl tick (*Argas persicus*), *Ornithodoros hermsi*, and *Ornithodoros turicata;* from the family Acaridae, for example, cereal mite (*Tyrophagus putrescentiae*) and grassland mite (*Tyrophagus similis*);

from the family Pyroglyphidae, for example, American house dust mite (*Dermatophagoides farinae*) and European house dust mite (*Dermatophagoides pteronyssinus*); from the family Cheyletidae, for example, *Cheyletus eruditus, Cheyletus malaccensis, Chelacaropsis moorei*, and *Cheyletiella yasguri;* from the family Psoroptidae, for example, sheep scab mite (*Psoroptes ovis*), horse psoroptic mange mite (*Psoroptes equi*), *Knemidocoptes mutans*, ear mange mite (*Otodectes cynotis*), and Chorioptes spp.;

from the family Sarcoptidae, for example, *Notoedres cati, Notoedres muris*, and itch mite (*Sarcoptes scabiei*); from the family Listrophoridae, for example, *Listrophorus gibbus;* from the family Dermanyssidae, for example, bird mite (*Dermanyssus gallinae*);

from the family Macronyssidae, for example, feather mite (*Ornithonyssus sylviarum*) and tropical rat mite (*Ornithonyssus bacoti*);

from the family Varroidae, for example, *Varroa jacobsoni;* from the family Demodicidae, for example, dog follicle mite (*Demodex canis*) and cat follicle mite (*Demodex cati*); from the family Trombiculidae, for example, *Leptotrombidium akamushi, Leptotrombidium pallidum*, and *Leptotrombidium scutellare;* and the others.

Araneae:

from the family Eutichuridae, for example, *Cheiracanthium japonicum;* from the family Theridiidae, for example, red-back spider (*Latrodectus hasseltii*);

and the others.

Polydesmida:

from the family Paradoxosomatidae, for example, flat-backed millipede (*Oxidus gracilis*) and *Nedyopus tambanus;* and the others.

Isopoda:

from the family Armadillidiidae, for example, common pill bug (*Armadillidium vulgare*);

and the others.

Chilopoda:

from the family Scutigeridae, for example, *Thereuonema hilgendorfi;* from the family Scolopendridae, for example, giant tropical centipede (*Scolopendra subspinipes*);

from the family Ethopolyidae, for example, *Bothropolys rugosus;* and the others.

Gastropoda:

from the family Limacidae, for example, tree slug (*Limax marginatus*) and garden tawny slug (*Limax flavus*); from the family Philomycidae, for example, *Meghimatium bilineatum;* from the family Ampullariidae, for example, golden apple snail (*Pomacea canaliculata*);

from the family Lymnaeidae, for example, *Austropeplea ollula;* and the others.

Nematoda:

from the family Aphelenchoididae, for example, rice white-tip nematode (*Aphelenchoides besseyi*);

from the family Pratylenchidae, for example, root lesion nematode (*Pratylenchus* coffeae), *Pratylenchus brachyurus*, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), guava root-knot nematodes (*Meloidogyne enterolobii*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (*Nothotylenchus acris*), and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*); and the others.

The harmful arthropods such as harmful insects and harmful mites, harmful mollusks, and harmful nematodes may be those having a reduced susceptibility to or a developed resistance to an insecticide, a miticide, a molluscicide, or a nematicide.

The method for controlling harmful arthropods of the present invention is carried out by applying an effective amount of the Present compound or the Composition A to a harmful arthropod directly and/or a habitat thereof (for example, plant bodies, soil, an interior of a house, animal bodies). Examples of the method for controlling harmful arthropods of the present invention include foliage treatment, soil treatment, root treatment, shower treatment, smoking treatment, water surface treatment, and seed treatment.

The Present compound or the Composition A is usually used by mixing it with inert carrier(s) such as solid carrier(s), liquid carrier(s), and gaseous carrier(s), surfactant(s), and the like, and as needed, adding thereto auxiliary agent(s) for formulation such as binder(s), dispersant(s), and stabilizer(s) to be formulated into an aqueous suspension formulation, an oily suspension formulation, an oil solution, an emulsifiable concentrate, an emulsion formulation, a microemulsion formulation, a microcapsule formulation, a wettable powder, a granular wettable powder, a dust formulation, a granule, a tablet, an aerosol formulation, a resin formulation, or the like. In addition to these formulations, the Present compound or the Composition A may be used by formulating it into a dosage form described in Manual on development and use of FAO and WHO Specifications for pesticides, FAO Plant Production and Protection Papers-271-276, prepared by the FAO/WHO Joint Meeting on Pesticide Specifications, 2016, ISSN:0259-2517.

These formulations usually comprise 0.0001 to 99% by weight ratio of the Present compound or the Composition A.

Examples of the solid carrier include fine powders and granules of clays (for example, pyrophyllite clay and kaolin clay), talc, calcium carbonate, diatomaceous earth, zeolite, bentonite, acid white clay, attapulgite, white carbon, ammonium sulfate, vermiculite, perlite, pumice, silica sand, chemical fertilizers (for example, ammonium sulfate, ammonium phosphate, ammonium nitrate, urea, and ammonium chloride), and the others; as well as resins (for example, polypropylene, polypropylene, polyester, polyurethane, polyamide, and polyvinyl chloride).

Examples of the liquid carrier include water, alcohols (for example, ethanol, cyclohexanol, benzyl alcohol, propylene glycol, and polyethylene glycol), ketones (for example, acetone and cyclohexanone), aromatic hydrocarbons (for example, xylene, phenyl xylyl ethane, and methylnaphthalene), aliphatic hydrocarbons (for example, hexane and cyclohexane), esters (for example, ethyl acetate, methyl oleate, and propylene carbonate), nitriles (for example, acetonitrile), ethers (for example, ethylene glycol dimethyl ether), amides (for example, N,N-dimethylformamide and N,N-dimethyloctanamide), sulfoxides (for example, dimethyl sulfoxide), lactams (for example, N-methylpyrrolidone and N-octylpyrrolidone), fatty acids (for example, oleic acid), and vegetable oils (for example, soybean oil).

Examples of the gaseous carrier include fluorocarbon, butane gas, LPG (liquefied petroleum gas), dimethyl ether, nitrogen, and carbon dioxide.

Examples of the surfactant include nonionic surfactants (for example, polyoxyethylene alkyl ethers, polyoxyethylene alkyl aryl ethers, and polyethylene glycol fatty acid esters), and anionic surfactants (for example, alkyl sulfonates, alkyl aryl sulfonates, and alkyl sulfates). The specific examples thereof include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

Examples of the other auxiliary agent for formulation include binders, dispersants, colorants, and stabilizers, and the specific examples thereof include polysaccharides (for example, starch, gum arabic, cellulose derivatives, and alginic acid), lignin derivatives, water-soluble synthetic polymers (for example, polyvinyl alcohol, polyvinyl pyrrolidone, and polyacrylic acids), acidic isopropyl phosphate, and dibutylhydroxytoluene.

As used herein, examples of the plant include whole plant, stem and leaf, flower, ear, fruit, tree stem, branch, crown, seed, vegetative reproductive organ, and seedling.

A vegetative reproductive organ means a part of plant such as root, stem, and leaf which has a growth capability even when said part is separated from the plant body and placed into soil. Examples of the vegetative reproductive organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

Examples of a method for controlling harmful arthropods by applying an effective amount of the Present compound or the Composition A to soils include a method of applying an effective amount of the Present compound or the Composition A to soil before planting plants or after planting plants, a method of applying an effective amount of the Present compound or the Composition A to a root part of a crop to be protected from damage such as ingestion by harmful arthropods, and a method of controlling harmful arthropods that ingest a plant by permeating and transferring an effective amount of the Present compound or the Composition A from a root into the interior of the plant body. Specifically, examples of the application method include planting hole treatment (for example, spraying into planting holes and soil mixing after planting hole treatment), plant foot treatment (for example, plant foot spraying, soil mixing after plant foot treatment, irrigation at plant foot, and plant foot treatment at a later seeding raising stage), planting furrow treatment (for example, planting furrow spraying and soil mixing after planting furrow treatment), planting row treatment (for example, planting row spraying, soil mixing after planting row treatment, and planting row spraying at a growing stage), planting row treatment at the time of sowing (for example, planting row spraying at the time of sowing and soil mixing after planting row treatment at the time of sowing), broadcast treatment (for example, overall soil surface spraying and soil mixing after broadcast treatment), side-article treatment, treatment of water surface (for example, application to water surface and application to water surface after flooding), other soil spraying treatment (for example, spraying of a granular formulation on leaves at a growing stage, spraying under a canopy or around a tree stem, spraying on the soil surface, mixing with surface soil, spraying into seed holes, spraying on the ground surfaces of furrows, and spraying between plants), other irrigation treatment (for example, soil irrigation, irrigation at a seedling raising stage, chemical solution injection treatment, irrigation of a plant part just above the ground, chemical solution drip irrigation, and chemigation), seedling raising box treatment (for example, spraying into a seedling raising box, irrigation of a seedling raising box, and flooding into a seedling raising box with chemical solution), seedling raising tray treatment (for example, spraying on a seedling raising tray, irrigation of a seedling raising tray, and flooding into a seedling raising tray with chemical solution), seedbed treatment (for example, spraying on a seedbed, irrigation of a seedbed, spraying on a lowland rice nursery, and immersion of seedlings), seedbed soil incorporation treatment (for example, mixing with seedbed soil, mixing with seedbed soil before sowing, spraying at sowing before covering with soils, spraying at sowing after covering with soils, and mixing with covering with soils), and other treatment (for example, mixing with culture soil, plowing under, mixing with surface soil, mixing with soil at the place where raindrops fall from a canopy, treatment at a planting position, spraying of a granule formulation on flower clusters, and mixing with a paste fertilizer).

In the present invention, the seed or the vegetative reproductive organ holding the Present compound or the Composition A means a seed or a vegetative reproductive organ in the state where the Present compound or the Composition A is attached to the surface of the seed or the vegetative reproductive organ. Also, the Present compound or the Composition A attached to the surface may permeate from the surface to the inside.

Also, when the Composition A is attached to the surface of a seed or a vegetative reproductive organ, a plurality of layers comprising a single active ingredient may overlap each other, a plurality of active ingredients may be mixed with each other to form a single layer, layers comprising a single active ingredient and layers comprising a plurality of active ingredients may overlap each other, or a plurality of layers comprising a plurality of active ingredients may overlap each other.

The seed or the vegetative reproductive organ used in the seed treatment may be directly used, or a material other than the Present compound or the Composition A may be attached thereto before or after the Present compound or the Composition A is treated.

Examples of the application to seeds (or seed treatments) include an application of the Present compound or the Composition A to seeds or vegetative reproductive organs, and specific examples thereof include spraying treatment in which a suspension of the Present compound or the Composition A is sprayed onto seed surface or the vegetative reproductive organ surface in the form of mist; smearing treatment in which the Present compound or the Composition A is coated on a surface of seeds or the vegetative reproductive organs; a soaking treatment in which the seeds or vegetative reproductive organs are soaked into the solution of the Present compound or the Composition A for a certain time; and a method for coating the seeds or the vegetative reproductive organs with a carrier containing the Present compound or the Composition A (for example, film coating treatment and pellet coating treatment). Examples of the above-described vegetative reproductive organ include particularly seed potato.

When the Composition A is applied to seeds or vegetative reproductive organs, the Composition A may be also applied to seeds or vegetative reproductive organs as a single formulation, or the Composition A may be applied to seeds or vegetative reproductive organs as multiple different formulations by multiple times. Examples of the method in which the Composition A is applied as multiple different formulations by multiple times include, for example, a method in which the formulations comprising as an active component the Present compound only are applied, and seeds or vegetative reproductive organs are air dried, followed by applying the formulations comprising the Present ingredient: and a method in which the formulations comprising as an active component the Present compound and the Present ingredients are applied, and seeds or vegetative reproductive organs are air dried, followed by applying the formulations comprising the Present ingredients other than the already-applied Present ingredients, are included.

As used herein, seeds or vegetative reproductive organs holding the Present compound or the Composition A mean seeds or vegetative reproductive organs in the state where the Present compound or the Composition A is adhered to a surface of the seeds or the vegetative reproductive organs. The above-described seeds or vegetative reproductive organs holding the Present compound or the Composition A may be adhered by any other materials that are different from the Present compound or the Composition A before or after being adhered the Present compound or the Composition A to the seeds or vegetative reproductive organs.

Also, when the Composition A is adhered in a form of layer(s) to a surface of seeds or vegetative reproductive organs, the layer(s) is/are composed of one layer or a multiple layers. Also, when multiple layers are formed, each of the layer may be composed of a layer comprising one or more active ingredients, or a combination of a layer comprising one or more active ingredients and a layer not comprising an active ingredient.

Seeds or vegetative reproductive organs holding the Present compound or the Composition A can be obtained, for example, by applying the formulations comprising the Present compound or the Composition A by the above-described application method to seeds or vegetative reproductive organs.

When the Present compound or the Composition A is applied for harmful arthropods control in agricultural fields, the application dose thereof is usually within a range of 1 to 10,000 g of the Present compound per 10,000 $m^2$. In the case of being applied to seeds or vegetative reproductive organs, the application dose thereof is usually within a range of 0.001 to 100 g of the Present compound per 1 Kg of seeds or vegetative reproductive organs. When the Present compound or the Composition A is formulated into an emulsifiable concentrate, a wettable powder, or a flowable, etc., they are usually applied by diluting them with water so as to make an effective concentration of the active ingredients 0.01 to 10,000 ppm, and the granular formulation, the dust formulation, or the like is usually applied as itself without diluting them.

Also, the resin preparation of the Present compound or the Composition A which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the Present compound or the Composition A is used to control harmful arthropods that live inside a house, the application dose as an amount of the Present compound is usually within a range from 0.01 to 1,000 mg per 1 $m^2$ of an area to be treated, in the case of using it on a planar area. In the case of using it spatially, the application dose as an amount of the Present compound is usually within a range from 0.01 to 500 mg per 1 $m^3$ of the space to be treated. When the Present compound or the Composition A is formulated into emulsifiable concentrates, wettable powders, flowables, or the others, such formulations are usually applied after diluting them with water in such a way that a concentration of the active ingredient is within a range from 0.1 to 10,000 ppm. In the case of being formulated into oil solutions, aerosols, smoking agents, poison baits, and the others, such formulations are used as themselves without diluting them.

When the Present compound or the Composition A is used for controlling external parasites of livestock such as cows, horses, pigs, sheep, goats, and chickens and small animals such as dogs, cats, rats, and mice, the composition of the present invention may be applied to the animals by a known method in the veterinary field. Specifically, when systemic control is intended, the composition of the present invention is administered to the animals as a tablet, a mixture with feed or a suppository, or by injection (including intramuscular, subcutaneous, intravenous, and intraperitoneal injections). On the other hand, when non-systemic control is intended, the composition of the present invention is applied to the animals by means of spraying of the oil solution or aqueous solution, pour-on or spot-on treatment, washing of the animals with a shampoo formulation, or by putting a collar or ear tag made of the resin formulations to the animals. In the case of being administered to an animal body, the dose of the Present compound is usually within a range from 0.1 to 1,000 mg per 1 kg of an animal body weight.

Also, the Present compound or the Composition A may be used as an agent for controlling harmful arthropods in agricultural lands such as fields, paddy fields, turfs, and orchards. Examples of the plants include the followings.

corn (dent corn, flint corn, flour corn, popcorn, waxy corn, sweet corn, and field corn), rice (long grain rice, short grain rice, medium grain rice, japonica rice, tropical japonica rice, indica rice, javanica rice, paddy rice, upland rice, floating rice, direct-seeded rice, transplanted rice, and glutinous rice), wheat (bread wheat (hard wheat, soft wheat, medium wheat, red wheat, and white wheat), durum wheat, spelt wheat, and club wheat, winter wheat and spring wheat of them), barley (two-rowed barley (=barley for brewery), six-rowed barley, hull-less barley, and pearl barley, winter barley and spring barley of them), rye (winter rye and spring rye), triticale (winter triticale and spring triticale), oat (winter oat and spring oat), sorghum, cotton (upland cotton and Pima cotton), soybean (ripe seed harvest soybean, green soybeans, and early harvest soybeans, indeterminate type, determinate type, and semi-determinate type of them), peanut, buckwheat, beet (beets for sugar production, beets for feed, beets for root vegetable, beets for leaf vegetable, and beets for fuel), rapeseed (winter rapeseed and spring rapeseed), canola (winter canola and spring canola), sunflower (sunflowers for oil extraction, edible sunflowers, and sunflowers for ornamental purpose), sugar cane, tobacco, tea, mulberry, solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, perilla, mint, and basil), strawberry, sweet potato, glutinous yam, eddoe, pomaceous fruits (for example, apple, pear, Japanese pear, Chinese white pear, Chinese quince, and quince), stone fleshy fruits (for example, peach, plum, nectarine, Japanese apricot (*Prunus mume*), cherry fruit, apricot, and prune), citrus fruits (for example, *Citrus unshiu*, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, fig, olive, Japanese plum, banana, coffee, date palm, coconuts, ornamental plants, forest plants, turfs, grasses, and the others.

The above plants are not specifically limited as long as they are generally cultivated cultivars. The above plants also include plants which may be produced by natural breeding, plants which may be generated by mutation, F1 hybrid plants, and genetically modified crops. Examples of the genetically modified crops include plants which have resistance to HPPD (4-hydroxyphenylpyruvate dioxygenase enzyme) inhibitors such as isoxaflutole, ALS (acetolactate synthase) inhibitors such as imazethapyr and thifensulfuron-methyl, EPSP (5-enolpyruvylshikimate-3-phosphate synthase) inhibitors, glutamine synthetase inhibitors, PPO (protoporphyrinogen oxidase) inhibitors, or herbicide such as bromoxynil and dicamba; plants which can synthesize a selective toxin known in *Bacillus* spp. such as *Bacillus thuringiensis* or the like; and plants which can synthesize a gene fragment or the like which is partially identical to an endogenous gene derived from a harmful insect, and induce a gene silencing (RNAi; RNA interference) in the target harmful insect to achieve a specific insecticidal activity.

EXAMPLES

Hereinafter, the present invention is illustrated more in detail by Preparation Examples, Formulation Examples, Test Examples, and the like, but the present invention is not limited to these Examples only.

In the present description, Me represents a methyl group, Et represents an ethyl group, iPr represents an isopropyl group, Bu represents a butyl group, cPr represents a cyclopropyl group, and $C_3F_7$ represents $CF_2CF_2CF_3$.

First, Preparation Examples of the Present compounds and the production intermediate compounds thereof are shown below.

When a physical property of a compound is measured by liquid chromatography/mass spectrometry (hereinafter referred to as "LCMS"), the measured molecular ion value $[M+H]^+$ or $[M-H]^-$, and retention time (hereinafter referred to as "RT") are described. The conditions of liquid chromatography (hereinafter referred to as "LC") are as follows.

[LC Conditions]

Column: L-column2 ODS, inner diameter: 4.6 mm, length: 30 mm, particle size: 3 μm (Chemicals Evaluation and Research Institute, Japan)

UV measurement wavelength: 254 nm

Mobile phase: Solution A: 0.1% formic acid in water, Solution B: 0.1% formic acid in acetonitrile Flow rate: 2.0 mL/min Gradient conditions: sending a solution with the concentration gradient described in Table LC1.

TABLE LC1

| Time (min) | Solution A (%) | Solution B (%) |
|---|---|---|
| 0.01 | 90 | 10 |
| 2.00 | 0 | 100 |
| 4.00 | 0 | 100 |
| 4.01 | 90 | 10 |

Reference Preparation Example 1

A mixture of 3-(bromoacetyl)coumarin (0.9 g), 2-amino-5-(trifluoromethyl)pyridine (0.55 g), and ethanol (5 mL) was stirred under reflux for 8 hours. The resulting mixture was cooled to room temperature, and the precipitated crystals were filtered. The resulting crystals were dried to give the Intermediate compound 1 represented by the following formula (0.45 g).

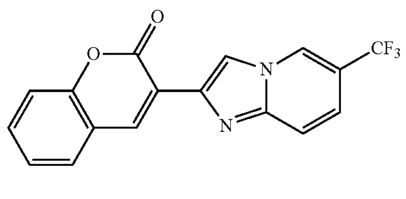 [SMILES: O=c1oc2ccccc2cc1-c1cn2cc(C(F)(F)F)ccc2n1]

Intermediate compound 1: $^1$H-NMR (DMSO-$D_6$) δ: 9.36 (1H, s), 8.93 (1H, s), 8.81 (1H, s), 7.98 (1H, d), 7.80 (1H, d), 7.69-7.65 (1H, m), 7.57 (1H, dd), 7.49 (1H, d), 7.43 (1H, t).

Reference Preparation Example 2

A mixture of the Intermediate compound 1 (0.45 g), NIS (0.34 g), and DMF (5 mL) was stirred at room temperature for 4 hours. To the resulting mixture was added water, and the resulting mixture was subjected to extraction with ethyl acetate. The resulting organic layer was washed with saturated brine, dried over anhydrous sodium sulfate, and concentrated under reduced pressure. The resulting residue was purified by silica gel column chromatography to give the Intermediate compound 2 represented by the following formula (0.2 g).

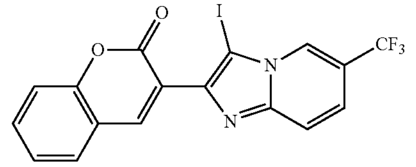 [SMILES: O=c1oc2ccccc2cc1-c1nc2ccc(C(F)(F)F)cn2c1I]

Intermediate compound 2: $^1$H-NMR ($CDCl_3$) δ: 8.60 (1H, s), 8.18 (1H, s), 7.76 (1H, d), 7.64-7.59 (2H, m), 7.44 (2H, t), 7.37-7.33 (1H, m).

Reference Preparation Example 3

To a mixture of ethyl 2-[6-(trifluoromethyl)imidazo[1,2-a]pyridin-2-yl]acetate (200 g) and DMF (800 mL) was added NIS (181.5 g) under ice-cooling, and the resulting mixture was stirred at room temperature for 40 minutes. The precipitated solids were filtered, the resulting crystals were washed with water, and dried under reduced pressure to give a crude product. The crude product was purified by silica gel column chromatography to give the Intermediate compound 3 represented by the following formula (237 g).

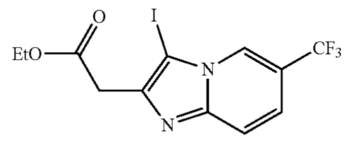 [SMILES: CCOC(=O)Cc1nc2ccc(C(F)(F)F)cn2c1I]

Intermediate compound 3: $^1$H-NMR ($CDCl_3$) δ: $^1$H-NMR ($CDCl_3$) δ: 8.45 (1H, s), 7.67 (1H, d), 7.39 (1H, dd), 4.21 (2H, q), 3.90 (2H, s), 1.28 (3H, t).

Reference Preparation Example 4

To a mixture of the Intermediate compound 3 (216 g), Xantphos (12.7 g), 1,4-dioxane (600 mL), and diisopropylethylamine (100 mL) was added $Pd_2(dba)_3$ (10.2 g) under nitrogen atmosphere at 50° C., then added dropwise ethanethiol (50 mL) over 30 minutes, and the resulting mixture was stirred for 1 hour. The precipitated solids were filtered, the resulting solids were washed with 1,4-dioxane, and dried under reduced pressure to give the Intermediate compound 4 represented by the following formula (140 g).

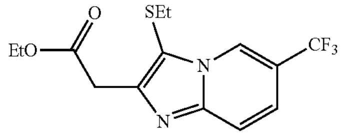

Intermediate compound 4: $^1$H-NMR ($CDCl_3$) δ: $^1$H-NMR ($CDCl_3$) δ: 8.76 (1H, s), 7.70 (1H, d), 7.42 (1H, dd), 4.21 (2H, q), 4.01 (2H, s), 2.72 (2H, q), 1.28 (3H, t), 1.21 (3H, t).

Reference Preparation Example 5

To a mixture of the Intermediate compound 4 (140 g) and chloroform (700 mL) was added mCPBA (218 g) (purity: 70%, comprising 30% of water) under ice-cooling, and the resulting mixture was stirred under ice-cooling for 2 hours. The resulting mixture was filtered, to the resulting filtrate were sequentially added water (500 mL) and sodium sulfite (20 g), and the resulting mixture was stirred at room temperature for 30 minutes. To the resulting mixture was added sodium hydrogen carbonate (84 g) little by little, and the resulting mixture was stirred for 30 minutes. The resulting mixture was filtered, and liquids were separated. The resulting organic layer was sequentially washed with a saturated aqueous solution of sodium hydrogen carbonate and saturated brine, dried over anhydrous sodium sulfate, and concentrated under reduced pressure to give the Intermediate compound 5 represented by the following formula (139.3 g).

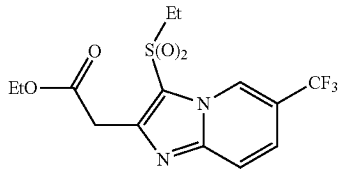

Intermediate compound 5: $^1$H-NMR ($CDCl_3$) δ: $^1$H-NMR ($CDCl_3$) δ: 9.22 (1H, s), 7.82 (1H, d), 7.61 (1H, dd), 4.23 (2H, s), 4.22 (2H, q), 3.39 (2H, q), 1.39 (3H, t), 1.30 (3H, t).

Reference Preparation Example 6

A mixture of the Intermediate compound 5 (5 g) and concentrated hydrochloric acid (10 mL) was stirred at 80° C. for 6 hours. The resulting mixture was cooled to room temperature, and then concentrated under reduced pressure. The resulting residue was sequentially washed with water and chloroform to give the Intermediate compound 6 represented by the following formula (4 g).

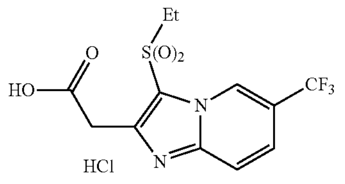

Intermediate compound 6: $^1$H-NMR ($CDCl_3$) δ: $^1$H-NMR (DMSO-D6) δ: 9.08 (1H, s), 8.01 (1H, d), 7.90 (1H, dd), 4.03 (2H, s), 3.58 (2H, q), 1.21 (3H, t).

Reference Preparation Example 7

A mixture of ethyl 2-(6-bromoimidazo[1,2-a]pyridin-2-yl)acetate (1.0 g), 2-amino-5-(trifluoromethyl)pyridine (1.1 g), and dimethylformamide dimethyl acetal (3 mL) was stirred at 90° C. for 2 hours. The resulting mixture was cooled to room temperature, and then concentrated under reduced pressure. To the resulting residue was added propionic acid (1.5 mL), and the resulting mixture was stirred at 120° C. for 1 hour. The resulting mixture was cooled to room temperature, and then a saturated aqueous solution of sodium hydrogen carbonate was added thereto to neutralize the mixture. The precipitated solids were filtered, the resulting solids were washed with methanol, and dried under reduced pressure to give the Intermediate compound 7-1 represented by the following formula (0.40 g).

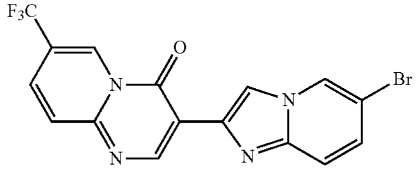 [SMILES: O=c1c(-c2cn3cc(Br)ccc3n2)cnc2ccc(C(F)(F)F)cn12]

Intermediate compound 7-1: LCMS: 409 [M+H]+, RT=2.501 min.

Reference Preparation Example 8

The compounds prepared according to the Reference Preparation Example 7 and physical properties thereof are shown below.

A compound represented by formula (A-1)

(A-1)

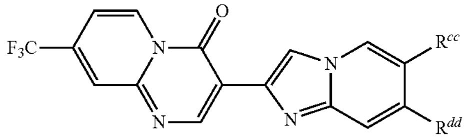

wherein the combination of $R^{cc}$ and $R^{dd}$ represents any one combination indicated in Table A1.

TABLE A1

| Intermediate compound | $R^{cc}$ | $R^{dd}$ |
|---|---|---|
| 7-2 | H | $CF_3$ |
| 7-3 | Cl | H |
| 7-4 | I | H |

Intermediate compound 7-3: $^1$H-NMR ($DMSO-D_6$) δ: 9.33 (1H, s), 9.26 (1H, d), 9.08 (1H, t), 8.73 (1H, s), 8.21 (1H, s), 7.64 (1H, dd), 7.47 (2H, d).

Intermediate compound 7-4: $^1$H-NMR ($DMSO-D_6$) δ: 9.31 (1H, s), 9.24 (1H, d), 8.96 (1H, d), 8.75 (1H, s), 8.19 (1H, s), 7.64 (2H, d), 7.34-7.31 (1H, m).

Preparation Example 1

To a mixture of the Intermediate compound 2 (0.20 g), diisopropylethylamine (0.084 mL), $Pd_2$ ($dba_3$) (0.036 g), Xantphos (0.052 g), and 1,4-dioxane (5 mL) was slowly added dropwise ethanethiol (0.038 mL) at 50° C., and the resulting mixture was stirred at 50° C. for 3 hours. The resulting mixture was cooled to room temperature, and then concentrated under reduced pressure. The resulting residue was purified by silica gel column chromatography (hexane: ethyl acetate=20:80) to give the Present compound 1 represented by the following formula (0.10 g).

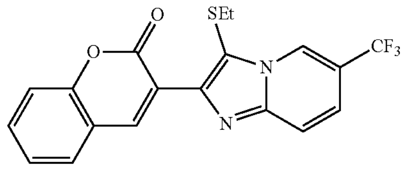

Present compound 1: $^1$H-NMR ($CDCl_3$) δ: 8.85 (1H, s), 8.13 (1H, s), 7.79 (1H, d), 7.62-7.58 (2H, m), 7.48 (1H, dd), 7.42 (1H, d), 7.34 (1H, t), 2.82 (2H, q), 1.20 (3H, t).

Preparation Example 2

To a solution of the Present compound 1 (0.10 g) and chloroform (5 mL) was added mCPBA (purity: 70%, comprising 30% of water) (0.14 g) at 0° C., and the resulting mixture was stirred at room temperature for 1 hour. To the resulting mixture was added a saturated aqueous solution of sodium thiosulfate, and the resulting mixture was subjected to extraction with chloroform. The resulting organic layer was sequentially washed with a saturated aqueous solution of sodium hydrogen carbonate and saturated brine, dried over anhydrous sodium sulfate, and concentrated under reduced pressure. The resulting residue was purified by silica gel chromatography (ethyl acetate) to give the Present compound 2 represented by the following formula (0.1 g).

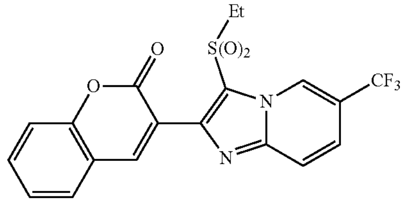

Present compound 2: $^1$H-NMR ($CDCl_3$) δ: 9.25 (1H, s), 8.14 (1H, s), 7.89 (1H, d), 7.67-7.60 (3H, m), 7.42 (1H, d), 7.35 (1H, t), 3.73 (2H, q), 1.51 (3H, t).

Preparation Example 2-1

The compound prepared according to the Preparation Example 1 and physical property thereof are shown below.

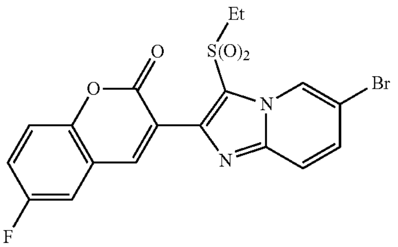

Present compound 3: LCMS: 451 [M+H]+, RT=1.721 min.

Preparation Example 3

A mixture of the Intermediate compound 6 (1.0 g), 1-ethyl-3-(3-dimethylaminopropyl)carbodiimide hydrochloride (1.0 g), 2-amino-5-(trifluoromethyl)pyridine (1.2 g), and pyridine (10 mL) was stirred at 100° C. for 4 hours. The resulting mixture was cooled to room temperature, and then concentrated under reduced pressure. To the resulting residue was added saturated brine, and the resulting mixture was subjected to extraction with ethyl acetate. The resulting organic layer was sequentially washed with 5% hydrochloric acid, a saturated aqueous solution of sodium hydrogen carbonate, and saturated brine, dried over anhydrous sodium sulfate, and concentrated under reduced pressure. To the resulting residue was added N,N-dimethylformamide dimethyl acetal (10 mL), and the resulting mixture was stirred at 50° C. for 2 hours. To the resulting mixture was added saturated brine, and the resulting mixture was subjected to extraction with ethyl acetate. The resulting organic layer was washed with saturated brine, dried over anhydrous sodium sulfate, and concentrated under reduced pressure. To the resulting residue was added acetic acid (12 mL), and the resulting mixture was stirred at room temperature for 1 hour. The resulting mixture was concentrated under reduced pressure, to the resulting residue was added saturated brine, and the resulting mixture was subjected to extraction with ethyl acetate. The resulting organic layer was sequentially washed with a saturated aqueous solution of sodium hydrogen carbonate and saturated brine, dried over anhydrous sodium sulfate, and concentrated under reduced pressure. The resulting residue was purified by silica gel chromatography (hexane:ethyl acetate=10:90) to give the Present compound 4 represented by the following formula (0.5 g).

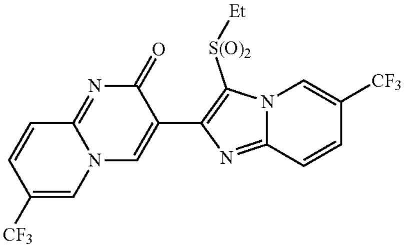

Present compound 4: $^1$H-NMR ($CDCl_3$) δ: 9.26 (1H, s), 8.18 (1H, s), 8.00 (1H, s), 7.86 (1H, d), 7.68-7.65 (2H, m), 7.46 (1H, d), 3.86 (2H, q), 1.50 (3H, t).

Preparation Example 3-1

The compound prepared according to the Preparation Example 3 and physical property thereof are shown below.

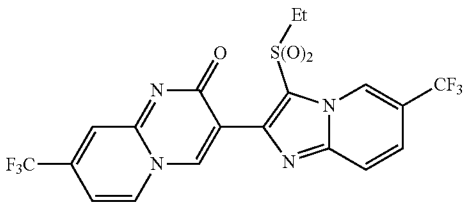

Present compound 9: $^1$H-NMR ($CDCl_3$) δ: $^1$H-NMR ($CDCl_3$) δ: 9.27 (1H, s), 8.20 (1H, s), 7.86 (1H, d), 7.77 (1H, d), 7.67-7.63 (2H, m), 6.97 (1H, dd), 3.88 (2H, q), 1.50 (3H, t).

Preparation Example 3-2

The compounds prepared according to the Preparation Example 3 and physical properties thereof are shown below. A compound represented by formula (A-3)

(A-3)

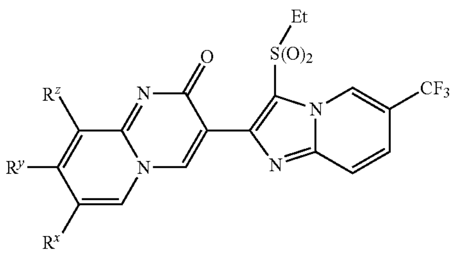

wherein the combination of $R^X$, $R^Y$, and $R^Z$ represents any one combination indicated in Table A3.

TABLE A3

| Present compound | $R^x$ | $R^y$ | $R^z$ |
|---|---|---|---|
| 10 | H | Cl | H |
| 11 | I | H | H |
| 12 | Cl | H | H |
| 13 | H | Br | H |
| 14 | H | H | Br |
| 15 | H | H | Cl |
| 16 | H | H | $CF_3$ |

Present compound 10: $^1$H-NMR ($CDCl_3$) δ: 9.26 (1H, s), 8.11 (1H, s), 7.85 (1H, d), 7.64 (1H, dd), 7.59 (1H, d), 7.37 (1H, d), 6.84 (1H, dd), 3.89 (2H, q), 1.50 (3H, t).

Present compound 11: $^1$H-NMR ($CDCl_3$) δ: 9.26 (1H, s), 8.06 (1H, s), 7.90 (1H, d), 7.86 (1H, d), 7.69 (1H, dd), 7.64 (1H, dd), 7.16 (1H, d), 3.88 (2H, q), 1.49 (3H, t).

Present compound 12: $^1$H-NMR ($CDCl_3$) δ: 9.27 (1H, s), 8.08 (1H, s), 7.86 (1H, d), 7.71 (1H, d), 7.65 (1H, dd), 7.53 (1H, dd), 7.35 (1H, d), 3.89 (2H, q), 1.50 (3H, t).

Present compound 13: $^1$H-NMR ($CDCl_3$) δ: 9.26 (1H, s), 8.10 (1H, s), 7.85 (1H, d), 7.64 (1H, dd), 7.58 (1H, d), 7.49 (1H, d), 6.96 (1H, dd), 3.89 (2H, q), 1.50 (3H, t).

Present compound 14: $^1$H-NMR ($CDCl_3$) δ: 9.27 (1H, s), 8.14 (1H, s), 7.99 (1H, dd), 7.85 (1H, d), 7.65 (2H, dt), 6.75 (1H, t), 3.92 (2H, q), 1.51 (3H, t).

Present compound 15: $^1$H-NMR ($CDCl_3$) δ: 9.26 (1H, s), 8.17 (1H, s), 7.85 (1H, d), 7.77 (1H, dd), 7.66-7.61 (2H, m), 6.82 (1H, t), 3.91 (2H, q), 1.50 (3H, t).

Present compound 16: $^1$H-NMR ($CDCl_3$) δ: 9.33-9.29 (2H, m), 8.78 (1H, s), 8.23 (1H, d), 7.91 (1H, d), 7.65 (1H, dd), 7.30 (1H, t), 3.79 (2H, q), 1.49 (3H, t).

Preparation Example 4

A mixture of the Intermediate compound 7-1 (0.20 g), diethyl disulfide (0.24 mL), iodine (0.50 g), and NMP (5 mL) was stirred at 110° C. for 4 hours. To the resulting mixture was added water, and the precipitated solids were filtered. To the resulting solids were sequentially added chloroform (5 mL) and mCPBA (purity: 70%, comprising 30% of water) (0.25 g), and the resulting mixture was stirred at room temperature for 4 hours. To the resulting mixture were sequentially added an aqueous solution of sodium thiosulfate and a saturated aqueous solution of sodium hydrogen carbonate, and the resulting mixture was subjected to extraction with chloroform. The resulting organic layer was dried over anhydrous sodium sulfate, and concentrated under reduced pressure. The resulting residue was purified by silica gel column chromatography (hexane:ethyl acetate=10:90) to give the Present compound 5 represented by the following formula (0.045 g).

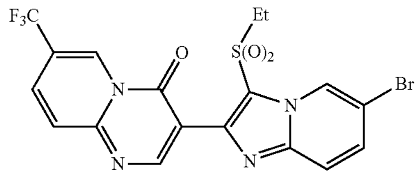

Present compound 5: $^1$H-NMR ($CDCl_3$) δ: 9.47 (1H, s), 9.06 (1H, d), 8.73 (1H, s), 7.89 (1H, s), 7.84 (1H, d), 7.69 (1H, d), 7.56 (1H, dd), 3.77 (2H, q), 1.50 (3H, t).

Preparation Example 4-1

The compounds prepared according to the Preparation Example 4 and physical properties thereof are shown below. A compound represented by formula (A-2)

(A-2)

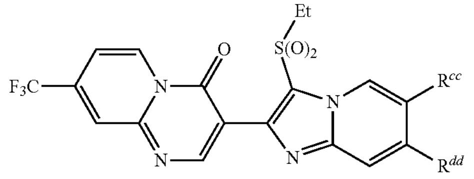

wherein the combination of $R^{cc}$ and $R^{dd}$ represents any one combination indicated in Table A2.

TABLE A2

| Present compound | $R^{cc}$ | $R^{dd}$ |
|---|---|---|
| 6 | H | $CF_3$ |
| 7 | Cl | H |
| 8 | I | H |

Present compound 6: $^1$H-NMR ($CDCl_3$) δ: 9.25 (1H, d), 9.07 (1H, d), 8.77 (1H, t), 8.10 (1H, s), 8.04 (1H, s), 7.35 (1H, d), 7.25 (1H, s), 3.79 (2H, q), 1.48 (3H, t).

Present compound 7: $^1$H-NMR ($CDCl_3$) δ: 9.24 (1H, d), 9.15 (1H, s), 8.74 (1H, s), 8.02 (1H, s), 7.69 (1H, dd), 7.57 (1H, d), 7.32 (1H, dd), 3.73 (2H, q), 1.47 (3H, t).

Present compound 8: $^1$H-NMR ($CDCl_3$) δ: 9.24 (1H, d), 8.98 (1H, dd), 8.75 (1H, s), 8.02 (1H, t), 7.74 (1H, dd), 7.48 (1H, dd), 7.33 (1H, dd), 3.74 (2H, q), 1.48 (3H, t).

Next, examples of the Present compounds prepared according to any one of the Preparation Examples described in EXAMPLES and the Production methods disclosed in the present description are shown below.

A compound represented by formula (L-1)

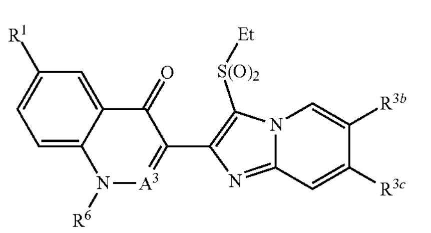

(L-1)

wherein the combination of the symbol n, and the substituents $A^3$, $R^6$, $R^{3b}$, $R^{3c}$, and $R^1$ represents any one combination indicated in the Combination AA (hereinafter referred to as "Compound group SX1").

The Combination AA consists of substituent numbers AA1 to AA6930. The substituent numbers AA1 to AA6930 represent the combinations of the symbol n, and the substituents $A^3$, $R^6$, $R^{3b}$, $R^{3c}$, and $R^1$, and hereinafter referred to as "[substituent number; n, $A^3$, $R^6$, $R^{3b}$, $R^{3c}$, $R^1$]". For example, substituent number AA2 means a combination wherein n represents 0, $A^3$ represents CH, $R^6$ represents a hydrogen atom, $R^{3b}$ represents a fluorine atom, $R^{3c}$ represents a hydrogen atom, and $R^1$ represents $CF_3$.

Combination AA: [AA1; 0, CH, H, H, H, $CF_3$], [AA2; 0, CH, H, F, H, $CF_3$], [AA3; 0, CH, H, Cl, H, $CF_3$], [AA4; 0, CH, H, Br, H, $CF_3$], [AA5; 0, CH, H, I, H, $CF_3$], [AA6; 0, CH, H, $CF_3$, H, $CF_3$], [AA7; 0, CH, H, $CF_2H$, H, $CF_3$], [AA8; 0, CH, H, $C_2F_5$, H, $CF_3$], [AA9; 0, CH, H, $C_3F_7$, H, $CF_3$], [AA10; 0, CH, H, $CH_2CF_3$, H, $CF_3$], [AA11; 0, CH, H, $CH_2CHF_2$, H, $CF_3$], [AA12; 1, CH, H, H, H, $CF_3$], [AA13; 1, CH, H, F, H, $CF_3$], [AA14; 1, CH, H, Cl, H, $CF_3$], [AA15; 1, CH, H, Br, H, $CF_3$], [AA16; 1, CH, H, I, H, $CF_3$], [AA17; 1, CH, H, $CF_3$, H, $CF_3$], [AA18; 1, CH, H, $CF_2H$, H, $CF_3$], [AA19; 1, CH, H, $C_2F_5$, H, $CF_3$], [AA20; 1, CH, H, $C_3F_7$, H, $CF_3$], [AA21; 1, CH, H, $CH_2CF_3$, H, $CF_3$], [AA22; 1, CH, H, $CH_2CHF_2$, H, $CF_3$], [AA23; 2, CH, H, H, H, $CF_3$], [AA24; 2, CH, H, F, H, $CF_3$], [AA25; 2, CH, H, Cl, H, $CF_3$], [AA26; 2, CH, H, Br, H, $CF_3$], [AA27; 2, CH, H, I, H, $CF_3$], [AA28; 2, CH, H, $CF_3$, H, $CF_3$], [AA29; 2, CH, H, $CF_2H$, H, $CF_3$], [AA30; 2, CH, H, $C_2F_5$, H, $CF_3$], [AA31; 2, CH, H, $C_3F_7$, H, $CF_3$], [AA32; 2, CH, H, $CH_2CF_3$, H, $CF_3$], [AA33; 2, CH, H, $CH_2CHF_2$, H, $CF_3$], [AA34; 0, N, H, H, H, $CF_3$], [AA35; 0, N, H, F, H, $CF_3$], [AA36; 0, N, H, Cl, H, $CF_3$], [AA37; 0, N, H, Br, H, $CF_3$], [AA38; 0, N, H, I, H, $CF_3$], [AA39; 0, N, H, $CF_3$, H, $CF_3$], [AA40; 0, N, H, $CF_2H$, H, $CF_3$], [AA41; 0, N, H, $C_2F_5$, H, $CF_3$], [AA42; O, N, H, $C_3F_7$, H, $CF_3$], [AA43; 0, N, H, $CH_2CF_3$, H, $CF_3$], [AA44; 0, N, H, $CH_2CHF_2$, H, $CF_3$], [AA45; 1, N, H, H, H, $CF_3$], [AA46; 1, N, H, F, H, $CF_3$], [AA47; 1, N, H, Cl, H, $CF_3$], [AA48; 1, N, H, Br, H, $CF_3$], [AA49; 1, N, H, I, H, $CF_3$], [AA50; 1, N, H, $CF_3$, H, $CF_3$], [AA51; 1, N, H, $CF_2H$, H, $CF_3$], [AA52; 1, N, H, $C_2F_5$, H, $CF_3$], [AA53; 1, N, H, $C_3F_7$, H, $CF_3$], [AA54; 1, N, H, $CH_2CF_3$, H, $CF_3$], [AA55; 1, N, H, $CH_2CHF_2$, H, $CF_3$], [AA56; 2, N, H, H, H, $CF_3$], [AA57; 2, N, H, F, H, $CF_3$], [AA58; 2, N, H, Cl, H, $CF_3$], [AA59; 2, N, H, Br, H, $CF_3$], [AA60; 2, N, H, I, H, $CF_3$], [AA61; 2, N, H, $CF_3$, H, $CF_3$], [AA62; 2, N, H, $CF_2H$, H, $CF_3$], [AA63; 2, N, H, $C_2F_5$, H, $CF_3$], [AA64; 2, N, H, $C_3F_7$, H, $CF_3$], [AA65; 2, N, H, $CH_2CF_3$, H, $CF_3$], [AA66; 2, N, H, $CH_2CHF_2$, H, $CF_3$], [AA67; 0, CH, Me, H, H, $CF_3$], [AA68; 0, CH, Me, F, H, $CF_3$], [AA69; 0, CH, Me, Cl, H, $CF_3$], [AA70; 0, CH, Me, Br, H, $CF_3$], [AA71; 0, CH, Me, I, H, $CF_3$], [AA72; 0, CH, Me, $CF_3$, H, $CF_3$], [AA73; 0, CH, Me, $CF_2H$, H, $CF_3$], [AA74; 0, CH, Me, $C_2F_5$, H, $CF_3$], [AA75; 0, CH, Me, $C_3F_7$, H, $CF_3$], [AA76; 0, CH, Me, $CH_2CF_3$, H, $CF_3$], [AA77; 0, CH, Me, $CH_2CHF_2$, H, $CF_3$], [AA78; 1, CH, Me, H, H, $CF_3$], [AA79; 1, CH, Me, F, H, $CF_3$], [AA80; 1, CH, Me, C1, H, $CF_3$], [AA81; 1, CH, Me, Br, H, $CF_3$], [AA82; 1, CH, Me, I, H, $CF_3$], [AA83; 1, CH, Me, $CF_3$, H, $CF_3$], [AA84; 1, CH, Me, $CF_2H$, H, $CF_3$], [AA85; 1, CH, Me, $C_2F_5$, H, $CF_3$], [AA86; 1, CH, Me, $C_3F_7$, H, $CF_3$], [AA87; 1, CH, Me, $CH_2CF_3$, H, $CF_3$], [AA88; 1, CH, Me, $CH_2CHF_2$, H, $CF_3$], [AA89; 2, CH, Me, H, H, $CF_3$], [AA90; 2, CH, Me, F, H, $CF_3$], [AA91; 2, CH, Me, Cl, H, $CF_3$], [AA92; 2, CH, Me, Br, H, $CF_3$], [AA93; 2, CH, Me, I, H, $CF_3$], [AA94; 2, CH, Me, $CF_3$, H, $CF_3$], [AA95; 2, CH, Me, $CF_2H$, H, $CF_3$], [AA96; 2, CH, Me, $C_2F_5$, H, $CF_3$], [AA97; 2, CH, Me, $C_3F_7$, H, $CF_3$], [AA98; 2, CH, Me, $CH_2CF_3$, H, $CF_3$], [AA99; 2, CH, Me, $CH_2CHF_2$, H, $CF_3$], [AA100; 0, N, Me, H, H, $CF_3$], [AA101; 0, N, Me, F, H, $CF_3$], [AA102; 0, N, Me, C1, H, $CF_3$], [AA103; 0, N, Me, Br, H, $CF_3$], [AA104; 0, N, Me, I, H, $CF_3$], [AA105; 0, N, Me, $CF_3$, H, $CF_3$], [AA106; 0, N, Me, $CF_2H$, H, $CF_3$], [AA107; 0, N, Me, $C_2F_5$, H, $CF_3$], [AA108; 0, N, Me, $C_3F_7$, H, $CF_3$], [AA109; 0, N, Me, $CH_2CF_3$, H, $CF_3$], [AA110; 0, N, Me, $CH_2CHF_2$, H, $CF_3$], [AA111; 1, N, Me, H, H, $CF_3$], [AA112; 1, N, Me, F, H, $CF_3$], [AA113; 1, N, Me, Cl, H, $CF_3$], [AA114; 1, N, Me, Br, H, $CF_3$], [AA115; 1, N, Me, I, H, $CF_3$], [AA116; 1, N, Me, $CF_3$, H, $CF_3$], [AA117; 1, N, Me, $CF_2H$, H, $CF_3$], [AA118; 1, N, Me, $C_2F_5$, H, $CF_3$], [AA119; 1, N, Me, $C_3F_7$, H, $CF_3$], [AA120; 1, N, Me, $CH_2CF_3$, H, $CF_3$], [AA121; 1, N, Me, $CH_2CHF_2$, H, $CF_3$], [AA122; 2, N, Me, H, H, $CF_3$], [AA123; 2, N, Me, F, H, $CF_3$], [AA124; 2, N, Me, Cl, H, $CF_3$], [AA125; 2, N, Me, Br, H, $CF_3$], [AA126; 2, N, Me, I, H, $CF_3$], [AA127; 2, N, Me, $CF_3$, H, $CF_3$], [AA128; 2, N, Me, $CF_2H$, H, $CF_3$], [AA129; 2, N, Me, $C_2F_5$, H, $CF_3$], [AA130; 2, N, Me, $C_3F_7$, H, $CF_3$], [AA131; 2, N, Me, $CH_2CF_3$, H, $CF_3$], [AA132; 2, N, Me, $CH_2CHF_2$, H, $CF_3$], [AA133; 0, CH, Et, H, H, $CF_3$], [AA134; 0, CH, Et, F, H, $CF_3$], [AA135; 0, CH, Et, Cl, H, $CF_3$], [AA136; 0, CH, Et, Br, H, $CF_3$], [AA137; 0, CH, Et, I, H, $CF_3$], [AA138; 0, CH, Et, $CF_3$, H, $CF_3$], [AA139; 0, CH, Et, $CF_2H$, H, $CF_3$], [AA140; 0, CH, Et, $C_2F_5$, H, $CF_3$], [AA141; 0, CH, Et, $C_3F_7$, H, $CF_3$], [AA142; 0, CH, Et, $CH_2CF_3$, H, $CF_3$], [AA143; 0, CH, Et, $CH_2CHF_2$, H, $CF_3$], [AA144; 1, CH, Et, H, H, $CF_3$], [AA145; 1, CH, Et, F, H, $CF_3$], [AA146; 1, CH, Et, Cl, H, $CF_3$], [AA147; 1, CH, Et, Br, H, $CF_3$], [AA148; 1, CH, Et, I, H, $CF_3$], [AA149; 1, CH, Et, $CF_3$, H, $CF_3$], [AA150; 1, CH, Et, $CF_2H$, H, $CF_3$], [AA151; 1, CH, Et, $C_2F_5$, H, $CF_3$], [AA152; 1, CH, Et, $C_3F_7$, H, $CF_3$], [AA153; 1, CH, Et, $CH_2CF_3$, H, $CF_3$], [AA154; 1, CH, Et, $CH_2CHF_2$, H, $CF_3$], [AA155; 2, CH, Et, H, H, $CF_3$], [AA156; 2, CH, Et, F, H, $CF_3$], [AA157; 2, CH, Et, Cl, H, $CF_3$], [AA158; 2, CH, Et, Br, H, $CF_3$], [AA159; 2, CH, Et, I, H, $CF_3$], [AA160; 2, CH, Et, $CF_3$, H, $CF_3$], [AA161; 2, CH, Et, $CF_2H$, H, $CF_3$], [AA162; 2, CH, Et, $C_2F_5$, H, $CF_3$], [AA163; 2, CH, Et, $C_3F_7$, H, $CF_3$], [AA164; 2, CH, Et, $CH_2CF_3$, H, $CF_3$], [AA165; 2, CH, Et, $CH_2CHF_2$, H, $CF_3$], [AA166; 0, N, Et, H, H, $CF_3$], [AA167; 0, N, Et, F, H, $CF_3$], [AA168; 0, N, Et, Cl, H, $CF_3$], [AA169; 0, N, Et, Br, H, $CF_3$], [AA170; 0, N, Et, I, H, $CF_3$], [AA171; 0, N, Et, $CF_3$, H, $CF_3$], [AA172; 0, N, Et, $CF_2H$, H, $CF_3$], [AA173; 0, N, Et, $C_2F_5$, H, $CF_3$], [AA174; 0, N, Et, $C_3F_7$, H, $CF_3$], [AA175; 0, N, Et, $CH_2CF_3$, H, $CF_3$], [AA176; 0, N, Et, $CH_2CHF_2$, H, $CF_3$], [AA177; 1, N, Et, H, H, $CF_3$], [AA178; 1, N, Et, F, H, $CF_3$], [AA179; 1, N, Et, Cl, H, $CF_3$], [AA180; 1, N, Et, Br, H, $CF_3$], [AA181; 1, N, Et, I, H, $CF_3$], [AA182; 1, N, Et, $CF_3$, H, $CF_3$], [AA183; 1, N, Et, $CF_2H$, H, $CF_3$], [AA184; 1, N, Et, $C_2F_5$, H, $CF_3$], [AA185; 1, N, Et, $C_3F_7$, H, $CF_3$], [AA186; 1, N, Et, $CH_2CF_3$, H, $CF_3$], [AA187; 1, N, Et, $CH_2CHF_2$, H, $CF_3$], [AA188; 2, N, Et, H, H, $CF_3$], [AA189; 2, N, Et, F, H, $CF_3$], [AA190; 2, N, Et, Cl, H, $CF_3$], [AA191; 2, N, Et, Br, H, $CF_3$], [AA192; 2, N, Et, I, H, $CF_3$], [AA193; 2, N, Et, $CF_3$, H, $CF_3$], [AA194; 2, N, Et, $CF_2H$, H, $CF_3$], [AA195; 2, N, Et, $C_2F_5$, H, $CF_3$], [AA196; 2, N, Et, $C_3F_7$, H, $CF_3$], [AA197; 2, N, Et, $CH_2CF_3$, H, $CF_3$], [AA198; 2, N, Et, $CH_2CHF_2$, H, $CF_3$], [AA199; 0, CH, iPr, H, H, $CF_3$], [AA200; 0, CH, iPr, F, H, $CF_3$], [AA201; 0, CH, iPr, Cl, H, $CF_3$], [AA202; 0, CH, iPr, Br, H, $CF_3$], [AA203; 0, CH, iPr, I, H, $CF_3$], [AA204; 0, CH, iPr, $CF_3$, H, $CF_3$], [AA205; 0, CH, iPr, $CF_2H$, H, $CF_3$], [AA206; 0, CH, iPr, $C_2F_5$, H, $CF_3$], [AA207; 0, CH, iPr, $C_3F_7$, H, $CF_3$], [AA208; 0, CH, iPr, $CH_2CF_3$, H, $CF_3$], [AA209; 0, CH, iPr, $CH_2CHF_2$, H, $CF_3$], [AA210; 1, CH, iPr, H, H, $CF_3$], [AA211; 1, CH, iPr, F, H, $CF_3$], [AA212; 1, CH, iPr, Cl, H, $CF_3$], [AA213; 1, CH, iPr, Br, H, $CF_3$], [AA214; 1, CH, iPr, I, H, $CF_3$], [AA215; 1, CH, iPr, $CF_3$, H, $CF_3$], [AA216; 1, CH, iPr, $CF_2H$, H, $CF_3$], [AA217; 1, CH, iPr, $C_2F_5$, H, $CF_3$], [AA218; 1, CH, iPr, $C_3F_7$, H, $CF_3$], [AA219; 1, CH, iPr, $CH_2CF_3$, H, $CF_3$], [AA220; 1, CH, iPr, $CH_2CHF_2$, H, $CF_3$], [AA221; 2, CH, iPr, H, H, $CF_3$], [AA222; 2, CH, iPr, F, H, $CF_3$], [AA223; 2, CH, iPr, Cl, H, $CF_3$], [AA224; 2, CH, iPr, Br, H, $CF_3$], [AA225; 2, CH, iPr, I, H, $CF_3$], [AA226; 2, CH, iPr, $CF_3$, H, $CF_3$], [AA227; 2, CH, iPr, $CF_2H$, H, $CF_3$], [AA228; 2, CH, iPr, $C_2F$ %, H, $CF_3$], [AA229; 2, CH, iPr, $C_3F_3$, H, $CF_3$], [AA230; 2, CH, iPr, $CH_2CF_3$, H, $CF_3$], [AA231; 2, CH, iPr, $CH_2CHF_2$, H, $CF_3$], [AA232; 0, N, iPr, H, H, $CF_3$], [AA233; 0, N, iPr, F, H, $CF_3$], [AA234; 0, N, iPr, Cl, H, $CF_3$], [AA235; 0, N, iPr, Br, H, $CF_3$], [AA236; 0, N, iPr, I, H, $CF_3$], [AA237; 0, N, iPr, $CF_3$, H, $CF_3$], [AA238; 0, N, iPr, $CF_2H$, H, $CF_3$], [AA239; 0, N, iPr, $C_2F_5$, H, $CF_3$], [AA240; 0, N, iPr, $C_3F_7$, H, $CF_3$], [AA241; 0, N, iPr, $CH_2CF_3$, H, $CF_3$], [AA242; 0, N, iPr, $CH_2CHF_2$, H, $CF_3$], [AA243; 1, N, iPr, H, H, $CF_3$], [AA244; 1, N, iPr, F, H, $CF_3$], [AA245; 1, N, iPr, Cl, H, $CF_3$], [AA246; 1, N, iPr, Br, H, $CF_3$], [AA247; 1, N, iPr, I, H, $CF_3$], [AA248; 1, N, iPr, $CF_3$, H, $CF_3$], [AA249; 1, N, iPr, $CF_2H$, H, $CF_3$], [AA250; 1, N, iPr, $C_2F_5$, H, $CF_3$], [AA251; 1, N, iPr, $C_3F_7$, H, $CF_3$], [AA252; 1, N, iPr, $CH_2CF_3$, H, $CF_3$], [AA253; 1, N, iPr, $CH_2CHF_2$, H, $CF_3$], [AA254; 2, N, iPr, H, H, $CF_3$], [AA255; 2, N, iPr, F, H, $CF_3$], [AA256; 2, N, iPr, Cl, H, $CF_3$], [AA257; 2, N, iPr, Br, H, $CF_3$], [AA258; 2, N, iPr, I, H, $CF_3$], [AA259; 2, N, iPr, $CF_3$, H, $CF_3$], [AA260; 2, N, iPr, $CF_2H$, H, $CF_3$], [AA261; 2, N, iPr, $C_2F_5$, H, $CF_3$], [AA262; 2, N, iPr, $C_3F_7$, H, $CF_3$], [AA263; 2, N, iPr, $CH_2CF_3$, H, $CF_3$], [AA264; 2, N, iPr, $CH_2CHF_2$, H, $CF_3$], [AA265; 0, CH, cPr, H, H, $CF_3$], [AA266; 0, CH, cPr, F, H, $CF_3$], [AA267; 0, CH, cPr, Cl, H, $CF_3$], [AA268; 0, CH, cPr, Br, H, $CF_3$], [AA269; 0, CH, cPr, I, H, $CF_3$], [AA270; 0, CH, cPr, $CF_3$, H, $CF_3$], [AA271; 0, CH, cPr, $CF_2H$, H, $CF_3$], [AA272; 0, CH, cPr, $C_2F_5$, H, $CF_3$], [AA273; 0, CH, cPr, $C_3F_7$, H, $CF_3$], [AA274; 0, CH, cPr, $CH_2CF_3$, H, $CF_3$], [AA275; 0, CH, cPr, $CH_2CHF_2$, H, $CF_3$], [AA276; 1, CH, cPr, H, H, $CF_3$], [AA277; 1, CH, cPr, F, H, $CF_3$], [AA278; 1, CH, cPr, Cl, H, $CF_3$], [AA279; 1, CH, cPr, Br, H, $CF_3$], [AA280; 1, CH, cPr, I, H, $CF_3$], [AA281; 1, CH, cPr, $CF_3$, H, $CF_3$], [AA282; 1, CH, cPr, $CF_2H$, H, $CF_3$], [AA283; 1, CH, cPr, $C_2F_5$, H, $CF_3$], [AA284; 1, CH, cPr, $C_3F_7$, H, $CF_3$], [AA285; 1, CH, cPr, $CH_2CF_3$, H, $CF_3$], [AA286; 1, CH, cPr, $CH_2CHF_2$, H, $CF_3$], [AA287; 2, CH, cPr, H, H, $CF_3$], [AA288; 2, CH, cPr, F, H, $CF_3$], [AA289; 2, CH, cPr, Cl, H, $CF_3$], [AA290; 2, CH, cPr, Br, H, $CF_3$], [AA291; 2, CH, cPr, I, H, $CF_3$], [AA292; 2, CH, cPr, $CF_3$, H, $CF_3$], [AA293; 2, CH, cPr, $CF_2H$, H, $CF_3$], [AA294; 2, CH, cPr, $C_2F_5$, H, $CF_3$], [AA295; 2, CH, cPr, $C_3F_7$, H, $CF_3$], [AA296; 2, CH, cPr, $CH_2CF_3$, H, $CF_3$], [AA297; 2, CH, cPr, $CH_2CHF_2$, H, $CF_3$], [AA298; 0, N, cPr, H, H, $CF_3$], [AA299; 0, N, cPr, F, H, $CF_3$], [AA300; 0, N, cPr, Cl, H, $CF_3$], [AA301; 0, N, cPr, Br, H, $CF_3$], [AA302; 0, N, cPr, I, H, $CF_3$], [AA303; 0, N, cPr, $CF_3$, H, $CF_3$], [AA304; 0, N, cPr, $CF_2H$, H, $CF_3$], [AA305; 0, N, cPr, C2F5, H, $CF_3$], [AA306; 0, N, cPr, $C_3F_7$, H, $CF_3$], [AA307; 0, N, cPr, $CH_2CF_3$, H, $CF_3$], [AA308; 0, N, cPr, $CH_2CHF_2$, H, $CF_3$], [AA309; 1, N, cPr, H, H, $CF_3$], [AA310; 1, N, cPr, F, H, $CF_3$], [AA311; 1, N, cPr, Cl, H, $CF_3$], [AA312; 1, N, cPr, Br, H, $CF_3$], [AA313; 1, N, cPr, I, H, $CF_3$], [AA314; 1, N, cPr, $CF_3$, H, $CF_3$], [AA315; 1, N, cPr, $CF_2H$, H, $CF_3$], [AA316; 1, N, cPr, $C_2F_5$, H, $CF_3$], [AA317; 1, N, cPr, $C_3F_7$, H, $CF_3$], [AA318; 1, N, cPr, $CH_2CF_3$, H, $CF_3$], [AA319; 1, N, cPr, $CH_2CHF_2$, H, $CF_3$], [AA320; 2, N, cPr, H, H, $CF_3$], [AA321; 2, N, cPr, F, H, $CF_3$], [AA322; 2, N, cPr, Cl, H, $CF_3$], [AA323; 2, N, cPr, Br, H, $CF_3$], [AA324; 2, N, cPr, I, H, $CF_3$], [AA325; 2, N, cPr, $CF_3$, H, $CF_3$], [AA326; 2, N, cPr, $CF_2H$, H, $CF_3$], [AA327; 2, N, cPr, $C_2F_5$, H, $CF_3$], [AA328; 2, N, cPr, $C_3F_7$, H, $CF_3$], [AA329; 2, N, cPr, $CH_2CF_3$, H, $CF_3$], [AA330; 2, N, cPr, $CH_2CHF_2$, H, $CF_3$], [AA331; 0, CH, H, H, F, $CF_3$], [AA332; 0, CH, H, H, Cl, $CF_3$], [AA333; 0, CH, H, H, Br, $CF_3$], [AA334; 0, CH, H, H, I, $CF_3$], [AA335; 0, CH, H, H, $CF_3$, $CF_3$], [AA336; 0, CH, H, H, $CF_2H$, $CF_3$], [AA337; 0, CH, H, H, $C_2F_5$, $CF_3$], [AA338; 0, CH, H, H, $C_3F_7$, $CF_3$], [AA339; 0, CH, H, H, $CH_2CF_3$, $CF_3$], [AA340; 0, CH, H, H, $CH_2CHF_2$, $CF_3$], [AA341; 1, CH, H, H, F, $CF_3$], [AA342; 1, CH, H, H, Cl, $CF_3$], [AA343; 1, CH, H, H, Br, $CF_3$], [AA344; 1, CH, H, H, I, $CF_3$], [AA345; 1, CH, H, H, $CF_3$, $CF_3$], [AA346; 1, CH, H, H, $CF_2H$, $CF_3$], [AA347; 1, CH, H, H, $C_2F_5$, $CF_3$], [AA348; 1, CH, H, H, $C_3F_7$, $CF_3$], [AA349; 1, CH, H, H, $CH_2CF_3$, $CF_3$], [AA350; 1, CH, H, H, $CH_2CHF_2$, $CF_3$], [AA351; 2, CH, H, H, F, $CF_3$], [AA352; 2, CH, H, H, Cl, $CF_3$], [AA353; 2, CH, H, H, Br, $CF_3$], [AA354; 2, CH, H, H, I, $CF_3$], [AA355; 2, CH, H, H, $CF_3$, $CF_3$], [AA356; 2, CH, H, H, $CF_2H$, $CF_3$], [AA357; 2, CH, H, H, $C_2F_5$, $CF_3$], [AA358; 2, CH, H, H, $C_3F_7$, $CF_3$], [AA359; 2, CH, H, H, $CH_2CF_3$, $CF_3$], [AA360; 2, CH, H, H, $CH_2CHF_2$, $CF_3$], [AA361; 0, N, H, H, F, $CF_3$], [AA362; 0, N, H, H, Cl, $CF_3$], [AA363; 0, N, H, H, Br, $CF_3$], [AA364; 0, N, H, H, I, $CF_3$], [AA365; 0, N, H, H, $CF_3$, $CF_3$], [AA366; 0, N, H, H, $CF_2H$, $CF_3$], [AA367; 0, N, H, H, $C_2F_5$, $CF_3$], [AA368; 0, N, H, H, $C_3F_7$, $CF_3$], [AA369; 0, N, H, H, $CH_2CF_3$, $CF_3$], [AA370; 0, N, H, H, $CH_2CHF_2$, $CF_3$], [AA371; 1, N, H, H, F, $CF_3$], [AA372; 1, N, H, H, Cl, $CF_3$], [AA373; 1, N, H, H, Br, $CF_3$], [AA374; 1, N, H, H, I, $CF_3$], [AA375; 1, N, H, H, $CF_3$, $CF_3$], [AA376; 1, N, H, H, $CF_2H$, $CF_3$], [AA377; 1, N, H, H, $C_2F_5$, $CF_3$], [AA378; 1, N, H, H, $C_3F_7$, $CF_3$], [AA379; 1, N, H, H, $CH_2CF_3$, $CF_3$], [AA380; 1, N, H, H, $CH_2CHF_2$, $CF_3$], [AA381; 2, N, H, H, F, $CF_3$], [AA382; 2, N, H, H, Cl, $CF_3$], [AA383; 2, N, H, H, Br, $CF_3$], [AA384; 2, N, H, H, I, $CF_3$], [AA385; 2, N, H, H, $CF_3$, $CF_3$], [AA386; 2, N, H, H, $CF_2H$, $CF_3$], [AA387; 2, N, H, H, $C_2F_5$, $CF_3$], [AA388; 2, N, H, H, $C_3F_7$, $CF_3$], [AA389; 2, N, H, H, $CH_2CF_3$, $CF_3$], [AA390; 2, N, H, H, $CH_2CHF_2$, $CF_3$], [AA391; 0, CH, Me, H, F, $CF_3$], [AA392; 0, CH, Me, H, Cl, $CF_3$], [AA393; 0, CH, Me, H, Br, $CF_3$], [AA394; 0, CH, Me, H, I, $CF_3$], [AA395; 0, CH, Me, H, $CF_3$, $CF_3$], [AA396; 0, CH, Me, H, $CF_2H$, $CF_3$], [AA397; 0, CH, Me, H, $C_2F_5$, $CF_3$], [AA398; 0, CH, Me, H, $C_3F_7$, $CF_3$], [AA399; 0, CH, Me, H, $CH_2CF_3$, $CF_3$], [AA400; 0, CH, Me, H, $CH_2CHF_2$, $CF_3$], [AA401; 1, CH, Me, H, F, $CF_3$], [AA402; 1, CH, Me, H, Cl, $CF_3$], [AA403; 1, CH, Me, H, Br, $CF_3$], [AA404; 1, CH, Me, H, I, $CF_3$], [AA405; 1, CH, Me, H, $CF_3$, $CF_3$], [AA406; 1, CH, Me, H, $CF_2H$, $CF_3$], [AA407; 1, CH, Me, H, $C_2F_5$, $CF_3$], [AA408; 1, CH, Me, H, $C_3F_7$, $CF_3$], [AA409; 1, CH, Me, H, $CH_2CF_3$, $CF_3$], [AA410; 1, CH, Me, H, $CH_2CHF_2$, $CF_3$], [AA411; 2, CH, Me, H, F, $CF_3$], [AA412; 2, CH, Me, H, Cl, $CF_3$], [AA413; 2, CH, Me, H, Br, $CF_3$], [AA414; 2, CH, Me, H, I, $CF_3$], [AA415; 2, CH, Me, H, $CF_3$, $CF_3$], [AA416; 2, CH, Me, H, $CF_2H$, $CF_3$], [AA417; 2, CH, Me, H, $C_2F_5$, $CF_3$], [AA418; 2, CH, Me, H, $C_3F_7$, $CF_3$], [AA419; 2, CH, Me, H, $CH_2CF_3$, $CF_3$], [AA420; 2, CH, Me, H, $CH_2CHF_2$, $CF_3$], [AA421; 0, N, Me, H, F, $CF_3$], [AA422; 0, N, Me, H, Cl, $CF_3$], [AA423; 0, N, Me, H, Br, $CF_3$], [AA424; 0, N, Me, H, I, $CF_3$], [AA425; 0, N, Me, H, $CF_3$, $CF_3$], [AA426; 0, N, Me, H, $CF_2H$, $CF_3$], [AA427; 0, N, Me, H, $C_2F_5$, $CF_3$], [AA428; 0, N, Me, H, $C_3F_7$, $CF_3$], [AA429; 0, N, Me, H, $CH_2CF_3$, $CF_3$], [AA430; 0, N, Me, H, $CH_2CHF_2$, $CF_3$], [AA431; 1, N, Me, H, F, $CF_3$], [AA432; 1, N, Me, H, Cl, $CF_3$], [AA433; 1, N, Me, H, Br, $CF_3$], [AA434; 1, N, Me, H, I, $CF_3$], [AA435; 1, N, Me, H, $CF_3$, $CF_3$], [AA436; 1, N, Me, H, $CF_2H$, $CF_3$], [AA437; 1, N, Me, H, $C_2F_5$, $CF_3$], [AA438; 1, N, Me, H, $C_3F_7$, $CF_3$], [AA439; 1, N, Me, H, $CH_2CF_3$, $CF_3$], [AA440; 1, N, Me, H, $CH_2CHF_2$, $CF_3$], [AA441; 2, N, Me, H, F, $CF_3$], [AA442; 2, N, Me, H, Cl, $CF_3$], [AA443; 2, N, Me, H, Br, $CF_3$], [AA444; 2, N, Me, H, I, $CF_3$], [AA445; 2, N, Me, H, $CF_3$, $CF_3$], [AA446; 2, N, Me, H, $CF_2H$, $CF_3$], [AA447; 2, N, Me, H, $C_2F_5$, $CF_3$], [AA448; 2, N, Me, H, $C_3F_7$, $CF_3$], [AA449; 2, N, Me, H, $CH_2CF_3$, $CF_3$], [AA450; 2, N, Me, H, $CH_2CHF_2$, $CF_3$], [AA451; 0, CH, Et, H, F, $CF_3$], [AA452; 0, CH, Et, H, Cl, $CF_3$], [AA453; 0, CH, Et, H, Br, $CF_3$], [AA454; 0, CH, Et, H, I, $CF_3$], [AA455; 0, CH, Et, H, $CF_3$, $CF_3$], [AA456; 0, CH, Et, H, $CF_2H$, $CF_3$], [AA457; 0, CH, Et, H, $C_2F_5$, $CF_3$], [AA458; 0, CH, Et, H, $C_3F_7$, $CF_3$], [AA459; 0, CH, Et, H, $CH_2CF_3$, $CF_3$], [AA460; 0, CH, Et, H, $CH_2CHF_2$, $CF_3$], [AA461; 1, CH, Et, H, F, $CF_3$], [AA462; 1, CH, Et, H, Cl, $CF_3$], [AA463; 1, CH, Et, H, Br, $CF_3$], [AA464; 1, CH, Et, H, I, $CF_3$], [AA465; 1, CH, Et, H, $CF_3$, $CF_3$], [AA466; 1, CH, Et, H, $CF_2H$, $CF_3$], [AA467; 1, CH, Et, H, $C_2F_5$, $CF_3$], [AA468; 1, CH, Et, H, $C_3F_7$, $CF_3$], [AA469; 1, CH, Et, H, $CH_2CF_3$, $CF_3$], [AA470; 1, CH, Et, H, $CH_2CHF_2$, $CF_3$], [AA471; 2, CH, Et, H, F, $CF_3$], [AA472; 2, CH, Et, H, Cl, $CF_3$], [AA473; 2, CH, Et, H, Br, $CF_3$], [AA474; 2, CH, Et, H, I, $CF_3$], [AA475; 2, CH, Et, H, $CF_3$, $CF_3$], [AA476; 2, CH, Et, H, $CF_2H$, $CF_3$], [AA477; 2, CH, Et, H, $C_2F_5$, $CF_3$], [AA478; 2, CH, Et, H, $C_3F_7$, $CF_3$], [AA479; 2, CH, Et, H, $CH_2CF_3$, $CF_3$], [AA480; 2, CH, Et, H, $CH_2CHF_2$, $CF_3$], [AA481; 0, N, Et, H, F, $CF_3$], [AA482; 0, N, Et, H, Cl, $CF_3$], [AA483; 0, N, Et, H, Br, $CF_3$], [AA484; 0, N, Et, H, I, $CF_3$], [AA485; 0, N, Et, H, $CF_3$, $CF_3$], [AA486; 0, N, Et, H, $CF_2H$, $CF_3$], [AA487; 0, N, Et, H, $C_2F_5$, $CF_3$], [AA488; 0, N, Et, H, $C_3F_7$, $CF_3$], [AA489; 0, N, Et, H, $CH_2CF_3$, $CF_3$], [AA490; 0, N, Et, H, $CH_2CHF_2$, $CF_3$], [AA491; 1, N, Et, H, F, $CF_3$], [AA492; 1, N, Et, H, Cl, $CF_3$], [AA493; 1, N, Et, H, Br, $CF_3$], [AA494; 1, N, Et, H, I, $CF_3$], [AA495; 1, N, Et, H, $CF_3$, $CF_3$], [AA496; 1, N, Et, H, $CF_2H$, $CF_3$], [AA497; 1, N, Et, H, $C_2F_5$, $CF_3$], [AA498; 1, N, Et, H, $C_3F_7$, $CF_3$], [AA499; 1, N, Et, H, $CH_2CF_3$, $CF_3$], [AA500; 1, N, Et, H, $CH_2CHF_2$, $CF_3$], [AA501; 2, N, Et, H, F, $CF_3$], [AA502; 2, N, Et, H, Cl, $CF_3$], [AA503; 2, N, Et, H, Br, $CF_3$], [AA504; 2, N, Et, H, I, $CF_3$], [AA505; 2, N, Et, H, $CF_3$, $CF_3$], [AA506; 2, N, Et, H, $CF_2H$, $CF_3$], [AA507; 2, N, Et, H, $C_2F_5$, $CF_3$], [AA508; 2, N, Et, H, $C_3F_7$, $CF_3$], [AA509; 2, N, Et, H, $CH_2CF_3$, $CF_3$], [AA510; 2, N, Et, H, $CH_2CHF_2$, $CF_3$], [AA511; 0, CH, iPr, H, F, $CF_3$], [AA512; 0, CH, iPr, H, Cl, $CF_3$], [AA513; 0, CH, iPr, H, Br, $CF_3$], [AA514; 0, CH, iPr, H, I, $CF_3$], [AA515; 0, CH, iPr, H, $CF_3$, $CF_3$], [AA516; 0, CH, iPr, H, $CF_2H$, $CF_3$], [AA517; 0, CH, iPr, H, $C_2F_5$, $CF_3$], [AA518; 0, CH, iPr, H, $C_3F_7$, $CF_3$], [AA519; 0, CH, iPr, H, $CH_2CF_3$, $CF_3$], [AA520; 0, CH, iPr, H, $CH_2CHF_2$, $CF_3$], [AA521; 1, CH, iPr, H, F, $CF_3$], [AA522; 1, CH, iPr, H, Cl, $CF_3$], [AA523; 1, CH, iPr, H, Br, $CF_3$], [AA524; 1, CH, iPr, H, I, $CF_3$], [AA525; 1, CH, iPr, H, $CF_3$, CFs], [AA526; 1, CH, iPr, H, $CF_2H$, $CF_3$], [AA527; 1, CH, iPr, H, $C_2F_5$, $CF_3$], [AA528; 1, CH, iPr, H, $C_3F_7$, $CF_3$], [AA529; 1, CH, iPr, H, $CH_2CF_3$, $CF_3$], [AA530; 1, CH, iPr, H, $CH_2CHF_2$, $CF_3$], [AA531; 2, CH, iPr, H, F, $CF_3$], [AA532; 2, CH, iPr, H, Cl, $CF_3$], [AA533; 2, CH, iPr, H, Br, $CF_3$], [AA534; 2, CH, iPr, H, I, $CF_3$], [AA535; 2, CH, iPr, H, $CF_3$, $CF_3$], [AA536; 2, CH, iPr, H, $CF_2H$, $CF_3$], [AA537; 2, CH, iPr, H, $C_2F_5$, $CF_3$], [AA538; 2, CH, iPr, H, $C_3F_7$, $CF_3$], [AA539; 2, CH, iPr, H, $CH_2CF_3$, $CF_3$], [AA540; 2, CH, iPr, H, $CH_2CHF_2$, $CF_3$], [AA541; 0, N, iPr, H, F, $CF_3$], [AA542; 0, N, iPr, H, Cl, $CF_3$], [AA543; 0, N, iPr, H, Br, $CF_3$], [AA544; 0, N, iPr, H, I, $CF_3$], [AA545; 0, N, iPr, H, $CF_3$, $CF_3$], [AA546; 0, N, iPr, H, $CF_2H$, $CF_3$], [AA547; 0, N, iPr, H, $C_2F_5$, $CF_3$], [AA548; 0, N, iPr, H, $C_3F_7$, $CF_3$], [AA549; 0, N, iPr, H, $CH_2CF_3$, $CF_3$], [AA550; 0, N, iPr, H, $CH_2CHF_2$, $CF_3$], [AA551; 1, N, iPr, H, F, $CF_3$], [AA552; 1, N, iPr, H, Cl, $CF_3$], [AA553; 1, N, iPr, H, Br, $CF_3$], [AA554; 1, N, iPr, H, I, $CF_3$], [AA555; 1, N, iPr, H, $CF_3$, $CF_3$], [AA556; 1, N, iPr, H, $CF_2H$, $CF_3$], [AA557; 1, N, iPr, H, $C_2F_5$, $CF_3$], [AA558; 1, N, iPr, H, $C_3F_7$, $CF_3$], [AA559; 1, N, iPr, H, $CH_2CF_3$, $CF_3$], [AA560; 1, N, iPr, H, $CH_2CHF_2$, $CF_3$], [AA561; 2, N, iPr, H, F, $CF_3$], [AA562; 2, N, iPr, H, Cl, $CF_3$], [AA563; 2, N, iPr, H, Br, $CF_3$], [AA564; 2, N, iPr, H, I, $CF_3$], [AA565; 2, N, iPr, H, $CF_3$, $CF_3$], [AA566; 2, N, iPr, H, $CF_2H$, $CF_3$], [AA567; 2, N, iPr, H, $C_2F_5$, $CF_3$], [AA568; 2, N, iPr, H, $C_3F_7$, $CF_3$], [AA569; 2, N, iPr, H, $CH_2CF_3$, $CF_3$], [AA570; 2, N, iPr, H, $CH_2CHF_2$, $CF_3$], [AA571; 0, CH, cPr, H, F, $CF_3$], [AA572; 0, CH, cPr, H, Cl, $CF_3$], [AA573; 0, CH, cPr, H, Br, $CF_3$], [AA574; 0, CH, cPr, H, I, $CF_3$], [AA575; 0, CH, cPr, H, $CF_3$, CFs], [AA576; 0, CH, cPr, H, $CF_2H$, $CF_3$], [AA577; 0, CH, cPr, H, $C_2F_5$, $CF_3$], [AA578; 0, CH, cPr, H, $C_3F_7$, $CF_3$], [AA579; 0, CH, cPr, H, $CH_2CF_3$, $CF_3$], [AA580; 0, CH, cPr, H, $CH_2CHF_2$, $CF_3$], [AA581; 1, CH, cPr, H, F, $CF_3$], [AA582; 1, CH, cPr, H, Cl, $CF_3$], [AA583; 1, CH, cPr, H, Br, $CF_3$], [AA584; 1, CH, cPr, H, I, $CF_3$], [AA585; 1, CH, cPr, H, $CF_3$, $CF_3$], [AA586; 1, CH, cPr, H, $CF_2H$, $CF_3$], [AA587; 1, CH, cPr, H, $C_2F_5$, $CF_3$], [AA588; 1, CH, cPr, H, $C_3F_7$, $CF_3$], [AA589; 1, CH, cPr, H, $CH_2CF_3$, $CF_3$], [AA590; 1, CH, cPr, H, $CH_2CHF_2$, $CF_3$], [AA591; 2, CH, cPr, H, F, $CF_3$], [AA592; 2, CH, cPr, H, Cl, $CF_3$], [AA593; 2, CH, cPr, H, Br, $CF_3$], [AA594; 2, CH, cPr, H, I, $CF_3$], [AA595; 2, CH, cPr, H, $CF_3$, $CF_3$], [AA596; 2, CH, cPr, H, $CF_2H$, $CF_3$], [AA597; 2, CH, cPr, H, $C_2F_5$, $CF_3$], [AA598; 2, CH, cPr, H, $C_3F_7$, $CF_3$], [AA599; 2, CH, cPr, H, $CH_2CF_3$, $CF_3$], [AA600; 2, CH, cPr, H, $CH_2CHF_2$, $CF_3$], [AA601; 0, N, cPr, H, F, $CF_3$], [AA602; 0, N, cPr, H, Cl, $CF_3$], [AA603; 0, N, cPr, H, Br, $CF_3$], [AA604; 0, N, cPr, H, I, $CF_3$], [AA605; 0, N, cPr, H, $CF_3$, $CF_3$], [AA606; 0, N, cPr, H, $CF_2H$, $CF_3$], [AA607; 0, N, cPr, H, $C_{21}F$, $CF_3$], [AA608; 0, N, cPr, H, $C_3F_7$, $CF_3$], [AA609; 0, N, cPr, H, $CH_2CF_3$, $CF_3$], [AA610; 0, N, cPr, H, $CH_2CHF_2$, $CF_3$], [AA611; 1, N, cPr, H, F, $CF_3$], [AA612; 1, N, cPr, H, Cl, $CF_3$], [AA613; 1, N, cPr, H, Br, $CF_3$], [AA614; 1, N, cPr, H, I, $CF_3$], [AA615; 1, N, cPr, H, $CF_3$, $CF_3$], [AA616; 1, N, cPr, H, $CF_2H$, $CF_3$], [AA617; 1, N, cPr, H, $C_2F_5$, $CF_3$], [AA618; 1, N, cPr, H, $C_3F_7$, $CF_3$], [AA619; 1, N, cPr, H, $CH_2CF_3$, $CF_3$], [AA620; 1, N, cPr, H, $CH_2CHF_2$, $CF_3$][AA621; 2, N, cPr, H, F, $CF_3$], [AA622; 2, N, cPr, H, Cl, $CF_3$], [AA623; 2, N, cPr, H, Br, $CF_3$], [AA624; 2, N, cPr, H, I, $CF_3$], [AA625; 2, N, cPr, H, $CF_3$, $CF_3$], [AA626; 2, N, cPr, H, $CF_2H$, $CF_3$], [AA627; 2, N, cPr, H, $C_2F_5$, $CF_3$], [AA628; 2, N, cPr, H, $C_3F_7$, $CF_3$], [AA629; 2, N, cPr, H, $CH_2CF_3$, $CF_3$], [AA630; 2, N, cPr, H, $CH_2CHF_2$, $CF_3$], [AA631; 0, CH, H, H, H, $CHF_2$], [AA632; 0, CH, H, F, H, $CHF_2$], [AA633; 0, CH, H, Cl, H, $CHF_2$], [AA634; 0, CH, H, Br, H, $CHF_2$], [AA635; 0, CH, H, I, H, $CHF_2$], [AA636; 0, CH, H, $CF_3$, H, $CHF_2$], [AA637; 0, CH, H, $CF_2H$, H, $CHF_2$], [AA638; 0, CH, H, $C_2F_5$, H, $CHF_2$], [AA639; 0, CH, H, $C_3F_7$, H, $CHF_2$], [AA640; 0, CH, H, $CH_2CF_3$, H, $CHF_2$], [AA641; 0, CH, H, $CH_2CHF_2$, H, $CHF_2$], [AA642; 1, CH, H, H, H, $CHF_2$], [AA643; 1, CH, H, F, H, $CHF_2$], [AA644; 1, CH, H, Cl, H, $CHF_2$], [AA645; 1, CH, H, Br, H, $CHF_2$], [AA646; 1, CH, H, I, H, $CHF_2$], [AA647; 1, CH, H, $CF_3$, H, $CHF_2$], [AA648; 1, CH, H, $CF_2H$, H, $CHF_2$], [AA649; 1, CH, H, $C_2F_5$, H, $CHF_2$], [AA650; 1, CH, H, $C_3F_7$, H, $CHF_2$], [AA651; 1, CH, H, $CH_2CF_3$, H, $CHF_2$], [AA652; 1, CH, H, $CH_2CHF_2$, H, $CHF_2$], [AA653; 2, CH, H, H, H, $CHF_2$], [AA654; 2, CH, H, F, H, $CHF_2$], [AA655; 2, CH, H, Cl, H, $CHF_2$], [AA656; 2, CH, H, Br, H, $CHF_2$], [AA657; 2, CH, H, I, H, $CHF_2$], [AA658; 2, CH, H, $CF_3$, H, $CHF_2$], [AA659; 2, CH, H, $CF_2H$, H, $CHF_2$], [AA660; 2, CH, H, $C_2F_5$, H, $CHF_2$], [AA661; 2, CH, H, $C_3F_7$, H, $CHF_2$], [AA662; 2, CH, H, $CH_2CF_3$, H, $CHF_2$], [AA663; 2, CH, H, $CH_2CHF_2$, H, $CHF_2$], [AA664; 0, N, H, H, H, $CHF_2$], [AA665; 0, N, H, F, H, $CHF_2$], [AA666; 0, N, H, Cl, H, $CHF_2$], [AA667; 0, N, H, Br, H, $CHF_2$], [AA668; 0, N, H, I, H, $CHF_2$], [AA669; 0, N, H, $CF_3$, H, $CHF_2$], [AA670; 0, N, H, $CF_2H$, H, $CHF_2$], [AA671; 0, N, H, $C_2F_5$, H, $CHF_2$], [AA672; 0, N, H, $C_3F_7$, H, $CHF_2$], [AA673; 0, N, H, $CH_2CF_3$, H, $CHF_2$], [AA674; 0, N, H, $CH_2CHF_2$, H, $CHF_2$], [AA675; 1, N, H, H, H, $CHF_2$], [AA676; 1, N, H, F, H, $CHF_2$], [AA677; 1, N, H, Cl, H, $CHF_2$], [AA678; 1, N, H, Br, H, $CHF_2$], [AA679; 1, N, H, I, H, $CHF_2$], [AA680; 1, N, H, $CF_3$, H, $CHF_2$], [AA681; 1, N, H, $CF_2H$, H, $CHF_2$], [AA682; 1, N, H, $C_2F_5$, H, $CHF_2$], [AA683; 1, N, H, $C_3F_7$, H, $CHF_2$], [AA684; 1, N, H, $CH_2CF_3$, H, $CHF_2$], [AA685; 1, N, H, $CH_2CHF_2$, H, $CHF_2$], [AA686; 2, N, H, H, H, $CHF_2$], [AA687; 2, N, H, F, H, $CHF_2$], [AA688; 2, N, H, Cl, H, $CHF_2$], [AA689; 2, N, H, Br, H, $CHF_2$], [AA690; 2, N, H, I, H, $CHF_2$], [AA691; 2, N, H, $CF_3$, H, $CHF_2$], [AA692; 2, N, H, $CF_2H$, H, $CHF_2$], [AA693; 2, N, H, $C_2F_5$, H, $CHF_2$], [AA694; 2, N, H, $C_3F_7$, H, $CHF_2$], [AA695; 2, N, H, $CH_2CF_3$, H, $CHF_2$], [AA696; 2, N, H, $CH_2CHF_2$, H, $CHF_2$], [AA697; 0, CH, Me, H, H, $CHF_2$], [AA698; 0, CH, Me, F, H, $CHF_2$], [AA699; 0, CH, Me, Cl, H, $CHF_2$], [AA700; 0, CH, Me, Br, H, $CHF_2$], [AA701; 0, CH, Me, I, H, $CHF_2$], [AA702; 0, CH, Me, $CF_3$, H, $CHF_2$], [AA703; 0, CH, Me, $CF_2H$, H, $CHF_2$], [AA704; 0, CH, Me, $C_2F_5$, H, $CHF_2$], [AA705; 0, CH, Me, $C_3F_7$, H, $CHF_2$], [AA706; 0, CH, Me, $CH_2CF_3$, H, $CHF_2$], [AA707; 0, CH, Me, $CH_2CHF_2$, H, $CHF_2$], [AA708; 1, CH, Me, H, H, $CHF_2$], [AA709; 1, CH, Me, F, H, $CHF_2$], [AA710; 1, CH, Me, Cl, H, $CHF_2$], [AA711; 1, CH, Me, Br, H, $CHF_2$], [AA712; 1, CH, Me, I, H, $CHF_2$], [AA713; 1, CH, Me, $CF_3$, H, $CHF_2$], [AA714; 1, CH, Me, $CF_2H$, H, $CHF_2$], [AA715; 1, CH, Me, $C_2F_5$, H, $CHF_2$], [AA716; 1, CH, Me, $C_3F_7$, H, $CHF_2$], [AA717; 1, CH, Me, $CH_2CF_3$, H, $CHF_2$], [AA718; 1, CH, Me, $CH_2CHF_2$, H, $CHF_2$], [AA719; 2, CH, Me, H, H, $CHF_2$], [AA720; 2, CH, Me, F, H, $CHF_2$], [AA721; 2, CH, Me, Cl, H, $CHF_2$], [AA722; 2, CH, Me, Br, H, $CHF_2$], [AA723; 2, CH, Me, I, H, $CHF_2$], [AA724; 2, CH, Me, $CF_3$, H, $CHF_2$], [AA725; 2, CH, Me, $CF_2H$, H, $CHF_2$], [AA726; 2, CH, Me, $C_2F_5$, H, $CHF_2$], [AA727; 2, CH, Me, $C_3F_7$, H, $CHF_2$], [AA728; 2, CH, Me, $CH_2CF_3$, H, $CHF_2$], [AA729; 2, CH, Me, $CH_2CHF_2$, H, $CHF_2$], [AA730; 0, N, Me, H, H, $CHF_2$], [AA731; 0, N, Me, F, H, $CHF_2$], [AA732; 0, N, Me, Cl, H, $CHF_2$], [AA733; 0, N, Me, Br, H, $CHF_2$], [AA734; 0, N, Me, I, H, $CHF_2$], [AA735; 0, N, Me, $CF_3$, H, $CHF_2$], [AA736; 0, N, Me, $CF_2H$, H, $CHF_2$], [AA737; 0, N, Me, $C_2F_5$, H, $CHF_2$], [AA738; 0, N, Me, $C_3F_7$, H, $CHF_2$], [AA739; 0, N, Me, $CH_2CF_3$, H, $CHF_2$], [AA740; 0, N, Me, $CH_2CHF_2$, H, $CHF_2$], [AA741; 1, N, Me, H, H, $CHF_2$], [AA742; 1, N, Me, F, H, $CHF_2$], [AA743; 1, N, Me, Cl, H, $CHF_2$], [AA744; 1, N, Me, Br, H, $CHF_2$], [AA745; 1, N, Me, I, H, $CHF_2$], [AA746; 1, N, Me, $CF_3$, H, $CHF_2$], [AA747; 1, N, Me, $CF_2H$, H, $CHF_2$], [AA748; 1, N, Me, $C_2F_5$, H, $CHF_2$], [AA749; 1, N, Me, $C_3F_7$, H, $CHF_2$], [AA750; 1, N, Me, $CH_2CF_3$, H, $CHF_2$], [AA751; 1, N, Me, $CH_2CHF_2$, H, $CHF_2$], [AA752; 2, N, Me, H, H, $CHF_2$], [AA753; 2, N, Me, F, H, $CHF_2$], [AA754; 2, N, Me, Cl, H, $CHF_2$], [AA755; 2, N, Me, Br, H, $CHF_2$], [AA756; 2, N, Me, I, H, $CHF_2$], [AA757; 2, N, Me, $CF_3$, H, $CHF_2$], [AA758; 2, N, Me, $CF_2H$, H, $CHF_2$], [AA759; 2, N, Me, $C_2F_5$, H, $CHF_2$], [AA760; 2, N, Me, $C_3F_7$, H, $CHF_2$], [AA761; 2, N, Me, $CH_2CF_3$, H, $CHF_2$], [AA762; 2, N, Me, $CH_2CHF_2$, H, $CHF_2$], [AA763; 0, CH, Et, H, H, $CHF_2$], [AA764; 0, CH, Et, F, H, $CHF_2$], [AA765; 0, CH, Et, Cl, H, $CHF_2$], [AA766; 0, CH, Et, Br, H, $CHF_2$], [AA767; 0, CH, Et, I, H, $CHF_2$], [AA768; 0, CH, Et, $CF_3$, H, $CHF_2$], [AA769; 0, CH, Et, $CF_2H$, H, $CHF_2$], [AA770; 0, CH, Et, $C_2F_5$, H, $CHF_2$], [AA771; 0, CH, Et, $C_3F_5$, H, $CHF_2$], [AA772; 0, CH, Et, $CH_2CF_3$, H, $CHF_2$], [AA773; 0, CH, Et, $CH_2CHF_2$, H, $CHF_2$], [AA774; 1, CH, Et, H, H, $CHF_2$], [AA775; 1, CH, Et, F, H, $CHF_2$], [AA776; 1, CH, Et, Cl, H, $CHF_2$], [AA777; 1, CH, Et, Br, H, $CHF_2$], [AA778; 1, CH, Et, I, H, $CHF_2$], [AA779; 1, CH, Et, $CF_3$, H, $CHF_2$], [AA780; 1, CH, Et, $CF_2H$, H, $CHF_2$], [AA781; 1, CH, Et, $C_2F_5$, H, $CHF_2$], [AA782; 1, CH, Et, $C_3F_7$, H, $CHF_2$], [AA783; 1, CH, Et, $CH_2CF_3$, H, $CHF_2$], [AA784; 1, CH, Et, $CH_2CHF_2$, H, $CHF_2$], [AA785; 2, CH, Et, H, H, $CHF_2$], [AA786; 2, CH, Et, F, H, $CHF_2$], [AA787; 2, CH, Et, Cl, H, $CHF_2$], [AA788; 2, CH, Et, Br, H, $CHF_2$], [AA789; 2, CH, Et, I, H, $CHF_2$], [AA790; 2, CH, Et, $CF_3$, H, $CHF_2$], [AA791; 2, CH, Et, $CF_2H$, H, $CHF_2$], [AA792; 2, CH, Et, $C_2F_5$, H, $CHF_2$], [AA793; 2, CH, Et, $C_3F_7$, H, $CHF_2$], [AA794; 2, CH, Et, $CH_2CF_3$, H, $CHF_2$], [AA795; 2, CH, Et, $CH_2CHF_2$, H, $CHF_2$], [AA796; 0, N, Et, H, H, $CHF_2$], [AA797; 0, N, Et, F, H, $CHF_2$], [AA798; 0, N, Et, Cl, H, $CHF_2$], [AA799; 0, N, Et, Br, H, $CHF_2$], [AA800; 0, N, Et, I, H, $CHF_2$], [AA801; 0, N, Et, $CF_3$, H, $CHF_2$], [AA802; 0, N, Et, $CF_2H$, H, $CHF_2$], [AA803; 0, N, Et, $C_2F_5$, H, $CHF_2$], [AA804; 0, N, Et, $C_3F_2$, H, $CHF_2$], [AA805; 0, N, Et, $CH_2CF_3$, H, $CHF_2$], [AA806; 0, N, Et, $CH_2CHF_2$, H, $CHF_2$], [AA807; 1, N, Et, H, H, $CHF_2$], [AA808; 1, N, Et, F, H, $CHF_2$], [AA809; 1, N, Et, Cl, H, $CHF_2$], [AA810; 1, N, Et, Br, H, $CHF_2$], [AA811; 1, N, Et, I, H, $CHF_2$], [AA812; 1, N, Et, $CF_3$, H, $CHF_2$], [AA813; 1, N, Et, $CF_2H$, H, $CHF_2$], [AA814; 1, N, Et, $C_2F_5$, H, $CHF_2$], [AA815; 1, N, Et, $C_3F_7$, H, $CHF_2$], [AA816; 1, N, Et, $CH_2CF_3$, H, $CHF_2$], [AA817; 1, N, Et, $CH_2CHF_2$, H, $CHF_2$], [AA818; 2, N, Et, H, H, $CHF_2$], [AA819; 2, N, Et, F, H, $CHF_2$], [AA820; 2, N, Et, Cl, H, $CHF_2$], [AA821; 2, N, Et, Br, H, $CHF_2$], [AA822; 2, N, Et, I, H, $CHF_2$], [AA823; 2, N, Et, $CF_3$, H, $CHF_2$], [AA824; 2, N, Et, $CF_2H$, H, $CHF_2$], [AA825; 2, N, Et, $C_2F_5$, H, $CHF_2$], [AA826; 2, N, Et, $C_3F_7$, H, $CHF_2$], [AA827; 2, N, Et, $CH_2CF_3$, H, $CHF_2$], [AA828; 2, N, Et, $CH_2CHF_2$, H, $CHF_2$], [AA829; 0, CH, iPr, H, H, $CHF_2$], [AA830; 0, CH, iPr, F, H, $CHF_2$], [AA831; 0, CH, iPr, Cl, H, $CHF_2$], [AA832; 0, CH, iPr, Br, H, $CHF_2$], [AA833; 0, CH, iPr, I, H, $CHF_2$], [AA834; 0, CH, iPr, $CF_3$, H, $CHF_2$], [AA835; 0, CH, iPr, $CF_2H$, H, $CHF_2$], [AA836; 0, CH, iPr, $C_2F_5$, H, $CHF_2$], [AA837; 0, CH, iPr, $C_3F$-7, H, $CHF_2$], [AA838; 0, CH, iPr, $CH_2CF_3$, H, $CHF_2$], [AA839; 0, CH, iPr, $CH_2CHF_2$, H, $CHF_2$], [AA840; 1, CH, iPr, H, H, $CHF_2$], [AA841; 1, CH, iPr, F, H, $CHF_2$], [AA842; 1, CH, iPr, Cl, H, $CHF_2$], [AA843; 1, CH, iPr, Br, H, $CHF_2$], [AA844; 1, CH, iPr, I, H, $CHF_2$], [AA845; 1, CH, iPr, $CF_3$, H, $CHF_2$], [AA846; 1, CH, iPr, $CF_2H$, H, $CHF_2$], [AA847; 1, CH, iPr, $C_2F_5$, H, $CHF_2$], [AA848; 1, CH, iPr, $C_3F$-7, H, $CHF_2$], [AA849; 1, CH, iPr, $CH_2CF_3$, H, $CHF_2$], [AA850; 1, CH, iPr, $CH_2CHF_2$, H, $CHF_2$], [AA851; 2, CH, iPr, H, H, $CHF_2$], [AA852; 2, CH, iPr, F, H, $CHF_2$], [AA853; 2, CH, iPr, Cl, H, $CHF_2$], [AA854; 2, CH, iPr, Br, H, $CHF_2$], [AA855; 2, CH, iPr, I, H, $CHF_2$], [AA856; 2, CH, iPr, $CF_3$, H, $CHF_2$], [AA857; 2, CH, iPr, $CF_2H$, H, $CHF_2$], [AA858; 2, CH, iPr, $C_2F_5$, H, $CHF_2$], [AA859; 2, CH, iPr, $C_3F_7$, H, $CHF_2$], [AA860; 2, CH, iPr, $CH_2CF_3$, H, $CHF_2$], [AA861; 2, CH, iPr, $CH_2CHF_2$, H, $CHF_2$], [AA862; 0, N, iPr, H, H, $CHF_2$], [AA863; 0, N, iPr, F, H, $CHF_2$], [AA864; 0, N, iPr, Cl, H, $CHF_2$], [AA865; 0, N, iPr, Br, H, $CHF_2$], [AA866; 0, N, iPr, I, H, $CHF_2$], [AA867; 0, N, iPr, $CF_3$, H, $CHF_2$], [AA868; 0, N, iPr, $CF_2H$, H, $CHF_2$], [AA869; 0, N, iPr, $C_2F_5$, H, $CHF_2$], [AA870; 0, N, iPr, $C_3F_7$, H, $CHF_2$], [AA871; 0, N, iPr, $CH_2CF_3$, H, $CHF_2$], [AA872; 0, N, iPr, $CH_2CHF_2$, H, $CHF_2$], [AA873; 1, N, iPr, H, H, $CHF_2$], [AA874; 1, N, iPr, F, H, $CHF_2$], [AA875; 1, N, iPr, Cl, H, $CHF_2$], [AA876; 1, N, iPr, Br, H, $CHF_2$], [AA877; 1, N, iPr, I, H, $CHF_2$], [AA878; 1, N, iPr, $CF_3$, H, $CHF_2$], [AA879; 1, N, iPr, $CF_2H$, H, $CHF_2$], [AA880; 1, N, iPr, $C_2F_5$, H, $CHF_2$], [AA881; 1, N, iPr, $C_3F_7$, H, $CHF_2$], [AA882; 1, N, iPr, $CH_2CF_3$, H, $CHF_2$], [AA883; 1, N, iPr, $CH_2CHF_2$, H, $CHF_2$], [AA884; 2, N, iPr, H, H, $CHF_2$], [AA885; 2, N, iPr, F, H, $CHF_2$], [AA886; 2, N, iPr, Cl, H, $CHF_2$], [AA887; 2, N, iPr, Br, H, $CHF_2$], [AA888; 2, N, iPr, I, H, $CHF_2$], [AA889; 2, N, iPr, $CF_3$, H, $CHF_2$], [AA890; 2, N, iPr, $CF_2H$, H, $CHF_2$], [AA891; 2, N, iPr, $C_2F_5$, H, $CHF_2$], [AA892; 2, N, iPr, $C_3F_7$, H, $CHF_2$], [AA893; 2, N, iPr, $CH_2CF_3$, H, $CHF_2$], [AA894; 2, N, iPr, $CH_2CHF_2$, H, $CHF_2$], [AA895; 0, CH, cPr, H, H, $CHF_2$], [AA896; 0, CH, cPr, F, H, $CHF_2$], [AA897; 0, CH, cPr, Cl, H, $CHF_2$], [AA898; 0, CH, cPr, Br, H, $CHF_2$], [AA899; 0, CH, cPr, I, H, $CHF_2$], [AA900; 0, CH, cPr, $CF_3$, H, $CHF_2$], [AA901; 0, CH, cPr, $CF_2H$, H, $CHF_2$], [AA902; 0, CH, cPr, $C_2F$, H, $CHF_2$], [AA903; 0, CH, cPr, $C_3F_7$, H, $CHF_2$], [AA904; 0, CH, cPr, $CH_2CF_3$, H, $CHF_2$], [AA905; 0, CH, cPr, $CH_2CHF_2$, H, $CHF_2$], [AA906; 1, CH, cPr, H, H, $CHF_2$], [AA907; 1, CH, cPr, F, H, $CHF_2$], [AA908; 1, CH, cPr, Cl, H, $CHF_2$], [AA909; 1, CH, cPr, Br, H, $CHF_2$], [AA910; 1, CH, cPr, I, H, $CHF_2$], [AA911; 1, CH, cPr, $CF_3$, H, $CHF_2$], [AA912; 1, CH, cPr, $CF_2H$, H, $CHF_2$], [AA913; 1, CH, cPr, $C_2F_5$, H, $CHF_2$], [AA914; 1, CH, cPr, $C_3F_7$, H, $CHF_2$], [AA915; 1, CH, cPr, $CH_2CF_3$, H, $CHF_2$], [AA916; 1, CH, cPr, $CH_2CHF_2$, H, $CHF_2$], [AA917; 2, CH, cPr, H, H, $CHF_2$], [AA918; 2, CH, cPr, F, H, $CHF_2$], [AA919; 2, CH, cPr, Cl, H, $CHF_2$], [AA920; 2, CH, cPr, Br, H, $CHF_2$], [AA921; 2, CH, cPr, I, H, $CHF_2$], [AA922; 2, CH, cPr, $CF_3$, H, $CHF_2$], [AA923; 2, CH, cPr, $CF_2H$, H, $CHF_2$], [AA924; 2, CH, cPr, $C_2F_5$, H, $CHF_2$], [AA925; 2, CH, cPr, $C_3F_7$, H, $CHF_2$], [AA926; 2, CH, cPr, $CH_2CF_3$, H, $CHF_2$], [AA927; 2, CH, cPr, $CH_2CHF_2$, H, $CHF_2$], [AA928; 0, N, cPr, H, H, $CHF_2$], [AA929; 0, N, cPr, F, H, $CHF_2$], [AA930; 0, N, cPr, Cl, H, $CHF_2$], [AA931; 0, N, cPr, Br, H, $CHF_2$], [AA932; 0, N, cPr, I, H, $CHF_2$], [AA933; 0, N, cPr, $CF_3$, H, $CHF_2$], [AA934; 0, N, cPr, $CF_2H$, H, $CHF_2$], [AA935; 0, N, cPr, $C_2F_5$, H, $CHF_2$], [AA936; 0, N, cPr, $C_3F_7$, H, $CHF_2$], [AA937; 0, N, cPr, $CH_2CF_3$, H, $CHF_2$], [AA938; 0, N, cPr, $CH_2CHF_2$, H, $CHF_2$], [AA939; 1, N, cPr, H, H, $CHF_2$], [AA940; 1, N, cPr, F, H, $CHF_2$], [AA941; 1, N, cPr, Cl, H, $CHF_2$], [AA942; 1, N, cPr, Br, H, $CHF_2$], [AA943; 1, N, cPr, I, H, $CHF_2$], [AA944; 1, N, cPr, $CF_3$, H, $CHF_2$], [AA945; 1, N, cPr, $CF_2H$, H, $CHF_2$], [AA946; 1, N, cPr, $C_2F$, H, $CHF_2$], [AA947; 1, N, cPr, $C_3F_7$, H, $CHF_2$], [AA948; 1, N, cPr, $CH_2CF_3$, H, $CHF_2$], [AA949; 1, N, cPr, $CH_2CHF_2$, H, $CHF_2$], [AA950; 2, N, cPr, H, H, $CHF_2$], [AA951; 2, N, cPr, F, H, $CHF_2$], [AA952; 2, N, cPr, Cl, H, $CHF_2$], [AA953; 2, N, cPr, Br, H, $CHF_2$], [AA954; 2, N, cPr, I, H, $CHF_2$], [AA955; 2, N, cPr, $CF_3$, H, $CHF_2$], [AA956; 2, N, cPr, $CF_2H$, H, $CHF_2$], [AA957; 2, N, cPr, $C_2F_5$, H, $CHF_2$], [AA958; 2, N, cPr, $C_3F_7$, H, $CHF_2$], [AA959; 2, N, cPr, $CH_2CF_3$, H, $CHF_2$], [AA960; 2, N, cPr, $CH_2CHF_2$, H, $CHF_2$], [AA961; 0, CH, H, H, F, $CHF_2$], [AA962; 0, CH, H, H, Cl, $CHF_2$], [AA963; 0, CH, H, H, Br, $CHF_2$], [AA964; 0, CH, H, H, I, $CHF_2$], [AA965; 0, CH, H, H, $CF_3$, $CHF_2$], [AA966; 0, CH, H, H, $CF_2H$, $CHF_2$], [AA967; 0, CH, H, H, $C_2F_5$, $CHF_2$], [AA968; 0, CH, H, H, $C_3F_7$, $CHF_2$], [AA969; 0, CH, H, H, $CH_2CF_3$, $CHF_2$], [AA970; 0, CH, H, H, $CH_2CHF_2$, $CHF_2$], [AA971; 1, CH, H, H, F, $CHF_2$], [AA972; 1, CH, H, H, Cl, $CHF_2$], [AA973; 1, CH, H, H, Br, $CHF_2$], [AA974; 1, CH, H, H, I, $CHF_2$], [AA975; 1, CH, H, H, $CF_3$, $CHF_2$], [AA976; 1, CH, H, H, $CF_2H$, $CHF_2$], [AA977; 1, CH, H, H, $C_2F_5$, $CHF_2$], [AA978; 1, CH, H, H, $C_3F_7$, $CHF_2$], [AA979; 1, CH, H, H, $CH_2CF_3$, $CHF_2$], [AA980; 1, CH, H, H, $CH_2CHF_2$, $CHF_2$], [AA981; 2, CH, H, H, F, $CHF_2$], [AA982; 2, CH, H, H, Cl, $CHF_2$], [AA983; 2, CH, H, H, Br, $CHF_2$], [AA984; 2, CH, H, H, I, $CHF_2$], [AA985; 2, CH, H, H, $CF_3$, $CHF_2$], [AA986; 2, CH, H, H, $CF_2H$, $CHF_2$], [AA987; 2, CH, H, H, $C_2F_5$, $CHF_2$], [AA988; 2, CH, H, H, $C_3F_7$, $CHF_2$], [AA989; 2, CH, H, H, $CH_2CF_3$, $CHF_2$], [AA990; 2, CH, H, H, $CH_2CHF_2$, $CHF_2$], [AA991; 0, N, H, H, F, $CHF_2$], [AA992; 0, N, H, H, Cl, $CHF_2$], [AA993; 0, N, H, H, Br, $CHF_2$], [AA994; 0, N, H, H, I, $CHF_2$], [AA995; 0, N, H, H, $CF_3$, $CHF_2$], [AA996; 0, N, H, H, $CF_2H$, $CHF_2$], [AA997; 0, N, H, H, $C_2F_5$, $CHF_2$], [AA998; 0, N, H, H, $C_3F_7$, $CHF_2$], [AA999; 0, N, H, H, $CH_2CF_3$, $CHF_2$], [AA1000; 0, N, H, H, $CH_2CHF_2$, $CHF_2$], [AA1001; 1, N, H, H, F, $CHF_2$], [AA1002; 1, N, H, H, Cl, $CHF_2$], [AA1003; 1, N, H, H, Br, $CHF_2$], [AA1004; 1, N, H, H, I, $CHF_2$], [AA1005; 1, N, H, H, $CF_3$, $CHF_2$], [AA1006; 1, N, H, H, $CF_2H$, $CHF_2$], [AA1007; 1, N, H, H, $C_2F_5$, $CHF_2$], [AA1008; 1, N, H, H, $C_3F_7$, $CHF_2$], [AA1009; 1, N, H, H, $CH_2CF_3$, $CHF_2$], [AA1010; 1, N, H, H, $CH_2CHF_2$, $CHF_2$], [AA1011; 2, N, H, H, F, $CHF_2$], [AA1012; 2, N, H, H, Cl, $CHF_2$], [AA1013; 2, N, H, H, Br, $CHF_2$], [AA1014; 2, N, H, H, I, $CHF_2$], [AA1015; 2, N, H, H, $CF_3$, $CHF_2$], [AA1016; 2, N, H, H, $CF_2H$, $CHF_2$], [AA1017; 2, N, H, H, $C_2F_5$, $CHF_2$], [AA1018; 2, N, H, H, $C_3F_7$, $CHF_2$], [AA1019; 2, N, H, H, $CH_2CF_3$, $CHF_2$], [AA1020; 2, N, H, H, $CH_2CHF_2$, $CHF_2$], [AA1021; 0, CH, Me, H, F, $CHF_2$], [AA1022; 0, CH, Me, H, Cl, $CHF_2$], [AA1023; 0, CH, Me, H, Br, $CHF_2$], [AA1024; 0, CH, Me, H, I, $CHF_2$], [AA1025; 0, CH, Me, H, $CF_3$, $CHF_2$], [AA1026; 0, CH, Me, H, $CF_2H$, $CHF_2$], [AA1027; 0, CH, Me, H, $C_2F_5$, $CHF_2$], [AA1028; 0, CH, Me, H, $C_3F_7$, $CHF_2$], [AA1029; 0, CH, Me, H, $CH_2CF_3$, $CHF_2$], [AA1030; 0, CH, Me, H, $CH_2CHF_2$, $CHF_2$], [AA1031; 1, CH, Me, H, F, $CHF_2$], [AA1032; 1, CH, Me, H, Cl, $CHF_2$], [AA1033; 1, CH, Me, H, Br, $CHF_2$], [AA1034; 1, CH, Me, H, I, $CHF_2$], [AA1035; 1, CH, Me, H, $CF_3$, $CHF_2$], [AA1036; 1, CH, Me, H, $CF_2H$, $CHF_2$], [AA1037; 1, CH, Me, H, $C_2F_5$, $CHF_2$], [AA1038; 1, CH, Me, H, $C_3F_7$, $CHF_2$], [AA1039; 1, CH, Me, H, $CH_2CF_3$, $CHF_2$], [AA1040; 1, CH, Me, H, $CH_2CHF_2$, $CHF_2$], [AA1041; 2, CH, Me, H, F, $CHF_2$], [AA1042; 2, CH, Me, H, Cl, $CHF_2$], [AA1043; 2, CH, Me, H, Br, $CHF_2$], [AA1044; 2, CH, Me, H, I, $CHF_2$], [AA1045; 2, CH, Me, H, $CF_3$, $CHF_2$], [AA1046; 2, CH, Me, H, $CF_2H$, $CHF_2$], [AA1047; 2, CH, Me, H, $C_2F_5$, $CHF_2$], [AA1048; 2, CH, Me, H, $C_3F_7$, $CHF_2$], [AA1049; 2, CH, Me, H, $CH_2CF_3$, $CHF_2$], [AA1050; 2, CH, Me, H, $CH_2CHF_2$, $CHF_2$], [AA1051; 0, N, Me, H, F, $CHF_2$], [AA1052; 0, N, Me, H, Cl, $CHF_2$], [AA1053; 0, N, Me, H, Br, $CHF_2$], [AA1054; 0, N, Me, H, I, $CHF_2$], [AA1055; 0, N, Me, H, $CF_3$, $CHF_2$], [AA1056; 0, N, Me, H, $CF_2H$, $CHF_2$], [AA1057; 0, N, Me, H, $C_2F_5$, $CHF_2$], [AA1058; 0, N, Me, H, $C_3F_7$, $CHF_2$], [AA1059; 0, N, Me, H, $CH_2CF_3$, $CHF_2$], [AA1060; 0, N, Me, H, $CH_2CHF_2$, $CHF_2$], [AA1061; 1, N, Me, H, F, $CHF_2$], [AA1062; 1, N, Me, H, Cl, $CHF_2$], [AA1063; 1, N, Me, H, Br, $CHF_2$], [AA1064; 1, N, Me, H, I, $CHF_2$], [AA1065; 1, N, Me, H, $CF_3$, $CHF_2$], [AA1066; 1, N, Me, H, $CF_2H$, $CHF_2$], [AA1067; 1, N, Me, H, $C_2F_5$, $CHF_2$], [AA1068; 1, N, Me, H, $C_3F_7$, $CHF_2$], [AA1069; 1, N, Me, H, $CH_2CF_3$, $CHF_2$], [AA1070; 1, N, Me, H, $CH_2CHF_2$, $CHF_2$], [AA1071; 2, N, Me, H, F, $CHF_2$], [AA1072; 2, N, Me, H, Cl, $CHF_2$], [AA1073; 2, N, Me, H, Br, $CHF_2$], [AA1074; 2, N, Me, H, I, $CHF_2$], [AA1075; 2, N, Me, H, $CF_3$, $CHF_2$], [AA1076; 2, N, Me, H, $CF_2H$, $CHF_2$], [AA1077; 2, N, Me, H, $C_2F_5$, $CHF_2$], [AA1078; 2, N, Me, H, $C_3F_7$, $CHF_2$], [AA1079; 2, N, Me, H, $CH_2CF_3$, $CHF_2$], [AA1080; 2, N, Me, H, $CH_2CHF_2$, $CHF_2$], [AA1081; 0, CH, Et, H, F, $CHF_2$], [AA1082; 0, CH, Et, H, Cl, $CHF_2$], [AA1083; 0, CH, Et, H, Br, $CHF_2$], [AA1084; 0, CH, Et, H, I, $CHF_2$], [AA1085; 0, CH, Et, H, $CF_3$, $CHF_2$], [AA1086; 0, CH, Et, H, $CF_2H$, $CHF_2$], [AA1087; 0, CH, Et, H, $C_2F_5$, $CHF_2$], [AA1088; 0, CH, Et, H, $C_3F_7$, $CHF_2$], [AA1089; 0, CH, Et, H, $CH_2CF_3$, $CHF_2$], [AA1090; 0, CH, Et, H, $CH_2CHF_2$, $CHF_2$], [AA1091; 1, CH, Et, H, F, $CHF_2$], [AA1092; 1, CH, Et, H, Cl, $CHF_2$], [AA1093; 1, CH, Et, H, Br, $CHF_2$], [AA1094; 1, CH, Et, H, I, $CHF_2$], [AA1095; 1, CH, Et, H, $CF_3$, $CHF_2$], [AA1096; 1, CH, Et, H, $CF_2H$, $CHF_2$], [AA1097; 1, CH, Et, H, $C_2F_2$, $CHF_2$], [AA1098; 1, CH, Et, H, $C_3F_7$, $CHF_2$], [AA1099; 1, CH, Et, H, $CH_2CF_3$, $CHF_2$], [AA1100; 1, CH, Et, H, $CH_2CHF_2$, $CHF_2$], [AA1101; 2, CH, Et, H, F, $CHF_2$], [AA1102; 2, CH, Et, H, Cl, $CHF_2$], [AA1103; 2, CH, Et, H, Br, $CHF_2$], [AA1104; 2, CH, Et, H, I, $CHF_2$], [AA1105; 2, CH, Et, H, $CF_3$, $CHF_2$], [AA1106; 2, CH, Et, H, $CF_2H$, $CHF_2$], [AA1107; 2, CH, Et, H, $C_2F_5$, $CHF_2$], [AA1108; 2, CH, Et, H, $C_3F_7$, $CHF_2$], [AA1109; 2, CH, Et, H, $CH_2CF_3$, $CHF_2$], [AA1110; 2, CH, Et, H, $CH_2CHF_2$, $CHF_2$], [AA1111; 0, N, Et, H, F, $CHF_2$], [AA1112; 0, N, Et, H, Cl, $CHF_2$], [AA1113; 0, N, Et, H, Br, $CHF_2$], [AA1114; 0, N, Et, H, I, $CHF_2$], [AA1115; 0, N, Et, H, $CF_3$, $CHF_2$], [AA1116; 0, N, Et, H, $CF_2H$, $CHF_2$], [AA1117; 0, N, Et, H, $C_2F_5$, $CHF_2$], [AA1118; 0, N, Et, H, $C_3F_7$, $CHF_2$], [AA1119; 0, N, Et, H, $CH_2CF_3$, $CHF_2$], [AA1120; 0, N, Et, H, $CH_2CHF_2$, $CHF_2$], [AA1121; 1, N, Et, H, F, $CHF_2$], [AA1122; 1, N, Et, H, Cl, $CHF_2$], [AA1123; 1, N, Et, H, Br, $CHF_2$], [AA1124; 1, N, Et, H, Cl, $CHF_2$], [AA1125; 1, N, Et, H, $CF_3$, $CHF_2$], [AA1126; 1, N, Et, H, $CF_7H$, $CHF_2$], [AA1127; 1, N, Et, H, $CH_2F_5$, $CHF_2$], [AA1128; 1, N, Et, H, $C_3F_7$, $CHF_2$], [AA1129; 1, N, Et, H, $CH_2CF_3$, $CHF_2$], [AA1130; 1, N, Et, H, $CH_2CHF_2$, $CHF_2$], [AA1131; 2, N, Et, H, F, $CHF_2$], [AA1132; 2, N, Et, H, Cl, $CHF_2$], [AA1133; 2, N, Et, H, Br, $CHF_2$], [AA1134; 2, N, Et, H, I, $CHF_2$], [AA1135; 2, N, Et, H, $CF_3$, $CHF_2$], [AA1136; 2, N, Et, H, $CF_2H$, $CHF_2$], [AA1137; 2, N, Et, H, $C_2F_5$, $CHF_2$], [AA1138; 2, N, Et, H, $C_3F_7$, $CHF_2$], [AA1139; 2, N, Et, H, $CH_2CF_3$, $CHF_2$], [AA1140; 2, N, Et, H, $CH_2CHF_2$, $CHF_2$], [AA1141; 0, CH, iPr, H, F, $CHF_2$], [AA1142; 0, CH, iPr, H, Cl, $CHF_2$], [AA1143; 0, CH, iPr, H, Br, $CHF_2$], [AA1144; 0, CH, iPr, H, I, $CHF_2$], [AA1145; 0, CH, iPr, H, $CF_3$, $CHF_2$], [AA1146; 0, CH, iPr, H, $CF_2H$, $CHF_2$], [AA1147; 0, CH, iPr, H, $C_2F_5$, $CHF_2$], [AA1148; 0, CH, iPr, H, $C_3F_7$, $CHF_2$], [AA1149; 0, CH, iPr, H, $CH_2CF_3$, $CHF_2$], [AA1150; 0, CH, iPr, H, $CH_2CHF_2$, $CHF_2$], [AA1151; 1, CH, iPr, H, F, $CHF_2$], [AA1152; 1, CH, iPr, H, Cl, $CHF_2$], [AA1153; 1, CH, iPr, H, Br, $CHF_2$], [AA1154; 1, CH, iPr, H, I, $CHF_2$], [AA1155; 1, CH, iPr, H, $CF_3$, $CHF_2$], [AA1156; 1, CH, iPr, H, $CF_2H$, $CHF_2$], [AA1157; 1, CH, iPr, H, $C_2F_5$, $CHF_2$], [AA1158; 1, CH, iPr, H, $C_3F_7$, $CHF_2$], [AA1159; 1, CH, iPr, H, $CH_2CF_3$, $CHF_2$], [AA1160; 1, CH, iPr, H, $CH_2CHF_2$, $CHF_2$], [AA1161; 2, CH, iPr, H, F, $CHF_2$], [AA1162; 2, CH, iPr, H, Cl, $CHF_2$], [AA1163; 2, CH, iPr, H, Br, $CHF_2$], [AA1164; 2, CH, iPr, H, I, $CHF_2$], [AA1165; 2, CH, iPr, H, $CF_3$, $CHF_2$], [AA1166; 2, CH, iPr, H, $CF_2H$, $CHF_2$], [AA1167; 2, CH, iPr, H, $C_2F$, $CHF_2$], [AA1168; 2, CH, iPr, H, $C_3F_7$, $CHF_2$], [AA1169; 2, CH, iPr, H, $CH_2CF_3$, $CHF_2$], [AA1170; 2, CH, iPr, H, $CH_2CHF_2$, $CHF_2$], [AA1171; 0, N, iPr, H, F, $CHF_2$], [AA1172; 0, N, iPr, H, Cl, $CHF_2$], [AA1173; 0, N, iPr, H, Br, $CHF_2$], [AA1174; 0, N, iPr, H, I, $CHF_2$], [AA1175; 0, N, iPr, H, $CF_3$, $CHF_2$], [AA11176; 0, N, iPr, H, $CF_2H$, $CHF_2$], [AA1177; 0, N, iPr, H, $C_2F_5$, $CHF_2$], [AA1178; 0, N, iPr, H, $C_3F_7$, $CHF_2$], [AA1179; 0, N, iPr, H, $CH_2CF_3$, $CHF_2$], [AA1180; 0, N, iPr, H, $CH_2CHF_2$, $CHF_2$], [AA1181; 1, N, iPr, H, F, $CHF_2$], [AA1182; 1, N, iPr, H, Cl, $CHF_2$], [AA1183; 1, N, iPr, H, Br, $CHF_2$], [AA1184; 1, N, iPr, H, I, $CHF_2$], [AA1185; 1, N, iPr, H, $CF_3$, $CHF_2$], [AA1186; 1, N, iPr, H, $CF_2H$, $CHF_2$], [AA1187; 1, N, iPr, H, $C_2F_5$, $CHF_2$], [AA1188; 1, N, iPr, H, $C_3F_7$, $CHF_2$], [AA1189; 1, N, iPr, H, $CH_2CF_3$, $CHF_2$], [AA1190; 1, N, iPr, H, $CH_2CHF_2$, $CHF_2$], [AA1191; 2, N, iPr, H, F, $CHF_2$], [AA1192; 2, N, iPr, H, Cl, $CHF_2$], [AA1193; 2, N, iPr, H, Br, $CHF_2$], [AA1194; 2, N, iPr, H, I, $CHF_2$], [AA1195; 2, N, iPr, H, $CF_3$, $CHF_2$], [AA1196; 2, N, iPr, H, $CF_2H$, $CHF_2$], [AA1197; 2, N, iPr, H, $C_2F_5$, $CHF_2$], [AA1198; 2, N, iPr, H, $C_3F_7$, $CHF_2$], [AA1199; 2, N, iPr, H, $CH_2CF_3$, $CHF_2$], [AA1200; 2, N, iPr, H, $CH_2CHF_2$, $CHF_2$], [AA1201; 0, CH, cPr, H, F, $CHF_2$], [AA1202; 0, CH, cPr, H, Cl, $CHF_2$], [AA1203; 0, CH, cPr, H, Br, $CHF_2$], [AA1204; 0, CH, cPr, H, I, $CHF_2$], [AA1205; 0, CH, cPr, H, $CF_3$, $CHF_2$], [AA1206; 0, CH, cPr, H, $CF_2H$, $CHF_2$], [AA1207; 0, CH, cPr, H, $C_2F_5$, $CHF_2$], [AA1208; 0, CH, cPr, H, $C_3F_7$, $CHF_2$], [AA1209; 0, CH, cPr, H, $CH_2CF_3$, $CHF_2$], [AA1210; 0, CH, cPr, H, $CH_2CHF_2$, $CHF_2$], [AA1211; 1, CH, cPr, H, F, $CHF_2$], [AA1212; 1, CH, cPr, H, Cl, $CHF_2$], [AA1213; 1, CH, cPr, H, Br, $CHF_2$], [AA1214; 1, CH, cPr, H, I, $CHF_2$], [AA1215; 1, CH, cPr, H, $CF_3$, $CHF_2$], [AA1216; 1, CH, cPr, H, $CF_2H$, $CHF_2$], [AA1217; 1, CH, cPr, H, $C_2F_5$, $CHF_2$], [AA1218; 1, CH, cPr, H, $C_3F_7$, $CHF_2$], [AA1219; 1, CH, cPr, H, $CH_2CF_3$, $CHF_2$], [AA1220; 1, CH, cPr, H, $CH_2CHF_2$, $CHF_2$], [AA1221; 2, CH, cPr, H, F, $CHF_2$], [AA1222; 2, CH, cPr, H, Cl, $CHF_2$], [AA1223; 2, CH, cPr, H, Br, $CHF_2$], [AA1224; 2, CH, cPr, H, I, $CHF_2$], [AA1225; 2, CH, cPr, H, $CF_3$, $CHF_2$], [AA1226; 2, CH, cPr, H, $CF_2H$, $CHF_2$], [AA1227; 2, CH, cPr, H, $C_2F_5$, $CHF_2$], [AA1228; 2, CH, cPr, H, $C_3F_7$, $CHF_2$], [AA1229; 2, CH, cPr, H, $CH_2CF_3$, $CHF_2$], [AA1230; 2, CH, cPr, H, $CH_2CHF_2$, $CHF_2$], [AA1231; 0, N, cPr, H, F, $CHF_2$], [AA1232; 0, N, cPr, H, Cl, $CHF_2$], [AA1233; 0, N, cPr, H, Br, $CHF_2$], [AA1234; 0, N, cPr, H, I, $CHF_2$], [AA1235; 0, N, cPr, H, $CF_3$, $CHF_2$], [AA1236; 0, N, cPr, H, $CF_2H$, $CHF_2$], [AA1237; 0, N, cPr, H, $C_2F_5$, $CHF_2$], [AA1238; 0, N, cPr, H, $C_3F_7$, $CHF_2$], [AA1239; 0, N, cPr, H, $CH_2CF_3$, $CHF_2$], [AA1240; 0, N, cPr, H, $CH_2CHF_2$, $CHF_2$], [AA1241; 1, N, cPr, H, F, $CHF_2$], [AA1242; 1, N, cPr, H, Cl, $CHF_2$], [AA1243; 1, N, cPr, H, Br, $CHF_2$], [AA1244; 1, N, cPr, H, I, $CHF_2$], [AA1245; 1, N, cPr, H, $CF_3$, $CHF_2$], [AA1246; 1, N, cPr, H, $CF_2H$, $CHF_2$], [AA1247; 1, N, cPr, H, $C_2F_5$, $CHF_2$], [AA1248; 1, N, cPr, H, $C_3F_7$, $CHF_2$], [AA1249; 1, N, cPr, H, $CH_2CF_3$, $CHF_2$], [AA1250; 1, N, cPr, H, $CH_2CHF_2$, $CHF_2$], [AA1251; 2, N, cPr, H, F, $CHF_2$], [AA1252; 2, N, cPr, H, Cl, $CHF_2$], [AA1253; 2, N, cPr, H, Br, $CHF_2$], [AA1254; 2, N, cPr, H, I, $CHF_2$], [AA1255; 2, N, cPr, H, $CF_3$, $CHF_2$], [AA1256; 2, N, cPr, H, $CF_2H$, $CHF_2$], [AA1257; 2, N, cPr, H, $C_2F_5$, $CHF_2$], [AA1258; 2, N, cPr, H, $C_3F_7$, $CHF_2$], [AA1259; 2, N, cPr, H, $CH_2CF_3$, $CHF_2$], [AA1260; 2, N, cPr, H, $CH_2CHF_2$, $CHF_2$], [AA1261; 0, CH, H, H, H, $CH_2CF_3$], [AA1262; 0, CH, H, F, H, $CH_2CF_3$], [AA1263; 0, CH, H, Cl, H, $CH_2CF_3$], [AA1264; 0, CH, H, Br, H, $CH_2CF_3$], [AA1265; 0, CH, H, I, H, $CH_2CF_3$], [AA1266; 0, CH, H, $CF_3$, H, $CH_2CF_3$], [AA1267; 0, CH, H, $CF_2H$, H, $CH_2CF_3$], [AA1268; 0, CH, H, $C_F$, H, CH $CF_3$], [AA1269; 0, CH, H, $C_3F_7$, H, $CH_2CF_3$], [AA1270; 0, CH, H, $CH_2CF_3$, H, $CH_2CF_3$], [AA1271; 0, CH, H, $CH_2CHF_2$, H, $CH_2CF_3$], [AA1272; 1, CH, H, H, H, $CH_2CF_3$], [AA1273; 1, CH, H, F, H, $CH_2CF_3$], [AA1274; 1, CH, H, Cl, H, $CH_2CF_3$], [AA1275; 1, CH, H, Br, H, $CH_2CF_3$], [AA1276; 1, CH, H, I, H, $CH_2CF_3$], [AA1277; 1, CH, H, $CF_3$, H, $CH_2CF_3$], [AA1278; 1, CH, H, $CF_2H$, H, $CH_2CF_3$], [AA1279; 1, CH, H, $C_2F$, H, $CH_2CF_3$], [AA1280; 1, CH, H, $C_3F_7$, H, $CH_2CF_3$], [AA1281; 1, CH, H, $CH_2CF_3$, H, $CH_2CF_3$], [AA1282; 1, CH, H, CH CHF, H, CH $CF_3$], [AA1283; 2, CH, H, H, H, $CH_2CF_3$], [AA1284; 2, CH, H, F, H, $CH_2CF_3$], [AA1285; 2, CH, H, Cl, H, $CH_2CF_3$], [AA1286; 2, CH, H, Br, H, $CH_2CF_3$], [AA1287; 2, CH, H, I, H, $CH_2CF_3$], [AA1288; 2, CH, H, $CF_3$, H, $CH_2CF_3$], [AA1289; 2, CH, H, $CF_2H$, H, $CH_2CF_3$], [AA1290; 2, CH, H, $C_2F_5$, H, $CH_2CF_3$], [AA1291; 2, CH, H, $C_3F_7$, H, $CH_2CF_3$], [AA1292; 2, CH, H, $CH_2CF_3$, H, $CH_2CF_3$], [AA1293; 2, CH, H, $CH_2CHF_2$, H, $CH_2CF_3$], [AA1294; 0, N, H, H, H, $CH_2CF_3$], [AA1295; 0, N, H, F, H, $CH_2CF_3$], [AA1296; 0, N, H, Cl, H, $CH_2CF_3$], [AA1297; 0, N, H, Br, H, $CH_2CF_3$], [AA1298; 0, N, H, I, H, $CH_2CF_3$], [AA1299; 0, N, H, $CF_3$, H, $CH_2CF_3$], [AA1300; 0, N, H, $CF_2H$, H, $CH_2CF_3$], [AA1301; 0, N, H, $C_2F_5$, H, $CH_2CF_3$], [AA1302; 0, N, H, $C_3F_7$, H, $CH_2CF_3$], [AA1303; 0, N, H, $CH_2CF_3$, H, $CH_2CF_3$], [AA1304; 0, N, H, $CH_2CHF_2$, H, $CH_2CF_3$], [AA1305; 1, N, H, H, H, $CH_2CF_3$], [AA1306; 1, N, H, F, H, $CH_2CF_3$], [AA1307; 1, N, H, Cl, H, $CH_2CF_3$], [AA1308; 1, N, H, Br, H, $CH_2CF_3$], [AA1309; 1, N, H, I, H, $CH_2CF_3$], [AA1310; 1, N, H, $CF_3$, H, $CH_2CF_3$], [AA1311; 1, N, H, $CF_2H$, H, $CH_2CF_3$], [AA1312; 1, N, H, $C_2F_5$, H, $CH_2CF_3$], [AA1313; 1, N, H, $C_3F_7$, H, $CH_2CF_3$], [AA1314; 1, N, H, $CH_2CF_3$, H, $CH_2CF_3$], [AA1315; 1, N, H, $CH_2CHF_2$, H, $CH_2CF_3$], [AA1316; 2, N, H, H, H, $CH_2CF_3$], [AA1317; 2, N, H, F, H, $CH_2CF_3$], [AA1318; 2, N, H, Cl, H, $CH_2CF_3$], [AA1319; 2, N, H, Br, H, $CH_2CF_3$], [AA1320; 2, N, H, I, H, $CH_2CF_3$], [AA1321; 2, N, H, $CF_3$, H, $CH_2CF_3$], [AA1322; 2, N, H, $CF_2H$, H, $CH_2CF_3$], [AA1323; 2, N, H, $C_2F_5$, H, $CH_2CF_3$], [AA1324; 2, N, H, $C_3F_7$, H, $CH_2CF_3$], [AA1325; 2, N, H, $CH_2CF_3$, H, $CH_2CF_3$], [AA1326; 2, N, H, $CH_2CHF_2$, H, $CH_2CF_3$], [AA1327; 0, CH, Me, H, H, $CH_2CF_3$], [AA1328; 0, CH, Me, F, H, $CH_2CF_3$], [AA1329; 0, CH, Me, Cl, H, $CH_2CF_3$], [AA1330; 0, CH, Me, Br, H, $CH_2CF_3$], [AA1331; 0, CH, Me, I, H, $CH_2CF_3$], [AA1332; 0, CH, Me, $CF_3$, H, $CH_2CF_3$], [AA1333; 0, CH, Me, $CF_2H$, H, $CH_2CF_3$], [AA1334; 0, CH, Me, $C_2F_5$, H, $CH_2CF_3$], [AA1335; 0, CH, Me, $C_3F$-7, H, $CH_2CF_3$], [AA1336; 0, CH, Me, $CH_2CF_3$, H, $CH_2CF_3$], [AA1337; 0, CH, Me, $CH_2CHF_2$, H, $CH_2CF_3$], [AA1338; 1, CH, Me, H, H, $CH_2CF_3$], [AA1339; 1, CH, Me, F, H, $CH_2CF_3$], [AA1340; 1, CH, Me, Cl, H, $CH_2CF_3$], [AA1341; 1, CH, Me, Br, H, $CH_2CF_3$], [AA1342; 1, CH, Me, I, H, $CH_2CF_3$], [AA1343; 1, CH, Me, $CF_3$, H, $CH_2CF_3$], [AA1344; 1, CH, Me, $CF_2H$, H, $CH_2CF_3$], [AA1345; 1, CH, Me, $C_2F_5$, H, $CH_2CF_3$], [AA1346; 1, CH, Me, $C_3F_7$, H, $CH_2CF_3$], [AA1347; 1, CH, Me, $CH_2CF_3$, H, $CH_2CF_3$], [AA1348; 1, CH, Me, $CH_2CHF_2$, H, $CH_2CF_3$], [AA1349; 2, CH, Me, H, H, $CH_2CF_3$], [AA1350; 2, CH, Me, F, H, $CH_2CF_3$], [AA1351; 2, CH, Me, Cl, H, $CH_2CF_3$], [AA1352; 2, CH, Me, Br, H, $CH_2CF_3$], [AA1353; 2, CH, Me, I, H, $CH_2CF_3$], [AA1354; 2, CH, Me, $CF_3$, H, $CH_2CF_3$], [AA1355; 2, CH, Me, $CF_2H$, H, $CH_2CF_3$], [AA1356; 2, CH, Me, $C_2F_5$, H, $CH_2CF_3$], [AA1357; 2, CH, Me, $C_3F_7$, H, $CH_2CF_3$], [AA1358; 2, CH, Me, $CH_2CF_3$, H, $CH_2CF_3$], [AA1359; 2, CH, Me, $CH_2CHF_2$, H, $CH_2CF_3$], [AA1360; 0, N, Me, H, H, $CH_2CF_3$], [AA1361; 0, N, Me, F, H, $CH_2CF_3$], [AA1362; 0, N, Me, Cl, H, $CH_2CF_3$], [AA1363; 0, N, Me, Br, H, $CH_2CF_3$], [AA1364; 0, N, Me, I, H, $CH_2CF_3$], [AA1365; 0, N, Me, $CF_3$, H, $CH_2CF_3$], [AA1366; 0, N, Me, $CF_2H$, H, $CH_2CF_3$], [AA1367; 0, N, Me, $C_2F_5$, H, $CH_2CF_3$], [AA1368; 0, N, Me, $C_3F_7$, H, $CH_2CF_3$], [AA1369; 0, N, Me, $CH_2CF_3$, H, $CH_2CF_3$], [AA1370; 0, N, Me, $CH_2CHF_2$, H, $CH_2CF_3$], [AA1371; 1, N, Me, H, H, $CH_2CF_3$], [AA1372; 1, N, Me, F, H, $CH_2CF_3$], [AA1373; 1, N, Me, Cl, H, $CH_2CF_3$], [AA1374; 1, N, Me, Br, H, $CH_2CF_3$], [AA1375; 1, N, Me, I, H, $CH_2CF_3$], [AA1376; 1, N, Me, $CF_3$, H, $CH_2CF_3$], [AA1377; 1, N, Me, $CF_2H$, H, $CH_2CF_3$], [AA1378; 1, N, Me, $C_2F_5$, H, $CH_2CF_3$], [AA1379; 1, N, Me, $C_3F_7$, H, $CH_2CF_3$], [AA1380; 1, N, Me, $CH_2CF_3$, H, $CH_2CF_3$], [AA1381; 1, N, Me, $CH_2CHF_2$, H, $CH_2CF_3$], [AA1382; 2, N, Me, H, H, $CH_2CF_3$], [AA1383; 2, N, Me, F, H, $CH_2CF_3$], [AA1384; 2, N, Me, Cl, H, $CH_2CF_3$], [AA1385; 2, N, Me, Br, H, $CH_2CF_3$], [AA1386; 2, N, Me, I, H, $CH_2CF_3$], [AA1387; 2, N, Me, $CF_3$, H, $CH_2CF_3$], [AA1388; 2, N, Me, $CF_2H$, H, $CH_2CF_3$], [AA1389; 2, N, Me, $C_2F_5$, H, $CH_2CF_3$], [AA1390; 2, N, Me, $C_3F_7$, H, $CH_2CF_3$], [AA1391; 2, N, Me, $CH_2CF_3$, H, $CH_2CF_3$], [AA1392; 2, N, Me, $CH_2CHF_2$, H, $CH_2CF_3$], [AA1393; 0, CH, Et, H, H, $CH_2CF_3$], [AA1394; 0, CH, Et, F, H, $CH_2CF_3$], [AA1395; 0, CH, Et, Cl, H, $CH_2CF_3$], [AA1396; 0, CH, Et, Br, H, $CH_2CF_3$], [AA1397; 0, CH, Et, I, H, $CH_2CF_3$], [AA1398; 0, CH, Et, $CF_3$, H, $CH_2CF_3$], [AA1399; 0, CH, Et, $CF_2H$, H, $CH_2CF_3$], [AA1400; 0, CH, Et, $C_2F_5$, H, $CH_2CF_3$], [AA1401; 0, CH, Et, $C_3F_7$, H, $CH_2CF_3$], [AA1402; 0, CH, Et, $CH_2CF_3$, H, $CH_2CF_3$], [AA1403; 0, CH, Et, $CH_2CHF_2$, H, $CH_2CF_3$], [AA1404; 1, CH, Et, H, H, $CH_2CF_3$], [AA1405; 1, CH, Et, F, H, $CH_2CF_3$], [AA1406; 1, CH, Et, Cl, H, $CH_2CF_3$], [AA1407; 1, CH, Et, Br, H, $CH_2CF_3$], [AA1408; 1, CH, Et, I, H, $CH_2CF_3$], [AA1409; 1, CH, Et, $CF_3$, H, $CH_2CF_3$], [AA1410; 1, CH, Et, $CF_2H$, H, $CH_2CF_3$], [AA1411; 1, CH, Et, $C_2F_5$, H, $CH_2CF_3$], [AA1412; 1, CH, Et, $C_3F_7$, H, $CH_2CF_3$], [AA1413; 1, CH, Et, $CH_2CF_3$, H, $CH_2CF_3$], [AA1414; 1, CH, Et, $CH_2CHF_2$, H, $CH_2CF_3$], [AA1415; 2, CH, Et, H, H, $CH_2CF_3$], [AA1416; 2, CH, Et, F, H, $CH_2CF_3$], [AA1417; 2, CH, Et, Cl, H, $CH_2CF_3$], [AA1418; 2, CH, Et, Br, H, $CH_2CF_3$], [AA1419; 2, CH, Et, I, H, $CH_2CF_3$], [AA1420; 2, CH, Et, $CF_3$, H, $CH_2CF_3$], [AA1421; 2, CH, Et, $CF_2H$, H, $CH_2CF_3$], [AA1422; 2, CH, Et, $C_2F_5$, H, $CH_2CF_3$], [AA1423; 2, CH, Et, $C_3F_7$, H, $CH_2CF_3$], [AA1424; 2, CH, Et, $CH_2CF_3$, H, $CH_2CF_3$], [AA1425; 2, CH, Et, $CH_2CHF_2$, H, $CH_2CF_3$], [AA1426; 0, N, Et, H, H, $CH_2CF_3$], [AA1427; 0, N, Et, F, H, $CH_2CF_3$], [AA1428; 0, N, Et, Cl, H, $CH_2CF_3$], [AA1429; 0, N, Et, Br, H, $CH_2CF_3$], [AA1430; 0, N, Et, I, H, $CH_2CF_3$], [AA1431; 0, N, Et, $CF_3$, H, $CH_2CF_3$], [AA1432; 0, N, Et, $CF_2H$, H, $CH_2CF_3$], [AA1433; 0, N, Et, $C_2F_5$, H, $CH_2CF_3$], [AA1434; 0, N, Et, $C_3F_7$, H, $CH_2CF_3$], [AA1435; 0, N, Et, $CH_2CF_3$, H, $CH_2CF_3$], [AA1436; 0, N, Et, $CH_2CHF_2$, H, $CH_2CF_3$], [AA1437; 1, N, Et, H, H, $CH_2CF_3$], [AA1438; 1, N, Et, F, H, $CH_2CF_3$], [AA1439; 1, N, Et, Cl, H, $CH_2CF_3$], [AA1440; 1, N, Et, Br, H, $CH_2CF_3$], [AA1441; 1, N, Et, I, H, $CH_2CF_3$], [AA1442; 1, N, Et, $CF_3$, H, $CH_2CF_3$], [AA1443; 1, N, Et, $CF_2H$, H, $CH_2CF_3$], [AA1444; 1, N, Et, $C_2F_5$, H, $CH_2CF_3$], [AA1445; 1, N, Et, $C_3F_7$, H, $CH_2CF_3$], [AA1446; 1, N, Et, $CH_2CF_3$, H, $CH_2CF_3$], [AA1447; 1, N, Et, $CH_2CHF_2$, H, $CH_2CF_3$], [AA1448; 2, N, Et, H, H, $CH_2CF_3$], [AA1449; 2, N, Et, F, H, $CH_2CF_3$], [AA1450; 2, N, Et, Cl, H, $CH_2CF_3$],

[AA1451; 2, N, Et, Br, H, $CH_2CF_3$], [AA1452; 2, N, Et, I, H, $CH_2CF_3$], [AA1453; 2, N, Et, $CF_3$, H, $CH_2CF_3$], [AA1454; 2, N, Et, $CF_2H$, H, $CH_2CF_3$], [AA1455; 2, N, Et, $C_2F_5$, H, $CH_2CF_3$], [AA1456; 2, N, Et, $C_3F_7$, H, $CH_2CF_3$], [AA1457; 2, N, Et, $CH_2CF_3$, H, $CH_2CF_3$], [AA1458; 2, N, Et, $CH_2CHF_2$, H, $CH_2CF_3$], [AA1459; 0, CH, iPr, H, H, $CH_2CF_3$], [AA1460; 0, CH, iPr, F, H, $CH_2CF_3$], [AA1461; 0, CH, iPr, Cl, H, $CH_2CF_3$], [AA1462; 0, CH, iPr, Br, H, $CH_2CF_3$], [AA1463; 0, CH, iPr, I, H, $CH_2CF_3$], [AA1464; 0, CH, iPr, $CF_3$, H, $CH_2CF_3$], [AA1465; 0, CH, iPr, $CF_2H$, H, $CH_2CF_3$], [AA1466; 0, CH, iPr, $C_2F_5$, H, $CH_2CF_3$], [AA1467; 0, CH, iPr, $C_3F_7$, H, $CH_2CF_3$], [AA1468; 0, CH, iPr, $CH_2CF_3$, H, $CH_2CF_3$], [AA1469; 0, CH, iPr, $CH_2CHF_2$, H, $CH_2CF_3$], [AA1470; 1, CH, iPr, H, H, $CH_2CF_3$], [AA1471; 1, CH, iPr, F, H, $CH_2CF_3$], [AA1472; 1, CH, iPr, Cl, H, $CH_2CF_3$], [AA1473; 1, CH, iPr, Br, H, $CH_2CF_3$], [AA1474; 1, CH, iPr, I, H, $CH_2CF_3$], [AA1475; 1, CH, iPr, $CF_3$, H, $CH_2CF_3$], [AA1476; 1, CH, iPr, $CF_2H$, H, $CH_2CF_3$], [AA1477; 1, CH, iPr, $C_2F_5$, H, $CH_2CF_3$], [AA1478; 1, CH, iPr, $C_3F_7$, H, $CH_2CF_3$], [AA1479; 1, CH, iPr, $CH_2CF_3$, H, $CH_2CF_3$], [AA1480; 1, CH, iPr, $CH_2CHF_2$, H, $CH_2CF_3$], [AA1481; 2, CH, iPr, H, H, $CH_2CF_3$], [AA1482; 2, CH, iPr, F, H, $CH_2CF_3$], [AA1483; 2, CH, iPr, Cl, H, $CH_2CF_3$], [AA1484; 2, CH, iPr, Br, H, $CH_2CF_3$], [AA1485; 2, CH, iPr, I, H, $CH_2CF_3$], [AA1486; 2, CH, iPr, $CF_3$, H, $CH_2CF_3$], [AA1487; 2, CH, iPr, $CF_2H$, H, $CH_2CF_3$], [AA1488; 2, CH, iPr, $C_2F_5$, H, $CH_2CF_3$], [AA1489; 2, CH, iPr, $C_3F_7$, H, $CH_2CF_3$], [AA1490; 2, CH, iPr, $CH_2CF_3$, H, $CH_2CF_3$], [AA1491; 2, CH, iPr, $CH_2CHF_2$, H, $CH_2CF_3$], [AA1492; 0, N, iPr, H, H, $CH_2CF_3$], [AA1493; 0, N, iPr, F, H, $CH_2CF_3$], [AA1494; 0, N, iPr, Cl, H, $CH_2CF_3$], [AA1495; 0, N, iPr, Br, H, $CH_2CF_3$], [AA1496; 0, N, iPr, I, H, $CH_2CF_3$], [AA1497; 0, N, iPr, $CF_3$, H, $CH_2CF_3$], [AA1498; 0, N, iPr, $CF_2H$, H, $CH_2CF_3$], [AA1499; 0, N, iPr, $C_2F_5$, H, $CH_2CF_3$], [AA1500; 0, N, iPr, $C_3F_7$, H, $CH_2CF_3$], [AA1501; 0, N, iPr, $CH_2CF_3$, H, $CH_2CF_3$], [AA1502; 0, N, iPr, $CH_2CHF_2$, H, $CH_2CF_3$], [AA1503; 1, N, iPr, H, H, $CH_2CF_3$], [AA1504; 1, N, iPr, F, H, $CH_2CF_3$], [AA1505; 1, N, iPr, Cl, H, $CH_2CF_3$], [AA1506; 1, N, iPr, Br, H, $CH_2CF_3$], [AA1507; 1, N, iPr, I, H, $CH_2CF_3$], [AA1508; 1, N, iPr, $CF_3$, H, $CH_2CF_3$], [AA1509; 1, N, iPr, $CF_2H$, H, $CH_2CF_3$], [AA1510; 1, N, iPr, $C_2F_5$, H, $CH_2CF_3$], [AA1511; 1, N, iPr, $C_3F_7$, H, $CH_2CF_3$], [AA1512; 1, N, iPr, $CH_2CF_3$, H, $CH_2CF_3$], [AA1513; 1, N, iPr, $CH_2CHF_2$, H, $CH_2CF_3$], [AA1514; 2, N, iPr, H, H, $CH_2CF_3$], [AA1515; 2, N, iPr, F, H, $CH_2CF_3$], [AA1516; 2, N, iPr, Cl, H, $CH_2CF_3$], [AA1517; 2, N, iPr, Br, H, $CH_2CF_3$], [AA1518; 2, N, iPr, I, H, $CH_2CF_3$], [AA1519; 2, N, iPr, $CF_3$, H, $CH_2CF_3$], [AA1520; 2, N, iPr, $CF_2H$, H, $CH_2CF_3$], [AA1521; 2, N, iPr, $C_2F_5$, H, $CH_2CF_3$], [AA1522; 2, N, iPr, $C_3F_7$, H, $CH_2CF_3$], [AA1523; 2, N, iPr, $CH_2CF_3$, H, $CH_2CF_3$], [AA1524; 2, N, iPr, $CH_2CHF_2$, H, $CH_2CF_3$], [AA1525; 0, CH, cPr, H, H, $CH_2CF_3$], [AA1526; 0, CH, cPr, F, H, $CH_2CF_3$], [AA1527; 0, CH, cPr, Cl, H, $CH_2CF_3$], [AA1528; 0, CH, cPr, Br, H, $CH_2CF_3$], [AA1529; 0, CH, cPr, I, H, $CH_2CF_3$], [AA1530; 0, CH, cPr, $CF_3$, H, $CH_2CF_3$], [AA1531; 0, CH, cPr, $CF_2H$, H, $CH_2CF_3$], [AA1532; 0, CH, cPr, $C_2F_5$, H, $CH_2CF_3$], [AA1533; 0, CH, cPr, $C_3F_7$, H, $CH_2CF_3$], [AA1534; 0, CH, cPr, $CH_2CF_3$, H, $CH_2CF_3$], [AA1535; 0, CH, cPr, $CH_2CHF_2$, H, $CH_2CF_3$], [AA1536; 1, CH, cPr, H, H, $CH_2CF_3$], [AA1537; 1, CH, cPr, F, H, $CH_2CF_3$], [AA1538; 1, CH, cPr, Cl, H, $CH_2CF_3$], [AA1539; 1, CH, cPr, Br, H, $CH_2CF_3$], [AA1540; 1, CH, cPr, I, H, $CH_2CF_3$], [AA1541; 1, CH, cPr, $CF_3$, H, $CH_2CF_3$], [AA1542; 1, CH, cPr, $CF_2H$, H, $CH_2CF_3$], [AA1543; 1, CH, cPr, $C_2F_5$, H, $CH_2CF_3$], [AA1544; 1, CH, cPr, $C_3F_7$, H, $CH_2CF_3$], [AA1545; 1, CH, cPr, $CH_2CF_3$, H, $CH_2CF_3$], [AA1546; 1, CH, cPr, $CH_2CHF_2$, H, $CH_2CF_3$], [AA1547; 2, CH, cPr, H, H, $CH_2CF_3$], [AA1548; 2, CH, cPr, F, H, $CH_2CF_3$], [AA1549; 2, CH, cPr, Cl, H, $CH_2CF_3$], [AA1550; 2, CH, cPr, Br, H, $CH_2CF_3$], [AA1551; 2, CH, cPr, I, H, $CH_2CF_3$], [AA1552; 2, CH, cPr, $CF_3$, H, $CH_2CF_3$], [AA1553; 2, CH, cPr, $CF_2H$, H, $CH_2CF_3$], [AA1554; 2, CH, cPr, $C_2F_5$, H, $CH_2CF_3$], [AA1555; 2, CH, cPr, $C_3F_7$, H, $CH_2CF_3$], [AA1556; 2, CH, cPr, $CH_2CF_3$, H, $CH_2CF_3$], [AA1557; 2, CH, cPr, $CH_2CHF_2$, H, $CH_2CF_3$], [AA1558; 0, N, cPr, H, H, $CH_2CF_3$], [AA1559; 0, N, cPr, F, H, $CH_2CF_3$], [AA1560; 0, N, cPr, Cl, H, $CH_2CF_3$], [AA1561; 0, N, cPr, Br, H, $CH_2CF_3$], [AA1562; 0, N, cPr, I, H, $CH_2CF_3$], [AA1563; 0, N, cPr, $CF_3$, H, $CH_2CF_3$], [AA1564; 0, N, cPr, $CF_2H$, H, $CH_2CF_3$], [AA1565; 0, N, cPr, $C_2F_5$, H, $CH_2CF_3$], [AA1566; 0, N, cPr, $C_3F_7$, H, $CH_2CF_3$], [AA1567; 0, N, cPr, $CH_2CF_3$, H, $CH_2CF_3$], [AA1568; 0, N, cPr, $CH_2CHF_2$, H, $CH_2CF_3$], [AA1569; 1, N, cPr, H, H, $CH_2CF_3$], [AA1570; 1, N, cPr, F, H, $CH_2CF_3$], [AA1571; 1, N, cPr, Cl, H, $CH_2CF_3$], [AA1572; 1, N, cPr, Br, H, $CH_2CF_3$], [AA1573; 1, N, cPr, I, H, $CH_2CF_3$], [AA1574; 1, N, cPr, $CF_3$, H, $CH_2CF_3$], [AA1575; 1, N, cPr, $CF_2H$, H, $CH_2CF_3$], [AA1576; 1, N, cPr, $C_2F$, H, $CH_2CF_3$], [AA1577; 1, N, cPr, $C_3F_7$, H, $CH_2CF_3$], [AA1578; 1, N, cPr, $CH_2CF_3$, H, $CH_2CF_3$], [AA1579; 1, N, cPr, $CH_2CHF_2$, H, $CH_2CF_3$], [AA1580; 2, N, cPr, H, H, $CH_2CF_3$], [AA1581; 2, N, cPr, F, H, $CH_2CF_3$], [AA1582; 2, N, cPr, Cl, H, $CH_2CF_3$], [AA1583; 2, N, cPr, Br, H, $CH_2CF_3$], [AA1584; 2, N, cPr, I, H, $CH_2CF_3$], [AA1585; 2, N, cPr, $CF_3$, H, $CH_2CF_3$], [AA1586; 2, N, cPr, $CF_2H$, H, $CH_2CF_3$], [AA1587; 2, N, cPr, $C_2F_5$, H, $CH_2CF_3$], [AA1588; 2, N, cPr, $C_3F_7$, H, $CH_2CF_3$], [AA1589; 2, N, cPr, $CH_2CF_3$, H, $CH_2CF_3$], [AA1590; 2, N, cPr, $CH_2CHF_2$, H, $CH_2CF_3$], [AA1591; 0, CH, H, H, F, $CH_2CF_3$], [AA1592; 0, CH, H, H, Cl, $CH_2CF_3$], [AA1593; 0, CH, H, H, Br, $CH_2CF_3$], [AA1594; 0, CH, H, H, I, $CH_2CF_3$], [AA1595; 0, CH, H, H, $CF_3$, $CH_2CF_3$], [AA1596; 0, CH, H, H, $CF_2H$, $CH_2CF_3$], [AA1597; 0, CH, H, H, $C_2F_5$, $CH_2CF_3$], [AA1598; 0, CH, H, H, $C_3F_7$, $CH_2CF_3$], [AA1599; 0, CH, H, H, $CH_2CF_3$, $CH_2CF_3$], [AA1600; 0, CH, H, H, $CH_2CHF_2$, $CH_2CF_3$], [AA1601; 1, CH, H, H, F, $CH_2CF_3$], [AA1602; 1, CH, H, H, Cl, $CH_2CF_3$], [AA1603; 1, CH, H, H, Br, $CH_2CF_3$], [AA1604; 1, CH, H, H, I, $CH_2CF_3$], [AA1605; 1, CH, H, H, $CF_3$, $CH_2CF_3$], [AA1606; 1, CH, H, H, $CF_2H$, $CH_2CF_3$], [AA1607; 1, CH, H, H, $C_2F_5$, $CH_2CF_3$], [AA1608; 1, CH, H, H, $C_3F_7$, $CH_2CF_3$], [AA1609; 1, CH, H, H, $CH_2CF_3$, $CH_2CF_3$], [AA1610; 1, CH, H, H, $CH_2CHF_2$, $CH_2CF_3$], [AA1611; 2, CH, H, H, F, $CH_2CF_3$], [AA1612; 2, CH, H, H, Cl, $CH_2CF_3$], [AA1613; 2, CH, H, H, Br, $CH_2CF_3$], [AA1614; 2, CH, H, H, I, $CH_2CF_3$], [AA1615; 2, CH, H, H, $CF_3$, $CH_2CF_3$], [AA1616; 2, CH, H, H, $CF_2H$, $CH_2CF_3$], [AA1617; 2, CH, H, H, $C_2F_5$, $CH_2CF_3$], [AA1618; 2, CH, H, H, $C_3F_7$, $CH_2CF_3$], [AA1619; 2, CH, H, H, $CH_2CF_3$, $CH_2CF_3$], [AA1620; 2, CH, H, H, $CH_2CHF_2$, $CH_2CF_3$], [AA1621; 0, N, H, H, F, $CH_2CF_3$], [AA1622; 0, N, H, H, Cl, $CH_2CF_3$], [AA1623; 0, N, H, H, Br, $CH_2CF_3$], [AA1624; 0, N, H, H, I, $CH_2CF_3$], [AA1625; 0, N, H, H, $CF_3$, $CH_2CF_3$], [AA1626; 0, N, H, H, $CF_2H$, $CH_2CF_3$], [AA1627; 0, N, H, H, $C_2F_5$, $CH_2CF_3$], [AA1628; 0, N, H, H, $C_3F_7$, $CH_2CF_3$], [AA1629; 0, N, H, H, $CH_2CF_3$, $CH_2CF_3$], [AA1630; 0, N, H, H, $CH_2CHF_2$, $CH_2CF_3$], [AA1631; 1, N, H, H, F, $CH_2CF_3$], [AA1632; 1, N, H, H, Cl, $CH_2CF_3$], [AA1633; 1, N, H, H, Br, $CH_2CF_3$], [AA1634; 1, N, H, H, I, $CH_2CF_3$], [AA1635; 1, N, H, H, $CF_3$, $CH_2CF_3$], [AA1636; 1, N, H, H, $CF_2H$, $CH_2CF_3$], [AA1637; 1, N, H, H, $C_2F_5$, $CH_2CF_3$], [AA1638; 1, N, H, H, $C_3F_7$, $CH_2CF_3$], [AA1639; 1, N, H, H, $CH_2CF_3$, $CH_2CF_3$], [AA1640; 1, N, H, H, $CH_2CHF_2$, $CH_2CF_3$], [AA1641; 2, N, H, H, F, $CH_2CF_3$], [AA1642; 2, N, H, H, Cl, $CH_2CF_3$], [AA1643; 2, N, H, H, Br, $CH_2CF_3$], [AA1644; 2, N, H, H, I, $CH_2CF_3$],

[AA1645; 2, N, H, H, $CF_3$, $CH_2CF_3$], [AA1646; 2, N, H, H, $CF_2H$, $CH_2CF_3$], [AA1647; 2, N, H, H, $C_2F_5$, $CH_2CF_3$], [AA1648; 2, N, H, H, $C_3F_7$, $CH_2CF_3$], [AA1649; 2, N, H, H, $CH_2CF_3$, $CH_2CF_3$], [AA1650; 2, N, H, H, $CH_2CHF_2$, $CH_2CF_3$], [AA1651; 0, CH, Me, H, F, $CH_2CF_3$], [AA1652; 0, CH, Me, H, Cl, $CH_2CF_3$], [AA1653; 0, CH, Me, H, Br, $CH_2CF_3$], [AA1654; 0, CH, Me, H, I, $CH_2CF_3$], [AA1655; 0, CH, Me, H, $CF_3$, $CH_2CF_3$], [AA1656; 0, CH, Me, H, $CF_2H$, $CH_2CF_3$], [AA1657; 0, CH, Me, H, $C_2F_5$, $CH_2CF_3$], [AA1658; 0, CH, Me, H, $C_3F_7$, $CH_2CF_3$], [AA1659; 0, CH, Me, H, $CH_2CF_3$, $CH_2CF_3$], [AA1660; 0, CH, Me, H, $CH_2CHF_2$, $CH_2CF_3$], [AA1661; 1, CH, Me, H, F, $CH_2CF_3$], [AA1662; 1, CH, Me, H, Cl, $CH_2CF_3$], [AA1663; 1, CH, Me, H, Br, $CH_2CF_3$], [AA1664; 1, CH, Me, H, I, $CH_2CF_3$], [AA1665; 1, CH, Me, H, $CF_3$, $CH_2CF_3$], [AA1666; 1, CH, Me, H, $CF_2H$, $CH_2CF_3$], [AA1667; 1, CH, Me, H, $C_2F_5$, $CH_2CF_3$], [AA1668; 1, CH, Me, H, $C_3F_7$, $CH_2CF_3$], [AA1669; 1, CH, Me, H, $CH_2CF_3$, $CH_2CF_3$], [AA1670; 1, CH, Me, H, $CH_2CHF_2$, $CH_2CF_3$], [AA1671; 2, CH, Me, H, F, $CH_2CF_3$], [AA1672; 2, CH, Me, H, Cl, $CH_2CF_3$], [AA1673; 2, CH, Me, H, Br, $CH_2CF_3$], [AA1674; 2, CH, Me, H, I, $CH_2CF_3$], [AA1675; 2, CH, Me, H, $CF_3$, $CH_2CF_3$], [AA1676; 2, CH, Me, H, $CF_2H$, $CH_2CF_3$], [AA1677; 2, CH, Me, H, $C_2F_5$, $CH_2CF_3$], [AA1678; 2, CH, Me, H, $C_3F_7$, $CH_2CF_3$], [AA1679; 2, CH, Me, H, $CH_2CF_3$, $CH_2CF_3$], [AA1680; 2, CH, Me, H, $CH_2CHF_2$, $CH_2CF_3$], [AA1681; 0, N, Me, H, F, $CH_2CF_3$], [AA1682; 0, N, Me, H, Cl, $CH_2CF_3$], [AA1683; 0, N, Me, H, Br, $CH_2CF_3$], [AA1684; 0, N, Me, H, I, $CH_2CF_3$], [AA1685; 0, N, Me, H, $CF_3$, $CH_2CF_3$], [AA1686; 0, N, Me, H, $CF_2H$, $CH_2CF_3$], [AA1687; 0, N, Me, H, $C_2F_5$, $CH_2CF_3$], [AA1688; 0, N, Me, H, $C_3F_7$, $CH_2CF_3$], [AA1689; 0, N, Me, H, $CH_2CF_3$, $CH_2CF_3$], [AA1690; 0, N, Me, H, $CH_2CHF_2$, $CH_2CF_3$], [AA1691; 1, N, Me, H, F, $CH_2CF_3$], [AA1692; 1, N, Me, H, Cl, $CH_2CF_3$], [AA1693; 1, N, Me, H, Br, $CH_2CF_3$], [AA1694; 1, N, Me, H, I, $CH_2CF_3$], [AA1695; 1, N, Me, H, $CF_3$, $CH_2CF_3$], [AA1696; 1, N, Me, H, $CF_2H$, $CH_2CF_3$], [AA1697; 1, N, Me, H, $C_2F_5$, $CH_2CF_3$], [AA1698; 1, N, Me, H, $C_3F_7$, $CH_2CF_3$], [AA1699; 1, N, Me, H, $CH_2CF_3$, $CH_2CF_3$], [AA1700; 1, N, Me, H, $CH_2CHF_2$, $CH_2CF_3$], [AA1701; 2, N, Me, H, F, $CH_2CF_3$], [AA1702; 2, N, Me, H, Cl, $CH_2CF_3$], [AA1703; 2, N, Me, H, Br, $CH_2CF_3$], [AA1704; 2, N, Me, H, I, $CH_2CF_3$], [AA1705; 2, N, Me, H, $CF_3$, $CH_2CF_3$], [AA1706; 2, N, Me, H, $CF_2H$, $CH_2CF_3$], [AA1707; 2, N, Me, H, $C_2F_5$, $CH_2CF_3$], [AA1708; 2, N, Me, H, $C_3F_7$, $CH_2CF_3$], [AA1709; 2, N, Me, H, $CH_2CF_3$, $CH_2CF_3$], [AA1710; 2, N, Me, H, $CH_2CHF_2$, $CH_2CF_3$], [AA1711; 0, CH, Et, H, F, $CH_2CF_3$], [AA1712; 0, CH, Et, H, Cl, $CH_2CF_3$], [AA1713; 0, CH, Et, H, Br, $CH_2CF_3$], [AA1714; 0, CH, Et, H, I, $CH_2CF_3$], [AA1715; 0, CH, Et, H, $CF_3$, $CH_2CF_3$], [AA1716; 0, CH, Et, H, $CF_2H$, $CH_2CF_3$], [AA1717; 0, CH, Et, H, $C_2F$, $CH_2CF_3$], [AA1718; 0, CH, Et, H, $C_3F_7$, CH $CF_3$], [AA1719; 0, CH, Et, H, $CH_2CF_3$, $CH_2CF_3$], [AA1720; 0, CH, Et, H, $CH_2CHF_2$, $CH_2CF_3$], [AA1721; 1, CH, Et, H, F, $CH_2CF_3$], [AA1722; 1, CH, Et, H, Cl, $CH_2CF_3$], [AA1723; 1, CH, Et, H, Br, $CH_2CF_3$], [AA1724; 1, CH, Et, H, I, $CH_2CF_3$], [AA1725; 1, CH, Et, H, $CF_3$, $CH_2CF_3$], [AA1726; 1, CH, Et, H, $CF_2H$, $CH_2CF_3$], [AA1727; 1, CH, Et, H, $C_2F_5$, $CH_2CF_3$], [AA1728; 1, CH, Et, H, $C_3F_7$, $CH_2CF_3$], [AA1729; 1, CH, Et, H, $CH_2CF_3$, $CH_2CF_3$], [AA1730; 1, CH, Et, H, $CH_2CHF_2$, $CH_2CF_3$], [AA1731; 2, CH, Et, H, F, $CH_2CF_3$], [AA1732; 2, CH, Et, H, Cl, $CH_2CF_3$], [AA1733; 2, CH, Et, H, Br, $CH_2CF_3$], [AA1734; 2, CH, Et, H, I, $CH_2CF_3$], [AA1735; 2, CH, Et, H, $CF_3$, $CH_2CF_3$], [AA1736; 2, CH, Et, H, $CF_2H$, $CH_2CF_3$], [AA1737; 2, CH, Et, H, $C_2F_5$, $CH_2CF_3$], [AA1738; 2, CH, Et, H, $C_3F_7$, $CH_2CF_3$], [AA1739; 2, CH, Et, H, $CH_2CF_3$, $CH_2CF_3$], [AA1740; 2, CH, Et, H, $CH_2CHF_2$, $CH_2CF_3$], [AA1741; 0, N, Et, H, F, $CH_2CF_3$], [AA1742; 0, N, Et, H, Cl, $CH_2CF_3$], [AA1743; 0, N, Et, H, Br, $CH_2CF_3$], [AA1744; 0, N, Et, H, I, $CH_2CF_3$], [AA1745; 0, N, Et, H, $CF_3$, $CH_2CF_3$], [AA1746; 0, N, Et, H, $CF_2H$, $CH_2CF_3$], [AA1747; 0, N, Et, H, $C_2F_5$, $CH_2CF_3$], [AA1748; 0, N, Et, H, $C_3F_7$, $CH_2CF_3$], [AA1749; 0, N, Et, H, $CH_2CF_3$, $CH_2CF_3$], [AA1750; 0, N, Et, H, $CH_2CHF_2$, $CH_2CF_3$], [AA1751; 1, N, Et, H, F, $CH_2CF_3$], [AA1752; 1, N, Et, H, Cl, $CH_2CF_3$], [AA1753; 1, N, Et, H, Br, $CH_2CF_3$], [AA1754; 1, N, Et, H, I, $CH_2CF_3$], [AA1755; 1, N, Et, H, $CF_3$, $CH_2CF_3$], [AA1756; 1, N, Et, H, $CF_2H$, $CH_2CF_3$], [AA1757; 1, N, Et, H, $C_2F_5$, $CH_2CF_3$], [AA1758; 1, N, Et, H, $C_3F_7$, $CH_2CF_3$], [AA1759; 1, N, Et, H, $CH_2CF_3$, $CH_2CF_3$], [AA1760; 1, N, Et, H, $CH_2CHF_2$, $CH_2CF_3$], [AA1761; 2, N, Et, H, F, $CH_2CF_3$], [AA1762; 2, N, Et, H, Cl, $CH_2CF_3$], [AA1763; 2, N, Et, H, Br, $CH_2CF_3$], [AA1764; 2, N, Et, H, I, $CH_2CF_3$], [AA1765; 2, N, Et, H, $CF_3$, $CH_2CF_3$], [AA1766; 2, N, Et, H, $CF_2H$, $CH_2CF_3$], [AA1767; 2, N, Et, H, $C_2F$, $CH_2CF_3$], [AA1768; 2, N, Et, H, $C_3F_7$, $CH_2CF_3$], [AA1769; 2, N, Et, H, $CH_2CF_3$, $CH_2CF_3$], [AA1770; 2, N, Et, H, $CH_2CHF_2$, $CH_2CF_3$], [AA1771; 0, CH, iPr, H, F, $CH_2CF_3$], [AA1772; 0, CH, iPr, H, Cl, $CH_2CF_3$], [AA1773; 0, CH, iPr, H, Br, $CH_2CF_3$], [AA1774; 0, CH, iPr, H, I, $CH_2CF_3$], [AA1775; 0, CH, iPr, H, $CF_3$, $CH_2CF_3$], [AA1776; 0, CH, iPr, H, $CF_2H$, $CH_2CF_3$], [AA1777; 0, CH, iPr, H, $C_2F$, $CH_2CF_3$], [AA1778; 0, CH, iPr, H, $C_3F_7$, $CH_2CF_3$], [AA1779; 0, CH, iPr, H, $CH_2CF_3$, $CH_2CF_3$], [AA1780; 0, CH, iPr, H, $CH_2CHF_2$, $CH_2CF_3$], [AA1781; 1, CH, iPr, H, F, $CH_2CF_3$], [AA1782; 1, CH, iPr, H, Cl, $CH_2CF_3$], [AA1783; 1, CH, iPr, H, Br, $CH_2CF_3$], [AA1784; 1, CH, iPr, H, I, $CH_2CF_3$], [AA1785; 1, CH, iPr, H, $CF_3$, $CH_2CF_3$], [AA1786; 1, CH, iPr, H, $CF_2H$, $CH_2CF_3$], [AA1787; 1, CH, iPr, H, $C_2F_5$, $CH_2CF_3$], [AA1788; 1, CH, iPr, H, $C_3F_7$, $CH_2CF_3$], [AA1789; 1, CH, iPr, H, $CH_2CF_3$, $CH_2CF_3$], [AA1790; 1, CH, iPr, H, $CH_2CHF_2$, $CH_2CF_3$], [AA1791; 2, CH, iPr, H, F, $CH_2CF_3$], [AA1792; 2, CH, iPr, H, Cl, $CH_2CF_3$], [AA1793; 2, CH, iPr, H, Br, $CH_2CF_3$], [AA1794; 2, CH, iPr, H, I, $CH_2CF_3$], [AA1795; 2, CH, iPr, H, $CF_3$, $CH_2CF_3$], [AA1796; 2, CH, iPr, H, $CF_2H$, CH $CF_3$], [AA1797; 2, CH, iPr, H, $C_2F_5$, $CH_2CF_3$], [AA1798; 2, CH, iPr, H, $C_3F_7$, $CH_2CF_3$], [AA1799; 2, CH, iPr, H, $CH_2CF_3$, $CH_2CF_3$], [AA1800; 2, CH, iPr, H, $CH_2CHF_2$, $CH_2CF_3$], [AA1801; 0, N, iPr, H, F, $CH_2CF_3$], [AA1802; 0, N, iPr, H, Cl, $CH_2CF_3$], [AA1803; 0, N, iPr, H, Br, $CH_2CF_3$], [AA1804; 0, N, iPr, H, I, $CH_2CF_3$], [AA1805; 0, N, iPr, H, $CF_3$, $CH_2CF_3$], [AA1806; 0, N, iPr, H, $CF_2H$, $CH_2CF_3$], [AA1807; 0, N, iPr, H, $C_2F_5$, $CH_2CF_3$], [AA1808; 0, N, iPr, H, $C_3F_7$, $CH_2CF_3$], [AA1809; 0, N, iPr, H, $CH_2CF_3$, $CH_2CF_3$], [AA1810; 0, N, iPr, H, $CH_2CHF_2$, $CH_2CF_3$], [AA1811; 1, N, iPr, H, F, $CH_2CF_3$], [AA1812; 1, N, iPr, H, Cl, $CH_2CF_3$], [AA1813; 1, N, iPr, H, Br, $CH_2CF_3$], [AA1814; 1, N, iPr, H, I, $CH_2CF_3$], [AA1815; 1, N, iPr, H, $CF_3$, $CH_2CF_3$], [AA1816; 1, N, iPr, H, $CF_2H$, $CH_2CF_3$], [AA1817; 1, N, iPr, H, $C_2F_5$, $CH_2CF_3$], [AA1818; 1, N, iPr, H, $C_3F_7$, $CH_2CF_3$], [AA1819; 1, N, iPr, H, $CH_2CF_3$, $CH_2CF_3$], [AA1820; 1, N, iPr, H, $CH_2CHF_2$, $CH_2CF_3$], [AA1821; 2, N, iPr, H, F, $CH_2CF_3$], [AA1822; 2, N, iPr, H, Cl, $CH_2CF_3$], [AA1823; 2, N, iPr, H, Br, $CH_2CF_3$], [AA1824; 2, N, iPr, H, I, $CH_2CF_3$], [AA1825; 2, N, iPr, H, $CF_3$, $CH_2CF_3$], [AA1826; 2, N, iPr, H, $CF_2H$, $CH_2CF_3$], [AA1827; 2, N, iPr, H, $C_2F_5$, $CH_2CF_3$], [AA1828; 2, N, iPr, H, $C_3F_7$, $CH_2CF_3$], [AA1829; 2, N, iPr, H, $CH_2CF_3$, $CH_2CF_3$], [AA1830; 2, N, iPr, H, $CH_2CHF_2$, $CH_2CF_3$], [AA1831; 0, CH, cPr, H, F, $CH_2CF_3$], [AA1832; 0, CH, cPr, H, Cl, $CH_2CF_3$], [AA1833; 0, CH, cPr, H, Br, $CH_2CF_3$], [AA1834; 0, CH, cPr, H, I, $CH_2CF_3$], [AA1835; 0, CH, cPr,

H, $CF_3$, $CH_2CF_3$], [AA1836; 0, CH, cPr, H, $CF_2H$, $CH_2CF_3$], [AA1837; 0, CH, cPr, H, $C_2F_5$, $CH_2CF_3$], [AA1838; 0, CH, cPr, H, $C_3F_7$, $CH_2CF_3$], [AA1839; 0, CH, cPr, H, $CH_2CF_3$, $CH_2CF_3$], [AA1840; 0, CH, cPr, H, $CH_2CHF_2$, $CH_2CF_3$], [AA1841; 1, CH, cPr, H, F, $CH_2CF_3$], [AA1842; 1, CH, cPr, H, Cl, $CH_2CF_3$], [AA1843; 1, CH, cPr, H, Br, $CH_2CF_3$], [AA1844; 1, CH, cPr, H, I, $CH_2CF_3$], [AA1845; 1, CH, cPr, H, $CF_3$, $CH_2CF_3$], [AA1846; 1, CH, cPr, H, $CF_2H$, $CH_2CF_3$], [AA1847; 1, CH, cPr, H, $C_2F_5$, $CH_2CF_3$], [AA1848; 1, CH, cPr, H, $C_3F_7$, $CH_2CF_3$], [AA1849; 1, CH, cPr, H, $CH_2CF_3$, $CH_2CF_3$], [AA1850; 1, CH, cPr, H, $CH_2CHF_2$, $CH_2CF_3$], [AA1851; 2, CH, cPr, H, F, $CH_2CF_3$], [AA1852; 2, CH, cPr, H, Cl, $CH_2CF_3$], [AA1853; 2, CH, cPr, H, Br, $CH_2CF_3$], [AA1854; 2, CH, cPr, H, I, $CH_2CF_3$], [AA1855; 2, CH, cPr, H, $CF_3$, $CH_2CF_3$], [AA1856; 2, CH, cPr, H, $CF_2H$, $CH_2CF_3$], [AA1857; 2, CH, cPr, H, $C_2F_5$, $CH_2CF_3$], [AA1858; 2, CH, cPr, H, $C_3F_7$, $CH_2CF_3$], [AA1859; 2, CH, cPr, H, $CH_2CF_3$, $CH_2CF_3$], [AA1860; 2, CH, cPr, H, $CH_2CHF_2$, $CH_2CF_3$], [AA1861; 0, N, cPr, H, F, $CH_2CF_3$], [AA1862; 0, N, cPr, H, Cl, $CH_2CF_3$], [AA1863; 0, N, cPr, H, Br, $CH_2CF_3$], [AA1864; 0, N, cPr, H, I, $CH_2CF_3$], [AA1865; 0, N, cPr, H, $CF_3$, $CH_2CF_3$], [AA1866; 0, N, cPr, H, $CF_2H$, $CH_2CF_3$], [AA1867; 0, N, cPr, H, $C_2F_5$, $CH_2CF_3$], [AA1868; 0, N, cPr, H, $C_3F_7$, $CH_2CF_3$], [AA1869; 0, N, cPr, H, $CH_2CF_3$, $CH_2CF_3$], [AA1870; 0, N, cPr, H, $CH_2CHF_2$, $CH_2CF_3$], [AA1871; 1, N, cPr, H, F, $CH_2CF_3$], [AA1872; 1, N, cPr, H, Cl, $CH_2CF_3$], [AA1873; 1, N, cPr, H, Br, $CH_2CF_3$], [AA1874; 1, N, cPr, H, I, $CH_2CF_3$], [AA1875; 1, N, cPr, H, $CF_3$, $CH_2CF_3$], [AA1876; 1, N, cPr, H, $CF_2H$, $CH_2CF_3$], [AA1877; 1, N, cPr, H, $C_2F_5$, $CH_2CF_3$], [AA1878; 1, N, cPr, H, $C_3F_7$, $CH_2CF_3$], [AA1879; 1, N, cPr, H, $CH_2CF_3$, $CH_2CF_3$], [AA1880; 1, N, cPr, H, $CH_2CHF_2$, $CH_2CF_3$], [AA1881; 2, N, cPr, H, F, $CH_2CF_3$], [AA1882; 2, N, cPr, H, Cl, $CH_2CF_3$], [AA1883; 2, N, cPr, H, Br, $CH_2CF_3$], [AA1884; 2, N, cPr, H, I, $CH_2CF_3$], [AA1885; 2, N, cPr, H, $CF_3$, $CH_2CF_3$], [AA1886; 2, N, cPr, H, $CF_2H$, $CH_2CF_3$], [AA1887; 2, N, cPr, H, $C_2F_5$, $CH_2CF_3$], [AA1888; 2, N, cPr, H, $C_3F_7$, $CH_2CF_3$], [AA1889; 2, N, cPr, H, $CH_2CF_3$, $CH_2CF_3$], [AA1890; 2, N, cPr, H, $CH_2CHF_2$, $CH_2CF_3$], [AA1891; 0, CH, H, H, H, $CH_2CHF_2$], [AA1892; 0, CH, H, F, H, $CH_2CHF_2$], [AA1893; 0, CH, H, Cl, H, $CH_2CHF_2$], [AA1894; 0, CH, H, Br, H, $CH_2CHF_2$], [AA1895; 0, CH, H, I, H, $CH_2CHF_2$], [AA1896; 0, CH, H, $CF_3$, H, $CH_2CHF_2$], [AA1897; 0, CH, H, $CF_2H$, H, $CH_2CHF_2$], [AA1898; 0, CH, H, $C_2F_5$, H, $CH_2CHF_2$], [AA1899; 0, CH, H, $C_3F_7$, H, $CH_2CHF_2$], [AA1900; 0, CH, H, $CH_2CF_3$, H, $CH_2CHF_2$], [AA1901; 0, CH, H, $CH_2CHF_2$, H, $CH_2CHF_2$], [AA1902; 1, CH, H, H, H, $CH_2CHF_2$], [AA1903; 1, CH, H, F, H, $CH_2CHF_2$], [AA1904; 1, CH, H, Cl, H, $CH_2CHF_2$], [AA1905; 1, CH, H, Br, H, $CH_2CHF_2$], [AA1906; 1, CH, H, I, H, $CH_2CHF_2$], [AA1907; 1, CH, H, $CF_3$, H, $CH_2CHF_2$], [AA1908; 1, CH, H, $CF_2H$, H, $CH_2CHF_2$], [AA1909; 1, CH, H, $C_2F_5$, H, $CH_2CHF_2$], [AA1910; 1, CH, H, $C_3F_7$, H, $CH_2CHF_2$], [AA1911; 1, CH, H, $CH_2CF_3$, H, $CH_2CHF_2$], [AA1912; 1, CH, H, $CH_2CHF_2$, H, $CH_2CHF_2$], [AA1913; 2, CH, H, H, H, $CH_2CHF_2$], [AA1914; 2, CH, H, F, H, $CH_2CHF_2$], [AA1915; 2, CH, H, Cl, H, $CH_2CHF_2$], [AA1916; 2, CH, H, Br, H, $CH_2CHF_2$], [AA1917; 2, CH, H, I, H, $CH_2CHF_2$], [AA1918; 2, CH, H, $CF_3$, H, $CH_2CHF_2$], [AA1919; 2, CH, H, $CF_2H$, H, $CH_2CHF_2$], [AA1920; 2, CH, H, $C_2F_5$, H, $CH_2CHF_2$], [AA1921; 2, CH, H, $C_3F_7$, H, $CH_2CHF_2$], [AA1922; 2, CH, H, $CH_2CF_3$, H, $CH_2CHF_2$], [AA1923; 2, CH, H, $CH_2CHF_2$, H, $CH_2CHF_2$], [AA1924; 0, N, H, H, H, $CH_2CHF_2$], [AA1925; 0, N, H, F, H, $CH_2CHF_2$], [AA1926; 0, N, H, Cl, H, $CH_2CHF_2$], [AA1927; 0, N, H, Br, H, $CH_2CHF_2$], [AA1928; 0, N, H, I, H, $CH_2CHF_2$], [AA1929; 0, N, H, $CF_3$, H, $CH_2CHF_2$], [AA1930; 0, N, H, $CF_2H$, H, $CH_2CHF_2$], [AA1931; 0, N, H, $C_2F_5$, H, $CH_2CHF_7$], [AA1932; 0, N, H, $C_3F_7$, H, $CH_2CHF_2$], [AA1933; 0, N, H, $CH_2CF_3$, H, $CH_2CHF_2$], [AA1934; 0, N, H, $CH_2CHF_2$, H, $CH_2CHF_2$], [AA1935; 1, N, H, H, H, $CH_2CHF_2$], [AA1936; 1, N, H, F, H, $CH_2CHF_2$], [AA1937; 1, N, H, Cl, H, $CH_2CHF_2$], [AA1938; 1, N, H, Br, H, $CH_2CHF_2$], [AA1939; 1, N, H, I, H, $CH_2CHF_2$], [AA1940; 1, N, H, $CF_3$, H, $CH_2CHF_2$], [AA1941; 1, N, H, $CF_2H$, H, $CH_2CHF_2$], [AA1942; 1, N, H, $C_2F_5$, H, $CH_2CHF_2$], [AA1943; 1, N, H, $C_3F_7$, H, $CH_2CHF_2$], [AA1944; 1, N, H, $CH_2CF_3$, H, $CH_2CHF_2$], [AA1945; 1, N, H, $CH_2CHF_2$, H, $CH_2CHF_2$], [AA1946; 2, N, H, H, H, $CH_2CHF_2$], [AA1947; 2, N, H, F, H, $CH_2CHF_2$], [AA1948; 2, N, H, Cl, H, $CH_2CHF_2$], [AA1949; 2, N, H, Br, H, $CH_2CHF_2$], [AA1950; 2, N, H, I, H, $CH_2CHF_2$], [AA1951; 2, N, H, $CF_3$, H, $CH_2CHF_2$], [AA1952; 2, N, H, $CF_2H$, H, $CH_2CHF_2$], [AA1953; 2, N, H, $C_2F_5$, H, $CH_2CHF_2$], [AA1954; 2, N, H, $C_3F_7$, H, $CH_2CHF_2$], [AA1955; 2, N, H, $CH_2CF_3$, H, $CH_2CHF_2$], [AA1956; 2, N, H, $CH_2CHF_2$, H, $CH_2CHF_2$], [AA1957; 0, CH, Me, H, H, $CH_2CHF_2$], [AA1958; 0, CH, Me, F, H, $CH_2CHF_2$], [AA1959; 0, CH, Me, Cl, H, $CH_2CHF_2$], [AA1960; 0, CH, Me, Br, H, $CH_2CHF_2$], [AA1961; 0, CH, Me, I, H, $CH_2CHF_2$], [AA1962; 0, CH, Me, $CF_3$, H, $CH_2CHF_2$], [AA1963; 0, CH, Me, $CF_2H$, H, $CH_2CHF_2$], [AA1964; 0, CH, Me, $C_2F_5$, H, $CH_2CHF_2$], [AA1965; 0, CH, Me, $C_3F_7$, H, $CH_2CHF_2$], [AA1966; 0, CH, Me, $CH_2CF_3$, H, $CH_2CHF_2$], [AA1967; 0, CH, Me, $CH_2CHF_2$, H, $CH_2CHF_2$], [AA1968; 1, CH, Me, H, H, $CH_2CHF_2$], [AA1969; 1, CH, Me, F, H, $CH_2CHF_2$], [AA1970; 1, CH, Me, Cl, H, $CH_2CHF_2$], [AA1971; 1, CH, Me, Br, H, $CH_2CHF_2$], [AA1972; 1, CH, Me, I, H, $CH_2CHF_2$], [AA1973; 1, CH, Me, $CF_3$, H, $CH_2CHF_2$], [AA1974; 1, CH, Me, $CF_2H$, H, $CH_2CHF_2$], [AA1975; 1, CH, Me, $C_2F_5$, H, $CH_2CHF_2$], [AA1976; 1, CH, Me, $C_3F_7$, H, $CH_2CHF_2$], [AA1977; 1, CH, Me, $CH_2CF_3$, H, $CH_2CHF_2$], [AA1978; 1, CH, Me, $CH_2CHF_2$, H, $CH_2CHF_2$], [AA1979; 2, CH, Me, H, H, $CH_2CHF_2$], [AA1980; 2, CH, Me, F, H, $CH_2CHF_2$], [AA1981; 2, CH, Me, Cl, H, $CH_2CHF_2$], [AA11982; 2, CH, Me, Br, H, $CH_2CHF_2$], [AA1983; 2, CH, Me, I, H, $CH_2CHF_2$], [AA1984; 2, CH, Me, $CF_3$, H, $CH_2CHF_2$], [AA1985; 2, CH, Me, $CF_2H$, H, $CH_2CHF_2$], [AA1986; 2, CH, Me, $C_2F_5$, H, $CH_2CHF_2$], [AA1987; 2, CH, Me, $C_3F_7$, H, $CH_2CHF_2$], [AA1988; 2, CH, Me, $CH_2CF_3$, H, $CH_2CHF_2$], [AA1989; 2, CH, Me, $CH_2CHF_2$, H, $CH_2CHF_2$], [AA1990; 0, N, Me, H, H, $CH_2CHF_2$], [AA1991; 0, N, Me, F, H, $CH_2CHF_2$], [AA1992; 0, N, Me, Cl, H, $CH_2CHF_2$], [AA1993; 0, N, Me, Br, H, $CH_2CHF_2$], [AA1994; 0, N, Me, I, H, $CH_2CHF_2$], [AA1995; 0, N, Me, $CF_3$, H, $CH_2CHF_2$], [AA1996; 0, N, Me, $CF_2H$, H, $CH_2CHF_2$], [AA1997; 0, N, Me, $C_2F_5$, H, $CH_2CHF_2$], [AA1998; 0, N, Me, $C_3F_7$, H, $CH_2CHF_2$], [AA1999; 0, N, Me, $CH_2CF_3$, H, $CH_2CHF_2$], [AA2000; 0, N, Me, $CH_2CHF_2$, H, $CH_2CHF_2$], [AA2001; 1, N, Me, H, H, $CH_2CHF_2$], [AA2002; 1, N, Me, F, H, $CH_2CHF_2$], [AA2003; 1, N, Me, Cl, H, $CH_2CHF_2$], [AA2004; 1, N, Me, Br, H, $CH_2CHF_2$], [AA2005; 1, N, Me, I, H, $CH_2CHF_2$], [AA2006; 1, N, Me, $CF_3$, H, $CH_2CHF_2$], [AA2007; 1, N, Me, $CF_2H$, H, $CH_2CHF_2$], [AA2008; 1, N, Me, $C_2F_5$, H, $CH_2CHF_2$], [AA2009; 1, N, Me, $C_3F_7$, H, $CH_2CHF_2$], [AA2010; 1, N, Me, $CH_2CF_3$, H, $CH_2CHF_2$], [AA2011; 1, N, Me, $CH_2CHF_2$, H, $CH_2CHF_2$], [AA2012; 2, N, Me, H, H, $CH_2CHF_2$], [AA2013; 2, N, Me, F, H, $CH_2CHF_2$], [AA2014; 2, N, Me, Cl, H, $CH_2CHF_2$], [AA2015; 2, N, Me, Br, H, $CH_2CHF_2$], [AA2016; 2, N, Me, I, H, $CH_2CHF_2$], [AA2017; 2, N, Me, $CF_3$, H, $CH_2CHF_2$], [AA2018; 2, N, Me, $CF_2H$, H, $CH_2CHF_2$], [AA2019; 2, N, Me, $C_2F_5$, H, $CH_2CHF_2$], [AA2020; 2, N, Me, $C_3F_7$, H, $CH_2CHF_2$], [AA2021; 2, N, Me, $CH_2CF_3$, H, $CH_2CHF_2$], [AA2022; 2, N, Me, $CH_2CHF_2$, H, $CH_2CHF_2$], [AA2023; 0, CH, Et, H, H, $CH_2CHF_2$], [AA2024; 0, CH, Et, F, H, $CH_2CHF_2$], [AA2025; 0, CH, Et, Cl, H, $CH_2CHF_2$], [AA2026; 0, CH, Et, Br, H, $CH_2CHF_2$], [AA2027; 0, CH, Et, I, H, $CH_2CHF_2$], [AA2028; 0, CH, Et, $CF_3$, H, $CH_2CHF_2$], [AA2029; 0, CH, Et, $CF_2H$, H, $CH_2CHF_2$], [AA2030; 0, CH, Et, $C_2F_5$, H, $CH_2CHF_2$], [AA2031; 0, CH, Et, $C_3F_7$, H, $CH_2CHF_2$], [AA2032; 0, CH, Et, $CH_2CF_3$, H, $CH_2CHF_2$], [AA2033; 0, CH, Et, $CH_2CHF_2$, H, $CH_2CHF_2$], [AA2034; 1, CH, Et, H, H, $CH_2CHF_2$], [AA2035; 1, CH, Et, F, H, $CH_2CHF_2$], [AA2036; 1, CH, Et, Cl, H, $CH_2CHF_2$], [AA2037; 1, CH, Et, Br, H, $CH_2CHF_2$], [AA2038; 1, CH, Et, I, H, $CH_2CHF_2$], [AA2039; 1, CH, Et, $CF_3$, H, $CH_2CHF_2$], [AA2040; 1, CH, Et, $CF_2H$, H, $CH_2CHF_2$], [AA2041; 1, CH, Et, $C_2F_5$, H, $CH_2CHF_2$], [AA2042; 1, CH, Et, $C_3F_7$, H, $CH_2CHF_2$], [AA2043; 1, CH, Et, $CH_2CF_3$, H, $CH_2CHF_2$], [AA2044; 1, CH, Et, $CH_2CHF_2$, H, $CH_2CHF_2$], [AA2045; 2, CH, Et, H, H, $CH_2CHF_2$], [AA2046; 2, CH, Et, F, H, $CH_2CHF_2$], [AA2047; 2, CH, Et, Cl, H, $CH_2CHF_2$], [AA2048; 2, CH, Et, Br, H, $CH_2CHF_2$], [AA2049; 2, CH, Et, I, H, $CH_2CHF_2$], [AA2050; 2, CH, Et, $CF_3$, H, $CH_2CHF_2$], [AA2051; 2, CH, Et, $CF_2H$, H, $CH_2CHF_2$], [AA2052; 2, CH, Et, $C_2F_5$, H, $CH_2CHF_2$], [AA2053; 2, CH, Et, $C_3F_7$, H, $CH_2CHF_2$], [AA2054; 2, CH, Et, $CH_2CF_3$, H, $CH_2CHF_2$], [AA2055; 2, CH, Et, CH CHF, H, CH, $CHF_2$], [AA2056; 0, N, Et, H, H, $CH_2CHF_2$], [AA2057; 0, N, Et, F, H, $CH_2CHF_2$], [AA2058; 0, N, Et, Cl, H, $CH_2CHF_2$], [AA2059; 0, N, Et, Br, H, $CH_2CHF_2$], [AA2060; 0, N, Et, I, H, $CH_2CHF_2$], [AA2061; 0, N, Et, $CF_3$, H, $CH_2CHF_2$], [AA2062; 0, N, Et, $CF_2H$, H, $CH_2CHF_2$], [AA2063; 0, N, Et, $C_2F_5$, H, $CH_2CHF_2$], [AA2064; 0, N, Et, $C_3F_7$, H, $CH_2CHF_2$], [AA2065; 0, N, Et, $CH_2CF_3$, H, $CH_2CHF_2$], [AA2066; 0, N, Et, $CH_2CHF_2$, H, $CH_2CHF_2$], [AA2067; 1, N, Et, H, H, $CH_2CHF_2$], [AA2068; 1, N, Et, F, H, $CH_2CHF_2$], [AA2069; 1, N, Et, Cl, H, $CH_2CHF_2$], [AA2070; 1, N, Et, Br, H, $CH_2CHF_2$], [AA2071; 1, N, Et, I, H, $CH_2CHF_2$], [AA2072; 1, N, Et, $CF_3$, H, $CH_2CHF_2$], [AA2073; 1, N, Et, $CF_2H$, H, $CH_2CHF_2$], [AA2074; 1, N, Et, $C_2F_5$, H, $CH_2CHF_2$], [AA2075; 1, N, Et, $C_3F_7$, H, $CH_2CHF_2$], [AA2076; 1, N, Et, $CH_2CF_3$, H, $CH_2CHF_2$], [AA2077; 1, N, Et, $CH_2CHF_2$, H, $CH_2CHF_2$], [AA2078; 2, N, Et, H, H, $CH_2CHF_2$], [AA2079; 2, N, Et, F, H, $CH_2CHF_2$], [AA2080; 2, N, Et, Cl, H, $CH_2CHF_2$], [AA2081; 2, N, Et, Br, H, $CH_2CHF_2$], [AA2082; 2, N, Et, I, H, $CH_2CHF_2$], [AA2083; 2, N, Et, $CF_3$, H, $CH_2CHF_2$], [AA2084; 2, N, Et, $CF_2H$, H, $CH_2CHF_2$], [AA2085; 2, N, Et, $C_2F_5$, H, $CH_2CHF_2$], [AA2086; 2, N, Et, $C_3F_7$, H, $CH_2CHF_2$], [AA2087; 2, N, Et, $CH_2CF_3$, H, $CH_2CHF_2$], [AA2088; 2, N, Et, $CH_2CHF_2$, H, $CH_2CHF_2$], [AA2089; 0, CH, iPr, H, H, $CH_2CHF_2$], [AA2090; 0, CH, iPr, F, H, $CH_2CHF_2$], [AA2091; 0, CH, iPr, Cl, H, $CH_2CHF_2$], [AA2092; 0, CH, iPr, Br, H, $CH_2CHF_2$], [AA2093; 0, CH, iPr, I, H, $CH_2CHF_2$], [AA2094; 0, CH, iPr, $CF_3$, H, $CH_2CHF_2$], [AA2095; 0, CH, iPr, $CF_2H$, H, $CH_2CHF_2$], [AA2096; 0, CH, iPr, $C_2F_5$, H, $CH_2CHF_2$], [AA2097; 0, CH, iPr, $C_3F_7$, H, $CH_2CHF_2$], [AA2098; 0, CH, iPr, $CH_2CF_3$, H, $CH_2CHF_2$], [AA2099; 0, CH, iPr, $CH_2CHF_2$, H, $CH_2CHF_2$], [AA2100; 1, CH, iPr, H, H, $CH_2CHF_2$], [AA2101; 1, CH, iPr, F, H, $CH_2CHF_2$], [AA2102; 1, CH, iPr, Cl, H, $CH_2CHF_2$], [AA2103; 1, CH, iPr, Br, H, $CH_2CHF_2$], [AA2104; 1, CH, iPr, I, H, $CH_2CHF_2$], [AA2105; 1, CH, iPr, $CF_3$, H, $CH_2CHF_2$], [AA2106; 1, CH, iPr, $CF_2H$, H, $CH_2CHF_2$], [AA2107; 1, CH, iPr, $C_2F_5$, H, $CH_2CHF_2$], [AA2108; 1, CH, iPr, $C_3F_7$, H, $CH_2CHF_2$], [AA2109; 1, CH, iPr, $CH_2CF_3$, H, $CH_2CHF_2$], [AA2110; 1, CH, iPr, $CH_2CHF_2$, H, $CH_2CHF_2$], [AA2111; 2, CH, iPr, H, H, $CH_2CHF_2$], [AA2112; 2, CH, iPr, F, H, $CH_2CHF_2$], [AA2113; 2, CH, iPr, Cl, H, $CH_2CHF_2$], [AA2114; 2, CH, iPr, Br, H, $CH_2CHF_2$], [AA2115; 2, CH, iPr, I, H, $CH_2CHF_2$], [AA2116; 2, CH, iPr, $CF_3$, H, $CH_2CHF_2$], [AA2117; 2, CH, iPr, $CF_2H$, H, $CH_2CHF_2$], [AA2118; 2, CH, iPr, $C_2F_5$, H, $CH_2CHF_2$], [AA2119; 2, CH, iPr, $C_3F_7$, H, $CH_2CHF_2$], [AA2120; 2, CH, iPr, $CH_2CF_3$, H, $CH_2CHF_2$], [AA2121; 2, CH, iPr, $CH_2CHF_2$, H, $CH_2CHF_2$], [AA2122; 0, N, iPr, H, H, $CH_2CHF_2$], [AA2123; 0, N, iPr, F, H, $CH_2CHF_2$], [AA2124; 0, N, iPr, Cl, H, $CH_2CHF_2$], [AA2125; 0, N, iPr, Br, H, $CH_2CHF_2$], [AA2126; 0, N, iPr, I, H, $CH_2CHF_2$], [AA2127; 0, N, iPr, $CF_3$, H, $CH_2CHF_2$], [AA2128; 0, N, iPr, $CF_2H$, H, $CH_2CHF_2$], [AA2129; 0, N, iPr, $C_2F_5$, H, $CH_2CHF_2$], [AA2130; 0, N, iPr, $C_3F_7$, H, $CH_2CHF_2$], [AA2131; 0, N, iPr, $CH_2CF_3$, H, $CH_2CHF_2$], [AA2132; 0, N, iPr, $CH_2CHF_2$, H, $CH_2CHF_2$], [AA2133; 1, N, iPr, H, H, $CH_2CHF_2$], [AA2134; 1, N, iPr, F, H, $CH_2CHF_2$], [AA2135; 1, N, iPr, Cl, H, $CH_2CHF_2$], [AA2136; 1, N, iPr, Br, H, $CH_2CHF_2$], [AA2137; 1, N, iPr, I, H, $CH_2CHF_2$], [AA2138; 1, N, iPr, $CF_3$, H, $CH_2CHF_2$], [AA2139; 1, N, iPr, $CF_2H$, H, $CH_2CHF_2$], [AA2140; 1, N, iPr, $C_2F_5$, H, $CH_2CHF_2$], [AA2141; 1, N, iPr, $C_3F_7$, H, $CH_2CHF_2$], [AA2142; 1, N, iPr, $CH_2CF_3$, H, $CH_2CHF_2$], [AA2143; 1, N, iPr, $CH_2CHF_2$, H, $CH_2CHF_2$], [AA2144; 2, N, iPr, H, H, $CH_2CHF_2$], [AA2145; 2, N, iPr, F, H, $CH_2CHF_2$], [AA2146; 2, N, iPr, Cl, H, $CH_2CHF_2$], [AA2147; 2, N, iPr, Br, H, $CH_2CHF_2$], [AA2148; 2, N, iPr, I, H, $CH_2CHF_2$], [AA2149; 2, N, iPr, $CF_3$, H, $CH_2CHF_2$], [AA2150; 2, N, iPr, $CF_2H$, H, $CH_2CHF_2$], [AA2151; 2, N, iPr, $C_2F_5$, H, $CH_2CHF_2$], [AA2152; 2, N, iPr, $C_3F_7$, H, $CH_2CHF_2$], [AA2153; 2, N, iPr, $CH_2CF_3$, H, $CH_2CHF_2$], [AA2154; 2, N, iPr, $CH_2CHF_2$, H, $CH_2CHF_2$], [AA2155; 0, CH, cPr, H, H, $CH_2CHF_2$], [AA2156; 0, CH, cPr, F, H, $CH_2CHF_2$], [AA2157; 0, CH, cPr, Cl, H, $CH_2CHF_2$], [AA2158; 0, CH, cPr, Br, H, $CH_2CHF_2$], [AA2159; 0, CH, cPr, I, H, $CH_2CHF_2$], [AA2160; 0, CH, cPr, $CF_3$, H, $CH_2CHF_2$], [AA2161; 0, CH, cPr, $CF_2H$, H, $CH_2CHF_2$], [AA2162; 0, CH, cPr, $C_2F_5$, H, $CH_2CHF_2$], [AA2163; 0, CH, cPr, $C_3F_7$, H, $CH_2CHF_2$], [AA2164; 0, CH, cPr, $CH_2CF_3$, H, $CH_2CHF_2$], [AA2165; 0, CH, cPr, $CH_2CHF_2$, H, $CH_2CHF_2$], [AA2166; 1, CH, cPr, H, H, $CH_2CHF_2$], [AA2167; 1, CH, cPr, F, H, $CH_2CHF_2$], [AA2168; 1, CH, cPr, Cl, H, $CH_2CHF_2$], [AA2169; 1, CH, cPr, Br, H, $CH_2CHF_2$], [AA2170; 1, CH, cPr, I, H, $CH_2CHF_2$], [AA2171; 1, CH, cPr, $CF_3$, H, $CH_2CHF_2$], [AA2172; 1, CH, cPr, $CF_2H$, H, $CH_2CHF_2$], [AA2173; 1, CH, cPr, $C_2F_5$, H, $CH_2CHF_2$], [AA2174; 1, CH, cPr, $C_3F_7$, H, $CH_2CHF_2$], [AA2175; 1, CH, cPr, $CH_2CF_3$, H, $CH_2CHF_2$], [AA2176; 1, CH, cPr, $CH_2CHF_2$, H, $CH_2CHF_2$], [AA2177; 2, CH, cPr, H, H, $CH_2CHF_2$], [AA2178; 2, CH, cPr, F, H, $CH_2CHF_2$], [AA2179; 2, CH, cPr, Cl, H, $CH_2CHF_2$], [AA2180; 2, CH, cPr, Br, H, $CH_2CHF_2$], [AA2181; 2, CH, cPr, I, H, $CH_2CHF_2$], [AA2182; 2, CH, cPr, $CF_3$, H, $CH_2CHF_2$], [AA2183; 2, CH, cPr, $CF_2H$, H, $CH_2CHF_2$], [AA2184; 2, CH, cPr, $C_2F_5$, H, $CH_2CHF_2$], [AA2185; 2, CH, cPr, $C_3F_7$, H, $CH_2CHF_2$], [AA2186; 2, CH, cPr, $CH_2CF_3$, H, $CH_2CHF_2$], [AA2187; 2, CH, cPr, $CH_2CHF_2$, H, $CH_2CHF_2$], [AA2188; 0, N, cPr, H, H, $CH_2CHF_2$], [AA2189; 0, N, cPr, F, H, $CH_2CHF_2$], [AA2190; 0, N, cPr, Cl, H, $CH_2CHF_2$], [AA2191; 0, N, cPr, Br, H, $CH_2CHF_2$], [AA2192; 0, N, cPr, I, H, $CH_2CHF_2$], [AA2193; 0, N, cPr, $CF_3$, H, $CH_2CHF_2$], [AA2194; 0, N, cPr, $CF_2H$, H, $CH_2CHF_2$], [AA2195; 0, N, cPr, $C_2F_5$, H, $CH_2CHF_2$], [AA2196; 0, N, cPr, $C_3F_7$, H, $CH_2CHF_2$], [AA2197; 0, N, cPr, $CH_2CF_3$, H, $CH_2CHF_2$], [AA2198; 0, N, cPr, $CH_2CHF_2$, H, $CH_2CHF_2$], [AA2199; 1, N, cPr, H, H, $CH_2CHF_2$], [AA2200; 1, N, cPr, F, H, $CH_2CHF_2$],

[AA2201; 1, N, cPr, Cl, H, $CH_2CHF_2$], [AA2202; 1, N, cPr, Br, H, $CH_2CHF_2$], [AA2203; 1, N, cPr, I, H, $CH_2CHF_2$], [AA2204; 1, N, cPr, $CF_3$, H, $CH_2CHF_2$], [AA2205; 1, N, cPr, $CF_2H$, H, $CH_2CHF_2$], [AA2206; 1, N, cPr, $C_2F_5$, H, $CH_2CHF_2$], [AA2207; 1, N, cPr, $C_3F_7$, H, $CH_2CHF_2$], [AA2208; 1, N, cPr, $CH_2CF_3$, H, $CH_2CHF_2$], [AA2209; 1, N, cPr, $CH_2CHF_2$, H, $CH_2CHF_2$], [AA2210; 2, N, cPr, H, H, $CH_2CHF_2$], [AA2211; 2, N, cPr, F, H, $CH_2CHF_2$], [AA2212; 2, N, cPr, Cl, H, $CH_2CHF_2$], [AA2213; 2, N, cPr, Br, H, $CH_2CHF_2$], [AA2214; 2, N, cPr, I, H, $CH_2CHF_2$], [AA2215; 2, N, cPr, $CF_3$, H, $CH_2CHF_2$], [AA2216; 2, N, cPr, $CF_2H$, H, $CH_2CHF_2$], [AA2217; 2, N, cPr, $C_2F_5$, H, $CH_2CHF_2$], [AA2218; 2, N, cPr, $C_3F_7$, H, $CH_2CHF_2$], [AA2219; 2, N, cPr, $CH_2CF_3$, H, $CH_2CHF_2$], [AA2220; 2, N, cPr, $CH_2CHF_2$, H, $CH_2CHF_2$], [AA2221; 0, CH, H, H, F, $CH_2CHF_2$], [AA2222; 0, CH, H, H, Cl, $CH_2CHF_2$], [AA2223; 0, CH, H, H, Br, $CH_2CHF_2$], [AA2224; 0, CH, H, H, I, $CH_2CHF_2$], [AA2225; 0, CH, H, H, $CF_3$, $CH_2CHF_2$], [AA2226; 0, CH, H, H, $CF_2H$, $CH_2CHF_2$], [AA2227; 0, CH, H, H, $C_2F_5$, $CH_2CHF_2$], [AA2228; 0, CH, H, H, $C_3F$, CH CHF], [AA2229; 0, CH, H, H, $CH_2CF_3$, $CH_2CHF_2$], [AA2230; 0, CH, H, H, $CH_2CHF_2$, $CH_2CHF_2$], [AA2231; 1, CH, H, H, F, $CH_2CHF_2$], [AA2232; 1, CH, H, H, Cl, $CH_2CHF_2$], [AA2233; 1, CH, H, H, Br, $CH_2CHF_2$], [AA2234; 1, CH, H, H, I, $CH_2CHF_2$], [AA2235; 1, CH, H, H, $CF_3$, $CH_2CHF_2$], [AA2236; 1, CH, H, H, $CF_2H$, $CH_2CHF_2$], [AA2237; 1, CH, H, H, $C_2F_5$, $CH_2CHF_2$], [AA2238; 1, CH, H, H, $C_3F_7$, $CH_2CHF_2$], [AA2239; 1, CH, H, H, $CH_2CF_3$, $CH_2CHF_2$], [AA2240; 1, CH, H, H, $CH_2CHF_2$, $CH_2CHF_2$], [AA2241; 2, CH, H, H, F, $CH_2CHF_2$], [AA2242; 2, CH, H, H, Cl, $CH_2CHF_2$], [AA2243; 2, CH, H, H, Br, $CH_2CHF_2$], [AA2244; 2, CH, H, H, I, $CH_2CHF_2$], [AA2245; 2, CH, H, H, $CF_3$, $CH_2CHF_2$], [AA2246; 2, CH, H, H, $CF_2H$, CH $CHF_2$], [AA2247; 2, CH, H, H, $C_2F_5$, $CH_2CHF_2$], [AA2248; 2, CH, H, H, $C_3F_7$, $CH_2CHF_2$], [AA2249; 2, CH, H, H, $CH_2CF_3$, $CH_2CHF_2$], [AA2250; 2, CH, H, H, $CH_2CHF_2$, $CH_2CHF_2$], [AA2251; 0, N, H, H, F, $CH_2CHF_2$], [AA2252; 0, N, H, H, Cl, $CH_2CHF_2$], [AA2253; 0, N, H, H, Br, $CH_2CHF_2$], [AA2254; 0, N, H, H, I, $CH_2CHF_2$], [AA2255; 0, N, H, H, $CF_3$, $CH_2CHF_2$], [AA2256; 0, N, H, H, $CF_2H$, $CH_2CHF_2$], [AA2257; 0, N, H, H, $C_2F_5$, $CH_2CHF_2$], [AA2258; 0, N, H, H, $C_3F_7$, $CH_2CHF_2$], [AA2259; 0, N, H, H, $CH_2CF_3$, $CH_2CHF_2$], [AA2260; 0, N, H, H, CH $CHF_2$, $CH_2CHF_2$], [AA2261; 1, N, H, H, F, $CH_2CHF_2$], [AA2262; 1, N, H, H, Cl, $CH_2CHF_2$], [AA2263; 1, N, H, H, Br, $CH_2CHF_2$], [AA2264; 1, N, H, H, I, $CH_2CHF_2$], [AA2265; 1, N, H, H, $CF_3$, $CH_2CHF_2$], [AA2266; 1, N, H, H, $CF_2H$, $CH_2CHF_2$], [AA2267; 1, N, H, H, $C_2F_5$, $CH_2CHF_2$], [AA2268; 1, N, H, H, $C_3F_7$, $CH_2CHF_2$], [AA2269; 1, N, H, H, $CH_2CF_3$, $CH_2CHF_2$], [AA2270; 1, N, H, H, $CH_2CHF_2$, $CH_2CHF_2$], [AA2271; 2, N, H, H, F, $CH_2CHF_2$], [AA2272; 2, N, H, H, Cl, $CH_2CHF_2$], [AA2273; 2, N, H, H, Br, $CH_2CHF_2$], [AA2274; 2, N, H, H, I, $CH_2CHF_2$], [AA2275; 2, N, H, H, $CF_3$, $CH_2CHF_2$], [AA2276; 2, N, H, H, $CF_2H$, $CH_2CHF_2$], [AA2277; 2, N, H, H, $C_2F_5$, $CH_2CHF_2$], [AA2278; 2, N, H, H, $C_3F_7$, $CH_2CHF_2$], [AA2279; 2, N, H, H, $CH_2CF_3$, $CH_2CHF_2$], [AA2280; 2, N, H, H, $CH_2CHF_2$, $CH_2CHF_2$], [AA2281; 0, CH, Me, H, F, $CH_2CHF_2$], [AA2282; 0, CH, Me, H, Cl, $CH_2CHF_2$], [AA2283; 0, CH, Me, H, Br, $CH_2CHF_2$], [AA2284; 0, CH, Me, H, I, $CH_2CHF_2$], [AA2285; 0, CH, Me, H, $CF_3$, $CH_2CHF_2$], [AA2286; 0, CH, Me, H, $CF_2H$, $CH_2CHF_2$], [AA2287; 0, CH, Me, H, $C_2F_5$, $CH_2CHF_2$], [AA22288; 0, CH, Me, H, $C_3F_7$, $CH_2CHF_2$], [AA2289; 0, CH, Me, H, $CH_2CF_3$, $CH_2CHF_2$], [AA2290; 0, CH, Me, H, $CH_2CHF_2$, $CH_2CHF_2$], [AA2291; 1, CH, Me, H, F, $CH_2CHF_2$], [AA2292; 1, CH, Me, H, Cl, $CH_2CHF_2$], [AA2293; 1, CH, Me, H, Br, $CH_2CHF_2$], [AA2294; 1, CH, Me, H, I, $CH_2CHF_2$], [AA2295; 1, CH, Me, H, $CF_3$, $CH_2CHF_2$], [AA2296; 1, CH, Me, H, $CF_2H$, $CH_2CHF_2$], [AA2297; 1, CH, Me, H, $C_2F_5$, $CH_2CHF_2$], [AA2298; 1, CH, Me, H, $C_3F_7$, $CH_2CHF_2$], [AA2299; 1, CH, Me, H, $CH_2CF_3$, $CH_2CHF_2$], [AA2300; 1, CH, Me, H, $CH_2CHF_2$, $CH_2CHF_2$], [AA2301; 2, CH, Me, H, F, $CH_2CHF_2$], [AA2302; 2, CH, Me, H, Cl, $CH_2CHF_2$], [AA2303; 2, CH, Me, H, Br, $CH_2CHF_2$], [AA2304; 2, CH, Me, H, I, $CH_2CHF_2$], [AA2305; 2, CH, Me, H, $CF_3$, $CH_2CHF_2$], [AA2306; 2, CH, Me, H, $CF_2H$, $CH_2CHF_2$], [AA2307; 2, CH, Me, H, $C_2F_5$, $CH_2CHF_2$], [AA2308; 2, CH, Me, H, $C_3F_7$, $CH_2CHF_2$], [AA2309; 2, CH, Me, H, $CH_2CF_3$, $CH_2CHF_2$], [AA2310; 2, CH, Me, H, $CH_2CHF_2$, $CH_2CHF_2$], [AA2311; 0, N, Me, H, F, $CH_2CHF_2$], [AA2312; 0, N, Me, H, Cl, $CH_2CHF_2$], [AA2313; 0, N, Me, H, Br, $CH_2CHF_2$], [AA2314; 0, N, Me, H, I, $CH_2CHF_2$], [AA2315; 0, N, Me, H, $CF_3$, $CH_2CHF_2$], [AA2316; 0, N, Me, H, $CF_2H$, $CH_2CHF_2$], [AA2317; 0, N, Me, H, $C_2F_5$, $CH_2CHF_2$], [AA2318; 0, N, Me, H, $C_3F_7$, $CH_2CHF_2$], [AA2319; 0, N, Me, H, $CH_2CF_3$, $CH_2CHF_2$], [AA2320; 0, N, Me, H, $CH_2CHF_2$, $CH_2CHF_2$], [AA2321; 1, N, Me, H, F, $CH_2CHF_2$], [AA2322; 1, N, Me, H, Cl, $CH_2CHF_2$], [AA2323; 1, N, Me, H, Br, $CH_2CHF_2$], [AA2324; 1, N, Me, H, I, $CH_2CHF_2$], [AA2325; 1, N, Me, H, $CF_3$, $CH_2CHF_2$], [AA2326; 1, N, Me, H, $CF_2H$, $CH_2CHF_2$], [AA2327; 1, N, Me, H, $C_2F_5$, $CH_2CHF_2$], [AA2328; 1, N, Me, H, $C_3F_7$, $CH_2CHF_2$], [AA2329; 1, N, Me, H, $CH_2CF_3$, $CH_2CHF_2$], [AA2330; 1, N, Me, H, $CH_2CHF_2$, $CH_2CHF_2$], [AA2331; 2, N, Me, H, F, $CH_2CHF_2$], [AA2332; 2, N, Me, H, Cl, $CH_2CHF_2$], [AA2333; 2, N, Me, H, Br, $CH_2CHF_2$], [AA2334; 2, N, Me, H, I, $CH_2CHF_2$], [AA2335; 2, N, Me, H, $CF_3$, $CH_2CHF_2$], [AA2336; 2, N, Me, H, $CF_2H$, $CH_2CHF_2$], [AA2337; 2, N, Me, H, $C_2F_5$, $CH_2CHF_2$], [AA2338; 2, N, Me, H, $C_3F_7$, $CH_2CHF_2$], [AA2339; 2, N, Me, H, $CH_2CF_3$, $CH_2CHF_2$], [AA2340; 2, N, Me, H, $CH_2CHF_2$, $CH_2CHF_2$], [AA2341; 0, CH, Et, H, F, $CH_2CHF_2$], [AA2342; 0, CH, Et, H, Cl, $CH_2CHF_2$], [AA2343; 0, CH, Et, H, Br, $CH_2CHF_2$], [AA2344; 0, CH, Et, H, I, $CH_2CHF_2$], [AA2345; 0, CH, Et, H, $CF_3$, $CH_2CHF_2$], [AA2346; 0, CH, Et, H, $CF_2H$, $CH_2CHF_2$], [AA2347; 0, CH, Et, H, $C_2F_5$, $CH_2CHF_2$], [AA2348; 0, CH, Et, H, $C_3F_7$, $CH_2CHF_2$], [AA2349; 0, CH, Et, H, $CH_2CF_3$, $CH_2CHF_2$], [AA2350; 0, CH, Et, H, $CH_2CHF_2$, $CH_2CHF_2$], [AA2351; 1, CH, Et, H, F, $CH_2CHF_2$], [AA2352; 1, CH, Et, H, Cl, $CH_2CHF_2$], [AA2353; 1, CH, Et, H, Br, $CH_2CHF_2$], [AA2354; 1, CH, Et, H, I, $CH_2CHF_2$], [AA2355; 1, CH, Et, H, $CF_3$, $CH_2CHF_2$], [AA2356; 1, CH, Et, H, $CF_2H$, $CH_2CHF_2$], [AA2357; 1, CH, Et, H, $C_2F_5$, $CH_3CHF_7$], [AA2358; 1, CH, Et, H, $C_3F_7$, $CH_2CHF_2$], [AA2359; 1, CH, Et, H, $CH_2CF_3$, $CH_2CHF_2$], [AA2360; 1, CH, Et, H, $CH_2CHF_2$, $CH_2CHF_2$], [AA2361; 2, CH, Et, H, F, $CH_2CHF_2$], [AA2362; 2, CH, Et, H, Cl, $CH_2CHF_2$], [AA2363; 2, CH, Et, H, Br, $CH_2CHF_2$], [AA2364; 2, CH, Et, H, I, $CH_2CHF_2$], [AA2365; 2, CH, Et, H, $CF_3$, $CH_2CHF_2$], [AA2366; 2, CH, Et, H, $CF_2H$, $CH_2CHF_2$], [AA2367; 2, CH, Et, H, $C_2F_5$, $CH_2CHF_2$], [AA2368; 2, CH, Et, H, $C_3F_7$, $CH_2CHF_2$], [AA2369; 2, CH, Et, H, $CH_2CF_3$, $CH_2CHF_2$], [AA2370; 2, CH, Et, H, $CH_2CHF_2$, $CH_2CHF_2$], [AA2371; 0, N, Et, H, F, $CH_2CHF_2$], [AA2372; 0, N, Et, H, Cl, $CH_2CHF_2$], [AA2373; 0, N, Et, H, Br, $CH_2CHF_2$], [AA2374; 0, N, Et, H, I, $CH_2CHF_2$], [AA2375; 0, N, Et, H, $CF_3$, $CH_2CHF_2$], [AA2376; 0, N, Et, H, $CF_2H$, $CH_2CHF_2$], [AA2377; 0, N, Et, H, $C_2F_5$, $CH_2CHF_2$], [AA2378; 0, N, Et, H, $C_3F_7$, $CH_2CHF_2$], [AA2379; 0, N, Et, H, $CH_2CF_3$, $CH_2CHF_2$], [AA2380; 0, N, Et, H, $CH_2CHF_2$, $CH_2CHF_2$], [AA2381; 1, N, Et, H, F, $CH_2CHF_2$], [AA2382; 1, N, Et, H,

Cl, $CH_2CHF_2$], [AA2383; 1, N, Et, H, Br, $CH_2CHF_2$], [AA2384; 1, N, Et, H, I, $CH_2CHF_2$], [AA2385; 1, N, Et, H, $CF_3$, $CH_2CHF_2$], [AA2386; 1, N, Et, H, $CF_2H$, $CH_2CHF_2$], [AA2387; 1, N, Et, H, $C_2F_5$, $CH_2CHF_2$], [AA2388; 1, N, Et, H, $C_3F_7$, $CH_2CHF_2$], [AA2389; 1, N, Et, H, $CH_2CF_3$, $CH_2CHF_2$], [AA2390; 1, N, Et, H, $CH_2CHF_2$, $CH_2CHF_2$], [AA2391; 2, N, Et, H, F, $CH_2CHF_2$], [AA2392; 2, N, Et, H, Cl, $CH_2CHF_2$], [AA2393; 2, N, Et, H, Br, $CH_2CHF_2$], [AA2394; 2, N, Et, H, I, $CH_2CHF_2$], [AA2395; 2, N, Et, H, $CF_3$, $CH_2CHF_2$], [AA2396; 2, N, Et, H, $CF_2H$, $CH_2CHF_2$], [AA2397; 2, N, Et, H, $C_2F_5$, $CH_2CHF_2$], [AA2398; 2, N, Et, H, $C_3F_7$, $CH_2CHF_2$], [AA2399; 2, N, Et, H, $CH_2CF_3$, $CH_2CHF_2$], [AA2400; 2, N, Et, H, $CH_2CHF_2$, $CH_2CHF_2$], [AA2401; 0, CH, iPr, H, F, $CH_2CHF_2$], [AA2402; 0, CH, iPr, H, Cl, $CH_2CHF_2$], [AA2403; 0, CH, iPr, H, Br, $CH_2CHF_2$], [AA2404; 0, CH, iPr, H, I, $CH_2CHF_2$], [AA2405; 0, CH, iPr, H, $CF_3$, $CH_2CHF_2$], [AA2406; 0, CH, iPr, H, $CF_2H$, $CH_2CHF_2$], [AA2407; 0, CH, iPr, H, $C_2F_5$, $CH_2CHF_2$], [AA2408; 0, CH, iPr, H, $C_3F_7$, $CH_2CHF_2$], [AA2409; 0, CH, iPr, H, $CH_2CF_3$, $CH_2CHF_2$], [AA2410; 0, CH, iPr, H, $CH_2CHF_2$, $CH_2CHF_2$], [AA2411; 1, CH, iPr, H, F, $CH_2CHF_2$], [AA2412; 1, CH, iPr, H, Cl, $CH_2CHF_2$], [AA2413; 1, CH, iPr, H, Br, $CH_2CHF_2$], [AA2414; 1, CH, iPr, H, I, $CH_2CHF_2$], [AA2415; 1, CH, iPr, H, $CF_3$, $CH_2CHF_2$], [AA2416; 1, CH, iPr, H, $CF_2H$, $CH_2CHF_2$], [AA2417; 1, CH, iPr, H, $C_2F_5$, $CH_2CHF_2$], [AA2418; 1, CH, iPr, H, $C_3F_7$, $CH_2CHF_2$], [AA2419; 1, CH, iPr, H, $CH_2CF_3$, $CH_2CHF_2$], [AA2420; 1, CH, iPr, H, $CH_2CHF_2$, $CH_2CHF_2$], [AA2421; 2, CH, iPr, H, F, $CH_2CHF_2$], [AA2422; 2, CH, iPr, H, Cl, $CH_2CHF_2$], [AA2423; 2, CH, iPr, H, Br, $CH_2CHF_2$], [AA2424; 2, CH, iPr, H, I, $CH_2CHF_2$], [AA2425; 2, CH, iPr, H, $CF_3$, $CH_2CHF_2$], [AA2426; 2, CH, iPr, H, $CF_2H$, $CH_2CHF_2$], [AA2427; 2, CH, iPr, H, $C_2F_5$, $CH_2CHF_2$], [AA2428; 2, CH, iPr, H, $C_3F_7$, $CH_2CHF_2$], [AA2429; 2, CH, iPr, H, $CH_2CF_3$, $CH_2CHF_2$], [AA2430; 2, CH, iPr, H, $CH_2CHF_2$, $CH_2CHF_2$], [AA2431; 0, N, iPr, H, F, $CH_2CHF_2$], [AA2432; 0, N, iPr, H, Cl, $CH_2CHF_2$], [AA2433; 0, N, iPr, H, Br, $CH_2CHF_2$], [AA2434; 0, N, iPr, H, I, $CH_2CHF_2$], [AA2435; 0, N, iPr, H, $CF_3$, $CH_2CHF_2$], [AA2436; 0, N, iPr, H, $CF_2H$, $CH_2CHF_2$], [AA2437; 0, N, iPr, H, $C_2F_5$, $CH_2CHF_2$], [AA2438; 0, N, iPr, H, $C_3F_7$, $CH_2CHF_2$], [AA2439; 0, N, iPr, H, $CH_2CF_3$, $CH_2CHF_2$], [AA2440; 0, N, iPr, H, $CH_2CHF_2$, $CH_2CHF_2$], [AA2441; 1, N, iPr, H, F, $CH_2CHF_2$], [AA2442; 1, N, iPr, H, Cl, $CH_2CHF_2$], [AA2443; 1, N, iPr, H, Br, $CH_2CHF_2$], [AA2444; 1, N, iPr, H, I, $CH_2CHF_2$], [AA2445; 1, N, iPr, H, $CF_3$, $CH_2CHF_2$], [AA2446; 1, N, iPr, H, $CF_2H$, $CH_2CHF_2$], [AA2447; 1, N, iPr, H, $C_2F_5$, $CH_2CHF_2$], [AA2448; 1, N, iPr, H, $C_3F_7$, $CH_2CHF_2$], [AA2449; 1, N, iPr, H, $CH_2CF_3$, $CH_2CHF_2$], [AA2450; 1, N, iPr, H, $CH_2CHF_2$, $CH_2CHF_2$], [AA2451; 2, N, iPr, H, F, $CH_2CHF_2$], [AA2452; 2, N, iPr, H, Cl, $CH_2CHF_2$], [AA2453; 2, N, iPr, H, Br, $CH_2CHF_2$], [AA2454; 2, N, iPr, H, I, $CH_2CHF_2$], [AA2455; 2, N, iPr, H, $CF_3$, $CH_2CHF_2$], [AA2456; 2, N, iPr, H, $CF_2H$, $CH_2CHF_2$], [AA2457; 2, N, iPr, H, $C_2F_5$, $CH_2CHF_2$], [AA2458; 2, N, iPr, H, $C_3F_7$, $CH_2CHF_2$], [AA2459; 2, N, iPr, H, $CH_2CF_3$, $CH_2CHF_2$], [AA2460; 2, N, iPr, H, $CH_2CHF_2$, $CH_2CHF_2$], [AA2461; 0, CH, cPr, H, F, $CH_2CHF_2$], [AA2462; 0, CH, cPr, H, Cl, $CH_2CHF_2$], [AA2463; 0, CH, cPr, H, Br, $CH_2CHF_2$], [AA2464; 0, CH, cPr, H, I, $CH_2CHF_2$], [AA2465; 0, CH, cPr, H, $CF_3$, $CH_2CHF_2$], [AA2466; 0, CH, cPr, H, $CF_2H$, $CH_2CHF_2$], [AA2467; 0, CH, cPr, H, $C_2F_5$, $CH_2CHF_2$], [AA2468; 0, CH, cPr, H, $C_3F_7$, $CH_2CHF_2$], [AA2469; 0, CH, cPr, H, $CH_2CF_3$, $CH_2CHF_2$], [AA2470; 0, CH, cPr, H, $CH_2CHF_2$, $CH_2CHF_2$], [AA2471; 1, CH, cPr, H, F, $CH_2CHF_2$], [AA2472; 1, CH, cPr, H, Cl, $CH_2CHF_2$], [AA2473; 1, CH, cPr, H, Br, $CH_2CHF_2$], [AA2474; 1, CH, cPr, H, I, $CH_2CHF_2$], [AA2475; 1, CH, cPr, H, $CF_3$, $CH_2CHF_2$], [AA2476; 1, CH, cPr, H, $CF_2H$, $CH_2CHF_2$], [AA2477; 1, CH, cPr, H, $C_2F_5$, $CH_2CHF_2$], [AA2478; 1, CH, cPr, H, $C_3F_7$, $CH_2CHF_2$], [AA2479; 1, CH, cPr, H, $CH_2CF_3$, $CH_2CHF_2$], [AA2480; 1, CH, cPr, H, $CH_2CHF_2$, $CH_2CHF_2$], [AA2481; 2, CH, cPr, H, F, $CH_2CHF_2$], [AA2482; 2, CH, cPr, H, Cl, $CH_2CHF_2$], [AA2483; 2, CH, cPr, H, Br, $CH_2CHF_2$], [AA2484; 2, CH, cPr, H, I, $CH_2CHF_2$], [AA2485; 2, CH, cPr, H, $CF_3$, $CH_2CHF_2$], [AA2486; 2, CH, cPr, H, $CF_2H$, $CH_2CHF_2$], [AA2487; 2, CH, cPr, H, $C_2F_5$, $CH_2CHF_2$], [AA2488; 2, CH, cPr, H, $C_3F_7$, $CH_2CHF_2$], [AA2489; 2, CH, cPr, H, $CH_2CF_3$, $CH_2CHF_2$], [AA2490; 2, CH, cPr, H, $CH_2CHF_2$, $CH_2CHF_2$], [AA2491; 0, N, cPr, H, F, $CH_2CHF_2$], [AA2492; 0, N, cPr, H, Cl, $CH_2CHF_2$], [AA2493; 0, N, cPr, H, Br, $CH_2CHF_2$], [AA2494; 0, N, cPr, H, I, $CH_2CHF_2$], [AA2495; 0, N, cPr, H, $CF_3$, $CH_2CHF_2$], [AA2496; 0, N, cPr, H, $CF_2H$, $CH_2CHF_2$], [AA2497; 0, N, cPr, H, $C_2F_5$, $CH_2CHF_2$], [AA2498; 0, N, cPr, H, $C_3F$, $CH_2CHF_2$], [AA2499; 0, N, cPr, H, $CH_2CF_3$, $CH_2CHF_2$], [AA2500; 0, N, cPr, H, $CH_2CHF_2$, $CH_2CHF_2$], [AA2501; 1, N, cPr, H, F, $CH_2CHF_2$], [AA2502; 1, N, cPr, H, Cl, $CH_2CHF_2$], [AA2503; 1, N, cPr, H, Br, $CH_2CHF_2$], [AA2504; 1, N, cPr, H, I, $CH_2CHF_2$], [AA2505; 1, N, cPr, H, $CF_3$, $CH_2CHF_2$], [AA2506; 1, N, cPr, H, $CF_2H$, $CH_2CHF_2$], [AA2507; 1, N, cPr, H, $C_2F_5$, $CH_2CHF_2$], [AA2508; 1, N, cPr, H, $C_3F_7$, $CH_2CHF_2$], [AA2509; 1, N, cPr, H, $CH_2CF_3$, $CH_2CHF_2$], [AA2510; 1, N, cPr, H, $CH_2CHF_2$, $CH_2CHF_2$], [AA2511; 2, N, cPr, H, F, $CH_2CHF_2$], [AA2512; 2, N, cPr, H, Cl, $CH_2CHF_2$], [AA2513; 2, N, cPr, H, Br, $CH_2CHF_2$], [AA2514; 2, N, cPr, H, I, $CH_2CHF_2$], [AA2515; 2, N, cPr, H, $CF_3$, $CH_2CHF_2$], [AA2516; 2, N, cPr, H, $CF_2H$, $CH_2CHF_2$], [AA2517; 2, N, cPr, H, $C_2F_5$, $CH_2CHF_2$], [AA2518; 2, N, cPr, H, $C_3F_7$, $CH_2CHF_2$], [AA2519; 2, N, cPr, H, $CH_2CF_3$, $CH_2CHF_2$], [AA2520; 2, N, cPr, H, $CH_2CHF_2$, $CH_2CHF_2$], [AA2521; 0, CH, H, H, H, $SCF_3$], [AA2522; 0, CH, H, F, H, $SCF_3$], [AA2523; 0, CH, H, Cl, H, $SCF_3$], [AA2524; 0, CH, H, Br, H, $SCF_3$], [AA2525; 0, CH, H, I, H, $SCF_3$], [AA2526; 0, CH, H, $CF_3$, H, $SCF_3$], [AA2527; 0, CH, H, $CF_2H$, H, $SCF_3$], [AA2528; 0, CH, H, $C_2F_5$, H, $SCF_3$], [AA2529; 0, CH, H, $C_3F_7$, H, $SCF_3$], [AA2530; 0, CH, H, $CH_2CF_3$, H, $SCF_3$], [AA2531; 0, CH, H, $CH_2CHF_2$, H, $SCF_3$], [AA2532; 1, CH, H, H, H, $SCF_3$], [AA2533; 1, CH, H, F, H, $SCF_3$], [AA2534; 1, CH, H, Cl, H, $SCF_3$], [AA2535; 1, CH, H, Br, H, $SCF_3$], [AA2536; 1, CH, H, I, H, $SCF_3$], [AA2537; 1, CH, H, $CF_3$, H, $SCF_3$], [AA2538; 1, CH, H, $CF_2H$, H, $SCF_3$], [AA2539; 1, CH, H, $C_2F_5$, H, $SCF_3$], [AA2540; 1, CH, H, $C_3F_5$, H, $SCF_3$], [AA2541; 1, CH, H, $CH_2CF_3$, H, $SCF_3$], [AA2542; 1, CH, H, $CH_2CHF_2$, H, $SCF_3$], [AA2543; 2, CH, H, H, H, $SCF_3$], [AA2544; 2, CH, H, F, H, $SCF_3$], [AA2545; 2, CH, H, Cl, H, $SCF_3$], [AA2546; 2, CH, H, Br, H, $SCF_3$], [AA2547; 2, CH, H, I, H, $SCF_3$], [AA2548; 2, CH, H, $CF_3$, H, $SCF_3$], [AA2549; 2, CH, H, $CF_2H$, H, $SCF_3$], [AA2550; 2, CH, H, $C_2F_5$, H, $SCF_3$], [AA2551; 2, CH, H, $C_3F_7$, H, $SCF_3$], [AA2552; 2, CH, H, $CH_2CF_3$, H, $SCF_3$], [AA2553; 2, CH, H, $CH_2CHF_2$, H, $SCF_3$], [AA2554; 0, N, H, H, H, $SCF_3$], [AA2555; 0, N, H, F, H, $SCF_3$], [AA2556; 0, N, H, Cl, H, $SCF_3$], [AA2557; 0, N, H, Br, H, $SCF_3$], [AA2558; 0, N, H, I, H, $SCF_3$], [AA2559; 0, N, H, $CF_3$, H, $SCF_3$], [AA2560; 0, N, H, $CF_2H$, H, $SCF_3$], [AA2561; 0, N, H, $C_2F_5$, H, $SCF_3$], [AA2562; 0, N, H, $C_3F_7$, H, $SCF_3$], [AA2563; 0, N, H, $CH_2CF_3$, H, $SCF_3$], [AA2564; 0, N, H, $CH_2CHF_2$, H, $SCF_3$], [AA2565; 1, N, H, H, H, $SCF_3$], [AA2566; 1, N, H, F, H, $SCF_3$], [AA2567; 1, N, H, Cl, H, $SCF_3$], [AA2568; 1, N, H, Br, H, $SCF_3$], [AA2569; 1, N, H, I, H, $SCF_3$], [AA2570; 1, N, H, $CF_3$, H, $SCF_3$], [AA2571; 1, N, H, $CF_2H$,

H, $SCF_3$], [AA2572; 1, N, H, $C_2F_5$, H, $SCF_3$], [AA2573; 1, N, H, $C_3F_7$, H, $SCF_3$], [AA2574; 1, N, H, $CH_2CF_3$, H, $SCF_3$], [AA2575; 1, N, H, $CH_2CHF_2$, H, $SCF_3$], [AA2576; 2, N, H, H, H, $SCF_3$], [AA2577; 2, N, H, F, H, $SCF_3$], [AA2578; 2, N, H, Cl, H, $SCF_3$], [AA2579; 2, N, H, Br, H, $SCF_3$], [AA2580; 2, N, H, I, H, $SCF_3$], [AA2581; 2, N, H, $CF_3$, H, $SCF_3$], [AA2582; 2, N, H, $CF_2H$, H, $SCF_3$], [AA2583; 2, N, H, $C_2F_5$, H, $SCF_3$], [AA2584; 2, N, H, $C_3F_7$, H, $SCF_3$], [AA2585; 2, N, H, $CH_2CF_3$, H, $SCF_3$], [AA2586; 2, N, H, $CH_2CHF_2$, H, $SCF_3$], [AA2587; 0, CH, Me, H, H, $SCF_3$], [AA2588; 0, CH, Me, F, H, $SCF_3$], [AA2589; 0, CH, Me, Cl, H, $SCF_3$], [AA2590; 0, CH, Me, Br, H, $SCF_3$], [AA2591; 0, CH, Me, I, H, $SCF_3$], [AA2592; 0, CH, Me, $CF_3$, H, $SCF_3$], [AA2593; 0, CH, Me, $CF_2H$, H, $SCF_3$], [AA2594; 0, CH, Me, $C_2F_5$, H, $SCF_3$], [AA2595; 0, CH, Me, $C_3F_7$, H, $SCF_3$], [AA2596; 0, CH, Me, $CH_2CF_3$, H, $SCF_3$], [AA2597; 0, CH, Me, $CH_2CHF_2$, H, $SCF_3$], [AA2598; 1, CH, Me, H, H, $SCF_3$], [AA2599; 1, CH, Me, F, H, $SCF_3$], [AA2600; 1, CH, Me, Cl, H, $SCF_3$], [AA2601; 1, CH, Me, Br, H, $SCF_3$], [AA2602; 1, CH, Me, I, H, $SCF_3$], [AA2603; 1, CH, Me, $CF_3$, H, $SCF_3$], [AA2604; 1, CH, Me, $CF_2H$, H, $SCF_3$], [AA2605; 1, CH, Me, $C_2F_5$, H, $SCF_3$], [AA2606; 1, CH, Me, $C_3F_7$, H, $SCF_3$], [AA2607; 1, CH, Me, $CH_2CF_3$, H, $SCF_3$], [AA2608; 1, CH, Me, $CH_2CHF_2$, H, $SCF_3$], [AA2609; 2, CH, Me, H, H, $SCF_3$], [AA2610; 2, CH, Me, F, H, $SCF_3$], [AA2611; 2, CH, Me, Cl, H, $SCF_3$], [AA2612; 2, CH, Me, Br, H, $SCF_3$], [AA2613; 2, CH, Me, I, H, $SCF_3$], [AA2614; 2, CH, Me, $CF_3$, H, $SCF_3$], [AA2615; 2, CH, Me, $CF_2H$, H, $SCF_3$], [AA2616; 2, CH, Me, $C_2F_5$, H, $SCF_3$], [AA2617; 2, CH, Me, $C_3F_7$, H, $SCF_3$], [AA2618; 2, CH, Me, $CH_2CF_3$, H, $SCF_3$], [AA2619; 2, CH, Me, $CH_2CHF_2$, H, $SCF_3$], [AA2620; 0, N, Me, H, H, $SCF_3$], [AA2621; 0, N, Me, F, H, $SCF_3$], [AA2622; 0, N, Me, Cl, H, $SCF_3$], [AA2623; 0, N, Me, Br, H, $SCF_3$], [AA2624; 0, N, Me, I, H, $SCF_3$], [AA2625; 0, N, Me, $CF_3$, H, $SCF_3$], [AA2626; 0, N, Me, $CF_2H$, H, $SCF_3$], [AA2627; 0, N, Me, $C_2F_5$, H, $SCF_3$], [AA2628; 0, N, Me, $C_3F_7$, H, $SCF_3$], [AA2629; 0, N, Me, $CH_2CF_3$, H, $SCF_3$], [AA2630; 0, N, Me, $CH_2CHF_2$, H, $SCF_3$], [AA2631; 1, N, Me, H, H, $SCF_3$], [AA2632; 1, N, Me, F, H, $SCF_3$], [AA2633; 1, N, Me, Cl, H, $SCF_3$], [AA2634; 1, N, Me, Br, H, $SCF_3$], [AA2635; 1, N, Me, I, H, $SCF_3$], [AA2636; 1, N, Me, $CF_3$, H, $SCF_3$], [AA2637; 1, N, Me, $CF_2H$, H, $SCF_3$], [AA2638; 1, N, Me, $C_2F_5$, H, $SCF_3$], [AA2639; 1, N, Me, $C_3F_7$, H, $SCF_3$], [AA2640; 1, N, Me, $CH_2CF_3$, H, $SCF_3$], [AA2641; 1, N, Me, $CH_2CHF_2$, H, $SCF_3$], [AA2642; 2, N, Me, H, H, $SCF_3$], [AA2643; 2, N, Me, F, H, $SCF_3$], [AA2644; 2, N, Me, Cl, H, $SCF_3$], [AA2645; 2, N, Me, Br, H, $SCF_3$], [AA2646; 2, N, Me, I, H, $SCF_3$], [AA2647; 2, N, Me, $CF_3$, H, $SCF_3$], [AA2648; 2, N, Me, $CF_2H$, H, $SCF_3$], [AA2649; 2, N, Me, $C_2F_5$, H, $SCF_3$], [AA2650; 2, N, Me, $C_3F_7$, H, $SCF_3$], [AA2651; 2, N, Me, $CH_2CF_3$, H, $SCF_3$], [AA2652; 2, N, Me, $CH_2CHF_2$, H, $SCF_3$], [AA2653; 0, CH, Et, H, H, $SCF_3$], [AA2654; 0, CH, Et, F, H, $SCF_3$], [AA2655; 0, CH, Et, Cl, H, $SCF_3$], [AA2656; 0, CH, Et, Br, H, $SCF_3$], [AA2657; 0, CH, Et, I, H, $SCF_3$], [AA2658; 0, CH, Et, $CF_3$, H, $SCF_3$], [AA2659; 0, CH, Et, $CF_2H$, H, $SCF_3$], [AA2660; 0, CH, Et, $C_2F_5$, H, $SCF_3$], [AA2661; 0, CH, Et, $C_3F_7$, H, $SCF_3$], [AA2662; 0, CH, Et, $CH_2CF_3$, H, $SCF_3$], [AA2663; 0, CH, Et, $CH_2CHF_2$, H, $SCF_3$], [AA2664; 1, CH, Et, H, H, $SCF_3$], [AA2665; 1, CH, Et, F, H, $SCF_3$], [AA2666; 1, CH, Et, Cl, H, $SCF_3$], [AA2667; 1, CH, Et, Br, H, $SCF_3$], [AA2668; 1, CH, Et, I, H, $SCF_3$], [AA2669; 1, CH, Et, $CF_3$, H, $SCF_3$], [AA2670; 1, CH, Et, $CF_2H$, H, $SCF_3$], [AA2671; 1, CH, Et, $C_2F_5$, H, $SCF_3$], [AA2672; 1, CH, Et, $C_3F_7$, H, $SCF_3$], [AA2673; 1, CH, Et, $CH_2CF_3$, H, $SCF_3$], [AA2674; 1, CH, Et, $CH_2CHF_2$, H, $SCF_3$], [AA2675; 2, CH, Et, H, H, $SCF_3$], [AA2676; 2, CH, Et, F, H, $SCF_3$], [AA2677; 2, CH, Et, Cl, H, $SCF_3$], [AA2678; 2, CH, Et, Br, H, $SCF_3$], [AA2679; 2, CH, Et, I, H, $SCF_3$], [AA2680; 2, CH, Et, $CF_3$, H, $SCF_3$], [AA2681; 2, CH, Et, $CF_2H$, H, $SCF_3$], [AA2682; 2, CH, Et, $C_2F_5$, H, $SCF_3$], [AA2683; 2, CH, Et, $C_3F_7$, H, $SCF_3$], [AA2684; 2, CH, Et, $CH_2CF_3$, H, $SCF_3$], [AA2685; 2, CH, Et, $CH_2CHF_2$, H, $SCF_3$], [AA2686; 0, N, Et, H, H, $SCF_3$], [AA2687; 0, N, Et, F, H, $SCF_3$], [AA2688; 0, N, Et, Cl, H, $SCF_3$], [AA2689; 0, N, Et, Br, H, $SCF_3$], [AA2690; 0, N, Et, I, H, $SCF_3$], [AA2691; 0, N, Et, $CF_3$, H, $SCF_3$], [AA2692; 0, N, Et, $CF_2H$, H, $SCF_3$], [AA2693; 0, N, Et, $C_2F_5$, H, $SCF_3$], [AA2694; 0, N, Et, $C_3F_7$, H, $SCF_3$], [AA2695; 0, N, Et, $CH_2CF_3$, H, $SCF_3$], [AA2696; 0, N, Et, $CH_2CHF_2$, H, $SCF_3$], [AA2697; 1, N, Et, H, H, $SCF_3$], [AA2698; 1, N, Et, F, H, $SCF_3$], [AA2699; 1, N, Et, Cl, H, $SCF_3$], [AA2700; 1, N, Et, Br, H, $SCF_3$], [AA2701; 1, N, Et, I, H, $SCF_3$], [AA2702; 1, N, Et, $CF_3$, H, $SCF_3$], [AA2703; 1, N, Et, $CF_2H$, H, $SCF_3$], [AA2704; 1, N, Et, $C_2F_5$, H, $SCF_3$], [AA2705; 1, N, Et, $C_3F_7$, H, $SCF_3$], [AA2706; 1, N, Et, $CH_2CF_3$, H, $SCF_3$], [AA2707; 1, N, Et, $CH_2CHF_2$, H, $SCF_3$], [AA2708; 2, N, Et, H, H, $SCF_3$], [AA2709; 2, N, Et, F, H, $SCF_3$], [AA2710; 2, N, Et, Cl, H, $SCF_3$], [AA2711; 2, N, Et, Br, H, $SCF_3$], [AA2712; 2, N, Et, I, H, $SCF_3$], [AA2713; 2, N, Et, $CF_3$, H, $SCF_3$], [AA2714; 2, N, Et, $CF_2H$, H, $SCF_3$], [AA2715; 2, N, Et, $C_2F_5$, H, $SCF_3$], [AA2716; 2, N, Et, $C_3F_7$, H, $SCF_3$], [AA2717; 2, N, Et, $CH_2CF_3$, H, $SCF_3$], [AA2718; 2, N, Et, $CH_2CHF_2$, H, $SCF_3$], [AA2719; 0, CH, iPr, H, H, $SCF_3$], [AA2720; 0, CH, iPr, F, H, $SCF_3$], [AA2721; 0, CH, iPr, Cl, H, $SCF_3$], [AA2722; 0, CH, iPr, Br, H, $SCF_3$], [AA2723; 0, CH, iPr, I, H, $SCF_3$], [AA2724; 0, CH, iPr, $CF_3$, H, $SCF_3$], [AA2725; 0, CH, iPr, $CF_2H$, H, $SCF_3$], [AA2726; 0, CH, iPr, $C_2F_5$, H, $SCF_3$], [AA2727; 0, CH, iPr, $C_3F_7$, H, $SCF_3$], [AA2728; 0, CH, iPr, $CH_2CF_3$, H, $SCF_3$], [AA2729; 0, CH, iPr, $CH_2CHF_2$, H, $SCF_3$], [AA2730; 1, CH, iPr, H, H, $SCF_3$], [AA2731; 1, CH, iPr, F, H, $SCF_3$], [AA2732; 1, CH, iPr, Cl, H, $SCF_3$], [AA2733; 1, CH, iPr, Br, H, $SCF_3$], [AA2734; 1, CH, iPr, I, H, $SCF_3$], [AA2735; 1, CH, iPr, $CF_3$, H, $SCF_3$], [AA2736; 1, CH, iPr, $CF_2H$, H, $SCF_3$], [AA2737; 1, CH, iPr, $C_2F_5$, H, $SCF_3$], [AA2738; 1, CH, iPr, $C_3F_7$, H, $SCF_3$], [AA2739; 1, CH, iPr, $CH_2CF_3$, H, $SCF_3$], [AA2740; 1, CH, iPr, $CH_2CHF_2$, H, $SCF_3$], [AA2741; 2, CH, iPr, H, H, $SCF_3$], [AA2742; 2, CH, iPr, F, H, $SCF_3$], [AA2743; 2, CH, iPr, Cl, H, $SCF_3$], [AA2744; 2, CH, iPr, Br, H, $SCF_3$], [AA2745; 2, CH, iPr, I, H, $SCF_3$], [AA2746; 2, CH, iPr, $CF_3$, H, $SCF_3$], [AA2747; 2, CH, iPr, $CF_2H$, H, $SCF_3$], [AA2748; 2, CH, iPr, $C_2F_5$, H, $SCF_3$], [AA2749; 2, CH, iPr, $C_3F_7$, H, $SCF_3$], [AA2750; 2, CH, iPr, $CH_2CF_3$, H, $SCF_3$], [AA2751; 2, CH, iPr, $CH_2CHF_2$, H, $SCF_3$], [AA2752; 0, N, iPr, H, H, $SCF_3$], [AA2753; 0, N, iPr, F, H, $SCF_3$], [AA2754; 0, N, iPr, Cl, H, $SCF_3$], [AA2755; 0, N, iPr, Br, H, $SCF_3$], [AA2756; 0, N, iPr, I, H, $SCF_3$], [AA2757; 0, N, iPr, $CF_3$, H, $SCF_3$], [AA2758; 0, N, iPr, $CF_2H$, H, $SCF_3$], [AA2759; 0, N, iPr, $C_2F_5$, H, $SCF_3$], [AA2760; 0, N, iPr, $C_3F_7$, H, $SCF_3$], [AA2761; 0, N, iPr, $CH_2CF_3$, H, $SCF_3$], [AA2762; 0, N, iPr, $CH_2CHF_2$, H, $SCF_3$], [AA2763; 1, N, iPr, H, H, $SCF_3$], [AA2764; 1, N, iPr, F, H, $SCF_3$], [AA2765; 1, N, iPr, Cl, H, $SCF_3$], [AA2766; 1, N, iPr, Br, H, $SCF_3$], [AA2767; 1, N, iPr, I, H, $SCF_3$], [AA2768; 1, N, iPr, $CF_3$, H, $SCF_3$], [AA2769; 1, N, iPr, $CF_2H$, H, $SCF_3$], [AA2770; 1, N, iPr, $C_2F$, H, $SCF_3$], [AA2771; 1, N, iPr, $C_3F_7$, H, $SCF_3$], [AA2772; 1, N, iPr, $CH_2CF_3$, H, $SCF_3$], [AA2773; 1, N, iPr, $CH_2CHF_2$, H, $SCF_3$], [AA2774; 2, N, iPr, H, H, $SCF_3$], [AA2775; 2, N, iPr, F, H, $SCF_3$], [AA2776; 2, N, iPr, Cl, H, $SCF_3$], [AA2777; 2, N, iPr, Br, H, $SCF_3$], [AA2778; 2, N, iPr, I, H, $SCF_3$], [AA2779; 2, N, iPr, $CF_3$, H, $SCF_3$], [AA2780; 2, N, iPr, $CF_2H$, H, $SCF_3$], [AA2781; 2, N, iPr, $C_2F_5$, H, $SCF_3$], [AA2782; 2, N, iPr, $C_3F_7$, H, $SCF_3$], [AA2783; 2, N, iPr, $CH_2CF_3$, H, $SCF_3$], [AA2784; 2, N, iPr, $CH_2CHF_2$, H, $SCF_3$], [AA2785; 0, CH, cPr, H, H, $SCF_3$], [AA2786; 0, CH, cPr, F, H, $SCF_3$], [AA2787; 0, CH, cPr, Cl, H, $SCF_3$], [AA2788; 0, CH, cPr, Br, H, $SCF_3$], [AA2789; 0, CH, cPr, I, H, $SCF_3$], [AA2790; 0, CH, cPr, $CF_3$, H, $SCF_3$], [AA2791; 0, CH, cPr, $CF_2H$, H, $SCF_3$], [AA2792; 0, CH, cPr, $C_2F_5$, H, $SCF_3$], [AA2793; 0, CH, cPr, $C_3F_7$, H, $SCF_3$], [AA2794; 0, CH, cPr, $CH_2CF_3$, H, $SCF_3$], [AA2795; 0, CH, cPr, $CH_2CHF_2$, H, $SCF_3$], [AA2796; 1, CH, cPr, H, H, $SCF_3$], [AA2797; 1, CH, cPr, F, H, $SCF_3$], [AA2798; 1, CH, cPr, Cl, H, $SCF_3$], [AA2799; 1, CH, cPr, Br, H, $SCF_3$], [AA2800; 1, CH, cPr, I, H, $SCF_3$], [AA2801; 1, CH, cPr, $CF_3$, H, $SCF_3$], [AA2802; 1, CH, cPr, $CF_2H$, H, $SCF_3$], [AA2803; 1, CH, cPr, $C_2F_5$, H, $SCF_3$], [AA2804; 1, CH, cPr, $C_3F_7$, H, $SCF_3$], [AA2805; 1, CH, cPr, $CH_2CF_3$, H, $SCF_3$], [AA2806; 1, CH, cPr, $CH_2CHF_2$, H, $SCF_3$], [AA2807; 2, CH, cPr, H, H, $SCF_3$], [AA2808; 2, CH, cPr, F, H, $SCF_3$], [AA2809; 2, CH, cPr, Cl, H, $SCF_3$], [AA2810; 2, CH, cPr, Br, H, $SCF_3$], [AA2811; 2, CH, cPr, I, H, $SCF_3$], [AA2812; 2, CH, cPr, $CF_3$, H, $SCF_3$], [AA2813; 2, CH, cPr, $CF_2H$, H, $SCF_3$], [AA2814; 2, CH, cPr, $C_2F_5$, H, $SCF_3$], [AA2815; 2, CH, cPr, $C_3F_7$, H, $SCF_3$], [AA2816; 2, CH, cPr, $CH_2CF_3$, H, $SCF_3$], [AA2817; 2, CH, cPr, $CH_2CHF_2$, H, $SCF_3$], [AA2818; 0, N, cPr, H, H, $SCF_3$], [AA2819; 0, N, cPr, F, H, $SCF_3$], [AA2820; 0, N, cPr, Cl, H, $SCF_3$], [AA2821; 0, N, cPr, Br, H, $SCF_3$], [AA2822; 0, N, cPr, I, H, $SCF_3$], [AA2823; 0, N, cPr, $CF_3$, H, $SCF_3$], [AA2824; 0, N, cPr, $CF_2H$, H, $SCF_3$], [AA2825; 0, N, cPr, $C_2F_5$, H, $SCF_3$], [AA2826; 0, N, cPr, $C_3F_7$, H, $SCF_3$], [AA2827; 0, N, cPr, $CH_2CF_3$, H, $SCF_3$], [AA2828; 0, N, cPr, $CH_2CHF_2$, H, $SCF_3$], [AA2829; 1, N, cPr, H, H, $SCF_3$], [AA2830; 1, N, cPr, F, H, $SCF_3$], [AA2831; 1, N, cPr, Cl, H, $SCF_3$], [AA2832; 1, N, cPr, Br, H, $SCF_3$], [AA2833; 1, N, cPr, I, H, $SCF_3$], [AA2834; 1, N, cPr, $CF_3$, H, $SCF_3$], [AA2835; 1, N, cPr, $CF_2H$, H, $SCF_3$], [AA2836; 1, N, cPr, $C_2F_5$, H, $SCF_3$], [AA2837; 1, N, cPr, $C_3F_7$, H, $SCF_3$], [AA2838; 1, N, cPr, $CH_2CF_3$, H, $SCF_3$], [AA2839; 1, N, cPr, $CH_2CHF_2$, H, $SCF_3$], [AA2840; 2, N, cPr, H, H, $SCF_3$], [AA2841; 2, N, cPr, F, H, $SCF_3$], [AA2842; 2, N, cPr, Cl, H, $SCF_3$], [AA2843; 2, N, cPr, Br, H, $SCF_3$], [AA2844; 2, N, cPr, I, H, $SCF_3$], [AA2845; 2, N, cPr, $CF_3$, H, $SCF_3$], [AA2846; 2, N, cPr, $CF_2H$, H, $SCF_3$], [AA2847; 2, N, cPr, $C_2F_5$, H, $SCF_3$], [AA2848; 2, N, cPr, $C_3F_7$, H, $SCF_3$], [AA2849; 2, N, cPr, $CH_2CF_3$, H, $SCF_3$], [AA2850; 2, N, cPr, $CH_2CHF_2$, H, $SCF_3$], [AA2851; 0, CH, H, H, F, $SCF_3$], [AA2852; 0, CH, H, H, Cl, $SCF_3$], [AA2853; 0, CH, H, H, Br, $SCF_3$], [AA2854; 0, CH, H, H, I, $SCF_3$], [AA2855; 0, CH, H, H, $CF_3$, $SCF_3$], [AA2856; 0, CH, H, H, $CF_2H$, $SCF_3$], [AA2857; 0, CH, H, H, $C_2F_5$, $SCF_3$], [AA2858; 0, CH, H, H, $C_3F_7$, $SCF_3$], [AA2859; 0, CH, H, H, $CH_2CF_3$, $SCF_3$], [AA2860; 0, CH, H, H, $CH_2CHF_2$, $SCF_3$], [AA2861; 1, CH, H, H, F, $SCF_3$], [AA2862; 1, CH, H, H, Cl, $SCF_3$], [AA2863; 1, CH, H, H, Br, $SCF_3$], [AA2864; 1, CH, H, H, I, $SCF_3$], [AA2865; 1, CH, H, H, $CF_3$, $SCF_3$], [AA2866; 1, CH, H, H, $CF_2H$, $SCF_3$], [AA2867; 1, CH, H, H, $C_2F_5$, $SCF_3$], [AA2868; 1, CH, H, H, $C_3F_7$, $SCF_3$], [AA2869; 1, CH, H, H, $CH_2CF_3$, $SCF_3$], [AA2870; 1, CH, H, H, $CH_2CHF_2$, $SCF_3$], [AA2871; 2, CH, H, H, F, $SCF_3$], [AA2872; 2, CH, H, H, Cl, $SCF_3$], [AA2873; 2, CH, H, H, Br, $SCF_3$], [AA2874; 2, CH, H, H, I, $SCF_3$], [AA2875; 2, CH, H, H, $CF_3$, $SCF_3$], [AA2876; 2, CH, H, H, $CF_2H$, $SCF_3$], [AA2877; 2, CH, H, H, $C_2F_5$, $SCF_3$], [AA2878; 2, CH, H, H, $C_3F_7$, $SCF_3$], [AA2879; 2, CH, H, H, $CH_2CF_3$, $SCF_3$], [AA2880; 2, CH, H, H, $CH_2CHF_2$, $SCF_3$], [AA2881; 0, N, H, H, F, $SCF_3$], [AA2882; 0, N, H, H, Cl, $SCF_3$], [AA2883; 0, N, H, H, Br, $SCF_3$], [AA2884; 0, N, H, H, I, $SCF_3$], [AA2885; 0, N, H, H, $CF_3$, $SCF_3$], [AA2886; 0, N, H, H, $CF_2H$, $SCF_3$], [AA2887; 0, N, H, H, $C_2F_5$, $SCF_3$], [AA2888; 0, N, H, H, $C_3F_7$, $SCF_3$], [AA2889; 0, N, H, H, $CH_2CF_3$, $SCF_3$], [AA2890; 0, N, H, H, $CH_2CHF_2$, $SCF_3$], [AA2891; 1, N, H, H, F, $SCF_3$], [AA2892; 1, N, H, H, Cl, $SCF_3$], [AA2893; 1, N, H, H, Br, $SCF_3$], [AA2894; 1, N, H, H, I, $SCF_3$], [AA2895; 1, N, H, H, $CF_3$, $SCF_3$], [AA2896; 1, N, H, H, $CF_2H$, $SCF_3$], [AA2897; 1, N, H, H, $C_2F_5$, $SCF_3$], [AA2898; 1, N, H, H, $C_3F_7$, $SCF_3$], [AA2899; 1, N, H, H, $CH_2CF_3$, $SCF_3$], [AA2900; 1, N, H, H, $CH_2CHF_2$, $SCF_3$], [AA2901; 2, N, H, H, F, $SCF_3$], [AA2902; 2, N, H, H, Cl, $SCF_3$], [AA2903; 2, N, H, H, Br, $SCF_3$], [AA2904; 2, N, H, H, I, $SCF_3$], [AA2905; 2, N, H, H, $CF_3$, $SCF_3$], [AA2906; 2, N, H, H, $CF_2H$, $SCF_3$], [AA2907; 2, N, H, H, $C_2F_5$, $SCF_3$], [AA2908; 2, N, H, H, $C_3F_7$, $SCF_3$], [AA2909; 2, N, H, H, $CH_2CF_3$, $SCF_3$], [AA2910; 2, N, H, H, $CH_2CHF_2$, $SCF_3$], [AA2911; 0, CH, Me, H, F, $SCF_3$], [AA2912; 0, CH, Me, H, Cl, $SCF_3$], [AA2913; 0, CH, Me, H, Br, $SCF_3$], [AA2914; 0, CH, Me, H, I, $SCF_3$], [AA2915; 0, CH, Me, H, $CF_3$, $SCF_3$], [AA2916; 0, CH, Me, H, $CF_2H$, $SCF_3$], [AA2917; 0, CH, Me, H, $C_2F_5$, $SCF_3$], [AA2918; 0, CH, Me, H, $C_3F_7$, $SCF_3$], [AA2919; 0, CH, Me, H, $CH_2CF_3$, $SCF_3$], [AA2920; 0, CH, Me, H, $CH_2CHF_2$, $SCF_3$], [AA2921; 1, CH, Me, H, F, $SCF_3$], [AA2922; 1, CH, Me, H, Cl, $SCF_3$], [AA2923; 1, CH, Me, H, Br, $SCF_3$], [AA2924; 1, CH, Me, H, I, $SCF_3$], [AA2925; 1, CH, Me, H, $CF_3$, $SCF_3$], [AA2926; 1, CH, Me, H, $CF_2H$, $SCF_3$], [AA2927; 1, CH, Me, H, $C_2F_5$, $SCF_3$], [AA2928; 1, CH, Me, H, $C_3F_7$, $SCF_3$], [AA2929; 1, CH, Me, H, $CH_2CF_3$, $SCF_3$], [AA2930; 1, CH, Me, H, $CH_2CHF_2$, $SCF_3$], [AA2931; 2, CH, Me, H, F, $SCF_3$], [AA2932; 2, CH, Me, H, Cl, $SCF_3$], [AA2933; 2, CH, Me, H, Br, $SCF_3$], [AA2934; 2, CH, Me, H, I, $SCF_3$], [AA2935; 2, CH, Me, H, $CF_3$, $SCF_3$], [AA2936; 2, CH, Me, H, $CF_2H$, $SCF_3$], [AA2937; 2, CH, Me, H, $C_2F_5$, $SCF_3$], [AA2938; 2, CH, Me, H, $C_3F_7$, $SCF_3$], [AA2939; 2, CH, Me, H, $CH_2CF_3$, $SCF_3$], [AA2940; 2, CH, Me, H, $CH_2CHF_2$, $SCF_3$], [AA2941; 0, N, Me, H, F, $SCF_3$], [AA2942; 0, N, Me, H, Cl, $SCF_3$], [AA2943; 0, N, Me, H, Br, $SCF_3$], [AA2944; 0, N, Me, H, I, $SCF_3$], [AA2945; 0, N, Me, H, $CF_3$, $SCF_3$], [AA2946; 0, N, Me, H, $CF_2H$, $SCF_3$], [AA2947; 0, N, Me, H, $C_2F_5$, $SCF_3$], [AA2948; 0, N, Me, H, $C_3F_7$, $SCF_3$], [AA2949; 0, N, Me, H, $CH_2CF_3$, $SCF_3$], [AA2950; 0, N, Me, H, $CH_2CHF_2$, $SCF_3$], [AA2951; 1, N, Me, H, F, $SCF_3$], [AA2952; 1, N, Me, H, Cl, $SCF_3$], [AA2953; 1, N, Me, H, Br, $SCF_3$], [AA2954; 1, N, Me, H, I, $SCF_3$], [AA2955; 1, N, Me, H, $CF_3$, $SCF_3$], [AA2956; 1, N, Me, H, $CF_2H$, $SCF_3$], [AA2957; 1, N, Me, H, $C_2F_5$, $SCF_3$], [AA2958; 1, N, Me, H, $C_3F_7$, $SCF_3$], [AA2959; 1, N, Me, H, $CH_2CF_3$, $SCF_3$], [AA2960; 1, N, Me, H, $CH_2CHF_2$, $SCF_3$], [AA2961; 2, N, Me, H, F, $SCF_3$], [AA2962; 2, N, Me, H, Cl, $SCF_3$], [AA2963; 2, N, Me, H, Br, $SCF_3$], [AA2964; 2, N, Me, H, I, $SCF_3$], [AA2965; 2, N, Me, H, $CF_3$, $SCF_3$], [AA2966; 2, N, Me, H, $CF_2H$, $SCF_3$], [AA2967; 2, N, Me, H, $C_2F_5$, $SCF_3$], [AA2968; 2, N, Me, H, $C_3F_7$, $SCF_3$], [AA2969; 2, N, Me, H, $CH_2CF_3$, $SCF_3$], [AA2970; 2, N, Me, H, $CH_2CHF_2$, $SCF_3$], [AA2971; 0, CH, Et, H, F, $SCF_3$], [AA2972; 0, CH, Et, H, Cl, $SCF_3$], [AA2973; 0, CH, Et, H, Br, $SCF_3$], [AA2974; 0, CH, Et, H, I, $SCF_3$], [AA2975; 0, CH, Et, H, $CF_3$, $SCF_3$], [AA2976; 0, CH, Et, H, $CF_2H$, $SCF_3$], [AA2977; 0, CH, Et, H, $C_2F_5$, $SCF_3$], [AA2978; 0, CH, Et, H, $C_3F_7$, $SCF_3$], [AA2979; 0, CH, Et, H, $CH_2CF_3$, $SCF_3$], [AA2980; 0, CH, Et, H, $CH_2CHF_2$, $SCF_3$], [AA2981; 1, CH, Et, H, F, $SCF_3$], [AA2982; 1, CH, Et, H, Cl, $SCF_3$], [AA2983; 1, CH, Et, H, Br, $SCF_3$], [AA2984; 1, CH, Et, H, I, $SCF_3$], [AA2985; 1, CH, Et, H, $CF_3$, $SCF_3$], [AA2986; 1, CH, Et, H, $CF_2H$, $SCF_3$], [AA2987; 1, CH, Et, H, $C_2F_5$, $SCF_3$], [AA2988; 1,

CH, Et, H, $C_3F_7$, $SCF_3$], [AA2989; 1, CH, Et, H, $CH_2CF_3$, $SCF_3$], [AA2990; 1, CH, Et, H, $CH_2CHF_2$, $SCF_3$], [AA2991; 2, CH, Et, H, F, $SCF_3$], [AA2992; 2, CH, Et, H, Cl, $SCF_3$], [AA2993; 2, CH, Et, H, Br, $SCF_3$], [AA2994; 2, CH, Et, H, I, $SCF_3$], [AA2995; 2, CH, Et, H, $CF_3$, $SCF_3$], [AA2996; 2, CH, Et, H, $CF_2H$, $SCF_3$], [AA2997; 2, CH, Et, H, $C_2F_5$, $SCF_3$], [AA2998; 2, CH, Et, H, $C_3F_7$, $SCF_3$], [AA2999; 2, CH, Et, H, $CH_2CF_3$, $SCF_3$], [AA3000; 2, CH, Et, H, $CH_2CHF_2$, $SCF_3$], [AA3001; 0, N, Et, H, F, $SCF_3$], [AA3002; 0, N, Et, H, Cl, $SCF_3$], [AA3003; 0, N, Et, H, Br, $SCF_3$], [AA3004; 0, N, Et, H, I, $SCF_3$], [AA3005; 0, N, Et, H, $CF_3$, $SCF_3$], [AA3006; 0, N, Et, H, $CF_2H$, $SCF_3$], [AA3007; 0, N, Et, H, $C_2F_5$, $SCF_3$], [AA3008; 0, N, Et, H, $C_3F_7$, $SCF_3$], [AA3009; 0, N, Et, H, $CH_2CF_3$, $SCF_3$], [AA3010; 0, N, Et, H, $CH_2CHF_2$, $SCF_3$], [AA3011; 1, N, Et, H, F, $SCF_3$], [AA3012; 1, N, Et, H, Cl, $SCF_3$], [AA3013; 1, N, Et, H, Br, $SCF_3$], [AA3014; 1, N, Et, H, I, $SCF_3$], [AA3015; 1, N, Et, H, $CF_3$, $SCF_3$], [AA3016; 1, N, Et, H, $CF_2H$, $SCF_3$], [AA3017; 1, N, Et, H, $C_2F_5$, $SCF_3$], [AA3018; 1, N, Et, H, $C_3F_7$, $SCF_3$], [AA3019; 1, N, Et, H, $CH_2CF_3$, $SCF_3$], [AA3020; 1, N, Et, H, $CH_2CHF_2$, $SCF_3$], [AA3021; 2, N, Et, H, F, $SCF_3$], [AA3022; 2, N, Et, H, Cl, $SCF_3$], [AA3023; 2, N, Et, H, Br, $SCF_3$], [AA3024; 2, N, Et, H, I, $SCF_3$], [AA3025; 2, N, Et, H, $CF_3$, $SCF_3$], [AA3026; 2, N, Et, H, $CF_2H$, $SCF_3$], [AA3027; 2, N, Et, H, $C_2F_5$, $SCF_3$], [AA3028; 2, N, Et, H, $C_3F_7$, $SCF_3$], [AA3029; 2, N, Et, H, $CH_2CF_3$, $SCF_3$], [AA3030; 2, N, Et, H, $CH_2CHF_2$, $SCF_3$], [AA3031; 0, CH, iPr, H, F, $SCF_3$], [AA3032; 0, CH, iPr, H, Cl, $SCF_3$], [AA3033; 0, CH, iPr, H, Br, $SCF_3$], [AA3034; 0, CH, iPr, H, I, $SCF_3$], [AA3035; 0, CH, iPr, H, $CF_3$, $SCF_3$], [AA3036; 0, CH, iPr, H, $CF_2H$, $SCF_3$], [AA3037; 0, CH, iPr, H, $C_2F_5$, $SCF_3$], [AA3038; 0, CH, iPr, H, $C_3F_7$, $SCF_3$], [AA3039; 0, CH, iPr, H, $CH_2CF_3$, $SCF_3$], [AA3040; 0, CH, iPr, H, $CH_2CHF_2$, $SCF_3$], [AA3041; 1, CH, iPr, H, F, $SCF_3$], [AA3042; 1, CH, iPr, H, Cl, $SCF_3$], [AA3043; 1, CH, iPr, H, Br, $SCF_3$], [AA3044; 1, CH, iPr, H, I, $SCF_3$], [AA3045; 1, CH, iPr, H, $CF_3$, $SCF_3$], [AA3046; 1, CH, iPr, H, $CF_2H$, $SCF_3$], [AA3047; 1, CH, iPr, H, $C_2F_5$, $SCF_3$], [AA3048; 1, CH, iPr, H, $C_3F_7$, $SCF_3$], [AA3049; 1, CH, iPr, H, $CH_2CF_3$, $SCF_3$], [AA3050; 1, CH, iPr, H, $CH_2CHF_2$, $SCF_3$], [AA3051; 2, CH, iPr, H, F, $SCF_3$], [AA3052; 2, CH, iPr, H, Cl, $SCF_3$], [AA3053; 2, CH, iPr, H, Br, $SCF_3$], [AA3054; 2, CH, iPr, H, I, $SCF_3$], [AA3055; 2, CH, iPr, H, $CF_3$, $SCF_3$], [AA3056; 2, CH, iPr, H, $CF_2H$, $SCF_3$], [AA3057; 2, CH, iPr, H, $C_2F_5$, $SCF_3$], [AA3058; 2, CH, iPr, H, $C_3F_7$, $SCF_3$], [AA3059; 2, CH, iPr, H, $CH_2CF_3$, $SCF_3$], [AA3060; 2, CH, iPr, H, $CH_2CHF_2$, $SCF_3$], [AA3061; 0, N, iPr, H, F, $SCF_3$], [AA3062; 0, N, iPr, H, Cl, $SCF_3$], [AA3063; 0, N, iPr, H, Br, $SCF_3$], [AA3064; 0, N, iPr, H, I, $SCF_3$], [AA3065; 0, N, iPr, H, $CF_3$, $SCF_3$], [AA3066; 0, N, iPr, H, $CF_2H$, $SCF_3$], [AA3067; 0, N, iPr, H, $C_2F_5$, $SCF_3$], [AA3068; 0, N, iPr, H, $C_3F_7$, $SCF_3$], [AA3069; 0, N, iPr, H, $CH_2CF_3$, $SCF_3$], [AA3070; 0, N, iPr, H, $CH_2CHF_2$, $SCF_3$], [AA3071; 1, N, iPr, H, F, $SCF_3$], [AA3072; 1, N, iPr, H, Cl, $SCF_3$], [AA3073; 1, N, iPr, H, Br, $SCF_3$], [AA3074; 1, N, iPr, H, I, $SCF_3$], [AA3075; 1, N, iPr, H, $CF_3$, $SCF_3$], [AA3076; 1, N, iPr, H, $CF_2H$, $SCF_3$], [AA3077; 1, N, iPr, H, $C_2F_5$, $SCF_3$], [AA3078; 1, N, iPr, H, $C_3F_7$, $SCF_3$], [AA3079; 1, N, iPr, H, $CH_2CF_3$, $SCF_3$], [AA3080; 1, N, iPr, H, $CH_2CHF_2$, $SCF_3$], [AA3081; 2, N, iPr, H, F, $SCF_3$], [AA3082; 2, N, iPr, H, Cl, $SCF_3$], [AA3083; 2, N, iPr, H, Br, $SCF_3$], [AA3084; 2, N, iPr, H, I, $SCF_3$], [AA3085; 2, N, iPr, H, $CF_3$, $SCF_3$], [AA3086; 2, N, iPr, H, $CF_2H$, $SCF_3$], [AA3087; 2, N, iPr, H, $C_2F_5$, $SCF_3$], [AA3088; 2, N, iPr, H, $C_3F_7$, $SCF_3$], [AA3089; 2, N, iPr, H, $CH_2CF_3$, $SCF_3$], [AA3090; 2, N, iPr, H, $CH_2CHF_2$, $SCF_3$], [AA3091; 0, CH, cPr, H, F, $SCF_3$], [AA3092; 0, CH, cPr, H, Cl, $SCF_3$], [AA3093; 0, CH, cPr, H, Br, $SCF_3$], [AA3094; 0, CH, cPr, H, I, $SCF_3$], [AA3095; 0, CH, cPr, H, $CF_3$, $SCF_3$], [AA3096; 0, CH, cPr, H, $CF_2H$, $SCF_3$], [AA3097; 0, CH, cPr, H, $C_2F_5$, $SCF_3$], [AA3098; 0, CH, cPr, H, $C_3F_7$, $SCF_3$], [AA3099; 0, CH, cPr, H, $CH_2CF_3$, $SCF_3$], [AA3100; 0, CH, cPr, H, $CH_2CHF_2$, $SCF_3$], [AA3101; 1, CH, cPr, H, F, $SCF_3$], [AA3102; 1, CH, cPr, H, Cl, $SCF_3$], [AA3103; 1, CH, cPr, H, Br, $SCF_3$], [AA3104; 1, CH, cPr, H, I, $SCF_3$], [AA3105; 1, CH, cPr, H, $CF_3$, $SCF_3$], [AA3106; 1, CH, cPr, H, $CF_2H$, $SCF_3$], [AA3107; 1, CH, cPr, H, $C_2F_3$, $SCF_3$], [AA3108; 1, CH, cPr, H, $C_3F_7$, $SCF_3$], [AA3109; 1, CH, cPr, H, $CH_2CF_3$, $SCF_3$], [AA3110; 1, CH, cPr, H, $CH_2CHF_2$, $SCF_3$], [AA3111; 2, CH, cPr, H, F, $SCF_3$], [AA3112; 2, CH, cPr, H, Cl, $SCF_3$], [AA3113; 2, CH, cPr, H, Br, $SCF_3$], [AA3114; 2, CH, cPr, H, I, $SCF_3$], [AA3115; 2, CH, cPr, H, $CF_3$, $SCF_3$], [AA3116; 2, CH, cPr, H, $CF_2H$, $SCF_3$], [AA3117; 2, CH, cPr, H, $C_2F_5$, $SCF_3$], [AA3118; 2, CH, cPr, H, $C_3F$, $SCF_3$], [AA3119; 2, CH, cPr, H, $CH_2CF_3$, $SCF_3$], [AA3120; 2, CH, cPr, H, $CH_2CHF_2$, $SCF_3$], [AA3121; 0, N, cPr, H, F, $SCF_3$], [AA3122; 0, N, cPr, H, Cl, $SCF_3$], [AA3123; 0, N, cPr, H, Br, $SCF_3$], [AA3124; 0, N, cPr, H, I, $SCF_3$], [AA3125; 0, N, cPr, H, $CF_3$, $SCF_3$], [AA3126; 0, N, cPr, H, $CF_2H$, $SCF_3$], [AA3127; 0, N, cPr, H, $C_2F_5$, $SCF_3$], [AA3128; 0, N, cPr, H, $C_3F_7$, $SCF_3$], [AA3129; 0, N, cPr, H, $CH_2CF_3$, $SCF_3$], [AA3130; 0, N, cPr, H, $CH_2CHF_2$, $SCF_3$], [AA3131; 1, N, cPr, H, F, $SCF_3$], [AA3132; 1, N, cPr, H, Cl, $SCF_3$], [AA3133; 1, N, cPr, H, Br, $SCF_3$], [AA3134; 1, N, cPr, H, I, $SCF_3$], [AA3135; 1, N, cPr, H, $CF_3$, $SCF_3$], [AA3136; 1, N, cPr, H, $CF_2H$, $SCF_3$], [AA3137; 1, N, cPr, H, $C_2F_5$, $SCF_3$], [AA3138; 1, N, cPr, H, $C_3F_7$, $SCF_3$], [AA3139; 1, N, cPr, H, $CH_2CF_3$, $SCF_3$], [AA3140; 1, N, cPr, H, $CH_2CHF_2$, $SCF_3$], [AA3141; 2, N, cPr, H, F, $SCF_3$], [AA3142; 2, N, cPr, H, Cl, $SCF_3$], [AA3143; 2, N, cPr, H, Br, $SCF_3$], [AA3144; 2, N, cPr, H, I, $SCF_3$], [AA3145; 2, N, cPr, H, $CF_3$, $SCF_3$], [AA3146; 2, N, cPr, H, $CF_2H$, $SCF_3$], [AA3147; 2, N, cPr, H, $C_2F_5$, $SCF_3$], [AA3148; 2, N, cPr, H, $C_3F_7$, $SCF_3$], [AA3149; 2, N, cPr, H, $CH_2CF_3$, $SCF_3$], [AA3150; 2, N, cPr, H, $CH_2CHF_2$, $SCF_3$], [AA3151; 0, CH, H, H, H, $OCF_3$], [AA3152; 0, CH, H, F, H, $OCF_3$], [AA3153; 0, CH, H, Cl, H, $OCF_3$], [AA3154; 0, CH, H, Br, H, $OCF_3$], [AA3155; 0, CH, H, I, H, $OCF_3$], [AA3156; 0, CH, H, $CF_3$, H, $OCF_3$], [AA3157; 0, CH, H, $CF_2H$, H, $OCF_3$], [AA3158; 0, CH, H, $C_2F_5$, H, $OCF_3$], [AA3159; 0, CH, H, $C_3F_7$, H, $OCF_3$], [AA3160; 0, CH, H, $CH_2CF_3$, H, $OCF_3$], [AA3161; 0, CH, H, $CH_2CHF_2$, H, $OCF_3$], [AA3162; 1, CH, H, H, H, $OCF_3$], [AA3163; 1, CH, H, F, H, $OCF_3$], [AA3164; 1, CH, H, Cl, H, $OCF_3$], [AA3165; 1, CH, H, Br, H, $OCF_3$], [AA3166; 1, CH, H, I, H, $OCF_3$], [AA3167; 1, CH, H, $CF_3$, H, $OCF_3$], [AA3168; 1, CH, H, $CF_2H$, H, $OCF_3$], [AA3169; 1, CH, H, $C_2F_5$, H, $OCF_3$], [AA3170; 1, CH, H, $C_3F_7$, H, $OCF_3$], [AA3171; 1, CH, H, $CH_2CF_3$, H, $OCF_3$], [AA3172; 1, CH, H, $CH_2CHF_2$, H, $OCF_3$], [AA3173; 2, CH, H, H, H, $OCF_3$], [AA3174; 2, CH, H, F, H, $OCF_3$], [AA3175; 2, CH, H, Cl, H, $OCF_3$], [AA3176; 2, CH, H, Br, H, $OCF_3$], [AA3177; 2, CH, H, I, H, $OCF_3$], [AA3178; 2, CH, H, $CF_3$, H, $OCF_3$], [AA3179; 2, CH, H, $CF_2H$, H, $OCF_3$], [AA3180; 2, CH, H, $C_2F_5$, H, $OCF_3$], [AA3181; 2, CH, H, $C_3F_7$, H, $OCF_3$], [AA3182; 2, CH, H, $CH_2CF_3$, H, $OCF_3$], [AA3183; 2, CH, H, $CH_2CHF_2$, H, $OCF_3$], [AA3184; 0, N, H, H, H, $OCF_3$], [AA3185; 0, N, H, F, H, $OCF_3$], [AA3186; 0, N, H, Cl, H, $OCF_3$], [AA3187; 0, N, H, Br, H, $OCF_3$], [AA3188; 0, N, H, I, H, $OCF_3$], [AA3189; 0, N, H, $CF_3$, H, $OCF_3$], [AA3190; 0, N, H, $CF_2H$, H, $OCF_3$], [AA3191; 0, N, H, $C_2F_3$, H, $OCF_3$], [AA3192; 0, N, H, $C_3F_7$, H, $OCF_3$], [AA3193; 0, N, H, $CH_2CF_3$, H, $OCF_3$], [AA3194; 0, N, H, $CH_2CHF_2$, H, $OCF_3$], [AA3195; 1, N, H, H, H, $OCF_3$], [AA3196; 1, N, H,

F, H, $OCF_3$], [AA3197; 1, N, H, Cl, H, $OCF_3$], [AA3198; 1, N, H, Br, H, $OCF_3$], [AA3199; 1, N, H, I, H, $OCF_3$], [AA3200; 1, N, H, $CF_3$, H, $OCF_3$], [AA3201; 1, N, H, $CF_2H$, H, $OCF_3$], [AA3202; 1, N, H, $C_2F_5$, H, $OCF_3$], [AA3203; 1, N, H, $C_3F_7$, H, $OCF_3$], [AA3204; 1, N, H, $CH_2CF_3$, H, $OCF_3$], [AA3205; 1, N, H, $CH_2CHF_2$, H, $OCF_3$], [AA3206; 2, N, H, H, H, $OCF_3$], [AA3207; 2, N, H, F, H, $OCF_3$], [AA3208; 2, N, H, Cl, H, $OCF_3$], [AA3209; 2, N, H, Br, H, $OCF_3$], [AA3210; 2, N, H, I, H, $OCF_3$], [AA3211; 2, N, H, $CF_3$, H, $OCF_3$], [AA3212; 2, N, H, $CF_2H$, H, $OCF_3$], [AA3213; 2, N, H, $C_2F_5$, H, $OCF_3$], [AA3214; 2, N, H, $C_3F_7$, H, $OCF_3$], [AA3215; 2, N, H, $CH_2CF_3$, H, $OCF_3$], [AA3216; 2, N, H, $CH_2CHF_2$, H, $OCF_3$], [AA3217; 0, CH, Me, H, H, $OCF_3$], [AA3218; 0, CH, Me, F, H, $OCF_3$], [AA3219; 0, CH, Me, Cl, H, $OCF_3$], [AA3220; 0, CH, Me, Br, H, $OCF_3$], [AA3221; 0, CH, Me, I, H, $OCF_3$], [AA3222; 0, CH, Me, $CF_3$, H, $OCF_3$], [AA3223; 0, CH, Me, $CF_2H$, H, $OCF_3$], [AA3224; 0, CH, Me, $C_2F_5$, H, $OCF_3$], [AA3225; 0, CH, Me, $C_3F_7$, H, $OCF_3$], [AA3226; 0, CH, Me, $CH_2CF_3$, H, $OCF_3$], [AA3227; 0, CH, Me, $CH_2CHF_2$, H, $OCF_3$], [AA3228; 1, CH, Me, H, H, $OCF_3$], [AA3229; 1, CH, Me, F, H, $OCF_3$], [AA3230; 1, CH, Me, Cl, H, $OCF_3$], [AA3231; 1, CH, Me, Br, H, $OCF_3$], [AA3232; 1, CH, Me, I, H, $OCF_3$], [AA3233; 1, CH, Me, $CF_3$, H, $OCF_3$], [AA3234; 1, CH, Me, $CF_2H$, H, $OCF_3$], [AA3235; 1, CH, Me, $C_2F_5$, H, $OCF_3$], [AA3236; 1, CH, Me, $C_3F_7$, H, $OCF_3$], [AA3237; 1, CH, Me, $CH_2CF_3$, H, $OCF_3$], [AA3238; 1, CH, Me, $CH_2CHF_2$, H, $OCF_3$], [AA3239; 2, CH, Me, H, H, $OCF_3$], [AA3240; 2, CH, Me, F, H, $OCF_3$], [AA3241; 2, CH, Me, Cl, H, $OCF_3$], [AA3242; 2, CH, Me, Br, H, $OCF_3$], [AA3243; 2, CH, Me, I, H, $OCF_3$], [AA3244; 2, CH, Me, $CF_3$, H, $OCF_3$], [AA3245; 2, CH, Me, $CF_2H$, H, $OCF_3$], [AA3246; 2, CH, Me, $C_2F_5$, H, $OCF_3$], [AA3247; 2, CH, Me, $C_3F_7$, H, $OCF_3$], [AA3248; 2, CH, Me, $CH_2CF_3$, H, $OCF_3$], [AA3249; 2, CH, Me, $CH_2CHF_2$, H, $OCF_3$], [AA3250; 0, N, Me, H, H, $OCF_3$], [AA3251; 0, N, Me, F, H, $OCF_3$], [AA3252; 0, N, Me, Cl, H, $OCF_3$], [AA3253; 0, N, Me, Br, H, $OCF_3$], [AA3254; 0, N, Me, I, H, $OCF_3$], [AA3255; 0, N, Me, $CF_3$, H, $OCF_3$], [AA3256; 0, N, Me, $CF_2H$, H, $OCF_3$], [AA3257; 0, N, Me, $C_2F_5$, H, $OCF_3$], [AA3258; 0, N, Me, $C_3F_7$, H, $OCF_3$], [AA3259; 0, N, Me, $CH_2CF_3$, H, $OCF_3$], [AA3260; 0, N, Me, $CH_2CHF_2$, H, $OCF_3$], [AA3261; 1, N, Me, H, H, $OCF_3$], [AA3262; 1, N, Me, F, H, $OCF_3$], [AA3263; 1, N, Me, Cl, H, $OCF_3$], [AA3264; 1, N, Me, Br, H, $OCF_3$], [AA3265; 1, N, Me, I, H, $OCF_3$], [AA3266; 1, N, Me, $CF_3$, H, $OCF_3$], [AA3267; 1, N, Me, $CF_2H$, H, $OCF_3$], [AA3268; 1, N, Me, $C_2F_5$, H, $OCF_3$], [AA3269; 1, N, Me, $C_3F_7$, H, $OCF_3$], [AA3270; 1, N, Me, $CH_2CF_3$, H, $OCF_3$], [AA3271; 1, N, Me, $CH_2CHF_2$, H, $OCF_3$], [AA3272; 2, N, Me, H, H, $OCF_3$], [AA3273; 2, N, Me, F, H, $OCF_3$], [AA3274; 2, N, Me, Cl, H, $OCF_3$], [AA3275; 2, N, Me, Br, H, $OCF_3$], [AA3276; 2, N, Me, I, H, $OCF_3$], [AA3277; 2, N, Me, $CF_3$, H, $OCF_3$], [AA3278; 2, N, Me, $CF_2H$, H, $OCF_3$], [AA3279; 2, N, Me, $C_2F_5$, H, $OCF_3$], [AA3280; 2, N, Me, $C_3F_7$, H, $OCF_3$], [AA3281; 2, N, Me, $CH_2CF_3$, H, $OCF_3$], [AA3282; 2, N, Me, $CH_2CHF_2$, H, $OCF_3$], [AA3283; 0, CH, Et, H, H, $OCF_3$], [AA3284; 0, CH, Et, F, H, $OCF_3$], [AA3285; 0, CH, Et, Cl, H, $OCF_3$], [AA3286; 0, CH, Et, Br, H, $OCF_3$], [AA3287; 0, CH, Et, I, H, $OCF_3$], [AA3288; 0, CH, Et, $CF_3$, H, $OCF_3$], [AA3289; 0, CH, Et, $CF_2H$, H, $OCF_3$], [AA3290; 0, CH, Et, $C_2F_5$, H, $OCF_3$], [AA3291; 0, CH, Et, $C_3F_7$, H, $OCF_3$], [AA3292; 0, CH, Et, $CH_2CF_3$, H, $OCF_3$], [AA3293; 0, CH, Et, $CH_2CHF_2$, H, $OCF_3$], [AA3294; 1, CH, Et, H, H, $OCF_3$], [AA3295; 1, CH, Et, F, H, $OCF_3$], [AA3296; 1, CH, Et, Cl, H, $OCF_3$], [AA3297; 1, CH, Et, Br, H, $OCF_3$], [AA3298; 1, CH, Et, I, H, $OCF_3$], [AA3299; 1, CH, Et, $CF_3$, H, $OCF_3$], [AA3300; 1, CH, Et, $CF_2H$, H, $OCF_3$], [AA3301; 1, CH, Et, $C_2F_5$, H, $OCF_3$], [AA3302; 1, CH, Et, $C_3F_7$, H, $OCF_3$], [AA3303; 1, CH, Et, $CH_2CF_3$, H, $OCF_3$], [AA3304; 1, CH, Et, $CH_2CHF_2$, H, $OCF_3$], [AA3305; 2, CH, Et, H, H, $OCF_3$], [AA3306; 2, CH, Et, F, H, $OCF_3$], [AA3307; 2, CH, Et, Cl, H, $OCF_3$], [AA3308; 2, CH, Et, Br, H, $OCF_3$], [AA3309; 2, CH, Et, I, H, $OCF_3$], [AA3310; 2, CH, Et, $CF_3$, H, $OCF_3$], [AA3311; 2, CH, Et, $CF_2H$, H, $OCF_3$], [AA3312; 2, CH, Et, $C_2F_5$, H, $OCF_3$], [AA3313; 2, CH, Et, $C_3F_7$, H, $OCF_3$], [AA3314; 2, CH, Et, $CH_2CF_3$, H, $OCF_3$], [AA3315; 2, CH, Et, $CH_2CHF_2$, H, $OCF_3$], [AA3316; 0, N, Et, H, H, $OCF_3$], [AA3317; 0, N, Et, F, H, $OCF_3$], [AA3318; 0, N, Et, Cl, H, $OCF_3$], [AA3319; 0, N, Et, Br, H, $OCF_3$], [AA3320; 0, N, Et, I, H, $OCF_3$], [AA3321; 0, N, Et, $CF_3$, H, $OCF_3$], [AA3322; 0, N, Et, $CF_2H$, H, $OCF_3$], [AA3323; 0, N, Et, $C_2F_5$, H, $OCF_3$], [AA3324; 0, N, Et, $C_3F_7$, H, $OCF_3$], [AA3325; 0, N, Et, $CH_2CF_3$, H, $OCF_3$], [AA3326; 0, N, Et, $CH_2CHF_2$, H, $OCF_3$], [AA3327; 1, N, Et, H, H, $OCF_3$], [AA3328; 1, N, Et, F, H, $OCF_3$], [AA3329; 1, N, Et, Cl, H, $OCF_3$], [AA3330; 1, N, Et, Br, H, $OCF_3$], [AA3331; 1, N, Et, I, H, $OCF_3$], [AA3332; 1, N, Et, $CF_3$, H, $OCF_3$], [AA3333; 1, N, Et, $CF_2H$, H, $OCF_3$], [AA3334; 1, N, Et, $C_2F_5$, H, $OCF_3$], [AA3335; 1, N, Et, $C_3F_7$, H, $OCF_3$], [AA3336; 1, N, Et, $CH_2CF_3$, H, $OCF_3$], [AA3337; 1, N, Et, $CH_2CHF_2$, H, $OCF_3$], [AA3338; 2, N, Et, H, H, $OCF_3$], [AA3339; 2, N, Et, F, H, $OCF_3$], [AA3340; 2, N, Et, Cl, H, $OCF_3$], [AA3341; 2, N, Et, Br, H, $OCF_3$], [AA3342; 2, N, Et, I, H, $OCF_3$], [AA3343; 2, N, Et, $CF_3$, H, $OCF_3$], [AA3344; 2, N, Et, $CF_2H$, H, $OCF_3$], [AA3345; 2, N, Et, $C_2F_5$, H, $OCF_3$], [AA3346; 2, N, Et, $C_3F_7$, H, $OCF_3$], [AA3347; 2, N, Et, $CH_2CF_3$, H, $OCF_3$], [AA3348; 2, N, Et, $CH_2CHF_2$, H, $OCF_3$], [AA3349; 0, CH, iPr, H, H, $OCF_3$], [AA3350; 0, CH, iPr, F, H, $OCF_3$], [AA3351; 0, CH, iPr, Cl, H, $OCF_3$], [AA3352; 0, CH, iPr, Br, H, $OCF_3$], [AA3353; 0, CH, iPr, I, H, $OCF_3$], [AA3354; 0, CH, iPr, $CF_3$, H, $OCF_3$], [AA3355; 0, CH, iPr, $CF_2H$, H, $OCF_3$], [AA3356; 0, CH, iPr, $C_2F_5$, H, $OCF_3$], [AA3357; 0, CH, iPr, $C_3F_7$, H, $OCF_3$], [AA3358; 0, CH, iPr, $CH_2CF_3$, H, $OCF_3$], [AA3359; 0, CH, iPr, $CH_2CHF_2$, H, $OCF_3$], [AA3360; 1, CH, iPr, H, H, $OCF_3$], [AA3361; 1, CH, iPr, F, H, $OCF_3$], [AA3362; 1, CH, iPr, Cl, H, $OCF_3$], [AA3363; 1, CH, iPr, Br, H, $OCF_3$], [AA3364; 1, CH, iPr, I, H, $OCF_3$], [AA3365; 1, CH, iPr, $CF_3$, H, $OCF_3$], [AA3366; 1, CH, iPr, $CF_2H$, H, $OCF_3$], [AA3367; 1, CH, iPr, $C_2F_5$, H, $OCF_3$], [AA3368; 1, CH, iPr, $C_3F_7$, H, $OCF_3$], [AA3369; 1, CH, iPr, $CH_2CF_3$, H, $OCF_3$], [AA3370; 1, CH, iPr, $CH_2CHF_2$, H, $OCF_3$], [AA3371; 2, CH, iPr, H, H, $OCF_3$], [AA3372; 2, CH, iPr, F, H, $OCF_3$], [AA3373; 2, CH, iPr, Cl, H, $OCF_3$], [AA3374; 2, CH, iPr, Br, H, $OCF_3$], [AA3375; 2, CH, iPr, I, H, $OCF_3$], [AA3376; 2, CH, iPr, $CF_3$, H, $OCF_3$], [AA3377; 2, CH, iPr, $CF_2H$, H, $OCF_3$], [AA3378; 2, CH, iPr, $C_2F_5$, H, $OCF_3$], [AA3379; 2, CH, iPr, $C_3F_7$, H, $OCF_3$], [AA3380; 2, CH, iPr, $CH_2CF_3$, H, $OCF_3$], [AA33381; 2, CH, iPr, $CH_2CHF_2$, H, $OCF_3$], [AA3382; 0, N, iPr, H, H, $OCF_3$], [AA3383; 0, N, iPr, F, H, $OCF_3$], [AA3384; 0, N, iPr, Cl, H, $OCF_3$], [AA3385; 0, N, iPr, Br, H, $OCF_3$], [AA3386; 0, N, iPr, I, H, $OCF_3$], [AA3387; 0, N, iPr, $CF_3$, H, $OCF_3$], [AA3388; 0, N, iPr, $CF_2H$, H, $OCF_3$], [AA3389; 0, N, iPr, $C_2F_5$, H, $OCF_3$], [AA3390; 0, N, iPr, $C_3F_7$, H, $OCF_3$], [AA3391; 0, N, iPr, $CH_2CF_3$, H, $OCF_3$], [AA3392; 0, N, iPr, $CH_2CHF_2$, H, $OCF_3$], [AA3393; 1, N, iPr, H, H, $OCF_3$], [AA3394; 1, N, iPr, F, H, $OCF_3$], [AA3395; 1, N, iPr, Cl, H, $OCF_3$], [AA3396; 1, N, iPr, Br, H, $OCF_3$], [AA3397; 1, N, iPr, I, H, $OCF_3$], [AA3398; 1, N, iPr, $CF_3$, H, $OCF_3$], [AA3399; 1, N, iPr, $CF_2H$, H, $OCF_3$], [AA3400; 1, N, iPr, $C_2F_5$, H, $OCF_3$], [AA3401; 1, N, iPr, $C_3F_7$, H, $OCF_3$], [AA3402; 1, N, iPr, $CH_2CF_3$, H, $OCF_3$], [AA3403; 1, N, iPr, $CH_2CHF_2$, H, $OCF_3$], [AA3404; 2, N, iPr, H, H, $OCF_3$], [AA3405; 2, N, iPr, F, H, $OCF_3$], [AA3406; 2, N, iPr, Cl, H, $OCF_3$], [AA3407; 2, N, iPr, Br, H, $OCF_3$], [AA3408; 2, N, iPr, I, H, $OCF_3$], [AA3409; 2, N, iPr, $CF_3$, H, $OCF_3$], [AA3410; 2, N, iPr, $CF_2H$, H, $OCF_3$], [AA3411; 2, N, iPr, $C_2F$, H, $OCF_3$], [AA3412; 2, N, iPr, $C_3F_7$, H, $OCF_3$], [AA3413; 2, N, iPr, $CH_2CF_3$, H, $OCF_3$], [AA3414; 2, N, iPr, $CH_2CHF_2$, H, $OCF_3$], [AA3415; 0, CH, cPr, H, H, $OCF_3$], [AA3416; 0, CH, cPr, F, H, $OCF_3$], [AA3417; 0, CH, cPr, Cl, H, $OCF_3$], [AA3418; 0, CH, cPr, Br, H, $OCF_3$], [AA3419; 0, CH, cPr, I, H, $OCF_3$], [AA3420; 0, CH, cPr, $CF_3$, H, $OCF_3$], [AA3421; 0, CH, cPr, $CF_2H$, H, $OCF_3$], [AA3422; 0, CH, cPr, $C_2F_5$, H, $OCF_3$], [AA3423; 0, CH, cPr, $C_3F_7$, H, $OCF_3$], [AA3424; 0, CH, cPr, $CH_2CF_3$, H, $OCF_3$], [AA3425; 0, CH, cPr, $CH_2CHF_2$, H, $OCF_3$], [AA3426; 1, CH, cPr, H, H, $OCF_3$], [AA3427; 1, CH, cPr, F, H, $OCF_3$], [AA3428; 1, CH, cPr, Cl, H, $OCF_3$], [AA3429; 1, CH, cPr, Br, H, $OCF_3$], [AA3430; 1, CH, cPr, I, H, $OCF_3$], [AA3431; 1, CH, cPr, $CF_3$, H, $OCF_3$], [AA3432; 1, CH, cPr, $CF_2H$, H, $OCF_3$], [AA3433; 1, CH, cPr, $C_2F_5$, H, $OCF_3$], [AA3434; 1, CH, cPr, $C_3F_7$, H, $OCF_3$], [AA3435; 1, CH, cPr, $CH_2CF_3$, H, $OCF_3$], [AA3436; 1, CH, cPr, $CH_2CHF_2$, H, $OCF_3$], [AA3437; 2, CH, cPr, H, H, $OCF_3$], [AA3438; 2, CH, cPr, F, H, $OCF_3$], [AA3439; 2, CH, cPr, Cl, H, $OCF_3$], [AA3440; 2, CH, cPr, Br, H, $OCF_3$], [AA3441; 2, CH, cPr, I, H, $OCF_3$], [AA3442; 2, CH, cPr, $CF_3$, H, $OCF_3$], [AA3443; 2, CH, cPr, $CF_2H$, H, $OCF_3$], [AA3444; 2, CH, cPr, $C_2F_5$, H, $OCF_3$], [AA3445; 2, CH, cPr, $C_3F_7$, H, $OCF_3$], [AA3446; 2, CH, cPr, $CH_2CF_3$, H, $OCF_3$], [AA3447; 2, CH, cPr, $CH_2CHF_2$, H, $OCF_3$], [AA3448; 0, N, cPr, H, H, $OCF_3$], [AA3449; 0, N, cPr, F, H, $OCF_3$], [AA3450; 0, N, cPr, Cl, H, $OCF_3$], [AA3451; 0, N, cPr, Br, H, $OCF_3$], [AA3452; 0, N, cPr, I, H, $OCF_3$], [AA3453; 0, N, cPr, $CF_3$, H, $OCF_3$], [AA3454; 0, N, cPr, $CF_2H$, H, $OCF_3$], [AA3455; 0, N, cPr, $C_2F_5$, H, $OCF_3$], [AA3456; 0, N, cPr, $C_3F_7$, H, $OCF_3$], [AA3457; 0, N, cPr, $CH_2CF_3$, H, $OCF_3$], [AA3458; 0, N, cPr, $CH_2CHF_2$, H, $OCF_3$], [AA3459; 1, N, cPr, H, H, $OCF_3$], [AA3460; 1, N, cPr, F, H, $OCF_3$], [AA3461; 1, N, cPr, Cl, H, $OCF_3$], [AA3462; 1, N, cPr, Br, H, $OCF_3$], [AA3463; 1, N, cPr, I, H, $OCF_3$], [AA3464; 1, N, cPr, $CF_3$, H, $OCF_3$], [AA3465; 1, N, cPr, $CF_2H$, H, $OCF_3$], [AA3466; 1, N, cPr, $C_2F_5$, H, $OCF_3$], [AA3467; 1, N, cPr, $C_3F_7$, H, $OCF_3$], [AA3468; 1, N, cPr, $CH_2CF_3$, H, $OCF_3$], [AA3469; 1, N, cPr, $CH_2CHF_2$, H, $OCF_3$], [AA3470; 2, N, cPr, H, H, $OCF_3$], [AA3471; 2, N, cPr, F, H, $OCF_3$], [AA3472; 2, N, cPr, Cl, H, $OCF_3$], [AA3473; 2, N, cPr, Br, H, $OCF_3$], [AA3474; 2, N, cPr, I, H, $OCF_3$], [AA3475; 2, N, cPr, $CF_3$, H, $OCF_3$], [AA3476; 2, N, cPr, $CF_2H$, H, $OCF_3$], [AA3477; 2, N, cPr, $C_2F_5$, H, $OCF_3$], [AA3478; 2, N, cPr, $C_3F_7$, H, $OCF_3$], [AA3479; 2, N, cPr, $CH_2CF_3$, H, $OCF_3$], [AA3480; 2, N, cPr, $CH_2CHF_2$, H, $OCF_3$], [AA3481; 0, CH, H, H, F, $OCF_3$], [AA3482; 0, CH, H, H, Cl, $OCF_3$], [AA3483; 0, CH, H, H, Br, $OCF_3$], [AA3484; 0, CH, H, H, I, $OCF_3$], [AA3485; 0, CH, H, H, $CF_3$, $OCF_3$], [AA3486; 0, CH, H, H, $CF_2H$, $OCF_3$], [AA3487; 0, CH, H, H, $C_2F_5$, $OCF_3$], [AA3488; 0, CH, H, H, $C_3F_7$, $OCF_3$], [AA3489; 0, CH, H, H, $CH_2CF_3$, $OCF_3$], [AA3490; 0, CH, H, H, $CH_2CHF_2$, $OCF_3$], [AA3491; 1, CH, H, H, F, $OCF_3$], [AA3492; 1, CH, H, H, Cl, $OCF_3$], [AA3493; 1, CH, H, H, Br, $OCF_3$], [AA3494; 1, CH, H, H, I, $OCF_3$], [AA3495; 1, CH, H, H, $CF_3$, $OCF_3$], [AA3496; 1, CH, H, H, $CF_2H$, $OCF_3$], [AA3497; 1, CH, H, H, $C_2F_5$, $OCF_3$], [AA3498; 1, CH, H, H, $C_3F_7$, $OCF_3$], [AA3499; 1, CH, H, H, $CH_2CF_3$, $OCF_3$], [AA3500; 1, CH, H, H, $CH_2CHF_2$, $OCF_3$], [AA3501; 2, CH, H, H, F, $OCF_3$], [AA3502; 2, CH, H, H, Cl, $OCF_3$], [AA3503; 2, CH, H, H, Br, $OCF_3$], [AA3504; 2, CH, H, H, I, $OCF_3$], [AA3505; 2, CH, H, H, $CF_3$, $OCF_3$], [AA3506; 2, CH, H, H, $CF_2H$, $OCF_3$], [AA3507; 2, CH, H, H, $C_2F_5$, $OCF_3$], [AA3508; 2, CH, H, H, $C_3F_7$, $OCF_3$], [AA3509; 2, CH, H, H, $CH_2CF_3$, $OCF_3$], [AA3510; 2, CH, H, H, $CH_2CHF_2$, $OCF_3$], [AA3511; 0, N, H, H, F, $OCF_3$], [AA3512; 0, N, H, H, Cl, $OCF_3$], [AA3513; 0, N, H, H, Br, $OCF_3$], [AA3514; 0, N, H, H, I, $OCF_3$], [AA3515; 0, N, H, H, $CF_3$, $OCF_3$], [AA3516; 0, N, H, H, $CF_2H$, $OCF_3$], [AA3517; 0, N, H, H, $C_2F_5$, $OCF_3$], [AA3518; 0, N, H, H, $C_3F_7$, $OCF_3$], [AA3519; 0, N, H, H, $CH_2CF_3$, $OCF_3$], [AA3520; 0, N, H, H, $CH_2CHF_2$, $OCF_3$], [AA3521; 1, N, H, H, F, $OCF_3$], [AA3522; 1, N, H, H, Cl, $OCF_3$], [AA3523; 1, N, H, H, Br, $OCF_3$], [AA3524; 1, N, H, H, I, $OCF_3$], [AA3525; 1, N, H, H, $CF_3$, $OCF_3$], [AA3526; 1, N, H, H, $CF_2H$, $OCF_3$], [AA3527; 1, N, H, H, $C_2F_5$, $OCF_3$], [AA3528; 1, N, H, H, $C_3F$-7, $OCF_3$], [AA3529; 1, N, H, H, $CH_2CF_3$, $OCF_3$], [AA3530; 1, N, H, H, $CH_2CHF_2$, $OCF_3$], [AA3531; 2, N, H, H, F, $OCF_3$], [AA3532; 2, N, H, H, Cl, $OCF_3$], [AA3533; 2, N, H, H, Br, $OCF_3$], [AA3534; 2, N, H, H, I, $OCF_3$], [AA3535; 2, N, H, H, $CF_3$, $OCF_3$], [AA3536; 2, N, H, H, $CF_2H$, $OCF_3$], [AA3537; 2, N, H, H, $C_2F_5$, $OCF_3$], [AA3538; 2, N, H, H, $C_3F$-7, $OCF_3$], [AA3539; 2, N, H, H, $CH_2CF_3$, $OCF_3$], [AA3540; 2, N, H, H, $CH_2CHF_2$, $OCF_3$], [AA3541; 0, CH, Me, H, F, $OCF_3$], [AA3542; 0, CH, Me, H, Cl, $OCF_3$], [AA3543; 0, CH, Me, H, Br, $OCF_3$], [AA3544; 0, CH, Me, H, I, $OCF_3$], [AA3545; 0, CH, Me, H, $CF_3$, $OCF_3$], [AA3546; 0, CH, Me, H, $CF_2H$, $OCF_3$], [AA3547; 0, CH, Me, H, $C_2F_5$, $OCF_3$], [AA3548; 0, CH, Me, H, $C_3F_7$, $OCF_3$], [AA3549; 0, CH, Me, H, $CH_2CF_3$, $OCF_3$], [AA3550; 0, CH, Me, H, $CH_2CHF_2$, $OCF_3$], [AA3551; 1, CH, Me, H, F, $OCF_3$], [AA3552; 1, CH, Me, H, Cl, $OCF_3$], [AA3553; 1, CH, Me, H, Br, $OCF_3$], [AA3554; 1, CH, Me, H, I, $OCF_3$], [AA3555; 1, CH, Me, H, $CF_3$, $OCF_3$], [AA3556; 1, CH, Me, H, $CF_2H$, $OCF_3$], [AA3557; 1, CH, Me, H, $C_2F_5$, $OCF_3$], [AA3558; 1, CH, Me, H, $C_3F_7$, $OCF_3$], [AA3559; 1, CH, Me, H, $CH_2CF_3$, $OCF_3$], [AA3560; 1, CH, Me, H, $CH_2CHF_2$, $OCF_3$], [AA3561; 2, CH, Me, H, F, $OCF_3$], [AA3562; 2, CH, Me, H, Cl, $OCF_3$], [AA3563; 2, CH, Me, H, Br, $OCF_3$], [AA3564; 2, CH, Me, H, I, $OCF_3$], [AA3565; 2, CH, Me, H, $CF_3$, $OCF_3$], [AA3566; 2, CH, Me, H, $CF_2H$, $OCF_3$], [AA3567; 2, CH, Me, H, $C_2F_5$, $OCF_3$], [AA3568; 2, CH, Me, H, $C_3F_7$, $OCF_3$], [AA3569; 2, CH, Me, H, $CH_2CF_3$, $OCF_3$], [AA3570; 2, CH, Me, H, $CH_2CHF_2$, $OCF_3$], [AA3571; 0, N, Me, H, F, $OCF_3$], [AA3572; 0, N, Me, H, Cl, $OCF_3$], [AA3573; 0, N, Me, H, Br, $OCF_3$], [AA3574; 0, N, Me, H, I, $OCF_3$], [AA3575; 0, N, Me, H, $CF_3$, $OCF_3$], [AA3576; 0, N, Me, H, $CF_2H$, $OCF_3$], [AA3577; 0, N, Me, H, $C_2F_5$, $OCF_3$], [AA3578; 0, N, Me, H, $C_3F_7$, $OCF_3$], [AA3579; 0, N, Me, H, $CH_2CF_3$, $OCF_3$], [AA3580; 0, N, Me, H, $CH_2CHF_2$, $OCF_3$], [AA3581; 1, N, Me, H, F, $OCF_3$], [AA3582; 1, N, Me, H, Cl, $OCF_3$], [AA3583; 1, N, Me, H, Br, $OCF_3$], [AA3584; 1, N, Me, H, I, $OCF_3$], [AA3585; 1, N, Me, H, $CF_3$, $OCF_3$], [AA3586; 1, N, Me, H, $CF_2H$, $OCF_3$], [AA3587; 1, N, Me, H, $C_2F_5$, $OCF_3$], [AA3588; 1, N, Me, H, $C_3F_7$, $OCF_3$], [AA3589; 1, N, Me, H, $CH_2CF_3$, $OCF_3$], [AA3590; 1, N, Me, H, $CH_2CHF_2$, $OCF_3$], [AA3591; 2, N, Me, H, F, $OCF_3$], [AA3592; 2, N, Me, H, Cl, $OCF_3$], [AA3593; 2, N, Me, H, Br, $OCF_3$], [AA3594; 2, N, Me, H, I, $OCF_3$], [AA3595; 2, N, Me, H, $CF_3$, $OCF_3$], [AA3596; 2, N, Me, H, $CF_2H$, $OCF_3$], [AA3597; 2, N, Me, H, $C_2F_5$, $OCF_3$], [AA3598; 2, N, Me, H, $C_3F_7$, $OCF_3$], [AA3599; 2, N, Me, H, $CH_2CF_3$, $OCF_3$], [AA3600; 2, N, Me, H, $CH_2CHF_2$, $OCF_3$], [AA3601; 0, CH, Et, H, F, $OCF_3$], [AA3602; 0, CH, Et, H, Cl, $OCF_3$], [AA3603; 0, CH, Et, H, Br, $OCF_3$], [AA3604; 0, CH, Et, H, I, $OCF_3$], [AA3605; 0, CH, Et, H, $CF_3$, $OCF_3$], [AA3606; 0, CH, Et, H, $CF_2H$, $OCF_3$], [AA3607; 0, CH, Et, H, $C_2F_5$, $OCF_3$], [AA3608; 0, CH, Et, H, $C_3F_7$, $OCF_3$], [AA3609; 0, CH, Et, H, $CH_2CF_3$, $OCF_3$], [AA3610; 0, CH, Et, H, $CH_2CHF_2$, $OCF_3$], [AA3611; 1, CH, Et, H, F, $OCF_3$], [AA3612; 1, CH, Et, H, Cl, $OCF_3$], [AA3613; 1, CH, Et, H, Br, $OCF_3$], [AA3614; 1, CH, Et, H, I, $OCF_3$], [AA3615; 1, CH, Et, H, $CF_3$, $OCF_3$], [AA3616; 1, CH, Et, H, $CF_2H$, $OCF_3$], [AA3617; 1, CH, Et, H, $C_2F_5$, $OCF_3$], [AA3618; 1, CH, Et, H, $C_3F_7$, $OCF_3$], [AA3619; 1, CH, Et, H, $CH_2CF_3$, $OCF_3$], [AA3620; 1, CH, Et, H, $CH_2CHF_2$, $OCF_3$], [AA3621; 2, CH, Et, H, F, $OCF_3$], [AA3622; 2, CH, Et, H, Cl, $OCF_3$], [AA3623; 2, CH, Et, H, Br, $OCF_3$], [AA3624; 2, CH, Et, H, I, $OCF_3$], [AA3625; 2, CH, Et, H, $CF_3$, $OCF_3$], [AA3626; 2, CH, Et, H, $CF_2H$, $OCF_3$], [AA3627; 2, CH, Et, H, $C_2F_5$, $OCF_3$], [AA3628; 2, CH, Et, H, $C_3F_7$, $OCF_3$], [AA3629; 2, CH, Et, H, $CH_2CF_3$, $OCF_3$], [AA3630; 2, CH, Et, H, $CH_2CHF_2$, $OCF_3$], [AA3631; 0, N, Et, H, F, $OCF_3$], [AA3632; 0, N, Et, H, Cl, $OCF_3$], [AA3633; 0, N, Et, H, Br, $OCF_3$], [AA3634; 0, N, Et, H, I, $OCF_3$], [AA3635; 0, N, Et, H, $CF_3$, $OCF_3$], [AA3636; 0, N, Et, H, $CF_2H$, $OCF_3$], [AA3637; 0, N, Et, H, $C_2F_5$, $OCF_3$], [AA3638; 0, N, Et, H, $C_3F_7$, $OCF_3$], [AA3639; 0, N, Et, H, $CH_2CF_3$, $OCF_3$], [AA3640; 0, N, Et, H, $CH_2CHF_2$, $OCF_3$], [AA3641; 1, N, Et, H, F, $OCF_3$], [AA3642; 1, N, Et, H, Cl, $OCF_3$], [AA3643; 1, N, Et, H, Br, $OCF_3$], [AA3644; 1, N, Et, H, I, $OCF_3$], [AA3645; 1, N, Et, H, $CF_3$, $OCF_3$], [AA3646; 1, N, Et, H, $CF_2H$, $OCF_3$], [AA3647; 1, N, Et, H, $C_2F_5$, $OCF_3$], [AA3648; 1, N, Et, H, $C_3F_7$, $OCF_3$], [AA3649; 1, N, Et, H, $CH_2CF_3$, $OCF_3$], [AA3650; 1, N, Et, H, $CH_2CHF_2$, $OCF_3$], [AA3651; 2, N, Et, H, F, $OCF_3$], [AA3652; 2, N, Et, H, Cl, $OCF_3$], [AA3653; 2, N, Et, H, Br, $OCF_3$], [AA3654; 2, N, Et, H, I, $OCF_3$], [AA3655; 2, N, Et, H, $CF_3$, $OCF_3$], [AA3656; 2, N, Et, H, $CF_2H$, $OCF_3$], [AA3657; 2, N, Et, H, $C_2F_5$, $OCF_3$], [AA3658; 2, N, Et, H, $C_3F_7$, $OCF_3$], [AA3659; 2, N, Et, H, $CH_2CF_3$, $OCF_3$], [AA3660; 2, N, Et, H, $CH_2CHF_2$, $OCF_3$], [AA3661; 0, CH, iPr, H, F, $OCF_3$], [AA3662; 0, CH, iPr, H, Cl, $OCF_3$], [AA3663; 0, CH, iPr, H, Br, $OCF_3$], [AA3664; 0, CH, iPr, H, I, $OCF_3$], [AA3665; 0, CH, iPr, H, $CF_3$, $OCF_3$], [AA3666; 0, CH, iPr, H, $CF_2H$, $OCF_3$], [AA3667; 0, CH, iPr, H, $C_2F_5$, $OCF_3$], [AA3668; 0, CH, iPr, H, $C_3F_7$, $OCF_3$], [AA3669; 0, CH, iPr, H, $CH_2CF_3$, $OCF_3$], [AA3670; 0, CH, iPr, H, $CH_2CHF_2$, $OCF_3$], [AA3671; 1, CH, iPr, H, F, $OCF_3$], [AA3672; 1, CH, iPr, H, Cl, $OCF_3$], [AA3673; 1, CH, iPr, H, Br, $OCF_3$], [AA3674; 1, CH, iPr, H, I, $OCF_3$], [AA3675; 1, CH, iPr, H, $CF_3$, $OCF_3$], [AA3676; 1, CH, iPr, H, $CF_2H$, $OCF_3$], [AA3677; 1, CH, iPr, H, $C_2F_5$, $OCF_3$], [AA3678; 1, CH, iPr, H, $C_3F_7$, $OCF_3$], [AA3679; 1, CH, iPr, H, $CH_2CF_3$, $OCF_3$], [AA3680; 1, CH, iPr, H, $CH_2CHF_2$, $OCF_3$], [AA3681; 2, CH, iPr, H, F, $OCF_3$], [AA3682; 2, CH, iPr, H, Cl, $OCF_3$], [AA3683; 2, CH, iPr, H, Br, $OCF_3$], [AA3684; 2, CH, iPr, H, I, $OCF_3$], [AA3685; 2, CH, iPr, H, $CF_3$, $OCF_3$], [AA3686; 2, CH, iPr, H, $CF_2H$, $OCF_3$], [AA3687; 2, CH, iPr, H, $C_2F_5$, $OCF_3$], [AA3688; 2, CH, iPr, H, $C_3F_7$, $OCF_3$], [AA3689; 2, CH, iPr, H, $CH_2CF_3$, $OCF_3$], [AA3690; 2, CH, iPr, H, $CH_2CHF_2$, $OCF_3$], [AA3691; 0, N, iPr, H, F, $OCF_3$], [AA3692; 0, N, iPr, H, Cl, $OCF_3$], [AA3693; 0, N, iPr, H, Br, $OCF_3$], [AA3694; 0, N, iPr, H, I, $OCF_3$], [AA3695; 0, N, iPr, H, $CF_3$, $OCF_3$], [AA3696; 0, N, iPr, H, $CF_2H$, $OCF_3$], [AA3697; 0, N, iPr, H, $C_2F_5$, $OCF_3$], [AA3698; 0, N, iPr, H, $C_3F_7$, $OCF_3$], [AA3699; 0, N, iPr, H, $CH_2CF_3$, $OCF_3$], [AA3700; 0, N, iPr, H, $CH_2CHF_2$, $OCF_3$], [AA3701; 1, N, iPr, H, F, $OCF_3$], [AA3702; 1, N, iPr, H, Cl, $OCF_3$], [AA3703; 1, N, iPr, H, Br, $OCF_3$], [AA3704; 1, N, iPr, H, I, $OCF_3$], [AA3705; 1, N, iPr, H, $CF_3$, $OCF_3$], [AA3706; 1, N, iPr, H, $CF_2H$, $OCF_3$], [AA3707; 1, N, iPr, H, $C_2F_5$, $OCF_3$], [AA3708; 1, N, iPr, H, $C_3F_7$, $OCF_3$], [AA3709; 1, N, iPr, H, $CH_2CF_3$, $OCF_3$], [AA3710; 1, N, iPr, H, $CH_2CHF_2$, $OCF_3$], [AA3711; 2, N, iPr, H, F, $OCF_3$], [AA3712; 2, N, iPr, H, Cl, $OCF_3$], [AA3713; 2, N, iPr, H, Br, $OCF_3$], [AA3714; 2, N, iPr, H, I, $OCF_3$], [AA3715; 2, N, iPr, H, $CF_3$, $OCF_3$], [AA3716; 2, N, iPr, H, $CF_2H$, $OCF_3$], [AA3717; 2, N, iPr, H, $C_2F_5$, $OCF_3$], [AA3718; 2, N, iPr, H, $C_3F_7$, $OCF_3$], [AA3719; 2, N, iPr, H, $CH_2CF_3$, $OCF_3$], [AA3720; 2, N, iPr, H, $CH_2CHF_2$, $OCF_3$], [AA3721; 0, CH, cPr, H, F, $OCF_3$], [AA3722; 0, CH, cPr, H, Cl, $OCF_3$], [AA3723; 0, CH, cPr, H, Br, $OCF_3$], [AA3724; 0, CH, cPr, H, I, $OCF_3$], [AA3725; 0, CH, cPr, H, $CF_3$, $OCF_3$], [AA3726; 0, CH, cPr, H, $CF_2H$, $OCF_3$], [AA3727; 0, CH, cPr, H, $C_2F_5$, $OCF_3$], [AA3728; 0, CH, cPr, H, $C_3F_7$, $OCF_3$], [AA3729; 0, CH, cPr, H, $CH_2CF_3$, $OCF_3$], [AA3730; 0, CH, cPr, H, $CH_2CHF_2$, $OCF_3$], [AA3731; 1, CH, cPr, H, F, $OCF_3$], [AA3732; 1, CH, cPr, H, Cl, $OCF_3$], [AA3733; 1, CH, cPr, H, Br, $OCF_3$], [AA3734; 1, CH, cPr, H, I, $OCF_3$], [AA3735; 1, CH, cPr, H, $CF_3$, $OCF_3$], [AA3736; 1, CH, cPr, H, $CF_2H$, $OCF_3$], [AA3737; 1, CH, cPr, H, $C_2F_5$, $OCF_3$], [AA3738; 1, CH, cPr, H, $C_3F_7$, $OCF_3$], [AA3739; 1, CH, cPr, H, $CH_2CF_3$, $OCF_3$], [AA3740; 1, CH, cPr, H, $CH_2CHF_2$, $OCF_3$], [AA3741; 2, CH, cPr, H, F, $OCF_3$], [AA3742; 2, CH, cPr, H, Cl, $OCF_3$], [AA3743; 2, CH, cPr, H, Br, $OCF_3$], [AA3744; 2, CH, cPr, H, I, $OCF_3$], [AA3745; 2, CH, cPr, H, $CF_3$, $OCF_3$], [AA3746; 2, CH, cPr, H, $CF_2H$, $OCF_3$], [AA3747; 2, CH, cPr, H, $C_2F_3$, $OCF_3$], [AA3748; 2, CH, cPr, H, $C_3F_7$, $OCF_3$], [AA3749; 2, CH, cPr, H, $CH_2CF_3$, $OCF_3$], [AA3750; 2, CH, cPr, H, $CH_2CHF_2$, $OCF_3$], [AA3751; 0, N, cPr, H, F, $OCF_3$], [AA3752; 0, N, cPr, H, Cl, $OCF_3$], [AA3753; 0, N, cPr, H, Br, $OCF_3$], [AA3754; 0, N, cPr, H, I, $OCF_3$], [AA3755; 0, N, cPr, H, $CF_3$, $OCF_3$], [AA3756; 0, N, cPr, H, $CF_2H$, $OCF_3$], [AA3757; 0, N, cPr, H, $C_2F_5$, $OCF_3$], [AA3758; 0, N, cPr, H, $C_3F_7$, $OCF_3$], [AA3759; 0, N, cPr, H, $CH_2CF_3$, $OCF_3$], [AA3760; 0, N, cPr, H, $CH_2CHF_2$, $OCF_3$], [AA3761; 1, N, cPr, H, F, $OCF_3$], [AA3762; 1, N, cPr, H, Cl, $OCF_3$], [AA3763; 1, N, cPr, H, Br, $OCF_3$], [AA3764; 1, N, cPr, H, I, $OCF_3$], [AA3765; 1, N, cPr, H, $CF_3$, $OCF_3$], [AA3766; 1, N, cPr, H, $CF_2H$, $OCF_3$], [AA3767; 1, N, cPr, H, $C_2F_5$, $OCF_3$], [AA3768; 1, N, cPr, H, $C_3F_7$, $OCF_3$], [AA3769; 1, N, cPr, H, $CH_2CF_3$, $OCF_3$], [AA3770; 1, N, cPr, H, $CH_2CHF_2$, $OCF_3$], [AA3771; 2, N, cPr, H, F, $OCF_3$], [AA3772; 2, N, cPr, H, Cl, $OCF_3$], [AA3773; 2, N, cPr, H, Br, $OCF_3$], [AA3774; 2, N, cPr, H, I, $OCF_3$], [AA3775; 2, N, cPr, H, $CF_3$, $OCF_3$], [AA3776; 2, N, cPr, H, $CF_2H$, $OCF_3$], [AA3777; 2, N, cPr, H, $C_2F_5$, $OCF_3$], [AA3778; 2, N, cPr, H, $C_3F_7$, $OCF_3$], [AA3779; 2, N, cPr, H, $CH_2CF_3$, $OCF_3$], [AA3780; 2, N, cPr, H, $CH_2CHF_2$, $OCF_3$], [AA3781; 0, CH, H, H, H, $OCHF_2$], [AA3782; 0, CH, H, F, H, $OCHF_2$], [AA3783; 0, CH, H, Cl, H, $OCHF_2$], [AA3784; 0, CH, H, Br, H, $OCHF_2$], [AA3785; 0, CH, H, I, H, $OCHF_2$], [AA3786; 0, CH, H, $CF_3$, H, $OCHF_2$], [AA3787; 0, CH, H, $CF_2H$, H, $OCHF_2$], [AA3788; 0, CH, H, $C_2F_5$, H, $OCHF_2$], [AA3789; 0, CH, H, $C_3F_7$, H, $OCHF_2$], [AA3790; 0, CH, H, $CH_2CF_3$, H, $OCHF_2$], [AA3791; 0, CH, H, $CH_2CHF_2$, H, $OCHF_2$], [AA3792; 1, CH, H, H, H, $OCHF_2$], [AA3793; 1, CH, H, F, H, $OCHF_2$], [AA3794; 1, CH, H, Cl, H, $OCHF_2$], [AA3795; 1, CH, H, Br, H, $OCHF_2$], [AA3796; 1, CH, H, I, H, $OCHF_2$], [AA3797; 1, CH, H, $CF_3$, H, $OCHF_2$], [AA3798; 1, CH, H, $CF_2H$, H, $OCHF_2$], [AA3799; 1, CH, H, $C_2F_5$, H, $OCHF_2$], [AA3800; 1, CH, H, $C_3F_7$, H, $OCHF_2$], [AA3801; 1, CH, H, $CH_2CF_3$, H, $OCHF_2$], [AA3802; 1, CH, H, $CH_2CHF_2$, H, $OCHF_2$], [AA3803; 2, CH, H, H, H, $OCHF_2$], [AA3804; 2, CH, H, F, H, $OCHF_2$], [AA3805; 2, CH, H, Cl, H, $OCHF_2$], [AA3806; 2, CH, H, Br, H, $OCHF_2$], [AA3807; 2, CH, H, I, H, $OCHF_2$], [AA3808; 2, CH, H, $CF_3$, H, $OCHF_2$], [AA3809; 2, CH, H, $CF_2H$, H, $OCHF_2$], [AA3810; 2, CH, H, $C_2F_5$, H, $OCHF_2$], [AA3811; 2, CH, H, $C_3F_7$, H, $OCHF_2$], [AA3812; 2, CH, H, $CH_2CF_3$, H, $OCHF_2$], [AA3813; 2, CH, H, $CH_2CHF_2$, H, $OCHF_2$], [AA3814; 0, N,

H, H, H, $OCHF_2$], [AA3815; 0, N, H, F, H, $OCHF_2$], [AA3816; 0, N, H, Cl, H, $OCHF_2$], [AA3817; 0, N, H, Br, H, $OCHF_2$], [AA3818; 0, N, H, I, H, $OCHF_2$], [AA3819; 0, N, H, $CF_3$, H, $OCHF_2$], [AA3820; 0, N, H, $CF_2H$, H, $OCHF_2$], [AA3821; 0, N, H, $C_2F_5$, H, $OCHF_2$], [AA3822; 0, N, H, $C_3F_7$, H, $OCHF_2$], [AA3823; 0, N, H, $CH_2CF_3$, H, $OCHF_2$], [AA3824; 0, N, H, $CH_2CHF_2$, H, $OCHF_2$], [AA3825; 1, N, H, H, H, $OCHF_2$], [AA3826; 1, N, H, F, H, $OCHF_2$], [AA3827; 1, N, H, Cl, H, $OCHF_2$], [AA3828; 1, N, H, Br, H, $OCHF_2$], [AA3829; 1, N, H, I, H, $OCHF_2$], [AA3830; 1, N, H, $CF_3$, H, $OCHF_2$], [AA3831; 1, N, H, $CF_2H$, H, $OCHF_2$], [AA3832; 1, N, H, $C_2F_5$, H, $OCHF_2$], [AA3833; 1, N, H, $C_3F_7$, H, $OCHF_2$], [AA3834; 1, N, H, $CH_2CF_3$, H, $OCHF_2$], [AA3835; 1, N, H, $CH_2CHF_2$, H, $OCHF_2$], [AA3836; 2, N, H, H, H, $OCHF_2$], [AA3837; 2, N, H, F, H, $OCHF_2$], [AA3838; 2, N, H, Cl, H, $OCHF_2$], [AA3839; 2, N, H, Br, H, $OCHF_2$], [AA3840; 2, N, H, I, H, $OCHF_2$], [AA3841; 2, N, H, $CF_3$, H, $OCHF_2$], [AA3842; 2, N, H, $CF_2H$, H, $OCHF_2$], [AA3843; 2, N, H, $C_2F_5$, H, $OCHF_2$], [AA3844; 2, N, H, $C_3F_7$, H, $OCHF_2$], [AA3845; 2, N, H, $CH_2CF_3$, H, $OCHF_2$], [AA3846; 2, N, H, $CH_2CHF_2$, H, $OCHF_2$], [AA3847; 0, CH, Me, H, H, $OCHF_2$], [AA3848; 0, CH, Me, F, H, $OCHF_2$], [AA3849; 0, CH, Me, Cl, H, $OCHF_2$], [AA3850; 0, CH, Me, Br, H, $OCHF_2$], [AA3851; 0, CH, Me, I, H, $OCHF_2$], [AA3852; 0, CH, Me, $CF_3$, H, $OCHF_2$], [AA3853; 0, CH, Me, $CF_2H$, H, $OCHF_2$], [AA3854; 0, CH, Me, $C_2F_5$, H, $OCHF_2$], [AA3855; 0, CH, Me, $C_3F_7$, H, $OCHF_2$], [AA3856; 0, CH, Me, $CH_2CF_3$, H, $OCHF_2$], [AA3857; 0, CH, Me, $CH_2CHF_2$, H, $OCHF_2$], [AA3858; 1, CH, Me, H, H, $OCHF_2$], [AA3859; 1, CH, Me, F, H, $OCHF_2$], [AA3860; 1, CH, Me, Cl, H, $OCHF_2$], [AA3861; 1, CH, Me, Br, H, $OCHF_2$], [AA3862; 1, CH, Me, I, H, $OCHF_2$], [AA3863; 1, CH, Me, $CF_3$, H, $OCHF_2$], [AA3864; 1, CH, Me, $CF_2H$, H, $OCHF_2$], [AA3865; 1, CH, Me, $C_2F_5$, H, $OCHF_2$], [AA3866; 1, CH, Me, $C_3F_7$, H, $OCHF_2$], [AA3867; 1, CH, Me, $CH_2CF_3$, H, $OCHF_2$], [AA3868; 1, CH, Me, $CH_2CHF_2$, H, $OCHF_2$], [AA3869; 2, CH, Me, H, H, $OCHF_2$], [AA3870; 2, CH, Me, F, H, $OCHF_2$], [AA3871; 2, CH, Me, Cl, H, $OCHF_2$], [AA3872; 2, CH, Me, Br, H, $OCHF_2$], [AA3873; 2, CH, Me, I, H, $OCHF_2$], [AA3874; 2, CH, Me, $CF_3$, H, $OCHF_2$], [AA3875; 2, CH, Me, $CF_2H$, H, $OCHF_2$], [AA3876; 2, CH, Me, $C_2F_5$, H, $OCHF_2$], [AA3877; 2, CH, Me, $C_3F_7$, H, $OCHF_2$], [AA3878; 2, CH, Me, $CH_2CF_3$, H, $OCHF_2$], [AA3879; 2, CH, Me, $CH_2CHF_2$, H, $OCHF_2$], [AA3880; 0, N, Me, H, H, $OCHF_2$], [AA3881; 0, N, Me, F, H, $OCHF_2$], [AA3882; 0, N, Me, Cl, H, $OCHF_2$], [AA3883; 0, N, Me, Br, H, $OCHF_2$], [AA3884; 0, N, Me, I, H, $OCHF_2$], [AA3885; 0, N, Me, $CF_3$, H, $OCHF_2$], [AA3886; 0, N, Me, $CF_2H$, H, $OCHF_2$], [AA3887; 0, N, Me, $C_2F_5$, H, $OCHF_2$], [AA3888; 0, N, Me, $C_3F_7$, H, $OCHF_2$], [AA3889; 0, N, Me, $CH_2CF_3$, H, $OCHF_2$], [AA3890; 0, N, Me, $CH_2CHF_2$, H, $OCHF_2$], [AA3891; 1, N, Me, H, H, $OCHF_2$], [AA3892; 1, N, Me, F, H, $OCHF_2$], [AA3893; 1, N, Me, Cl, H, $OCHF_2$], [AA3894; 1, N, Me, Br, H, $OCHF_2$], [AA3895; 1, N, Me, I, H, $OCHF_2$], [AA3896; 1, N, Me, $CF_3$, H, $OCHF_2$], [AA3897; 1, N, Me, $CF_2H$, H, $OCHF_2$], [AA3898; 1, N, Me, $C_2F_5$, H, $OCHF_2$], [AA3899; 1, N, Me, $C_3F_7$, H, $OCHF_2$], [AA3900; 1, N, Me, $CH_2CF_3$, H, $OCHF_2$], [AA3901; 1, N, Me, $CH_2CHF_2$, H, $OCHF_2$], [AA3902; 2, N, Me, H, H, $OCHF_2$], [AA3903; 2, N, Me, F, H, $OCHF_2$], [AA3904; 2, N, Me, Cl, H, $OCHF_2$], [AA3905; 2, N, Me, Br, H, $OCHF_2$], [AA3906; 2, N, Me, I, H, $OCHF_2$], [AA3907; 2, N, Me, $CF_3$, H, $OCHF_2$], [AA3908; 2, N, Me, $CF_2H$, H, $OCHF_2$], [AA3909; 2, N, Me, $C_2F_5$, H, $OCHF_2$], [AA3910; 2, N, Me, $C_3F_7$, H, $OCHF_2$], [AA3911; 2, N, Me, $CH_2CF_3$, H, $OCHF_2$], [AA3912; 2, N, Me, $CH_2CHF_2$, H, $OCHF_2$], [AA3913; 0, CH, Et, H, H, $OCHF_2$], [AA3914; 0, CH, Et, F, H, $OCHF_2$], [AA3915; 0, CH, Et, Cl, H, $OCHF_2$], [AA3916; 0, CH, Et, Br, H, $OCHF_2$], [AA3917; 0, CH, Et, I, H, $OCHF_2$], [AA3918; 0, CH, Et, $CF_3$, H, $OCHF_2$], [AA3919; 0, CH, Et, $CF_2H$, H, $OCHF_2$], [AA3920; 0, CH, Et, $C_2F_5$, H, $OCHF_2$], [AA3921; 0, CH, Et, $C_3F_2$, H, $OCHF_2$], [AA3922; 0, CH, Et, $CH_2CF_3$, H, $OCHF_2$], [AA3923; 0, CH, Et, $CH_2CHF_2$, H, $OCHF_2$], [AA3924; 1, CH, Et, H, H, $OCHF_2$], [AA3925; 1, CH, Et, F, H, $OCHF_2$], [AA3926; 1, CH, Et, Cl, H, $OCHF_2$], [AA3927; 1, CH, Et, Br, H, $OCHF_2$], [AA3928; 1, CH, Et, I, H, $OCHF_2$], [AA3929; 1, CH, Et, $CF_3$, H, $OCHF_2$], [AA3930; 1, CH, Et, $CF_2H$, H, $OCHF_2$], [AA3931; 1, CH, Et, $C_2F_5$, H, $OCHF_2$], [AA3932; 1, CH, Et, $C_3F$-7, H, $OCHF_2$], [AA3933; 1, CH, Et, $CH_2CF_3$, H, $OCHF_2$], [AA3934; 1, CH, Et, $CH_2CHF_2$, H, $OCHF_2$], [AA3935; 2, CH, Et, H, H, $OCHF_2$], [AA3936; 2, CH, Et, F, H, $OCHF_2$], [AA3937; 2, CH, Et, Cl, H, $OCHF_2$], [AA3938; 2, CH, Et, Br, H, $OCHF_2$], [AA3939; 2, CH, Et, I, H, $OCHF_2$], [AA3940; 2, CH, Et, $CF_3$, H, $OCHF_2$], [AA3941; 2, CH, Et, $CF_2H$, H, $OCHF_2$], [AA3942; 2, CH, Et, $C_2F_5$, H, $OCHF_2$], [AA3943; 2, CH, Et, $C_3F_7$, H, $OCHF_2$], [AA3944; 2, CH, Et, $CH_2CF_3$, H, $OCHF_2$], [AA3945; 2, CH, Et, $CH_2CHF_2$, H, $OCHF_2$], [AA3946; 0, N, Et, H, H, $OCHF_2$], [AA3947; 0, N, Et, F, H, $OCHF_2$], [AA3948; 0, N, Et, Cl, H, $OCHF_2$], [AA3949; 0, N, Et, Br, H, $OCHF_2$], [AA3950; 0, N, Et, I, H, $OCHF_2$], [AA3951; 0, N, Et, $CF_3$, H, $OCHF_2$], [AA3952; 0, N, Et, $CF_2H$, H, $OCHF_2$], [AA3953; 0, N, Et, $C_2F_5$, H, $OCHF_2$], [AA3954; 0, N, Et, $C_3F_7$, H, $OCHF_2$], [AA3955; 0, N, Et, $CH_2CF_3$, H, $OCHF_2$], [AA3956; 0, N, Et, $CH_2CHF_2$, H, $OCHF_2$], [AA3957; 1, N, Et, H, H, $OCHF_2$], [AA3958; 1, N, Et, F, H, $OCHF_2$], [AA3959; 1, N, Et, Cl, H, $OCHF_2$], [AA3960; 1, N, Et, Br, H, $OCHF_2$], [AA3961; 1, N, Et, I, H, $OCHF_2$], [AA3962; 1, N, Et, $CF_3$, H, $OCHF_2$], [AA3963; 1, N, Et, $CF_2H$, H, $OCHF_2$], [AA3964; 1, N, Et, $C_2F_5$, H, $OCHF_2$], [AA3965; 1, N, Et, $C_3F_7$, H, $OCHF_2$], [AA3966; 1, N, Et, $CH_2CF_3$, H, $OCHF_2$], [AA3967; 1, N, Et, $CH_2CHF_2$, H, $OCHF_2$], [AA3968; 2, N, Et, H, H, $OCHF_2$], [AA3969; 2, N, Et, F, H, $OCHF_2$], [AA3970; 2, N, Et, Cl, H, $OCHF_2$], [AA3971; 2, N, Et, Br, H, $OCHF_2$], [AA3972; 2, N, Et, I, H, $OCHF_2$], [AA3973; 2, N, Et, $CF_3$, H, $OCHF_2$], [AA3974; 2, N, Et, $CF_2H$, H, $OCHF_2$], [AA3975; 2, N, Et, $C_2F_5$, H, $OCHF_2$], [AA3976; 2, N, Et, $C_3F_7$, H, $OCHF_2$], [AA3977; 2, N, Et, $CH_2CF_3$, H, $OCHF_2$], [AA3978; 2, N, Et, $CH_2CHF_2$, H, $OCHF_2$], [AA3979; 0, CH, iPr, H, H, $OCHF_2$], [AA3980; 0, CH, iPr, F, H, $OCHF_2$], [AA3981; 0, CH, iPr, Cl, H, $OCHF_2$], [AA3982; 0, CH, iPr, Br, H, $OCHF_2$], [AA3983; 0, CH, iPr, I, H, $OCHF_2$], [AA3984; 0, CH, iPr, $CF_3$, H, $OCHF_2$], [AA3985; 0, CH, iPr, $CF_2H$, H, $OCHF_2$], [AA3986; 0, CH, iPr, $C_2F_5$, H, $OCHF_2$], [AA3987; 0, CH, iPr, $C_3F_7$, H, $OCHF_2$], [AA3988; 0, CH, iPr, $CH_2CF_3$, H, $OCHF_2$], [AA3989; 0, CH, iPr, $CH_2CHF_2$, H, $OCHF_2$], [AA3990; 1, CH, iPr, H, H, $OCHF_2$], [AA3991; 1, CH, iPr, F, H, $OCHF_2$], [AA3992; 1, CH, iPr, Cl, H, $OCHF_2$], [AA3993; 1, CH, iPr, Br, H, $OCHF_2$], [AA3994; 1, CH, iPr, I, H, $OCHF_2$], [AA3995; 1, CH, iPr, $CF_3$, H, $OCHF_2$], [AA3996; 1, CH, iPr, $CF_2H$, H, $OCHF_2$], [AA3997; 1, CH, iPr, $C_2F_5$, H, $OCHF_2$], [AA3998; 1, CH, iPr, $C_3F_7$, H, $OCHF_2$], [AA3999; 1, CH, iPr, $CH_2CF_3$, H, $OCHF_2$], [AA4000; 1, CH, iPr, $CH_2CHF_2$, H, $OCHF_2$], [AA4001; 2, CH, iPr, H, H, $OCHF_2$], [AA4002; 2, CH, iPr, F, H, $OCHF_2$], [AA4003; 2, CH, iPr, Cl, H, $OCHF_2$], [AA4004; 2, CH, iPr, Br, H, $OCHF_2$], [AA4005; 2, CH, iPr, I, H, $OCHF_2$], [AA4006; 2, CH, iPr, $CF_3$, H, $OCHF_2$], [AA4007; 2, CH, iPr, $CF_2H$, H, $OCHF_2$], [AA4008; 2, CH, iPr, $C_2F_5$, H, $OCHF_2$], [AA4009; 2, CH, iPr, $C_3F_7$, H, $OCHF_2$], [AA4010; 2, CH, iPr, $CH_2CF_3$, H, $OCHF_2$],

[AA4011; 2, CH, iPr, $CH_2CHF_2$, H, $OCHF_2$], [AA4012; 0, N, iPr, H, H, $OCHF_2$], [AA4013; 0, N, iPr, F, H, $OCHF_2$], [AA4014; 0, N, iPr, Cl, H, $OCHF_2$], [AA4015; 0, N, iPr, Br, H, $OCHF_2$], [AA4016; 0, N, iPr, I, H, $OCHF_2$], [AA4017; 0, N, iPr, $CF_3$, H, $OCHF_2$], [AA4018; 0, N, iPr, $CF_2H$, H, $OCHF_2$], [AA4019; 0, N, iPr, $C_2F_5$, H, $OCHF_2$], [AA4020; 0, N, iPr, $C_3F_7$, H, $OCHF_2$], [AA4021; 0, N, iPr, $CH_2CF_3$, H, $OCHF_2$], [AA4022; 0, N, iPr, $CH_2CHF_2$, H, $OCHF_2$], [AA4023; 1, N, iPr, H, H, $OCHF_2$], [AA4024; 1, N, iPr, F, H, $OCHF_2$], [AA4025; 1, N, iPr, Cl, H, $OCHF_2$], [AA4026; 1, N, iPr, Br, H, $OCHF_2$], [AA4027; 1, N, iPr, I, H, $OCHF_2$], [AA4028; 1, N, iPr, $CF_3$, H, $OCHF_2$], [AA4029; 1, N, iPr, $CF_2H$, H, $OCHF_2$], [AA4030; 1, N, iPr, $C_2F_5$, H, $OCHF_2$], [AA4031; 1, N, iPr, $C_3F_7$, H, $OCHF_2$], [AA4032; 1, N, iPr, $CH_2CF_3$, H, $OCHF_2$], [AA4033; 1, N, iPr, $CH_2CHF_2$, H, $OCHF_2$], [AA4034; 2, N, iPr, H, H, $OCHF_2$], [AA4035; 2, N, iPr, F, H, $OCHF_2$], [AA4036; 2, N, iPr, Cl, H, $OCHF_2$], [AA4037; 2, N, iPr, Br, H, $OCHF_2$], [AA4038; 2, N, iPr, I, H, $OCHF_2$], [AA4039; 2, N, iPr, $CF_3$, H, $OCHF_2$], [AA4040; 2, N, iPr, $CF_2H$, H, $OCHF_2$], [AA4041; 2, N, iPr, $C_2F_5$, H, $OCHF_2$], [AA4042; 2, N, iPr, $C_3F_7$, H, $OCHF_2$], [AA4043; 2, N, iPr, $CH_2CF_3$, H, $OCHF_2$], [AA4044; 2, N, iPr, $CH_2CHF_2$, H, $OCHF_2$], [AA4045; 0, CH, cPr, H, H, $OCHF_2$], [AA4046; 0, CH, cPr, F, H, $OCHF_2$], [AA4047; 0, CH, cPr, Cl, H, $OCHF_2$], [AA4048; 0, CH, cPr, Br, H, $OCHF_2$], [AA4049; 0, CH, cPr, I, H, $OCHF_2$], [AA4050; 0, CH, cPr, $CF_3$, H, $OCHF_2$], [AA4051; 0, CH, cPr, $CF_2H$, H, $OCHF_2$], [AA4052; 0, CH, cPr, $C_2F_5$, H, $OCHF_2$], [AA4053; 0, CH, cPr, $C_3F_7$, H, $OCHF_2$], [AA4054; 0, CH, cPr, $CH_2CF_3$, H, $OCHF_2$], [AA4055; 0, CH, cPr, $CH_2CHF_2$, H, $OCHF_2$], [AA4056; 1, CH, cPr, H, H, $OCHF_2$], [AA4057; 1, CH, cPr, F, H, $OCHF_2$], [AA4058; 1, CH, cPr, Cl, H, $OCHF_2$], [AA4059; 1, CH, cPr, Br, H, $OCHF_2$], [AA4060; 1, CH, cPr, I, H, $OCHF_2$], [AA4061; 1, CH, cPr, $CF_3$, H, $OCHF_2$], [AA4062; 1, CH, cPr, $CF_2H$, H, $OCHF_2$], [AA4063; 1, CH, cPr, $C_2Fa$, H, $OCHF_2$], [AA4064; 1, CH, cPr, $C_3F_7$, H, $OCHF_2$], [AA4065; 1, CH, cPr, $CH_2CF_3$, H, $OCHF_2$], [AA4066; 1, CH, cPr, $CH_2CHF_2$, H, $OCHF_2$], [AA4067; 2, CH, cPr, H, H, $OCHF_2$], [AA4068; 2, CH, cPr, F, H, $OCHF_2$], [AA4069; 2, CH, cPr, Cl, H, $OCHF_2$], [AA4070; 2, CH, cPr, Br, H, $OCHF_2$], [AA4071; 2, CH, cPr, I, H, $OCHF_2$], [AA4072; 2, CH, cPr, $CF_3$, H, $OCHF_2$], [AA4073; 2, CH, cPr, $CF_2H$, H, $OCHF_2$], [AA4074; 2, CH, cPr, $C_2F_5$, H, $OCHF_2$], [AA4075; 2, CH, cPr, $C_3F_7$, H, $OCHF_2$], [AA4076; 2, CH, cPr, $CH_2CF_3$, H, $OCHF_2$], [AA4077; 2, CH, cPr, $CH_2CHF_2$, H, $OCHF_2$], [AA4078; 0, N, cPr, H, H, $OCHF_2$], [AA4079; 0, N, cPr, F, H, $OCHF_2$], [AA4080; 0, N, cPr, Cl, H, $OCHF_2$], [AA4081; 0, N, cPr, Br, H, $OCHF_2$], [AA4082; 0, N, cPr, I, H, $OCHF_2$], [AA4083; 0, N, cPr, $CF_3$, H, $OCHF_2$], [AA4084; 0, N, cPr, $CF_2H$, H, $OCHF_2$], [AA4085; 0, N, cPr, $C_2F_5$, H, $OCHF_2$], [AA4086; 0, N, cPr, $C_3F_7$, H, $OCHF_2$], [AA4087; 0, N, cPr, $CH_2CF_3$, H, $OCHF_2$], [AA44088; 0, N, cPr, $CH_2CHF_2$, H, $OCHF_2$], [AA4089; 1, N, cPr, H, H, $OCHF_2$], [AA4090; 1, N, cPr, F, H, $OCHF_2$], [AA4091; 1, N, cPr, Cl, H, $OCHF_2$], [AA4092; 1, N, cPr, Br, H, $OCHF_2$], [AA4093; 1, N, cPr, I, H, $OCHF_2$], [AA4094; 1, N, cPr, $CF_3$, H, $OCHF_2$], [AA4095; 1, N, cPr, $CF_2H$, H, $OCHF_2$], [AA4096; 1, N, cPr, $C_2F_5$, H, $OCHF_2$], [AA4097; 1, N, cPr, $C_3F_7$, H, $OCHF_2$], [AA4098; 1, N, cPr, $CH_2CF_3$, H, $OCHF_2$], [AA4099; 1, N, cPr, $CH_2CHF_2$, H, $OCHF_2$], [AA4100; 2, N, cPr, H, H, $OCHF_2$], [AA4101; 2, N, cPr, F, H, $OCHF_2$], [AA4102; 2, N, cPr, Cl, H, $OCHF_2$], [AA4103; 2, N, cPr, Br, H, $OCHF_2$], [AA4104; 2, N, cPr, I, H, $OCHF_2$], [AA4105; 2, N, cPr, $CF_3$, H, $OCHF_2$], [AA4106; 2, N, cPr, $CF_2H$, H, $OCHF_2$], [AA4107; 2, N, cPr, $C_2F$, H, $OCHF_2$], [AA4108; 2, N, cPr, $C_3F_7$, H, $OCHF_2$], [AA4109; 2, N, cPr, $CH_2CF_3$, H, $OCHF_2$], [AA4110; 2, N, cPr, $CH_2CHF_2$, H, $OCHF_2$], [AA4111; 0, CH, H, H, F, $OCHF_2$], [AA4112; 0, CH, H, H, Cl, $OCHF_2$], [AA4113; 0, CH, H, H, Br, $OCHF_2$], [AA4114; 0, CH, H, H, I, $OCHF_2$], [AA4115; 0, CH, H, H, $CF_3$, $OCHF_2$], [AA4116; 0, CH, H, H, $CF_2H$, $OCHF_2$], [AA4117; 0, CH, H, H, $C_2F_5$, $OCHF_2$], [AA4118; 0, CH, H, H, $C_3F_7$, $OCHF_2$], [AA4119; 0, CH, H, H, $CH_2CF_3$, $OCHF_2$], [AA4120; 0, CH, H, H, $CH_2CHF_2$, $OCHF_2$], [AA4121; 1, CH, H, H, F, $OCHF_2$], [AA4122; 1, CH, H, H, Cl, $OCHF_2$], [AA4123; 1, CH, H, H, Br, $OCHF_2$], [AA4124; 1, CH, H, H, I, $OCHF_2$], [AA4125; 1, CH, H, H, $CF_3$, $OCHF_2$], [AA4126; 1, CH, H, H, $CF_2H$, $OCHF_2$], [AA4127; 1, CH, H, H, $C_2F_5$, $OCHF_2$], [AA4128; 1, CH, H, H, $C_3F_7$, $OCHF_2$], [AA4129; 1, CH, H, H, $CH_2CF_3$, $OCHF_2$], [AA4130; 1, CH, H, H, $CH_2CHF_2$, $OCHF_2$], [AA4131; 2, CH, H, H, F, $OCHF_2$], [AA4132; 2, CH, H, H, Cl, $OCHF_2$], [AA4133; 2, CH, H, H, Br, $OCHF_2$], [AA4134; 2, CH, H, H, I, $OCHF_2$], [AA4135; 2, CH, H, H, $CF_3$, $OCHF_2$], [AA4136; 2, CH, H, H, $CF_2H$, $OCHF_2$], [AA4137; 2, CH, H, H, $C_2F_5$, $OCHF_2$], [AA4138; 2, CH, H, H, $C_3F_7$, $OCHF_2$], [AA4139; 2, CH, H, H, $CH_2CF_3$, $OCHF_2$], [AA4140; 2, CH, H, H, $CH_2CHF_2$, $OCHF_2$], [AA4141; 0, N, H, H, F, $OCHF_2$], [AA4142; 0, N, H, H, Cl, $OCHF_2$], [AA4143; 0, N, H, H, Br, $OCHF_2$], [AA4144; 0, N, H, H, I, $OCHF_2$], [AA4145; 0, N, H, H, $CF_3$, $OCHF_2$], [AA4146; 0, N, H, H, $CF_2H$, $OCHF_2$], [AA4147; 0, N, H, H, $C_2F_5$, $OCHF_2$], [AA4148; 0, N, H, H, $C_3F_7$, $OCHF_2$], [AA4149; 0, N, H, H, $CH_2CF_3$, $OCHF_2$], [AA4150; 0, N, H, H, $CH_2CHF_2$, $OCHF_2$], [AA4151; 1, N, H, H, F, $OCHF_2$], [AA4152; 1, N, H, H, Cl, $OCHF_2$], [AA4153; 1, N, H, H, Br, $OCHF_2$], [AA4154; 1, N, H, H, I, $OCHF_2$], [AA4155; 1, N, H, H, $CF_3$, $OCHF_2$], [AA4156; 1, N, H, H, $CF_2H$, $OCHF_2$], [AA4157; 1, N, H, H, $C_2F_5$, $OCHF_2$], [AA4158; 1, N, H, H, $C_3F_7$, $OCHF_2$], [AA4159; 1, N, H, H, $CH_2CF_3$, $OCHF_2$], [AA4160; 1, N, H, H, $CH_2CHF_2$, $OCHF_2$], [AA4161; 2, N, H, H, F, $OCHF_2$], [AA4162; 2, N, H, H, Cl, $OCHF_2$], [AA4163; 2, N, H, H, Br, $OCHF_2$], [AA4164; 2, N, H, H, I, $OCHF_2$], [AA4165; 2, N, H, H, $CF_3$, $OCHF_2$], [AA4166; 2, N, H, H, $CF_2H$, $OCHF_2$], [AA4167; 2, N, H, H, $C_2F_5$, $OCHF_2$], [AA4168; 2, N, H, H, $C_3F_7$, $OCHF_2$], [AA4169; 2, N, H, H, $CH_2CF_3$, $OCHF_2$], [AA4170; 2, N, H, H, $CH_2CHF_2$, $OCHF_2$], [AA4171; 0, CH, Me, H, F, $OCHF_2$], [AA4172; 0, CH, Me, H, Cl, $OCHF_2$], [AA4173; 0, CH, Me, H, Br, $OCHF_2$], [AA4174; 0, CH, Me, H, I, $OCHF_2$], [AA4175; 0, CH, Me, H, $CF_3$, $OCHF_2$], [AA4176; 0, CH, Me, H, $CF_2H$, $OCHF_2$], [AA4177; 0, CH, Me, H, $C_2F_5$, $OCHF_2$], [AA4178; 0, CH, Me, H, $C_3F_7$, $OCHF_2$], [AA4179; 0, CH, Me, H, $CH_2CF_3$, $OCHF_2$], [AA4180; 0, CH, Me, H, $CH_2CHF_2$, $OCHF_2$], [AA4181; 1, CH, Me, H, F, $OCHF_2$], [AA4182; 1, CH, Me, H, Cl, $OCHF_2$], [AA4183; 1, CH, Me, H, Br, $OCHF_2$], [AA4184; 1, CH, Me, H, I, $OCHF_2$], [AA4185; 1, CH, Me, H, $CF_3$, $OCHF_2$], [AA4186; 1, CH, Me, H, $CF_2H$, $OCHF_2$], [AA4187; 1, CH, Me, H, $C_2F_5$, $OCHF_2$], [AA4188; 1, CH, Me, H, $C_3F_7$, $OCHF_2$], [AA4189; 1, CH, Me, H, $CH_2CF_3$, $OCHF_2$], [AA4190; 1, CH, Me, H, $CH_2CHF_2$, $OCHF_2$], [AA4191; 2, CH, Me, H, F, $OCHF_2$], [AA4192; 2, CH, Me, H, Cl, $OCHF_2$], [AA4193; 2, CH, Me, H, Br, $OCHF_2$], [AA4194; 2, CH, Me, H, I, $OCHF_2$], [AA4195; 2, CH, Me, H, $CF_3$, $OCHF_2$], [AA4196; 2, CH, Me, H, $CF_2H$, $OCHF_2$], [AA4197; 2, CH, Me, H, $C_2F_5$, $OCHF_2$], [AA4198; 2, CH, Me, H, $C_3F_7$, $OCHF_2$], [AA4199; 2, CH, Me, H, $CH_2CF_3$, $OCHF_2$], [AA4200; 2, CH, Me, H, $CH_2CHF_2$, $OCHF_2$], [AA4201; 0, N, Me, H, F, $OCHF_2$], [AA4202; 0, N, Me, H, Cl, $OCHF_2$], [AA4203; 0, N, Me, H, Br, $OCHF_2$], [AA4204; 0, N, Me, H, I, $OCHF_2$], [AA4205; 0, N, Me, H, $CF_3$, $OCHF_2$], [AA4206; 0, N, Me, H, $CF_2H$, $OCHF_2$], [AA4207; 0, N, Me, H, $C_2F_5$, $OCHF_2$], [AA4208; 0, N, Me, H, $C_3F_7$, $OCHF_2$], [AA4209; 0, N, Me, H, $CH_2CF_3$, $OCHF_2$], [AA4210; 0, N, Me, H, $CH_2CHF_2$, $OCHF_2$], [AA4211; 1, N, Me, H, F, $OCHF_2$], [AA4212; 1, N, Me, H, Cl, $OCHF_2$], [AA4213; 1, N, Me, H, Br, $OCHF_2$], [AA4214; 1, N, Me, H, I, $OCHF_2$], [AA4215; 1, N, Me, H, $CF_3$, $OCHF_2$], [AA4216; 1, N, Me, H, $CF_2H$, $OCHF_2$], [AA4217; 1, N, Me, H, $C_2F_5$, $OCHF_2$], [AA4218; 1, N, Me, H, $C_3F_7$, $OCHF_2$], [AA4219; 1, N, Me, H, $CH_2CF_3$, $OCHF_2$], [AA4220; 1, N, Me, H, $CH_2CHF_2$, $OCHF_2$], [AA4221; 2, N, Me, H, F, $OCHF_2$], [AA4222; 2, N, Me, H, Cl, $OCHF_2$], [AA4223; 2, N, Me, H, Br, $OCHF_2$], [AA4224; 2, N, Me, H, I, $OCHF_2$], [AA4225; 2, N, Me, H, $CF_3$, $OCHF_2$], [AA4226; 2, N, Me, H, $CF_2H$, $OCHF_2$], [AA4227; 2, N, Me, H, $C_2F_5$, $OCHF_2$], [AA4228; 2, N, Me, H, $C_3F_7$, $OCHF_2$], [AA4229; 2, N, Me, H, $CH_2CF_3$, $OCHF_2$], [AA4230; 2, N, Me, H, $CH_2CHF_2$, $OCHF_2$], [AA4231; 0, CH, Et, H, F, $OCHF_2$], [AA4232; 0, CH, Et, H, Cl, $OCHF_2$], [AA4233; 0, CH, Et, H, Br, $OCHF_2$], [AA4234; 0, CH, Et, H, I, $OCHF_2$], [AA4235; 0, CH, Et, H, $CF_3$, $OCHF_2$], [AA4236; 0, CH, Et, H, $CF_2H$, $OCHF_2$], [AA4237; 0, CH, Et, H, $C_2F_5$, $OCHF_2$], [AA4238; 0, CH, Et, H, $C_3F_7$, $OCHF_2$], [AA4239; 0, CH, Et, H, $CH_2CF_3$, $OCHF_2$], [AA4240; 0, CH, Et, H, $CH_2CHF_2$, $OCHF_2$], [AA4241; 1, CH, Et, H, F, $OCHF_2$], [AA4242; 1, CH, Et, H, Cl, $OCHF_2$], [AA4243; 1, CH, Et, H, Br, $OCHF_2$], [AA4244; 1, CH, Et, H, I, $OCHF_2$], [AA4245; 1, CH, Et, H, $CF_3$, $OCHF_2$], [AA4246; 1, CH, Et, H, $CF_2H$, $OCHF_2$], [AA4247; 1, CH, Et, H, $C_2F_5$, $OCHF_2$], [AA4248; 1, CH, Et, H, $C_3F_7$, $OCHF_2$], [AA4249; 1, CH, Et, H, $CH_2CF_3$, $OCHF_2$], [AA4250; 1, CH, Et, H, $CH_2CHF_2$, $OCHF_2$], [AA4251; 2, CH, Et, H, F, $OCHF_2$], [AA4252; 2, CH, Et, H, Cl, $OCHF_2$], [AA4253; 2, CH, Et, H, Br, $OCHF_2$], [AA4254; 2, CH, Et, H, I, $OCHF_2$], [AA4255; 2, CH, Et, H, $CF_3$, $OCHF_2$], [AA4256; 2, CH, Et, H, $CF_2H$, $OCHF_2$], [AA4257; 2, CH, Et, H, $C_2F_5$, $OCHF_2$], [AA4258; 2, CH, Et, H, $C_3F_7$, $OCHF_2$], [AA4259; 2, CH, Et, H, $CH_2CF_3$, $OCHF_2$], [AA4260; 2, CH, Et, H, $CH_2CHF$, $OCHF_2$], [AA4261; 0, N, Et, H, F, $OCHF_2$], [AA4262; 0, N, Et, H, Cl, $OCHF_2$], [AA4263; 0, N, Et, H, Br, $OCHF_2$], [AA4264; 0, N, Et, H, I, $OCHF_2$], [AA4265; 0, N, Et, H, $CF_3$, $OCHF_2$], [AA4266; 0, N, Et, H, $CF_2H$, $OCHF_2$], [AA4267; 0, N, Et, H, $C_2F_5$, $OCHF_2$], [AA4268; 0, N, Et, H, $C_3F_7$, $OCHF_2$], [AA4269; 0, N, Et, H, $CH_2CF_3$, $OCHF_2$], [AA4270; 0, N, Et, H, $CH_2CHF_2$, $OCHF_2$], [AA4271; 1, N, Et, H, F, $OCHF_2$], [AA4272; 1, N, Et, H, Cl, $OCHF_2$], [AA4273; 1, N, Et, H, Br, $OCHF_2$], [AA4274; 1, N, Et, H, I, $OCHF_2$], [AA4275; 1, N, Et, H, $CF_3$, $OCHF_2$], [AA4276; 1, N, Et, H, $CF_2H$, $OCHF_2$], [AA4277; 1, N, Et, H, $C_2F_5$, $OCHF_2$], [AA4278; 1, N, Et, H, $C_3F_7$, $OCHF_2$], [AA4279; 1, N, Et, H, $CH_2CF_3$, $OCHF_2$], [AA4280; 1, N, Et, H, $CH_2CHF_2$, $OCHF_2$], [AA4281; 2, N, Et, H, F, $OCHF_2$], [AA4282; 2, N, Et, H, Cl, $OCHF_2$], [AA4283; 2, N, Et, H, Br, $OCHF_2$], [AA4284; 2, N, Et, H, I, $OCHF_2$], [AA4285; 2, N, Et, H, $CF_3$, $OCHF_2$], [AA4286; 2, N, Et, H, $CF_2H$, $OCHF_2$], [AA4287; 2, N, Et, H, $C_2F_5$, $OCHF_2$], [AA4288; 2, N, Et, H, $C_3F_7$, $OCHF_2$], [AA4289; 2, N, Et, H, $CH_2CF_3$, $OCHF_2$], [AA4290; 2, N, Et, H, $CH_2CHF_2$, $OCHF_2$], [AA4291; 0, CH, iPr, H, F, $OCHF_2$], [AA4292; 0, CH, iPr, H, Cl, $OCHF_2$], [AA4293; 0, CH, iPr, H, Br, $OCHF_2$], [AA4294; 0, CH, iPr, H, I, $OCHF_2$], [AA4295; 0, CH, iPr, H, $CF_3$, $OCHF_2$], [AA4296; 0, CH, iPr, H, $CF_2H$, $OCHF_2$], [AA4297; 0, CH, iPr, H, $C_2F_5$, $OCHF_2$], [AA4298; 0, CH, iPr, H, $C_3F_7$, $OCHF_2$], [AA4299; 0, CH, iPr, H, $CH_2CF_3$, $OCHF_2$], [AA4300; 0, CH, iPr, H, $CH_2CHF_2$, $OCHF_2$], [AA4301; 1, CH, iPr, H, F, $OCHF_2$], [AA4302; 1, CH, iPr, H, Cl, $OCHF_2$], [AA4303; 1, CH, iPr, H, Br, $OCHF_2$], [AA4304; 1, CH, iPr, H, I, $OCHF_2$], [AA4305; 1, CH, iPr, H, $CF_3$, $OCHF_2$], [AA4306; 1, CH, iPr, H, $CF_2H$, $OCHF_2$], [AA4307; 1, CH, iPr, H, $C_2F_5$, $OCHF_2$], [AA4308; 1, CH, iPr, H, $C_3F_7$, $OCHF_2$], [AA4309; 1, CH, iPr, H, $CH_2CF_3$, $OCHF_2$], [AA4310; 1, CH, iPr, H, $CH_2CHF_2$, $OCHF_2$], [AA4311; 2, CH, iPr, H, F, $OCHF_2$], [AA4312; 2, CH, iPr, H, Cl, $OCHF_2$], [AA4313; 2, CH, iPr, H, Br, $OCHF_2$], [AA4314; 2, CH, iPr, H, I, $OCHF_2$], [AA4315; 2, CH, iPr, H, $CF_3$, $OCHF_2$], [AA4316; 2, CH, iPr, H, $CF_2H$, $OCHF_2$], [AA4317; 2, CH, iPr, H, $C_2F_5$, $OCHF_2$], [AA4318; 2, CH, iPr, H, $C_3F_7$, $OCHF_2$], [AA4319; 2, CH, iPr, H, $CH_2CF_3$, $OCHF_2$], [AA4320; 2, CH, iPr, H, $CH_2CHF_2$, $OCHF_2$], [AA4321; 0, N, iPr, H, F, $OCHF_2$], [AA4322; 0, N, iPr, H, Cl, $OCHF_2$], [AA4323; 0, N, iPr, H, Br, $OCHF_2$], [AA4324; 0, N, iPr, H, I, $OCHF_2$], [AA4325; 0, N, iPr, H, $CF_3$, $OCHF_2$], [AA4326; 0, N, iPr, H, $CF_2H$, $OCHF_2$], [AA4327; 0, N, iPr, H, $C_2F_5$, $OCHF_2$], [AA4328; 0, N, iPr, H, $C_3F_7$, $OCHF_2$], [AA4329; 0, N, iPr, H, $CH_2CF_3$, $OCHF_2$], [AA4330; 0, N, iPr, H, $CH_2CHF_2$, $OCHF_2$], [AA4331; 1, N, iPr, H, F, $OCHF_2$], [AA4332; 1, N, iPr, H, Cl, $OCHF_2$], [AA4333; 1, N, iPr, H, Br, $OCHF_2$], [AA4334; 1, N, iPr, H, I, $OCHF_2$], [AA4335; 1, N, iPr, H, $CF_3$, $OCHF_2$], [AA4336; 1, N, iPr, H, $CF_2H$, $OCHF_2$], [AA4337; 1, N, iPr, H, $C_2F_5$, $OCHF_2$], [AA4338; 1, N, iPr, H, $C_3F_7$, $OCHF_2$], [AA4339; 1, N, iPr, H, $CH_2CF_3$, $OCHF_2$], [AA4340; 1, N, iPr, H, $CH_2CHF_2$, $OCHF_2$], [AA4341; 2, N, iPr, H, F, $OCHF_2$], [AA4342; 2, N, iPr, H, Cl, $OCHF_2$], [AA4343; 2, N, iPr, H, Br, $OCHF_2$], [AA4344; 2, N, iPr, H, I, $OCHF_2$], [AA4345; 2, N, iPr, H, $CF_3$, $OCHF_2$], [AA4346; 2, N, iPr, H, $CF_2H$, $OCHF_2$], [AA4347; 2, N, iPr, H, $C_2F_5$, $OCHF_2$], [AA4348; 2, N, iPr, H, $C_3F_7$, $OCHF_2$], [AA4349; 2, N, iPr, H, $CH_2CF_3$, $OCHF_2$], [AA4350; 2, N, iPr, H, $CH_2CHF_2$, $OCHF_2$], [AA4351; 0, CH, cPr, H, F, $OCHF_2$], [AA4352; 0, CH, cPr, H, Cl, $OCHF_2$], [AA4353; 0, CH, cPr, H, Br, $OCHF_2$], [AA4354; 0, CH, cPr, H, I, $OCHF_2$], [AA4355; 0, CH, cPr, H, $CF_3$, $OCHF_2$], [AA4356; 0, CH, cPr, H, $CF_2H$, $OCHF_2$], [AA4357; 0, CH, cPr, H, $C_2F_5$, $OCHF_2$], [AA4358; 0, CH, cPr, H, $C_3F_7$, $OCHF_2$], [AA4359; 0, CH, cPr, H, $CH_2CF_3$, $OCHF_2$], [AA4360; 0, CH, cPr, H, $CH_2CHF_2$, $OCHF_2$], [AA4361; 1, CH, cPr, H, F, $OCHF_2$], [AA4362; 1, CH, cPr, H, Cl, $OCHF_2$], [AA4363; 1, CH, cPr, H, Br, $OCHF_2$], [AA4364; 1, CH, cPr, H, I, $OCHF_2$], [AA4365; 1, CH, cPr, H, $CF_3$, $OCHF_2$], [AA4366; 1, CH, cPr, H, $CF_2H$, $OCHF_2$], [AA4367; 1, CH, cPr, H, $C_2F_5$, $OCHF_2$], [AA4368; 1, CH, cPr, H, $C_3F_7$, $OCHF_2$], [AA4369; 1, CH, cPr, H, $CH_2CF_3$, $OCHF_2$], [AA4370; 1, CH, cPr, H, $CH_2CHF_2$, $OCHF_2$], [AA4371; 2, CH, cPr, H, F, $OCHF_2$], [AA4372; 2, CH, cPr, H, Cl, $OCHF_2$], [AA4373; 2, CH, cPr, H, Br, $OCHF_2$], [AA4374; 2, CH, cPr, H, I, $OCHF_2$], [AA4375; 2, CH, cPr, H, $CF_3$, $OCHF_2$], [AA4376; 2, CH, cPr, H, $CF_2H$, $OCHF_2$], [AA4377; 2, CH, cPr, H, $C_2F_5$, $OCHF_2$], [AA4378; 2, CH, cPr, H, $C_3F_7$, $OCHF_2$], [AA4379; 2, CH, cPr, H, $CH_2CF_3$, $OCHF_2$], [AA4380; 2, CH, cPr, H, $CH_2CHF_2$, $OCHF_2$], [AA4381; 0, N, cPr, H, F, $OCHF_2$], [AA4382; 0, N, cPr, H, Cl, $OCHF_2$], [AA4383; 0, N, cPr, H, Br, $OCHF_2$], [AA4384; 0, N, cPr, H, I, $OCHF_2$], [AA4385; 0, N, cPr, H, $CF_3$, $OCHF_2$], [AA4386; 0, N, cPr, H, $CF_2H$, $OCHF_2$], [AA4387; 0, N, cPr, H, $C_2F_5$, $OCHF_2$], [AA4388; 0, N, cPr, H, $C_3F_7$, $OCHF_2$], [AA4389; 0, N, cPr, H, $CH_2CF_3$, $OCHF_2$], [AA4390; 0, N, cPr, H, $CH_2CHF_2$, $OCHF_2$], [AA4391; 1, N, cPr, H, F, $OCHF_2$], [AA4392; 1, N, cPr, H, Cl, $OCHF_2$], [AA4393; 1, N, cPr, H, Br, $OCHF_2$], [AA4394; 1, N, cPr, H, I, $OCHF_2$], [AA4395; 1, N, cPr, H, $CF_3$, $OCHF_2$], [AA4396; 1, N, cPr, H, $CF_2H$, $OCHF_2$], [AA4397; 1, N, cPr, H, $C_2F_5$, $OCHF_2$], [AA4398; 1, N, cPr, H, $C_3F_7$, $OCHF_2$], [AA4399; 1, N, cPr, H, $CH_2CF_3$, $OCHF_2$], [AA4400; 1, N, cPr, H, $CH_2CHF_2$, $OCHF_2$], [AA4401; 2, N, cPr, H, F, $OCHF_2$], [AA4402; 2, N, cPr, H, Cl, $OCHF_2$], [AA4403; 2, N, cPr, H, Br, $OCHF_2$], [AA4404; 2, N, cPr, H, I, $OCHF_2$], [AA4405;

2, N, cPr, H, $CF_3$, $OCHF_2$], [AA4406; 2, N, cPr, H, $CF_2H$, $OCHF_2$], [AA4407; 2, N, cPr, H, $C_2F_5$, $OCHF_2$], [AA4408; 2, N, cPr, H, $C_3F_7$, $OCHF_2$], [AA4409; 2, N, cPr, H, $CH_2CF_3$, $OCHF_2$], [AA4410; 2, N, cPr, H, $CH_2CHF_2$, $OCHF_2$], [AA4411; 0, CH, H, H, H, Br], [AA4412; 0, CH, H, F, H, Br], [AA4413; 0, CH, H, Cl, H, Br], [AA4414; 0, CH, H, Br, H, Br], [AA4415; 0, CH, H, I, H, Br], [AA4416; 0, CH, H, $CF_3$, H, Br], [AA4417; 0, CH, H, $CF_2H$, H, Br], [AA4418; 0, CH, H, $C_2F_5$, H, Br], [AA4419; 0, CH, H, $C_3F_7$, H, Br], [AA4420; 0, CH, H, $CH_2CF_3$, H, Br], [AA4421; 0, CH, H, $CH_2CHF_2$, H, Br], [AA4422; 1, CH, H, H, H, Br], [AA4423; 1, CH, H, F, H, Br], [AA4424; 1, CH, H, Cl, H, Br], [AA4425; 1, CH, H, Br, H, Br], [AA4426; 1, CH, H, I, H, Br], [AA4427; 1, CH, H, $CF_3$, H, Br], [AA4428; 1, CH, H, $CF_2H$, H, Br], [AA4429; 1, CH, H, $C_2F_5$, H, Br], [AA4430; 1, CH, H, $C_3F_7$, H, Br], [AA4431; 1, CH, H, $CH_2CF_3$, H, Br], [AA4432; 1, CH, H, $CH_2CHF_2$, H, Br], [AA4433; 2, CH, H, H, H, Br], [AA4434; 2, CH, H, F, H, Br], [AA4435; 2, CH, H, Cl, H, Br], [AA4436; 2, CH, H, Br, H, Br], [AA4437; 2, CH, H, I, H, Br], [AA4438; 2, CH, H, $CF_3$, H, Br], [AA4439; 2, CH, H, $CF_2H$, H, Br], [AA4440; 2, CH, H, $C_2F_5$, H, Br], [AA4441; 2, CH, H, $C_3F_7$, H, Br], [AA4442; 2, CH, H, $CH_2CF_3$, H, Br], [AA4443; 2, CH, H, $CH_2CHF_2$, H, Br], [AA4444; 0, N, H, H, H, Br], [AA4445; 0, N, H, F, H, Br], [AA4446; 0, N, H, Cl, H, Br], [AA4447; 0, N, H, Br, H, Br], [AA4448; 0, N, H, I, H, Br], [AA4449; 0, N, H, $CF_3$, H, Br], [AA4450; 0, N, H, $CF_2H$, H, Br], [AA4451; 0, N, H, $C_2F_5$, H, Br], [AA4452; 0, N, H, $C_3F_7$, H, Br], [AA4453; 0, N, H, $CH_2CF_3$, H, Br], [AA4454; 0, N, H, $CH_2CHF_2$, H, Br], [AA4455; 1, N, H, H, H, Br], [AA4456; 1, N, H, F, H, Br], [AA4457; 1, N, H, Cl, H, Br], [AA4458; 1, N, H, Br, H, Br], [AA4459; 1, N, H, I, H, Br], [AA4460; 1, N, H, $CF_3$, H, Br], [AA4461; 1, N, H, $CF_2H$, H, Br], [AA4462; 1, N, H, $C_2F_5$, H, Br], [AA4463; 1, N, H, $C_3F_7$, H, Br], [AA4464; 1, N, H, $CH_2CF_3$, H, Br], [AA4465; 1, N, H, $CH_2CHF_2$, H, Br], [AA4466; 2, N, H, H, H, Br], [AA4467; 2, N, H, F, H, Br], [AA4468; 2, N, H, Cl, H, Br], [AA4469; 2, N, H, Br, H, Br], [AA4470; 2, N, H, I, H, Br], [AA4471; 2, N, H, $CF_3$, H, Br], [AA4472; 2, N, H, $CF_2H$, H, Br], [AA4473; 2, N, H, $C_2F_5$, H, Br], [AA4474; 2, N, H, $C_3F_7$, H, Br], [AA4475; 2, N, H, $CH_2CF_3$, H, Br], [AA4476; 2, N, H, $CH_2CHF_2$, H, Br], [AA4477; 0, CH, Me, H, H, Br], [AA4478; 0, CH, Me, F, H, Br], [AA4479; 0, CH, Me, Cl, H, Br], [AA4480; 0, CH, Me, Br, H, Br], [AA4481; 0, CH, Me, I, H, Br], [AA4482; 0, CH, Me, $CF_3$, H, Br], [AA4483; 0, CH, Me, $CF_2H$, H, Br], [AA4484; 0, CH, Me, $C_2F_5$, H, Br], [AA4485; 0, CH, Me, $C_3F_7$, H, Br], [AA4486; 0, CH, Me, $CH_2CF_3$, H, Br], [AA4487; 0, CH, Me, $CH_2CHF_2$, H, Br], [AA4488; 1, CH, Me, H, H, Br], [AA4489; 1, CH, Me, F, H, Br], [AA4490; 1, CH, Me, Cl, H, Br], [AA4491; 1, CH, Me, Br, H, Br], [AA4492; 1, CH, Me, I, H, Br], [AA4493; 1, CH, Me, $CF_3$, H, Br], [AA4494; 1, CH, Me, $CF_2H$, H, Br], [AA4495; 1, CH, Me, $C_2F_5$, H, Br], [AA4496; 1, CH, Me, $C_3F_7$, H, Br], [AA4497; 1, CH, Me, $CH_2CF_3$, H, Br], [AA4498; 1, CH, Me, $CH_2CHF_2$, H, Br], [AA4499; 2, CH, Me, H, H, Br], [AA4500; 2, CH, Me, F, H, Br], [AA4501; 2, CH, Me, Cl, H, Br], [AA4502; 2, CH, Me, Br, H, Br], [AA4503; 2, CH, Me, I, H, Br], [AA4504; 2, CH, Me, $CF_3$, H, Br], [AA4505; 2, CH, Me, $CF_2H$, H, Br], [AA4506; 2, CH, Me, $C_2F_5$, H, Br], [AA4507; 2, CH, Me, $C_3F_7$, H, Br], [AA4508; 2, CH, Me, $CH_2CF_3$, H, Br], [AA4509; 2, CH, Me, $CH_2CHF_2$, H, Br], [AA4510; 0, N, Me, H, H, Br], [AA4511; 0, N, Me, F, H, Br], [AA4512; 0, N, Me, Cl, H, Br], [AA4513; 0, N, Me, Br, H, Br], [AA4514; 0, N, Me, I, H, Br], [AA4515; 0, N, Me, $CF_3$, H, Br], [AA4516; 0, N, Me, $CF_2H$, H, Br], [AA4517; 0, N, Me, $C_2F_5$, H, Br], [AA4518; 0, N, Me, $C_3F_7$, H, Br], [AA4519; 0, N, Me, $CH_2CF_3$, H, Br], [AA4520; 0, N, Me, $CH_2CHF_2$, H, Br], [AA4521; 1, N, Me, H, H, Br], [AA4522; 1, N, Me, F, H, Br], [AA4523; 1, N, Me, Cl, H, Br], [AA4524; 1, N, Me, Br, H, Br], [AA4525; 1, N, Me, I, H, Br], [AA4526; 1, N, Me, $CF_3$, H, Br], [AA4527; 1, N, Me, $CF_2H$, H, Br], [AA4528; 1, N, Me, $C_2F_5$, H, Br], [AA4529; 1, N, Me, $C_3F_7$, H, Br], [AA4530; 1, N, Me, $CH_2CF_3$, H, Br], [AA4531; 1, N, Me, $CH_2CHF_2$, H, Br], [AA4532; 2, N, Me, H, H, Br], [AA4533; 2, N, Me, F, H, Br], [AA4534; 2, N, Me, Cl, H, Br], [AA4535; 2, N, Me, Br, H, Br], [AA4536; 2, N, Me, I, H, Br], [AA4537; 2, N, Me, $CF_3$, H, Br], [AA4538; 2, N, Me, $CF_2H$, H, Br], [AA4539; 2, N, Me, $C_2F_5$, H, Br], [AA4540; 2, N, Me, $C_3F_7$, H, Br], [AA4541; 2, N, Me, $CH_2CF_3$, H, Br], [AA4542; 2, N, Me, $CH_2CHF_2$, H, Br], [AA4543; 0, CH, Et, H, H, Br], [AA4544; 0, CH, Et, F, H, Br], [AA4545; 0, CH, Et, Cl, H, Br], [AA4546; 0, CH, Et, Br, H, Br], [AA4547; 0, CH, Et, I, H, Br], [AA4548; 0, CH, Et, $CF_3$, H, Br], [AA4549; 0, CH, Et, $CF_2H$, H, Br], [AA4550; 0, CH, Et, $C_2F_5$, H, Br], [AA4551; 0, CH, Et, $C_3F_7$, H, Br], [AA4552; 0, CH, Et, $CH_2CF_3$, H, Br], [AA4553; 0, CH, Et, $CH_2CHF_2$, H, Br], [AA4554; 1, CH, Et, H, H, Br], [AA4555; 1, CH, Et, F, H, Br], [AA4556; 1, CH, Et, Cl, H, Br], [AA4557; 1, CH, Et, Br, H, Br], [AA4558; 1, CH, Et, I, H, Br], [AA4559; 1, CH, Et, $CF_3$, H, Br], [AA4560; 1, CH, Et, $CF_2H$, H, Br], [AA4561; 1, CH, Et, $C_2F_5$, H, Br], [AA4562; 1, CH, Et, $C_3F_7$, H, Br], [AA4563; 1, CH, Et, $CH_2CF_3$, H, Br], [AA4564; 1, CH, Et, $CH_2CHF_2$, H, Br], [AA4565; 2, CH, Et, H, H, Br], [AA4566; 2, CH, Et, F, H, Br], [AA4567; 2, CH, Et, Cl, H, Br], [AA4568; 2, CH, Et, Br, H, Br], [AA4569; 2, CH, Et, I, H, Br], [AA4570; 2, CH, Et, $CF_3$, H, Br], [AA4571; 2, CH, Et, $CF_2H$, H, Br], [AA4572; 2, CH, Et, $C_2F_5$, H, Br], [AA4573; 2, CH, Et, $C_3F_7$, H, Br], [AA4574; 2, CH, Et, $CH_2CF_3$, H, Br], [AA4575; 2, CH, Et, $CH_2CHF_2$, H, Br], [AA4576; 0, N, Et, H, H, Br], [AA4577; 0, N, Et, F, H, Br], [AA4578; 0, N, Et, Cl, H, Br], [AA4579; 0, N, Et, Br, H, Br], [AA4580; 0, N, Et, I, H, Br], [AA4581; 0, N, Et, $CF_3$, H, Br], [AA4582; 0, N, Et, $CF_2H$, H, Br], [AA4583; 0, N, Et, $C_2F_5$, H, Br], [AA4584; 0, N, Et, $C_3F_7$, H, Br], [AA4585; 0, N, Et, $CH_2CF_3$, H, Br], [AA4586; 0, N, Et, $CH_2CHF_2$, H, Br], [AA4587; 1, N, Et, H, H, Br], [AA4588; 1, N, Et, F, H, Br], [AA4589; 1, N, Et, Cl, H, Br], [AA4590; 1, N, Et, Br, H, Br], [AA4591; 1, N, Et, I, H, Br], [AA4592; 1, N, Et, $CF_3$, H, Br], [AA4593; 1, N, Et, $CF_2H$, H, Br], [AA4594; 1, N, Et, $C_2F_5$, H, Br], [AA4595; 1, N, Et, $C_3F_7$, H, Br], [AA4596; 1, N, Et, $CH_2CF_3$, H, Br], [AA4597; 1, N, Et, $CH_2CHF_2$, H, Br], [AA4598; 2, N, Et, H, H, Br], [AA4599; 2, N, Et, F, H, Br], [AA4600; 2, N, Et, Cl, H, Br], [AA4601; 2, N, Et, Br, H, Br], [AA4602; 2, N, Et, I, H, Br], [AA4603; 2, N, Et, $CF_3$, H, Br], [AA4604; 2, N, Et, $CF_2H$, H, Br], [AA4605; 2, N, Et, $C_2F_5$, H, Br], [AA4606; 2, N, Et, $C_3F_7$, H, Br], [AA4607; 2, N, Et, $CH_2CF_3$, H, Br], [AA4608; 2, N, Et, $CH_2CHF_2$, H, Br], [AA4609; 0, CH, iPr, H, H, Br], [AA4610; 0, CH, iPr, F, H, Br], [AA4611; 0, CH, iPr, Cl, H, Br], [AA4612; 0, CH, iPr, Br, H, Br], [AA4613; 0, CH, iPr, I, H, Br], [AA4614; 0, CH, iPr, $CF_3$, H, Br], [AA4615; 0, CH, iPr, $CF_2H$, H, Br], [AA4616; 0, CH, iPr, $C_2F_5$, H, Br], [AA4617; 0, CH, iPr, $C_3F_7$, H, Br], [AA4618; 0, CH, iPr, $CH_2CF_3$, H, Br], [AA4619; 0, CH, iPr, $CH_2CHF_2$, H, Br], [AA4620; 1, CH, iPr, H, H, Br], [AA4621; 1, CH, iPr, F, H, Br], [AA4622; 1, CH, iPr, Cl, H, Br], [AA4623; 1, CH, iPr, Br, H, Br], [AA4624; 1, CH, iPr, I, H, Br], [AA4625; 1, CH, iPr, $CF_3$, H, Br], [AA4626; 1, CH, iPr, $CF_2H$, H, Br], [AA4627; 1, CH, iPr, $C_2F_5$, H, Br], [AA4628; 1, CH, iPr, $C_3F_7$, H, Br], [AA4629; 1, CH, iPr, $CH_2CF_3$, H, Br], [AA4630; 1, CH, iPr, $CH_2CHF_2$, H, Br], [AA4631; 2, CH, iPr, H, H, Br], [AA4632; 2, CH, iPr, F, H, Br], [AA4633; 2,

CH, iPr, Cl, H, Br], [AA4634; 2, CH, iPr, Br, H, Br], [AA4635; 2, CH, iPr, I, H, Br], [AA4636; 2, CH, iPr, $CF_3$, H, Br], [AA4637; 2, CH, iPr, $CF_2H$, H, Br], [AA4638; 2, CH, iPr, $C_2F_5$, H, Br], [AA4639; 2, CH, iPr, $C_3F_7$, H, Br], [AA4640; 2, CH, iPr, $CH_2CF_3$, H, Br], [AA4641; 2, CH, iPr, $CH_2CHF_2$, H, Br], [AA4642; 0, N, iPr, H, H, Br], [AA4643; 0, N, iPr, F, H, Br], [AA4644; 0, N, iPr, Cl, H, Br], [AA4645; 0, N, iPr, Br, H, Br], [AA4646; 0, N, iPr, I, H, Br], [AA4647; 0, N, iPr, $CF_3$, H, Br], [AA4648; 0, N, iPr, $CF_2H$, H, Br], [AA4649; 0, N, iPr, $C_2F_5$, H, Br], [AA4650; 0, N, iPr, $C_3F_7$, H, Br], [AA4651; 0, N, iPr, $CH_2CF_3$, H, Br], [AA4652; 0, N, iPr, $CH_2CHF_2$, H, Br], [AA4653; 1, N, iPr, H, H, Br], [AA4654; 1, N, iPr, F, H, Br], [AA4655; 1, N, iPr, Cl, H, Br], [AA4656; 1, N, iPr, Br, H, Br], [AA4657; 1, N, iPr, I, H, Br], [AA4658; 1, N, iPr, $CF_3$, H, Br], [AA4659; 1, N, iPr, $CF_2H$, H, Br], [AA4660; 1, N, iPr, $C_2F_5$, H, Br], [AA4661; 1, N, iPr, $C_3F_7$, H, Br], [AA4662; 1, N, iPr, $CH_2CF_3$, H, Br], [AA4663; 1, N, iPr, $CH_2CHF_2$, H, Br], [AA4664; 2, N, iPr, H, H, Br], [AA4665; 2, N, iPr, F, H, Br], [AA4666; 2, N, iPr, Cl, H, Br], [AA4667; 2, N, iPr, Br, H, Br], [AA4668; 2, N, iPr, I, H, Br], [AA4669; 2, N, iPr, $CF_3$, H, Br], [AA4670; 2, N, iPr, $CF_2H$, H, Br], [AA4671; 2, N, iPr, $C_2F_5$, H, Br], [AA4672; 2, N, iPr, $C_3F_7$, H, Br], [AA4673; 2, N, iPr, $CH_2CF_3$, H, Br], [AA4674; 2, N, iPr, $CH_2CHF_2$, H, Br], [AA4675; 0, CH, cPr, H, H, Br], [AA4676; 0, CH, cPr, F, H, Br], [AA4677; 0, CH, cPr, Cl, H, Br], [AA4678; 0, CH, cPr, Br, H, Br], [AA4679; 0, CH, cPr, I, H, Br], [AA4680; 0, CH, cPr, $CF_3$, H, Br], [AA4681; 0, CH, cPr, $CF_2H$, H, Br], [AA4682; 0, CH, cPr, $C_2F_5$, H, Br], [AA4683; 0, CH, cPr, $C_3F_7$, H, Br], [AA4684; 0, CH, cPr, $CH_2CF_3$, H, Br], [AA4685; 0, CH, cPr, $CH_2CHF_2$, H, Br], [AA4686; 1, CH, cPr, H, H, Br], [AA4687; 1, CH, cPr, F, H, Br], [AA4688; 1, CH, cPr, Cl, H, Br], [AA4689; 1, CH, cPr, Br, H, Br], [AA4690; 1, CH, cPr, I, H, Br], [AA4691; 1, CH, cPr, $CF_3$, H, Br], [AA4692; 1, CH, cPr, $CF_2H$, H, Br], [AA4693; 1, CH, cPr, $C_2F_5$, H, Br], [AA4694; 1, CH, cPr, $C_3F_7$, H, Br], [AA4695; 1, CH, cPr, $CH_2CF_3$, H, Br], [AA4696; 1, CH, cPr, $CH_2CHF_2$, H, Br], [AA4697; 2, CH, cPr, H, H, Br], [AA4698; 2, CH, cPr, F, H, Br], [AA4699; 2, CH, cPr, Cl, H, Br], [AA4700; 2, CH, cPr, Br, H, Br], [AA4701; 2, CH, cPr, I, H, Br], [AA4702; 2, CH, cPr, $CF_3$, H, Br], [AA4703; 2, CH, cPr, $CF_2H$, H, Br], [AA4704; 2, CH, cPr, $C_2F_5$, H, Br], [AA4705; 2, CH, cPr, $C_3F_7$, H, Br], [AA4706; 2, CH, cPr, $CH_2CF_3$, H, Br], [AA4707; 2, CH, cPr, $CH_2CHF_2$, H, Br], [AA4708; 0, N, cPr, H, H, Br], [AA4709; 0, N, cPr, F, H, Br], [AA4710; 0, N, cPr, Cl, H, Br], [AA4711; 0, N, cPr, Br, H, Br], [AA4712; 0, N, cPr, I, H, Br], [AA4713; 0, N, cPr, $CF_3$, H, Br], [AA4714; 0, N, cPr, $CF_2H$, H, Br], [AA4715; 0, N, cPr, $C_2F_5$, H, Br], [AA4716; 0, N, cPr, $C_3F_7$, H, Br], [AA4717; 0, N, cPr, $CH_2CF_3$, H, Br], [AA4718; 0, N, cPr, $CH_2CHF_2$, H, Br], [AA4719; 1, N, cPr, H, H, Br], [AA4720; 1, N, cPr, F, H, Br], [AA4721; 1, N, cPr, Cl, H, Br], [AA4722; 1, N, cPr, Br, H, Br], [AA4723; 1, N, cPr, I, H, Br], [AA4724; 1, N, cPr, $CF_3$, H, Br], [AA4725; 1, N, cPr, $CF_2H$, H, Br], [AA4726; 1, N, cPr, $C_2F_5$, H, Br], [AA4727; 1, N, cPr, $C_3F_7$, H, Br], [AA4728; 1, N, cPr, $CH_2CF_3$, H, Br], [AA4729; 1, N, cPr, $CH_2CHF_2$, H, Br], [AA4730; 2, N, cPr, H, H, Br], [AA4731; 2, N, cPr, F, H, Br], [AA4732; 2, N, cPr, Cl, H, Br], [AA4733; 2, N, cPr, Br, H, Br], [AA4734; 2, N, cPr, I, H, Br], [AA4735; 2, N, cPr, $CF_3$, H, Br], [AA4736; 2, N, cPr, $CF_2H$, H, Br], [AA4737; 2, N, cPr, $C_2F_5$, H, Br], [AA4738; 2, N, cPr, $C_3F_7$, H, Br], [AA4739; 2, N, cPr, $CH_2CF_3$, H, Br], [AA4740; 2, N, cPr, $CH_2CHF_2$, H, Br], [AA4741; 0, CH, H, H, F, Br], [AA4742; 0, CH, H, H, Cl, Br], [AA4743; 0, CH, H, H, Br, Br], [AA4744; 0, CH, H, H, I, Br], [AA4745; 0, CH, H, H, $CF_3$, Br], [AA4746; 0, CH, H, H, $CF_2H$, Br], [AA4747; 0, CH, H, H, $C_2F_5$, Br], [AA4748; 0, CH, H, H, $C_3F_7$, Br], [AA4749; 0, CH, H, H, $CH_2CF_3$, Br], [AA4750; 0, CH, H, H, $CH_2CHF_2$, Br], [AA4751; 1, CH, H, H, F, Br], [AA4752; 1, CH, H, H, Cl, Br], [AA4753; 1, CH, H, H, Br, Br], [AA4754; 1, CH, H, H, I, Br], [AA4755; 1, CH, H, H, $CF_3$, Br], [AA4756; 1, CH, H, H, $CF_2H$, Br], [AA4757; 1, CH, H, H, $C_2F_5$, Br], [AA4758; 1, CH, H, H, $C_3F_7$, Br], [AA4759; 1, CH, H, H, $CH_2CF_3$, Br], [AA4760; 1, CH, H, H, $CH_2CHF_2$, Br], [AA4761; 2, CH, H, H, F, Br], [AA4762; 2, CH, H, H, Cl, Br], [AA4763; 2, CH, H, H, Br, Br], [AA4764; 2, CH, H, H, I, Br], [AA4765; 2, CH, H, H, $CF_3$, Br], [AA4766; 2, CH, H, H, $CF_2H$, Br], [AA4767; 2, CH, H, H, $C_2F_5$, Br], [AA4768; 2, CH, H, H, $C_3F_7$, Br], [AA4769; 2, CH, H, H, $CH_2CF_3$, Br], [AA4770; 2, CH, H, H, $CH_2CHF_2$, Br], [AA4771; 0, N, H, H, F, Br], [AA4772; 0, N, H, H, Cl, Br], [AA4773; 0, N, H, H, Br, Br], [AA4774; 0, N, H, H, I, Br], [AA4775; 0, N, H, H, $CF_3$, Br], [AA4776; 0, N, H, H, $CF_2H$, Br], [AA4777; 0, N, H, H, $C_2F_5$, Br], [AA4778; 0, N, H, H, $C_3F_7$, Br], [AA4779; 0, N, H, H, $CH_2CF_3$, Br], [AA4780; 0, N, H, H, $CH_2CHF_2$, Br], [AA4781; 1, N, H, H, F, Br], [AA4782; 1, N, H, H, Cl, Br], [AA4783; 1, N, H, H, Br, Br], [AA4784; 1, N, H, H, I, Br], [AA4785; 1, N, H, H, $CF_3$, Br], [AA4786; 1, N, H, H, $CF_2H$, Br], [AA4787; 1, N, H, H, $C_2F_5$, Br], [AA4788; 1, N, H, H, $C_3F_7$, Br], [AA4789; 1, N, H, H, $CH_2CF_3$, Br], [AA4790; 1, N, H, H, $CH_2CHF_2$, Br], [AA4791; 2, N, H, H, F, Br], [AA4792; 2, N, H, H, Cl, Br], [AA4793; 2, N, H, H, Br, Br], [AA4794; 2, N, H, H, I, Br], [AA4795; 2, N, H, H, $CF_3$, Br], [AA4796; 2, N, H, H, $CF_2H$, Br], [AA4797; 2, N, H, H, $C_2F_5$, Br], [AA4798; 2, N, H, H, $C_3F_7$, Br], [AA4799; 2, N, H, H, $CH_2CF_3$, Br], [AA4800; 2, N, H, H, $CH_2CHF_2$, Br], [AA4801; 0, CH, Me, H, F, Br], [AA4802; 0, CH, Me, H, Cl, Br], [AA4803; 0, CH, Me, H, Br, Br], [AA4804; 0, CH, Me, H, I, Br], [AA4805; 0, CH, Me, H, $CF_3$, Br], [AA4806; 0, CH, Me, H, $CF_2H$, Br], [AA4807; 0, CH, Me, H, $C_2F_5$, Br], [AA4808; 0, CH, Me, H, $C_3F_7$, Br], [AA4809; 0, CH, Me, H, $CH_2CF_3$, Br], [AA4810; 0, CH, Me, H, $CH_2CHF_2$, Br], [AA4811; 1, CH, Me, H, F, Br], [AA4812; 1, CH, Me, H, Cl, Br], [AA4813; 1, CH, Me, H, Br, Br], [AA4814; 1, CH, Me, H, I, Br], [AA4815; 1, CH, Me, H, $CF_3$, Br], [AA4816; 1, CH, Me, H, $CF_2H$, Br], [AA4817; 1, CH, Me, H, $C_2F_5$, Br], [AA4818; 1, CH, Me, H, $C_3F_7$, Br], [AA4819; 1, CH, Me, H, $CH_2CF_3$, Br], [AA4820; 1, CH, Me, H, $CH_2CHF_2$, Br], [AA4821; 2, CH, Me, H, F, Br], [AA4822; 2, CH, Me, H, Cl, Br], [AA4823; 2, CH, Me, H, Br, Br], [AA4824; 2, CH, Me, H, I, Br], [AA4825; 2, CH, Me, H, $CF_3$, Br], [AA4826; 2, CH, Me, H, $CF_2H$, Br], [AA4827; 2, CH, Me, H, $C_2F_5$, Br], [AA4828; 2, CH, Me, H, $C_3F_7$, Br], [AA4829; 2, CH, Me, H, $CH_2CF_3$, Br], [AA4830; 2, CH, Me, H, $CH_2CHF_2$, Br], [AA4831; 0, N, Me, H, F, Br], [AA4832; 0, N, Me, H, Cl, Br], [AA4833; 0, N, Me, H, Br, Br], [AA4834; 0, N, Me, H, I, Br], [AA4835; 0, N, Me, H, $CF_3$, Br], [AA4836; 0, N, Me, H, $CF_2H$, Br], [AA4837; 0, N, Me, H, $C_2F_5$, Br], [AA4838; 0, N, Me, H, $C_3F_7$, Br], [AA4839; 0, N, Me, H, $CH_2CF_3$, Br], [AA4840; 0, N, Me, H, $CH_2CHF_2$, Br], [AA4841; 1, N, Me, H, F, Br], [AA4842; 1, N, Me, H, Cl, Br], [AA4843; 1, N, Me, H, Br, Br], [AA4844; 1, N, Me, H, I, Br], [AA4845; 1, N, Me, H, $CF_3$, Br], [AA4846; 1, N, Me, H, $CF_2H$, Br], [AA4847; 1, N, Me, H, $C_2F_5$, Br], [AA4848; 1, N, Me, H, $C_3F_7$, Br], [AA4849; 1, N, Me, H, $CH_2CF_3$, Br], [AA4850; 1, N, Me, H, $CH_2CHF_2$, Br], [AA4851; 2, N, Me, H, F, Br], [AA4852; 2, N, Me, H, Cl, Br], [AA4853; 2, N, Me, H, Br, Br], [AA4854; 2, N, Me, H, I, Br], [AA4855; 2, N, Me, H, $CF_3$, Br], [AA4856; 2, N, Me, H, $CF_2H$, Br], [AA4857; 2, N, Me, H, $C_2F_5$, Br], [AA4858; 2, N, Me, H, $C_3F_7$, Br], [AA4859; 2, N, Me, H, $CH_2CF_3$, Br], [AA4860; 2, N, Me, H, $CH_2CHF_2$, Br], [AA4861; 0, CH, Et, H, F, Br], [AA4862;

0, CH, Et, H, Cl, Br], [AA4863; 0, CH, Et, H, Br, Br], [AA4864; 0, CH, Et, H, I, Br], [AA4865; 0, CH, Et, H, $CF_3$, Br], [AA4866; 0, CH, Et, H, $CF_2H$, Br], [AA4867; 0, CH, Et, H, $C_2F_5$, Br], [AA4868; 0, CH, Et, H, $C_3F_7$, Br], [AA4869; 0, CH, Et, H, $CH_2CF_3$, Br], [AA4870; 0, CH, Et, H, $CH_2CHF_2$, Br], [AA4871; 1, CH, Et, H, F, Br], [AA4872; 1, CH, Et, H, Cl, Br], [AA4873; 1, CH, Et, H, Br, Br], [AA4874; 1, CH, Et, H, I, Br], [AA4875; 1, CH, Et, H, $CF_3$, Br], [AA4876; 1, CH, Et, H, $CF_2H$, Br], [AA4877; 1, CH, Et, H, $C_2F_5$, Br], [AA4878; 1, CH, Et, H, $C_3F_7$, Br], [AA4879; 1, CH, Et, H, $CH_2CF_3$, Br], [AA4880; 1, CH, Et, H, $CH_2CHF_2$, Br], [AA4881; 2, CH, Et, H, F, Br], [AA4882; 2, CH, Et, H, Cl, Br], [AA4883; 2, CH, Et, H, Br, Br], [AA4884; 2, CH, Et, H, I, Br], [AA4885; 2, CH, Et, H, $CF_3$, Br], [AA4886; 2, CH, Et, H, $CF_2H$, Br], [AA4887; 2, CH, Et, H, $C_2F_5$, Br], [AA4888; 2, CH, Et, H, $C_3F_7$, Br], [AA4889; 2, CH, Et, H, $CH_2CF_3$, Br], [AA4890; 2, CH, Et, H, $CH_2CHF_2$, Br], [AA4891; 0, N, Et, H, F, Br], [AA4892; 0, N, Et, H, Cl, Br], [AA4893; 0, N, Et, H, Br, Br], [AA4894; 0, N, Et, H, I, Br], [AA4895; 0, N, Et, H, $CF_3$, Br], [AA4896; 0, N, Et, H, $CF_2H$, Br], [AA4897; 0, N, Et, H, $C_2F_5$, Br], [AA4898; 0, N, Et, H, $C_3F_7$, Br], [AA4899; 0, N, Et, H, $CH_2CF_3$, Br], [AA4900; 0, N, Et, H, $CH_2CHF_2$, Br], [AA4901; 1, N, Et, H, F, Br], [AA4902; 1, N, Et, H, Cl, Br], [AA4903; 1, N, Et, H, Br, Br], [AA4904; 1, N, Et, H, I, Br], [AA4905; 1, N, Et, H, $CF_3$, Br], [AA4906; 1, N, Et, H, $CF_2H$, Br], [AA4907; 1, N, Et, H, $C_2F_5$, Br], [AA4908; 1, N, Et, H, $C_3F_7$, Br], [AA4909; 1, N, Et, H, $CH_2CF_3$, Br], [AA4910; 1, N, Et, H, $CH_2CHF_2$, Br], [AA4911; 2, N, Et, H, F, Br], [AA4912; 2, N, Et, H, Cl, Br], [AA4913; 2, N, Et, H, Br, Br], [AA4914; 2, N, Et, H, I, Br], [AA4915; 2, N, Et, H, $CF_3$, Br], [AA4916; 2, N, Et, H, $CF_2H$, Br], [AA4917; 2, N, Et, H, $C_2F_5$, Br], [AA4918; 2, N, Et, H, $C_3F_7$, Br], [AA4919; 2, N, Et, H, $CH_2CF_3$, Br], [AA4920; 2, N, Et, H, $CH_2CHF_2$, Br], [AA4921; 0, CH, iPr, H, F, Br], [AA4922; 0, CH, iPr, H, Cl, Br], [AA4923; 0, CH, iPr, H, Br, Br], [AA4924; 0, CH, iPr, H, I, Br], [AA4925; 0, CH, iPr, H, $CF_3$, Br], [AA4926; 0, CH, iPr, H, $CF_2H$, Br], [AA4927; 0, CH, iPr, H, $C_2F_5$, Br], [AA4928; 0, CH, iPr, H, $C_3F_7$, Br], [AA4929; 0, CH, iPr, H, $CH_2CF_3$, Br], [AA4930; 0, CH, iPr, H, $CH_2CHF_2$, Br], [AA4931; 1, CH, iPr, H, F, Br], [AA4932; 1, CH, iPr, H, Cl, Br], [AA4933; 1, CH, iPr, H, Br, Br], [AA4934; 1, CH, iPr, H, I, Br], [AA4935; 1, CH, iPr, H, $CF_3$, Br], [AA4936; 1, CH, iPr, H, $CF_2H$, Br], [AA4937; 1, CH, iPr, H, $C_2F_5$, Br], [AA4938; 1, CH, iPr, H, $C_3F_7$, Br], [AA4939; 1, CH, iPr, H, $CH_2CF_3$, Br], [AA4940; 1, CH, iPr, H, $CH_2CHF_2$, Br], [AA4941; 2, CH, iPr, H, F, Br], [AA4942; 2, CH, iPr, H, Cl, Br], [AA4943; 2, CH, iPr, H, Br, Br], [AA4944; 2, CH, iPr, H, I, Br], [AA4945; 2, CH, iPr, H, $CF_3$, Br], [AA4946; 2, CH, iPr, H, $CF_2H$, Br], [AA4947; 2, CH, iPr, H, $C_2F_5$, Br], [AA4948; 2, CH, iPr, H, $C_3F_7$, Br], [AA4949; 2, CH, iPr, H, $CH_2CF_3$, Br], [AA4950; 2, CH, iPr, H, $CH_2CHF_2$, Br], [AA4951; 0, N, iPr, H, F, Br], [AA4952; 0, N, iPr, H, Cl, Br], [AA4953; 0, N, iPr, H, Br, Br], [AA4954; 0, N, iPr, H, I, Br], [AA4955; 0, N, iPr, H, $CF_3$, Br], [AA4956; 0, N, iPr, H, $CF_2H$, Br], [AA4957; 0, N, iPr, H, $C_2F_5$, Br], [AA4958; 0, N, iPr, H, $C_3F_7$, Br], [AA4959; 0, N, iPr, H, $CH_2CF_3$, Br], [AA4960; 0, N, iPr, H, $CH_2CHF_2$, Br], [AA4961; 1, N, iPr, H, F, Br], [AA4962; 1, N, iPr, H, Cl, Br], [AA4963; 1, N, iPr, H, Br, Br], [AA4964; 1, N, iPr, H, I, Br], [AA4965; 1, N, iPr, H, $CF_3$, Br], [AA4966; 1, N, iPr, H, $CF_2H$, Br], [AA4967; 1, N, iPr, H, $C_2F_5$, Br], [AA4968; 1, N, iPr, H, $C_3F_7$, Br], [AA4969; 1, N, iPr, H, $CH_2CF_3$, Br], [AA4970; 1, N, iPr, H, $CH_2CHF_2$, Br], [AA4971; 2, N, iPr, H, F, Br], [AA4972; 2, N, iPr, H, Cl, Br], [AA4973; 2, N, iPr, H, Br, Br], [AA4974; 2, N, iPr, H, I, Br], [AA4975; 2, N, iPr, H, $CF_3$, Br], [AA4976; 2, N, iPr, H, $CF_2H$, Br], [AA4977; 2, N, iPr, H, $C_2F_5$, Br], [AA4978; 2, N, iPr, H, $C_3F_7$, Br], [AA4979; 2, N, iPr, H, $CH_2CF_3$, Br], [AA4980; 2, N, iPr, H, $CH_2CHF_2$, Br], [AA4981; 0, CH, cPr, H, F, Br], [AA4982; 0, CH, cPr, H, Cl, Br], [AA4983; 0, CH, cPr, H, Br, Br], [AA4984; 0, CH, cPr, H, I, Br], [AA4985; 0, CH, cPr, H, $CF_3$, Br], [AA4986; 0, CH, cPr, H, $CF_2H$, Br], [AA4987; 0, CH, cPr, H, $C_2F_5$, Br], [AA4988; 0, CH, cPr, H, $C_3F_7$, Br], [AA4989; 0, CH, cPr, H, $CH_2CF_3$, Br], [AA4990; 0, CH, cPr, H, $CH_2CHF_2$, Br], [AA4991; 1, CH, cPr, H, F, Br], [AA4992; 1, CH, cPr, H, Cl, Br], [AA4993; 1, CH, cPr, H, Br, Br], [AA4994; 1, CH, cPr, H, I, Br], [AA4995; 1, CH, cPr, H, $CF_3$, Br], [AA4996; 1, CH, cPr, H, $CF_2H$, Br], [AA4997; 1, CH, cPr, H, $C_2F_5$, Br], [AA4998; 1, CH, cPr, H, $C_3F_7$, Br], [AA4999; 1, CH, cPr, H, $CH_2CF_3$, Br], [AA5000; 1, CH, cPr, H, $CH_2CHF_2$, Br], [AA5001; 2, CH, cPr, H, F, Br], [AA5002; 2, CH, cPr, H, Cl, Br], [AA5003; 2, CH, cPr, H, Br, Br], [AA5004; 2, CH, cPr, H, I, Br], [AA5005; 2, CH, cPr, H, $CF_3$, Br], [AA5006; 2, CH, cPr, H, $CF_2H$, Br], [AA5007; 2, CH, cPr, H, $C_2F_5$, Br], [AA5008; 2, CH, cPr, H, $C_3F_7$, Br], [AA5009; 2, CH, cPr, H, $CH_2CF_3$, Br], [AA5010; 2, CH, cPr, H, $CH_2CHF_2$, Br], [AA5011; 0, N, cPr, H, F, Br], [AA5012; 0, N, cPr, H, Cl, Br], [AA5013; 0, N, cPr, H, Br, Br], [AA5014; 0, N, cPr, H, I, Br], [AA5015; 0, N, cPr, H, $CF_3$, Br], [AA5016; 0, N, cPr, H, $CF_2H$, Br], [AA5017; 0, N, cPr, H, $C_2F_5$, Br], [AA5018; 0, N, cPr, H, $C_3F_7$, Br], [AA5019; 0, N, cPr, H, $CH_2CF_3$, Br], [AA5020; 0, N, cPr, H, $CH_2CHF_2$, Br], [AA5021; 1, N, cPr, H, F, Br], [AA5022; 1, N, cPr, H, Cl, Br], [AA5023; 1, N, cPr, H, Br, Br], [AA5024; 1, N, cPr, H, I, Br], [AA5025; 1, N, cPr, H, $CF_3$, Br], [AA5026; 1, N, cPr, H, $CF_2H$, Br], [AA5027; 1, N, cPr, H, $C_2F_5$, Br], [AA5028; 1, N, cPr, H, $C_3F_7$, Br], [AA5029; 1, N, cPr, H, $CH_2CF_3$, Br], [AA5030; 1, N, cPr, H, $CH_2CHF_2$, Br], [AA5031; 2, N, cPr, H, F, Br], [AA5032; 2, N, cPr, H, Cl, Br], [AA5033; 2, N, cPr, H, Br, Br], [AA5034; 2, N, cPr, H, I, Br], [AA5035; 2, N, cPr, H, $CF_3$, Br], [AA5036; 2, N, cPr, H, $CF_2H$, Br], [AA5037; 2, N, cPr, H, $C_2F_5$, Br], [AA5038; 2, N, cPr, H, $C_3F_7$, Br], [AA5039; 2, N, cPr, H, $CH_2CF_3$, Br], [AA5040; 2, N, cPr, H, $CH_2CHF_2$, Br], [AA5041; 0, CH, H, H, H, Cl], [AA5042; 0, CH, H, F, H, Cl], [AA5043; 0, CH, H, Cl, H, Cl], [AA5044; 0, CH, H, Br, H, Cl], [AA5045; 0, CH, H, I, H, Cl], [AA5046; 0, CH, H, $CF_3$, H, Cl], [AA5047; 0, CH, H, $CF_2H$, H, Cl], [AA5048; 0, CH, H, $C_2F_5$, H, Cl], [AA5049; 0, CH, H, $C_3F_7$, H, Cl], [AA5050; 0, CH, H, $CH_2CF_3$, H, Cl], [AA5051; 0, CH, H, $CH_2CHF_2$, H, Cl], [AA5052; 1, CH, H, H, H, Cl], [AA5053; 1, CH, H, F, H, Cl], [AA5054; 1, CH, H, Cl, H, Cl], [AA5055; 1, CH, H, Br, H, Cl], [AA5056; 1, CH, H, I, H, Cl], [AA5057; 1, CH, H, $CF_3$, H, Cl], [AA5058; 1, CH, H, $CF_2H$, H, Cl], [AA5059; 1, CH, H, $C_2F_5$, H, Cl], [AA5060; 1, CH, H, $C_3F_7$, H, Cl], [AA5061; 1, CH, H, $CH_2CF_3$, H, Cl], [AA5062; 1, CH, H, $CH_2CHF_2$, H, Cl], [AA5063; 2, CH, H, H, H, Cl], [AA5064; 2, CH, H, F, H, Cl], [AA5065; 2, CH, H, Cl, H, Cl], [AA5066; 2, CH, H, Br, H, Cl], [AA5067; 2, CH, H, I, H, Cl], [AA5068; 2, CH, H, $CF_3$, H, Cl], [AA5069; 2, CH, H, $CF_2H$, H, Cl], [AA5070; 2, CH, H, $C_2F_5$, H, Cl], [AA5071; 2, CH, H, $C_3F_7$, H, Cl], [AA5072; 2, CH, H, $CH_2CF_3$, H, Cl], [AA5073; 2, CH, H, $CH_2CHF_2$, H, Cl], [AA5074; 0, N, H, H, H, Cl], [AA5075; 0, N, H, F, H, Cl], [AA5076; 0, N, H, Cl, H, Cl], [AA5077; 0, N, H, Br, H, Cl], [AA5078; 0, N, H, I, H, Cl], [AA5079; 0, N, H, $CF_3$, H, Cl], [AA5080; 0, N, H, $CF_2H$, H, Cl], [AA5081; 0, N, H, $C_2F_5$, H, Cl], [AA5082; 0, N, H, $C_3F_7$, H, Cl], [AA5083; 0, N, H, $CH_2CF_3$, H, Cl], [AA5084; 0, N, H, $CH_2CHF_2$, H, Cl], [AA5085; 1, N, H, H, H, Cl], [AA5086; 1, N, H, F, H, Cl], [AA5087; 1, N, H, Cl, H, Cl], [AA5088; 1, N, H, Br, H, Cl], [AA5089; 1, N, H, I, H, Cl], [AA5090; 1, N, H, $CF_3$, H, Cl], [AA5091; 1, N, H, $CF_2H$, H, Cl], [AA5092; 1, N, H, $C_2F_5$, H, Cl], [AA5093; 1, N, H, $C_3F_7$, H, Cl], [AA5094; 1, N, H, $CH_2CF_3$, H, Cl], [AA5095; 1, N, H, $CH_2CHF_2$, H, Cl], [AA5096; 2, N, H, H, H, Cl], [AA5097; 2, N, H, F, H, Cl], [AA5098; 2, N, H, Cl, H, Cl], [AA5099; 2, N, H, Br, H, Cl], [AA5100; 2, N, H, I, H, Cl], [AA5101; 2, N, H, $CF_3$, H, Cl], [AA5102; 2, N, H, $CF_2H$, H, Cl], [AA5103; 2, N, H, $C_2F_5$, H, Cl], [AA5104; 2, N, H, $C_3F_7$, H, Cl], [AA5105; 2, N, H, $CH_2CF_3$, H, Cl], [AA5106; 2, N, H, $CH_2CHF_2$, H, Cl], [AA5107; 0, CH, Me, H, H, Cl], [AA5108; 0, CH, Me, F, H, Cl], [AA5109; 0, CH, Me, Cl, H, Cl], [AA5110; 0, CH, Me, Br, H, Cl], [AA5111; 0, CH, Me, I, H, Cl], [AA5112; 0, CH, Me, $CF_3$, H, Cl], [AA5113; 0, CH, Me, $CF_2H$, H, Cl], [AA5114; 0, CH, Me, $C_2F_5$, H, Cl], [AA5115; 0, CH, Me, $C_3F_7$, H, Cl], [AA5116; 0, CH, Me, $CH_2CF_3$, H, Cl], [AA5117; 0, CH, Me, $CH_2CHF_2$, H, Cl], [AA5118; 1, CH, Me, H, H, Cl], [AA5119; 1, CH, Me, F, H, Cl], [AA5120; 1, CH, Me, Cl, H, Cl], [AA5121; 1, CH, Me, Br, H, Cl], [AA5122; 1, CH, Me, I, H, Cl], [AA5123; 1, CH, Me, $CF_3$, H, Cl], [AA5124; 1, CH, Me, $CF_2H$, H, Cl], [AA5125; 1, CH, Me, $C_2F_5$, H, Cl], [AA5126; 1, CH, Me, $C_3F_7$, H, HCl], [AA5127; 1, CH, Me, $CH_2CF_3$, H, $C_1$], [AA5128; 1, CH, Me, $CH_2CHF_2$, H, Cl], [AA5129; 2, CH, Me, H, H, Cl], [AA5130; 2, CH, Me, F, H, Cl], [AA5131; 2, CH, Me, Cl, H, Cl], [AA5132; 2, CH, Me, Br, H, Cl], [AA5133; 2, CH, Me, I, H, Cl], [AA5134; 2, CH, Me, $CF_3$, H, Cl], [AA5135; 2, CH, Me, $CF_2H$, H, Cl], [AA5136; 2, CH, Me, $C_2F_5$, H, Cl], [AA5137; 2, CH, Me, $C_3F_7$, H, Cl], [AA5138; 2, CH, Me, $CH_2CF_3$, H, Cl], [AA5139; 2, CH, Me, $CH_2CHF_2$, H, Cl], [AA5140; 0, N, Me, H, H, Cl], [AA5141; 0, N, Me, F, H, Cl], [AA5142; 0, N, Me, Cl, H, Cl], [AA5143; 0, N, Me, Br, H, Cl], [AA5144; 0, N, Me, I, H, Cl], [AA5145; 0, N, Me, $CF_3$, H, Cl], [AA5146; 0, N, Me, $CF_2H$, H, Cl], [AA5147; 0, N, Me, $C_2F_5$, H, Cl], [AA5148; 0, N, Me, $C_3F_3$, H, Cl], [AA5149; 0, N, Me, $CH_2CF_3$, H, Cl], [AA5150; 0, N, Me, $CH_2CHF_2$, H, Cl], [AA5151; 1, N, Me, H, H, Cl], [AA5152; 1, N, Me, F, H, Cl], [AA5153; 1, N, Me, Cl, H, Cl], [AA5154; 1, N, Me, Br, H, Cl], [AA5155; 1, N, Me, I, H, Cl], [AA5156; 1, N, Me, $CF_3$, H, Cl], [AA5157; 1, N, Me, $CF_2H$, H, Cl], [AA5158; 1, N, Me, $C_2F_5$, H, Cl], [AA5159; 1, N, Me, $C_3F_7$, H, Cl], [AA5160; 1, N, Me, $CH_2CF_3$, H, Cl], [AA5161; 1, N, Me, $CH_2CHF_2$, H, Cl], [AA5162; 2, N, Me, H, H, Cl], [AA5163; 2, N, Me, F, H, Cl], [AA5164; 2, N, Me, Cl, H, Cl], [AA5165; 2, N, Me, Br, H, Cl], [AA5166; 2, N, Me, I, H, Cl], [AA5167; 2, N, Me, $CF_3$, H, Cl], [AA5168; 2, N, Me, $CF_2H$, H, Cl], [AA5169; 2, N, Me, $C_2F_5$, H, Cl], [AA5170; 2, N, Me, $C_3F_7$, H, Cl], [AA5171; 2, N, Me, $CH_2CF_3$, H, Cl], [AA5172; 2, N, Me, $CH_2CHF_2$, H, Cl], [AA5173; 0, CH, Et, H, H, Cl], [AA5174; 0, CH, Et, F, H, Cl], [AA5175; 0, CH, Et, Cl, H, Cl], [AA5176; 0, CH, Et, Br, H, Cl], [AA5177; 0, CH, Et, I, H, Cl], [AA5178; 0, CH, Et, $CF_3$, H, Cl], [AA5179; 0, CH, Et, $CF_2H$, H, Cl], [AA5180; 0, CH, Et, $C_2F_5$, H, Cl], [AA5181; 0, CH, Et, $C_3F_7$, H, Cl], [AA5182; 0, CH, Et, $CH_2CF_3$, H, Cl], [AA5183; 0, CH, Et, $CH_2CHF_2$, H, Cl], [AA5184; 1, CH, Et, H, H, Cl], [AA5185; 1, CH, Et, F, H, Cl], [AA5186; 1, CH, Et, Cl, H, Cl], [AA5187; 1, CH, Et, Br, H, Cl], [AA5188; 1, CH, Et, I, H, Cl], [AA5189; 1, CH, Et, $CF_3$, H, Cl], [AA5190; 1, CH, Et, $CF_2H$, H, Cl], [AA5191; 1, CH, Et, $C_2F_5$, H, $C_1$], [AA5192; 1, CH, Et, $C_3F_7$, H, Cl], [AA5193; 1, CH, Et, $CH_2CF_3$, H, Cl], [AA5194; 1, CH, Et, $CH_2CHF_2$, H, Cl][AA5195; 2, CH, Et, H, H, Cl], [AA5196; 2, CH, Et, F, H, Cl], [AA5197; 2, CH, Et, Cl, H, Cl], [AA5198; 2, CH, Et, Br, H, Cl], [AA5199; 2, CH, Et, I, H, Cl], [AA5200; 2, CH, Et, $CF_3$, H, Cl], [AA5201; 2, CH, Et, $CF_2H$, H, Cl], [AA5202; 2, CH, Et, $C_2F_5$, H, Cl], [AA5203; 2, CH, Et, $C_3F_7$, H, Cl], [AA5204; 2, CH, Et, $CH_2CF_3$, H, Cl], [AA5205; 2, CH, Et, $CH_2CHF_2$, H, Cl], [AA5206; 0, N, Et, H, H, Cl], [AA5207; 0, N, Et, F, H, Cl], [AA5208; 0, N, Et, Cl, H, Cl], [AA5209; 0, N, Et, Br, H, Cl], [AA5210; 0, N, Et, I, H, Cl], [AA5211; 0, N, Et, $CF_3$, H, Cl], [AA5212; 0, N, Et, $CF_2H$, H, Cl], [AA5213; 0, N, Et, $C_2F_5$, H, Cl], [AA5214; 0, N, Et, $C_3F_7$, H, Cl], [AA5215; 0, N, Et, $CH_2CF_3$, H, Cl], [AA5216; 0, N, Et, $CH_2CHF_2$, H, Cl][AA5217; 1, N, Et, H, H, Cl], [AA5218; 1, N, Et, F, H, Cl], [AA5219; 1, N, Et, Cl, H, Cl], [AA5220; 1, N, Et, Br, H, Cl], [AA5221; 1, N, Et, I, H, Cl], [AA5222; 1, N, Et, $CF_3$, H, Cl], [AA5223; 1, N, Et, $CF_2H$, H, Cl], [AA5224; 1, N, Et, $C_2F_5$, H, Cl], [AA5225; 1, N, Et, $C_3F_7$, H, Cl], [AA5226; 1, N, Et, $CH_2CF_3$, H, Cl], [AA5227; 1, N, Et, $CH_2CHF_2$, H, Cl], [AA5228; 2, N, Et, H, H, Cl], [AA5229; 2, N, Et, F, H, Cl], [AA5230; 2, N, Et, Cl, H, Cl], [AA5231; 2, N, Et, Br, H, Cl], [AA5232; 2, N, Et, I, H, Cl], [AA5233; 2, N, Et, $CF_3$, H, Cl], [AA5234; 2, N, Et, $CF_2H$, H, Cl], [AA5235; 2, N, Et, $C_2F_5$, H, Cl], [AA5236; 2, N, Et, $C_3F_7$, H, Cl], [AA5237; 2, N, Et, $CH_2CF_3$, H, Cl], [AA5238; 2, N, Et, $CH_2CHF_2$, H, Cl][AA5239; 0, CH, iPr, H, H, Cl], [AA5240; 0, CH, iPr, F, H, Cl], [AA5241; 0, CH, iPr, Cl, H, Cl], [AA5242; 0, CH, iPr, Br, H, Cl], [AA5243; 0, CH, iPr, I, H, Cl], [AA5244; 0, CH, iPr, $CF_3$, H, Cl], [AA5245; 0, CH, iPr, $CF_2H$, H, Cl], [AA5246; 0, CH, iPr, $C_2F_5$, H, Cl], [AA5247; 0, CH, iPr, $C_3F_7$, H, Cl], [AA5248; 0, CH, iPr, $CH_2CF_3$, H, Cl], [AA5249; 0, CH, iPr, $CH_2CHF_2$, H, Cl], [AA5250; 1, CH, iPr, H, H, Cl], [AA5251; 1, CH, iPr, F, H, Cl], [AA5252; 1, CH, iPr, Cl, H, Cl], [AA5253; 1, CH, iPr, Br, H, Cl], [AA5254; 1, CH, iPr, I, H, Cl], [AA5255; 1, CH, iPr, $CF_3$, H, Cl], [AA5256; 1, CH, iPr, $CF_2H$, H, Cl], [AA5257; 1, CH, iPr, $C_2F_5$, H, Cl], [AA5258; 1, CH, iPr, $C_3F_{77}$, H, Cl], [AA5259; 1, CH, iPr, $CH_2CF_3$, H, Cl], [AA5260; 1, CH, iPr, $CH_2CHF_2$, H, Cl], [AA5261; 2, CH, iPr, H, H, Cl], [AA5262; 2, CH, iPr, F, H, Cl], [AA5263; 2, CH, iPr, Cl, H, Cl], [AA5264; 2, CH, iPr, Br, H, Cl], [AA5265; 2, CH, iPr, I, H, Cl], [AA5266; 2, CH, iPr, $CF_3$, H, Cl], [AA5267; 2, CH, iPr, $CF_2H$, H, Cl], [AA5268; 2, CH, iPr, $C_2F_5$, H, Cl], [AA5269; 2, CH, iPr, $C_3F_7$, H, Cl], [AA5270; 2, CH, iPr, $CH_2CF_3$, H, Cl], [AA5271; 2, CH, iPr, $CH_2CHF_2$, H, Cl], [AA5272; 0, N, iPr, H, H, Cl], [AA5273; 0, N, iPr, F, H, Cl], [AA5274; 0, N, iPr, Cl, H, Cl], [AA5275; 0, N, iPr, Br, H, Cl], [AA5276; 0, N, iPr, I, H, Cl], [AA5277; 0, N, iPr, $CF_3$, H, Cl], [AA5278; 0, N, iPr, $CF_2H$, H, Cl], [AA5279; 0, N, iPr, $C_2F_5$, H, Cl], [AA5280; 0, N, iPr, $C_3F_3$, H, Cl], [AA5281; 0, N, iPr, $CH_2CF_3$, H, Cl], [AA5282; 0, N, iPr, $CH_2CHF_2$, H, Cl], [AA5283; 1, N, iPr, H, H, Cl], [AA5284; 1, N, iPr, F, H, Cl], [AA5285; 1, N, iPr, Cl, H, Cl], [AA5286; 1, N, iPr, Br, H, Cl], [AA5287; 1, N, iPr, I, H, Cl], [AA5288; 1, N, iPr, $CF_3$, H, Cl], [AA5289; 1, N, iPr, $CF_2H$, H, Cl], [AA5290; 1, N, iPr, $C_2F_5$, H, Cl], [AA5291; 1, N, iPr, $C_3F_7$, H, Cl], [AA5292; 1, N, iPr, $CH_2CF_3$, H, Cl], [AA5293; 1, N, iPr, $CH_2CHF_2$, H, Cl], [AA5294; 2, N, iPr, H, H, Cl], [AA5295; 2, N, iPr, F, H, Cl], [AA5296; 2, N, iPr, Cl, H, Cl], [AA5297; 2, N, iPr, Br, H, Cl], [AA5298; 2, N, iPr, I, H, Cl], [AA5299; 2, N, iPr, $CF_3$, H, Cl], [AA5300; 2, N, iPr, $CF_2H$, H, Cl], [AA5301; 2, N, iPr, $C_2F_5$, H, Cl], [AA5302; 2, N, iPr, $C_3F_7$, H, Cl], [AA5303; 2, N, iPr, $CH_2CF_3$, H, Cl], [AA5304; 2, N, iPr, $CH_2CHF_2$, H, Cl], [AA5305; 0, CH, cPr, H, H, Cl], [AA5306; 0, CH, cPr, F, H, Cl], [AA5307; 0, CH, cPr, Cl, H, Cl], [AA5308; 0, CH, cPr, Br, H, Cl], [AA5309; 0, CH, cPr, I, H, Cl], [AA5310; 0, CH, cPr, $CF_3$, H, Cl], [AA5311; 0, CH, cPr, $CF_2H$, H, Cl], [AA5312; 0, CH, cPr, $C_2F_5$, H, Cl], [AA5313; 0, CH, cPr, $C_3F_7$, H, Cl], [AA5314; 0, CH, cPr, $CH_2CF_3$, H, Cl], [AA5315; 0, CH, cPr, $CH_2CHF_2$, H, Cl], [AA5316; 1, CH, cPr, H, H, Cl], [AA5317; 1, CH, cPr, F, H, Cl], [AA5318; 1, CH, cPr, Cl, H, Cl], [AA5319; 1, CH, cPr, Br, H, Cl], [AA5320; 1, CH, cPr, I, H, Cl], [AA5321; 1, CH, cPr, $CF_3$,

H, Cl], [AA5322; 1, CH, cPr, $CF_2H$, H, Cl], [AA5323; 1, CH, cPr, $C_2F_5$, H, Cl], [AA5324; 1, CH, cPr, $C_3F_7$, H, Cl], [AA5325; 1, CH, cPr, $CH_2CF_3$, H, Cl], [AA5326; 1, CH, cPr, $CH_2CHF_2$, H, Cl], [AA5327; 2, CH, cPr, H, H, Cl], [AA5328; 2, CH, cPr, F, H, Cl], [AA5329; 2, CH, cPr, Cl, H, Cl], [AA5330; 2, CH, cPr, Br, H, Cl], [AA5331; 2, CH, cPr, I, H, Cl], [AA5332; 2, CH, cPr, $CF_3$, H, Cl], [AA5333; 2, CH, cPr, $CF_2H$, H, Cl], [AA5334; 2, CH, cPr, $C_2F_3$, H, Cl], [AA5335; 2, CH, cPr, $C_3F$-7, H, Cl], [AA5336; 2, CH, cPr, $CH_2CF_3$, H, Cl], [AA5337; 2, CH, cPr, $CH_2CHF_2$, H, Cl], [AA5338; 0, N, cPr, H, H, Cl], [AA5339; 0, N, cPr, F, H, Cl], [AA5340; 0, N, cPr, Cl, H, Cl], [AA5341; 0, N, cPr, Br, H, Cl], [AA5342; 0, N, cPr, I, H, Cl], [AA5343; 0, N, cPr, $CF_3$, H, Cl], [AA5344; 0, N, cPr, $CF_2H$, H, Cl], [AA5345; 0, N, cPr, $C_2F_5$, H, Cl], [AA5346; 0, N, cPr, $C_3F_7$, H, Cl], [AA5347; 0, N, cPr, $CH_2CF_3$, H, Cl], [AA5348; 0, N, cPr, $CH_2CHF_2$, H, Cl], [AA5349; 1, N, cPr, H, H, Cl], [AA5350; 1, N, cPr, F, H, Cl], [AA5351; 1, N, cPr, Cl, H, Cl], [AA5352; 1, N, cPr, Br, H, Cl], [AA5353; 1, N, cPr, I, H, Cl], [AA5354; 1, N, cPr, $CF_3$, H, Cl], [AA5355; 1, N, cPr, $CF_2H$, H, Cl], [AA5356; 1, N, cPr, $C_2F_5$, H, Cl], [AA5357; 1, N, cPr, $C_3F_7$, H, Cl], [AA5358; 1, N, cPr, $CH_2CF_3$, H, Cl], [AA5359; 1, N, cPr, $CH_2CHF_2$, H, Cl], [AA5360; 2, N, cPr, H, H, Cl], [AA5361; 2, N, cPr, F, H, Cl], [AA5362; 2, N, cPr, Cl, H, Cl], [AA5363; 2, N, cPr, Br, H, Cl], [AA5364; 2, N, cPr, I, H, Cl], [AA5365; 2, N, cPr, $CF_3$, H, Cl], [AA5366; 2, N, cPr, $CF_2H$, H, Cl], [AA5367; 2, N, cPr, $C_2F_5$, H, Cl], [AA5368; 2, N, cPr, $C_3F_7$, H, Cl], [AA5369; 2, N, cPr, $CH_2CF_3$, H, Cl], [AA5370; 2, N, cPr, $CH_2CHF_2$, H, Cl], [AA5371; 0, CH, H, H, F, Cl], [AA5372; 0, CH, H, H, Cl, Cl], [AA5373; 0, CH, H, H, Br, Cl], [AA5374; 0, CH, H, H, I, Cl], [AA5375; 0, CH, H, H, $CF_3$, Cl], [AA5376; 0, CH, H, H, $CF_2H$, Cl], [AA5377; 0, CH, H, H, $C_2F_3$, Cl], [AA5378; 0, CH, H, H, $C_3F_7$, Cl], [AA5379; 0, CH, H, H, $CH_2CF_3$, Cl], [AA5380; 0, CH, H, H, $CH_2CHF_2$, Cl], [AA5381; 1, CH, H, H, F, Cl], [AA5382; 1, CH, H, H, Cl, Cl], [AA5383; 1, CH, H, H, Br, Cl], [AA5384; 1, CH, H, H, I, Cl], [AA5385; 1, CH, H, H, $CF_3$, Cl], [AA5386; 1, CH, H, H, $CF_2H$, Cl], [AA5387; 1, CH, H, H, $C_2F_5$, Cl], [AA5388; 1, CH, H, H, $C_3F_7$, Cl], [AA5389; 1, CH, H, H, $CH_2CF_3$, Cl], [AA5390; 1, CH, H, H, $CH_2CHF_2$, Cl], [AA5391; 2, CH, H, H, F, Cl], [AA5392; 2, CH, H, H, Cl, Cl], [AA5393; 2, CH, H, H, Br, Cl], [AA5394; 2, CH, H, H, I, Cl], [AA5395; 2, CH, H, H, $CF_3$, Cl], [AA5396; 2, CH, H, H, $CF_2H$, Cl], [AA5397; 2, CH, H, H, $C_2F_5$, Cl], [AA5398; 2, CH, H, H, $C_3F_7$, Cl], [AA5399; 2, CH, H, H, $CH_2CF_3$, Cl], [AA5400; 2, CH, H, H, $CH_2CHF_2$, Cl], [AA5401; 0, N, H, H, F, Cl], [AA5402; 0, N, H, H, Cl, Cl], [AA5403; 0, N, H, H, Br, Cl], [AA5404; 0, N, H, H, I, Cl], [AA5405; 0, N, H, H, $CF_3$, Cl], [AA5406; 0, N, H, H, $CF_2H$, Cl], [AA5407; 0, N, H, H, $C_2F_5$, Cl], [AA5408; 0, N, H, H, $C_3F_7$, Cl], [AA5409; 0, N, H, H, $CH_2CF_3$, Cl], [AA5410; 0, N, H, H, $CH_2CHF_2$, Cl], [AA5411; 1, N, H, H, F, Cl], [AA5412; 1, N, H, H, Cl, Cl], [AA5413; 1, N, H, H, Br, Cl], [AA5414; 1, N, H, H, I, Cl], [AA5415; 1, N, H, H, $CF_3$, Cl], [AA5416; 1, N, H, H, $CF_2H$, Cl], [AA5417; 1, N, H, H, $C_2F_5$, Cl], [AA5418; 1, N, H, H, $C_3F_7$, Cl], [AA5419; 1, N, H, H, $CH_2CF_3$, Cl], [AA5420; 1, N, H, H, $CH_2CHF_2$, Cl], [AA5421; 2, N, H, H, F, Cl], [AA5422; 2, N, H, H, Cl, Cl], [AA5423; 2, N, H, H, Br, Cl], [AA5424; 2, N, H, H, I, Cl], [AA5425; 2, N, H, H, $CF_3$, Cl], [AA5426; 2, N, H, H, $CF_2H$, Cl], [AA5427; 2, N, H, H, $C_2F_5$, Cl], [AA5428; 2, N, H, H, $C_3F_7$, Cl], [AA5429; 2, N, H, H, $CH_2CF_3$, Cl], [AA5430; 2, N, H, H, $CH_2CHF_2$, Cl], [AA5431; 0, CH, Me, H, F, Cl], [AA5432; 0, CH, Me, H, Cl, Cl], [AA5433; 0, CH, Me, H, Br, Cl], [AA5434; 0, CH, Me, H, I, Cl], [AA5435; 0, CH, Me, H, $CF_3$, Cl], [AA5436; 0, CH, Me, H, $CF_2H$, Cl], [AA5437; 0, CH, Me, H, $C_2F_5$, Cl], [AA5438; 0, CH, Me, H, $C_3F_7$, Cl], [AA5439; 0, CH, Me, H, $CH_2CF_3$, Cl], [AA5440; 0, CH, Me, H, $CH_2CHF_2$, Cl][AA5441; 1, CH, Me, H, F, Cl], [AA5442; 1, CH, Me, H, Cl, Cl], [AA5443; 1, CH, Me, H, Br, Cl], [AA5444; 1, CH, Me, H, I, Cl], [AA5445; 1, CH, Me, H, $CF_3$, Cl], [AA5446; 1, CH, Me, H, $CF_2H$, Cl], [AA5447; 1, CH, Me, H, $C_2F_5$, Cl], [AA5448; 1, CH, Me, H, $C_3F_7$, Cl], [AA5449; 1, CH, Me, H, $CH_2CF_3$, Cl], [AA5450; 1, CH, Me, H, $CH_2CHF_2$, Cl], [AA5451; 2, CH, Me, H, F, Cl], [AA5452; 2, CH, Me, H, Cl, Cl], [AA5453; 2, CH, Me, H, Br, Cl], [AA5454; 2, CH, Me, H, I, Cl], [AA5455; 2, CH, Me, H, $CF_3$, Cl], [AA5456; 2, CH, Me, H, $CF_2H$, Cl], [AA5457; 2, CH, Me, H, $C_2F_5$, Cl], [AA5458; 2, CH, Me, H, $C_3F_7$, Cl], [AA5459; 2, CH, Me, H, $CH_2CF_3$, Cl], [AA5460; 2, CH, Me, H, $CH_2CHF_2$, Cl], [AA5461; 0, N, Me, H, F, Cl], [AA5462; 0, N, Me, H, Cl, Cl], [AA5463; 0, N, Me, H, Br, Cl], [AA5464; 0, N, Me, H, I, Cl], [AA5465; 0, N, Me, H, $CF_3$, Cl], [AA5466; 0, N, Me, H, $CF_2H$, Cl], [AA5467; 0, N, Me, H, $C_2F_5$, Cl], [AA5468; 0, N, Me, H, $C_3F_7$, Cl], [AA5469; 0, N, Me, H, $CH_2CF_3$, Cl], [AA5470; 0, N, Me, H, $CH_2CHF_2$, Cl], [AA5471; 1, N, Me, H, F, Cl], [AA5472; 1, N, Me, H, Cl, Cl], [AA5473; 1, N, Me, H, Br, Cl], [AA5474; 1, N, Me, H, I, Cl], [AA5475; 1, N, Me, H, $CF_3$, Cl], [AA5476; 1, N, Me, H, $CF_2H$, Cl], [AA5477; 1, N, Me, H, $C_2F_5$, Cl], [AA5478; 1, N, Me, H, $C_3F_7$, Cl], [AA5479; 1, N, Me, H, $CH_2CF_3$, Cl], [AA5480; 1, N, Me, H, $CH_2CHF_2$, Cl], [AA5481; 2, N, Me, H, F, Cl], [AA5482; 2, N, Me, H, Cl, Cl], [AA5483; 2, N, Me, H, Br, Cl], [AA5484; 2, N, Me, H, I, Cl], [AA5485; 2, N, Me, H, $CF_3$, Cl], [AA5486; 2, N, Me, H, $CF_2H$, Cl], [AA5487; 2, N, Me, H, $C_2F_5$, Cl], [AA5488; 2, N, Me, H, $C_3F_7$, Cl], [AA5489; 2, N, Me, H, $CH_2CF_3$, Cl], [AA5490; 2, N, Me, H, $CH_2CHF_2$, Cl], [AA5491; 0, CH, Et, H, F, Cl], [AA5492; 0, CH, Et, H, Cl, Cl], [AA5493; 0, CH, Et, H, Br, Cl], [AA5494; 0, CH, Et, H, I, Cl], [AA5495; 0, CH, Et, H, $CF_3$, Cl], [AA5496; 0, CH, Et, H, $CF_2H$, Cl], [AA5497; 0, CH, Et, H, $C_2F_5$, Cl], [AA5498; 0, CH, Et, H, $C_3F_7$, Cl], [AA5499; 0, CH, Et, H, $CH_2CF_3$, Cl], [AA5500; 0, CH, Et, H, $CH_2CHF_2$, Cl], [AA5501; 1, CH, Et, H, F, Cl], [AA5502; 1, CH, Et, H, Cl, Cl], [AA5503; 1, CH, Et, H, Br, Cl], [AA5504; 1, CH, Et, H, I, Cl], [AA5505; 1, CH, Et, H, $CF_3$, Cl], [AA5506; 1, CH, Et, H, $CF_2H$, Cl], [AA5507; 1, CH, Et, H, $C_2F_5$, Cl], [AA5508; 1, CH, Et, H, $C_3F_7$, Cl], [AA5509; 1, CH, Et, H, $CH_2CF_3$, Cl], [AA5510; 1, CH, Et, H, $CH_2CHF_2$, Cl], [AA5511; 2, CH, Et, H, F, Cl], [AA5512; 2, CH, Et, H, Cl, Cl], [AA5513; 2, CH, Et, H, Br, Cl], [AA5514; 2, CH, Et, H, I, Cl], [AA5515; 2, CH, Et, H, $CF_3$, Cl], [AA5516; 2, CH, Et, H, $CF_2H$, Cl], [AA5517; 2, CH, Et, H, $C_2F_5$, Cl], [AA5518; 2, CH, Et, H, $C_3F_7$, Cl], [AA5519; 2, CH, Et, H, $CH_2CF_3$, Cl], [AA5520; 2, CH, Et, H, $CH_2CHF_2$, Cl], [AA5521; 0, N, Et, H, F, Cl], [AA5522; 0, N, Et, H, Cl, Cl], [AA5523; 0, N, Et, H, Br, Cl], [AA5524; 0, N, Et, H, I, Cl], [AA5525; 0, N, Et, H, $CF_3$, Cl], [AA5526; 0, N, Et, H, $CF_2H$, Cl], [AA5527; 0, N, Et, H, $C_2F$, Cl], [AA5528; 0, N, Et, H, $C_3F$, Cl], [AA5529; 0, N, Et, H, $CH_2CF_3$, Cl], [AA5530; 0, N, Et, H, $CH_2CHF_2$, Cl], [AA5531; 1, N, Et, H, F, Cl], [AA5532; 1, N, Et, H, Cl, Cl], [AA5533; 1, N, Et, H, Br, Cl], [AA5534; 1, N, Et, H, I, Cl], [AA5535; 1, N, Et, H, $CF_3$, Cl], [AA5536; 1, N, Et, H, $CF_2H$, Cl], [AA5537; 1, N, Et, H, $C_2F_5$, Cl], [AA5538; 1, N, Et, H, $C_3F_7$, Cl], [AA5539; 1, N, Et, H, $CH_2CF_3$, Cl], [AA5540; 1, N, Et, H, $CH_2CHF_2$, Cl], [AA5541; 2, N, Et, H, F, Cl], [AA5542; 2, N, Et, H, Cl, Cl], [AA5543; 2, N, Et, H, Br, Cl], [AA5544; 2, N, Et, H, I, Cl], [AA5545; 2, N, Et, H, $CF_3$, Cl], [AA5546; 2, N, Et, H, $CF_2H$, Cl], [AA5547; 2, N, Et, H, $C_2F_5$, Cl], [AA5548; 2, N, Et, H, $C_3F_7$, Cl], [AA5549; 2, N, Et, H, $CH_2CF_3$, Cl], [AA5550; 2, N, Et, H, $CH_2CHF_2$, Cl], [AA5551; 0, CH, iPr, H, F, Cl], [AA5552; 0,

CH, iPr, H, Cl, Cl], [AA5553; 0, CH, iPr, H, Br, Cl], [AA5554; 0, CH, iPr, H, I, Cl], [AA5555; 0, CH, iPr, H, $CF_3$, Cl], [AA5556; 0, CH, iPr, H, $CF_2H$, Cl], [AA5557; 0, CH, iPr, H, $C_2F_5$, Cl], [AA5558; 0, CH, iPr, H, $C_3F_7$, Cl], [AA5559; 0, CH, iPr, H, $CH_2CF_3$, Cl], [AA5560; 0, CH, iPr, H, $CH_2CHF_2$, Cl], [AA5561; 1, CH, iPr, H, F, Cl], [AA5562; 1, CH, iPr, H, Cl, Cl], [AA5563; 1, CH, iPr, H, Br, Cl], [AA5564; 1, CH, iPr, H, I, Cl], [AA5565; 1, CH, iPr, H, $CF_3$, Cl], [AA5566; 1, CH, iPr, H, $CF_2H$, Cl], [AA5567; 1, CH, iPr, H, $C_2F_5$, Cl], [AA5568; 1, CH, iPr, H, $C_3F_7$, Cl], [AA5569; 1, CH, iPr, H, $CH_2CF_3$, Cl], [AA5570; 1, CH, iPr, H, $CH_2CHF_2$, Cl], [AA5571; 2, CH, iPr, H, F, Cl], [AA5572; 2, CH, iPr, H, Cl, Cl], [AA5573; 2, CH, iPr, H, Br, Cl], [AA5574; 2, CH, iPr, H, I, Cl], [AA5575; 2, CH, iPr, H, $CF_3$, Cl], [AA5576; 2, CH, iPr, H, $CF_2H$, Cl], [AA5577; 2, CH, iPr, H, $C_2F_5$, Cl], [AA5578; 2, CH, iPr, H, $C_3F_7$, Cl], [AA5579; 2, CH, iPr, H, $CH_2CF_3$, Cl], [AA5580; 2, CH, iPr, H, $CH_2CHF_2$, Cl], [AA5581; 0, N, iPr, H, F, Cl], [AA5582; 0, N, iPr, H, Cl, Cl], [AA5583; 0, N, iPr, H, Br, Cl], [AA5584; 0, N, iPr, H, I, Cl], [AA5585; 0, N, iPr, H, $CF_3$, Cl], [AA5586; 0, N, iPr, H, $CF_2H$, Cl], [AA5587; 0, N, iPr, H, $C_2F_5$, Cl], [AA5588; 0, N, iPr, H, $C_3F_7$, Cl], [AA5589; 0, N, iPr, H, $CH_2CF_3$, Cl], [AA5590; 0, N, iPr, H, $CH_2CHF_2$, Cl], [AA5591; 1, N, iPr, H, F, Cl], [AA5592; 1, N, iPr, H, Cl, Cl], [AA5593; 1, N, iPr, H, Br, Cl], [AA5594; 1, N, iPr, H, I, Cl], [AA5595; 1, N, iPr, H, $CF_3$, Cl], [AA5596; 1, N, iPr, H, $CF_2H$, Cl], [AA5597; 1, N, iPr, H, $C_2F_5$, Cl], [AA5598; 1, N, iPr, H, $C_3F_7$, Cl], [AA5599; 1, N, iPr, H, $CH_2CF_3$, Cl], [AA5600; 1, N, iPr, H, $CH_2CHF_2$, Cl], [AA5601; 2, N, iPr, H, F, Cl], [AA5602; 2, N, iPr, H, Cl, Cl], [AA5603; 2, N, iPr, H, Br, Cl], [AA5604; 2, N, iPr, H, I, Cl], [AA5605; 2, N, iPr, H, $CF_3$, Cl], [AA5606; 2, N, iPr, H, $CF_2H$, Cl], [AA5607; 2, N, iPr, H, $C_2F_5$, Cl], [AA5608; 2, N, iPr, H, $C_3F_7$, Cl], [AA5609; 2, N, iPr, H, $CH_2CF_3$, Cl], [AA5610; 2, N, iPr, H, $CH_2CHF_2$, Cl], [AA5611; 0, CH, cPr, H, F, Cl], [AA5612; 0, CH, cPr, H, Cl, Cl], [AA5613; 0, CH, cPr, H, Br, Cl], [AA5614; 0, CH, cPr, H, I, Cl], [AA5615; 0, CH, cPr, H, $CF_3$, Cl], [AA5616; 0, CH, cPr, H, $CF_2H$, Cl], [AA5617; 0, CH, cPr, H, $C_2F_5$, Cl], [AA5618; 0, CH, cPr, H, $C_3F_7$, Cl], [AA5619; 0, CH, cPr, H, $CH_2CF_3$, Cl], [AA5620; 0, CH, cPr, H, $CH_2CHF_2$, Cl], [AA5621; 1, CH, cPr, H, F, Cl], [AA5622; 1, CH, cPr, H, Cl, Cl], [AA5623; 1, CH, cPr, H, Br, Cl], [AA5624; 1, CH, cPr, H, I, Cl], [AA5625; 1, CH, cPr, H, $CF_3$, Cl], [AA5626; 1, CH, cPr, H, $CF_2H$, Cl], [AA5627; 1, CH, cPr, H, $C_2F_5$, Cl], [AA5628; 1, CH, cPr, H, $C_3F_7$, Cl], [AA5629; 1, CH, cPr, H, $CH_2CF_3$, Cl], [AA5630; 1, CH, cPr, H, $CH_2CHF_2$, $C_1$], [AA5631; 2, CH, cPr, H, F, Cl], [AA5632; 2, CH, cPr, H, Cl, Cl], [AA5633; 2, CH, cPr, H, Br, Cl], [AA5634; 2, CH, cPr, H, I, Cl], [AA5635; 2, CH, cPr, H, $CF_3$, Cl], [AA5636; 2, CH, cPr, H, $CF_2H$, Cl], [AA5637; 2, CH, cPr, H, $C_2F_5$, Cl], [AA5638; 2, CH, cPr, H, $C_3F_7$, Cl], [AA5639; 2, CH, cPr, H, $CH_2CF_3$, Cl], [AA5640; 2, CH, cPr, H, $CH_2CHF_2$, Cl], [AA5641; 0, N, cPr, H, F, Cl], [AA5642; 0, N, cPr, H, Cl, Cl], [AA5643; 0, N, cPr, H, Br, Cl], [AA5644; 0, N, cPr, H, I, Cl], [AA5645; 0, N, cPr, H, $CF_3$, Cl], [AA5646; 0, N, cPr, H, $CF_2H$, Cl], [AA5647; 0, N, cPr, H, $C_2F_5$, Cl], [AA5648; 0, N, cPr, H, $C_3F_7$, Cl], [AA5649; 0, N, cPr, H, $CH_2CF_3$, Cl], [AA5650; 0, N, cPr, H, $CH_2CHF_2$, Cl], [AA5651; 1, N, cPr, H, F, Cl], [AA5652; 1, N, cPr, H, Cl, Cl], [AA5653; 1, N, cPr, H, Br, Cl], [AA5654; 1, N, cPr, H, I, Cl], [AA5655; 1, N, cPr, H, $CF_3$, Cl], [AA5656; 1, N, cPr, H, $CF_2H$, Cl], [AA5657; 1, N, cPr, H, $C_2F_5$, Cl], [AA5658; 1, N, cPr, H, $C_3F_7$, Cl], [AA5659; 1, N, cPr, H, $CH_2CF_3$, Cl], [AA5660; 1, N, cPr, H, $CH_2CHF_2$, Cl], [AA5661; 2, N, cPr, H, F, Cl], [AA5662; 2, N, cPr, H, Cl, Cl], [AA5663; 2, N, cPr, H, Br, Cl], [AA5664; 2, N, cPr, H, I, Cl], [AA5665; 2, N, cPr, H, $CF_3$, Cl], [AA5666; 2, N, cPr, H, $CF_2H$, Cl], [AA5667; 2, N, cPr, H, $C_2F_5$, Cl], [AA5668; 2, N, cPr, H, $C_3F_7$, Cl], [AA5669; 2, N, cPr, H, $CH_2CF_3$, Cl], [AA5670; 2, N, cPr, H, $CH_2CHF_2$, Cl], [AA5671; 0, CH, H, H, H, I], [AA5672; 0, CH, H, F, H, I], [AA5673; 0, CH, H, Cl, H, I], [AA5674; 0, CH, H, Br, H, I], [AA5675; 0, CH, H, I, H, I], [AA5676; 0, CH, H, $CF_3$, H, I], [AA5677; 0, CH, H, $CF_2H$, H, I], [AA5678; 0, CH, H, $C_2F_5$, H, I], [AA5679; 0, CH, H, $C_3F_7$, H, I], [AA5680; 0, CH, H, $CH_2CF_3$, H, I], [AA5681; 0, CH, H, $CH_2CHF_2$, H, I], [AA5682; 1, CH, H, H, H, I], [AA5683; 1, CH, H, F, H, I], [AA5684; 1, CH, H, Cl, H, I], [AA5685; 1, CH, H, Br, H, I], [AA5686; 1, CH, H, I, H, I], [AA5687; 1, CH, H, $CF_3$, H, I], [AA5688; 1, CH, H, $CF_2H$, H, I], [AA5689; 1, CH, H, $C_2F_5$, H, I], [AA5690; 1, CH, H, $C_3F_7$, H, I], [AA5691; 1, CH, H, $CH_2CF_3$, H, I], [AA5692; 1, CH, H, $CH_2CHF_2$, H, I], [AA5693; 2, CH, H, H, H, I], [AA5694; 2, CH, H, F, H, I], [AA5695; 2, CH, H, Cl, H, I], [AA5696; 2, CH, H, Br, H, I], [AA5697; 2, CH, H, I, H, I], [AA5698; 2, CH, H, $CF_3$, H, I], [AA5699; 2, CH, H, $CF_2H$, H, I], [AA5700; 2, CH, H, $C_2F_5$, H, I], [AA5701; 2, CH, H, $C_3F_7$, H, I], [AA5702; 2, CH, H, $CH_2CF_3$, H, I], [AA5703; 2, CH, H, $CH_2CHF_2$, H, I], [AA5704; 0, N, H, H, H, I], [AA5705; 0, N, H, F, H, I], [AA5706; 0, N, H, Cl, H, I], [AA5707; 0, N, H, Br, H, I], [AA5708; 0, N, H, I, H, I], [AA5709; 0, N, H, $CF_3$, H, I], [AA5710; 0, N, H, $CF_2H$, H, I], [AA5711; 0, N, H, $C_2F_5$, H, I], [AA5712; 0, N, H, $C_3F_7$, H, I], [AA5713; 0, N, H, $CH_2CF_3$, H, I], [AA5714; 0, N, H, $CH_2CHF_2$, H, I], [AA5715; 1, N, H, H, H, I], [AA5716; 1, N, H, F, H, I], [AA5717; 1, N, H, Cl, H, I], [AA5718; 1, N, H, Br, H, I], [AA5719; 1, N, H, I, H, I], [AA5720; 1, N, H, $CF_3$, H, I], [AA5721; 1, N, H, $CF_2H$, H, I], [AA5722; 1, N, H, $C_2F_5$, H, I], [AA5723; 1, N, H, $C_3F_5$, H, I], [AA5724; 1, N, H, $CH_2CF_3$, H, I], [AA5725; 1, N, H, $CH_2CHF_2$, H, I], [AA5726; 2, N, H, H, H, I], [AA5727; 2, N, H, F, H, I], [AA5728; 2, N, H, Cl, H, I], [AA5729; 2, N, H, Br, H, I], [AA5730; 2, N, H, I, H, I], [AA5731; 2, N, H, $CF_3$, H, I], [AA5732; 2, N, H, $CF_2H$, H, I], [AA5733; 2, N, H, $C_2F_5$, H, I], [AA5734; 2, N, H, $C_3F_7$, H, I], [AA5735; 2, N, H, $CH_2CF_3$, H, I], [AA5736; 2, N, H, $CH_2CHF_2$, H, I], [AA5737; 0, CH, Me, H, H, I], [AA5738; 0, CH, Me, F, H, I], [AA5739; 0, CH, Me, Cl, H, I], [AA5740; 0, CH, Me, Br, H, I], [AA5741; 0, CH, Me, I, H, I], [AA5742; 0, CH, Me, $CF_3$, H, I], [AA5743; 0, CH, Me, $CF_2H$, H, I], [AA5744; 0, CH, Me, $C_2F_5$, H, I], [AA5745; 0, CH, Me, $C_3F_7$, H, I], [AA5746; 0, CH, Me, $CH_2CF_3$, H, I], [AA5747; 0, CH, Me, $CH_2CHF_2$, H, I], [AA5748; 1, CH, Me, H, H, I], [AA5749; 1, CH, Me, F, H, I], [AA5750; 1, CH, Me, Cl, H, I], [AA5751; 1, CH, Me, Br, H, I], [AA5752; 1, CH, Me, I, H, I], [AA5753; 1, CH, Me, $CF_3$, H, I], [AA5754; 1, CH, Me, $CF_2H$, H, I], [AA5755; 1, CH, Me, $C_2F_5$, H, I], [AA5756; 1, CH, Me, $C_3F_7$, H, I], [AA5757; 1, CH, Me, $CH_2CF_3$, H, I], [AA5758; 1, CH, Me, $CH_2CHF_2$, H, I], [AA5759; 2, CH, Me, H, H, I], [AA5760; 2, CH, Me, F, H, I], [AA5761; 2, CH, Me, Cl, H, I], [AA5762; 2, CH, Me, Br, H, I], [AA5763; 2, CH, Me, I, H, I], [AA5764; 2, CH, Me, $CF_3$, H, I], [AA5765; 2, CH, Me, $CF_2H$, H, I], [AA5766; 2, CH, Me, $C_2F_5$, H, I], [AA5767; 2, CH, Me, $C_3F_7$, H, I], [AA5768; 2, CH, Me, $CH_2CF_3$, H, I], [AA5769; 2, CH, Me, $CH_2CHF_2$, H, I], [AA5770; 0, N, Me, H, H, I], [AA5771; 0, N, Me, F, H, I], [AA5772; 0, N, Me, Cl, H, I], [AA5773; 0, N, Me, Br, H, I], [AA5774; 0, N, Me, I, H, I], [AA5775; 0, N, Me, $CF_3$, H, I], [AA5776; 0, N, Me, $CF_2H$, H, I], [AA5777; 0, N, Me, $C_2F_5$, H, I], [AA5778; 0, N, Me, $C_3F_7$, H, I], [AA5779; 0, N, Me, $CH_2CF_3$, H, I], [AA5780; 0, N, Me, $CH_2CHF_2$, H, I], [AA5781; 1, N, Me, H, H, I], [AA5782; 1, N, Me, F, H, I], [AA5783; 1, N, Me, Cl, H, I], [AA5784; 1, N, Me, Br, H, I], [AA5785; 1, N, Me, I, H, I], [AA5786; 1, N, Me, $CF_3$, H,

I], [AA5787; 1, N, Me, $CF_2H$, H, I], [AA5788; 1, N, Me, $C_2F_5$, H, I], [AA5789; 1, N, Me, $C_3F_7$, H, I], [AA5790; 1, N, Me, $CH_2CF_3$, H, I], [AA5791; 1, N, Me, $CH_2CHF_2$, H, I], [AA5792; 2, N, Me, H, H, I], [AA5793; 2, N, Me, F, H, I], [AA5794; 2, N, Me, Cl, H, I], [AA5795; 2, N, Me, Br, H, I], [AA5796; 2, N, Me, I, H, I], [AA5797; 2, N, Me, $CF_3$, H, I], [AA5798; 2, N, Me, $CF_2H$, H, I], [AA5799; 2, N, Me, $C_2F_5$, H, I], [AA5800; 2, N, Me, $C_3F_7$, H, I], [AA5801; 2, N, Me, $CH_2CF_3$, H, I], [AA5802; 2, N, Me, $CH_2CHF_2$, H, I], [AA5803; 0, CH, Et, H, H, I], [AA5804; 0, CH, Et, F, H, I], [AA5805; 0, CH, Et, Cl, H, I], [AA5806; 0, CH, Et, Br, H, I], [AA5807; 0, CH, Et, I, H, I], [AA5808; 0, CH, Et, $CF_3$, H, I], [AA5809; 0, CH, Et, $CF_2H$, H, I], [AA5810; 0, CH, Et, $C_2F_5$, H, I], [AA5811; 0, CH, Et, $C_3F_7$, H, I], [AA5812; 0, CH, Et, $CH_2CF_3$, H, I], [AA5813; 0, CH, Et, $CH_2CHF_2$, H, I], [AA5814; 1, CH, Et, H, H, I], [AA5815; 1, CH, Et, F, H, I], [AA5816; 1, CH, Et, Cl, H, I], [AA5817; 1, CH, Et, Br, H, I], [AA5818; 1, CH, Et, I, H, I], [AA5819; 1, CH, Et, $CF_3$, H, I], [AA5820; 1, CH, Et, $CF_2H$, H, I], [AA5821; 1, CH, Et, $C_2F_5$, H, I], [AA5822; 1, CH, Et, $C_3F_7$, H, I], [AA5823; 1, CH, Et, $CH_2CF_3$, H, I], [AA5824; 1, CH, Et, $CH_2CHF_2$, H, I], [AA5825; 2, CH, Et, H, H, I], [AA5826; 2, CH, Et, F, H, I], [AA5827; 2, CH, Et, Cl, H, I], [AA5828; 2, CH, Et, Br, H, I], [AA5829; 2, CH, Et, I, H, I], [AA5830; 2, CH, Et, $CF_3$, H, I], [AA5831; 2, CH, Et, $CF_2H$, H, I], [AA5832; 2, CH, Et, $C_2F_5$, H, I], [AA5833; 2, CH, Et, $C_3F_7$, H, I], [AA5834; 2, CH, Et, $CH_2CF_3$, H, I], [AA5835; 2, CH, Et, $CH_2CHF_2$, H, I], [AA5836; 0, N, Et, H, H, I], [AA5837; 0, N, Et, F, H, I], [AA5838; 0, N, Et, Cl, H, I], [AA5839; 0, N, Et, Br, H, I], [AA5840; 0, N, Et, I, H, I], [AA5841; 0, N, Et, $CF_3$, H, I], [AA5842; 0, N, Et, $CF_2H$, H, I], [AA5843; 0, N, Et, $C_2F_5$, H, I], [AA5844; 0, N, Et, $C_3F_7$, H, I], [AA5845; 0, N, Et, $CH_2CF_3$, H, I], [AA5846; 0, N, Et, $CH_2CHF_2$, H, I], [AA5847; 1, N, Et, H, H, I], [AA5848; 1, N, Et, F, H, I], [AA5849; 1, N, Et, Cl, H, I], [AA5850; 1, N, Et, Br, H, I], [AA5851; 1, N, Et, I, H, I], [AA5852; 1, N, Et, $CF_3$, H, I], [AA5853; 1, N, Et, $CF_2H$, H, I], [AA5854; 1, N, Et, $C_2F_5$, H, I], [AA5855; 1, N, Et, $C_3F_7$, H, I], [AA5856; 1, N, Et, $CH_2CF_3$, H, I], [AA5857; 1, N, Et, $CH_2CHF_2$, H, I], [AA5858; 2, N, Et, H, H, I], [AA5859; 2, N, Et, F, H, I], [AA5860; 2, N, Et, Cl, H, I], [AA5861; 2, N, Et, Br, H, I], [AA5862; 2, N, Et, I, H, I], [AA5863; 2, N, Et, $CF_3$, H, I], [AA5864; 2, N, Et, $CF_2H$, H, I], [AA5865; 2, N, Et, $C_2F_5$, H, I], [AA5866; 2, N, Et, $C_3F_7$, H, I], [AA5867; 2, N, Et, $CH_2CF_3$, H, I], [AA5868; 2, N, Et, $CH_2CHF_2$, H, I], [AA5869; 0, CH, iPr, H, H, I], [AA5870; 0, CH, iPr, F, H, I], [AA5871; 0, CH, iPr, Cl, H, I], [AA5872; 0, CH, iPr, Br, H, I], [AA5873; 0, CH, iPr, I, H, I], [AA5874; 0, CH, iPr, $CF_3$, H, H, I], [AA5875; 0, CH, iPr, $CF_2H$, H, I], [AA5876; 0, CH, iPr, $C_2F_5$, H, I], [AA5877; 0, CH, iPr, $C_3F_7$, H, I], [AA5878; 0, CH, iPr, $CH_2CF_3$, H, I], [AA5879; 0, CH, iPr, $CH_2CHF_2$, H, I], [AA5880; 1, CH, iPr, H, H, I], [AA5881; 1, CH, iPr, F, H, I], [AA5882; 1, CH, iPr, Cl, H, I], [AA5883; 1, CH, iPr, Br, H, I], [AA5884; 1, CH, iPr, I, H, I], [AA5885; 1, CH, iPr, $CF_3$, H, I], [AA5886; 1, CH, iPr, $CF_2H$, H, I], [AA5887; 1, CH, iPr, $C_2F_5$, H, I], [AA5888; 1, CH, iPr, $C_3F_7$, H, I], [AA5889; 1, CH, iPr, $CH_2CF_3$, H, I], [AA5890; 1, CH, iPr, $CH_2CHF_2$, H, I][AA5891; 2, CH, iPr, H, H, I], [AA5892; 2, CH, iPr, F, H, I], [AA5893; 2, CH, iPr, Cl, H, I], [AA5894; 2, CH, iPr, Br, H, I], [AA5895; 2, CH, iPr, I, H, I], [AA5896; 2, CH, iPr, $CF_3$, H, I], [AA5897; 2, CH, iPr, $CF_2H$, H, I], [AA5898; 2, CH, iPr, $C_2F_5$, H, I], [AA5899; 2, CH, iPr, $C_3F_7$, H, I], [AA5900; 2, CH, iPr, $CH_2CF_3$, H, I], [AA5901; 2, CH, iPr, $CH_2CHF_2$, H, I], [AA5902; 0, N, iPr, H, H, I], [AA5903; 0, N, iPr, F, H, I], [AA5904; 0, N, iPr, Cl, H, I], [AA5905; 0, N, iPr, Br, H, I], [AA5906; 0, N, iPr, I, H, I], [AA5907; 0, N, iPr, $CF_3$, H, I], [AA5908; 0, N, iPr, $CF_2H$, H, I], [AA5909; 0, N, iPr, $C_2F_5$, H, I], [AA5910; 0, N, iPr, $C_3F_7$, H, I], [AA5911; 0, N, iPr, $CH_2CF_3$, H, I], [AA5912; 0, N, iPr, $CH_2CHF_2$, H, I], [AA5913; 1, N, iPr, H, H, I], [AA5914; 1, N, iPr, F, H, I], [AA5915; 1, N, iPr, Cl, H, I], [AA5916; 1, N, iPr, Br, H, I], [AA5917; 1, N, iPr, I, H, I], [AA5918; 1, N, iPr, $CF_3$, H, I], [AA5919; 1, N, iPr, $CF_2H$, H, I], [AA5920; 1, N, iPr, $C_2F_5$, H, I], [AA5921; 1, N, iPr, $C_3F_7$, H, I], [AA5922; 1, N, iPr, $CH_2CF_3$, H, I], [AA5923; 1, N, iPr, $CH_2CHF_2$, H, I], [AA5924; 2, N, iPr, H, H, I], [AA5925; 2, N, iPr, F, H, I], [AA5926; 2, N, iPr, Cl, H, I], [AA5927; 2, N, iPr, Br, H, I], [AA5928; 2, N, iPr, I, H, I], [AA5929; 2, N, iPr, $CF_3$, H, I], [AA5930; 2, N, iPr, $CF_2H$, H, I], [AA5931; 2, N, iPr, $C_2F_5$, H, I], [AA5932; 2, N, iPr, $C_3F_7$, H, I], [AA5933; 2, N, iPr, $CH_2CF_3$, H, I], [AA5934; 2, N, iPr, $CH_2CHF_2$, H, I], [AA5935; 0, CH, cPr, H, H, I], [AA5936; 0, CH, cPr, F, H, I], [AA5937; 0, CH, cPr, Cl, H, I], [AA5938; 0, CH, cPr, Br, H, I], [AA5939; 0, CH, cPr, I, H, I], [AA5940; 0, CH, cPr, $CF_3$, H, I], [AA5941; 0, CH, cPr, $CF_2H$, H, I], [AA5942; 0, CH, cPr, $C_2F_5$, H, I], [AA5943; 0, CH, cPr, $C_3F_7$, H, I], [AA5944; 0, CH, cPr, $CH_2CF_3$, H, I], [AA5945; 0, CH, cPr, $CH_2CHF_2$, H, I], [AA5946; 1, CH, cPr, H, H, I], [AA5947; 1, CH, cPr, F, H, I], [AA5948; 1, CH, cPr, Cl, H, I], [AA5949; 1, CH, cPr, Br, H, I], [AA5950; 1, CH, cPr, I, H, I], [AA5951; 1, CH, cPr, $CF_3$, H, I], [AA5952; 1, CH, cPr, $CF_2H$, H, I], [AA5953; 1, CH, cPr, $C_2F_5$, H, I], [AA5954; 1, CH, cPr, $C_3F_7$, H, I], [AA5955; 1, CH, cPr, $CH_2CF_3$, H, I], [AA5956; 1, CH, cPr, $CH_2CHF_2$, H, I], [AA5957; 2, CH, cPr, H, H, I], [AA5958; 2, CH, cPr, F, H, I], [AA5959; 2, CH, cPr, Cl, H, I], [AA5960; 2, CH, cPr, Br, H, I], [AA5961; 2, CH, cPr, I, H, I], [AA5962; 2, CH, cPr, $CF_3$, H, I], [AA5963; 2, CH, cPr, $CF_2H$, H, I], [AA5964; 2, CH, cPr, $C_2F_5$, H, I], [AA5965; 2, CH, cPr, $C_3F_7$, H, I], [AA5966; 2, CH, cPr, $CH_2CF_3$, H, I], [AA5967; 2, CH, cPr, $CH_2CHF_2$, H, I], [AA5968; 0, N, cPr, H, H, I], [AA5969; 0, N, cPr, F, H, I], [AA5970; 0, N, cPr, Cl, H, I], [AA5971; 0, N, cPr, Br, H, I], [AA5972; 0, N, cPr, I, H, I], [AA5973; 0, N, cPr, $CF_3$, H, I], [AA5974; 0, N, cPr, $CF_2H$, H, I], [AA5975; 0, N, cPr, $C_2F_5$, H, I], [AA5976; 0, N, cPr, $C_3F_7$, H, I], [AA5977; 0, N, cPr, $CH_2CF_3$, H, I], [AA5978; 0, N, cPr, $CH_2CHF_2$, H, I], [AA5979; 1, N, cPr, H, H, I], [AA5980; 1, N, cPr, F, H, I], [AA5981; 1, N, cPr, Cl, H, I], [AA5982; 1, N, cPr, Br, H, I], [AA5983; 1, N, cPr, I, H, I], [AA5984; 1, N, cPr, $CF_3$, H, I], [AA5985; 1, N, cPr, $CF_2H$, H, I], [AA5986; 1, N, cPr, $C_2F_5$, H, I], [AA5987; 1, N, cPr, $C_3F_7$, H, I], [AA5988; 1, N, cPr, $CH_2CF_3$, H, I][AA5989; 1, N, cPr, $CH_2CHF_2$, H, I], [AA5990; 2, N, cPr, H, H, I], [AA5991; 2, N, cPr, F, H, I], [AA5992; 2, N, cPr, Cl, H, I], [AA5993; 2, N, cPr, Br, H, I], [AA5994; 2, N, cPr, I, H, I], [AA5995; 2, N, cPr, $CF_3$, H, I], [AA5996; 2, N, cPr, $CF_2H$, H, I], [AA5997; 2, N, cPr, $C_2F_5$, H, I], [AA5998; 2, N, cPr, $C_3F_7$, H, I], [AA5999; 2, N, cPr, $CH_2CF_3$, H, I], [AA6000; 2, N, cPr, $CH_2CHF_2$, H, I], [AA6001; 0, CH, H, H, F, I], [AA6002; 0, CH, H, H, Cl, I], [AA6003; 0, CH, H, H, Br, I], [AA6004; 0, CH, H, H, I, I], [AA6005; 0, CH, H, H, $CF_3$, I], [AA6006; 0, CH, H, H, $CF_2H$, I], [AA6007; 0, CH, H, H, $C_2F_5$, I], [AA6008; 0, CH, H, H, $C_3F_7$, I], [AA6009; 0, CH, H, H, $CH_2CF_3$, I], [AA6010; 0, CH, H, H, $CH_2CHF_2$, I], [AA6011; 1, CH, H, H, F, I], [AA6012; 1, CH, H, H, Cl, I], [AA6013; 1, CH, H, H, Br, I], [AA6014; 1, CH, H, H, I, I], [AA6015; 1, CH, H, H, $CF_3$, I], [AA6016; 1, CH, H, H, $CF_2H$, I], [AA6017; 1, CH, H, H, $C_2F_5$, I], [AA6018; 1, CH, H, H, $C_3F_7$, I], [AA6019; 1, CH, H, H, $CH_2CF_3$, I], [AA6020; 1, CH, H, H, $CH_2CHF_2$, I], [AA6021; 2, CH, H, H, F, I], [AA6022; 2, CH, H, H, Cl, I], [AA6023; 2, CH, H, H, Br, I], [AA6024; 2, CH, H, H, I, I], [AA6025; 2, CH, H, H, $CF_3$, I], [AA6026; 2, CH, H, H, $CF_2H$, I], [AA6027; 2, CH, H, H, $C_2F_5$, I], [AA6028; 2, CH, H, H, $C_3F_7$, I],

[AA6029; 2, CH, H, H, $CH_2CF_3$, I], [AA6030; 2, CH, H, H, $CH_2CHF_2$, I], [AA6031; 0, N, H, H, F, I], [AA6032; 0, N, H, H, Cl, I], [AA6033; 0, N, H, H, Br, I], [AA6034; 0, N, H, H, I, I], [AA6035; 0, N, H, H, $CF_3$, I], [AA6036; 0, N, H, H, $CF_2H$, I], [AA6037; 0, N, H, H, $C_2F_5$, I], [AA6038; 0, N, H, H, $C_3F_7$, I], [AA6039; 0, N, H, H, $CH_2CF_3$, I], [AA6040; 0, N, H, H, $CH_2CHF_2$, I], [AA6041; 1, N, H, H, F, I], [AA6042; 1, N, H, H, Cl, I], [AA6043; 1, N, H, H, Br, I], [AA6044; 1, N, H, H, I, I], [AA6045; 1, N, H, H, $CF_3$, I], [AA6046; 1, N, H, H, $CF_2H$, I], [AA6047; 1, N, H, H, $C_2F_5$, I], [AA6048; 1, N, H, H, $C_3F_7$, I], [AA6049; 1, N, H, H, $CH_2CF_3$, I], [AA6050; 1, N, H, H, $CH_2CHF_2$, I], [AA6051; 2, N, H, H, F, I], [AA6052; 2, N, H, H, Cl, I], [AA6053; 2, N, H, H, Br, I], [AA6054; 2, N, H, H, I, I], [AA6055; 2, N, H, H, $CF_3$, I], [AA6056; 2, N, H, H, $CF_2H$, I], [AA6057; 2, N, H, H, $C_2F_5$, I], [AA6058; 2, N, H, H, $C_3F$-7, I], [AA6059; 2, N, H, H, $CH_2CF_3$, I], [AA6060; 2, N, H, H, $CH_2CHF_2$, I], [AA6061; 0, CH, Me, H, F, I], [AA6062; 0, CH, Me, H, Cl, I], [AA6063; 0, CH, Me, H, Br, I], [AA6064; 0, CH, Me, H, I, I], [AA6065; 0, CH, Me, H, $CF_3$, I], [AA6066; 0, CH, Me, H, $CF_2H$, I], [AA6067; 0, CH, Me, H, $C_2F_5$, I], [AA6068; 0, CH, Me, H, $C_3F_7$, I], [AA6069; 0, CH, Me, H, $CH_2CF_3$, I], [AA6070; 0, CH, Me, H, $CH_2CHF_2$, I], [AA6071; 1, CH, Me, H, F, I], [AA6072; 1, CH, Me, H, Cl, I], [AA6073; 1, CH, Me, H, Br, I], [AA6074; 1, CH, Me, H, I, I], [AA6075; 1, CH, Me, H, $CF_3$, I], [AA6076; 1, CH, Me, H, $CF_2H$, I], [AA6077; 1, CH, Me, H, $C_2F_5$, I], [AA6078; 1, CH, Me, H, $C_3F_3$, I], [AA6079; 1, CH, Me, H, $CH_2CF_3$, I], [AA6080; 1, CH, Me, H, $CH_2CHF_2$, I], [AA6081; 2, CH, Me, H, F, I], [AA6082; 2, CH, Me, H, Cl, I], [AA6083; 2, CH, Me, H, Br, I], [AA6084; 2, CH, Me, H, I, I], [AA6085; 2, CH, Me, H, $CF_3$, I], [AA6086; 2, CH, Me, H, $CF_2H$, I], [AA6087; 2, CH, Me, H, $C_2F_5$, I], [AA6088; 2, CH, Me, H, $C_3F_7$, I], [AA6089; 2, CH, Me, H, $CH_2CF_5$, I], [AA6090; 2, CH, Me, H, $CH_2CHF_2$, I], [AA6091; 0, N, Me, H, F, I], [AA6092; 0, N, Me, H, Cl, I], [AA6093; 0, N, Me, H, Br, I], [AA6094; 0, N, Me, H, I, I], [AA6095; 0, N, Me, H, $CF_3$, I], [AA6096; 0, N, Me, H, $CF_2H$, I], [AA6097; 0, N, Me, H, $C_2F_5$, I], [AA6098; 0, N, Me, H, $C_3F_7$, I], [AA6099; 0, N, Me, H, $CH_2CF_3$, I], [AA6100; 0, N, Me, H, $CH_2CHF_2$, I], [AA6101; 1, N, Me, H, F, I], [AA6102; 1, N, Me, H, Cl, I], [AA6103; 1, N, Me, H, Br, I], [AA6104; 1, N, Me, H, I, I], [AA6105; 1, N, Me, H, $CF_3$, I], [AA6106; 1, N, Me, H, $CF_2H$, I], [AA6107; 1, N, Me, H, $C_2F_5$, I], [AA6108; 1, N, Me, H, $C_3F_7$, I], [AA6109; 1, N, Me, H, $CH_2CF_3$, I], [AA6110; 1, N, Me, H, $CH_2CHF_2$, I], [AA6111; 2, N, Me, H, F, I], [AA6112; 2, N, Me, H, Cl, I], [AA6113; 2, N, Me, H, Br, I], [AA6114; 2, N, Me, H, I, I], [AA6115; 2, N, Me, H, $CF_3$, I], [AA6116; 2, N, Me, H, $CF_2H$, I], [AA6117; 2, N, Me, H, $C_2F_5$, I], [AA6118; 2, N, Me, H, $C_3F_7$, I], [AA6119; 2, N, Me, H, $CH_2CF_3$, I], [AA6120; 2, N, Me, H, $CH_2CHF_2$, I], [AA6121; 0, CH, Et, H, F, I], [AA6122; 0, CH, Et, H, Cl, I], [AA6123; 0, CH, Et, H, Br, I], [AA6124; 0, CH, Et, H, I, I], [AA6125; 0, CH, Et, H, $CF_3$, I], [AA6126; 0, CH, Et, H, $CF_2H$, I], [AA6127; 0, CH, Et, H, $C_2F_5$, I], [AA6128; 0, CH, Et, H, $C_3F_7$, I], [AA6129; 0, CH, Et, H, $CH_2CF_3$, I], [AA6130; 0, CH, Et, H, $CH_2CHF_2$, I], [AA6131; 1, CH, Et, H, F, I], [AA6132; 1, CH, Et, H, Cl, I], [AA6133; 1, CH, Et, H, Br, I], [AA6134; 1, CH, Et, H, I, I], [AA6135; 1, CH, Et, H, $CF_3$, I], [AA6136; 1, CH, Et, H, $CF_2H$, I], [AA6137; 1, CH, Et, H, $C_2F_2$, I], [AA6138; 1, CH, Et, H, $C_3F_7$, I], [AA6139; 1, CH, Et, H, $CH_2CF_3$, I], [AA6140; 1, CH, Et, H, $CH_2CHF_2$, I], [AA6141; 2, CH, Et, H, F, I], [AA6142; 2, CH, Et, H, Cl, I], [AA6143; 2, CH, Et, H, Br, I], [AA6144; 2, CH, Et, H, I, I], [AA6145; 2, CH, Et, H, $CF_3$, I], [AA6146; 2, CH, Et, H, $CF_2H$, I], [AA6147; 2, CH, Et, H, $C_2F_5$, I], [AA6148; 2, CH, Et, H, $C_3F_7$, I], [AA6149; 2, CH, Et, H, $CH_2CF_3$, I], [AA6150; 2, CH, Et, H, $CH_2CHF_2$, I], [AA6151; 0, N, Et, H, F, I], [AA6152; 0, N, Et, H, Cl, I], [AA6153; 0, N, Et, H, Br, I], [AA6154; 0, N, Et, H, I, I], [AA6155; 0, N, Et, H, $CF_3$, I], [AA6156; 0, N, Et, H, $CF_2H$, I], [AA6157; 0, N, Et, H, $C_2F_5$, I], [AA6158; 0, N, Et, H, $C_3F_7$, I], [AA6159; 0, N, Et, H, $CH_2CF_3$, I], [AA6160; 0, N, Et, H, $CH_2CHF_2$, I], [AA6161; 1, N, Et, H, F, I], [AA6162; 1, N, Et, H, Cl, I], [AA6163; 1, N, Et, H, Br, I], [AA6164; 1, N, Et, H, I, I], [AA6165; 1, N, Et, H, $CF_3$, I], [AA6166; 1, N, Et, H, $CF_2H$, I], [AA6167; 1, N, Et, H, $C_2F_5$, I], [AA6168; 1, N, Et, H, $C_3F_7$, I], [AA6169; 1, N, Et, H, $CH_2CF_3$, I], [AA6170; 1, N, Et, H, $CH_2CHF_2$, I], [AA6171; 2, N, Et, H, F, I], [AA6172; 2, N, Et, H, Cl, I], [AA6173; 2, N, Et, H, Br, I], [AA6174; 2, N, Et, H, I, I], [AA6175; 2, N, Et, H, $CF_3$, I], [AA6176; 2, N, Et, H, $CF_2H$, I], [AA6177; 2, N, Et, H, $C_2F_5$, I], [AA6178; 2, N, Et, H, $C_3F_7$, I], [AA6179; 2, N, Et, H, $CH_2CF_3$, I], [AA6180; 2, N, Et, H, $CH_2CHF_2$, I], [AA6181; 0, CH, iPr, H, F, I], [AA6182; 0, CH, iPr, H, Cl, I], [AA6183; 0, CH, iPr, H, Br, I], [AA6184; 0, CH, iPr, H, I, I], [AA6185; 0, CH, iPr, H, $CF_3$, I], [AA6186; 0, CH, iPr, H, $CF_2H$, I], [AA6187; 0, CH, iPr, H, $C_2F_5$, I], [AA6188; 0, CH, iPr, H, $C_3F_7$, I], [AA6189; 0, CH, iPr, H, $CH_2CF_3$, I], [AA6190; 0, CH, iPr, H, $CH_2CHF_2$, I], [AA6191; 1, CH, iPr, H, F, I], [AA6192; 1, CH, iPr, H, Cl, I], [AA6193; 1, CH, iPr, H, Br, I], [AA6194; 1, CH, iPr, H, I, I], [AA6195; 1, CH, iPr, H, $CF_3$, I], [AA6196; 1, CH, iPr, H, $CF_2H$, I], [AA6197; 1, CH, iPr, H, $C_2F_5$, I], [AA6198; 1, CH, iPr, H, $C_3F_7$, I], [AA6199; 1, CH, iPr, H, $CH_2CF_3$, I], [AA6200; 1, CH, iPr, H, $CH_2CHF_2$, I], [AA6201; 2, CH, iPr, H, F, I], [AA6202; 2, CH, iPr, H, Cl, I], [AA6203; 2, CH, iPr, H, Br, I], [AA6204; 2, CH, iPr, H, I, I], [AA6205; 2, CH, iPr, H, $CF_3$, I], [AA6206; 2, CH, iPr, H, $CF_2H$, I], [AA6207; 2, CH, iPr, H, $C_2F_5$, I], [AA6208; 2, CH, iPr, H, $C_3F_7$, I], [AA6209; 2, CH, iPr, H, $CH_2CF_3$, I], [AA6210; 2, CH, iPr, H, $CH_2CHF_2$, I], [AA6211; 0, N, iPr, H, F, I], [AA6212; 0, N, iPr, H, Cl, I], [AA6213; 0, N, iPr, H, Br, I], [AA6214; 0, N, iPr, H, I, I], [AA6215; 0, N, iPr, H, $CF_3$, I], [AA6216; 0, N, iPr, H, $CF_2H$, I], [AA6217; 0, N, iPr, H, $C_2F_5$, I], [AA6218; 0, N, iPr, H, $C_3F_7$, I], [AA6219; 0, N, iPr, H, $CH_2CF_3$, I], [AA6220; 0, N, iPr, H, $CH_2CHF_2$, I], [AA6221; 1, N, iPr, H, F, I], [AA6222; 1, N, iPr, H, Cl, I], [AA6223; 1, N, iPr, H, Br, I], [AA6224; 1, N, iPr, H, I, I], [AA6225; 1, N, iPr, H, $CF_3$, I], [AA6226; 1, N, iPr, H, $CF_2H$, I], [AA6227; 1, N, iPr, H, $C_2F$, I], [AA6228; 1, N, iPr, H, $C_3F_7$, I], [AA6229; 1, N, iPr, H, $CH_2CF_3$, I], [AA6230; 1, N, iPr, H, $CH_2CHF_2$, I], [AA6231; 2, N, iPr, H, F, I], [AA6232; 2, N, iPr, H, Cl, I], [AA6233; 2, N, iPr, H, Br, I], [AA6234; 2, N, iPr, H, I, I], [AA6235; 2, N, iPr, H, $CF_3$, I], [AA6236; 2, N, iPr, H, $CF_2H$, I], [AA6237; 2, N, iPr, H, $C_2F_5$, I], [AA6238; 2, N, iPr, H, $C_3F_7$, I], [AA6239; 2, N, iPr, H, $CH_2CF_3$, I], [AA6240; 2, N, iPr, H, $CH_2CHF_2$, I], [AA6241; 0, CH, cPr, H, F, I], [AA6242; 0, CH, cPr, H, Cl, I], [AA6243; 0, CH, cPr, H, Br, I], [AA6244; 0, CH, cPr, H, I, I], [AA6245; 0, CH, cPr, H, $CF_3$, I], [AA6246; 0, CH, cPr, H, $CF_2H$, I], [AA6247; 0, CH, cPr, H, $C_2F_5$, I], [AA6248; 0, CH, cPr, H, $C_3F_7$, I], [AA6249; 0, CH, cPr, H, $CH_2CF_3$, I], [AA6250; 0, CH, cPr, H, $CH_2CHF_2$, I], [AA6251; 1, CH, cPr, H, F, I], [AA6252; 1, CH, cPr, H, Cl, I], [AA6253; 1, CH, cPr, H, Br, I], [AA6254; 1, CH, cPr, H, I, I], [AA6255; 1, CH, cPr, H, $CF_3$, I], [AA6256; 1, CH, cPr, H, $CF_2H$, I], [AA6257; 1, CH, cPr, H, $C_2F_5$, I], [AA6258; 1, CH, cPr, H, $C_3F_7$, I], [AA6259; 1, CH, cPr, H, $CH_2CF_3$, I], [AA6260; 1, CH, cPr, H, $CH_2CHF_2$, I], [AA6261; 2, CH, cPr, H, F, I], [AA6262; 2, CH, cPr, H, Cl, I], [AA6263; 2, CH, cPr, H, Br, I], [AA6264; 2, CH, cPr, H, I, I], [AA6265; 2, CH, cPr, H, $CF_3$, I], [AA6266; 2, CH, cPr, H, $CF_2H$, I], [AA6267; 2, CH, cPr,

H, $C_2F_5$, I], [AA6268; 2, CH, cPr, H, $C_3F_7$, I], [AA6269; 2, CH, cPr, H, $CH_2CF_3$, I], [AA6270; 2, CH, cPr, H, $CH_2CHF_2$, I], [AA6271; 0, N, cPr, H, F, I], [AA6272; 0, N, cPr, H, Cl, I], [AA6273; 0, N, cPr, H, Br, I], [AA6274; 0, N, cPr, H, I, I], [AA6275; 0, N, cPr, H, $CF_3$, I], [AA6276; 0, N, cPr, H, $CF_2H$, I], [AA6277; 0, N, cPr, H, $C_2F$, I], [AA6278; 0, N, cPr, H, $C_3F_7$, I], [AA6279; 0, N, cPr, H, $CH_2CF_3$, I], [AA6280; 0, N, cPr, H, $CH_2CHF_2$, I], [AA6281; 1, N, cPr, H, F, I], [AA6282; 1, N, cPr, H, Cl, I], [AA6283; 1, N, cPr, H, Br, I], [AA6284; 1, N, cPr, H, I, I], [AA6285; 1, N, cPr, H, $CF_3$, I], [AA6286; 1, N, cPr, H, $CF_2H$, I], [AA6287; 1, N, cPr, H, $C_2F$, I], [AA6288; 1, N, cPr, H, $C_3F_7$, I], [AA6289; 1, N, cPr, H, $CH_2CF_3$, I], [AA6290; 1, N, cPr, H, $CH_2CHF_2$, I], [AA6291; 2, N, cPr, H, F, I], [AA6292; 2, N, cPr, H, Cl, I], [AA6293; 2, N, cPr, H, Br, I], [AA6294; 2, N, cPr, H, I, I], [AA6295; 2, N, cPr, H, $CF_3$, I], [AA6296; 2, N, cPr, H, $CF_2H$, I], [AA6297; 2, N, cPr, H, $C_2F_5$, I], [AA6298; 2, N, cPr, H, $C_3F_7$, I], [AA6299; 2, N, cPr, H, $CH_2CF_3$, I], [AA6300; 2, N, cPr, H, $CH_2CHF_2$, I], [AA6301; 0, CH, H, H, H, F], [AA6302; 0, CH, H, F, H, F], [AA6303; 0, CH, H, Cl, H, F], [AA6304; 0, CH, H, Br, H, F], [AA6305; 0, CH, H, I, H, F], [AA6306; 0, CH, H, $CF_3$, H, F], [AA6307; 0, CH, H, $CF_2H$, H, F], [AA6308; 0, CH, H, $C_2F_5$, H, F], [AA6309; 0, CH, H, $C_3F_7$, H, F], [AA6310; 0, CH, H, $CH_2CF_3$, H, F], [AA6311; 0, CH, H, $CH_2CHF_2$, H, F], [AA6312; 1, CH, H, H, H, F], [AA6313; 1, CH, H, F, H, F], [AA6314; 1, CH, H, Cl, H, F], [AA6315; 1, CH, H, Br, H, F], [AA6316; 1, CH, H, I, H, F], [AA6317; 1, CH, H, $CF_3$, H, F], [AA6318; 1, CH, H, $CF_2H$, H, F], [AA6319; 1, CH, H, $C_2F_5$, H, F], [AA6320; 1, CH, H, $C_3F_7$, H, F], [AA6321; 1, CH, H, $CH_2CF_3$, H, F], [AA6322; 1, CH, H, $CH_2CHF_2$, H, F], [AA6323; 2, CH, H, H, H, F], [AA6324; 2, CH, H, F, H, F], [AA6325; 2, CH, H, Cl, H, F], [AA6326; 2, CH, H, Br, H, F], [AA6327; 2, CH, H, I, H, F], [AA6328; 2, CH, H, $CF_3$, H, F], [AA6329; 2, CH, H, $CF_2H$, H, F], [AA6330; 2, CH, H, $C_2F_5$, H, F], [AA6331; 2, CH, H, $C_3F_7$, H, F], [AA6332; 2, CH, H, $CH_2CF_3$, H, F], [AA6333; 2, CH, H, $CH_2CHF_2$, H, F], [AA6334; 0, N, H, H, H, F], [AA6335; 0, N, H, F, H, F], [AA6336; 0, N, H, Cl, H, F], [AA6337; 0, N, H, Br, H, F], [AA6338; 0, N, H, I, H, F], [AA6339; 0, N, H, $CF_3$, H, F], [AA6340; 0, N, H, $CF_2H$, H, F], [AA6341; 0, N, H, $C_2F_5$, H, F], [AA6342; 0, N, H, $C_3F_7$, H, F], [AA6343; 0, N, H, $CH_2CF_3$, H, F], [AA6344; 0, N, H, $CH_2CHF_2$, H, F], [AA6345; 1, N, H, H, H, F], [AA6346; 1, N, H, F, H, F], [AA6347; 1, N, H, Cl, H, F], [AA6348; 1, N, H, Br, H, F], [AA6349; 1, N, H, I, H, F], [AA6350; 1, N, H, $CF_3$, H, F], [AA6351; 1, N, H, $CF_2H$, H, F], [AA6352; 1, N, H, $C_2F_5$, H, F], [AA6353; 1, N, H, $C_3F_7$, H, F], [AA6354; 1, N, H, $CH_2CF_3$, H, F], [AA6355; 1, N, H, $CH_2CHF_2$, H, F], [AA6356; 2, N, H, H, H, F], [AA6357; 2, N, H, F, H, F], [AA6358; 2, N, H, Cl, H, F], [AA6359; 2, N, H, Br, H, F], [AA6360; 2, N, H, I, H, F], [AA6361; 2, N, H, $CF_3$, H, F], [AA6362; 2, N, H, $CF_2H$, H, F], [AA6363; 2, N, H, $C_2F_5$, H, F], [AA6364; 2, N, H, $C_3F_7$, H, F], [AA6365; 2, N, H, $CH_2CF_3$, H, F], [AA6366; 2, N, H, $CH_2CHF_2$, H, F], [AA6367; 0, CH, Me, H, H, F], [AA6368; 0, CH, Me, F, H, F], [AA6369; 0, CH, Me, Cl, H, F], [AA6370; 0, CH, Me, Br, H, F], [AA6371; 0, CH, Me, I, H, F], [AA6372; 0, CH, Me, $CF_3$, H, F], [AA6373; 0, CH, Me, $CF_2H$, H, F], [AA6374; 0, CH, Me, $C_2F_5$, H, F], [AA6375; 0, CH, Me, $C_3F_7$, H, F], [AA6376; 0, CH, Me, $CH_2CF_3$, H, F], [AA6377; 0, CH, Me, $CH_2CHF_2$, H, F], [AA6378; 1, CH, Me, H, H, F], [AA6379; 1, CH, Me, F, H, F], [AA6380; 1, CH, Me, Cl, H, F], [AA6381; 1, CH, Me, Br, H, F], [AA6382; 1, CH, Me, I, H, F], [AA6383; 1, CH, Me, $CF_3$, H, F], [AA6384; 1, CH, Me, $CF_2H$, H, F], [AA6385; 1, CH, Me, $C_2F_5$, H, F], [AA6386; 1, CH, Me, $C_3F_7$, H, F], [AA6387; 1, CH, Me, $CH_2CF_3$, H, F], [AA6388; 1, CH, Me, $CH_2CHF_2$, H, F], [AA6389; 2, CH, Me, H, H, F], [AA6390; 2, CH, Me, F, H, F], [AA6391; 2, CH, Me, Cl, H, F], [AA6392; 2, CH, Me, Br, H, F], [AA6393; 2, CH, Me, I, H, F], [AA6394; 2, CH, Me, $CF_3$, H, F], [AA6395; 2, CH, Me, $CF_2H$, H, F], [AA6396; 2, CH, Me, $C_2F_5$, H, F], [AA6397; 2, CH, Me, $C_3F_7$, H, F], [AA6398; 2, CH, Me, $CH_2CF_3$, H, F], [AA6399; 2, CH, Me, $CH_2CHF_2$, H, F], [AA6400; 0, N, Me, H, H, F], [AA6401; 0, N, Me, F, H, F], [AA6402; 0, N, Me, Cl, H, F], [AA6403; 0, N, Me, Br, H, F], [AA6404; 0, N, Me, I, H, F], [AA6405; 0, N, Me, $CF_3$, H, F], [AA6406; 0, N, Me, $CF_2H$, H, F], [AA6407; 0, N, Me, $C_2F_5$, H, F], [AA6408; 0, N, Me, $C_3F_7$, H, F], [AA6409; 0, N, Me, $CH_2CF_3$, H, F], [AA6410; 0, N, Me, $CH_2CHF_2$, H, F], [AA6411; 1, N, Me, H, H, F], [AA6412; 1, N, Me, F, H, F], [AA6413; 1, N, Me, Cl, H, F], [AA6414; 1, N, Me, Br, H, F], [AA6415; 1, N, Me, I, H, F], [AA6416; 1, N, Me, $CF_3$, H, F], [AA6417; 1, N, Me, $CF_2H$, H, F], [AA6418; 1, N, Me, $C_2F_5$, H, F], [AA6419; 1, N, Me, $C_3F_7$, H, F], [AA6420; 1, N, Me, $CH_2CF_3$, H, F], [AA6421; 1, N, Me, $CH_2CHF_2$, H, F], [AA6422; 2, N, Me, H, H, F], [AA6423; 2, N, Me, F, H, F], [AA6424; 2, N, Me, Cl, H, F], [AA6425; 2, N, Me, Br, H, F], [AA6426; 2, N, Me, I, H, F], [AA6427; 2, N, Me, $CF_3$, H, F], [AA6428; 2, N, Me, $CF_2H$, H, F], [AA6429; 2, N, Me, $C_2F_5$, H, F], [AA6430; 2, N, Me, $C_3F_7$, H, F], [AA6431; 2, N, Me, $CH_2CF_3$, H, F], [AA6432; 2, N, Me, $CH_2CHF_2$, H, F], [AA6433; 0, CH, Et, H, H, F], [AA6434; 0, CH, Et, F, H, F], [AA6435; 0, CH, Et, Cl, H, F], [AA6436; 0, CH, Et, Br, H, F], [AA6437; 0, CH, Et, I, H, F], [AA6438; 0, CH, Et, $CF_3$, H, F], [AA6439; 0, CH, Et, $CF_2H$, H, F], [AA6440; 0, CH, Et, $C_2F_5$, H, F], [AA6441; 0, CH, Et, $C_3F_7$, H, F], [AA6442; 0, CH, Et, $CH_2CF_3$, H, F], [AA6443; 0, CH, Et, $CH_2CHF_2$, H, F], [AA6444; 1, CH, Et, H, H, F], [AA6445; 1, CH, Et, F, H, F], [AA6446; 1, CH, Et, Cl, H, F], [AA6447; 1, CH, Et, Br, H, F], [AA6448; 1, CH, Et, I, H, F], [AA6449; 1, CH, Et, $CF_3$, H, F], [AA6450; 1, CH, Et, $CF_2H$, H, F], [AA6451; 1, CH, Et, $C_2F_5$, H, F], [AA6452; 1, CH, Et, $C_3F_7$, H, F], [AA6453; 1, CH, Et, $CH_2CF_3$, H, F], [AA6454; 1, CH, Et, $CH_2CHF_2$, H, F], [AA6455; 2, CH, Et, H, H, F], [AA6456; 2, CH, Et, F, H, F], [AA6457; 2, CH, Et, Cl, H, F], [AA6458; 2, CH, Et, Br, H, F], [AA6459; 2, CH, Et, I, H, F], [AA6460; 2, CH, Et, $CF_3$, H, F], [AA6461; 2, CH, Et, $CF_2H$, H, F], [AA6462; 2, CH, Et, $C_2F_5$, H, F], [AA6463; 2, CH, Et, $C_3F_7$, H, F], [AA6464; 2, CH, Et, $CH_2CF_3$, H, F], [AA6465; 2, CH, Et, $CH_2CHF_2$, H, F], [AA6466; 0, N, Et, H, H, F], [AA6467; 0, N, Et, F, H, F], [AA6468; 0, N, Et, Cl, H, F], [AA6469; 0, N, Et, Br, H, F], [AA6470; 0, N, Et, I, H, F], [AA6471; 0, N, Et, $CF_3$, H, F], [AA6472; 0, N, Et, $CF_2H$, H, F], [AA6473; 0, N, Et, $C_2F_5$, H, F], [AA6474; 0, N, Et, $C_3F_7$, H, F], [AA6475; 0, N, Et, $CH_2CF_3$, H, F], [AA6476; 0, N, Et, $CH_2CHF_2$, H, F], [AA6477; 1, N, Et, H, H, F], [AA6478; 1, N, Et, F, H, F], [AA6479; 1, N, Et, Cl, H, F], [AA6480; 1, N, Et, Br, H, F], [AA6481; 1, N, Et, I, H, F], [AA6482; 1, N, Et, $CF_3$, H, F], [AA6483; 1, N, Et, $CF_2H$, H, F], [AA6484; 1, N, Et, $C_2F_5$, H, F], [AA6485; 1, N, Et, $C_3F_7$, H, F], [AA6486; 1, N, Et, $CH_2CF_3$, H, F], [AA6487; 1, N, Et, $CH_2CHF_2$, H, F], [AA6488; 2, N, Et, H, H, F], [AA6489; 2, N, Et, F, H, F], [AA6490; 2, N, Et, Cl, H, F], [AA6491; 2, N, Et, Br, H, F], [AA6492; 2, N, Et, I, H, F], [AA6493; 2, N, Et, $CF_3$, H, F], [AA6494; 2, N, Et, $CF_2H$, H, F], [AA6495; 2, N, Et, $C_2F_5$, H, F], [AA6496; 2, N, Et, $C_3F_7$, H, F], [AA6497; 2, N, Et, $CH_2CF_3$, H, F], [AA6498; 2, N, Et, $CH_2CHF_2$, H, F], [AA6499; 0, CH, iPr, H, H, F], [AA6500; 0, CH, iPr, F, H, F], [AA6501; 0, CH, iPr, Cl, H, F], [AA6502; 0, CH, iPr, Br, H, F], [AA6503; 0, CH, iPr, I, H, F], [AA6504; 0, CH, iPr, $CF_3$, H, F], [AA6505; 0, CH, iPr, $CF_2H$, H, F], [AA6506; 0, CH, iPr, $C_2F_5$, H, F],

[AA6507; 0, CH, iPr, $C_3F_7$, H, F], [AA6508; 0, CH, iPr, $CH_2CF_3$, H, F], [AA6509; 0, CH, iPr, $CH_2CHF_2$, H, F], [AA6510; 1, CH, iPr, H, H, F], [AA6511; 1, CH, iPr, F, H, F], [AA6512; 1, CH, iPr, Cl, H, F], [AA6513; 1, CH, iPr, Br, H, F], [AA6514; 1, CH, iPr, I, H, F], [AA6515; 1, CH, iPr, $CF_3$, H, F], [AA6516; 1, CH, iPr, $CF_2H$, H, F], [AA6517; 1, CH, iPr, $C_2F_5$, H, F], [AA6518; 1, CH, iPr, $C_3F_7$, H, F], [AA6519; 1, CH, iPr, $CH_2CF_3$, H, F], [AA6520; 1, CH, iPr, $CH_2CHF_2$, H, F], [AA6521; 2, CH, iPr, H, H, F], [AA6522; 2, CH, iPr, F, H, F], [AA6523; 2, CH, iPr, Cl, H, F], [AA6524; 2, CH, iPr, Br, H, F], [AA6525; 2, CH, iPr, I, H, F], [AA6526; 2, CH, iPr, $CF_3$, H, F], [AA6527; 2, CH, iPr, $CF_2H$, H, F], [AA6528; 2, CH, iPr, $C_2F_5$, H, F], [AA6529; 2, CH, iPr, $C_3F_7$, H, F], [AA6530; 2, CH, iPr, $CH_2CF_3$, H, F], [AA6531; 2, CH, iPr, $CH_2CHF_2$, H, F], [AA6532; 0, N, iPr, H, H, F], [AA6533; 0, N, iPr, F, H, F], [AA6534; 0, N, iPr, Cl, H, F], [AA6535; 0, N, iPr, Br, H, F], [AA6536; 0, N, iPr, I, H, F], [AA6537; 0, N, iPr, $CF_3$, H, F], [AA6538; 0, N, iPr, $CF_2H$, H, F], [AA6539; 0, N, iPr, $C_2F_5$, H, F], [AA6540; 0, N, iPr, $C_3F_7$, H, F], [AA6541; 0, N, iPr, $CH_2CF_3$, H, F], [AA6542; 0, N, iPr, $CH_2CHF_2$, H, F], [AA6543; 1, N, iPr, H, H, F], [AA6544; 1, N, iPr, F, H, F], [AA6545; 1, N, iPr, Cl, H, F], [AA6546; 1, N, iPr, Br, H, F], [AA6547; 1, N, iPr, I, H, F], [AA6548; 1, N, iPr, $CF_3$, H, F], [AA6549; 1, N, iPr, $CF_2H$, H, F], [AA6550; 1, N, iPr, $C_2F_5$, H, F], [AA6551; 1, N, iPr, $C_3F_7$, H, F], [AA6552; 1, N, iPr, $CH_2CF_3$, H, F], [AA6553; 1, N, iPr, $CH_2CHF_2$, H, F], [AA6554; 2, N, iPr, H, H, F], [AA6555; 2, N, iPr, F, H, F], [AA6556; 2, N, iPr, Cl, H, F], [AA6557; 2, N, iPr, Br, H, F], [AA6558; 2, N, iPr, I, H, F], [AA6559; 2, N, iPr, $CF_3$, H, F], [AA6560; 2, N, iPr, $CF_2H$, H, F], [AA6561; 2, N, iPr, $C_2F_5$, H, F], [AA6562; 2, N, iPr, $C_3F_7$, H, F], [AA6563; 2, N, iPr, $CH_2CF_3$, H, F], [AA6564; 2, N, iPr, $CH_2CHF_2$, H, F], [AA6565; 0, CH, cPr, H, H, F], [AA6566; 0, CH, cPr, F, H, F], [AA6567; 0, CH, cPr, Cl, H, F], [AA6568; 0, CH, cPr, Br, H, F], [AA6569; 0, CH, cPr, I, H, F], [AA6570; 0, CH, cPr, $CF_3$, H, F], [AA6571; 0, CH, cPr, $CF_2H$, H, F], [AA6572; 0, CH, cPr, $C_2F_5$, H, F], [AA6573; 0, CH, cPr, $C_3F_7$, H, F], [AA6574; 0, CH, cPr, $CH_2CF_3$, H, F], [AA6575; 0, CH, cPr, $CH_2CHF_2$, H, F], [AA6576; 1, CH, cPr, H, H, F], [AA6577; 1, CH, cPr, F, H, F], [AA6578; 1, CH, cPr, Cl, H, F], [AA6579; 1, CH, cPr, Br, H, F], [AA6580; 1, CH, cPr, I, H, F], [AA6581; 1, CH, cPr, $CF_3$, H, F], [AA6582; 1, CH, cPr, $CF_2H$, H, F], [AA6583; 1, CH, cPr, $C_2F_5$, H, F], [AA6584; 1, CH, cPr, $C_3F_7$, H, F], [AA6585; 1, CH, cPr, $CH_2CF_3$, H, F], [AA6586; 1, CH, cPr, $CH_2CHF_2$, H, F], [AA6587; 2, CH, cPr, H, H, F], [AA6588; 2, CH, cPr, F, H, F], [AA6589; 2, CH, cPr, Cl, H, F], [AA6590; 2, CH, cPr, Br, H, F], [AA6591; 2, CH, cPr, I, H, F], [AA6592; 2, CH, cPr, $CF_3$, H, F], [AA6593; 2, CH, cPr, $CF_2H$, H, F], [AA6594; 2, CH, cPr, $C_2F_5$, H, F], [AA6595; 2, CH, cPr, $C_3F_7$, H, F], [AA6596; 2, CH, cPr, $CH_2CF_3$, H, F], [AA6597; 2, CH, cPr, $CH_2CHF_2$, H, F], [AA6598; 0, N, cPr, H, H, F], [AA6599; 0, N, cPr, F, H, F], [AA6600; 0, N, cPr, Cl, H, F], [AA6601; 0, N, cPr, Br, H, F], [AA6602; 0, N, cPr, I, H, F], [AA6603; 0, N, cPr, $CF_3$, H, F], [AA6604; 0, N, cPr, $CF_2H$, H, F], [AA6605; 0, N, cPr, $C_2F_5$, H, F], [AA6606; 0, N, cPr, $C_3F_7$, H, F], [AA6607; 0, N, cPr, $CH_2CF_3$, H, F], [AA6608; 0, N, cPr, $CH_2CHF_2$, H, F], [AA6609; 1, N, cPr, H, H, F], [AA6610; 1, N, cPr, F, H, F], [AA6611; 1, N, cPr, Cl, H, F], [AA6612; 1, N, cPr, Br, H, F], [AA6613; 1, N, cPr, I, H, F], [AA6614; 1, N, cPr, $CF_3$, H, F], [AA6615; 1, N, cPr, $CF_2H$, H, F], [AA6616; 1, N, cPr, $C_2F_5$, H, F], [AA6617; 1, N, cPr, $C_3F_7$, H, F], [AA6618; 1, N, cPr, $CH_2CF_3$, H, F], [AA6619; 1, N, cPr, $CH_2CHF_2$, H, F], [AA6620; 2, N, cPr, H, H, F], [AA6621; 2, N, cPr, F, H, F], [AA6622; 2, N, cPr, Cl, H, F], [AA6623; 2, N, cPr, Br, H, F], [AA6624; 2, N, cPr, I, H, F], [AA6625; 2, N, cPr, $CF_3$, H, F], [AA6626; 2, N, cPr, $CF_2H$, H, F], [AA6627; 2, N, cPr, $C_2F_3$, H, F], [AA6628; 2, N, cPr, $C_3F_7$, H, F], [AA6629; 2, N, cPr, $CH_2CF_3$, H, F], [AA6630; 2, N, cPr, $CH_2CHF_2$, H, F], [AA6631; 0, CH, H, H, F, F], [AA6632; 0, CH, H, H, Cl, F], [AA6633; 0, CH, H, H, Br, F], [AA6634; 0, CH, H, H, I, F], [AA6635; 0, CH, H, H, $CF_3$, F], [AA6636; 0, CH, H, H, $CF_2H$, F], [AA6637; 0, CH, H, H, $C_2F_5$, F], [AA6638; 0, CH, H, H, $C_3F_7$, F], [AA6639; 0, CH, H, H, $CH_2CF_3$, F], [AA6640; 0, CH, H, H, $CH_2CHF_2$, F], [AA6641; 1, CH, H, H, F, F], [AA6642; 1, CH, H, H, Cl, F], [AA6643; 1, CH, H, H, Br, F], [AA6644; 1, CH, H, H, I, F], [AA6645; 1, CH, H, H, $CF_3$, F], [AA6646; 1, CH, H, H, $CF_2H$, F], [AA6647; 1, CH, H, H, $C_2F_5$, F], [AA6648; 1, CH, H, H, $C_3F_7$, F], [AA6649; 1, CH, H, H, $CH_2CF_3$, F], [AA6650; 1, CH, H, H, $CH_2CHF_2$, F], [AA6651; 2, CH, H, H, F, F], [AA6652; 2, CH, H, H, Cl, F], [AA6653; 2, CH, H, H, Br, F], [AA6654; 2, CH, H, H, I, F], [AA6655; 2, CH, H, H, $CF_3$, F], [AA6656; 2, CH, H, H, $CF_2H$, F], [AA6657; 2, CH, H, H, $C_2F_5$, F], [AA6658; 2, CH, H, H, $C_3F_7$, F], [AA6659; 2, CH, H, H, $CH_2CF_3$, F], [AA6660; 2, CH, H, H, $CH_2CHF_2$, F], [AA6661; 0, N, H, H, F, F], [AA6662; 0, N, H, H, Cl, F], [AA6663; 0, N, H, H, Br, F], [AA6664; 0, N, H, H, I, F], [AA6665; 0, N, H, H, $CF_3$, F], [AA6666; 0, N, H, H, $CF_2H$, F], [AA6667; 0, N, H, H, $C_2F_5$, F], [AA6668; 0, N, H, H, $C_3F_7$, F], [AA6669; 0, N, H, H, $CH_2CF_3$, F], [AA6670; 0, N, H, H, $CH_2CHF_2$, F], [AA6671; 1, N, H, H, F, F], [AA6672; 1, N, H, H, Cl, F], [AA6673; 1, N, H, H, Br, F], [AA6674; 1, N, H, H, I, F], [AA6675; 1, N, H, H, $CF_3$, F], [AA6676; 1, N, H, H, $CF_2H$, F], [AA6677; 1, N, H, H, $C_2F_5$, F], [AA6678; 1, N, H, H, $C_3F_7$, F], [AA6679; 1, N, H, H, $CH_2CF_3$, F], [AA6680; 1, N, H, H, $CH_2CHF_2$, F], [AA6681; 2, N, H, H, F, F], [AA6682; 2, N, H, H, Cl, F], [AA6683; 2, N, H, H, Br, F], [AA6684; 2, N, H, H, I, F], [AA6685; 2, N, H, H, $CF_3$, F], [AA6686; 2, N, H, H, $CF_2H$, F], [AA6687; 2, N, H, H, $C_2F_5$, F], [AA6688; 2, N, H, H, $C_3F_7$, F], [AA6689; 2, N, H, H, $CH_2CF_3$, F], [AA6690; 2, N, H, H, $CH_2CHF_2$, F], [AA6691; 0, CH, Me, H, F, F], [AA6692; 0, CH, Me, H, Cl, F], [AA6693; 0, CH, Me, H, Br, F], [AA6694; 0, CH, Me, H, I, F], [AA6695; 0, CH, Me, H, $CF_3$, F], [AA6696; 0, CH, Me, H, $CF_2H$, F], [AA6697; 0, CH, Me, H, $C_2F_5$, F], [AA6698; 0, CH, Me, H, $C_3F_7$, F], [AA6699; 0, CH, Me, H, $CH_2CF_3$, F], [AA6700; 0, CH, Me, H, $CH_2CHF_2$, F], [AA6701; 1, CH, Me, H, F, F], [AA6702; 1, CH, Me, H, Cl, F], [AA6703; 1, CH, Me, H, Br, F], [AA6704; 1, CH, Me, H, I, F], [AA6705; 1, CH, Me, H, $CF_3$, F], [AA6706; 1, CH, Me, H, $CF_2H$, F], [AA6707; 1, CH, Me, H, $C_2F_5$, F], [AA6708; 1, CH, Me, H, $C_3F_7$, F], [AA6709; 1, CH, Me, H, $CH_2CF_3$, F], [AA6710; 1, CH, Me, H, $CH_2CHF_2$, F], [AA6711; 2, CH, Me, H, F, F], [AA6712; 2, CH, Me, H, Cl, F], [AA6713; 2, CH, Me, H, Br, F], [AA6714; 2, CH, Me, H, I, F], [AA6715; 2, CH, Me, H, $CF_3$, F], [AA6716; 2, CH, Me, H, $CF_2H$, F], [AA6717; 2, CH, Me, H, $C_2F_5$, F], [AA6718; 2, CH, Me, H, $C_3F_7$, F], [AA6719; 2, CH, Me, H, $CH_2CF_3$, F], [AA6720; 2, CH, Me, H, $CH_2CHF_2$, F], [AA6721; 0, N, Me, H, F, F], [AA6722; 0, N, Me, H, Cl, F], [AA6723; 0, N, Me, H, Br, F], [AA6724; 0, N, Me, H, I, F], [AA6725; 0, N, Me, H, $CF_3$, F], [AA6726; 0, N, Me, H, $CF_2H$, F], [AA6727; 0, N, Me, H, $C_2F_5$, F], [AA6728; 0, N, Me, H, $C_3F_7$, F], [AA6729; 0, N, Me, H, $CH_2CF_3$, F], [AA6730; 0, N, Me, H, $CH_2CHF_2$, F], [AA6731; 1, N, Me, H, F, F], [AA6732; 1, N, Me, H, Cl, F], [AA6733; 1, N, Me, H, Br, F], [AA6734; 1, N, Me, H, I, F], [AA6735; 1, N, Me, H, $CF_3$, F], [AA6736; 1, N, Me, H, $CF_2H$, F], [AA6737; 1, N, Me, H, $C_2F_5$, F], [AA6738; 1, N, Me, H, $C_3F_7$, F], [AA6739; 1, N, Me, H, $CH_2CF_3$, F], [AA6740; 1, N, Me, H, $CH_2CHF_2$, F], [AA6741; 2, N, Me, H, F, F], [AA6742; 2, N,

Me, H, Cl, F], [AA6743; 2, N, Me, H, Br, F], [AA6744; 2, N, Me, H, I, F], [AA6745; 2, N, Me, H, $CF_3$, F], [AA6746; 2, N, Me, H, $CF_2H$, F], [AA6747; 2, N, Me, H, $C_2F_5$, F], [AA6748; 2, N, Me, H, $C_3F_7$, F], [AA6749; 2, N, Me, H, $CH_2CF_3$, F], [AA6750; 2, N, Me, H, $CH_2CHF_2$, F], [AA6751; 0, CH, Et, H, F, F], [AA6752; 0, CH, Et, H, Cl, F], [AA6753; 0, CH, Et, H, Br, F], [AA6754; 0, CH, Et, H, I, F], [AA6755; 0, CH, Et, H, $CF_3$, F], [AA6756; 0, CH, Et, H, $CF_2H$, F], [AA6757; 0, CH, Et, H, $C_2F_5$, F], [AA6758; 0, CH, Et, H, $C_3F_7$, F], [AA6759; 0, CH, Et, H, $CH_2CF_3$, F], [AA6760; 0, CH, Et, H, $CH_2CHF_2$, F], [AA6761; 1, CH, Et, H, F, F], [AA6762; 1, CH, Et, H, Cl, F], [AA6763; 1, CH, Et, H, Br, F], [AA6764; 1, CH, Et, H, I, F], [AA6765; 1, CH, Et, H, $CF_3$, F], [AA6766; 1, CH, Et, H, $CF_2H$, F], [AA6767; 1, CH, Et, H, $C_2F_5$, F], [AA6768; 1, CH, Et, H, $C_3F_7$, F], [AA6769; 1, CH, Et, H, $CH_2CF_3$, F], [AA6770; 1, CH, Et, H, $CH_2CHF_2$, F], [AA6771; 2, CH, Et, H, F, F], [AA6772; 2, CH, Et, H, Cl, F], [AA6773; 2, CH, Et, H, Br, F], [AA6774; 2, CH, Et, H, I, F], [AA6775; 2, CH, Et, H, $CF_3$, F], [AA6776; 2, CH, Et, H, $CF_2H$, F], [AA6777; 2, CH, Et, H, $C_2F_5$, F], [AA6778; 2, CH, Et, H, $C_3F_7$, F], [AA6779; 2, CH, Et, H, $CH_2CF_3$, F], [AA6780; 2, CH, Et, H, $CH_2CHF_2$, F], [AA6781; 0, N, Et, H, F, F], [AA6782; 0, N, Et, H, Cl, F], [AA6783; 0, N, Et, H, Br, F], [AA6784; 0, N, Et, H, I, F], [AA6785; 0, N, Et, H, $CF_3$, F], [AA6786; 0, N, Et, H, $CF_2H$, F], [AA6787; 0, N, Et, H, $C_2F_5$, F], [AA6788; 0, N, Et, H, $C_3F_7$, F], [AA6789; 0, N, Et, H, $CH_2CF_3$, F], [AA6790; 0, N, Et, H, $CH_2CHF_2$, F], [AA6791; 1, N, Et, H, F, F], [AA6792; 1, N, Et, H, Cl, F], [AA6793; 1, N, Et, H, Br, F], [AA6794; 1, N, Et, H, I, F], [AA6795; 1, N, Et, H, $CF_3$, F], [AA6796; 1, N, Et, H, $CF_2H$, F], [AA6797; 1, N, Et, H, $C_2F_5$, F], [AA6798; 1, N, Et, H, $C_3F_7$, F], [AA6799; 1, N, Et, H, $CH_2CF_3$, F], [AA6800; 1, N, Et, H, $CH_2CHF_2$, F], [AA6801; 2, N, Et, H, F, F], [AA6802; 2, N, Et, H, Cl, F], [AA6803; 2, N, Et, H, Br, F], [AA6804; 2, N, Et, H, I, F], [AA6805; 2, N, Et, H, $CF_3$, F], [AA6806; 2, N, Et, H, $CF_2H$, F], [AA6807; 2, N, Et, H, $C_2F_5$, F], [AA6808; 2, N, Et, H, $C_3F_7$, F], [AA6809; 2, N, Et, H, $CH_2CF_3$, F], [AA6810; 2, N, Et, H, $CH_2CHF_2$, F], [AA6811; 0, CH, iPr, H, F, F], [AA6812; 0, CH, iPr, H, Cl, F], [AA6813; 0, CH, iPr, H, Br, F], [AA6814; 0, CH, iPr, H, I, F], [AA6815; 0, CH, iPr, H, $CF_3$, F], [AA6816; 0, CH, iPr, H, $CF_2H$, F], [AA6817; 0, CH, iPr, H, $C_2F_5$, F], [AA6818; 0, CH, iPr, H, $C_3F_7$, F], [AA6819; 0, CH, iPr, H, $CH_2CF_3$, F], [AA6820; 0, CH, iPr, H, $CH_2CHF_2$, F], [AA6821; 1, CH, iPr, H, F, F], [AA6822; 1, CH, iPr, H, Cl, F], [AA6823; 1, CH, iPr, H, Br, F], [AA6824; 1, CH, iPr, H, I, F], [AA6825; 1, CH, iPr, H, $CF_3$, F], [AA6826; 1, CH, iPr, H, $CF_2H$, F], [AA6827; 1, CH, iPr, H, $C_2F_5$, F], [AA6828; 1, CH, iPr, H, $C_3F_7$, F], [AA6829; 1, CH, iPr, H, $CH_2CF_3$, F], [AA6830; 1, CH, iPr, H, $CH_2CHF_2$, F], [AA6831; 2, CH, iPr, H, F, F], [AA6832; 2, CH, iPr, H, Cl, F], [AA6833; 2, CH, iPr, H, Br, F], [AA6834; 2, CH, iPr, H, I, F], [AA6835; 2, CH, iPr, H, $CF_3$, F], [AA6836; 2, CH, iPr, H, $CF_2H$, F], [AA6837; 2, CH, iPr, H, $C_2F_5$, F], [AA6838; 2, CH, iPr, H, $C_3F_7$, F], [AA6839; 2, CH, iPr, H, $CH_2CF_3$, F], [AA6840; 2, CH, iPr, H, $CH_2CHF_2$, F], [AA6841; 0, N, iPr, H, F, F], [AA6842; 0, N, iPr, H, Cl, F], [AA6843; 0, N, iPr, H, Br, F], [AA6844; 0, N, iPr, H, I, F], [AA6845; 0, N, iPr, H, $CF_3$, F], [AA6846; 0, N, iPr, H, $CF_2H$, F], [AA6847; 0, N, iPr, H, $C_2F_5$, F], [AA6848; 0, N, iPr, H, $C_3F_7$, F], [AA6849; 0, N, iPr, H, $CH_2CF_3$, F], [AA6850; 0, N, iPr, H, $CH_2CHF_2$, F], [AA6851; 1, N, iPr, H, F, F], [AA6852; 1, N, iPr, H, Cl, F], [AA6853; 1, N, iPr, H, Br, F], [AA6854; 1, N, iPr, H, I, F], [AA6855; 1, N, iPr, H, $CF_3$, F], [AA6856; 1, N, iPr, H, $CF_2H$, F], [AA6857; 1, N, iPr, H, $C_2F_5$, F], [AA6858; 1, N, iPr, H, $C_3F_7$, F], [AA6859; 1, N, iPr, H, $CH_2CF_3$, F], [AA6860; 1, N, iPr, H, $CH_2CHF_2$, F], [AA6861; 2, N, iPr, H, F, F], [AA6862; 2, N, iPr, H, Cl, F], [AA6863; 2, N, iPr, H, Br, F], [AA6864; 2, N, iPr, H, I, F], [AA6865; 2, N, iPr, H, $CF_3$, F], [AA6866; 2, N, iPr, H, $CF_2H$, F], [AA6867; 2, N, iPr, H, $C_2F_5$, F], [AA6868; 2, N, iPr, H, $C_3F_7$, F], [AA6869; 2, N, iPr, H, $CH_2CF_3$, F], [AA6870; 2, N, iPr, H, $CH_2CHF_2$, F], [AA6871; 0, CH, cPr, H, F, F], [AA6872; 0, CH, cPr, H, Cl, F], [AA6873; 0, CH, cPr, H, Br, F], [AA6874; 0, CH, cPr, H, I, F], [AA6875; 0, CH, cPr, H, $CF_3$, F], [AA6876; 0, CH, cPr, H, $CF_2H$, F], [AA6877; 0, CH, cPr, H, $C_2F_5$, F], [AA6878; 0, CH, cPr, H, $C_3F_7$, F], [AA6879; 0, CH, cPr, H, $CH_2CF_3$, F], [AA6880; 0, CH, cPr, H, $CH_2CHF_2$, F], [AA6881; 1, CH, cPr, H, F, F], [AA6882; 1, CH, cPr, H, Cl, F], [AA6883; 1, CH, cPr, H, Br, F], [AA6884; 1, CH, cPr, H, I, F], [AA6885; 1, CH, cPr, H, $CF_3$, F], [AA6886; 1, CH, cPr, H, $CF_2H$, F], [AA6887; 1, CH, cPr, H, $C_2F_2$, F], [AA6888; 1, CH, cPr, H, $C_3F_7$, F], [AA6889; 1, CH, cPr, H, $CH_2CF_3$, F], [AA6890; 1, CH, cPr, H, $CH_2CHF_2$, F], [AA6891; 2, CH, cPr, H, F, F], [AA6892; 2, CH, cPr, H, Cl, F], [AA6893; 2, CH, cPr, H, Br, F], [AA6894; 2, CH, cPr, H, I, F], [AA6895; 2, CH, cPr, H, $CF_3$, F], [AA6896; 2, CH, cPr, H, $CF_2H$, F], [AA6897; 2, CH, cPr, H, $C_2F_5$, F], [AA6898; 2, CH, cPr, H, $C_3F_7$, F], [AA6899; 2, CH, cPr, H, $CH_2CF_3$, F], [AA6900; 2, CH, cPr, H, $CH_2CHF_2$, F], [AA6901; 0, N, cPr, H, F, F], [AA6902; 0, N, cPr, H, Cl, F], [AA6903; 0, N, cPr, H, Br, F], [AA6904; 0, N, cPr, H, I, F], [AA6905; 0, N, cPr, H, $CF_3$, F], [AA6906; 0, N, cPr, H, $CF_2H$, F], [AA6907; 0, N, cPr, H, $C_2F_5$, F], [AA6908; 0, N, cPr, H, $C_3F_7$, F], [AA6909; 0, N, cPr, H, $CH_2CF_3$, F], [AA6910; 0, N, cPr, H, $CH_2CHF_2$, F], [AA6911; 1, N, cPr, H, F, F], [AA6912; 1, N, cPr, H, Cl, F], [AA6913; 1, N, cPr, H, Br, F], [AA6914; 1, N, cPr, H, I, F], [AA6915; 1, N, cPr, H, $CF_3$, F], [AA6916; 1, N, cPr, H, $CF_2H$, F], [AA6917; 1, N, cPr, H, $C_2F_5$, F], [AA6918; 1, N, cPr, H, $C_3F_7$, F], [AA6919; 1, N, cPr, H, $CH_2CF_3$, F], [AA6920; 1, N, cPr, H, $CH_2CHF_2$, F], [AA6921; 2, N, cPr, H, F, F], [AA6922; 2, N, cPr, H, Cl, F], [AA6923; 2, N, cPr, H, Br, F], [AA6924; 2, N, cPr, H, I, F], [AA6925; 2, N, cPr, H, $CF_3$, F], [AA6926; 2, N, cPr, H, $CF_2H$, F], [AA6927; 2, N, cPr, H, $C_2F_5$, F], [AA6928; 2, N, cPr, H, $C_3F_7$, F], [AA6929; 2, N, cPr, H, $CH_2CF_3$, F], [AA6930; 2, N, cPr, H, $CH_2CHF_2$, F]

A compound represented by formula (L-2)

(L-2)

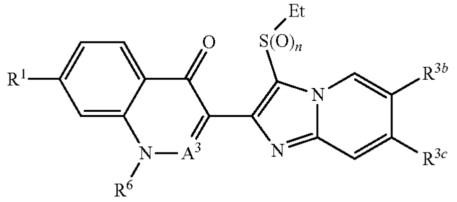

wherein the combination of the symbol n, and the substituents $A^3$, $R^6$, $R^{3b}$, $R^{3c}$, and $R^1$ represents any one combination indicated in the Combination AA (hereinafter referred to as "Compound group SX2").

A compound represented by formula (L-3)

(L-3)

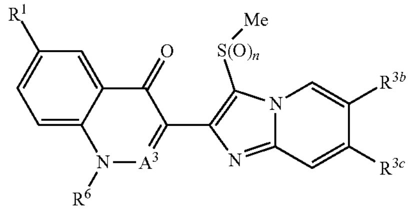

wherein the combination of the symbol n, and the substituents $A^3$, $R^6$, $R^{3b}$, $R^{3c}$, and $R^1$ represents any one combination indicated in the Combination AA (hereinafter referred to as "Compound group SX3").

A compound represented by formula (L-4)

(L-4)

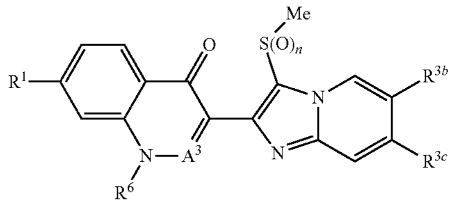

wherein the combination of the symbol n, and the substituents $A^3$, $R^6$, $R^{3b}$, $R^{3c}$, and $R^1$ represents any one combination indicated in the Combination AA (hereinafter referred to as "Compound group SX4").

A compound represented by formula (L-5)

(L-5)

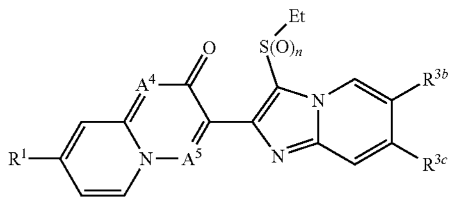

wherein the combination of the symbol n, and the substituents $A^4$, $A^5$, $R^{3b}$, $R^{3c}$, and $R^1$ represents any one combination indicated in the Combination BB (hereinafter referred to as "Compound group SX5").

The Combination BB consists of substituent numbers BB1 to BB693. The substituent numbers BB1 to BB693 represent combinations of the symbol n, and the substituents $A^4$, $A^5$, $R^{3b}$, $R^{3c}$, and $R^1$, and hereinafter referred to as "[substituent number; n, $A^4$, $A^5$, $R^{3b}$, $R^{3c}$, $R^1$]". For example, the substituent number BB2 means a combination wherein n represents 0, $A^4$ represents N, $A^5$ represents CH, $R^{3b}$ represents a fluorine atom, $R^{3c}$ represents a hydrogen atom, and $R^1$ represents $CF_3$.

Combination BB: [BB1; 0, N, CH, H, H, $CF_3$], [BB2; 0, N, CH, F, H, $CF_3$], [BB3; 0, N, CH, Cl, H, $CF_3$], [BB4; 0, N, CH, Br, H, $CF_3$], [BB5; 0, N, CH, I, H, $CF_3$], [BB6; 0, N, CH, $CF_3$, H, $CF_3$], [BB7; 0, N, CH, $CF_2H$, H, $CF_3$], [BB8; 0, N, CH, $C_2F_5$, H, $CF_3$], [BB9; 0, N, CH, $C_3F_7$, H, $CF_3$], [BB10; 0, N, CH, $CH_2CF_3$, H, $CF_3$], [BB11; 0, N, CH, $CH_2CHF_2$, H, $CF_3$], [BB12; 1, N, CH, H, H, $CF_3$], [BB13; 1, N, CH, F, H, $CF_3$], [BB14; 1, N, CH, Cl, H, $CF_3$], [BB15; 1, N, CH, Br, H, $CF_3$], [BB16; 1, N, CH, I, H, $CF_3$], [BB17; 1, N, CH, $CF_3$, H, $CF_3$], [BB18; 1, N, CH, $CF_2H$, H, $CF_3$], [BB19; 1, N, CH, $C_2F_5$, H, $CF_3$], [BB20; 1, N, CH, $C_3F_7$, H, $CF_3$], [BB21; 1, N, CH, $CH_2CF_3$, H, $CF_3$], [BB22; 1, N, CH, $CH_2CHF_2$, H, $CF_3$], [BB23; 2, N, CH, H, H, $CF_3$], [BB24; 2, N, CH, F, H, $CF_3$], [BB25; 2, N, CH, Cl, H, $CF_3$], [BB26; 2, N, CH, Br, H, $CF_3$], [BB27; 2, N, CH, I, H, $CF_3$], [BB28; 2, N, CH, $CF_3$, H, $CF_3$], [BB29; 2, N, CH, $CF_2H$, H, $CF_3$], [BB30; 2, N, CH, $C_2F_5$, H, $CF_3$], [BB31; 2, N, CH, $C_3F_7$, H, $CF_3$], [BB32; 2, N, CH, $CH_2CF_3$, H, $CF_3$], [BB33; 2, N, CH, $CH_2CHF_2$, H, $CF_3$], [BB34; 0, N, CH, H, F, $CF_3$], [BB35; 0, N, CH, H, Cl, $CF_3$], [BB36; 0, N, CH, H, Br, $CF_3$], [BB37; 0, N, CH, H, I, $CF_3$], [BB38; 0, N, CH, H, $CF_3$, $CF_3$], [BB39; 0, N, CH, H, $CF_2H$, $CF_3$], [BB40; 0, N, CH, H, $C_2F_5$, $CF_3$], [BB41; 0, N, CH, H, $C_3F_7$, $CF_3$], [BB42; 0, N, CH, H, $CH_2CF_3$, $CF_3$], [BB43; 0, N, CH, H, $CH_2CHF_2$, $CF_3$], [BB44; 1, N, CH, H, F, $CF_3$], [BB45; 1, N, CH, H, Cl, $CF_3$], [BB46; 1, N, CH, H, Br, $CF_3$], [BB47; 1, N, CH, H, I, $CF_3$], [BB48; 1, N, CH, H, $CF_3$, $CF_3$], [BB49; 1, N, CH, H, $CF_2H$, $CF_3$], [BB50; 1, N, CH, H, $C_2F_5$, $CF_3$], [BB51; 1, N, CH, H, $C_3F_7$, $CF_3$], [BB52; 1, N, CH, H, $CH_2CF_3$, $CF_3$], [BB53; 1, N, CH, H, $CH_2CHF_2$, $CF_3$], [BB54; 2, N, CH, H, F, $CF_3$], [BB55; 2, N, CH, H, Cl, $CF_3$], [BB56; 2, N, CH, H, Br, $CF_3$], [BB57; 2, N, CH, H, I, $CF_3$], [BB58; 2, N, CH, H, $CF_3$, $CF_3$], [BB59; 2, N, CH, H, $CF_2H$, $CF_3$], [BB60; 2, N, CH, H, $C_2F_5$, $CF_3$], [BB61; 2, N, CH, H, $C_3F_7$, $CF_3$], [BB62; 2, N, CH, H, $CH_2CF_3$, $CF_3$], [BB63; 2, N, CH, H, $CH_2CHF_2$, $CF_3$], [BB64; 0, N, CH, H, H, $CHF_2$], [BB65; 0, N, CH, F, H, $CHF_2$], [BB66; 0, N, CH, Cl, H, $CHF_2$], [BB67; 0, N, CH, Br, H, $CHF_2$], [BB68; 0, N, CH, I, H, $CHF_2$], [BB69; 0, N, CH, $CF_3$, H, $CHF_2$], [BB70; 0, N, CH, $CF_2H$, H, $CHF_2$], [BB71; O, N, CH, $C_2F_5$, H, $CHF_2$], [BB72; O, N, CH, $C_3F_7$, H, $CHF_2$], [BB73; 0, N, CH, $CH_2CF_3$, H, $CHF_2$], [BB74; 0, N, CH, $CH_2CHF_2$, H, $CHF_2$], [BB75; 1, N, CH, H, H, $CHF_2$], [BB76; 1, N, CH, F, H, $CHF_2$], [BB77; 1, N, CH, Cl, H, $CHF_2$], [BB78; 1, N, CH, Br, H, $CHF_2$], [BB79; 1, N, CH, I, H, $CHF_2$], [BB80; 1, N, CH, $CF_3$, H, $CHF_2$], [BB81; 1, N, CH, $CF_2H$, H, $CHF_2$], [BB82; 1, N, CH, $C_2F_5$, H, $CHF_2$], [BB83; 1, N, CH, $C_3F_7$, H, $CHF_2$], [BB84; 1, N, CH, $CH_2CF_3$, H, $CHF_2$], [BB85; 1, N, CH, $CH_2CHF_2$, H, $CHF_2$], [BB86; 2, N, CH, H, H, $CHF_2$], [BB87; 2, N, CH, F, H, $CHF_2$], [BB88; 2, N, CH, Cl, H, $CHF_2$], [BB89; 2, N, CH, Br, H, $CHF_2$], [BB90; 2, N, CH, I, H, $CHF_2$], [BB91; 2, N, CH, $CF_3$, H, $CHF_2$], [BB92; 2, N, CH, $CF_2H$, H, $CHF_2$], [BB93; 2, N, CH, $C_2F_5$, H, $CHF_2$], [BB94; 2, N, CH, $C_3F_7$, H, $CHF_2$], [BB95; 2, N, CH, $CH_2CF_3$, H, $CHF_2$], [BB96; 2, N, CH, $CH_2CHF_2$, H, $CHF_2$], [BB97; 0, N, CH, H, F, $CHF_2$], [BB98; 0, N, CH, H, Cl, $CHF_2$], [BB99; 0, N, CH, H, Br, $CHF_2$], [BB100; 0, N, CH, H, I, $CHF_2$], [BB101; 0, N, CH, H, $CF_3$, $CHF_2$], [BB102; 0, N, CH, H, $CF_2H$, $CHF_2$], [BB103; 0, N, CH, H, $C_2F_5$, $CHF_2$], [BB104; 0, N, CH, H, $C_3F_7$, $CHF_2$], [BB105; 0, N, CH, H, $CH_2CF_3$, $CHF_2$], [BB106; 0, N, CH, H, $CH_2CHF_2$, $CHF_2$], [BB107; 1, N, CH, H, F, $CHF_2$], [BB108; 1, N, CH, H, Cl, $CHF_2$], [BB109; 1, N, CH, H, Br, $CHF_2$], [BB110; 1, N, CH, H, I, $CHF_2$], [BB111; 1, N, CH, H, $CF_3$, $CHF_2$], [BB112; 1, N, CH, H, $CF_2H$, $CHF_2$], [BB113; 1, N, CH, H, $C_2F_5$, $CHF_2$], [BB114; 1, N, CH, H, $C_3F_7$, $CHF_2$], [BB115; 1, N, CH, H, $CH_2CF_3$, $CHF_2$], [BB116; 1, N, CH, H, $CH_2CHF_2$, $CHF_2$], [BB117; 2, N, CH, H, F, $CHF_2$], [BB118; 2, N, CH, H, Cl, $CHF_2$], [BB119; 2, N, CH, H, Br, $CHF_2$], [BB120; 2, N, CH, H, I, $CHF_2$], [BB121; 2, N, CH, H, $CF_3$, $CHF_2$], [BB122; 2, N, CH, H, $CF_2H$, $CHF_2$], [BB123; 2, N, CH, H, $C_2F_5$, $CHF_2$], [BB124; 2, N, CH, H, $C_3F_7$, $CHF_2$], [BB125; 2, N, CH, H, $CH_2CF_3$, $CHF_2$], [BB126; 2, N, CH, H, $CH_2CHF_2$, $CHF_2$], [BB127; 0, N, CH, H, H, $CH_2CF_3$], [BB128; 0, N, CH, F, H, $CH_2CF_3$], [BB129; 0, N, CH, Cl, H, $CH_2CF_3$], [BB130; 0, N, CH, Br, H, $CH_2CF_3$], [BB131; 0, N, CH, I, H, $CH_2CF_3$], [BB132; 0, N, CH, $CF_3$, H, $CH_2CF_3$], [BB133; 0, N, CH, $CF_2H$, H, $CH_2CF_3$], [BB134; 0, N, CH, $C_2F_5$, H, $CH_2CF_3$], [BB135; O, N, CH, $C_3F_7$, H, $CH_2CF_3$], [BB136; 0, N, CH, $CH_2CF_3$, H, $CH_2CF_3$], [BB137; 0, N, CH, $CH_2CHF_2$, H, $CH_2CF_3$], [BB138; 1, N, CH, H, H, $CH_2CF_3$], [BB139; 1, N, CH, F, H, $CH_2CF_3$], [BB140; 1, N, CH, Cl, H, $CH_2CF_3$], [BB141; 1, N, CH, Br, H, $CH_2CF_3$], [BB142; 1, N, CH, I, H, $CH_2CF_3$], [BB143; 1, N, CH, $CF_3$, H, $CH_2CF_3$], [BB144; 1, N, CH, $CF_2H$, H, $CH_2CF_3$], [BB145; 1, N, CH, $C_2F_5$, H, $CH_2CF_3$], [BB146; 1, N, CH, $C_3F_7$, H, $CH_2CF_3$], [BB147; 1, N, CH, $CH_2CF_3$, H, $CH_2CF_3$], [BB148; 1, N, CH, $CH_2CHF_2$, H, $CH_2CF_3$], [BB149; 2, N, CH, H, H, $CH_2CF_3$], [BB150; 2, N, CH, F, H, $CH_2CF_3$], [BB151; 2, N, CH, Cl, H, $CH_2CF_3$], [BB152; 2, N, CH, Br, H, $CH_2CF_3$], [BB153; 2, N, CH, I, H, $CH_2CF_3$], [BB154; 2, N, CH, $CF_3$, H, $CH_2CF_3$], [BB155; 2, N, CH, $CF_2H$, H, $CH_2CF_3$], [BB156; 2, N, CH, $C_2F_5$, H, $CH_2CF_3$], [BB157; 2, N, CH, $C_3F_7$, H, $CH_2CF_3$], [BB158; 2, N, CH, $CH_2CF_3$, H, $CH_2CF_3$], [BB159; 2, N, CH, $CH_2CHF_2$, H, $CH_2CF_3$], [BB160; 0, N, CH, H, F, $CH_2CF_3$], [BB161; 0, N, CH, H, Cl, $CH_2CF_3$], [BB162; 0, N, CH, H, Br, $CH_2CF_3$], [BB163; 0, N, CH, H, I, $CH_2CF_3$], [BB164; 0, N, CH, H, $CF_3$, $CH_2CF_3$], [BB165; 0, N, CH, H, $CF_2H$, $CH_2CF_3$], [BB166; 0, N, CH, H, $C_2F_5$, $CH_2CF_3$], [BB167; 0, N, CH, H, $C_3F_7$, $CH_2CF_3$], [BB168; 0, N, CH, H, $CH_2CF_3$, $CH_2CF_3$], [BB169; 0, N, CH, H, $CH_2CHF_2$, $CH_2CF_3$], [BB170; 1, N, CH, H, F, $CH_2CF_3$], [BB171; 1, N, CH, H, Cl, $CH_2CF_3$], [BB172; 1, N, CH, H, Br, $CH_2CF_3$], [BB173; 1, N, CH, H, I, $CH_2CF_3$], [BB174; 1, N, CH, H, $CF_3$, $CH_2CF_3$], [BB175; 1, N, CH, H, $CF_2H$, $CH_2CF_3$], [BB176; 1, N, CH, H, $C_2F_5$, $CH_2CF_3$], [BB177; 1, N, CH, H, $C_3F_7$, $CH_2CF_3$], [BB178; 1, N, CH, H, $CH_2CF_3$, $CH_2CF_3$], [BB179; 1, N, CH, H, $CH_2CHF_2$, $CH_2CF_3$], [BB180; 2, N, CH, H, F, $CH_2CF_3$], [BB181; 2, N, CH, H, Cl, $CH_2CF_3$], [BB182; 2, N, CH, H, Br, $CH_2CF_3$], [BB183; 2, N, CH, H, I, $CH_2CF_3$], [BB184; 2, N, CH, H, $CF_3$, $CH_2CF_3$], [BB185; 2, N, CH, H, $CF_2H$, $CH_2CF_3$], [BB186; 2, N, CH, H, $C_2F_5$, $CH_2CF_3$], [BB187; 2, N, CH, H, $C_3F_7$, $CH_2CF_3$], [BB188; 2, N, CH, H, $CH_2CF_3$, $CH_2CF_3$], [BB189; 2, N, CH, H, $CH_2CHF_2$, $CH_2CF_3$], [BB190; 0, N, CH, H, H, $CH_2CHF_2$], [BB191; 0, N, CH, F, H, $CH_2CHF_2$], [BB192; 0, N, CH, Cl, H, $CH_2CHF_2$], [BB193; 0, N, CH, Br, H, $CH_2CHF_2$], [BB194; 0, N, CH, I, H, $CH_2CHF_2$], [BB195; 0, N, CH, $CF_3$, H, $CH_2CHF_2$], [BB196; 0, N, CH, $CF_2H$, H, $CH_2CHF_2$], [BB197; 0, N, CH, $C_2F_5$, H, $CH_2CHF_2$], [BB198; O, N, CH, $C_3F_7$, H, $CH_2CHF_2$], [BB199; 0, N, CH, $CH_2CF_3$, H, $CH_2CHF_2$], [BB200; 0, N, CH, $CH_2CHF_2$, H, $CH_2CHF_2$], [BB201; 1, N, CH, H, H, $CH_2CHF_2$], [BB202; 1, N, CH, F, H, $CH_2CHF_2$], [BB203; 1, N, CH, Cl, H, $CH_2CHF_2$], [BB204; 1, N, CH, Br, H, $CH_2CHF_2$], [BB205; 1, N, CH, I, H, $CH_2CHF_2$], [BB206; 1, N, CH, $CF_3$, H, $CH_2CHF_2$], [BB207; 1, N, CH, $CF_2H$, H, $CH_2CHF_2$], [BB208; 1, N, CH, $C_2F_5$, H, $CH_2CHF_2$], [BB209; 1, N, CH, $C_3F_7$, H, $CH_2CHF_2$], [BB210; 1, N, CH, $CH_2CF_3$, H, $CH_2CHF_2$], [BB211; 1, N, CH, $CH_2CHF_2$, H, $CH_2CHF_2$], [BB212; 2, N, CH, H, H, $CH_2CHF_2$], [BB213; 2, N, CH, F, H, $CH_2CHF_2$], [BB214; 2, N, CH, Cl, H, $CH_2CHF_2$], [BB215; 2, N, CH, Br, H, $CH_2CHF_2$], [BB216; 2, N, CH, I, H, $CH_2CHF_2$], [BB217; 2, N, CH, $CF_3$, H, $CH_2CHF_2$], [BB218; 2, N, CH, $CF_2H$, H, $CH_2CHF_2$], [BB219; 2, N, CH, $C_2F_5$, H, $CH_2CHF_2$], [BB220; 2, N, CH, $C_3F_7$, H, $CH_2CHF_2$], [BB221; 2, N, CH, $CH_2CF_3$, H, $CH_2CHF_2$], [BB222; 2, N, CH, $CH_2CHF_2$, H, $C_H$ $CHF_2$], [BB223; 0, N, CH, H, F, $CH_2CHF_2$], [BB224; 0, N, CH, H, Cl, $CH_2CHF_2$], [BB225; 0, N, CH, H, Br, $CH_2CHF_2$], [BB226; 0, N, CH, H, I, $CH_2CHF_2$], [BB227; 0, N, CH, H, $CF_3$, $CH_2CHF_2$], [BB228; 0, N, CH, H, $CF_2H$, $CH_2CHF_2$], [BB229; 0, N, CH, H, $C_2F_5$, $CH_2CHF_2$], [BB230; 0, N, CH, H, $C_3F$-7, $CH_2CHF_2$], [BB231; 0, N, CH, H, $CH_2CF_3$, $CH_2CHF_2$], [BB232; 0, N, CH, H, $CH_2CHF_2$, $CH_2CHF_2$], [BB233; 1, N, CH, H, F, $CH_2CHF_2$], [BB234; 1, N, CH, H, Cl, $CH_2CHF_2$], [BB235; 1, N, CH, H, Br, $CH_2CHF_2$], [BB236; 1, N, CH, H, I, $CH_2CHF_2$], [BB237; 1, N, CH, H, $CF_3$, $CH_2CHF_2$], [BB238; 1, N, CH, H, $CF_2H$, $CH_2CHF_2$], [BB239; 1, N, CH, H, $C_2F_5$, $CH_2CHF_2$], [BB240; 1, N, CH, H, $C_3F_7$, $CH_2CHF_2$], [BB241; 1, N, CH, H, $CH_2CF_3$, $CH_2CHF_2$], [BB242; 1, N, CH, H, $CH_2CHF_2$, $CH_2CHF_2$], [BB243; 2, N, CH, H, F, $CH_2CHF_2$], [BB244; 2, N, CH, H, Cl, $CH_2CHF_2$], [BB245; 2, N, CH, H, Br, $CH_2CHF_2$], [BB246; 2, N, CH, H, I, $CH_2CHF_2$], [BB247; 2, N, CH, H, $CF_3$, $CH_2CHF_2$], [BB248; 2, N, CH, H, $CF_2H$, $CH_2CHF_2$], [BB249; 2, N, CH, H, $C_2F_5$, $CH_2CHF_2$], [BB250; 2, N, CH, H, $C_3F_7$, $CH_2CHF_2$], [BB251; 2, N, CH, H, $CH_2CF_3$, $CH_2CHF_2$], [BB252; 2, N, CH, H, $CH_2CHF_2$, $CH_2CHF_2$], [BB253; 0, N, CH, H, H, $SCF_3$], [BB254; 0, N, CH, F, H, $SCF_3$], [BB255; 0, N, CH, Cl, H, $SCF_3$], [BB256; 0, N, CH, Br, H, $SCF_3$], [BB257; 0, N, CH, I, H, $SCF_3$], [BB258; 0, N, CH, $CF_3$, H, $SCF_3$], [BB259; 0, N, CH, $CF_2H$, H, $SCF_3$], [BB260; 0, N, CH, $C_2F_5$, H, $SCF_3$], [BB261; 0, N, CH, $C_3F$, H, $SCF_3$], [BB262; 0, N, CH, $CH_2CF_3$, H, $SCF_3$], [BB263; 0, N, CH, $CH_2CHF_2$, H, $SCF_3$], [BB264; 1, N, CH, H, H, $SCF_3$], [BB265; 1, N, CH, F, H, $SCF_3$], [BB266; 1, N, CH, Cl, H, $SCF_3$], [BB267; 1, N, CH, Br, H, $SCF_3$], [BB268; 1, N, CH, I, H, $SCF_3$], [BB269; 1, N, CH, $CF_3$, H, $SCF_3$], [BB270; 1, N, CH, $CF_2H$, H, $SCF_3$], [BB271; 1, N, CH, $C_2F_5$, H, $SCF_3$], [BB272; 1, N, CH, $C_3F_7$, H, $SCF_3$], [BB273; 1, N, CH, $CH_2CF_3$, H, $SCF_3$], [BB274; 1, N, CH, $CH_2CHF_2$, H, $SCF_3$], [BB275; 2, N, CH, H, H, $SCF_3$], [BB276; 2, N, CH, F, H, $SCF_3$], [BB277; 2, N, CH, Cl, H, $SCF_3$], [BB278; 2, N, CH, Br, H, $SCF_3$], [BB279; 2, N, CH, I, H, $SCF_3$], [BB280; 2, N, CH, $CF_3$, H, $SCF_3$], [BB281; 2, N, CH, $CF_2H$, H, $SCF_3$], [BB282; 2, N, CH, $C_2F_5$, H, $SCF_3$], [BB283; 2, N, CH, $C_3F_7$, H, $SCF_3$], [BB284; 2, N, CH, $CH_2CF_3$, H, $SCF_3$], [BB285; 2, N, CH, $CH_2CHF_2$, H, $SCF_3$], [BB286; 0, N, CH, H, F, $SCF_3$], [BB287; 0, N, CH, H, Cl, $SCF_3$], [BB288; 0, N, CH, H, Br, $SCF_3$], [BB289; 0, N, CH, H, I, $SCF_3$], [BB290; 0, N, CH, H, $CF_3$, $SCF_3$], [BB291; 0, N, CH, H, $CF_2H$, $SCF_3$], [BB292; 0, N, CH, H, $C_2F_5$, $SCF_3$], [BB293; 0, N, CH, H, $C_3F_7$, $SCF_3$], [BB294; 0, N, CH, H, $CH_2CF_3$, $SCF_3$], [BB295; 0, N, CH, H, $CH_2CHF_2$, $SCF_3$], [BB296; 1, N, CH, H, F, $SCF_3$], [BB297; 1, N, CH, H, Cl, $SCF_3$], [BB298; 1, N, CH, H, Br, $SCF_3$], [BB299; 1, N, CH, H, I, $SCF_3$], [BB300; 1, N, CH, H, $CF_3$, $SCF_3$], [BB301; 1, N, CH, H, $CF_2H$, $SCF_3$], [BB302; 1, N, CH, H, $C_2F_5$, $SCF_3$], [BB303; 1, N, CH, H, $C_3F_7$, $SCF_3$], [BB304; 1, N, CH, H, $CH_2CF_3$, $SCF_3$], [BB305; 1, N, CH, H, $CH_2CHF_2$, $SCF_3$], [BB306; 2, N, CH, H, F, $SCF_3$], [BB307; 2, N, CH, H, Cl, $SCF_3$], [BB308; 2, N, CH, H, Br, $SCF_3$], [BB309; 2, N, CH, H, I, $SCF_3$], [BB310; 2, N, CH, H, $CF_3$, $SCF_3$], [BB311; 2, N, CH, H, $CF_2H$, $SCF_3$], [BB312; 2, N, CH, H, $C_2F_5$, $SCF_3$], [BB313; 2, N, CH, H, $C_3F_7$, $SCF_3$], [BB314; 2, N, CH, H, $CH_2CF_3$, $SCF_3$], [BB315; 2, N, CH, H, $CH_2CHF_2$, $SCF_3$], [BB316; 0, N, CH, H, H, $OCF_3$], [BB317; 0, N, CH, F, H, $OCF_3$], [BB318; 0, N, CH, Cl, H, $OCF_3$], [BB319; 0, N, CH, Br, H, $OCF_3$], [BB320; 0, N, CH, I, H, $OCF_3$], [BB321; 0, N, CH, $CF_3$, H, $OCF_3$], [BB322; 0, N, CH, $CF_2H$, H, $OCF_3$], [BB323; 0, N, CH, $C_2F_5$, H, $OCF_3$], [BB324; 0, N, CH, $C_3F_7$, H, $OCF_3$], [BB325; 0, N, CH, $CH_2CF_3$, H, $OCF_3$], [BB326; 0, N, CH, $CH_2CHF_2$, H, $OCF_3$], [BB327; 1, N, CH, H, H, $OCF_3$], [BB328; 1, N, CH, F, H, $OCF_3$], [BB329; 1, N, CH, Cl, H, $OCF_3$], [BB330; 1, N, CH, Br, H, $OCF_3$], [BB331; 1, N, CH, I, H, $OCF_3$], [BB332; 1, N, CH, $CF_3$, H, $OCF_3$], [BB333; 1, N, CH, $CF_2H$, H, $OCF_3$], [BB334; 1, N, CH, $C_2F_5$, H, $OCF_3$], [BB335; 1, N, CH, $C_3F_7$, H, $OCF_3$], [BB336; 1, N, CH, $CH_2CF_3$, H, $OCF_3$], [BB337; 1, N, CH, $CH_2CHF_2$, H, $OCF_3$], [BB338; 2, N, CH, H, H, $OCF_3$], [BB339; 2, N, CH, F, H, $OCF_3$], [BB340; 2, N, CH, Cl, H, $OCF_3$], [BB341; 2, N, CH, Br, H, $OCF_3$], [BB342; 2, N, CH, I, H, $OCF_3$], [BB343; 2, N, CH, $CF_3$, H, $OCF_3$], [BB344; 2, N, CH, $CF_2H$, H, $OCF_3$], [BB345; 2, N, CH, $C_2F_5$, H, $OCF_3$], [BB346; 2, N, CH, $C_3F_7$, H, $OCF_3$], [BB347; 2, N, CH, $CH_2CF_3$, H, $OCF_3$], [BB348; 2, N, CH, $CH_2CHF_2$, H, $OCF_3$], [BB349; 0, N, CH, H, F, $OCF_3$], [BB350; 0, N, CH, H, Cl, $OCF_3$], [BB351; 0, N, CH, H, Br, $OCF_3$], [BB352; 0, N, CH, H, I, $OCF_3$], [BB353; 0, N, CH, H, $CF_3$, $OCF_3$], [BB354; 0, N, CH, H, $CF_2H$, $OCF_3$], [BB355; 0, N, CH, H, $C_2F_5$, $OCF_3$], [BB356; 0, N, CH, H, $C_3F_7$, $OCF_3$], [BB357; 0, N, CH, H, $CH_2CF_3$, $OCF_3$], [BB358; 0, N, CH, H, $CH_2CHF_2$, $OCF_3$], [BB359; 1, N, CH, H, F, $OCF_3$], [BB360; 1, N, CH, H, Cl, $OCF_3$], [BB361; 1, N, CH, H, Br, $OCF_3$], [BB362; 1, N, CH, H, I, $OCF_3$], [BB363; 1, N, CH, H, $CF_3$, $OCF_3$], [BB364; 1, N, CH, H, $CF_2H$, $OCF_3$], [BB365; 1, N, CH, H, $C_2F_5$, $OCF_3$], [BB366; 1, N, CH, H, $C_3F_7$, $OCF_3$], [BB367; 1, N, CH, H, $CH_2CF_3$, $OCF_3$], [BB368; 1, N, CH, H, $CH_2CHF_2$, $OCF_3$], [BB369; 2, N, CH, H, F, $OCF_3$], [BB370; 2, N, CH, H, Cl, $OCF_3$], [BB371; 2, N, CH, H, Br, $OCF_3$], [BB372; 2, N, CH, H, I, $OCF_3$], [BB373; 2, N, CH, H, $CF_3$, $OCF_3$], [BB374; 2, N, CH, H, $CF_2H$, $OCF_3$], [BB375; 2, N, CH, H, $C_2F_5$, $OCF_3$], [BB376; 2, N, CH, H, $C_3F_7$, $OCF_3$], [BB377; 2, N, CH, H, $CH_2CF_3$, $OCF_3$], [BB378; 2, N, CH, H, $CH_2CHF_2$, $OCF_3$], [BB379; 0, N, CH, H, H, $OCHF_2$], [BB380; 0, N, CH, F, H, $OCHF_2$], [BB381; 0, N, CH, Cl, H, $OCHF_2$], [BB382; 0, N, CH, Br, H, $OCHF_2$], [BB383; 0, N, CH, I, H, $OCHF_2$], [BB384; 0, N, CH, $CF_3$, H, $OCHF_2$], [BB385; 0, N, CH, $CF_2H$, H, $OCHF_2$], [BB386; 0, N, CH, $C_2F_5$, H, $OCHF_2$], [BB387; 0, N, CH, $C_3F_7$, H, $OCHF_2$], [BB388; 0, N, CH, $CH_2CF_3$, H, $OCHF_2$], [BB389; 0, N, CH, $CH_2CHF_2$, H, $OCHF_2$], [BB390; 1, N, CH, H, H, $OCHF_2$], [BB391; 1, N, CH, F, H, $OCHF_2$], [BB392; 1, N, CH, Cl, H, $OCHF_2$], [BB393; 1, N, CH, Br, H, $OCHF_2$], [BB394; 1, N, CH, I, H, $OCHF_2$], [BB395; 1, N, CH, $CF_3$, H, $OCHF_2$], [BB396; 1, N, CH, $CF_2H$, H, $OCHF_2$], [BB397; 1, N, CH, $C_2F_5$, H, $OCHF_2$], [BB398; 1, N, CH, $C_3F_7$, H, $OCHF_2$], [BB399; 1, N, CH, $CH_2CF_3$, H, $OCHF_2$], [BB400; 1, N, CH, $CH_2CHF_2$, H, $OCHF_2$], [BB401; 2, N, CH, H, H, $OCHF_2$], [BB402; 2, N, CH, F, H, $OCHF_2$], [BB403; 2, N, CH, Cl, H, $OCHF_2$], [BB404; 2, N, CH, Br, H, $OCHF_2$], [BB405; 2, N, CH, I, H, $OCHF_2$], [BB406; 2, N, CH, $CF_3$, H, $OCHF_2$], [BB407; 2, N, CH, $CF_2H$, H, $OCHF_2$], [BB408; 2, N, CH, $C_2F$, H, $OCHF_2$], [BB409; 2, N, CH, $C_3F_7$, H, $OCHF_2$], [BB410; 2, N, CH, $CH_2CF_3$, H, $OCHF_2$], [BB411; 2, N, CH, $CH_2CHF_2$, H, $OCHF_2$], [BB412; 0, N, CH, H, F, $OCHF_2$], [BB413; 0, N, CH, H, Cl, $OCHF_2$], [BB414; 0, N, CH, H, Br, $OCHF_2$], [BB415; 0, N, CH, H, I, $OCHF_2$], [BB416; 0, N, CH, H, $CF_3$, $OCHF_2$], [BB417; 0, N, CH, H, $CF_2H$, $OCHF_2$], [BB418; 0, N, CH, H, $C_2F$ %, $OCHF_2$], [BB419; 0, N, CH, H, $C_3F_7$, $OCHF_2$], [BB420; 0, N, CH, H, $CH_2CF_3$, $OCHF_2$], [BB421; 0, N, CH, H, $CH_2CHF_2$, $OCHF_2$], [BB422; 1, N, CH, H, F, $OCHF_2$], [BB423; 1, N, CH, H, Cl, $OCHF_2$], [BB424; 1, N, CH, H, Br, $OCHF_2$], [BB425; 1, N, CH, H, I, $OCHF_2$], [BB426; 1, N, CH, H, $CF_3$, $OCHF_2$], [BB427; 1, N, CH, H, $CF_2H$, $OCHF_2$], [BB428; 1, N, CH, H, $C_2F_5$, $OCHF_2$], [BB429; 1, N, CH, H, $C_3F_7$, $OCHF_2$], [BB430; 1, N, CH, H, $CH_2CF_3$, $OCHF_2$], [BB431; 1, N, CH, H, $CH_2CHF_2$, $OCHF_2$], [BB432; 2, N, CH, H, F, $OCHF_2$], [BB433; 2, N, CH, H, Cl, $OCHF_2$], [BB434; 2, N, CH, H, Br, $OCHF_2$], [BB435; 2, N, CH, H, I, $OCHF_2$], [BB436; 2, N, CH, H, $CF_3$, $OCHF_2$], [BB437; 2, N, CH, H, $CF_2H$, $OCHF_2$], [BB438; 2, N, CH, H, $C_2F_5$, $OCHF_2$], [BB439; 2, N, CH, H, $C_3F_7$, $OCHF_2$], [BB440; 2, N, CH, H, $CH_2CF_3$, $OCHF_2$], [BB441; 2, N, CH, H, $CH_2CHF_2$, $OCHF_2$], [BB442; 0, N, CH, H, H, Br], [BB443; 0, N, CH, F, H, Br], [BB444; 0, N, CH, Cl, H, Br], [BB445; 0, N, CH, Br, H, Br], [BB446; 0, N, CH, I, H, Br], [BB447; 0, N, CH, $CF_3$, H, Br], [BB448; 0, N, CH, $CF_2H$, H, Br], [BB449; 0, N, CH, $C_2F_5$, H, Br], [BB450; 0, N, CH, $C_3F_7$, H, Br], [BB451; 0, N, CH, $CH_2CF_3$, H, Br], [BB452; 0, N, CH, $CH_2CHF_2$, H, Br], [BB453; 1, N, CH, H, H, Br], [BB454; 1, N, CH, F, H, Br], [BB455; 1, N, CH, Cl, H, Br], [BB456; 1, N, CH, Br, H, Br], [BB457; 1, N, CH, I, H, Br], [BB458; 1, N, CH, $CF_3$, H, Br], [BB459; 1, N, CH, $CF_2H$, H, Br], [BB460; 1, N, CH, $C_2F_5$, H, Br], [BB461; 1, N, CH, $C_3F_7$, H, Br], [BB462; 1, N, CH, $CH_2CF_3$, H, Br], [BB463; 1, N, CH, $CH_2CHF_2$, H, Br], [BB464; 2, N, CH, H, H, Br], [BB465; 2, N, CH, F, H, Br], [BB466; 2, N, CH, Cl, H, Br], [BB467; 2, N, CH, Br, H, Br], [BB468; 2, N, CH, I, H, Br], [BB469; 2, N, CH, $CF_3$, H, Br], [BB470; 2, N, CH, $CF_2H$, H, Br], [BB471; 2, N, CH, $C_2F_5$, H, Br], [BB472; 2, N, CH, $C_3F_7$, H, Br], [BB473; 2, N, CH, $CH_2CF_3$, H, Br], [BB474; 2, N, CH, $CH_2CHF_2$, H, Br], [BB475; 0, N, CH, H, F, Br], [BB476; 0, N, CH, H, Cl, Br], [BB477; 0, N, CH, H, Br, Br], [BB478; 0, N, CH, H, I, Br], [BB479; 0, N, CH, H, $CF_3$, Br], [BB480; 0, N, CH, H, $CF_2H$, Br], [BB481; 0, N, CH, H, $C_2F_5$, Br], [BB482; 0, N, CH, H, $C_3F_7$, Br], [BB483; 0, N, CH, H, $CH_2CF_3$, Br], [BB484; 0, N, CH, H, $CH_2CHF_2$, Br], [BB485; 1, N, CH, H, F, Br], [BB486; 1, N, CH, H, Cl, Br], [BB487; 1, N, CH, H, Br, Br], [BB488; 1, N, CH, H, I, Br], [BB489; 1, N, CH, H, $CF_3$, Br], [BB490; 1, N, CH, H, $CF_2H$, Br], [BB491; 1, N, CH, H, $C_2F_5$, Br], [BB492; 1, N, CH, H, $C_3F_7$, Br], [BB493; 1, N, CH, H, $CH_2CF_3$, Br], [BB494; 1, N, CH, H, $CH_2CHF_2$, Br], [BB495; 2, N, CH, H, F, Br], [BB496; 2, N, CH, H, Cl, Br], [BB497; 2, N, CH, H, Br, Br], [BB498; 2, N, CH, H, I, Br], [BB499; 2, N, CH, H, $CF_3$, Br], [BB500; 2, N, CH, H, $CF_2H$, Br], [BB501; 2, N, CH, H, $C_2F_5$, Br], [BB502; 2, N, CH, H, $C_3F_7$, Br], [BB503; 2, N, CH, H, $CH_2CF_3$, Br], [BB504; 2, N, CH, H, $CH_2CHF_2$, Br], [BB505; 0, N, CH, H, H, Cl], [BB506; 0, N, CH, F, H, Cl], [BB507; 0, N, CH, Cl, H, Cl], [BB508; 0, N, CH, Br, H, Cl], [BB509; 0, N, CH, I, H, Cl], [BB510; 0, N, CH, $CF_3$, H, Cl], [BB511; 0, N, CH, $CF_2H$, H, Cl], [BB512; 0, N, CH, $C_2F_5$, H, Cl], [BB513; 0, N, CH, $C_3F_7$, H, Cl], [BB514; 0, N, CH, $CH_2CF_3$, H, Cl], [BB515; 0, N, CH, $CH_2CHF_2$, H, Cl], [BB516; 1, N, CH, H, H, Cl], [BB517; 1, N, CH, F, H, Cl], [BB518; 1, N, CH, Cl, H, Cl], [BB519; 1, N, CH, Br, H, Cl], [BB520; 1, N, CH, I, H, Cl], [BB521; 1, N, CH, $CF_3$, H, Cl], [BB522; 1, N, CH, $CF_2H$, H, Cl], [BB523; 1, N, CH, $C_2F_5$, H, Cl], [BB524; 1, N, CH, $C_3F_7$, H, Cl], [BB525; 1, N, CH, $CH_2CF_3$, H, Cl], [BB526; 1, N, CH, $CH_2CHF_2$, H, Cl], [BB527; 2, N, CH, H, H, Cl], [BB528; 2, N, CH, F, H, Cl], [BB529; 2, N, CH, Cl, H, Cl], [BB530; 2, N, CH, Br, H, Cl], [BB531; 2, N, CH, I, H, Cl], [BB532; 2, N, CH, $CF_3$, H, Cl], [BB533; 2, N, CH, $CF_2H$, H, Cl], [BB534; 2, N, CH, $C_2F_5$, H, Cl], [BB535; 2, N, CH, $C_3F_7$, H, Cl], [BB536; 2, N, CH, $CH_2CF_3$, H, Cl], [BB537; 2, N, CH, $CH_2CHF_2$, H, Cl], [BB538; 0, N, CH, H, F, Cl], [BB539; 0, N, CH, H, Cl, Cl], [BB540; 0, N, CH, H, Br, Cl], [BB541; 0, N, CH, H, I, Cl], [BB542; 0, N, CH, H, $CF_3$, Cl], [BB543; 0, N, CH, H, $CF_2H$, Cl], [BB544; 0, N, CH, H, $C_2F_5$, Cl], [BB545; 0, N, CH, H, $C_3F_7$, Cl], [BB546; 0, N, CH, H, $CH_2CF_3$, Cl], [BB547; 0, N, CH, H, $CH_2CHF_2$, Cl], [BB548; 1, N, CH, H, F, Cl], [BB549; 1, N, CH, H, Cl, Cl], [BB550; 1, N, CH, H, Br, Cl], [BB551; 1, N, CH, H, I, Cl], [BB552; 1, N, CH, H, $CF_3$, Cl], [BB553; 1, N, CH, H, $CF_2H$, Cl], [BB554; 1, N, CH, H, $C_2F_5$, Cl], [BB555; 1, N, CH, H, $C_3F_7$, Cl], [BB556; 1, N, CH, H, $CH_2CF_3$, Cl], [BB557; 1, N, CH, H, $CH_2CHF_2$, Cl], [BB558; 2, N, CH, H, F, Cl],

[BB559; 2, N, CH, H, Cl, Cl], [BB560; 2, N, CH, H, Br, Cl], [BB561; 2, N, CH, H, I, Cl], [BB562; 2, N, CH, H, $CF_3$, Cl], [BB563; 2, N, CH, H, $CF_2H$, Cl], [BB564; 2, N, CH, H, $C_2F_5$, Cl], [BB565; 2, N, CH, H, $C_3F_7$, Cl], [BB566; 2, N, CH, H, $CH_2CF_3$, Cl], [BB567; 2, N, CH, H, $CH_2CHF_2$, Cl], [BB568; 0, N, CH, H, H, I], [BB569; 0, N, CH, F, H, I], [BB570; 0, N, CH, Cl, H, I], [BB571; 0, N, CH, Br, H, I], [BB572; 0, N, CH, I, H, I], [BB573; 0, N, CH, $CF_3$, H, I], [BB574; 0, N, CH, $CF_2H$, H, I], [BB575; 0, N, CH, $C_2F_5$, H, I], [BB576; 0, N, CH, $C_3F_7$, H, I], [BB577; 0, N, CH, $CH_2CF_3$, H, I], [BB578; 0, N, CH, $CH_2CHF_2$, H, I], [BB579; 1, N, CH, H, H, I], [BB580; 1, N, CH, F, H, I], [BB581; 1, N, CH, Cl, H, I], [BB582; 1, N, CH, Br, H, I], [BB583; 1, N, CH, I, H, I], [BB584; 1, N, CH, $CF_3$, H, I], [BB585; 1, N, CH, $CF_2H$, H, I], [BB586; 1, N, CH, $C_2F_5$, H, I], [BB587; 1, N, CH, $C_3F_7$, H, I], [BB588; 1, N, CH, $CH_2CF_3$, H, I], [BB589; 1, N, CH, $CH_2CHF_2$, H, I], [BB590; 2, N, CH, H, H, I], [BB591; 2, N, CH, F, H, I], [BB592; 2, N, CH, Cl, H, I], [BB593; 2, N, CH, Br, H, I], [BB594; 2, N, CH, I, H, I], [BB595; 2, N, CH, $CF_3$, H, I], [BB596; 2, N, CH, $CF_2H$, H, I], [BB597; 2, N, CH, $C_2F_5$, H, I], [BB598; 2, N, CH, $C_3F_7$, H, I], [BB599; 2, N, CH, $CH_2CF_3$, H, I], [BB600; 2, N, CH, $CH_2CHF_2$, H, I], [BB601; 0, N, CH, H, F, I], [BB602; 0, N, CH, H, Cl, I], [BB603; 0, N, CH, H, Br, I], [BB604; 0, N, CH, H, I, I], [BB605; 0, N, CH, H, $CF_3$, I], [BB606; 0, N, CH, H, $CF_2H$, I], [BB607; 0, N, CH, H, $C_2F_5$, I], [BB608; 0, N, CH, H, $C_3F_7$, I], [BB609; 0, N, CH, H, $CH_2CF_3$, I], [BB610; 0, N, CH, H, $CH_2CHF_2$, I], [BB611; 1, N, CH, H, F, I], [BB612; 1, N, CH, H, Cl, I], [BB613; 1, N, CH, H, Br, I], [BB614; 1, N, CH, H, I, I], [BB615; 1, N, CH, H, $CF_3$, I], [BB616; 1, N, CH, H, $CF_2H$, I], [BB617; 1, N, CH, H, $C_2F_2$, I], [BB618; 1, N, CH, H, $C_3F_7$, I], [BB619; 1, N, CH, H, $CH_2CF_3$, I], [BB620; 1, N, CH, H, $CH_2CHF_2$, I], [BB621; 2, N, CH, H, F, I], [BB622; 2, N, CH, H, Cl, I], [BB623; 2, N, CH, H, Br, I], [BB624; 2, N, CH, H, I, I], [BB625; 2, N, CH, H, $CF_3$, I], [BB626; 2, N, CH, H, $CF_2H$, I], [BB627; 2, N, CH, H, $C_2F_5$, I], [BB628; 2, N, CH, H, $C_3F_7$, I], [BB629; 2, N, CH, H, $CH_2CF_3$, I], [BB630; 2, N, CH, H, $CH_2CHF_2$, I], [BB631; 0, N, CH, H, H, F], [BB632; 0, N, CH, F, H, F], [BB633; 0, N, CH, Cl, H, F], [BB634; 0, N, CH, Br, H, F], [BB635; 0, N, CH, I, H, F], [BB636; 0, N, CH, $CF_3$, H, F], [BB637; 0, N, CH, $CF_2H$, H, F], [BB638; 0, N, CH, $C_2F_5$, H, F], [BB639; 0, N, CH, $C_3F_7$, H, F], [BB640; 0, N, CH, $CH_2CF_3$, H, F], [BB641; 0, N, CH, $CH_2CHF_2$, H, F], [BB642; 1, N, CH, H, H, F], [BB643; 1, N, CH, F, H, F], [BB644; 1, N, CH, Cl, H, F], [BB645; 1, N, CH, Br, H, F], [BB646; 1, N, CH, I, H, F], [BB647; 1, N, CH, $CF_3$, H, F], [BB648; 1, N, CH, $CF_2H$, H, F], [BB649; 1, N, CH, $C_2F_5$, H, F], [BB650; 1, N, CH, $C_3F_7$, H, F], [BB651; 1, N, CH, $CH_2CF_3$, H, F], [BB652; 1, N, CH, $CH_2CHF_2$, H, F], [BB653; 2, N, CH, H, H, F], [BB654; 2, N, CH, F, H, F], [BB655; 2, N, CH, Cl, H, F], [BB656; 2, N, CH, Br, H, F], [BB657; 2, N, CH, I, H, F], [BB658; 2, N, CH, $CF_3$, H, F], [BB659; 2, N, CH, $CF_2H$, H, F], [BB660; 2, N, CH, $C_2F_5$, H, F], [BB661; 2, N, CH, $C_3F_7$, H, F], [BB662; 2, N, CH, $CH_2CF_3$, H, F], [BB663; 2, N, CH, $CH_2CHF_2$, H, F], [BB664; 0, N, CH, H, F, F], [BB665; 0, N, CH, H, Cl, F], [BB666; 0, N, CH, H, Br, F], [BB667; 0, N, CH, H, I, F], [BB668; 0, N, CH, H, $CF_3$, F], [BB669; 0, N, CH, H, $CF_2H$, F], [BB670; 0, N, CH, H, $C_2F_5$, F], [BB671; 0, N, CH, H, $C_3F_7$, F], [BB672; 0, N, CH, H, $CH_2CF_3$, F], [BB673; 0, N, CH, H, $CH_2CHF_2$, F], [BB674; 1, N, CH, H, F, F], [BB675; 1, N, CH, H, Cl, F], [BB676; 1, N, CH, H, Br, F], [BB677; 1, N, CH, H, I, F], [BB678; 1, N, CH, H, $CF_3$, F], [BB679; 1, N, CH, H, $CF_2H$, F], [BB680; 1, N, CH, H, $C_2F_5$, F], [BB681; 1, N, CH, H, $C_3F_7$, F], [BB682; 1, N, CH, H, $CH_2CF_3$, F], [BB683; 1, N, CH, H, $CH_2CHF_2$, F], [BB684; 2, N, CH, H, F, F], [BB685; 2, N, CH, H, Cl, F], [BB686; 2, N, CH, H, Br, F], [BB687; 2, N, CH, H, I, F], [BB688; 2, N, CH, H, $CF_3$, F], [BB689; 2, N, CH, H, $CF_2H$, F], [BB690; 2, N, CH, H, $C_2F_5$, F], [BB691; 2, N, CH, H, $C_3F_7$, F], [BB692; 2, N, CH, H, $CH_2CF_3$, F], [BB693; 2, N, CH, H, $CH_2CHF_2$, F]

A compound represented by formula (L-6)

(L-6)

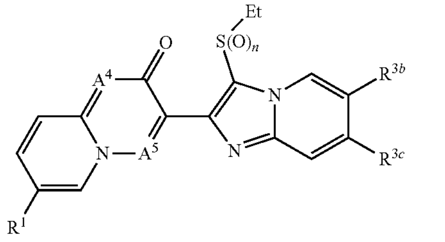

wherein the combination of the symbol n, and the substituents $A^4$, $A^5$, $R^{3b}$, $R^{3c}$, and $R^1$ represents any one combination indicated in the Combination BB (hereinafter referred to as "Compound group SX6").

A compound represented by formula (L-7)

(L-7)

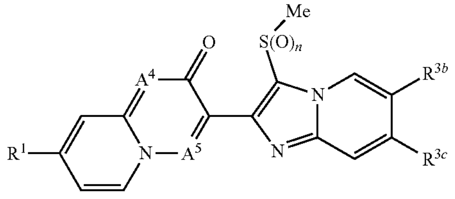

wherein the combination of the symbol n, and the substituents $A^4$, $A^5$, $R^{3b}$, $R^{3c}$, and $R^1$ represents any one combination indicated in the Combination BB (hereinafter referred to as "Compound group SX7").

A compound represented by formula (L-8)

(L-8)

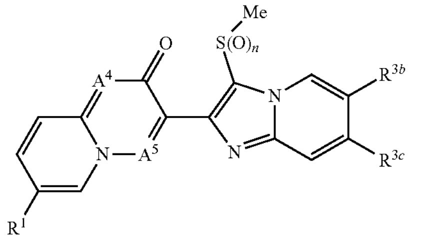

wherein the combination of the symbol n, and the substituents $A^4$, $A^5$, $R^{3b}$, $R^{3c}$, and $R^1$ represents any one combination indicated in the Combination BB (hereinafter referred to as "Compound group SX8").

A compound represented by formula (L-9)

(L-9)

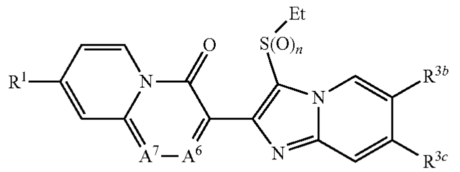

wherein the combination of the symbol n, and the substituents $A^6$, $A^7$, $R^{3b}$, $R^{3c}$, and $R^1$ represents any one combination indicated in the Combination CC (hereinafter referred to as "Compound group SX9").

The Combination CC consists of substituent numbers CC1 to CC2904. The substituent numbers CC1 to CC2904 represent the combinations of the symbol n, and the substituents $A^6$, $A^7$, $R^{3b}$, $R^{3c}$, and $R^1$, and hereinafter referred to as "[substituent number; n, $A^6$, $A^7$, $R^{3b}$, $R^{3c}$, $R^1$]". For example, the substituent number CC2 means a combination wherein n represents 0, $A^6$ represents CH, $A^7$ represents CH, $R^{3b}$ represents a fluorine atom, $R^{3c}$ represents a hydrogen atom, and $R^1$ represents $CF_3$.

Combination CC: [CC1; 0, CH, CH, H, H, $CF_3$], [CC2; 0, CH, CH, F, H, $CF_3$], [CC3; 0, CH, CH, Cl, H, $CF_3$], [CC4; 0, CH, CH, Br, H, $CF_3$], [CC5; 0, CH, CH, I, H, $CF_3$], [CC6; 0, CH, CH, $CF_3$, H, $CF_3$], [CC7; 0, CH, CH, $CF_2$, H, H, $CF_3$], [CC8; 0, CH, CH, $C_2F$, H, $CF_3$], [CC9; 0, CH, CH, $C_3F_7$, H, $CF_3$], [CC10; 0, CH, CH, CH $CF_3$, H, $CF_3$], [CC11; 0, CH, CH, CH $CHF_2$, H, $CF_3$], [CC12; 1, CH, CH, H, H, $CF_3$], [CC13; 1, CH, CH, F, H, $CF_3$], [CC14; 1, CH, CH, Cl, H, $CF_3$], [CC15; 1, CH, CH, Br, H, $CF_3$], [CC16; 1, CH, CH, I, H, $CF_3$], [CC17; 1, CH, CH, $CF_3$, H, $CF_3$], [CC18; 1, CH, CH, $CF_2H$, H, $CF_3$], [CC19; 1, CH, CH, $C_2F_5$, H, $CF_3$], [CC20; 1, CH, CH, $C_3F_7$, H, $CF_3$], [CC21; 1, CH, CH, $CH_2CF_3$, H, $CF_3$], [CC22; 1, CH, CH, $CH_2CHF_2$, H, $CF_3$], [CC23; 2, CH, CH, H, H, $CF_3$], [CC24; 2, CH, CH, F, H, $CF_3$], [CC25; 2, CH, CH, Cl, H, $CF_3$], [CC26; 2, CH, CH, Br, H, $CF_3$], [CC27; 2, CH, CH, I, H, $CF_3$], [CC28; 2, CH, CH, $CF_3$, H, $CF_3$], [CC29; 2, CH, CH, $CF_2H$, H, $CF_3$], [CC30; 2, CH, CH, $C_2F_5$, H, $CF_3$], [CC31; 2, CH, CH, $C_3F_7$, H, $CF_3$], [CC32; 2, CH, CH, $CH_2CF_3$, H, $CF_3$], [CC33; 2, CH, CH, $CH_2CHF_2$, H, $CF_3$], [CC34; 0, N, CH, H, H, $CF_3$], [CC35; 0, N, CH, F, H, $CF_3$], [CC36; 0, N, CH, Cl, H, $CF_3$], [CC37; 0, N, CH, Br, H, $CF_3$], [CC38; 0, N, CH, I, H, $CF_3$], [CC39; 0, N, CH, $CF_3$, H, $CF_3$], [CC40; 0, N, CH, $CF_2H$, H, $CF_3$], [CC41; 0, N, CH, $C_2F_5$, H, $CF_3$], [CC42; 0, N, CH, $C_3F_7$, H, $CF_3$], [CC43; 0, N, CH, $CH_2CF_3$, H, $CF_3$], [CC44; 0, N, CH, $CH_2CHF_2$, H, $CF_3$], [CC45; 1, N, CH, H, H, $CF_3$], [CC46; 1, N, CH, F, H, $CF_3$], [CC47; 1, N, CH, Cl, H, $CF_3$], [CC48; 1, N, CH, Br, H, $CF_3$], [CC49; 1, N, CH, I, H, $CF_3$], [CC50; 1, N, CH, $CF_3$, H, $CF_3$], [CC51; 1, N, CH, $CF_2H$, H, $CF_3$], [CC52; 1, N, CH, $C_2F_5$, H, $CF_3$], [CC53; 1, N, CH, $C_3F_7$, H, $CF_3$], [CC54; 1, N, CH, $CH_2CF_3$, H, $CF_3$], [CC55; 1, N, CH, $CH_2CHF_2$, H, $CF_3$], [CC56; 2, N, CH, H, H, $CF_3$], [CC57; 2, N, CH, F, H, $CF_3$], [CC58; 2, N, CH, Cl, H, $CF_3$], [CC59; 2, N, CH, Br, H, $CF_3$], [CC60; 2, N, CH, I, H, $CF_3$], [CC61; 2, N, CH, $CF_3$, H, $CF_3$], [CC62; 2, N, CH, $CF_2H$, H, $CF_3$], [CC63; 2, N, CH, $C_2F$, H, $CF_3$], [CC64; 2, N, CH, $C_3F_2$, H, $CF_3$], [CC65; 2, N, CH, $CH_2CF_3$, H, $CF_3$], [CC66; 2, N, CH, $CH_2CHF_2$, H, $CF_3$], [CC67; 0, CH, N, H, H, $CF_3$], [CC68; 0, CH, N, F, H, $CF_3$], [CC69; 0, CH, N, Cl, H, $CF_3$], [CC70; 0, CH, N, Br, H, $CF_3$], [CC71; 0, CH, N, I, H, $CF_3$], [CC72; 0, CH, N, $CF_3$, H, $CF_3$], [CC73; 0, CH, N, $CF_2H$, H, $CF_3$], [CC74; 0, CH, N, $C_2F_5$, H, $CF_3$], [CC75; 0, CH, N, $C_3F_7$, H, $CF_3$], [CC76; 0, CH, N, $CH_2CF_3$, H, $CF_3$], [CC77; 0, CH, N, $CH_2CHF_2$, H, $CF_3$], [CC78; 1, CH, N, H, H, $CF_3$], [CC79; 1, CH, N, F, H, $CF_3$], [CC80; 1, CH, N, Cl, H, $CF_3$], [CC81; 1, CH, N, Br, H, $CF_3$], [CC82; 1, CH, N, I, H, $CF_3$], [CC83; 1, CH, N, $CF_3$, H, $CF_3$], [CC84; 1, CH, N, $CF_2H$, H, $CF_3$], [CC85; 1, CH, N, $C_2F_3$, H, $CF_3$], [CC86; 1, CH, N, $C_3F_7$, H, $CF_3$], [CC87; 1, CH, N, $CH_2CF_3$, H, $CF_3$], [CC88; 1, CH, N, $CH_2CHF_2$, H, $CF_3$], [CC89; 2, CH, N, H, H, $CF_3$], [CC90; 2, CH, N, F, H, $CF_3$], [CC91; 2, CH, N, Cl, H, $CF_3$], [CC92; 2, CH, N, Br, H, $CF_3$], [CC93; 2, CH, N, I, H, $CF_3$], [CC94; 2, CH, N, $CF_3$, H, $CF_3$], [CC95; 2, CH, N, $CF_2H$, H, $CF_3$], [CC96; 2, CH, N, $C_2F_5$, H, $CF_3$], [CC97; 2, CH, N, $C_3F_7$, H, $CF_3$], [CC98; 2, CH, N, $CH_2CF_3$, H, $CF_3$], [CC99; 2, CH, N, $CH_2CHF_2$, H, $CF_3$], [CC100; 0, N,N, H, H, $CF_3$], [CC101; 0, N,N, F, H, $CF_3$], [CC102; 0, N, N, Cl, H, $CF_3$], [CC103; 0, N, N, Br, H, $CF_3$], [CC104; 0, N,N, I, H, $CF_3$], [CC105; 0, N, N, $CF_3$, H, $CF_3$], [CC106; 0, N, N, $CF_2H$, H, $CF_3$], [CC107; 0, N, N, $C_2F_5$, H, $CF_3$], [CC108; 0, N, N, $C_3F_7$, H, $CF_3$], [CC109; 0, N, N, $CH_2CF_3$, H, $CF_3$], [CC110; 0, N, N, $CH_2CHF_2$, H, $CF_3$], [CC111; 1, N,N, H, H, $CF_3$], [CC112; 1, N,N, F, H, $CF_3$], [CC113; 1, N, N, Cl, H, $CF_3$], [CC114; 1, N, N, Br, H, $CF_3$], [CC115; 1, N,N, I, H, $CF_3$], [CC116; 1, N, N, $CF_3$, H, $CF_3$], [CC117; 1, N, N, $CF_2H$, H, $CF_3$], [CC118; 1, N, N, $C_2F_5$, H, $CF_3$], [CC119; 1, N, N, $C_3F_7$, H, $CF_3$], [CC120; 1, N, N, $CH_2CF_3$, H, $CF_3$], [CC121; 1, N, N, $CH_2CHF_2$, H, $CF_3$], [CC122; 2, N,N, H, H, $CF_3$], [CC123; 2, N,N, F, H, $CF_3$], [CC124; 2, N, N, Cl, H, $CF_3$], [CC125; 2, N, N, Br, H, $CF_3$], [CC126; 2, N,N, I, H, $CF_3$], [CC127; 2, N, N, $CF_3$, H, $CF_3$], [CC128; 2, N, N, $CF_2H$, H, $CF_3$], [CC129; 2, N, N, $C_2F_5$, H, $CF_3$], [CC130; 2, N, N, $C_3F_7$, H, $CF_3$], [CC131; 2, N, N, $CH_2CF_3$, H, $CF_3$], [CC132; 2, N, N, $CH_2CHF_2$, H, $CF_3$], [CC133; 0, CH, CH, H, H, $CF_3$], [CC134; 0, CH, CH, H, F, $CF_3$], [CC135; 0, CH, CH, H, Cl, $CF_3$], [CC136; 0, CH, CH, H, Br, $CF_3$], [CC137; 0, CH, CH, H, I, $CF_3$], [CC138; 0, CH, CH, H, $CF_3$, $CF_3$], [CC139; 0, CH, CH, H, $CF_2H$, $CF_3$], [CC140; 0, CH, CH, H, $C_2F_5$, $CF_3$], [CC141; 0, CH, CH, H, $C_3F_7$, $CF_3$], [CC142; 0, CH, CH, H, $CH_2CF_3$, $CF_3$], [CC143; 0, CH, CH, H, $CH_2CHF_2$, $CF_3$], [CC144; 1, CH, CH, H, H, $CF_3$], [CC145; 1, CH, CH, H, F, $CF_3$], [CC146; 1, CH, CH, H, Cl, $CF_3$], [CC147; 1, CH, CH, H, Br, $CF_3$], [CC148; 1, CH, CH, H, I, $CF_3$], [CC149; 1, CH, CH, H, $CF_3$, $CF_3$], [CC150; 1, CH, CH, H, $CF_2H$, $CF_3$], [CC151; 1, CH, CH, H, $C_2F_5$, $CF_3$], [CC152; 1, CH, CH, H, $C_3F_7$, $CF_3$], [CC153; 1, CH, CH, H, $CH_2CF_3$, $CF_3$], [CC154; 1, CH, CH, H, $CH_2CHF_2$, $CF_3$], [CC155; 2, CH, CH, H, H, $CF_3$], [CC156; 2, CH, CH, H, F, $CF_3$], [CC157; 2, CH, CH, H, Cl, $CF_3$], [CC158; 2, CH, CH, H, Br, $CF_3$], [CC159; 2, CH, CH, H, I, $CF_3$], [CC160; 2, CH, CH, H, $CF_3$, $CF_3$], [CC161; 2, CH, CH, H, $CF_2H$, $CF_3$], [CC162; 2, CH, CH, H, $C_2F_5$, $CF_3$], [CC163; 2, CH, CH, H, $C_3F_7$, $CF_3$], [CC164; 2, CH, CH, H, $CH_2CF_3$, $CF_3$], [CC165; 2, CH, CH, H, $CH_2CHF_2$, $CF_3$], [CC166; 0, N, CH, H, H, $CF_3$], [CC167; 0, N, CH, H, F, $CF_3$], [CC168; 0, N, CH, H, Cl, $CF_3$], [CC169; 0, N, CH, H, Br, $CF_3$], [CC170; 0, N, CH, H, I, $CF_3$], [CC171; 0, N, CH, H, $CF_3$, $CF_3$], [CC172; 0, N, CH, H, $CF_2H$, $CF_3$], [CC173; 0, N, CH, H, $C_2F_5$, $CF_3$], [CC174; 0, N, CH, H, $C_3F_7$, $CF_3$], [CC175; 0, N, CH, H, $CH_2CF_3$, $CF_3$], [CC176; 0, N, CH, H, $CH_2CHF_2$, $CF_3$], [CC177; 1, N, CH, H, H, $CF_3$], [CC178; 1, N, CH, H, F, $CF_3$], [CC179; 1, N, CH, H, Cl, $CF_3$], [CC180; 1, N, CH, H, Br, $CF_3$], [CC181; 1, N, CH, H, I, $CF_3$], [CC182; 1, N, CH, H, $CF_3$, $CF_3$], [CC183; 1, N, CH, H, $CF_2H$, $CF_3$], [CC184; 1, N, CH, H, $C_2F_5$, $CF_3$], [CC185; 1, N, CH, H, $C_3F_7$, $CF_3$], [CC186; 1, N, CH, H, $CH_2CF_3$, $CF_3$], [CC187; 1, N, CH, H, $CH_2CHF_2$, $CF_3$], [CC188; 2, N, CH, H, H, $CF_3$], [CC189; 2, N, CH, H, F, $CF_3$], [CC190; 2, N, CH, H, Cl, $CF_3$], [CC191; 2, N, CH, H, Br, $CF_3$], [CC192; 2, N, CH, H, I, $CF_3$],

[CC193; 2, N, CH, H, $CF_3$, $CF_3$], [CC194; 2, N, CH, H, $CF_2H$, $CF_3$], [CC195; 2, N, CH, H, $C_2F_5$, $CF_3$], [CC196; 2, N, CH, H, $C_3F_7$, $CF_3$], [CC197; 2, N, CH, H, $CH_2CF_3$, $CF_3$], [CC198; 2, N, CH, H, $CH_2CHF_2$, $CF_3$], [CC199; 0, CH, N, H, H, $CF_3$], [CC200; 0, CH, N, H, F, $CF_3$], [CC201; 0, CH, N, H, Cl, $CF_3$], [CC202; 0, CH, N, H, Br, $CF_3$], [CC203; 0, CH, N, H, I, $CF_3$], [CC204; 0, CH, N, H, $CF_3$, $CF_3$], [CC205; 0, CH, N, H, $CF_2H$, $CF_3$], [CC206; 0, CH, N, H, $C_2F_5$, $CF_3$], [CC207; 0, CH, N, H, $C_3F_7$, $CF_3$], [CC208; 0, CH, N, H, $CH_2CF_3$, $CF_3$], [CC209; 0, CH, N, H, $CH_2CHF_2$, $CF_3$], [CC210; 1, CH, N, H, H, $CF_3$], [CC211; 1, CH, N, H, F, $CF_3$], [CC212; 1, CH, N, H, Cl, $CF_3$], [CC213; 1, CH, N, H, Br, $CF_3$], [CC214; 1, CH, N, H, I, $CF_3$], [CC215; 1, CH, N, H, $CF_3$, $CF_3$], [CC216; 1, CH, N, H, $CF_2H$, $CF_3$], [CC217; 1, CH, N, H, $C_2F_5$, $CF_3$], [CC218; 1, CH, N, H, $C_3F_7$, $CF_3$], [CC219; 1, CH, N, H, $CH_2CF_3$, $CF_3$], [CC220; 1, CH, N, H, $CH_2CHF_2$, $CF_3$], [CC221; 2, CH, N, H, H, $CF_3$], [CC222; 2, CH, N, H, F, $CF_3$], [CC223; 2, CH, N, H, Cl, $CF_3$], [CC224; 2, CH, N, H, Br, $CF_3$], [CC225; 2, CH, N, H, I, $CF_3$], [CC226; 2, CH, N, H, $CF_3$, $CF_3$], [CC227; 2, CH, N, H, $CF_2H$, $CF_3$], [CC228; 2, CH, N, H, $C_2F_5$, $CF_3$], [CC229; 2, CH, N, H, $C_3F_7$, $CF_3$], [CC230; 2, CH, N, H, $CH_2CF_3$, $CF_3$], [CC231; 2, CH, N, H, $CH_2CHF_2$, $CF_3$], [CC232; 0, N,N, H, H, $CF_3$], [CC233; 0, N,N, H, F, $CF_3$], [CC234; 0, N,N, H, Cl, $CF_3$], [CC235; 0, N,N, H, Br, $CF_3$], [CC236; 0, N,N, H, I, $CF_3$], [CC237; 0, N,N, H, $CF_3$, $CF_3$], [CC238; 0, N,N, H, $CF_2H$, $CF_3$], [CC239; 0, N,N, H, $C_2F_5$, $CF_3$], [CC240; 0, N,N, H, $C_3F_7$, $CF_3$], [CC241; 0, N,N, H, $CH_2CF_3$, $CF_3$], [CC242; 0, N,N, H, $CH_2CHF_2$, $CF_3$], [CC243; 1, N,N, H, H, $CF_3$], [CC244; 1, N,N, H, F, $CF_3$], [CC245; 1, N,N, H, Cl, $CF_3$], [CC246; 1, N,N, H, Br, $CF_3$], [CC247; 1, N,N, H, I, $CF_3$], [CC248; 1, N,N, H, $CF_3$, $CF_3$], [CC249; 1, N,N, H, $CF_2H$, $CF_3$], [CC250; 1, N,N, H, $C_2F_5$, $CF_3$], [CC251; 1, N,N, H, $C_3F_7$, $CF_3$], [CC252; 1, N,N, H, $CH_2CF_3$, $CF_3$], [CC253; 1, N,N, H, $CH_2CHF_2$, $CF_3$], [CC254; 2, N,N, H, H, $CF_3$], [CC255; 2, N,N, H, F, $CF_3$], [CC256; 2, N,N, H, Cl, $CF_3$], [CC257; 2, N,N, H, Br, $CF_3$], [CC258; 2, N,N, H, I, $CF_3$], [CC259; 2, N,N, H, $CF_3$, $CF_3$], [CC260; 2, N,N, H, $CF_2H$, $CF_3$], [CC261; 2, N,N, H, $C_{2F}5$, $CF_3$], [CC262; 2, N,N, H, $C_3F_7$, $CF_3$], [CC263; 2, N,N, H, $CH_2CF_3$, $CF_3$], [CC264; 2, N,N, H, $CH_2CHF_2$, $CF_3$], [CC265; 0, CH, CH, H, H, $CHF_2$], [CC266; 0, CH, CH, F, H, $CHF_2$], [CC267; 0, CH, CH, Cl, H, $CHF_2$], [CC268; 0, CH, CH, Br, H, $CHF_2$], [CC269; 0, CH, CH, I, H, $CHF_2$], [CC270; 0, CH, CH, $CF_3$, H, $CHF_2$], [CC271; 0, CH, CH, $CF_2H$, H, $CHF_2$], [CC272; 0, CH, CH, $C_2F_5$, H, $CHF_2$], [CC273; 0, CH, CH, $C_3F_7$, H, $CHF_2$], [CC274; 0, CH, CH, $CH_2CF_3$, H, $CHF_2$], [CC275; 0, CH, CH, $CH_2CHF_2$, H, $CHF_2$], [CC276; 1, CH, CH, H, H, $CHF_2$], [CC277; 1, CH, CH, F, H, $CHF_2$], [CC278; 1, CH, CH, Cl, H, $CHF_2$], [CC279; 1, CH, CH, Br, H, $CHF_2$], [CC280; 1, CH, CH, I, H, $CHF_2$], [CC281; 1, CH, CH, $CF_3$, H, $CHF_2$], [CC282; 1, CH, CH, $CF_2H$, H, $CHF_2$], [CC283; 1, CH, CH, $C_2F_5$, H, $CHF_2$], [CC284; 1, CH, CH, $C_3F_7$, H, $CHF_2$], [CC285; 1, CH, CH, $CH_2CF_3$, H, $CHF_2$], [CC286; 1, CH, CH, $CH_2CHF_2$, H, $CHF_2$], [CC287; 2, CH, CH, H, H, $CHF_2$], [CC288; 2, CH, CH, F, H, $CHF_2$], [CC289; 2, CH, CH, Cl, H, $CHF_2$], [CC290; 2, CH, CH, Br, H, $CHF_2$], [CC291; 2, CH, CH, I, H, $CHF_2$], [CC292; 2, CH, CH, $CF_3$, H, $CHF_2$], [CC293; 2, CH, CH, $CF_2H$, H, $CHF_2$], [CC294; 2, CH, CH, $C_2F_5$, H, $CHF_2$], [CC295; 2, CH, CH, $C_3F_7$, H, $CHF_2$], [CC296; 2, CH, CH, $CH_2CF_3$, H, $CHF_2$], [CC297; 2, CH, CH, $CH_2CHF_2$, H, $CHF_2$], [CC298; 0, N, CH, H, H, $CHF_2$], [CC299; 0, N, CH, F, H, $CHF_2$], [CC300; 0, N, CH, Cl, H, $CHF_2$], [CC301; 0, N, CH, Br, H, $CHF_2$], [CC302; 0, N, CH, I, H, $CHF_2$], [CC303; 0, N, CH, $CF_3$, H, $CHF_2$], [CC304; 0, N, CH, $CF_2H$, H, $CHF_2$], [CC305; 0, N, CH, $C_2F_5$, H, $CHF_2$], [CC306; 0, N, CH, $C_3F_7$, H, $CHF_2$], [CC307; 0, N, CH, $CH_2CF_3$, H, $CHF_2$], [CC308; 0, N, CH, $CH_2CHF_2$, H, $CHF_2$], [CC309; 1, N, CH, H, H, $CHF_2$], [CC310; 1, N, CH, F, H, $CHF_2$], [CC311; 1, N, CH, Cl, H, $CHF_2$], [CC312; 1, N, CH, Br, H, $CHF_2$], [CC313; 1, N, CH, I, H, $CHF_2$], [CC314; 1, N, CH, $CF_3$, H, $CHF_2$], [CC315; 1, N, CH, $CF_2H$, H, $CHF_2$], [CC316; 1, N, CH, $C_2F_5$, H, $CHF_2$], [CC317; 1, N, CH, $C_3F_7$, H, $CHF_2$], [CC318; 1, N, CH, $CH_2CF_3$, H, $CHF_2$], [CC319; 1, N, CH, $CH_2CHF_2$, H, $CHF_2$], [CC320; 2, N, CH, H, H, $CHF_2$], [CC321; 2, N, CH, F, H, $CHF_2$], [CC322; 2, N, CH, Cl, H, $CHF_2$], [CC323; 2, N, CH, Br, H, $CHF_2$], [CC324; 2, N, CH, I, H, $CHF_2$], [CC325; 2, N, CH, $CF_3$, H, $CHF_2$], [CC326; 2, N, CH, $CF_2$, H, H, $CHF_2$], [CC327; 2, N, CH, $C_2F_5$, H, $CHF_2$], [CC328; 2, N, CH, $C_3F_7$, H, $CHF_2$], [CC329; 2, N, CH, $CH_2CF_3$, H, $CHF_2$], [CC330; 2, N, CH, $CH_2CHF_2$, H, $CHF_2$], [CC331; 0, CH, N, H, H, $CHF_2$], [CC332; 0, CH, N, F, H, $CHF_2$], [CC333; 0, CH, N, Cl, H, $CHF_2$], [CC334; 0, CH, N, Br, H, $CHF_2$], [CC335; 0, CH, N, I, H, $CHF_2$], [CC336; 0, CH, N, $CF_3$, H, $CHF_2$], [CC337; 0, CH, N, $CF_2H$, H, $CHF_2$], [CC338; 0, CH, N, $C_2F_5$, H, $CHF_2$], [CC339; 0, CH, N, $C_3F_7$, H, $CHF_2$], [CC340; 0, CH, N, $CH_2CF_3$, H, $CHF_2$], [CC341; 0, CH, N, $CH_2CHF_2$, H, $CHF_2$], [CC342; 1, CH, N, H, H, $CHF_2$], [CC343; 1, CH, N, F, H, $CHF_2$], [CC344; 1, CH, N, Cl, H, $CHF_2$], [CC345; 1, CH, N, Br, H, $CHF_2$], [CC346; 1, CH, N, I, H, $CHF_2$], [CC347; 1, CH, N, $CF_3$, H, $CHF_2$], [CC348; 1, CH, N, $CF_2H$, H, $CHF_2$], [CC349; 1, CH, N, $C_2F_5$, H, $CHF_2$], [CC350; 1, CH, N, $C_3F_7$, H, $CHF_2$], [CC351; 1, CH, N, $CH_2CF_3$, H, $CHF_2$], [CC352; 1, CH, N, $CH_2CHF_2$, H, $CHF_2$], [CC353; 2, CH, N, H, H, $CHF_2$], [CC354; 2, CH, N, F, H, $CHF_2$], [CC355; 2, CH, N, Cl, H, $CHF_2$], [CC356; 2, CH, N, Br, H, $CHF_2$], [CC357; 2, CH, N, I, H, $CHF_2$], [CC358; 2, CH, N, $CF_3$, H, $CHF_2$], [CC359; 2, CH, N, $CF_2H$, H, $CHF_2$], [CC360; 2, CH, N, $C_2F_5$, H, $CHF_2$], [CC361; 2, CH, N, $C_3F_7$, H, $CHF_2$], [CC362; 2, CH, N, $CH_2CF_3$, H, $CHF_2$], [CC363; 2, CH, N, $CH_2CHF_2$, H, $CHF_2$], [CC364; 0, N,N, H, H, $CHF_2$], [CC365; 0, N,N, F, H, $CHF_2$], [CC366; 0, N, N, Cl, H, $CHF_2$], [CC367; 0, N, N, Br, H, $CHF_2$], [CC368; 0, N,N, I, H, $CHF_2$], [CC369; 0, N, N, $CF_3$, H, $CHF_2$], [CC370; 0, N, N, $CF_2H$, H, $CHF_2$], [CC371; 0, N, N, $C_2F_5$, H, $CHF_2$], [CC372; 0, N, N, $C_3F_7$, H, $CHF_2$], [CC373; 0, N, N, $CH_2CF_3$, H, $CHF_2$], [CC374; 0, N, N, $CH_2CHF_2$, H, $CHF_2$], [CC375; 1, N,N, H, H, $CHF_2$], [CC376; 1, N,N, F, H, $CHF_2$], [CC377; 1, N, N, Cl, H, $CHF_2$], [CC378; 1, N, N, Br, H, $CHF_2$], [CC379; 1, N,N, I, H, $CHF_2$], [CC380; 1, N, N, $CF_3$, H, $CHF_2$], [CC381; 1, N, N, $CF_2H$, H, $CHF_2$], [CC382; 1, N, N, $C_2F_5$, H, $CHF_2$], [CC383; 1, N, N, $C_3F_7$, H, $CHF_2$], [CC384; 1, N, N, $CH_2CF_3$, H, $CHF_2$], [CC385; 1, N, N, $CH_2CHF_2$, H, $CHF_2$], [CC386; 2, N,N, H, H, $CHF_2$], [CC387; 2, N,N, F, H, $CHF_2$], [CC388; 2, N, N, Cl, H, $CHF_2$], [CC389; 2, N, N, Br, H, $CHF_2$], [CC390; 2, N,N, I, H, $CHF_2$], [CC391; 2, N, N, $CF_3$, H, $CHF_2$], [CC392; 2, N, N, $CF_2H$, H, $CHF_2$], [CC393; 2, N, N, $C_2F_5$, H, $CHF_2$], [CC394; 2, N, N, $C_3F_7$, H, $CHF_2$], [CC395; 2, N, N, $CH_2CF_3$, H, $CHF_2$], [CC396; 2, N, N, $CH_2CHF_2$, H, $CHF_2$], [CC397; 0, CH, CH, H, H, $CHF_2$], [CC398; 0, CH, CH, H, F, $CHF_2$], [CC399; 0, CH, CH, H, Cl, $CHF_2$], [CC400; 0, CH, CH, H, Br, $CHF_2$], [CC401; 0, CH, CH, H, I, $CHF_2$], [CC402; 0, CH, CH, H, $CF_3$, $CHF_2$], [CC403; 0, CH, CH, H, $CF_2H$, $CHF_2$], [CC404; 0, CH, CH, H, $C_2F_5$, $CHF_2$], [CC405; 0, CH, CH, H, $C_3F_7$, $CHF_2$], [CC406; 0, CH, CH, H, $CH_2CF_3$, $CHF_2$], [CC407; 0, CH, CH, H, $CH_2CHF_2$, $CHF_2$], [CC408; 1, CH, CH, H, H, $CHF_2$], [CC409; 1, CH, CH, H, F, $CHF_2$], [CC410; 1, CH, CH, H, Cl, $CHF_2$], [CC411; 1, CH, CH, H, Br, $CHF_2$], [CC412; 1, CH, CH, H, I, $CHF_2$], [CC413; 1, CH, CH, H, $CF_3$, $CHF_2$], [CC414; 1, CH, CH, H, $CF_2H$, $CHF_2$], [CC415;

1, CH, CH, H, $C_2F_5$, $CHF_2$], [CC416; 1, CH, CH, H, $C_3F_7$, $CHF_2$], [CC417; 1, CH, CH, H, $CH_2CF_3$, $CHF_2$], [CC418; 1, CH, CH, H, $CH_2CHF_2$, $CHF_2$], [CC419; 2, CH, CH, H, H, $CHF_2$], [CC420; 2, CH, CH, H, F, $CHF_2$], [CC421; 2, CH, CH, H, Cl, $CHF_2$], [CC422; 2, CH, CH, H, Br, $CHF_2$], [CC423; 2, CH, CH, H, I, $CHF_2$], [CC424; 2, CH, CH, H, $CF_3$, $CHF_2$], [CC425; 2, CH, CH, H, $CF_2H$, $CHF_2$], [CC426; 2, CH, CH, H, $C_2F_5$, $CHF_2$], [CC427; 2, CH, CH, H, $C_3F_7$, $CHF_2$], [CC428; 2, CH, CH, H, $CH_2CF_3$, $CHF_2$], [CC429; 2, CH, CH, H, $CH_2CHF_2$, $CHF_2$], [CC430; 0, N, CH, H, H, $CHF_2$], [CC431; 0, N, CH, H, F, $CHF_2$], [CC432; 0, N, CH, H, Cl, $CHF_2$], [CC433; 0, N, CH, H, Br, $CHF_2$], [CC434; 0, N, CH, H, I, $CHF_2$], [CC435; 0, N, CH, H, $CF_3$, $CHF_2$], [CC436; 0, N, CH, H, $CF_2H$, $CHF_2$], [CC437; 0, N, CH, H, $C_2F_5$, $CHF_2$], [CC438; 0, N, CH, H, $C_3F_7$, $CHF_2$], [CC439; 0, N, CH, H, $CH_2CF_3$, $CHF_2$], [CC440; 0, N, CH, H, $CH_2CHF_2$, $CHF_2$], [CC441; 1, N, CH, H, H, $CHF_2$], [CC442; 1, N, CH, H, F, $CHF_2$], [CC443; 1, N, CH, H, Cl, $CHF_2$], [CC444; 1, N, CH, H, Br, $CHF_2$], [CC445; 1, N, CH, H, I, $CHF_2$], [CC446; 1, N, CH, H, $CF_3$, $CHF_2$], [CC447; 1, N, CH, H, $CF_2H$, $CHF_2$], [CC448; 1, N, CH, H, $C_2F_5$, $CHF_2$], [CC449; 1, N, CH, H, $C_3F$, $CHF_2$], [CC450; 1, N, CH, H, $CH_2CF_3$, $CHF_2$], [CC451; 1, N, CH, H, $CH_2CHF_2$, $CHF_2$], [CC452; 2, N, CH, H, H, $CHF_2$], [CC453; 2, N, CH, H, F, $CHF_2$], [CC454; 2, N, CH, H, Cl, $CHF_2$], [CC455; 2, N, CH, H, Br, $CHF_2$], [CC456; 2, N, CH, H, I, $CHF_2$], [CC457; 2, N, CH, H, $CF_3$, $CHF_2$], [CC458; 2, N, CH, H, $CF_2H$, $CHF_2$], [CC459; 2, N, CH, H, $C_2F_5$, $CHF_2$], [CC460; 2, N, CH, H, $C_3F_7$, $CHF_2$], [CC461; 2, N, CH, H, $CH_2CF_3$, $CHF_2$], [CC462; 2, N, CH, H, $CH_2CHF_2$, $CHF_2$], [CC463; 0, CH, N, H, H, $CHF_2$], [CC464; 0, CH, N, H, F, $CHF_2$], [CC465; 0, CH, N, H, Cl, $CHF_2$], [CC466; 0, CH, N, H, Br, $CHF_2$], [CC467; 0, CH, N, H, I, $CHF_2$], [CC468; 0, CH, N, H, $CF_3$, $CHF_2$], [CC469; 0, CH, N, H, $CF_2H$, $CHF_2$], [CC470; 0, CH, N, H, $C_2F_5$, $CHF_2$], [CC471; 0, CH, N, H, $C_3F_7$, $CHF_2$], [CC472; 0, CH, N, H, $CH_2CF_3$, $CHF_2$], [CC473; 0, CH, N, H, $CH_2CHF_2$, $CHF_2$], [CC474; 1, CH, N, H, H, $CHF_2$], [CC475; 1, CH, N, H, F, $CHF_2$], [CC476; 1, CH, N, H, Cl, $CHF_2$], [CC477; 1, CH, N, H, Br, $CHF_2$], [CC478; 1, CH, N, H, I, $CHF_2$], [CC479; 1, CH, N, H, $CF_3$, $CHF_2$], [CC480; 1, CH, N, H, $CF_2H$, $CHF_2$], [CC481; 1, CH, N, H, $C_2F_5$, $CHF_2$], [CC482; 1, CH, N, H, $C_3F_7$, $CHF_2$], [CC483; 1, CH, N, H, $CH_2CF_3$, $CHF_2$], [CC484; 1, CH, N, H, $CH_2CHF_2$, $CHF_2$], [CC485; 2, CH, N, H, H, $CHF_2$], [CC486; 2, CH, N, H, F, $CHF_2$], [CC487; 2, CH, N, H, Cl, $CHF_2$], [CC488; 2, CH, N, H, Br, $CHF_2$], [CC489; 2, CH, N, H, I, $CHF_2$], [CC490; 2, CH, N, H, $CF_3$, $CHF_2$], [CC491; 2, CH, N, H, $CF_2H$, $CHF_2$], [CC492; 2, CH, N, H, $C_2F_5$, $CHF_2$], [CC493; 2, CH, N, H, $C_3F_7$, $CHF_2$], [CC494; 2, CH, N, H, $CH_2CF_3$, $CHF_2$], [CC495; 2, CH, N, H, $CH_2CHF_2$, $CHF_2$], [CC496; 0, N,N, H, H, $CHF_2$], [CC497; 0, N,N, H, F, $CHF_2$], [CC498; 0, N,N, H, Cl, $CHF_2$], [CC499; 0, N,N, H, Br, $CHF_2$], [CC500; 0, N,N, H, I, $CHF_2$], [CC501; 0, N,N, H, $CF_3$, $CHF_2$], [CC502; 0, N,N, H, $CF_2H$, $CHF_2$], [CC503; 0, N,N, H, $C_2F_5$, $CHF_2$], [CC504; 0, N,N, H, $C_3F_7$, $CHF_2$], [CC505; 0, N,N, H, $CH_2CF_3$, $CHF_2$], [CC506; 0, N,N, H, $CH_2CHF_2$, $CHF_2$], [CC507; 1, N,N, H, H, $CHF_2$], [CC508; 1, N,N, H, F, $CHF_2$], [CC509; 1, N,N, H, Cl, $CHF_2$], [CC510; 1, N,N, H, Br, $CHF_2$], [CC511; 1, N,N, H, I, $CHF_2$], [CC512; 1, N,N, H, $CF_3$, $CHF_2$], [CC513; 1, N,N, H, $CF_2H$, $CHF_2$], [CC514; 1, N,N, H, $C_2F_5$, $CHF_2$], [CC515; 1, N,N, H, $C_3F_7$, $CHF_2$], [CC516; 1, N,N, H, $CH_2CF_3$, $CHF_2$], [CC517; 1, N,N, H, $CH_2CHF_2$, $CHF_2$], [CC518; 2, N,N, H, H, $CHF_2$], [CC519; 2, N,N, H, F, $CHF_2$], [CC520; 2, N,N, H, Cl, $CHF_2$], [CC521; 2, N,N, H, Br, $CHF_2$], [CC522; 2, N,N, H, I, $CHF_2$], [CC523; 2, N,N, H, $CF_3$, $CHF_2$], [CC524; 2, N,N, H, $CF_2H$, $CHF_2$], [CC525; 2, N,N, H, $C_2F_5$, $CHF_2$], [CC526; 2, N,N, H, $C_3F_7$, $CHF_2$], [CC527; 2, N,N, H, $CH_2CF_3$, $CHF_2$], [CC528; 2, N,N, H, $CH_2CHF_2$, $CHF_2$], [CC529; 0, CH, CH, H, H, $CH_2CF_3$], [CC530; 0, CH, CH, F, H, $CH_2CF_3$], [CC531; 0, CH, CH, Cl, H, $CH_2CF_3$], [CC532; 0, CH, CH, Br, H, $CH_2CF_3$], [CC533; 0, CH, CH, I, H, $CH_2CF_3$], [CC534; 0, CH, CH, $CF_3$, H, $CH_2CF_3$], [CC535; 0, CH, CH, $CF_2H$, H, $CH_2CF_3$], [CC536; 0, CH, CH, $C_2F_5$, H, $CH_2CF_3$], [CC537; 0, CH, CH, $C_3F_7$, H, $CH_2CF_3$], [CC538; 0, CH, CH, $CH_2CF_3$, H, $CH_2CF_3$], [CC539; 0, CH, CH, $CH_2CHF_2$, H, $CH_2CF_3$], [CC540; 1, CH, CH, H, H, $CH_2CF_3$], [CC541; 1, CH, CH, F, H, $CH_2CF_3$], [CC542; 1, CH, CH, Cl, H, $CH_2CF_3$], [CC543; 1, CH, CH, Br, H, $CH_2CF_3$], [CC544; 1, CH, CH, I, H, $CH_2CF_3$], [CC545; 1, CH, CH, $CF_3$, H, $CH_2CF_3$], [CC546; 1, CH, CH, $CF_2H$, H, $CH_2CF_3$], [CC547; 1, CH, CH, $C_2F_5$, H, $CH_2CF_3$], [CC548; 1, CH, CH, $C_3F_7$, H, $CH_2CF_3$], [CC549; 1, CH, CH, $CH_2CF_3$, H, $CH_2CF_3$], [CC550; 1, CH, CH, $CH_2CHF_2$, H, $CH_2CF_3$], [CC551; 2, CH, CH, H, H, $CH_2CF_3$], [CC552; 2, CH, CH, F, H, $CH_2CF_3$], [CC553; 2, CH, CH, Cl, H, $CH_2CF_3$], [CC554; 2, CH, CH, Br, H, $CH_2CF_3$], [CC555; 2, CH, CH, I, H, $CH_2CF_3$], [CC556; 2, CH, CH, $CF_3$, H, $CH_2CF_3$], [CC557; 2, CH, CH, $CF_2H$, H, $CH_2CF_3$], [CC558; 2, CH, CH, $C_2F_5$, H, $CH_2CF_3$], [CC559; 2, CH, CH, $C_3F_7$, H, CH $CF_3$], [CC560; 2, CH, CH, $CH_2CF_3$, H, $CH_2CF_3$], [CC561; 2, CH, CH, $CH_2CHF_2$, H, $CH_2CF_3$], [CC562; 0, N, CH, H, H, $CH_2CF_3$], [CC563; 0, N, CH, F, H, $CH_2CF_3$], [CC564; 0, N, CH, Cl, H, $CH_2CF_3$], [CC565; 0, N, CH, Br, H, $CH_2CF_3$], [CC566; 0, N, CH, I, H, $CH_2CF_3$], [CC567; 0, N, CH, $CF_3$, H, $CH_2CF_3$], [CC568; 0, N, CH, $CF_2H$, H, $CH_2CF_3$], [CC569; 0, N, CH, $C_2F_5$, H, $CH_2CF_3$], [CC570; 0, N, CH, $C_3F_7$, H, $CH_2CF_3$], [CC571; 0, N, CH, $CH_2CF_3$, H, $CH_2CF_3$], [CC572; 0, N, CH, $CH_2CHF_2$, H, $CH_2CF_3$], [CC573; 1, N, CH, H, H, $CH_2CF_3$], [CC574; 1, N, CH, F, H, $CH_2CF_3$], [CC575; 1, N, CH, Cl, H, $CH_2CF_3$], [CC576; 1, N, CH, Br, H, $CH_2CF_3$], [CC577; 1, N, CH, I, H, $CH_2CF_3$], [CC578; 1, N, CH, $CF_3$, H, $CH_2CF_3$], [CC579; 1, N, CH, $CF_2H$, H, $CH_2CF_3$], [CC580; 1, N, CH, $C_2F_5$, H, $CH_2CF_3$], [CC581; 1, N, CH, $C_3F_7$, H, $CH_2CF_3$], [CC582; 1, N, CH, $CH_2CF_3$, H, $CH_2CF_3$], [CC583; 1, N, CH, $CH_2CHF_2$, H, $CH_2CF_3$], [CC584; 2, N, CH, H, H, $CH_2CF_3$], [CC585; 2, N, CH, F, H, $CH_2CF_3$], [CC586; 2, N, CH, Cl, H, $CH_2CF_3$], [CC587; 2, N, CH, Br, H, $CH_2CF_3$], [CC588; 2, N, CH, I, H, $CH_2CF_3$], [CC589; 2, N, CH, $CF_3$, H, $CH_2CF_3$], [CC590; 2, N, CH, $CF_2H$, H, $CH_2CF_3$], [CC591; 2, N, CH, $C_2F_5$, H, $CH_2CF_3$], [CC592; 2, N, CH, $C_3F_7$, H, $CH_2CF_3$], [CC593; 2, N, CH, $CH_2CF_3$, H, $CH_2CF_3$], [CC594; 2, N, CH, $CH_2CHF_2$, H, $CH_2CF_3$], [CC595; 0, CH, N, H, H, $CH_2CF_3$], [CC596; 0, CH, N, F, H, $CH_2CF_3$], [CC597; 0, CH, N, Cl, H, $CH_2CF_3$], [CC598; 0, CH, N, Br, H, $CH_2CF_3$], [CC599; 0, CH, N, I, H, $CH_2CF_3$], [CC600; 0, CH, N, $CF_3$, H, $CH_2CF_3$], [CC601; 0, CH, N, $CF_2H$, H, $CH_2CF_3$], [CC602; 0, CH, N, $C_2F_5$, H, $CH_2CF_3$], [CC603; 0, CH, N, $C_3F_7$, H, $CH_2CF_3$], [CC604; 0, CH, N, $CH_2CF_3$, H, $CH_2CF_3$], [CC605; 0, CH, N, $CH_2CHF_2$, H, $CH_2CF_3$], [CC606; 1, CH, N, H, H, $CH_2CF_3$], [CC607; 1, CH, N, F, H, $CH_2CF_3$], [CC608; 1, CH, N, Cl, H, $CH_2CF_3$], [CC609; 1, CH, N, Br, H, $CH_2CF_3$], [CC610; 1, CH, N, I, H, $CH_2CF_3$], [CC611; 1, CH, N, $CF_3$, H, $CH_2CF_3$], [CC612; 1, CH, N, $CF_2H$, H, $CH_2CF_3$], [CC613; 1, CH, N, $C_2F_5$, H, $CH_2CF_3$], [CC614; 1, CH, N, $C_3F_7$, H, $CH_2CF_3$], [CC615; 1, CH, N, $CH_2CF_3$, H, $CH_2CF_3$], [CC616; 1, CH, N, $CH_2CHF_2$, H, $CH_2CF_3$], [CC617; 2, CH, N, H, H, $CH_2CF_3$], [CC618; 2, CH, N, F, H, $CH_2CF_3$], [CC619; 2, CH, N, Cl, H, $CH_2CF_3$], [CC620; 2, CH, N, Br, H, $CH_2CF_3$], [CC621; 2, CH, N, I, H, $CH_2CF_3$], [CC622; 2, CH, N, $CF_3$, H, $CH_2CF_3$], [CC623; 2, CH, N, $CF_2H$, H, $CH_2CF_3$], [CC624; 2, CH, N, $C_2F_5$, H, $CH_2CF_3$],

[CC625; 2, CH, N, $C_3F_7$, H, $CH_2CF_3$], [CC626; 2, CH, N, $CH_2CF_3$, H, $CH_2CF_3$], [CC627; 2, CH, N, $CH_2CHF_2$, H, $CH_2CF_3$], [CC628; 0, N,N, H, H, $CH_2CF_3$], [CC629; 0, N,N, F, H, $CH_2CF_3$], [CC630; 0, N, N, Cl, H, $CH_2CF_3$], [CC631; 0, N, N, Br, H, $CH_2CF_3$], [CC632; 0, N,N, I, H, $CH_2CF_3$], [CC633; 0, N, N, $CF_3$, H, $CH_2CF_3$], [CC634; 0, N, N, $CF_2H$, H, $CH_2CF_3$], [CC635; 0, N, N, $C_2F_5$, H, $CH_2CF_3$], [CC636; 0, N, N, $C_3F_7$, H, $CH_2CF_3$], [CC637; 0, N, N, $CH_2CF_3$, H, $CH_2CF_3$], [CC638; 0, N, N, $CH_2CHF_2$, H, $CH_2CF_3$], [CC639; 1, N,N, H, H, $CH_2CF_3$], [CC640; 1, N,N, F, H, $CH_2CF_3$], [CC641; 1, N, N, Cl, H, $CH_2CF_3$], [CC642; 1, N, N, Br, H, $CH_2CF_3$], [CC643; 1, N,N, I, H, $CH_2CF_3$], [CC644; 1, N, N, $CF_3$, H, $CH_2CF_3$], [CC645; 1, N, N, $CF_2H$, H, $CH_2CF_3$], [CC646; 1, N, N, $C_2F_5$, H, $CH_2CF_3$], [CC647; 1, N, N, $C_3F_7$, H, $CH_2CF_3$], [CC648; 1, N, N, $CH_2CF_3$, H, $CH_2CF_3$], [CC649; 1, N, N, $CH_2CHF_2$, H, $CH_2CF_3$], [CC650; 2, N,N, H, H, $CH_2CF_3$], [CC651; 2, N,N, F, H, $CH_2CF_3$], [CC652; 2, N, N, Cl, H, $CH_2CF_3$], [CC653; 2, N, N, Br, H, $CH_2CF_3$], [CC654; 2, N,N, I, H, $CH_2CF_3$], [CC655; 2, N, N, $CF_3$, H, $CH_2CF_3$], [CC656; 2, N, N, $CF_2H$, H, $CH_2CF_3$], [CC657; 2, N, N, $C_2F_5$, H, $CH_2CF_3$], [CC658; 2, N, N, $C_3F_7$, H, $CH_2CF_3$], [CC659; 2, N, N, $CH_2CF_3$, H, $CH_2CF_3$], [CC660; 2, N, N, $CH_2CHF_2$, H, $CH_2CF_3$], [CC661; 0, CH, CH, H, H, $CH_2CF_3$], [CC662; 0, CH, CH, H, F, $CH_2CF_3$], [CC663; 0, CH, CH, H, Cl, $CH_2CF_3$], [CC664; 0, CH, CH, H, Br, $CH_2CF_3$], [CC665; 0, CH, CH, H, I, $CH_2CF_3$], [CC666; 0, CH, CH, H, $CF_3$, $CH_2CF_3$], [CC667; 0, CH, CH, H, $CF_2H$, $CH_2CF_3$], [CC668; 0, CH, CH, H, $C_2F_5$, $CH_2CF_3$], [CC669; 0, CH, CH, H, $C_3F_7$, $CH_2CF_3$], [CC670; 0, CH, CH, H, $CH_2CF_3$, $CH_2CF_3$], [CC671; 0, CH, CH, H, $CH_2CHF_2$, $CH_2CF_3$], [CC672; 1, CH, CH, H, H, $CH_2CF_3$], [CC673; 1, CH, CH, H, F, $CH_2CF_3$], [CC674; 1, CH, CH, H, Cl, $CH_2CF_3$], [CC675; 1, CH, CH, H, Br, $CH_2CF_3$], [CC676; 1, CH, CH, H, I, $CH_2CF_3$], [CC677; 1, CH, CH, H, $CF_3$, $CH_2CF_3$], [CC678; 1, CH, CH, H, $CF_2H$, $CH_2CF_3$], [CC679; 1, CH, CH, H, $C_2F_5$, $CH_2CF_3$], [CC680; 1, CH, CH, H, $C_3F_7$, $CH_2CF_3$], [CC681; 1, CH, CH, H, $CH_2CF_3$, $CH_2CF_3$], [CC682; 1, CH, CH, H, $CH_2CHF_2$, $CH_2CF_3$], [CC683; 2, CH, CH, H, H, $CH_2CF_3$], [CC684; 2, CH, CH, H, F, $CH_2CF_3$], [CC685; 2, CH, CH, H, Cl, $CH_2CF_3$], [CC686; 2, CH, CH, H, Br, $CH_2CF_3$], [CC687; 2, CH, CH, H, I, $CH_2CF_3$], [CC688; 2, CH, CH, H, $CF_3$, $CH_2CF_3$], [CC689; 2, CH, CH, H, $CF_2H$, $CH_2CF_3$], [CC690; 2, CH, CH, H, $C_2F_5$, $CH_2CF_3$], [CC691; 2, CH, CH, H, $C_3F_7$, $CH_2CF_3$], [CC692; 2, CH, CH, H, $CH_2CF_3$, $CH_2CF_3$], [CC693; 2, CH, CH, H, $CH_2CHF_2$, $CH_2CF_3$], [CC694; 0, N, CH, H, H, $CH_2CF_3$], [CC695; 0, N, CH, H, F, $CH_2CF_3$], [CC696; 0, N, CH, H, Cl, $CH_2CF_3$], [CC697; 0, N, CH, H, Br, $CH_2CF_3$], [CC698; 0, N, CH, H, I, $CH_2CF_3$], [CC699; 0, N, CH, H, $CF_3$, $CH_2CF_3$], [CC700; 0, N, CH, H, $CF_2H$, $CH_2CF_3$], [CC701; 0, N, CH, H, $C_2F_5$, $CH_2CF_3$], [CC702; 0, N, CH, H, $C_3F_7$, $CH_2CF_3$], [CC703; 0, N, CH, H, $CH_2CF_3$, $CH_2CF_3$], [CC704; 0, N, CH, H, $CH_7CHF_7$, $CH_7CF_3$], [CC705; 1, N, CH, H, H, $CH_7CF_3$], [CC706; 1, N, CH, H, F, $CH_2CF_3$], [CC707; 1, N, CH, H, Cl, $CH_2CF_3$], [CC708; 1, N, CH, H, Br, $CH_2CF_3$], [CC709; 1, N, CH, H, I, $CH_2CF_3$], [CC710; 1, N, CH, H, $CF_3$, $CH_7CF_3$], [CC711; 1, N, CH, H, $CF_7H$, $CH_7CF_3$], [CC712; 1, N, CH, H, $C_2F_5$, $CH_2CF_3$], [CC713; 1, N, CH, H, $C_3F_7$, $CH_2CF_3$], [CC714; 1, N, CH, H, $CH_2CF_3$, $CH_2CF_3$], [CC715; 1, N, CH, H, $CH_2CHF_2$, $CH_2CF_3$], [CC716; 2, N, CH, H, H, $CH_2CF_3$], [CC717; 2, N, CH, H, F, $CH_2CF_3$], [CC718; 2, N, CH, H, Cl, $CH_2CF_3$], [CC719; 2, N, CH, H, Br, $CH_2CF_3$], [CC720; 2, N, CH, H, I, $CH_2CF_3$], [CC721; 2, N, CH, H, $CF_3$, $CH_2CF_3$], [CC722; 2, N, CH, H, $CF_2H$, $CH_2CF_3$], [CC723; 2, N, CH, H, $C_2F_5$, $CH_2CF_3$], [CC724; 2, N, CH, H, $C_3F_7$, $CH_2CF_3$], [CC725; 2, N, CH, H, $CH_2CF_3$, $CH_2CF_3$], [CC726; 2, N, CH, H, $CH_2CHF_2$, $CH_2CF_3$], [CC727; 0, CH, N, H, H, $CH_2CF_3$], [CC728; 0, CH, N, H, F, $CH_2CF_3$], [CC729; 0, CH, N, H, Cl, $CH_2CF_3$], [CC730; 0, CH, N, H, Br, $CH_2CF_3$], [CC731; 0, CH, N, H, I, $CH_2CF_3$], [CC732; 0, CH, N, H, $CF_3$, $CH_2CF_3$], [CC733; 0, CH, N, H, $CF_2H$, $CH_2CF_3$], [CC734; 0, CH, N, H, $C_2F_5$, $CH_2CF_3$], [CC735; 0, CH, N, H, $C_3F_7$, $CH_2CF_3$], [CC736; 0, CH, N, H, $CH_2CF_3$, $CH_2CF_3$], [CC737; 0, CH, N, H, $CH_2CHF_2$, $CH_2CF_3$], [CC738; 1, CH, N, H, H, $CH_2CF_3$], [CC739; 1, CH, N, H, F, $CH_2CF_3$], [CC740; 1, CH, N, H, Cl, $CH_2CF_3$], [CC741; 1, CH, N, H, Br, $CH_2CF_3$], [CC742; 1, CH, N, H, I, $CH_2CF_3$], [CC743; 1, CH, N, H, $CF_3$, $CH_2CF_3$], [CC744; 1, CH, N, H, $CF_2H$, $CH_2CF_3$], [CC745; 1, CH, N, H, $C_2F_5$, $CH_2CF_3$], [CC746; 1, CH, N, H, $C_3F_7$, $CH_2CF_3$], [CC747; 1, CH, N, H, $CH_2CF_3$, $CH_2CF_3$], [CC748; 1, CH, N, H, $CH_2CHF_2$, $CH_2CF_3$], [CC749; 2, CH, N, H, H, $CH_2CF_3$], [CC750; 2, CH, N, H, F, $CH_2CF_3$], [CC751; 2, CH, N, H, Cl, $CH_2CF_3$], [CC752; 2, CH, N, H, Br, $CH_2CF_3$], [CC753; 2, CH, N, H, I, $CH_2CF_3$], [CC754; 2, CH, N, H, $CF_3$, $CH_2CF_3$], [CC755; 2, CH, N, H, $CF_2H$, $CH_2CF_3$], [CC756; 2, CH, N, H, $C_2F_5$, $CH_2CF_3$], [CC757; 2, CH, N, H, $C_3F_7$, $CH_2CF_3$], [CC758; 2, CH, N, H, $CH_2CF_3$, $CH_2CF_3$], [CC759; 2, CH, N, H, $CH_2CHF_2$, $CH_2CF_3$], [CC760; 0, N,N, H, H, $CH_2CF_3$], [CC761; 0, N,N, H, F, $CH_2CF_3$], [CC762; 0, N,N, H, Cl, $CH_2CF_3$], [CC763; 0, N,N, H, Br, $CH_2CF_3$], [CC764; 0, N,N, H, I, $CH_2CF_3$], [CC765; 0, N,N, H, $CF_3$, $CH_2CF_3$], [CC766; 0, N,N, H, $CF_2H$, $CH_2CF_3$], [CC767; 0, N,N, H, $C_2F_5$, $CH_2CF_3$], [CC768; 0, N,N, H, $C_3F_7$, $CH_2CF_3$], [CC769; 0, N, N, H, $CH_2CF_3$, $CH_2CF_3$], [CC770; 0, N,N, H, $CH_2CHF_2$, $CH_2CF_3$], [CC771; 1, N,N, H, H, $CH_2CF_3$], [CC772; 1, N,N, H, F, $CH_2CF_3$], [CC773; 1, N,N, H, Cl, $CH_2CF_3$], [CC774; 1, N,N, H, Br, $CH_2CF_3$], [CC775; 1, N,N, H, I, $CH_2CF_3$], [CC776; 1, N,N, H, $CF_3$, $CH_2CF_3$], [CC777; 1, N,N, H, $CF_2H$, $CH_2CF_3$], [CC778; 1, N,N, H, $C_2F_5$, $CH_2CF_3$], [CC779; 1, N,N, H, $C_3F_7$, $CH_2CF_3$], [CC780; 1, N,N, H, $CH_2CF_3$, $CH_2CF_3$], [CC781; 1, N,N, H, $CH_2CHF_2$, $CH_2CF_3$], [CC782; 2, N,N, H, H, $CH_2CF_3$], [CC783; 2, N,N, H, F, $CH_2CF_3$], [CC784; 2, N,N, H, Cl, $CH_2CF_3$], [CC785; 2, N,N, H, Br, $CH_2CF_3$], [CC786; 2, N,N, H, I, $CH_2CF_3$], [CC787; 2, N,N, H, $CF_3$, $CH_2CF_3$], [CC788; 2, N,N, H, $CF_2H$, $CH_2CF_3$], [CC789; 2, N,N, H, $C_2F_5$, $CH_2CF_3$], [CC790; 2, N,N, H, $C_3F_7$, $CH_2CF_3$], [CC791; 2, N, N, H, $CH_2CF_3$, $CH_2CF_3$], [CC792; 2, N,N, H, $CH_2CHF_2$, $CH_2CF_3$], [CC793; 0, CH, CH, H, H, $CH_2CHF_2$], [CC794; 0, CH, CH, F, H, $CH_2CHF_2$], [CC795; 0, CH, CH, Cl, H, $CH_2CHF_2$], [CC796; 0, CH, CH, Br, H, $CH_2CHF_2$], [CC797; 0, CH, CH, I, H, $CH_2CHF_2$], [CC798; 0, CH, CH, $CF_3$, H, $CH_2CHF_2$], [CC799; 0, CH, CH, $CF_2H$, H, $CH_2CHF_2$], [CC800; 0, CH, CH, $C_2F_5$, H, $CH_2CHF_2$], [CC801; 0, CH, CH, $C_3F_7$, H, $CH_2CHF_2$], [CC802; 0, CH, CH, $CH_2CF_3$, H, $CH_2CHF_2$], [CC803; 0, CH, CH, $CH_2CHF_2$, H, $CH_2CHF_2$], [CC804; 1, CH, CH, H, H, $CH_2CHF_2$], [CC805; 1, CH, CH, F, H, $CH_2CHF_2$], [CC806; 1, CH, CH, Cl, H, $CH_2CHF_2$], [CC807; 1, CH, CH, Br, H, $CH_2CHF_2$], [CC808; 1, CH, CH, I, H, $CH_2CHF_2$], [CC809; 1, CH, CH, $CF_3$, H, $CH_2CHF_2$], [CC810; 1, CH, CH, $CF_2H$, H, $CH_2CHF_2$], [CC811; 1, CH, CH, $C_2F_5$, H, $CH_2CHF_2$], [CC812; 1, CH, CH, $C_3F_7$, H, $CH_2CHF_2$], [CC813; 1, CH, CH, $CH_2CF_3$, H, $CH_2CHF_2$], [CC814; 1, CH, CH, $CH_2CHF_2$, H, $CH_2CHF_2$], [CC815; 2, CH, CH, H, H, $CH_2CHF_2$], [CC816; 2, CH, CH, F, H, $CH_2CHF_2$], [CC817; 2, CH, CH, Cl, H, $CH_2CHF_2$], [CC818; 2, CH, CH, Br, H, $CH_2CHF_2$], [CC819; 2, CH, CH, I, H, $CH_2CHF_2$], [CC820; 2, CH, CH, $CF_3$, H, $CH_2CHF_2$], [CC821; 2, CH, CH, $CF_2H$, H, $CH_2CHF_2$], [CC822; 2, CH, CH, $C_2F_5$, H, $CH_2CHF_2$], [CC823; 2, CH, CH, $C_3F_7$, H, $CH_2CHF_2$], [CC824; 2, CH,

CH, $CH_2CF_3$, H, $CH_2CHF_2$], [CC825; 2, CH, CH, $CH_2CHF_2$, H, $CH_2CHF_2$], [CC826; 0, N, CH, H, H, $CH_2CHF_2$], [CC827; 0, N, CH, F, H, $CH_2CHF_2$], [CC828; 0, N, CH, Cl, H, $CH_2CHF_2$], [CC829; 0, N, CH, Br, H, $CH_2CHF_2$], [CC830; 0, N, CH, I, H, $CH_7CHF_2$], [CC831; 0, N, CH, $CF_3$, H, $CH_2CHF_2$], [CC832; 0, N, CH, $CF_2H$, H, $CH_2CHF_2$], [CC833; 0, N, CH, $C_2F_5$, H, $CH_2CHF_2$], [CC834; 0, N, CH, $C_3F_7$, H, $CH_7$ $CHF_7$], [CC835; 0, N, CH, $CH_2CF_3$, H, $CH_2CHF_2$], [CC836; 0, N, CH, $CH_2CHF_2$, H, $CH_2CHF_2$], [CC837; 1, N, CH, H, H, $CH_2CHF_2$], [CC838; 1, N, CH, F, H, $CH_2CHF_2$], [CC839; 1, N, CH, Cl, H, $CH_2CHF_2$], [CC840; 1, N, CH, Br, H, $CH_2CHF_2$], [CC841; 1, N, CH, I, H, $CH_2CHF_2$], [CC842; 1, N, CH, $CF_3$, H, $CH_2CHF_2$], [CC843; 1, N, CH, $CF_2H$, H, $CH_2CHF_2$], [CC844; 1, N, CH, $C_2F_5$, H, $CH_2CHF_2$], [CC845; 1, N, CH, $C_3F_5$, H, $CH_2CHF_2$], [CC846; 1, N, CH, $CH_2CF_3$, H, $CH_2CHF_2$], [CC847; 1, N, CH, $CH_2CHF_2$, H, $CH_2CHF_2$], [CC848; 2, N, CH, H, H, $CH_2CHF_2$], [CC849; 2, N, CH, F, H, $CH_2CHF_2$], [CC850; 2, N, CH, Cl, H, $CH_2CHF_2$], [CC851; 2, N, CH, Br, H, $CH_2CHF_2$], [CC852; 2, N, CH, I, H, $CH_2CHF_2$], [CC853; 2, N, CH, $CF_3$, H, $CH_2CHF_2$], [CC854; 2, N, CH, $CF_2H$, H, $CH_2CHF_2$], [CC855; 2, N, CH, $C_2F_5$, H, $CH_2CHF_2$], [CC856; 2, N, CH, $C_3F_7$, H, $CH_2CHF_2$], [CC857; 2, N, CH, $CH_2CF_3$, H, $CH_2CHF_2$], [CC858; 2, N, CH, $CH_2CHF_2$, H, $CH_2CHF_2$], [CC859; 0, CH, N, H, H, $CH_2CHF_2$], [CC860; 0, CH, N, F, H, $CH_2CHF_2$], [CC861; 0, CH, N, Cl, H, $CH_2CHF_2$], [CC862; 0, CH, N, Br, H, $CH_2CHF_2$], [CC863; 0, CH, N, I, H, $CH_2CHF_2$], [CC864; 0, CH, N, $CF_3$, H, $CH_2CHF_2$], [CC865; 0, CH, N, $CF_2H$, H, $CH_2CHF_2$], [CC866; 0, CH, N, $C_2F_5$, H, $CH_2CHF_2$], [CC867; 0, CH, N, $C_3F_2$, H, $CH_2CHF_2$], [CC868; 0, CH, N, $CH_2CF_3$, H, $CH_2CHF_2$], [CC869; 0, CH, N, $CH_2CHF_2$, H, $CH_2CHF_2$], [CC870; 1, CH, N, H, H, $CH_2CHF_2$], [CC871; 1, CH, N, F, H, $CH_2CHF_2$], [CC872; 1, CH, N, Cl, H, $CH_2CHF_2$], [CC873; 1, CH, N, Br, H, $CH_2CHF_2$], [CC874; 1, CH, N, I, H, $CH_2CHF_2$], [CC875; 1, CH, N, $CF_3$, H, $CH_2CHF_2$], [CC876; 1, CH, N, $CF_2H$, H, $CH_2CHF_2$], [CC877; 1, CH, N, $C_2F_5$, H, $CH_2CHF_2$], [CC878; 1, CH, N, $C_3F_7$, H, $CH_2CHF_2$], [CC879; 1, CH, N, $CH_2CF_3$, H, $CH_2CHF_2$], [CC880; 1, CH, N, $CH_2CHF_2$, H, $CH_2CHF_2$], [CC881; 2, CH, N, H, H, $CH_2CHF_2$], [CC882; 2, CH, N, F, H, $CH_2CHF_2$], [CC883; 2, CH, N, Cl, H, $CH_2CHF_2$], [CC884; 2, CH, N, Br, H, $CH_2CHF_2$], [CC885; 2, CH, N, I, H, $CH_2CHF_2$], [CC886; 2, CH, N, $CF_3$, H, $CH_2CHF_2$], [CC887; 2, CH, N, $CF_2H$, H, $CH_2CHF_2$], [CC888; 2, CH, N, $C_2F_5$, H, $CH_2CHF_2$], [CC889; 2, CH, N, $C_3F_7$, H, $CH_2CHF_2$], [CC890; 2, CH, N, $CH_2CF_3$, H, $CH_2CHF_2$], [CC891; 2, CH, N, $CH_2CHF_2$, H, $CH_2CHF_2$], [CC892; 0, N,N, H, H, $CH_2CHF_2$], [CC893; 0, N,N, F, H, $CH_2CHF_2$], [CC894; 0, N, N, Cl, H, $CH_2CHF_2$], [CC895; 0, N, N, Br, H, $CH_2CHF_2$], [CC896; 0, N,N, I, H, $CH_2CHF_2$], [CC897; 0, N, N, $CF_3$, H, $CH_2CHF_2$], [CC898; 0, N, N, $CF_2H$, H, $CH_2CHF_2$], [CC899; 0, N, N, $C_2F_5$, H, $CH_2CHF_2$], [CC900; 0, N, N, $C_3F_7$, H, $CH_2CHF_2$], [CC901; 0, N, N, $CH_2CF_3$, H, CH CHF], [CC902; 0, N, N, $CH_2CHF_2$, H, $CH_2CHF_2$], [CC903; 1, N,N, H, H, $CH_2CHF_2$], [CC904; 1, N,N, F, H, $CH_2CHF_2$], [CC905; 1, N, N, Cl, H, $CH_2CHF_2$], [CC906; 1, N, N, Br, H, $CH_2CHF_2$], [CC907; 1, N,N, I, H, $CH_2CHF$], [CC908; 1, N, N, $CF_3$, H, $CH_2CHF_2$], [CC909; 1, N, N, $CF_2H$, H, $CH_2CHF_2$], [CC910; 1, N, N, $C_2F_5$, H, $CH_2CHF_2$], [CC911; 1, N, N, $C_3F_7$, H, $CH_2CHF_2$], [CC912; 1, N, N, $CH_2CF_3$, H, $CH_2CHF_2$], [CC913; 1, N, N, $CH_2CHF_2$, H, $CH_2CHF_2$], [CC914; 2, N,N, H, H, $CH_2CHF_2$], [CC915; 2, N,N, F, H, $CH_2CHF_2$], [CC916; 2, N, N, Cl, H, $CH_2CHF_2$], [CC917; 2, N, N, Br, H, $CH_2CHF_2$], [CC918; 2, N,N, I, H, $CH_2CHF_2$], [CC919; 2, N, N, $CF_3$, H, $CH_2CHF_2$], [CC920; 2, N, N, $CF_2H$, H, $CH_2CHF_2$], [CC921; 2, N, N, $C_2F_5$, H, $CH_2CHF_2$], [CC922; 2, N, N, $C_3F_7$, H, $CH_2CHF_2$], [CC923; 2, N, N, $CH_2CF_3$, H, $CH_2CHF_2$], [CC924; 2, N, N, $CH_2CHF_2$, H, $CH_2CHF_2$], [CC925; 0, CH, CH, H, H, $CH_2CHF_2$], [CC926; 0, CH, CH, H, F, $CH_2CHF_2$], [CC927; 0, CH, CH, H, Cl, $CH_2CHF_2$], [CC928; 0, CH, CH, H, Br, $CH_2CHF_2$], [CC929; 0, CH, CH, H, I, $CH_2CHF_2$], [CC930; 0, CH, CH, H, $CF_3$, $CH_2CHF_2$], [CC931; 0, CH, CH, H, $CF_2H$, $CH_2CHF_2$], [CC932; 0, CH, CH, H, $C_2F_5$, $CH_2CHF_2$], [CC933; 0, CH, CH, H, $C_3F_7$, $CH_2CHF_2$], [CC934; 0, CH, CH, H, $CH_2CF_3$, $CH_2CHF_2$], [CC935; 0, CH, CH, H, $CH_2CHF_2$, $CH_2CHF_2$], [CC936; 1, CH, CH, H, H, $CH_2CHF_2$], [CC937; 1, CH, CH, H, F, $CH_2CHF_2$], [CC938; 1, CH, CH, H, Cl, $CH_2CHF_2$], [CC939; 1, CH, CH, H, Br, $CH_2CHF_2$], [CC940; 1, CH, CH, H, I, $CH_2CHF_2$], [CC941; 1, CH, CH, H, $CF_3$, $CH_2CHF_2$], [CC942; 1, CH, CH, H, $CF_2H$, $CH_2CHF_2$], [CC943; 1, CH, CH, H, $C_2F_5$, $CH_2CHF_2$], [CC944; 1, CH, CH, H, $C_3F_7$, $CH_2CHF_2$], [CC945; 1, CH, CH, H, $CH_2CF_3$, $CH_2CHF_2$], [CC946; 1, CH, CH, H, $CH_2CHF_2$, $CH_2CHF_2$], [CC947; 2, CH, CH, H, H, $CH_2CHF_2$], [CC948; 2, CH, CH, H, F, $CH_2CHF_2$], [CC949; 2, CH, CH, H, Cl, $CH_2CHF_2$], [CC950; 2, CH, CH, H, Br, $CH_2CHF_2$], [CC951; 2, CH, CH, H, I, $CH_2CHF_2$], [CC952; 2, CH, CH, H, $CF_3$, $CH_2CHF_2$], [CC953; 2, CH, CH, H, $CF_2H$, $CH_2CHF_2$], [CC954; 2, CH, CH, H, $C_2F_5$, $CH_2CHF_2$], [CC955; 2, CH, CH, H, $C_3F_7$, $CH_2CHF_2$], [CC956; 2, CH, CH, H, $CH_2CF_3$, $CH_2CHF_2$], [CC957; 2, CH, CH, H, $CH_2CHF_2$, $CH_2CHF_2$], [CC958; 0, N, CH, H, H, $CH_2CHF_2$], [CC959; 0, N, CH, H, F, $CH_2CHF_2$], [CC960; 0, N, CH, H, Cl, $CH_2CHF_2$], [CC961; 0, N, CH, H, Br, $CH_2CHF_2$], [CC962; 0, N, CH, H, I, $CH_2CHF_2$], [CC963; 0, N, CH, H, $CF_3$, $CH_2CHF_2$], [CC964; 0, N, CH, H, $CF_2H$, $CH_2CHF_2$], [CC965; 0, N, CH, H, $C_2F_5$, $CH_2CHF_2$], [CC966; 0, N, CH, H, $C_3F_7$, $CH_2CHF_2$], [CC967; 0, N, CH, H, $CH_2CF_3$, $CH_2CHF_2$], [CC968; 0, N, CH, H, $CH_2CHF_2$, $CH_2CHF_2$], [CC969; 1, N, CH, H, H, $CH_2CHF_2$], [CC970; 1, N, CH, H, F, $CH_2CHF_2$], [CC971; 1, N, CH, H, Cl, $CH_2CHF_2$], [CC972; 1, N, CH, H, Br, $CH_2CHF_2$], [CC973; 1, N, CH, H, I, $CH_2CHF_2$], [CC974; 1, N, CH, H, $CF_3$, $CH_2CHF_2$], [CC975; 1, N, CH, H, $CF_2H$, $CH_2CHF_2$], [CC976; 1, N, CH, H, $C_7F_5$, $CH_2$ $CHF_2$], [CC977; 1, N, CH, H, $C_3F_7$, $CH_2CHF_2$], [CC978; 1, N, CH, H, $CH_2CF_3$, $CH_2CHF_2$], [CC979; 1, N, CH, H, $CH_7CHF_7$, $CH_7CHF_2$], [CC980; 2, N, CH, H, H, $CH_2CHF_2$], [CC981; 2, N, CH, H, F, $CH_2CHF_2$], [CC982; 2, N, CH, H, Cl, $CH_2CHF_2$], [CC983; 2, N, CH, H, Br, $CH_2CHF_2$], [CC984; 2, N, CH, H, I, $CH_2CHF_2$], [CC985; 2, N, CH, H, $CF_3$, $CH_2CHF_2$], [CC986; 2, N, CH, H, $CF_2H$, $CH_2CHF_2$], [CC987; 2, N, CH, H, $C_2F_5$, $CH_2CHF_2$], [CC988; 2, N, CH, H, $C_3F_7$, $CH_2CHF_2$], [CC989; 2, N, CH, H, $CH_2CF_3$, $CH_2CHF_2$], [CC990; 2, N, CH, H, $CH_2CHF_2$, $CH_2CHF_2$], [CC991; 0, CH, N, H, H, $CH_2CHF_2$], [CC992; 0, CH, N, H, F, $CH_2CHF_2$], [CC993; 0, CH, N, H, Cl, $CH_2CHF_2$], [CC994; 0, CH, N, H, Br, $CH_2CHF_2$], [CC995; 0, CH, N, H, I, $CH_2CHF_2$], [CC996; 0, CH, N, H, $CF_3$, $CH_2CHF_2$], [CC997; 0, CH, N, H, $CF_2H$, $CH_2CHF_2$], [CC998; 0, CH, N, H, $C_2F_5$, $CH_2CHF_2$], [CC999; 0, CH, N, H, $C_3F_7$, $CH_2CHF_2$], [CC1000; 0, CH, N, H, $CH_2CF_3$, $CH_2CHF_2$], [CC1001; 0, CH, N, H, $CH_2CHF_2$, $CH_2CHF_2$], [CC1002; 1, CH, N, H, H, $CH_2CHF_2$], [CC1003; 1, CH, N, H, F, $CH_2CHF_2$], [CC1004; 1, CH, N, H, Cl, $CH_2CHF_2$], [CC1005; 1, CH, N, H, Br, $CH_2CHF_2$], [CC1006; 1, CH, N, H, I, $CH_2CHF_2$], [CC1007; 1, CH, N, H, $CF_3$, $CH_2CHF_2$], [CC1008; 1, CH, N, H, $CF_2H$, $CH_2CHF_2$], [CC1009; 1, CH, N, H, $C_2F_5$, $CH_2CHF_2$], [CC1010; 1, CH, N, H, $C_3F_7$, $CH_2CHF_2$], [CC1011; 1, CH, N, H, $CH_2CF_3$, $CH_2CHF_2$], [CC1012; 1, CH, N, H, $CH_2CHF_2$, $CH_2CHF_2$], [CC1013; 2,

CH, N, H, H, $CH_2CHF_2$], [CC1014; 2, CH, N, H, F, $CH_2CHF_2$], [CC1015; 2, CH, N, H, Cl, $CH_2CHF_2$], [CC1016; 2, CH, N, H, Br, $CH_2CHF_2$], [CC1017; 2, CH, N, H, I, $CH_2CHF_2$], [CC1018; 2, CH, N, H, $CF_3$, $CH_2CHF_2$], [CC1019; 2, CH, N, H, $CF_2H$, $CH_2CHF_2$], [CC1020; 2, CH, N, H, $C_2F_5$, $CH_2CHF_2$], [CC1021; 2, CH, N, H, $C_3F_7$, $CH_2CHF_2$], [CC1022; 2, CH, N, H, $CH_2CF_3$, $CH_2CHF_2$], [CC1023; 2, CH, N, H, $CH_2CHF_2$, $CH_2CHF_2$], [CC1024; 0, N,N, H, H, $CH_2CHF_2$], [CC1025; 0, N,N, H, F, $CH_2CHF_2$], [CC1026; 0, N,N, H, Cl, $CH_2CHF_2$], [CC1027; 0, N,N, H, Br, $CH_2CHF_2$], [CC1028; 0, N,N, H, I, $CH_2CHF_2$], [CC1029; 0, N,N, H, $CF_3$, $CH_2CHF_2$], [CC1030; 0, N, N, H, $CF_2H$, $CH_2CHF_2$], [CC1031; 0, N, N, H, $C_2F_5$, $CH_2CHF_2$], [CC1032; 0, N,N, H, $C_3F_7$, $CH_2CHF_2$], [CC1033; 0, N, N, H, $CH_2CF_3$, $CH_2CHF_2$], [CC1034; 0, N, N, H, $CH_2CHF_2$, $CH_2CHF_2$], [CC1035; 1, N,N, H, H, $CH_2CHF_2$], [CC1036; 1, N,N, H, F, $CH_2CHF_2$], [CC1037; 1, N,N, H, Cl, $CH_2CHF_2$], [CC1038; 1, N,N, H, Br, $CH_2CHF_2$], [CC1039; 1, N,N, H, I, $CH_2CHF_2$], [CC1040; 1, N,N, H, $CF_3$, $CH_2CHF_2$], [CC1041; 1, N, N, H, $CF_2H$, $CH_2CHF_2$], [CC1042; 1, N, N, H, $C_2F_5$, $CH_2CHF_2$], [CC1043; 1, N, N, H, $C_3F_7$, $CH_2CHF_2$], [CC1044; 1, N, N, H, $CH_2CF_3$, $CH_2CHF_2$], [CC1045; 1, N,N, H, $CH_2CHF_2$, $CH_2CHF_2$], [CC1046; 2, N,N, H, H, $CH_2CHF_2$], [CC1047; 2, N,N, H, F, $CH_2CHF_2$], [CC1048; 2, N,N, H, Cl, $CH_2CHF_2$], [CC1049; 2, N,N, H, Br, $CH_2CHF_2$], [CC1050; 2, N,N, H, I, $CH_2CHF_2$], [CC1051; 2, N,N, H, $CF_3$, $CH_2CHF_2$], [CC1052; 2, N, N, H, $CF_2H$, $CH_2CHF_2$], [CC1053; 2, N,N, H, $C_2F_5$, $CH_2CHF_2$], [CC1054; 2, N, N, H, $C_3F_7$, $CH_2CHF_2$], [CC1055; 2, N, N, H, $CH_2CF_3$, $CH_2CHF_2$], [CC1056; 2, N,N, H, $CH_2CHF_2$, $CH_2CHF_2$], [CC1057; 0, CH, CH, H, H, $SCF_3$], [CC1058; 0, CH, CH, F, H, $SCF_3$], [CC1059; 0, CH, CH, Cl, H, $SCF_3$], [CC1060; 0, CH, CH, Br, H, $SCF_3$], [CC1061; 0, CH, CH, I, H, $SCF_3$], [CC1062; 0, CH, CH, $CF_3$, H, $SCF_3$], [CC1063; 0, CH, CH, $CF_2H$, H, $SCF_3$], [CC1064; 0, CH, CH, $C_2F_5$, H, $SCF_3$], [CC1065; 0, CH, CH, $C_3F_7$, H, $SCF_3$], [CC1066; 0, CH, CH, $CH_2CF_3$, H, $SCF_3$], [CC1067; 0, CH, CH, $CH_2CHF_2$, H, $SCF_3$], [CC1068; 1, CH, CH, H, H, $SCF_3$], [CC1069; 1, CH, CH, F, H, $SCF_3$], [CC1070; 1, CH, CH, Cl, H, $SCF_3$], [CC1071; 1, CH, CH, Br, H, $SCF_3$], [CC1072; 1, CH, CH, I, H, $SCF_3$], [CC1073; 1, CH, CH, $CF_3$, H, $SCF_3$], [CC1074; 1, CH, CH, $CF_2H$, H, $SCF_3$], [CC1075; 1, CH, CH, $C_2F_5$, H, $SCF_3$], [CC1076; 1, CH, CH, $C_3F_7$, H, $SCF_3$], [CC1077; 1, CH, CH, $CH_2CF_3$, H, $SCF_3$], [CC1078; 1, CH, CH, $CH_2CHF_2$, H, $SCF_3$], [CC1079; 2, CH, CH, H, H, $SCF_3$], [CC1080; 2, CH, CH, F, H, $SCF_3$], [CC1081; 2, CH, CH, Cl, H, $SCF_3$], [CC1082; 2, CH, CH, Br, H, $SCF_3$], [CC1083; 2, CH, CH, I, H, $SCF_3$], [CC1084; 2, CH, CH, $CF_3$, H, $SCF_3$], [CC1085; 2, CH, CH, $CF_2H$, H, $SCF_3$], [CC1086; 2, CH, CH, $C_2F_7$, H, $SCF_3$], [CC1087; 2, CH, CH, $C_3F_7$, H, $SCF_3$], [CC1088; 2, CH, CH, $CH_2CF_3$, H, $SCF_3$], [CC1089; 2, CH, CH, $CH_2CHF_2$, H, $SCF_3$], [CC1090; 0, N, CH, H, H, $SCF_3$], [CC1091; 0, N, CH, F, H, $SCF_3$], [CC1092; 0, N, CH, Cl, H, $SCF_3$], [CC1093; 0, N, CH, Br, H, $SCF_3$], [CC1094; 0, N, CH, I, H, $SCF_3$], [CC1095; 0, N, CH, $CF_3$, H, $SCF_3$], [CC1096; 0, N, CH, $CF_2H$, H, $SCF_3$], [CC1097; 0, N, CH, $C_2F$, H, $SCF_3$], [CC1098; 0, N, CH, $C_3F_7$, H, $SCF_3$], [CC1099; 0, N, CH, $CH_2CF_3$, H, $SCF_3$], [CC1100; 0, N, CH, $CH_2CHF_2$, H, $SCF_3$], [CC1101; 1, N, CH, H, H, $SCF_3$], [CC1102; 1, N, CH, F, H, $SCF_3$], [CC1103; 1, N, CH, Cl, H, $SCF_3$], [CC1104; 1, N, CH, Br, H, $SCF_3$], [CC1105; 1, N, CH, I, H, $SCF_3$], [CC1106; 1, N, CH, $CF_3$, H, $SCF_3$], [CC1107; 1, N, CH, $CF_2H$, H, $SCF_3$], [CC1108; 1, N, CH, $C_2F_5$, H, $SCF_3$], [CC1109; 1, N, CH, $C_3F_7$, H, $SCF_3$], [CC1110; 1, N, CH, $CH_2CF_3$, H, $SCF_3$], [CC1111; 1, N, CH, $CH_2CHF_2$, H, $SCF_3$], [CC1112; 2, N, CH, H, H, $SCF_3$], [CC1113; 2, N, CH, F, H, $SCF_3$], [CC1114; 2, N, CH, Cl, H, $SCF_3$], [CC1115; 2, N, CH, Br, H, $SCF_3$], [CC1116; 2, N, CH, I, H, $SCF_3$], [CC1117; 2, N, CH, $CF_3$, H, $SCF_3$], [CC1118; 2, N, CH, $CF_2H$, H, $SCF_3$], [CC1119; 2, N, CH, $C_2F_5$, H, $SCF_3$], [CC1120; 2, N, CH, $C_3F_7$, H, $SCF_3$], [CC1121; 2, N, CH, $CH_2CF_3$, H, $SCF_3$], [CC1122; 2, N, CH, $CH_2CHF_2$, H, $SCF_3$], [CC1123; 0, CH, N, H, H, $SCF_3$], [CC1124; 0, CH, N, F, H, $SCF_3$], [CC1125; 0, CH, N, Cl, H, $SCF_3$], [CC1126; 0, CH, N, Br, H, $SCF_3$], [CC1127; 0, CH, N, I, H, $SCF_3$], [CC1128; 0, CH, N, $CF_3$, H, $SCF_3$], [CC1129; 0, CH, N, $CF_2H$, H, $SCF_3$], [CC1130; 0, CH, N, $C_2F_5$, H, $SCF_3$], [CC1131; 0, CH, N, $C_3F_7$, H, $SCF_3$], [CC1132; 0, CH, N, $CH_2CF_3$, H, $SCF_3$], [CC1133; 0, CH, N, $CH_2CHF_2$, H, $SCF_3$], [CC1134; 1, CH, N, H, H, $SCF_3$], [CC1135; 1, CH, N, F, H, $SCF_3$], [CC1136; 1, CH, N, Cl, H, $SCF_3$], [CC1137; 1, CH, N, Br, H, $SCF_3$], [CC1138; 1, CH, N, I, H, $SCF_3$], [CC1139; 1, CH, N, $CF_3$, H, $SCF_3$], [CC1140; 1, CH, N, $CF_2H$, H, $SCF_3$], [CC1141; 1, CH, N, $C_2F_5$, H, $SCF_3$], [CC1142; 1, CH, N, $C_3F_7$, H, $SCF_3$], [CC1143; 1, CH, N, $CH_2CF_3$, H, $SCF_3$], [CC1144; 1, CH, N, $CH_2CHF_2$, H, $SCF_3$], [CC1145; 2, CH, N, H, H, $SCF_3$], [CC1146; 2, CH, N, F, H, $SCF_3$], [CC1147; 2, CH, N, Cl, H, $SCF_3$], [CC1148; 2, CH, N, Br, H, $SCF_3$], [CC1149; 2, CH, N, I, H, $SCF_3$], [CC1150; 2, CH, N, $CF_3$, H, $SCF_3$], [CC1151; 2, CH, N, $CF_2H$, H, $SCF_3$], [CC1152; 2, CH, N, $C_2F_5$, H, $SCF_3$], [CC1153; 2, CH, N, $C_3F_7$, H, $SCF_3$], [CC1154; 2, CH, N, $CH_2CF_3$, H, $SCF_3$], [CC1155; 2, CH, N, $CH_2CHF_2$, H, $SCF_3$], [CC1156; 0, N,N, H, H, $SCF_3$], [CC1157; 0, N,N, F, H, $SCF_3$], [CC1158; 0, N, N, Cl, H, $SCF_3$], [CC1159; 0, N, N, Br, H, $SCF_3$], [CC1160; 0, N,N, I, H, $SCF_3$], [CC1161; 0, N, N, $CF_3$, H, $SCF_3$], [CC1162; 0, N, N, $CF_2H$, H, $SCF_3$], [CC1163; 0, N, N, $C_2F_5$, H, $SCF_3$], [CC1164; 0, N, N, $C_3F_7$, H, $SCF_3$], [CC1165; 0, N, N, $CH_2CF_3$, H, $SCF_3$], [CC1166; 0, N, N, $CH_2CHF_2$, H, $SCF_3$], [CC1167; 1, N,N, H, H, $SCF_3$], [CC1168; 1, N,N, F, H, $SCF_3$], [CC1169; 1, N, N, Cl, H, $SCF_3$], [CC1170; 1, N, N, Br, H, $SCF_3$], [CC1171; 1, N,N, I, H, $SCF_3$], [CC1172; 1, N, N, $CF_3$, H, $SCF_3$], [CC1173; 1, N, N, $CF_2H$, H, $SCF_3$], [CC1174; 1, N, N, $C_2F_5$, H, $SCF_3$], [CC1175; 1, N, N, $C_3F_7$, H, $SCF_3$], [CC1176; 1, N, N, $CH_2CF_3$, H, $SCF_3$], [CC1177; 1, N, N, $CH_2CHF_2$, H, $SCF_3$], [CC1178; 2, N,N, H, H, $SCF_3$], [CC1179; 2, N,N, F, H, $SCF_3$], [CC1180; 2, N, N, Cl, H, $SCF_3$], [CC1181; 2, N, N, Br, H, $SCF_3$], [CC1182; 2, N,N, I, H, $SCF_3$], [CC1183; 2, N, N, $CF_3$, H, $SCF_3$], [CC1184; 2, N, N, $CF_2H$, H, $SCF_3$], [CC1185; 2, N, N, $C_2F_5$, H, $SCF_3$], [CC1186; 2, N, N, $C_3F_7$, H, $SCF_3$], [CC1187; 2, N, N, $CH_2CF_3$, H, $SCF_3$], [CC1188; 2, N, N, $CH_2CHF_2$, H, $SCF_3$], [CC1189; 0, CH, CH, H, H, $SCF_3$], [CC1190; 0, CH, CH, H, F, $SCF_3$], [CC1191; 0, CH, CH, H, Cl, $SCF_3$], [CC1192; 0, CH, CH, H, Br, $SCF_3$], [CC1193; 0, CH, CH, H, I, $SCF_3$], [CC1194; 0, CH, CH, H, $CF_3$, $SCF_3$], [CC1195; 0, CH, CH, H, $CF_2H$, $SCF_3$], [CC1196; 0, CH, CH, H, $C_2F_5$, $SCF_3$], [CC1197; 0, CH, CH, H, $C_3F_7$, $SCF_3$], [CC1198; 0, CH, CH, H, $CH_2CF_3$, $SCF_3$], [CC1199; 0, CH, CH, H, $CH_2CHF_2$, $SCF_3$], [CC1200; 1, CH, CH, H, H, $SCF_3$], [CC1201; 1, CH, CH, H, F, $SCF_3$], [CC1202; 1, CH, CH, H, Cl, $SCF_3$], [CC1203; 1, CH, CH, H, Br, $SCF_3$], [CC1204; 1, CH, CH, H, I, $SCF_3$], [CC1205; 1, CH, CH, H, $CF_3$, $SCF_3$], [CC1206; 1, CH, CH, H, $CF_2H$, $SCF_3$], [CC1207; 1, CH, CH, H, $C_2F_5$, $SCF_3$], [CC1208; 1, CH, CH, H, $C_3F_7$, $SCF_3$], [CC1209; 1, CH, CH, H, $CH_2CF_3$, $SCF_3$], [CC1210; 1, CH, CH, H, $CH_2CHF_2$, $SCF_3$], [CC1211; 2, CH, CH, H, H, $SCF_3$], [CC1212; 2, CH, CH, H, F, $SCF_3$], [CC1213; 2, CH, CH, H, Cl, $SCF_3$], [CC1214; 2, CH, CH, H, Br, $SCF_3$], [CC1215; 2, CH, CH, H, I, $SCF_3$], [CC1216; 2, CH, CH, H, $CF_3$, $SCF_3$], [CC1217; 2, CH, CH, H, $CF_2H$, $SCF_3$], [CC1218; 2, CH, CH, H, $C_2F_5$, $SCF_3$], [CC1219; 2, CH, CH,

H, $C_3F_7$, $SCF_3$], [CC1220; 2, CH, CH, H, $CH_2CF_3$, $SCF_3$], [CC1221; 2, CH, CH, H, $CH_2CHF_2$, $SCF_3$], [CC1222; 0, N, CH, H, H, $SCF_3$], [CC1223; 0, N, CH, H, F, $SCF_3$], [CC1224; 0, N, CH, H, Cl, $SCF_3$], [CC1225; 0, N, CH, H, Br, $SCF_3$], [CC1226; 0, N, CH, H, I, $SCF_3$], [CC1227; 0, N, CH, H, $CF_3$, $SCF_3$], [CC1228; 0, N, CH, H, $CF_2H$, $SCF_3$], [CC1229; 0, N, CH, H, $C_2F_5$, $SCF_3$], [CC1230; 0, N, CH, H, $C_3F_7$, $SCF_3$], [CC1231; 0, N, CH, H, $CH_2CF_3$, $SCF_3$], [CC1232; 0, N, CH, H, $CH_2CHF_2$, $SCF_3$], [CC1233; 1, N, CH, H, H, $SCF_3$], [CC1234; 1, N, CH, H, F, $SCF_3$], [CC1235; 1, N, CH, H, Cl, $SCF_3$], [CC1236; 1, N, CH, H, Br, $SCF_3$], [CC1237; 1, N, CH, H, I, $SCF_3$], [CC1238; 1, N, CH, H, $CF_3$, $SCF_3$], [CC1239; 1, N, CH, H, $CF_2H$, $SCF_3$], [CC1240; 1, N, CH, H, $C_2F_5$, $SCF_3$], [CC1241; 1, N, CH, H, $C_3F_7$, $SCF_3$], [CC1242; 1, N, CH, H, $CH_2CF_3$, $SCF_3$], [CC1243; 1, N, CH, H, $CH_2CHF_2$, $SCF_3$], [CC1244; 2, N, CH, H, H, $SCF_3$], [CC1245; 2, N, CH, H, F, $SCF_3$], [CC1246; 2, N, CH, H, Cl, $SCF_3$], [CC1247; 2, N, CH, H, Br, $SCF_3$], [CC1248; 2, N, CH, H, I, $SCF_3$], [CC1249; 2, N, CH, H, $CF_3$, $SCF_3$], [CC1250; 2, N, CH, H, $CF_2H$, $SCF_3$], [CC1251; 2, N, CH, H, $C_2F_5$, $SCF_3$], [CC1252; 2, N, CH, H, $C_3F$, $SCF_3$], [CC1253; 2, N, CH, H, $CH_2CF_3$, $SCF_3$], [CC1254; 2, N, CH, H, $CH_2CHF_2$, $SCF_3$], [CC1255; 0, CH, N, H, H, $SCF_3$], [CC1256; 0, CH, N, H, F, $SCF_3$], [CC1257; 0, CH, N, H, Cl, $SCF_3$], [CC1258; 0, CH, N, H, Br, $SCF_3$], [CC1259; 0, CH, N, H, I, $SCF_3$], [CC1260; 0, CH, N, H, $CF_3$, $SCF_3$], [CC1261; 0, CH, N, H, $CF_2H$, $SCF_3$], [CC1262; 0, CH, N, H, $C_2F_5$, $SCF_3$], [CC1263; 0, CH, N, H, $C_3F_7$, $SCF_3$], [CC1264; 0, CH, N, H, $CH_2CF_3$, $SCF_3$], [CC1265; 0, CH, N, H, $CH_2CHF_2$, $SCF_3$], [CC1266; 1, CH, N, H, H, $SCF_3$], [CC1267; 1, CH, N, H, F, $SCF_3$], [CC1268; 1, CH, N, H, Cl, $SCF_3$], [CC1269; 1, CH, N, H, Br, $SCF_3$], [CC1270; 1, CH, N, H, I, $SCF_3$], [CC1271; 1, CH, N, H, $CF_3$, $SCF_3$], [CC1272; 1, CH, N, H, $CF_2H$, $SCF_3$], [CC1273; 1, CH, N, H, $C_2F_5$, $SCF_3$], [CC1274; 1, CH, N, H, $C_3F_7$, $SCF_3$], [CC1275; 1, CH, N, H, $CH_2CF_3$, $SCF_3$], [CC1276; 1, CH, N, H, $CH_2CHF_2$, $SCF_3$], [CC1277; 2, CH, N, H, H, $SCF_3$], [CC1278; 2, CH, N, H, F, $SCF_3$], [CC1279; 2, CH, N, H, Cl, $SCF_3$], [CC1280; 2, CH, N, H, Br, $SCF_3$], [CC1281; 2, CH, N, H, I, $SCF_3$], [CC1282; 2, CH, N, H, $CF_3$, $SCF_3$], [CC1283; 2, CH, N, H, $CF_2H$, $SCF_3$], [CC1284; 2, CH, N, H, $C_2F_5$, $SCF_3$], [CC1285; 2, CH, N, H, $C_3F_7$, $SCF_3$], [CC1286; 2, CH, N, H, $CH_2CF_3$, $SCF_3$], [CC1287; 2, CH, N, H, $CH_2CHF_2$, $SCF_3$], [CC1288; 0, N,N, H, H, $SCF_3$], [CC1289; 0, N,N, H, F, $SCF_3$], [CC1290; 0, N,N, H, Cl, $SCF_3$], [CC1291; 0, N,N, H, Br, $SCF_3$], [CC1292; 0, N,N, H, I, $SCF_3$], [CC1293; 0, N,N, H, $CF_3$, $SCF_3$], [CC1294; 0, N,N, H, $CF_2H$, $SCF_3$], [CC1295; 0, N,N, H, $C_2F_5$, $SCF_3$], [CC1296; 0, N,N, H, $C_3F_7$, $SCF_3$], [CC1297; 0, N,N, H, $CH_2CF_3$, $SCF_3$], [CC1298; 0, N,N, H, $CH_2CHF_2$, $SCF_3$], [CC1299; 1, N,N, H, H, $SCF_3$], [CC1300; 1, N,N, H, F, $SCF_3$], [CC1301; 1, N,N, H, Cl, $SCF_3$], [CC1302; 1, N,N, H, Br, $SCF_3$], [CC1303; 1, N,N, H, I, $SCF_3$], [CC1304; 1, N,N, H, $CF_3$, $SCF_3$], [CC1305; 1, N,N, H, $CF_2H$, $SCF_3$], [CC1306; 1, N,N, H, $C_2F_5$, $SCF_3$], [CC1307; 1, N,N, H, $C_3F_7$, $SCF_3$], [CC1308; 1, N,N, H, $CH_2CF_3$, $SCF_3$], [CC1309; 1, N,N, H, $CH_2CHF_2$, $SCF_3$], [CC1310; 2, N,N, H, H, $SCF_3$], [CC1311; 2, N,N, H, F, $SCF_3$], [CC1312; 2, N,N, H, Cl, $SCF_3$], [CC1313; 2, N,N, H, Br, $SCF_3$], [CC1314; 2, N,N, H, I, $SCF_3$], [CC1315; 2, N,N, H, $CF_3$, $SCF_3$], [CC1316; 2, N,N, H, $CF_2H$, $SCF_3$], [CC1317; 2, N, N, H, $C_2F_5$, $SCF_3$], [CC1318; 2, N, N, H, $C_3F_7$, $SCF_3$], [CC1319; 2, N,N, H, $CH_2CF_3$, $SCF_3$], [CC1320; 2, N,N, H, $CH_2CHF_2$, $SCF_3$], [CC1321; 0, CH, CH, H, H, $OCF_3$], [CC1322; 0, CH, CH, F, H, $OCF_3$], [CC1323; 0, CH, CH, Cl, H, $OCF_3$], [CC1324; 0, CH, CH, Br, H, $OCF_3$], [CC1325; 0, CH, CH, I, H, $OCF_3$], [CC1326; 0, CH, CH, $CF_3$, H, $OCF_3$], [CC1327; 0, CH, CH, $CF_2H$, H, $OCF_3$], [CC1328; 0, CH, CH, $C_2F_5$, H, $OCF_3$], [CC1329; 0, CH, CH, $C_3F_7$, H, $OCF_3$], [CC1330; 0, CH, CH, $CH_2CF_3$, H, $OCF_3$], [CC1331; 0, CH, CH, $CH_2CHF_2$, H, $OCF_3$], [CC1332; 1, CH, CH, H, H, $OCF_3$], [CC1333; 1, CH, CH, F, H, $OCF_3$], [CC1334; 1, CH, CH, Cl, H, $OCF_3$], [CC1335; 1, CH, CH, Br, H, $OCF_3$], [CC1336; 1, CH, CH, I, H, $OCF_3$], [CC1337; 1, CH, CH, $CF_3$, H, $OCF_3$], [CC1338; 1, CH, CH, $CF_2H$, H, $OCF_3$], [CC1339; 1, CH, CH, $C_2F_5$, H, $OCF_3$], [CC1340; 1, CH, CH, $C_3F_7$, H, $OCF_3$], [CC1341; 1, CH, CH, $CH_2CF_3$, H, $OCF_3$], [CC1342; 1, CH, CH, $CH_2CHF_2$, H, $OCF_3$], [CC1343; 2, CH, CH, H, H, $OCF_3$], [CC1344; 2, CH, CH, F, H, $OCF_3$], [CC1345; 2, CH, CH, Cl, H, $OCF_3$], [CC1346; 2, CH, CH, Br, H, $OCF_3$], [CC1347; 2, CH, CH, I, H, $OCF_3$], [CC1348; 2, CH, CH, $CF_3$, H, $OCF_3$], [CC1349; 2, CH, CH, $CF_2H$, H, $OCF_3$], [CC1350; 2, CH, CH, $C_2F_5$, H, $OCF_3$], [CC1351; 2, CH, CH, $C_3F_7$, H, $OCF_3$], [CC1352; 2, CH, CH, $CH_2CF_3$, H, $OCF_3$], [CC1353; 2, CH, CH, $CH_2CHF_2$, H, $OCF_3$], [CC1354; 0, N, CH, H, H, $OCF_3$], [CC1355; 0, N, CH, F, H, $OCF_3$], [CC1356; 0, N, CH, Cl, H, $OCF_3$], [CC1357; 0, N, CH, Br, H, $OCF_3$], [CC1358; 0, N, CH, I, H, $OCF_3$], [CC1359; 0, N, CH, $CF_3$, H, $OCF_3$], [CC1360; 0, N, CH, $CF_2H$, H, $OCF_3$], [CC1361; 0, N, CH, $C_2F_5$, H, $OCF_3$], [CC1362; 0, N, CH, $C_3F_7$, H, $OCF_3$], [CC1363; 0, N, CH, $CH_2CF_3$, H, $OCF_3$], [CC1364; 0, N, CH, $CH_2CHF_2$, H, $OCF_3$], [CC1365; 1, N, CH, H, H, $OCF_3$], [CC1366; 1, N, CH, F, H, $OCF_3$], [CC1367; 1, N, CH, Cl, H, $OCF_3$], [CC1368; 1, N, CH, Br, H, $OCF_3$], [CC1369; 1, N, CH, I, H, $OCF_3$], [CC1370; 1, N, CH, $CF_3$, H, $OCF_3$], [CC1371; 1, N, CH, $CF_2H$, H, $OCF_3$], [CC1372; 1, N, CH, $C_2F_5$, H, $OCF_3$], [CC1373; 1, N, CH, $C_3F_7$, H, $OCF_3$], [CC1374; 1, N, CH, $CH_2CF_3$, H, $OCF_3$], [CC1375; 1, N, CH, $CH_2CHF_2$, H, $OCF_3$], [CC1376; 2, N, CH, H, H, $OCF_3$], [CC1377; 2, N, CH, F, H, $OCF_3$], [CC1378; 2, N, CH, Cl, H, $OCF_3$], [CC1379; 2, N, CH, Br, H, $OCF_3$], [CC1380; 2, N, CH, I, H, $OCF_3$], [CC1381; 2, N, CH, $CF_3$, H, $OCF_3$], [CC1382; 2, N, CH, $CF_2H$, H, $OCF_3$], [CC1383; 2, N, CH, $C_2F_5$, H, $OCF_3$], [CC1384; 2, N, CH, $C_3F_7$, H, $OCF_3$], [CC1385; 2, N, CH, $CH_2CF_3$, H, $OCF_3$], [CC1386; 2, N, CH, $CH_2CHF_2$, H, $OCF_3$], [CC1387; 0, CH, N, H, H, $OCF_3$], [CC1388; 0, CH, N, F, H, $OCF_3$], [CC1389; 0, CH, N, Cl, H, $OCF_3$], [CC1390; 0, CH, N, Br, H, $OCF_3$], [CC1391; 0, CH, N, I, H, $OCF_3$], [CC1392; 0, CH, N, $CF_3$, H, $OCF_3$], [CC1393; 0, CH, N, $CF_2H$, H, $OCF_3$], [CC1394; 0, CH, N, $C_2F_5$, H, $OCF_3$], [CC1395; 0, CH, N, $C_3F_7$, H, $OCF_3$], [CC1396; 0, CH, N, $CH_2CF_3$, H, $OCF_3$], [CC1397; 0, CH, N, $CH_2CHF_2$, H, $OCF_3$], [CC1398; 1, CH, N, H, H, $OCF_3$], [CC1399; 1, CH, N, F, H, $OCF_3$], [CC1400; 1, CH, N, Cl, H, $OCF_3$], [CC1401; 1, CH, N, Br, H, $OCF_3$], [CC1402; 1, CH, N, I, H, $OCF_3$], [CC1403; 1, CH, N, $CF_3$, H, $OCF_3$], [CC1404; 1, CH, N, $CF_2H$, H, $OCF_3$], [CC1405; 1, CH, N, $C_2F_5$, H, $OCF_3$], [CC1406; 1, CH, N, $C_3F_7$, H, $OCF_3$], [CC1407; 1, CH, N, $CH_2CF_3$, H, $OCF_3$], [CC1408; 1, CH, N, $CH_2CHF_2$, H, $OCF_3$], [CC1409; 2, CH, N, H, H, $OCF_3$], [CC1410; 2, CH, N, F, H, $OCF_3$], [CC1411; 2, CH, N, Cl, H, $OCF_3$], [CC1412; 2, CH, N, Br, H, $OCF_3$], [CC1413; 2, CH, N, I, H, $OCF_3$], [CC1414; 2, CH, N, $CF_3$, H, $OCF_3$], [CC1415; 2, CH, N, $CF_2H$, H, $OCF_3$], [CC1416; 2, CH, N, $C_2F_5$, H, $OCF_3$], [CC1417; 2, CH, N, $C_3F_7$, H, $OCF_3$], [CC1418; 2, CH, N, $CH_2CF_3$, H, $OCF_3$], [CC1419; 2, CH, N, $CH_2CHF_2$, H, $OCF_3$], [CC1420; 0, N,N, H, H, $OCF_3$], [CC1421; 0, N,N, F, H, $OCF_3$], [CC1422; 0, N, N, Cl, H, $OCF_3$], [CC1423; 0, N, N, Br, H, $OCF_3$], [CC1424; 0, N,N, I, H, $OCF_3$], [CC1425; 0, N, N, $CF_3$, H, $OCF_3$], [CC1426; 0, N, N, $CF_2H$, H, $OCF_3$], [CC1427; 0, N, N, $C_2F_5$, H, $OCF_3$], [CC1428; 0, N, N, $C_3F_7$, H, $OCF_3$], [CC1429; 0, N, N, $CH_2CF_3$, H, $OCF_3$], [CC1430; 0, N, N, $CH_2CHF_2$, H, $OCF_3$], [CC1431; 1, N,N, H, H, $OCF_3$], [CC1432; 1, N,N, F, H, $OCF_3$], [CC1433; 1, N, N, Cl, H, $OCF_3$], [CC1434; 1, N, N, Br, H, $OCF_3$], [CC1435; 1, N,N, I, H, $OCF_3$], [CC1436; 1, N, N, $CF_3$, H, $OCF_3$], [CC1437; 1, N, N, $CF_2H$, H, $OCF_3$], [CC1438; 1, N, N, $C_2F_5$, H, $OCF_3$], [CC1439; 1, N, N, $C_3F_7$, H, $OCF_3$], [CC1440; 1, N, N, $CH_2CF_3$, H, $OCF_3$], [CC1441; 1, N, N, $CH_2CHF_2$, H, $OCF_3$], [CC1442; 2, N,N, H, H, $OCF_3$], [CC1443; 2, N,N, F, H, $OCF_3$], [CC1444; 2, N, N, Cl, H, $OCF_3$], [CC1445; 2, N, N, Br, H, $OCF_3$], [CC1446; 2, N,N, I, H, $OCF_3$], [CC1447; 2, N, N, $CF_3$, H, $OCF_3$], [CC1448; 2, N, N, $CF_2H$, H, $OCF_3$], [CC1449; 2, N, N, $C_2F_5$, H, $OCF_3$], [CC1450; 2, N, N, $C_3F_7$, H, $OCF_3$], [CC1451; 2, N, N, $CH_2CF_3$, H, $OCF_3$], [CC1452; 2, N, N, $CH_2CHF_2$, H, $OCF_3$], [CC1453; 0, CH, CH, H, H, $OCF_3$], [CC1454; 0, CH, CH, H, F, $OCF_3$], [CC1455; 0, CH, CH, H, Cl, $OCF_3$], [CC1456; 0, CH, CH, H, Br, $OCF_3$], [CC1457; 0, CH, CH, H, I, $OCF_3$], [CC1458; 0, CH, CH, H, $CF_3$, $OCF_3$], [CC1459; 0, CH, CH, H, $CF_2H$, $OCF_3$], [CC1460; 0, CH, CH, H, $C_2F_5$, $OCF_3$], [CC1461; 0, CH, CH, H, $C_3F_7$, $OCF_3$], [CC1462; 0, CH, CH, H, $CH_2CF_3$, $OCF_3$], [CC1463; 0, CH, CH, H, $CH_2CHF_2$, $OCF_3$], [CC1464; 1, CH, CH, H, H, $OCF_3$], [CC1465; 1, CH, CH, H, F, $OCF_3$], [CC1466; 1, CH, CH, H, Cl, $OCF_3$], [CC1467; 1, CH, CH, H, Br, $OCF_3$], [CC1468; 1, CH, CH, H, I, $OCF_3$], [CC1469; 1, CH, CH, H, $CF_3$, $OCF_3$], [CC1470; 1, CH, CH, H, $CF_2H$, $OCF_3$], [CC1471; 1, CH, CH, H, $C_2F_5$, $OCF_3$], [CC1472; 1, CH, CH, H, $C_3F_7$, $OCF_3$], [CC1473; 1, CH, CH, H, $CH_2CF_3$, $OCF_3$], [CC1474; 1, CH, CH, H, $CH_2CHF_2$, $OCF_3$], [CC1475; 2, CH, CH, H, H, $OCF_3$], [CC1476; 2, CH, CH, H, F, $OCF_3$], [CC1477; 2, CH, CH, H, Cl, $OCF_3$], [CC1478; 2, CH, CH, H, Br, $OCF_3$], [CC1479; 2, CH, CH, H, I, $OCF_3$], [CC1480; 2, CH, CH, H, $CF_3$, $OCF_3$], [CC1481; 2, CH, CH, H, $CF_2H$, $OCF_3$], [CC1482; 2, CH, CH, H, $C_2F_5$, $OCF_3$], [CC1483; 2, CH, CH, H, $C_3F_7$, $OCF_3$], [CC1484; 2, CH, CH, H, $CH_2CF_3$, $OCF_3$], [CC1485; 2, CH, CH, H, $CH_2CHF_2$, $OCF_3$], [CC1486; 0, N, CH, H, H, $OCF_3$], [CC1487; 0, N, CH, H, F, $OCF_3$], [CC1488; 0, N, CH, H, Cl, $OCF_3$], [CC1489; 0, N, CH, H, Br, $OCF_3$], [CC1490; 0, N, CH, H, I, $OCF_3$], [CC1491; 0, N, CH, H, $CF_3$, $OCF_3$], [CC1492; 0, N, CH, H, $CF_2H$, $OCF_3$], [CC1493; 0, N, CH, H, $C_2F_5$, $OCF_3$], [CC1494; 0, N, CH, H, $C_3F_7$, $OCF_3$], [CC1495; 0, N, CH, H, $CH_2CF_3$, $OCF_3$], [CC1496; 0, N, CH, H, $CH_2CHF_2$, $OCF_3$], [CC1497; 1, N, CH, H, H, $OCF_3$], [CC1498; 1, N, CH, H, F, $OCF_3$], [CC1499; 1, N, CH, H, Cl, $OCF_3$], [CC1500; 1, N, CH, H, Br, $OCF_3$], [CC1501; 1, N, CH, H, I, $OCF_3$], [CC1502; 1, N, CH, H, $CF_3$, $OCF_3$], [CC1503; 1, N, CH, H, $CF_2H$, $OCF_3$], [CC1504; 1, N, CH, H, $C_2F_5$, $OCF_3$], [CC1505; 1, N, CH, H, $C_3F_7$, $OCF_3$], [CC1506; 1, N, CH, H, $CH_2CF_3$, $OCF_3$], [CC1507; 1, N, CH, H, $CH_2CHF_2$, $OCF_3$], [CC1508; 2, N, CH, H, H, $OCF_3$], [CC1509; 2, N, CH, H, F, $OCF_3$], [CC1510; 2, N, CH, H, Cl, $OCF_3$], [CC1511; 2, N, CH, H, Br, $OCF_3$], [CC1512; 2, N, CH, H, I, $OCF_3$], [CC1513; 2, N, CH, H, $CF_3$, $OCF_3$], [CC1514; 2, N, CH, H, $CF_2H$, $OCF_3$], [CC1515; 2, N, CH, H, $C_2F_5$, $OCF_3$], [CC1516; 2, N, CH, H, $C_3F_7$, $OCF_3$], [CC1517; 2, N, CH, H, $CH_2CF_3$, $OCF_3$], [CC1518; 2, N, CH, H, $CH_2CHF_2$, $OCF_3$], [CC1519; 0, CH, N, H, H, $OCF_3$], [CC1520; 0, CH, N, H, F, $OCF_3$], [CC1521; 0, CH, N, H, Cl, $OCF_3$], [CC1522; 0, CH, N, H, Br, $OCF_3$], [CC1523; 0, CH, N, H, I, $OCF_3$], [CC1524; 0, CH, N, H, $CF_3$, $OCF_3$], [CC1525; 0, CH, N, H, $CF_2H$, $OCF_3$], [CC1526; 0, CH, N, H, $C_2F_5$, $OCF_3$], [CC1527; 0, CH, N, H, $C_3F_7$, $OCF_3$], [CC1528; 0, CH, N, H, $CH_2CF_3$, $OCF_3$], [CC1529; 0, CH, N, H, $CH_2CHF_2$, $OCF_3$], [CC1530; 1, CH, N, H, H, $OCF_3$], [CC1531; 1, CH, N, H, F, $OCF_3$], [CC1532; 1, CH, N, H, Cl, $OCF_3$], [CC1533; 1, CH, N, H, Br, $OCF_3$], [CC1534; 1, CH, N, H, I, $OCF_3$], [CC1535; 1, CH, N, H, $CF_3$, $OCF_3$], [CC1536; 1, CH, N, H, $CF_2H$, $OCF_3$], [CC1537; 1, CH, N, H, $C_2F_5$, $OCF_3$], [CC1538; 1, CH, N, H, $C_3F_7$, $OCF_3$], [CC1539; 1, CH, N, H, $CH_2CF_3$, $OCF_3$], [CC1540; 1, CH, N, H, $CH_2CHF_2$, $OCF_3$], [CC1541; 2, CH, N, H, H, $OCF_3$], [CC1542; 2, CH, N, H, F, $OCF_3$], [CC1543; 2, CH, N, H, Cl, $OCF_3$], [CC1544; 2, CH, N, H, Br, $OCF_3$], [CC1545; 2, CH, N, H, I, $OCF_3$], [CC1546; 2, CH, N, H, $CF_3$, $OCF_3$], [CC1547; 2, CH, N, H, $CF_2H$, $OCF_3$], [CC1548; 2, CH, N, H, $C_2F_5$, $OCF_3$], [CC1549; 2, CH, N, H, $C_3F_7$, $OCF_3$], [CC1550; 2, CH, N, H, $CH_2CF_3$, $OCF_3$], [CC1551; 2, CH, N, H, $CH_2CHF_2$, $OCF_3$], [CC1552; 0, N,N, H, H, $OCF_3$], [CC1553; 0, N,N, H, F, $OCF_3$], [CC1554; 0, N,N, H, Cl, $OCF_3$], [CC1555; 0, N,N, H, Br, $OCF_3$], [CC1556; 0, N,N, H, I, $OCF_3$], [CC1557; 0, N,N, H, $CF_3$, $OCF_3$], [CC1558; 0, N,N, H, $CF_2H$, $OCF_3$], [CC1559; 0, N,N, H, $C_2F_5$, $OCF_3$], [CC1560; 0, N,N, H, $C_3F_7$, $OCF_3$], [CC1561; 0, N,N, H, $CH_2CF_3$, $OCF_3$], [CC1562; 0, N,N, H, $CH_2CHF_2$, $OCF_3$], [CC1563; 1, N,N, H, H, $OCF_3$], [CC1564; 1, N,N, H, F, $OCF_3$], [CC1565; 1, N,N, H, Cl, $OCF_3$], [CC1566; 1, N,N, H, Br, $OCF_3$], [CC1567; 1, N,N, H, I, $OCF_3$], [CC1568; 1, N,N, H, $CF_3$, $OCF_3$], [CC1569; 1, N,N, H, $CF_2H$, $OCF_3$], [CC1570; 1, N,N, H, $C_2F_5$, $OCF_3$], [CC1571; 1, N,N, H, $C_3F_7$, $OCF_3$], [CC1572; 1, N,N, H, $CH_2CF_3$, $OCF_3$], [CC1573; 1, N,N, H, $CH_2CHF_2$, $OCF_3$], [CC1574; 2, N,N, H, H, $OCF_3$], [CC1575; 2, N,N, H, F, $OCF_3$], [CC1576; 2, N,N, H, Cl, $OCF_3$], [CC1577; 2, N,N, H, Br, $OCF_3$], [CC1578; 2, N,N, H, I, $OCF_3$], [CC1579; 2, N,N, H, $CF_3$, $OCF_3$], [CC1580; 2, N,N, H, $CF_2H$, $OCF_3$], [CC1581; 2, N,N, H, $C_2F_5$, $OCF_3$], [CC1582; 2, N,N, H, $C_3F_7$, $OCF_3$], [CC1583; 2, N,N, H, $CH_2CF_3$, $OCF_3$], [CC1584; 2, N,N, H, $CH_2CHF_2$, $OCF_3$], [CC1585; 0, CH, CH, H, H, $OCHF_2$], [CC1586; 0, CH, CH, F, H, $OCHF_2$], [CC1587; 0, CH, CH, Cl, H, $OCHF_2$], [CC1588; 0, CH, CH, Br, H, $OCHF_2$], [CC1589; 0, CH, CH, I, H, $OCHF_2$], [CC1590; 0, CH, CH, $CF_3$, H, $OCHF_2$], [CC1591; 0, CH, CH, $CF_2H$, H, $OCHF_2$], [CC1592; 0, CH, CH, $C_2F_5$, H, $OCHF_2$], [CC1593; 0, CH, CH, $C_3F_7$, H, $OCHF_2$], [CC1594; 0, CH, CH, $CH_2CF_3$, H, $OCHF_2$], [CC1595; 0, CH, CH, $CH_2CHF_2$, H, $OCHF_2$], [CC1596; 1, CH, CH, H, H, $OCHF_2$], [CC1597; 1, CH, CH, F, H, $OCHF_2$], [CC1598; 1, CH, CH, Cl, H, $OCHF_2$], [CC1599; 1, CH, CH, Br, H, $OCHF_2$], [CC1600; 1, CH, CH, I, H, $OCHF_2$], [CC1601; 1, CH, CH, $CF_3$, H, $OCHF_2$], [CC1602; 1, CH, CH, $CF_2H$, H, $OCHF_2$], [CC1603; 1, CH, CH, $C_2F_5$, H, $OCHF_2$], [CC1604; 1, CH, CH, $C_3F_7$, H, $OCHF_2$], [CC1605; 1, CH, CH, $CH_2CF_3$, H, $OCHF_2$], [CC1606; 1, CH, CH, $CH_2CHF_2$, H, $OCHF_2$], [CC1607; 2, CH, CH, H, H, $OCHF_2$], [CC1608; 2, CH, CH, F, H, $OCHF_2$], [CC1609; 2, CH, CH, Cl, H, $OCHF_2$], [CC1610; 2, CH, CH, Br, H, $OCHF_2$], [CC1611; 2, CH, CH, I, H, $OCHF_2$], [CC1612; 2, CH, CH, $CF_3$, H, $OCHF_2$], [CC1613; 2, CH, CH, $CF_2H$, H, $OCHF_2$], [CC1614; 2, CH, CH, $C_2F_5$, H, $OCHF_2$], [CC1615; 2, CH, CH, $C_3F_7$, H, $OCHF_2$], [CC1616; 2, CH, CH, $CH_2CF_3$, H, $OCHF_2$], [CC1617; 2, CH, CH, $CH_2CHF_2$, H, $OCHF_2$], [CC1618; 0, N, CH, H, H, $OCHF_2$], [CC1619; 0, N, CH, F, H, $OCHF_2$], [CC1620; 0, N, CH, Cl, H, $OCHF_2$], [CC1621; 0, N, CH, Br, H, $OCHF_2$], [CC1622; 0, N, CH, I, H, $OCHF_2$], [CC1623; 0, N, CH, $CF_3$, H, $OCHF_2$], [CC1624; 0, N, CH, $CF_2H$, H, $OCHF_2$], [CC1625; 0, N, CH, $C_2F_5$, H, $OCHF_2$], [CC1626; 0, N, CH, $C_3F_7$, H, $OCHF_2$], [CC1627; 0, N, CH, $CH_2CF_3$, H, $OCHF_2$], [CC1628; 0, N, CH, $CH_2CHF_2$, H, $OCHF_2$], [CC1629; 1, N, CH, H, H, $OCHF_2$], [CC1630; 1, N, CH, F, H, $OCHF_2$], [CC1631; 1, N, CH, Cl, H, $OCHF_2$], [CC1632; 1, N, CH, Br, H, $OCHF_2$], [CC1633; 1, N, CH, I, H, $OCHF_2$], [CC1634; 1, N, CH, $CF_3$, H, $OCHF_2$], [CC1635; 1, N, CH, $CF_2H$, H, $OCHF_2$], [CC1636; 1, N, CH, $C_2F_5$, H, $OCHF_2$], [CC1637; 1, N, CH, $C_3F_7$, H, $OCHF_2$], [CC1638; 1, N, CH, $CH_2CF_3$, H, $OCHF_2$], [CC1639; 1, N, CH, $CH_2CHF_2$, H, $OCHF_2$], [CC1640; 2, N, CH, H, H, $OCHF_2$], [CC1641; 2, N, CH, F, H, $OCHF_2$], [CC1642; 2, N, CH, Cl, H, $OCHF_2$], [CC1643; 2, N, CH, Br, H, $OCHF_2$], [CC1644; 2, N, CH, I, H, $OCHF_2$], [CC1645; 2, N, CH, $CF_3$, H, $OCHF_2$], [CC1646; 2, N, CH, $CF_2H$, H, $OCHF_2$], [CC1647; 2, N, CH, $C_2F_5$, H, $OCHF_2$], [CC1648; 2, N, CH, $C_3F_7$, H, $OCHF_2$], [CC1649; 2, N, CH, $CH_2CF_3$, H, $OCHF_2$], [CC1650; 2, N, CH, $CH_2CHF_2$, H, $OCHF_2$], [CC1651; 0, CH, N, H, H, $OCHF_2$], [CC1652; 0, CH, N, F, H, $OCHF_2$], [CC1653; 0, CH, N, Cl, H, $OCHF_2$], [CC1654; 0, CH, N, Br, H, $OCHF_2$], [CC1655; 0, CH, N, I, H, $OCHF_2$], [CC1656; 0, CH, N, $CF_3$, H, $OCHF_2$], [CC1657; 0, CH, N, $CF_2H$, H, $OCHF_2$], [CC1658; 0, CH, N, $C_2F_5$, H, $OCHF_2$], [CC1659; 0, CH, N, $C_3F_7$, H, $OCHF_2$], [CC1660; 0, CH, N, $CH_2CF_3$, H, $OCHF_2$], [CC1661; 0, CH, N, $CH_2CHF_2$, H, $OCHF_2$], [CC1662; 1, CH, N, H, H, $OCHF_2$], [CC1663; 1, CH, N, F, H, $OCHF_2$], [CC1664; 1, CH, N, Cl, H, $OCHF_2$], [CC1665; 1, CH, N, Br, H, $OCHF_2$], [CC1666; 1, CH, N, I, H, $OCHF_2$], [CC1667; 1, CH, N, $CF_3$, H, $OCHF_2$], [CC1668; 1, CH, N, $CF_2H$, H, $OCHF_2$], [CC1669; 1, CH, N, $C_2F_5$, H, $OCHF_2$], [CC1670; 1, CH, N, $C_3F_7$, H, $OCHF_2$], [CC1671; 1, CH, N, $CH_2CF_3$, H, $OCHF_2$], [CC1672; 1, CH, N, $CH_2CHF_2$, H, $OCHF_2$], [CC1673; 2, CH, N, H, H, $OCHF_2$], [CC1674; 2, CH, N, F, H, $OCHF_2$], [CC1675; 2, CH, N, Cl, H, $OCHF_2$], [CC1676; 2, CH, N, Br, H, $OCHF_2$], [CC1677; 2, CH, N, I, H, $OCHF_2$], [CC1678; 2, CH, N, $CF_3$, H, $OCHF_2$], [CC1679; 2, CH, N, $CF_2H$, H, $OCHF_2$], [CC1680; 2, CH, N, $C_2F$, H, $OCHF_2$], [CC1681; 2, CH, N, $C_3F_7$, H, $OCHF_2$], [CC1682; 2, CH, N, $CH_2CF_3$, H, $OCHF_2$], [CC1683; 2, CH, N, $CH_2CHF_2$, H, $OCHF_2$], [CC1684; 0, N, N, H, H, $OCHF_2$], [CC1685; 0, N,N, F, H, $OCHF_2$], [CC1686; 0, N, N, Cl, H, $OCHF_2$], [CC1687; 0, N, N, Br, H, $OCHF_2$], [CC1688; 0, N,N, I, H, $OCHF_2$], [CC1689; 0, N, N, $CF_3$, H, $OCHF_2$], [CC1690; 0, N, N, $CF_2H$, H, $OCHF_2$], [CC1691; 0, N, N, $C_2F_5$, H, $OCHF_2$], [CC1692; 0, N, N, $C_3F_7$, H, $OCHF_2$], [CC1693; 0, N, N, $CH_2CF_3$, H, $OCHF_2$], [CC1694; 0, N, N, $CH_2CHF_2$, H, $OCHF_2$], [CC1695; 1, N, N, H, H, $OCHF_2$], [CC1696; 1, N,N, F, H, $OCHF_2$], [CC1697; 1, N, N, Cl, H, $OCHF_2$], [CC1698; 1, N, N, Br, H, $OCHF_2$], [CC1699; 1, N,N, I, H, $OCHF_2$], [CC1700; 1, N, N, $CF_3$, H, $OCHF_2$], [CC1701; 1, N, N, $CF_2H$, H, $OCHF_2$], [CC1702; 1, N, N, $C_2F_5$, H, $OCHF_2$], [CC1703; 1, N, N, $C_3F_7$, H, $OCHF_2$], [CC1704; 1, N, N, $CH_2CF_3$, H, $OCHF_2$], [CC1705; 1, N, N, $CH_2CHF_2$, H, $OCHF_2$], [CC1706; 2, N, N, H, H, $OCHF_2$], [CC1707; 2, N,N, F, H, $OCHF_2$], [CC1708; 2, N, N, Cl, H, $OCHF_2$], [CC1709; 2, N, N, Br, H, $OCHF_2$], [CC1710; 2, N,N, I, H, $OCHF_2$], [CC1711; 2, N, N, $CF_3$, H, $OCHF_2$], [CC1712; 2, N, N, $CF_2H$, H, $OCHF_2$], [CC1713; 2, N, N, $C_2F_5$, H, $OCHF_2$], [CC1714; 2, N, N, $C_3F_7$, H, $OCHF_2$], [CC1715; 2, N, N, $CH_2CF_3$, H, $OCHF_2$], [CC1716; 2, N, N, $CH_2CHF_2$, H, $OCHF_2$], [CC1717; 0, CH, CH, H, H, $OCHF_2$], [CC1718; 0, CH, CH, H, F, $OCHF_2$], [CC1719; 0, CH, CH, H, Cl, $OCHF_2$], [CC1720; 0, CH, CH, H, Br, $OCHF_2$], [CC1721; 0, CH, CH, H, I, $OCHF_2$], [CC1722; 0, CH, CH, H, $CF_3$, $OCHF_2$], [CC1723; 0, CH, CH, H, $CF_2H$, $OCHF_2$], [CC1724; 0, CH, CH, H, $C_2F_5$, $OCHF_2$], [CC1725; 0, CH, CH, H, $C_3F_7$, $OCHF_2$], [CC1726; 0, CH, CH, H, $CH_2CF_3$, $OCHF_2$], [CC1727; 0, CH, CH, H, $CH_2CHF_2$, $OCHF_2$], [CC1728; 1, CH, CH, H, H, $OCHF_2$], [CC1729; 1, CH, CH, H, F, $OCHF_2$], [CC1730; 1, CH, CH, H, Cl, $OCHF_2$], [CC1731; 1, CH, CH, H, Br, $OCHF_2$], [CC1732; 1, CH, CH, H, I, $OCHF_2$], [CC1733; 1, CH, CH, H, $CF_3$, $OCHF_2$], [CC1734; 1, CH, CH, H, $CF_2H$, $OCHF_2$], [CC1735; 1, CH, CH, H, $C_2F_5$, $OCHF_2$], [CC1736; 1, CH, CH, H, $C_3F_7$, $OCHF_2$], [CC1737; 1, CH, CH, H, $CH_2CF_3$, $OCHF_2$], [CC1738; 1, CH, CH, H, $CH_2CHF_2$, $OCHF_2$], [CC1739; 2, CH, CH, H, H, $OCHF_2$], [CC1740; 2, CH, CH, H, F, $OCHF_2$], [CC1741; 2, CH, CH, H, Cl, $OCHF_2$], [CC1742; 2, CH, CH, H, Br, $OCHF_2$], [CC1743; 2, CH, CH, H, I, $OCHF_2$], [CC1744; 2, CH, CH, H, $CF_3$, $OCHF_2$], [CC1745; 2, CH, CH, H, $CF_2H$, $OCHF_2$], [CC1746; 2, CH, CH, H, $C_2F_5$, $OCHF_2$], [CC1747; 2, CH, CH, H, $C_3F_7$, $OCHF_2$], [CC1748; 2, CH, CH, H, $CH_2CF_3$, $OCHF_2$], [CC1749; 2, CH, CH, H, $CH_2CHF_2$, $OCHF_2$], [CC1750; 0, N, CH, H, H, $OCHF_2$], [CC1751; 0, N, CH, H, F, $OCHF_2$], [CC1752; 0, N, CH, H, Cl, $OCHF_2$], [CC1753; 0, N, CH, H, Br, $OCHF_2$], [CC1754; 0, N, CH, H, I, $OCHF_2$], [CC1755; 0, N, CH, H, $CF_3$, $OCHF_2$], [CC1756; 0, N, CH, H, $CF_2H$, $OCHF_2$], [CC1757; 0, N, CH, H, $C_2F_5$, $OCHF_2$], [CC1758; 0, N, CH, H, $C_3F_7$, $OCHF_2$], [CC1759; 0, N, CH, H, $CH_2CF_3$, $OCHF_2$], [CC1760; 0, N, CH, H, $CH_2CHF_2$, $OCHF_2$], [CC1761; 1, N, CH, H, H, $OCHF_2$], [CC1762; 1, N, CH, H, F, $OCHF_2$], [CC1763; 1, N, CH, H, Cl, $OCHF_2$], [CC1764; 1, N, CH, H, Br, $OCHF_2$], [CC1765; 1, N, CH, H, I, $OCHF_2$], [CC1766; 1, N, CH, H, $CF_3$, $OCHF_2$], [CC1767; 1, N, CH, H, $CF_2H$, $OCHF_2$], [CC1768; 1, N, CH, H, $C_2Fc$, $OCHF_2$], [CC1769; 1, N, CH, H, $C_3Fc$, $OCHF_2$], [CC1770; 1, N, CH, H, $CH_2CF_3$, $OCHF_2$], [CC1771; 1, N, CH, H, $CH_2CHF_2$, $OCHF_2$], [CC1772; 2, N, CH, H, H, $OCHF_2$], [CC1773; 2, N, CH, H, F, $OCHF_2$], [CC1774; 2, N, CH, H, Cl, $OCHF_2$], [CC1775; 2, N, CH, H, Br, $OCHF_2$], [CC1776; 2, N, CH, H, I, $OCHF_2$], [CC1777; 2, N, CH, H, $CF_3$, $OCHF_2$], [CC1778; 2, N, CH, H, $CF_2H$, $OCHF_2$], [CC1779; 2, N, CH, H, $C_2F_5$, $OCHF_2$], [CC1780; 2, N, CH, H, $C_3F_7$, $OCHF_2$], [CC1781; 2, N, CH, H, $CH_2CF_3$, $OCHF_2$], [CC1782; 2, N, CH, H, $CH_2CHF_2$, $OCHF_2$], [CC1783; 0, CH, N, H, H, $OCHF_2$], [CC1784; 0, CH, N, H, F, $OCHF_2$], [CC1785; 0, CH, N, H, Cl, $OCHF_2$], [CC1786; 0, CH, N, H, Br, $OCHF_2$], [CC1787; 0, CH, N, H, I, $OCHF_2$], [CC1788; 0, CH, N, H, $CF_3$, $OCHF_2$], [CC1789; 0, CH, N, H, $CF_2H$, $OCHF_2$], [CC1790; 0, CH, N, H, $C_2F_5$, $OCHF_2$], [CC1791; 0, CH, N, H, $C_3F_7$, $OCHF_2$], [CC1792; 0, CH, N, H, $CH_2CF_3$, $OCHF_2$], [CC1793; 0, CH, N, H, $CH_2CHF_2$, $OCHF_2$], [CC1794; 1, CH, N, H, H, $OCHF_2$], [CC1795; 1, CH, N, H, F, $OCHF_2$], [CC1796; 1, CH, N, H, Cl, $OCHF_2$], [CC1797; 1, CH, N, H, Br, $OCHF_2$], [CC1798; 1, CH, N, H, I, $OCHF_2$], [CC1799; 1, CH, N, H, $CF_3$, $OCHF_2$], [CC1800; 1, CH, N, H, $CF_2H$, $OCHF_2$], [CC1801; 1, CH, N, H, $C_2F_5$, $OCHF_2$], [CC1802; 1, CH, N, H, $C_3F_7$, $OCHF_2$], [CC1803; 1, CH, N, H, $CH_2CF_3$, $OCHF_2$], [CC1804; 1, CH, N, H, $CH_2CHF_2$, $OCHF_2$], [CC1805; 2, CH, N, H, H, $OCHF_2$], [CC1806; 2, CH, N, H, F, $OCHF_2$], [CC1807; 2, CH, N, H, Cl, $OCHF_2$], [CC1808; 2, CH, N, H, Br, $OCHF_2$], [CC1809; 2, CH, N, H, I, $OCHF_2$], [CC1810; 2, CH, N, H, $CF_3$, $OCHF_2$], [CC1811; 2, CH, N, H, $CF_2H$, $OCHF_2$], [CC1812; 2, CH, N, H, $C_2F_5$, $OCHF_2$], [CC1813; 2, CH, N, H, $C_3F_7$, $OCHF_2$], [CC1814; 2, CH, N, H, $CH_2CF_3$, $OCHF_2$], [CC1815; 2, CH, N, H, $CH_2CHF_2$, $OCHF_2$], [CC1816; 0, N, N, H, H, $OCHF_2$], [CC1817; 0, N,N, H, F, $OCHF_2$], [CC1818; 0, N,N, H, Cl, $OCHF_2$], [CC1819; 0, N,N, H, Br, $OCHF_2$], [CC1820; 0, N,N, H, I, $OCHF_2$], [CC1821; 0, N,N, H, $CF_3$, $OCHF_2$], [CC1822; 0, N,N, H, $CF_2H$, $OCHF_2$], [CC1823; 0, N,N, H, $C_2F_5$, $OCHF_2$], [CC1824; 0, N,N, H, $C_3F_3$, $OCHF_2$], [CC1825; 0, N, N, H, $CH_2CF_3$, $OCHF_2$], [CC1826; 0, N,N, H, $CH_2CHF_2$, $OCHF_2$], [CC1827; 1, N, N, H, H, $OCHF_2$], [CC1828; 1, N,N, H, F, $OCHF_2$], [CC1829; 1, N,N, H, Cl, $OCHF_2$], [CC1830; 1, N,N, H, Br, $OCHF_2$], [CC1831; 1, N,N, H, I, $OCHF_2$], [CC1832; 1, N,N, H, $CF_3$, $OCHF_2$], [CC1833; 1, N,N, H, $CF_2H$, $OCHF_2$], [CC1834; 1, N,N, H, $C_2F_3$, $OCHF_2$], [CC1835; 1, N,N, H, $C_3F_7$, $OCHF_2$], [CC1836; 1, N,N, H, $CH_2CF_3$, $OCHF_2$], [CC1837; 1, N,N, H, $CH_2CHF_2$, $OCHF_2$], [CC1838; 2, N,

N, H, H, $OCHF_2$], [CC1839; 2, N,N, H, F, $OCHF_2$], [CC1840; 2, N,N, H, Cl, $OCHF_2$], [CC1841; 2, N,N, H, Br, $OCHF_2$], [CC1842; 2, N,N, H, I, $OCHF_2$], [CC1843; 2, N,N, H, $CF_3$, $OCHF_2$], [CC1844; 2, N,N, H, $CF_2H$, $OCHF_2$], [CC1845; 2, N,N, H, $C_2F_5$, $OCHF_2$], [CC1846; 2, N,N, H, $C_3F_7$, $OCHF_2$], [CC1847; 2, N,N, H, $CH_2CF_3$, $OCHF_2$], [CC1848; 2, N,N, H, $CH_2CHF_2$, $OCHF_2$], [CC1849; 0, CH, CH, H, H, Br], [CC1850; 0, CH, CH, F, H, Br], [CC1851; 0, CH, CH, Cl, H, Br], [CC1852; 0, CH, CH, Br, H, Br], [CC1853; 0, CH, CH, I, H, Br], [CC1854; 0, CH, CH, $CF_3$, H, Br], [CC1855; 0, CH, CH, $CF_2H$, H, Br], [CC1856; 0, CH, CH, $C_2F_5$, H, Br], [CC1857; 0, CH, CH, $C_3F_7$, H, Br], [CC1858; 0, CH, CH, $CH_2CF_3$, H, Br], [CC1859; 0, CH, CH, $CH_2CHF_2$, H, Br], [CC1860; 1, CH, CH, H, H, Br], [CC1861; 1, CH, CH, F, H, Br], [CC1862; 1, CH, CH, Cl, H, Br], [CC1863; 1, CH, CH, Br, H, Br], [CC1864; 1, CH, CH, I, H, Br], [CC1865; 1, CH, CH, $CF_3$, H, Br], [CC1866; 1, CH, CH, $CF_2H$, H, Br], [CC1867; 1, CH, CH, $C_2F_5$, H, Br], [CC1868; 1, CH, CH, $C_3F_7$, H, Br], [CC1869; 1, CH, CH, $CH_2CF_3$, H, Br], [CC1870; 1, CH, CH, $CH_2CHF_2$, H, Br], [CC1871; 2, CH, CH, H, H, Br], [CC1872; 2, CH, CH, F, H, Br], [CC1873; 2, CH, CH, Cl, H, Br], [CC1874; 2, CH, CH, Br, H, Br], [CC1875; 2, CH, CH, I, H, Br], [CC1876; 2, CH, CH, $CF_3$, H, Br], [CC1877; 2, CH, CH, $CF_2H$, H, Br], [CC1878; 2, CH, CH, $C_2F_5$, H, Br], [CC1879; 2, CH, CH, $C_3F_7$, H, Br], [CC1880; 2, CH, CH, $CH_2CF_3$, H, Br], [CC1881; 2, CH, CH, $CH_2CHF_2$, H, Br][CC1882; 0, N, CH, H, H, Br], [CC1883; 0, N, CH, F, H, Br], [CC1884; 0, N, CH, Cl, H, Br], [CC1885; 0, N, CH, Br, H, Br], [CC1886; 0, N, CH, I, H, Br], [CC1887; 0, N, CH, $CF_3$, H, Br], [CC1888; 0, N, CH, $CF_2H$, H, Br], [CC1889; 0, N, CH, $C_2F_5$, H, Br], [CC1890; 0, N, CH, $C_3F_7$, H, Br], [CC1891; 0, N, CH, $CH_2CF_3$, H, Br], [CC1892; 0, N, CH, $CH_2CHF_2$, H, Br], [CC1893; 1, N, CH, H, H, Br], [CC1894; 1, N, CH, F, H, Br], [CC1895; 1, N, CH, Cl, H, Br], [CC1896; 1, N, CH, Br, H, Br], [CC1897; 1, N, CH, I, H, Br], [CC1898; 1, N, CH, $CF_3$, H, Br], [CC1899; 1, N, CH, $CF_2H$, H, Br], [CC1900; 1, N, CH, $C_2F_5$, H, Br], [CC1901; 1, N, CH, $C_3F_7$, H, Br], [CC1902; 1, N, CH, $CH_2CF_3$, H, Br], [CC1903; 1, N, CH, $CH_2CHF_2$, H, Br], [CC1904; 2, N, CH, H, H, Br], [CC1905; 2, N, CH, F, H, Br], [CC1906; 2, N, CH, Cl, H, Br], [CC1907; 2, N, CH, Br, H, Br], [CC1908; 2, N, CH, I, H, Br], [CC1909; 2, N, CH, $CF_3$, H, Br], [CC1910; 2, N, CH, $CF_2H$, H, Br], [CC1911; 2, N, CH, $C_2F_5$, H, Br], [CC1912; 2, N, CH, $C_3F_7$, H, Br], [CC1913; 2, N, CH, $CH_2CF_3$, H, Br], [CC1914; 2, N, CH, $CH_2CHF_2$, H, Br], [CC1915; 0, CH, N, H, H, Br], [CC1916; 0, CH, N, F, H, Br], [CC1917; 0, CH, N, Cl, H, Br], [CC1918; 0, CH, N, Br, H, Br], [CC1919; 0, CH, N, I, H, Br], [CC1920; 0, CH, N, $CF_3$, H, Br], [CC1921; 0, CH, N, $CF_2H$, H, Br], [CC1922; 0, CH, N, $C_2F_5$, H, Br], [CC1923; 0, CH, N, $C_3F_7$, H, Br], [CC1924; 0, CH, N, $CH_2CF_3$, H, Br], [CC1925; 0, CH, N, $CH_2CHF_2$, H, Br], [CC1926; 1, CH, N, H, H, Br], [CC1927; 1, CH, N, F, H, Br], [CC1928; 1, CH, N, Cl, H, Br], [CC1929; 1, CH, N, Br, H, Br], [CC1930; 1, CH, N, I, H, Br], [CC1931; 1, CH, N, $CF_3$, H, Br], [CC1932; 1, CH, N, $CF_2H$, H, Br], [CC1933; 1, CH, N, $C_2F_5$, H, Br], [CC1934; 1, CH, N, $C_3F_7$, H, Br], [CC1935; 1, CH, N, $CH_2CF_3$, H, Br], [CC1936; 1, CH, N, $CH_2CHF_2$, H, Br], [CC1937; 2, CH, N, H, H, Br], [CC1938; 2, CH, N, F, H, Br], [CC1939; 2, CH, N, Cl, H, Br], [CC1940; 2, CH, N, Br, H, Br], [CC1941; 2, CH, N, I, H, Br], [CC1942; 2, CH, N, $CF_3$, H, Br], [CC1943; 2, CH, N, $CF_2H$, H, Br], [CC1944; 2, CH, N, $C_2F_5$, H, Br], [CC1945; 2, CH, N, $C_3F_7$, H, Br], [CC1946; 2, CH, N, $CH_2CF_3$, H, Br], [CC1947; 2, CH, N, $CH_2CHF_2$, H, Br], [CC1948; 0, N, N, H, H, Br], [CC1949; 0, N,N, F, H, Br], [CC1950; 0, N, N, Cl, H, Br], [CC1951; 0, N, N, Br, H, Br], [CC1952; 0, N,N, I, H, Br], [CC1953; 0, N, N, $CF_3$, H, Br], [CC1954; 0, N, N, $CF_2H$, H, Br], [CC1955; 0, N, N, $C_2F_5$, H, Br], [CC1956; 0, N, N, $C_3F_7$, H, Br], [CC1957; 0, N, N, $CH_2CF_3$, H, Br], [CC1958; 0, N, N, $CH_2CHF_2$, H, Br], [CC1959; 1, N, N, H, H, Br], [CC1960; 1, N,N, F, H, Br], [CC1961; 1, N, N, Cl, H, Br], [CC1962; 1, N, N, Br, H, Br], [CC1963; 1, N,N, I, H, Br], [CC1964; 1, N, N, $CF_3$, H, Br], [CC1965; 1, N, N, $CF_2H$, H, Br], [CC1966; 1, N, N, $C_2F_5$, H, Br], [CC1967; 1, N, N, $C_3F_7$, H, Br], [CC1968; 1, N, N, $CH_2CF_3$, H, Br], [CC1969; 1, N, N, $CH_2CHF_2$, H, Br], [CC1970; 2, N, N, H, H, Br], [CC1971; 2, N,N, F, H, Br], [CC1972; 2, N, N, Cl, H, Br], [CC1973; 2, N, N, Br, H, Br], [CC1974; 2, N,N, I, H, Br], [CC1975; 2, N, N, $CF_3$, H, Br], [CC1976; 2, N, N, $CF_2H$, H, Br], [CC1977; 2, N, N, $C_2F_5$, H, Br], [CC1978; 2, N, N, $C_3F_7$, H, Br], [CC1979; 2, N, N, $CH_2CF_3$, H, Br], [CC1980; 2, N, N, $CH_2CHF_2$, H, Br], [CC1981; 0, CH, CH, H, H, Br], [CC1982; 0, CH, CH, H, F, Br], [CC1983; 0, CH, CH, H, Cl, Br], [CC1984; 0, CH, CH, H, Br, Br], [CC1985; 0, CH, CH, H, I, Br], [CC1986; 0, CH, CH, H, $CF_3$, Br], [CC1987; 0, CH, CH, H, $CF_2H$, Br], [CC1988; 0, CH, CH, H, $C_2F_5$, Br], [CC1989; 0, CH, CH, H, $C_3F_7$, Br], [CC1990; 0, CH, CH, H, $CH_2CF_3$, Br], [CC1991; 0, CH, CH, H, $CH_2CHF_2$, Br], [CC1992; 1, CH, CH, H, H, Br], [CC1993; 1, CH, CH, H, F, Br], [CC1994; 1, CH, CH, H, Cl, Br], [CC1995; 1, CH, CH, H, Br, Br], [CC1996; 1, CH, CH, H, I, Br], [CC1997; 1, CH, CH, H, $CF_3$, Br], [CC1998; 1, CH, CH, H, $CF_2H$, Br], [CC1999; 1, CH, CH, H, $C_2F_5$, Br], [CC2000; 1, CH, CH, H, $C_3F_7$, Br], [CC2001; 1, CH, CH, H, $CH_2CF_3$, Br], [CC2002; 1, CH, CH, H, $CH_2CHF_2$, Br], [CC2003; 2, CH, CH, H, H, Br], [CC2004; 2, CH, CH, H, F, Br], [CC2005; 2, CH, CH, H, Cl, Br], [CC2006; 2, CH, CH, H, Br, Br], [CC2007; 2, CH, CH, H, I, Br], [CC2008; 2, CH, CH, H, $CF_3$, Br], [CC2009; 2, CH, CH, H, $CF_2H$, Br], [CC2010; 2, CH, CH, H, $C_2F_5$, Br], [CC2011; 2, CH, CH, H, $C_3F_7$, Br], [CC2012; 2, CH, CH, H, $CH_2CF_3$, Br], [CC2013; 2, CH, CH, H, $CH_2CHF_2$, Br], [CC2014; 0, N, CH, H, H, Br], [CC2015; 0, N, CH, H, F, Br], [CC2016; 0, N, CH, H, Cl, Br], [CC2017; 0, N, CH, H, Br, Br], [CC2018; 0, N, CH, H, I, Br], [CC2019; 0, N, CH, H, $CF_3$, Br], [CC2020; 0, N, CH, H, $CF_2H$, Br], [CC2021; 0, N, CH, H, $C_2F_5$, Br], [CC2022; 0, N, CH, H, $C_3F_7$, Br], [CC2023; 0, N, CH, H, $CH_2CF_3$, Br], [CC2024; 0, N, CH, H, $CH_2CHF_2$, Br], [CC2025; 1, N, CH, H, H, Br], [CC2026; 1, N, CH, H, F, Br], [CC2027; 1, N, CH, H, Cl, Br], [CC2028; 1, N, CH, H, Br, Br], [CC2029; 1, N, CH, H, I, Br], [CC2030; 1, N, CH, H, $CF_3$, Br], [CC2031; 1, N, CH, H, $CF_2H$, Br], [CC2032; 1, N, CH, H, $C_2F_5$, Br], [CC2033; 1, N, CH, H, $C_3F_7$, Br], [CC2034; 1, N, CH, H, $CH_2CF_3$, Br], [CC2035; 1, N, CH, H, $CH_2CHF_2$, Br], [CC2036; 2, N, CH, H, H, Br], [CC2037; 2, N, CH, H, F, Br], [CC2038; 2, N, CH, H, Cl, Br], [CC2039; 2, N, CH, H, Br, Br], [CC2040; 2, N, CH, H, I, Br], [CC2041; 2, N, CH, H, $CF_3$, Br], [CC2042; 2, N, CH, H, $CF_2H$, Br], [CC2043; 2, N, CH, H, $C_2F_5$, Br], [CC2044; 2, N, CH, H, $C_3F_7$, Br], [CC2045; 2, N, CH, H, $CH_2CF_3$, Br], [CC2046; 2, N, CH, H, $CH_2CHF_2$, Br], [CC2047; 0, CH, N, H, H, Br], [CC2048; 0, CH, N, H, F, Br], [CC2049; 0, CH, N, H, Cl, Br], [CC2050; 0, CH, N, H, Br, Br], [CC2051; 0, CH, N, H, I, Br], [CC2052; 0, CH, N, H, $CF_3$, Br], [CC2053; 0, CH, N, H, $CF_2H$, Br], [CC2054; 0, CH, N, H, $C_2F_5$, Br], [CC2055; 0, CH, N, H, $C_3F_7$, Br], [CC2056; 0, CH, N, H, $CH_2CF_3$, Br], [CC2057; 0, CH, N, H, $CH_2CHF_2$, Br], [CC2058; 1, CH, N, H, H, Br], [CC2059; 1, CH, N, H, F, Br], [CC2060; 1, CH, N, H, Cl, Br], [CC2061; 1, CH, N, H, Br, Br], [CC2062; 1, CH, N, H, I, Br], [CC2063; 1, CH, N, H, $CF_3$, Br], [CC2064; 1, CH, N, H, $CF_2H$, Br], [CC2065; 1, CH, N, H, $C_2F_5$, Br], [CC2066; 1, CH, N, H, $C_3F_7$, Br], [CC2067; 1, CH, N, H, $CH_2CF_3$,

Br], [CC2068; 1, CH, N, H, $CH_2CHF_2$, Br], [CC2069; 2, CH, N, H, H, Br], [CC2070; 2, CH, N, H, F, Br], [CC2071; 2, CH, N, H, Cl, Br], [CC2072; 2, CH, N, H, Br, Br], [CC2073; 2, CH, N, H, I, Br], [CC2074; 2, CH, N, H, $CF_3$, Br], [CC2075; 2, CH, N, H, $CF_2H$, Br], [CC2076; 2, CH, N, H, $C_2F_5$, Br], [CC2077; 2, CH, N, H, $C_3F_7$, Br], [CC2078; 2, CH, N, H, $CH_2CF_3$, Br], [CC2079; 2, CH, N, H, $CH_2CHF_2$, Br], [CC2080; 0, N, N, H, H, Br], [CC2081; 0, N,N, H, F, Br], [CC2082; 0, N,N, H, Cl, Br], [CC2083; 0, N,N, H, Br, Br], [CC2084; 0, N,N, H, I, Br], [CC2085; 0, N,N, H, $CF_3$, Br], [CC2086; 0, N,N, H, $CF_2H$, Br], [CC2087; 0, N,N, H, $C_2F_5$, Br], [CC2088; 0, N,N, H, $C_3F_7$, Br], [CC2089; 0, N,N, H, $CH_2CF_3$, Br], [CC2090; 0, N,N, H, $CH_2CHF_2$, Br], [CC2091; 1, N, N, H, H, Br], [CC2092; 1, N,N, H, F, Br], [CC2093; 1, N,N, H, Cl, Br], [CC2094; 1, N,N, H, Br, Br], [CC2095; 1, N,N, H, I, Br], [CC2096; 1, N,N, H, $CF_3$, Br], [CC2097; 1, N,N, H, $CF_2H$, Br], [CC2098; 1, N,N, H, $C_2F_5$, Br], [CC2099; 1, N,N, H, $C_3F_7$, Br], [CC2100; 1, N, N, H, $CH_2CF_3$, Br], [CC2101; 1, N,N, H, $CH_2CHF_2$, Br], [CC2102; 2, N, N, H, H, Br], [CC2103; 2, N,N, H, F, Br], [CC2104; 2, N,N, H, Cl, Br], [CC2105; 2, N,N, H, Br, Br], [CC2106; 2, N,N, H, I, Br], [CC2107; 2, N,N, H, $CF_3$, Br], [CC2108; 2, N,N, H, $CF_2H$, Br], [CC2109; 2, N,N, H, $C_2F_5$, Br], [CC2110; 2, N,N, H, $C_3F_7$, Br], [CC2111; 2, N,N, H, $CH_2CF_3$, Br], [CC2112; 2, N,N, H, $CH_2CHF_2$, Br], [CC2113; 0, CH, CH, H, H, Cl], [CC2114; 0, CH, CH, F, H, Cl], [CC2115; 0, CH, CH, Cl, H, Cl], [CC2116; 0, CH, CH, Br, H, Cl], [CC2117; 0, CH, CH, I, H, Cl], [CC2118; 0, CH, CH, $CF_3$, H, Cl], [CC2119; 0, CH, CH, $CF_2H$, H, Cl], [CC2120; 0, CH, CH, $C_2F_5$, H, Cl], [CC2121; 0, CH, CH, $C_3F_7$, H, Cl], [CC2122; 0, CH, CH, $CH_2CF_3$, H, Cl], [CC2123; 0, CH, CH, $CH_2CHF_2$, H, Cl], [CC2124; 1, CH, CH, H, H, Cl], [CC2125; 1, CH, CH, F, H, Cl], [CC2126; 1, CH, CH, Cl, H, Cl], [CC2127; 1, CH, CH, Br, H, Cl], [CC2128; 1, CH, CH, I, H, Cl], [CC2129; 1, CH, CH, $CF_3$, H, Cl], [CC2130; 1, CH, CH, $CF_2H$, H, Cl], [CC2131; 1, CH, CH, $C_2F_5$, H, Cl], [CC2132; 1, CH, CH, $C_3F_7$, H, Cl], [CC2133; 1, CH, CH, $CH_2CF_3$, H, Cl], [CC2134; 1, CH, CH, $CH_2CHF_2$, H, Cl], [CC2135; 2, CH, CH, H, H, Cl], [CC2136; 2, CH, CH, F, H, Cl], [CC2137; 2, CH, CH, Cl, H, Cl], [CC2138; 2, CH, CH, Br, H, Cl], [CC2139; 2, CH, CH, I, H, Cl], [CC2140; 2, CH, CH, $CF_3$, H, Cl], [CC2141; 2, CH, CH, $CF_2H$, H, Cl], [CC2142; 2, CH, CH, $C_2F_5$, H, Cl], [CC2143; 2, CH, CH, $C_3F_7$, H, Cl], [CC2144; 2, CH, CH, $CH_2CF_3$, H, Cl], [CC2145; 2, CH, CH, $CH_2CHF_2$, H, Cl], [CC2146; 0, N, CH, H, H, Cl], [CC2147; 0, N, CH, F, H, Cl], [CC2148; 0, N, CH, Cl, H, Cl], [CC2149; 0, N, CH, Br, H, Cl], [CC2150; 0, N, CH, I, H, Cl], [CC2151; 0, N, CH, $CF_3$, H, Cl], [CC2152; 0, N, CH, $CF_2H$, H, Cl], [CC2153; 0, N, CH, $C_2F_5$, H, Cl], [CC2154; 0, N, CH, $C_3F_7$, H, Cl], [CC2155; 0, N, CH, $CH_2CF_3$, H, Cl], [CC2156; 0, N, CH, $CH_2CHF_2$, H, Cl], [CC2157; 1, N, CH, H, H, Cl], [CC2158; 1, N, CH, F, H, Cl], [CC2159; 1, N, CH, Cl, H, Cl], [CC2160; 1, N, CH, Br, H, Cl], [CC2161; 1, N, CH, I, H, Cl], [CC2162; 1, N, CH, $CF_3$, H, Cl], [CC2163; 1, N, CH, $CF_2H$, H, Cl], [CC2164; 1, N, CH, $C_2F_5$, H, Cl], [CC2165; 1, N, CH, $C_3F_7$, H, Cl], [CC2166; 1, N, CH, $CH_2CF_3$, H, Cl], [CC2167; 1, N, CH, $CH_2CHF_2$, H, Cl], [CC2168; 2, N, CH, H, H, Cl], [CC2169; 2, N, CH, F, H, Cl], [CC2170; 2, N, CH, Cl, H, Cl], [CC2171; 2, N, CH, Br, H, Cl], [CC2172; 2, N, CH, I, H, Cl], [CC2173; 2, N, CH, $CF_3$, H, Cl], [CC2174; 2, N, CH, $CF_2H$, H, Cl], [CC2175; 2, N, CH, $C_2F_5$, H, Cl], [CC2176; 2, N, CH, $C_3F_7$, H, Cl], [CC2177; 2, N, CH, $CH_2CF_3$, H, Cl], [CC2178; 2, N, CH, $CH_2CHF_2$, H, Cl] [CC2179; 0, CH, N, H, H, Cl], [CC2180; 0, CH, N, F, H, Cl], [CC2181; 0, CH, N, Cl, H, Cl], [CC2182; 0, CH, N, Br, H, Cl], [CC2183; 0, CH, N, I, H, Cl], [CC2184; 0, CH, N, $CF_3$, H, Cl], [CC2185; 0, CH, N, $CF_2H$, H, Cl], [CC2186; 0, CH, N, $C_2F_5$, H, Cl], [CC2187; 0, CH, N, $C_3F_7$, H, Cl], [CC2188; 0, CH, N, $CH_2CF_3$, H, Cl], [CC2189; 0, CH, N, $CH_2CHF_2$, H, Cl], [CC2190; 1, CH, N, H, H, Cl], [CC2191; 1, CH, N, F, H, Cl], [CC2192; 1, CH, N, Cl, H, Cl], [CC2193; 1, CH, N, Br, H, Cl], [CC2194; 1, CH, N, I, H, Cl], [CC2195; 1, CH, N, $CF_3$, H, Cl], [CC2196; 1, CH, N, $CF_2H$, H, Cl], [CC2197; 1, CH, N, $C_2F_5$, H, Cl], [CC2198; 1, CH, N, $C_3F_7$, H, Cl], [CC2199; 1, CH, N, $CH_2CF_3$, H, Cl], [CC2200; 1, CH, N, $CH_2CHF_2$, H, Cl][CC2201; 2, CH, N, H, H, Cl], [CC2202; 2, CH, N, F, H, Cl], [CC2203; 2, CH, N, Cl, H, Cl], [CC2204; 2, CH, N, Br, H, Cl], [CC2205; 2, CH, N, I, H, Cl], [CC2206; 2, CH, N, $CF_3$, H, Cl], [CC2207; 2, CH, N, $CF_2H$, H, Cl], [CC2208; 2, CH, N, $C_2F_5$, H, Cl], [CC2209; 2, CH, N, $C_3F_7$, H, Cl], [CC2210; 2, CH, N, $CH_2CF_3$, H, Cl], [CC2211; 2, CH, N, $CH_2CHF_2$, H, Cl], [CC2212; 0, N, N, H, H, Cl], [CC2213; 0, N,N, F, H, Cl], [CC2214; 0, N, N, Cl, H, Cl], [CC2215; 0, N, N, Br, H, Cl], [CC2216; 0, N,N, I, H, Cl], [CC2217; 0, N, N, $CF_3$, H, Cl], [CC2218; 0, N, N, $CF_2H$, H, Cl], [CC2219; 0, N, N, $C_2F_5$, H, Cl], [CC2220; 0, N, N, $C_3F_7$, H, Cl], [CC2221; 0, N, N, $CH_2CF_3$, H, Cl], [CC2222; 0, N, N, $CH_2CHF_2$, H, Cl], [CC2223; 1, N, N, H, H, Cl], [CC2224; 1, N,N, F, H, Cl], [CC2225; 1, N, N, Cl, H, Cl], [CC2226; 1, N, N, Br, H, Cl], [CC2227; 1, N,N, I, H, Cl], [CC2228; 1, N, N, $CF_3$, H, Cl], [CC2229; 1, N, N, $CF_2H$, H, Cl], [CC2230; 1, N, N, $C_2F_5$, H, Cl], [CC2231; 1, N, N, $C_3F_7$, H, Cl], [CC2232; 1, N, N, $CH_2CF_3$, H, Cl], [CC2233; 1, N, N, $CH_2CHF_2$, H, Cl], [CC2234; 2, N, N, H, H, Cl], [CC2235; 2, N,N, F, H, Cl], [CC2236; 2, N, N, Cl, H, Cl], [CC2237; 2, N, N, Br, H, Cl], [CC2238; 2, N,N, I, H, Cl], [CC2239; 2, N, N, $CF_3$, H, Cl], [CC2240; 2, N, N, $CF_2H$, H, Cl], [CC2241; 2, N, N, $C_2F_5$, H, Cl], [CC2242; 2, N, N, $C_3F_7$, H, Cl], [CC2243; 2, N, N, $CH_2CF_3$, H, Cl], [CC2244; 2, N, N, $CH_2CHF_2$, H, Cl], [CC2245; 0, CH, CH, H, H, Cl], [CC2246; 0, CH, CH, H, F, Cl], [CC2247; 0, CH, CH, H, C, Cl], [CC2248; 0, CH, CH, H, Br, Cl], [CC2249; 0, CH, CH, H, I, Cl], [CC2250; 0, CH, CH, H, $CF_3$, Cl], [CC2251; 0, CH, CH, H, $CF_2H$, Cl], [CC2252; 0, CH, CH, H, $C_2F_5$, Cl], [CC2253; 0, CH, CH, H, $C_3F_7$, Cl], [CC2254; 0, CH, CH, H, $CH_2CF_3$, Cl], [CC2255; 0, CH, CH, H, $CH_2CHF_2$, Cl], [CC2256; 1, CH, CH, H, H, Cl], [CC2257; 1, CH, CH, H, F, Cl], [CC2258; 1, CH, CH, H, Cl, Cl], [CC2259; 1, CH, CH, H, Br, Cl], [CC2260; 1, CH, CH, H, I, Cl], [CC2261; 1, CH, CH, H, $CF_3$, Cl], [CC2262; 1, CH, CH, H, $CF_2H$, Cl], [CC2263; 1, CH, CH, H, $C_2F_5$, Cl], [CC2264; 1, CH, CH, H, $C_3F_7$, Cl], [CC2265; 1, CH, CH, H, $CH_2CF_3$, Cl], [CC2266; 1, CH, CH, H, $CH_2CHF_2$, Cl][CC2267; 2, CH, CH, H, H, Cl], [CC2268; 2, CH, CH, H, F, Cl], [CC2269; 2, CH, CH, H, Cl, Cl], [CC2270; 2, CH, CH, H, Br, Cl], [CC2271; 2, CH, CH, H, I, Cl], [CC2272; 2, CH, CH, H, $CF_3$, Cl], [CC2273; 2, CH, CH, H, $CF_2H$, Cl], [CC2274; 2, CH, CH, H, $C_2F_5$, Cl], [CC2275; 2, CH, CH, H, $C_3F_7$, Cl], [CC2276; 2, CH, CH, H, $CH_2CF_3$, Cl], [CC2277; 2, CH, CH, H, $CH_2CHF_2$, Cl], [CC2278; 0, N, CH, H, H, Cl], [CC2279; 0, N, CH, H, F, Cl], [CC2280; 0, N, CH, H, Cl, Cl], [CC2281; 0, N, CH, H, Br, Cl], [CC2282; 0, N, CH, H, I, Cl], [CC2283; 0, N, CH, H, $CF_3$, Cl], [CC2284; 0, N, CH, H, $CF_2H$, Cl], [CC2285; 0, N, CH, H, $C_2F_5$, Cl], [CC2286; 0, N, CH, H, $C_3F_7$, Cl], [CC2287; 0, N, CH, H, $CH_2CF_3$, Cl], [CC2288; 0, N, CH, H, $CH_2CHF_2$, Cl], [CC2289; 1, N, CH, H, H, Cl], [CC2290; 1, N, CH, H, F, Cl], [CC2291; 1, N, CH, H, Cl, Cl], [CC2292; 1, N, CH, H, Br, Cl], [CC2293; 1, N, CH, H, I, Cl], [CC2294; 1, N, CH, H, $CF_3$, Cl], [CC2295; 1, N, CH, H, $CF_2H$, Cl], [CC2296; 1, N, CH, H, $C_2F_5$, Cl], [CC2297; 1, N, CH, H, $C_3F_7$, Cl], [CC2298; 1, N, CH, H, $CH_2CF_3$, Cl], [CC2299; 1, N, CH, H, $CH_2CHF_2$, Cl], [CC2300; 2, N, CH, H, H, Cl], [CC2301;

2, N, CH, H, F, Cl], [CC2302; 2, N, CH, H, Cl, Cl], [CC2303; 2, N, CH, H, Br, Cl], [CC2304; 2, N, CH, H, I, Cl], [CC2305; 2, N, CH, H, $CF_3$, Cl], [CC2306; 2, N, CH, H, $CF_2H$, Cl], [CC2307; 2, N, CH, H, $C_2F_5$, Cl], [CC2308; 2, N, CH, H, $C_3F_7$, Cl], [CC2309; 2, N, CH, H, $CH_2CF_3$, Cl], [CC2310; 2, N, CH, H, $CH_2CHF_2$, Cl], [CC2311; 0, CH, N, H, H, Cl], [CC2312; 0, CH, N, H, F, Cl], [CC2313; 0, CH, N, H, Cl, Cl], [CC2314; 0, CH, N, H, Br, Cl], [CC2315; 0, CH, N, H, I, Cl], [CC2316; 0, CH, N, H, $CF_3$, Cl], [CC2317; 0, CH, N, H, $CF_2H$, Cl], [CC2318; 0, CH, N, H, $C_2F_5$, Cl], [CC2319; 0, CH, N, H, $C_3F_7$, Cl], [CC2320; 0, CH, N, H, $CH_2CF_3$, Cl], [CC2321; 0, CH, N, H, $CH_2CHF_2$, Cl], [CC2322; 1, CH, N, H, H, Cl], [CC2323; 1, CH, N, H, F, Cl], [CC2324; 1, CH, N, H, Cl, Cl], [CC2325; 1, CH, N, H, Br, Cl], [CC2326; 1, CH, N, H, I, Cl], [CC2327; 1, CH, N, H, $CF_3$, Cl], [CC2328; 1, CH, N, H, $CF_2H$, Cl], [CC2329; 1, CH, N, H, $C_2F_5$, Cl], [CC2330; 1, CH, N, H, $C_3F_7$, Cl], [CC2331; 1, CH, N, H, $CH_2CF_3$, Cl], [CC2332; 1, CH, N, H, $CH_2CHF_2$, Cl], [CC2333; 2, CH, N, H, H, Cl], [CC2334; 2, CH, N, H, F, Cl], [CC2335; 2, CH, N, H, Cl, Cl], [CC2336; 2, CH, N, H, Br, Cl], [CC2337; 2, CH, N, H, I, Cl], [CC2338; 2, CH, N, H, $CF_3$, Cl], [CC2339; 2, CH, N, H, $CF_2H$, Cl], [CC2340; 2, CH, N, H, $C_2F_5$, Cl], [CC2341; 2, CH, N, H, $C_3F_7$, Cl], [CC2342; 2, CH, N, H, $CH_2CF_3$, Cl], [CC2343; 2, CH, N, H, $CH_2CHF_2$, Cl], [CC2344; 0, N, N, H, H, Cl], [CC2345; 0, N,N, H, F, Cl], [CC2346; 0, N,N, H, Cl, Cl], [CC2347; 0, N,N, H, Br, Cl], [CC2348; 0, N,N, H, I, Cl], [CC2349; 0, N,N, H, $CF_3$, Cl], [CC2350; 0, N,N, H, $CF_2H$, Cl], [CC2351; 0, N,N, H, $C_2F_5$, Cl], [CC2352; 0, N,N, H, $C_3F_7$, Cl], [CC2353; 0, N,N, H, $CH_2CF_3$, Cl], [CC2354; 0, N,N, H, $CH_2CHF_2$, Cl], [CC2355; 1, N, N, H, H, Cl], [CC2356; 1, N,N, H, F, Cl], [CC2357; 1, N,N, H, Cl, Cl], [CC2358; 1, N,N, H, Br, Cl], [CC2359; 1, N,N, H, I, Cl], [CC2360; 1, N,N, H, $CF_3$, Cl], [CC2361; 1, N,N, H, $CF_2H$, Cl], [CC2362; 1, N,N, H, $C_2F_5$, Cl], [CC2363; 1, N,N, H, $C_3F_7$, Cl], [CC2364; 1, N,N, H, $CH_2CF_3$, Cl], [CC2365; 1, N,N, H, $CH_2CHF_2$, Cl], [CC2366; 2, N, N, H, H, Cl], [CC2367; 2, N,N, H, F, Cl], [CC2368; 2, N,N, H, Cl, Cl], [CC2369; 2, N,N, H, Br, Cl], [CC2370; 2, N,N, H, I, Cl], [CC2371; 2, N,N, H, $CF_3$, Cl], [CC2372; 2, N,N, H, $CF_2H$, Cl], [CC2373; 2, N,N, H, $C_2F_5$, Cl], [CC2374; 2, N,N, H, $C_3F_7$, Cl], [CC2375; 2, N,N, H, $CH_2CF_3$, Cl], [CC2376; 2, N,N, H, $CH_2CHF_2$, Cl], [CC2377; 0, CH, CH, H, H, I], [CC2378; 0, CH, CH, F, H, I], [CC2379; 0, CH, CH, Cl, H, I], [CC2380; 0, CH, CH, Br, H, I], [CC2381; 0, CH, CH, I, H, I], [CC2382; 0, CH, CH, $CF_3$, H, I], [CC2383; 0, CH, CH, $CF_2H$, H, I], [CC2384; 0, CH, CH, $C_2F_5$, H, I], [CC2385; 0, CH, CH, $C_3F_7$, H, I], [CC2386; 0, CH, CH, $CH_2CF_3$, H, I], [CC2387; 0, CH, CH, $CH_2CHF_2$, H, I], [CC2388; 1, CH, CH, H, H, I], [CC2389; 1, CH, CH, F, H, I], [CC2390; 1, CH, CH, Cl, H, I], [CC2391; 1, CH, CH, Br, H, I], [CC2392; 1, CH, CH, I, H, I], [CC2393; 1, CH, CH, $CF_3$, H, I], [CC2394; 1, CH, CH, $CF_2H$, H, I], [CC2395; 1, CH, CH, $C_2F_5$, H, I], [CC2396; 1, CH, CH, $C_3F_7$, H, I], [CC2397; 1, CH, CH, $CH_2CF_3$, H, I], [CC2398; 1, CH, CH, $CH_2CHF_2$, H, I], [CC2399; 2, CH, CH, H, H, I], [CC2400; 2, CH, CH, F, H, I], [CC2401; 2, CH, CH, Cl, H, I], [CC2402; 2, CH, CH, Br, H, I], [CC2403; 2, CH, CH, I, H, I], [CC2404; 2, CH, CH, $CF_3$, H, I], [CC2405; 2, CH, CH, $CF_2H$, H, I], [CC2406; 2, CH, CH, $C_2F_5$, H, I], [CC2407; 2, CH, CH, $C_3F_7$, H, I], [CC2408; 2, CH, CH, $CH_2CF_3$, H, I], [CC2409; 2, CH, CH, $CH_2CHF_2$, H, I], [CC2410; 0, N, CH, H, H, I], [CC2411; 0, N, CH, F, H, I], [CC2412; 0, N, CH, Cl, H, I], [CC2413; 0, N, CH, Br, H, I], [CC2414; 0, N, CH, I, H, I], [CC2415; 0, N, CH, $CF_3$, H, I], [CC2416; 0, N, CH, $CF_2H$, H, I], [CC2417; 0, N, CH, $C_2F_5$, H, I], [CC2418; 0, N, CH, $C_3F_7$, H, I], [CC2419; 0, N, CH, $CH_2CF_3$, H, I], [CC2420; 0, N, CH, $CH_2CHF_2$, H, I], [CC2421; 1, N, CH, H, H, I], [CC2422; 1, N, CH, F, H, I], [CC2423; 1, N, CH, Cl, H, I], [CC2424; 1, N, CH, Br, H, I], [CC2425; 1, N, CH, I, H, I], [CC2426; 1, N, CH, $CF_3$, H, I], [CC2427; 1, N, CH, $CF_2H$, H, I], [CC2428; 1, N, CH, $C_2F_5$, H, I], [CC2429; 1, N, CH, $C_3F_7$, H, I], [CC2430; 1, N, CH, $CH_2CF_3$, H, I], [CC2431; 1, N, CH, $CH_2CHF_2$, H, I], [CC2432; 2, N, CH, H, H, I], [CC2433; 2, N, CH, F, H, I], [CC2434; 2, N, CH, Cl, H, I], [CC2435; 2, N, CH, Br, H, I], [CC2436; 2, N, CH, I, H, I], [CC2437; 2, N, CH, $CF_3$, H, I], [CC2438; 2, N, CH, $CF_2H$, H, I], [CC2439; 2, N, CH, $C_2F_5$, H, I], [CC2440; 2, N, CH, $C_3F_7$, H, I], [CC2441; 2, N, CH, $CH_2CF_3$, H, I], [CC2442; 2, N, CH, $CH_2CHF_2$, H, I], [CC2443; 0, CH, N, H, H, I], [CC2444; 0, CH, N, F, H, I], [CC2445; 0, CH, N, Cl, H, I], [CC2446; 0, CH, N, Br, H, I], [CC2447; 0, CH, N, I, H, I], [CC2448; 0, CH, N, $CF_3$, H, I], [CC2449; 0, CH, N, $CF_2H$, H, I], [CC2450; 0, CH, N, $C_2F_5$, H, I], [CC2451; 0, CH, N, $C_3F_7$, H, I], [CC2452; 0, CH, N, $CH_2CF_3$, H, I], [CC2453; 0, CH, N, $CH_2CHF_2$, H, I], [CC2454; 1, CH, N, H, H, I], [CC2455; 1, CH, N, F, H, I], [CC2456; 1, CH, N, Cl, H, I], [CC2457; 1, CH, N, Br, H, I], [CC2458; 1, CH, N, I, H, I], [CC2459; 1, CH, N, $CF_3$, H, I], [CC2460; 1, CH, N, $CF_2H$, H, I], [CC2461; 1, CH, N, $C_2F_5$, H, I], [CC2462; 1, CH, N, $C_3F_7$, H, I], [CC2463; 1, CH, N, $CH_2CF_3$, H, I], [CC2464; 1, CH, N, $CH_2CHF_2$, H, I], [CC2465; 2, CH, N, H, H, I], [CC2466; 2, CH, N, F, H, I], [CC2467; 2, CH, N, Cl, H, I], [CC2468; 2, CH, N, Br, H, I], [CC2469; 2, CH, N, I, H, I], [CC2470; 2, CH, N, $CF_3$, H, I], [CC2471; 2, CH, N, $CF_2H$, H, I], [CC2472; 2, CH, N, $C_2F_5$, H, I], [CC2473; 2, CH, N, $C_3F_7$, H, I], [CC2474; 2, CH, N, $CH_2CF_3$, H, I], [CC2475; 2, CH, N, $CH_2CHF_2$, H, I], [CC2476; 0, N, N, H, H, I], [CC2477; 0, N,N, F, H, I], [CC2478; 0, N, N, Cl, H, I], [CC2479; 0, N, N, Br, H, I], [CC2480; 0, N,N, I, H, I], [CC2481; 0, N, N, $CF_3$, H, I], [CC2482; 0, N, N, $CF_2H$, H, I], [CC2483; 0, N, N, $C_2F_5$, H, I], [CC2484; 0, N, N, $C_3F_7$, H, I], [CC2485; 0, N, N, $CH_2CF_3$, H, I], [CC2486; 0, N, N, $CH_2CHF_2$, H, I], [CC2487; 1, N, N, H, H, I], [CC2488; 1, N,N, F, H, I], [CC2489; 1, N, N, Cl, H, I], [CC2490; 1, N, N, Br, H, I], [CC2491; 1, N,N, I, H, I], [CC2492; 1, N, N, $CF_3$, H, I], [CC2493; 1, N, N, $CF_2H$, H, I], [CC2494; 1, N, N, $C_2F_5$, H, I], [CC2495; 1, N, N, $C_3F_7$, H, I], [CC2496; 1, N, N, $CH_2CF_3$, H, I], [CC2497; 1, N, N, $CH_2CHF_2$, H, I], [CC2498; 2, N, N, H, H, I], [CC2499; 2, N, N, F, H, I], [CC2500; 2, N, N, Cl, H, I], [CC2501; 2, N, N, Br, H, I], [CC2502; 2, N,N, I, H, I], [CC2503; 2, N, N, $CF_3$, H, I], [CC2504; 2, N, N, $CF_2H$, H, I], [CC2505; 2, N, N, $C_2F_5$, H, I], [CC2506; 2, N, N, $C_3F_7$, H, I], [CC2507; 2, N, N, $CH_2CF_3$, H, I], [CC2508; 2, N, N, $CH_2CHF_2$, H, I], [CC2509; 0, CH, CH, H, H, I], [CC2510; 0, CH, CH, H, F, I], [CC2511; 0, CH, CH, H, Cl, I], [CC2512; 0, CH, CH, H, Br, I], [CC2513; 0, CH, CH, H, I, I], [CC2514; 0, CH, CH, H, $CF_3$, I], [CC2515; 0, CH, CH, H, $CF_2H$, I], [CC2516; 0, CH, CH, H, $C_2F_5$, I], [CC2517; 0, CH, CH, H, $C_3F_7$, I], [CC2518; 0, CH, CH, H, $CH_2CF_3$, I], [CC2519; 0, CH, CH, H, $CH_2CHF_2$, I], [CC2520; 1, CH, CH, H, H, I], [CC2521; 1, CH, CH, H, F, I], [CC2522; 1, CH, CH, H, Cl, I], [CC2523; 1, CH, CH, H, Br, I], [CC2524; 1, CH, CH, H, I, I], [CC2525; 1, CH, CH, H, $CF_3$, I], [CC2526; 1, CH, CH, H, $CF_2H$, I], [CC2527; 1, CH, CH, H, $C_2F_5$, I], [CC2528; 1, CH, CH, H, $C_3F_7$, I], [CC2529; 1, CH, CH, H, $CH_2CF_3$, I], [CC2530; 1, CH, CH, H, $CH_2CHF_2$, I], [CC2531; 2, CH, CH, H, H, I], [CC2532; 2, CH, CH, H, F, I], [CC2533; 2, CH, CH, H, Cl, I], [CC2534; 2, CH, CH, H, Br, I], [CC2535; 2, CH, CH, H, I, I], [CC2536; 2, CH, CH, H, $CF_3$, I], [CC2537; 2, CH, CH, H, $CF_2H$, I], [CC2538; 2, CH, CH, H, $C_2F_5$, I], [CC2539; 2, CH, CH, H, $C_3F_7$, I], [CC2540; 2, CH, CH, H, $CH_2CF_3$, I], [CC2541; 2, CH, CH, H, $CH_2CHF_2$, I],

[CC2542; 0, N, CH, H, H, I], [CC2543; 0, N, CH, H, F, I], [CC2544; 0, N, CH, H, Cl, I], [CC2545; 0, N, CH, H, Br, I], [CC2546; 0, N, CH, H, I, I], [CC2547; 0, N, CH, H, $CF_3$, I], [CC2548; 0, N, CH, H, $CF_2H$, I], [CC2549; 0, N, CH, H, $C_2F_5$, I], [CC2550; 0, N, CH, H, $C_3F_7$, I], [CC2551; 0, N, CH, H, $CH_2CF_3$, I], [CC2552; 0, N, CH, H, $CH_2CHF_2$, I], [CC2553; 1, N, CH, H, H, I], [CC2554; 1, N, CH, H, F, I], [CC2555; 1, N, CH, H, Cl, I], [CC2556; 1, N, CH, H, Br, I], [CC2557; 1, N, CH, H, I, I], [CC2558; 1, N, CH, H, $CF_3$, I], [CC2559; 1, N, CH, H, $CF_2H$, I], [CC2560; 1, N, CH, H, $C_2F_5$, I], [CC2561; 1, N, CH, H, $C_3F_7$, I], [CC2562; 1, N, CH, H, $CH_2CF_3$, I], [CC2563; 1, N, CH, H, $CH_2CHF_2$, I], [CC2564; 2, N, CH, H, H, I], [CC2565; 2, N, CH, H, F, I], [CC2566; 2, N, CH, H, Cl, I], [CC2567; 2, N, CH, H, Br, I], [CC2568; 2, N, CH, H, I, I], [CC2569; 2, N, CH, H, $CF_3$, I], [CC2570; 2, N, CH, H, $CF_2H$, I], [CC2571; 2, N, CH, H, $C_2F_5$, I], [CC2572; 2, N, CH, H, $C_3F_7$, I], [CC2573; 2, N, CH, H, $CH_2CF_3$, I], [CC2574; 2, N, CH, H, $CH_2CHF_2$, I], [CC2575; 0, CH, N, H, H, I], [CC2576; 0, CH, N, H, F, I], [CC2577; 0, CH, N, H, Cl, I], [CC2578; 0, CH, N, H, Br, I], [CC2579; 0, CH, N, H, I, I], [CC2580; 0, CH, N, H, $CF_3$, I], [CC2581; 0, CH, N, H, $CF_2H$, I], [CC2582; 0, CH, N, H, $C_2F_5$, I], [CC2583; 0, CH, N, H, $C_3F_7$, I], [CC2584; 0, CH, N, H, $CH_2CF_3$, I], [CC2585; 0, CH, N, H, $CH_2CHF_2$, I], [CC2586; 1, CH, N, H, H, I], [CC2587; 1, CH, N, H, F, I], [CC2588; 1, CH, N, H, Cl, I], [CC2589; 1, CH, N, H, Br, I], [CC2590; 1, CH, N, H, I, I], [CC2591; 1, CH, N, H, $CF_3$, I], [CC2592; 1, CH, N, H, $CF_2H$, I], [CC2593; 1, CH, N, H, $C_2F_5$, I], [CC2594; 1, CH, N, H, $C_3F_7$, I], [CC2595; 1, CH, N, H, $CH_2CF_3$, I], [CC2596; 1, CH, N, H, $CH_2CHF_2$, I], [CC2597; 2, CH, N, H, H, I], [CC2598; 2, CH, N, H, F, I], [CC2599; 2, CH, N, H, Cl, I], [CC2600; 2, CH, N, H, Br, I], [CC2601; 2, CH, N, H, I, I], [CC2602; 2, CH, N, H, $CF_3$, I], [CC2603; 2, CH, N, H, $CF_2H$, I], [CC2604; 2, CH, N, H, $C_2F_5$, I], [CC2605; 2, CH, N, H, $C_3F_7$, I], [CC2606; 2, CH, N, H, $CH_2CF_3$, I], [CC2607; 2, CH, N, H, $CH_2CHF_2$, I], [CC2608; 0, N, N, H, H, I], [CC2609; 0, N,N, H, F, I], [CC2610; 0, N,N, H, Cl, I], [CC2611; 0, N,N, H, Br, I], [CC2612; 0, N,N, H, I, I], [CC2613; 0, N,N, H, $CF_3$, I], [CC2614; 0, N,N, H, $CF_2H$, I], [CC2615; 0, N,N, H, $C_2F_5$, I], [CC2616; 0, N,N, H, $C_3F_7$, I], [CC2617; 0, N,N, H, $CH_2CF_3$, I], [CC2618; 0, N,N, H, $CH_2CHF_2$, I], [CC2619; 1, N, N, H, H, I], [CC2620; 1, N,N, H, F, I], [CC2621; 1, N,N, H, Cl, I], [CC2622; 1, N,N, H, Br, I], [CC2623; 1, N,N, H, I, I], [CC2624; 1, N,N, H, $CF_3$, I], [CC2625; 1, N,N, H, $CF_2H$, I], [CC2626; 1, N,N, H, $C_2F_5$, I], [CC2627; 1, N,N, H, $C_3F_7$, I], [CC2628; 1, N,N, H, $CH_2CF_3$, I], [CC2629; 1, N,N, H, $CH_2CHF_2$, I], [CC2630; 2, N, N, H, H, I], [CC2631; 2, N,N, H, F, I], [CC2632; 2, N,N, H, Cl, I], [CC2633; 2, N,N, H, Br, I], [CC2634; 2, N,N, H, I, I], [CC2635; 2, N,N, H, $CF_3$, I], [CC2636; 2, N,N, H, $CF_2H$, I], [CC2637; 2, N,N, H, $C_2F_5$, I], [CC2638; 2, N,N, H, $C_3F_7$, I], [CC2639; 2, N,N, H, $CH_2CF_3$, I], [CC2640; 2, N,N, H, $CH_2CHF_2$, I], [CC2641; 0, CH, CH, H, H, F], [CC2642; 0, CH, CH, F, H, F], [CC2643; 0, CH, CH, Cl, H, F], [CC2644; 0, CH, CH, Br, H, F], [CC2645; 0, CH, CH, I, H, F], [CC2646; 0, CH, CH, $CF_3$, H, F], [CC2647; 0, CH, CH, $CF_2H$, H, F], [CC2648; 0, CH, CH, $C_2F_5$, H, F], [CC2649; 0, CH, CH, $C_3F_7$, H, F], [CC2650; 0, CH, CH, $CH_2CF_3$, H, F], [CC2651; 0, CH, CH, $CH_2CHF_2$, H, F], [CC2652; 1, CH, CH, H, H, F], [CC2653; 1, CH, CH, F, H, F], [CC2654; 1, CH, CH, Cl, H, F], [CC2655; 1, CH, CH, Br, H, F], [CC2656; 1, CH, CH, I, H, F], [CC2657; 1, CH, CH, $CF_3$, H, F], [CC2658; 1, CH, CH, $CF_2H$, H, F], [CC2659; 1, CH, CH, $C_2F_5$, H, F], [CC2660; 1, CH, CH, $C_3F_7$, H, F], [CC2661; 1, CH, CH, $CH_2CF_3$, H, F], [CC2662; 1, CH, CH, $CH_2CHF_2$, H, F], [CC2663; 2, CH, CH, H, H, F], [CC2664; 2, CH, CH, F, H, F], [CC2665; 2, CH, CH, Cl, H, F], [CC2666; 2, CH, CH, Br, H, F], [CC2667; 2, CH, CH, I, H, F], [CC2668; 2, CH, CH, $CF_3$, H, F], [CC2669; 2, CH, CH, $CF_2H$, H, F], [CC2670; 2, CH, CH, $C_2F_5$, H, F], [CC2671; 2, CH, CH, $C_3F_7$, H, F], [CC2672; 2, CH, CH, $CH_2CF_3$, H, F], [CC2673; 2, CH, CH, $CH_2CHF_2$, H, F], [CC2674; 0, N, CH, H, H, F], [CC2675; 0, N, CH, F, H, F], [CC2676; 0, N, CH, Cl, H, F], [CC2677; 0, N, CH, Br, H, F], [CC2678; 0, N, CH, I, H, F], [CC2679; 0, N, CH, $CF_3$, H, F], [CC2680; 0, N, CH, $CF_2H$, H, F], [CC2681; 0, N, CH, $C_2F_5$, H, F], [CC2682; 0, N, CH, $C_3F_7$, H, F], [CC2683; 0, N, CH, $CH_2CF_3$, H, F], [CC2684; 0, N, CH, $CH_2CHF_2$, H, F], [CC2685; 1, N, CH, H, H, F], [CC2686; 1, N, CH, F, H, F], [CC2687; 1, N, CH, Cl, H, F], [CC2688; 1, N, CH, Br, H, F], [CC2689; 1, N, CH, I, H, F], [CC2690; 1, N, CH, $CF_3$, H, F], [CC2691; 1, N, CH, $CF_2H$, H, F], [CC2692; 1, N, CH, $C_2F_5$, H, F], [CC2693; 1, N, CH, $C_3F_7$, H, F], [CC2694; 1, N, CH, $CH_2CF_3$, H, F], [CC2695; 1, N, CH, $CH_2CHF_2$, H, F], [CC2696; 2, N, CH, H, H, F], [CC2697; 2, N, CH, F, H, F], [CC2698; 2, N, CH, Cl, H, F], [CC2699; 2, N, CH, Br, H, F], [CC2700; 2, N, CH, I, H, F], [CC2701; 2, N, CH, $CF_3$, H, F], [CC2702; 2, N, CH, $CF_2H$, H, F], [CC2703; 2, N, CH, $C_2F_5$, H, F], [CC2704; 2, N, CH, $C_3F_7$, H, F], [CC2705; 2, N, CH, $CH_2CF_3$, H, F], [CC2706; 2, N, CH, $CH_2CHF_2$, H, F], [CC2707; 0, CH, N, H, H, F], [CC2708; 0, CH, N, F, H, F], [CC2709; 0, CH, N, Cl, H, F], [CC2710; 0, CH, N, Br, H, F], [CC2711; 0, CH, N, I, H, F], [CC2712; 0, CH, N, $CF_3$, H, F], [CC2713; 0, CH, N, $CF_2H$, H, F], [CC2714; 0, CH, N, $C_2F_5$, H, F], [CC2715; 0, CH, N, $C_3F_7$, H, F], [CC2716; 0, CH, N, $CH_2CF_3$, H, F], [CC2717; 0, CH, N, $CH_2CHF_2$, H, F], [CC2718; 1, CH, N, H, H, F], [CC2719; 1, CH, N, F, H, F], [CC2720; 1, CH, N, Cl, H, F], [CC2721; 1, CH, N, Br, H, F], [CC2722; 1, CH, N, I, H, F], [CC2723; 1, CH, N, $CF_3$, H, F], [CC2724; 1, CH, N, $CF_2H$, H, F], [CC2725; 1, CH, N, $C_2F_5$, H, F], [CC2726; 1, CH, N, $C_3F_7$, H, F], [CC2727; 1, CH, N, $CH_2CF_3$, H, F], [CC2728; 1, CH, N, $CH_2CHF_2$, H, F], [CC2729; 2, CH, N, H, H, F], [CC2730; 2, CH, N, F, H, F], [CC2731; 2, CH, N, Cl, H, F], [CC2732; 2, CH, N, Br, H, F], [CC2733; 2, CH, N, I, H, F], [CC2734; 2, CH, N, $CF_3$, H, F], [CC2735; 2, CH, N, $CF_2H$, H, F], [CC2736; 2, CH, N, $C_2F_5$, H, F], [CC2737; 2, CH, N, $C_3F_7$, H, F], [CC2738; 2, CH, N, $CH_2CF_3$, H, F], [CC2739; 2, CH, N, $CH_2CHF_2$, H, F], [CC2740; 0, N, N, H, H, F], [CC2741; 0, N,N, F, H, F], [CC2742; 0, N, N, Cl, H, F], [CC2743; 0, N, N, Br, H, F], [CC2744; 0, N,N, I, H, F], [CC2745; 0, N, N, $CF_3$, H, F], [CC2746; 0, N, N, $CF_2H$, H, F], [CC2747; 0, N, N, $C_2F_5$, H, F], [CC2748; 0, N, N, $C_3F_7$, H, F], [CC2749; 0, N, N, $CH_2CF_3$, H, F], [CC2750; 0, N, N, $CH_2CHF_2$, H, F], [CC2751; 1, N, N, H, H, F], [CC2752; 1, N,N, F, H, F], [CC2753; 1, N, N, Cl, H, F], [CC2754; 1, N, N, Br, H, F], [CC2755; 1, N,N, I, H, F], [CC2756; 1, N, N, $CF_3$, H, F], [CC2757; 1, N, N, $CF_2H$, H, F], [CC2758; 1, N, N, $C_2F_5$, H, F], [CC2759; 1, N, N, $C_3F_7$, H, F], [CC2760; 1, N, N, $CH_2CF_3$, H, F], [CC2761; 1, N, N, $CH_2CHF_2$, H, F], [CC2762; 2, N, N, H, H, F], [CC2763; 2, N,N, F, H, F], [CC2764; 2, N, N, Cl, H, F], [CC2765; 2, N, N, Br, H, F], [CC2766; 2, N,N, I, H, F], [CC2767; 2, N, N, $CF_3$, H, F], [CC2768; 2, N, N, $CF_2H$, H, F], [CC2769; 2, N, N, $C_2F_5$, H, F], [CC2770; 2, N, N, $C_3F_7$, H, F], [CC2771; 2, N, N, $CH_2CF_3$, H, F], [CC2772; 2, N, N, $CH_2CHF_2$, H, F], [CC2773; 0, CH, CH, H, H, F], [CC2774; 0, CH, CH, H, F, F], [CC2775; 0, CH, CH, H, Cl, F], [CC2776; 0, CH, CH, H, Br, F], [CC2777; 0, CH, CH, H, I, F], [CC2778; 0, CH, CH, H, $CF_3$, F], [CC2779; 0, CH, CH, H, $CF_2H$, F], [CC2780; 0, CH, CH, H, $C_2F_5$, F], [CC2781; 0, CH, CH, H, $C_3F_7$, F], [CC2782; 0, CH, CH, H, $CH_2CF_3$, F], [CC2783; 0, CH, CH, H, $CH_2CHF_2$, F], [CC2784; 1, CH, CH, H, H,

F], [CC2785; 1, CH, CH, H, F, F], [CC2786; 1, CH, CH, H, Cl, F], [CC2787; 1, CH, CH, H, Br, F], [CC2788; 1, CH, CH, H, I, F], [CC2789; 1, CH, CH, H, $CF_3$, F], [CC2790; 1, CH, CH, H, $CF_2H$, F], [CC2791; 1, CH, CH, H, $C_2F_5$, F], [CC2792; 1, CH, CH, H, $C_3F_7$, F], [CC2793; 1, CH, CH, H, $CH_2CF_3$, F], [CC2794; 1, CH, CH, H, $CH_2CHF_2$, F], [CC2795; 2, CH, CH, H, H, F], [CC2796; 2, CH, CH, H, F, F], [CC2797; 2, CH, CH, H, Cl, F], [CC2798; 2, CH, CH, H, Br, F], [CC2799; 2, CH, CH, H, I, F], [CC2800; 2, CH, CH, H, $CF_3$, F], [CC2801; 2, CH, CH, H, $CF_2H$, F], [CC2802; 2, CH, CH, H, $C_2F$, F], [CC2803; 2, CH, CH, H, $C_3F_7$, F], [CC2804; 2, CH, CH, H, $CH_2CF_3$, F], [CC2805; 2, CH, CH, H, $CH_2CHF_2$, F], [CC2806; 0, N, CH, H, H, F], [CC2807; 0, N, CH, H, F, F], [CC2808; 0, N, CH, H, Cl, F], [CC2809; 0, N, CH, H, Br, F], [CC2810; 0, N, CH, H, I, F], [CC2811; 0, N, CH, H, $CF_3$, F], [CC2812; 0, N, CH, H, $CF_2H$, F], [CC2813; 0, N, CH, H, $C_2F_5$, F], [CC2814; 0, N, CH, H, $C_3F_7$, F], [CC2815; 0, N, CH, H, $CH_2CF_3$, F], [CC2816; 0, N, CH, H, $CH_2CHF_2$, F], [CC2817; 1, N, CH, H, H, F], [CC2818; 1, N, CH, H, F, F], [CC2819; 1, N, CH, H, Cl, F], [CC2820; 1, N, CH, H, Br, F], [CC2821; 1, N, CH, H, I, F], [CC2822; 1, N, CH, H, $CF_3$, F], [CC2823; 1, N, CH, H, $CF_2H$, F], [CC2824; 1, N, CH, H, $C_2F_5$, F], [CC2825; 1, N, CH, H, $C_3F_7$, F], [CC2826; 1, N, CH, H, $CH_2CF_3$, F], [CC2827; 1, N, CH, H, $CH_2CHF_2$, F], [CC2828; 2, N, CH, H, H, F], [CC2829; 2, N, CH, H, F, F], [CC2830; 2, N, CH, H, Cl, F], [CC2831; 2, N, CH, H, Br, F], [CC2832; 2, N, CH, H, I, F], [CC2833; 2, N, CH, H, $CF_3$, F], [CC2834; 2, N, CH, H, $CF_2H$, F], [CC2835; 2, N, CH, H, $C_2F_5$, F], [CC2836; 2, N, CH, H, $C_3F_7$, F], [CC2837; 2, N, CH, H, $CH_2CF_3$, F], [CC2838; 2, N, CH, H, $CH_2CHF_2$, F], [CC2839; 0, CH, N, H, H, F], [CC2840; 0, CH, N, H, F, F], [CC2841; 0, CH, N, H, Cl, F], [CC2842; 0, CH, N, H, Br, F], [CC2843; 0, CH, N, H, I, F], [CC2844; 0, CH, N, H, $CF_3$, F], [CC2845; 0, CH, N, H, $CF_2H$, F], [CC2846; 0, CH, N, H, $C_2F_5$, F], [CC2847; 0, CH, N, H, $C_3F_7$, F], [CC2848; 0, CH, N, H, $CH_2CF_3$, F], [CC2849; 0, CH, N, H, $CH_2CHF_2$, F], [CC2850; 1, CH, N, H, H, F], [CC2851; 1, CH, N, H, F, F], [CC2852; 1, CH, N, H, Cl, F], [CC2853; 1, CH, N, H, Br, F], [CC2854; 1, CH, N, H, I, F], [CC2855; 1, CH, N, H, $CF_3$, F], [CC2856; 1, CH, N, H, $CF_2H$, F], [CC2857; 1, CH, N, H, $C_2F_1$, F], [CC2858; 1, CH, N, H, $C_3F_7$, F], [CC2859; 1, CH, N, H, $CH_2CF_3$, F], [CC2860; 1, CH, N, H, $CH_2CHF_2$, F], [CC2861; 2, CH, N, H, H, F], [CC2862; 2, CH, N, H, F, F], [CC2863; 2, CH, N, H, Cl, F], [CC2864; 2, CH, N, H, Br, F], [CC2865; 2, CH, N, H, I, F], [CC2866; 2, CH, N, H, $CF_3$, F], [CC2867; 2, CH, N, H, $CF_2H$, F], [CC2868; 2, CH, N, H, $C_2F_3$, F], [CC2869; 2, CH, N, H, $C_3F_7$, F], [CC2870; 2, CH, N, H, $CH_2CF_3$, F], [CC2871; 2, CH, N, H, $CH_2CHF_2$, F], [CC2872; 0, N, N, H, H, F], [CC2873; 0, N,N, H, F, F], [CC2874; 0, N,N, H, Cl, F], [CC2875; 0, N,N, H, Br, F], [CC2876; 0, N,N, H, I, F], [CC2877; 0, N,N, H, $CF_3$, F], [CC2878; 0, N,N, H, $CF_2H$, F], [CC2879; 0, N,N, H, $C_2F_5$, F], [CC2880; 0, N,N, H, $C_3F_7$, F], [CC2881; 0, N,N, H, $CH_2CF_3$, F], [CC2882; 0, N,N, H, $CH_2CHF_2$, F], [CC2883; 1, N, N, H, H, F], [CC2884; 1, N,N, H, F, F], [CC2885; 1, N,N, H, Cl, F], [CC2886; 1, N,N, H, Br, F], [CC2887; 1, N,N, H, I, F], [CC2888; 1, N,N, H, $CF_3$, F], [CC2889; 1, N,N, H, $CF_2H$, F], [CC2890; 1, N,N, H, $C_2F_5$, F], [CC2891; 1, N,N, H, $C_3F_7$, F], [CC2892; 1, N,N, H, $CH_2CF_3$, F], [CC2893; 1, N,N, H, $CH_2CHF_2$, F], [CC2894; 2, N, N, H, H, F], [CC2895; 2, N,N, H, F, F], [CC2896; 2, N,N, H, Cl, F], [CC2897; 2, N,N, H, Br, F], [CC2898; 2, N,N, H, I, F], [CC2899; 2, N,N, H, $CF_3$, F], [CC2900; 2, N,N, H, $CF_2H$, F], [CC2901; 2, N,N, H, $C_2F_5$, F], [CC2902; 2, N,N, H, $C_3F_7$, F], [CC2903; 2, N,N, H, $CH_2CF_3$, F], [CC2904; 2, N,N, H, $CH_2CHF_2$, F],

A compound represented by formula (L-10)

(L-10)

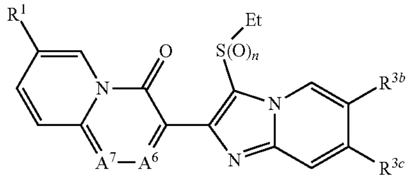

wherein the combination of the symbol n, and the substituents $A^6$, $A^7$, $R^{3b}$, $R^{3c}$, and $R^1$ represents any one combination indicated in the Combination CC (hereinafter referred to as "Compound group SX10").

A compound represented by formula (L-11)

(L-11)

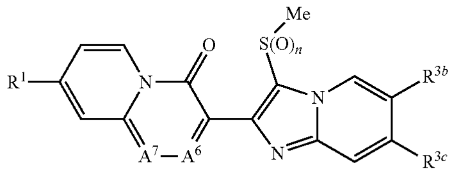

wherein the combination of the symbol n, and the substituents $A^6$, $A^7$, $R^{3b}$, $R^{3c}$, and $R^1$ represents any one combination indicated in the Combination CC (hereinafter referred to as "Compound group SX11").

A compound represented by formula (L-12)

(L-12)

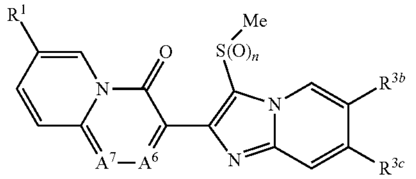

wherein the combination of the symbol n, and the substituents $A^6$, $A^7$, $R^{3b}$, $R^{3c}$, and $R^1$ represents any one combination indicated in the Combination CC (hereinafter referred to as "Compound group SX12").

A compound represented by formula (L-13)

(L-13)

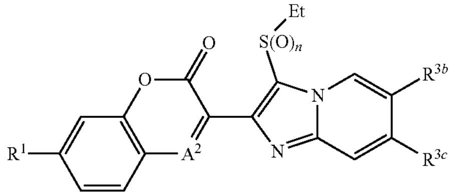

wherein the combination of the symbol n, and the substituents $A^2$, $R^{3b}$, $R^{3c}$, and $R^1$ represents any one combination indicated in the Combination DD (hereinafter referred to as "Compound group SX13").

The Combination DD consists of substituent numbers DD1 to DD1452. The substituent numbers DD1 to DD1452 represent the combinations of the symbol n, and the substituents $A^2$, $R^{3b}$, $R^{3c}$, and $R^1$, and hereinafter referred to as "[substituent number; n, $A^2$, $R^{3b}$, $R^{3c}$, $R^1$]". For example, the substituent number DD2 means a combination wherein n represents 0, $A^2$ represents N, $R^{3b}$ represents a fluorine atom, $R^{3c}$ represents a hydrogen atom, and $R^1$ represents $CF_3$ Combination DD: [DD1; 0, N, H, H, $CF_3$], [DD2; 0, N, F, H, $CF_3$], [DD3; 0, N, Cl, H, $CF_3$], [DD4; 0, N, Br, H, $CF_3$], [DD5; 0, N, I, H, $CF_3$], [DD6; 0, N, $CF_3$, H, $CF_3$], [DD7; 0, N, $CF_2H$, H, $CF_3$], [DD8; 0, N, $C_2F_3$, H, $CF_3$], [DD9; 0, N, $C_3F_7$, H, $CF_3$], [DD10; 0, N, $CH_2CF_3$, H, $CF_3$], [DD11; 0, N, $CH_2CHF_2$, H, $CF_3$], [DD12; 0, CH, H, H, $CF_3$], [DD13; 0, CH, F, H, $CF_3$], [DD14; 0, CH, Cl, H, $CF_3$], [DD15; 0, CH, Br, H, $CF_3$], [DD16; 0, CH, I, H, $CF_3$], [DD17; 0, CH, $CF_3$, H, $CF_3$], [DD18; 0, CH, $CF_2H$, H, $CF_3$], [DD19; 0, CH, $C_2F_5$, H, $CF_3$], [DD20; 0, CH, $C_3F_7$, H, $CF_3$], [DD21; 0, CH, $CH_2CF_3$, H, $CF_3$], [DD22; 0, CH, $CH_2CHF_2$, H, $CF_3$], [DD23; 1, N, H, H, $CF_3$], [DD24; 1, N, F, H, $CF_3$], [DD25; 1, N, Cl, H, $CF_3$], [DD26; 1, N, Br, H, $CF_3$], [DD27; 1, N, I, H, $CF_3$], [DD28; 1, N, $CF_3$, H, $CF_3$], [DD29; 1, N, $CF_2H$, H, $CF_3$], [DD30; 1, N, $C_2F_5$, H, $CF_3$], [DD31; 1, N, $C_3F_7$, H, $CF_3$], [DD32; 1, N, $CH_2CF_3$, H, $CF_3$], [DD33; 1, N, $CH_2CHF_2$, H, $CF_3$], [DD34; 1, CH, H, H, $CF_3$], [DD35; 1, CH, F, H, $CF_3$], [DD36; 1, CH, Cl, H, $CF_3$], [DD37; 1, CH, Br, H, $CF_3$], [DD38; 1, CH, I, H, $CF_3$], [DD39; 1, CH, $CF_3$, H, $CF_3$], [DD40; 1, CH, $CF_2H$, H, $CF_3$], [DD41; 1, CH, $C_2F$, H, $CF_3$], [DD42; 1, CH, $C_3F_7$, H, $CF_3$], [DD43; 1, CH, $CH_2CF_3$, H, $CF_3$], [DD44; 1, CH, $CH_2CHF_2$, H, $CF_3$], [DD45; 2, N, H, H, $CF_3$], [DD46; 2, N, F, H, $CF_3$], [DD47; 2, N, Cl, H, $CF_3$], [DD48; 2, N, Br, H, $CF_3$], [DD49; 2, N, I, H, $CF_3$], [DD50; 2, N, $CF_3$, H, $CF_3$], [DD51; 2, N, $CF_2H$, H, $CF_3$], [DD52; 2, N, $C_2F_5$, H, $CF_3$], [DD53; 2, N, $C_3F_7$, H, $CF_3$], [DD54; 2, N, $CH_2CF_3$, H, $CF_3$], [DD55; 2, N, $CH_2CHF_2$, H, $CF_3$], [DD56; 2, CH, H, H, $CF_3$], [DD57; 2, CH, F, H, $CF_3$], [DD58; 2, CH, Cl, H, $CF_3$], [DD59; 2, CH, Br, H, $CF_3$], [DD60; 2, CH, I, H, $CF_3$], [DD61; 2, CH, $CF_3$, H, $CF_3$], [DD62; 2, CH, $CF_2H$, H, $CF_3$], [DD63; 2, CH, $C_2F_5$, H, $CF_3$], [DD64; 2, CH, $C_3F_7$, H, $CF_3$], [DD65; 2, CH, $CH_2CF_3$, H, $CF_3$], [DD66; 2, CH, $CH_2CHF_2$, H, $CF_3$], [DD67; 0, N, H, H, $CF_3$], [DD68; 0, N, H, F, $CF_3$], [DD69; 0, N, H, Cl, $CF_3$], [DD70; 0, N, H, Br, $CF_3$], [DD71; 0, N, H, I, $CF_3$], [DD72; 0, N, H, $CF_3$, $CF_3$], [DD73; 0, N, H, $CF_2H$, $CF_3$], [DD74; 0, N, H, $C_2F_5$, $CF_3$], [DD75; 0, N, H, $C_3F_7$, $CF_3$], [DD76; 0, N, H, $CH_2CF_3$, $CF_3$], [DD77; 0, N, H, $CH_2CHF_2$, $CF_3$], [DD78; 0, CH, H, H, $CF_3$], [DD79; 0, CH, H, F, $CF_3$], [DD80; 0, CH, H, Cl, $CF_3$], [DD81; 0, CH, H, Br, $CF_3$], [DD82; 0, CH, H, I, $CF_3$], [DD83; 0, CH, H, $CF_3$, $CF_3$], [DD84; 0, CH, H, $CF_2H$, $CF_3$], [DD85; 0, CH, H, $C_2F_5$, $CF_3$], [DD86; 0, CH, H, $C_3F_7$, $CF_3$], [DD87; 0, CH, H, $CH_2CF_3$, $CF_3$], [DD88; 0, CH, H, $CH_2CHF_2$, $CF_3$], [DD89; 1, N, H, H, $CF_3$], [DD90; 1, N, H, F, $CF_3$], [DD91; 1, N, H, Cl, $CF_3$], [DD92; 1, N, H, Br, $CF_3$], [DD93; 1, N, H, I, $CF_3$], [DD94; 1, N, H, $CF_3$, $CF_3$], [DD95; 1, N, H, $CF_2H$, $CF_3$], [DD96; 1, N, H, $C_2F_5$, $CF_3$], [DD97; 1, N, H, $C_3F_7$, $CF_3$], [DD98; 1, N, H, $CH_2CF_3$, $CF_3$], [DD99; 1, N, H, $CH_2CHF_2$, $CF_3$], [DD100; 1, CH, H, H, $CF_3$], [DD101; 1, CH, H, F, $CF_3$], [DD102; 1, CH, H, Cl, $CF_3$], [DD103; 1, CH, H, Br, $CF_3$], [DD104; 1, CH, H, I, $CF_3$], [DD105; 1, CH, H, $CF_3$, $CF_3$], [DD106; 1, CH, H, $CF_2H$, $CF_3$], [DD107; 1, CH, H, $C_2F_5$, $CF_3$], [DD108; 1, CH, H, $C_3F_1$, $CF_3$], [DD109; 1, CH, H, $CH_2CF_3$, $CF_3$], [DD110; 1, CH, H, $CH_2CHF_2$, $CF_3$], [DD111; 2, N, H, H, $CF_3$], [DD112; 2, N, H, F, $CF_3$], [DD113; 2, N, H, Cl, $CF_3$], [DD114; 2, N, H, Br, $CF_3$], [DD115; 2, N, H, I, $CF_3$], [DD116; 2, N, H, $CF_3$, $CF_3$], [DD117; 2, N, H, $CF_2H$, $CF_3$], [DD118; 2, N, H, $C_2F_5$, $CF_3$], [DD119; 2, N, H, $C_3F_7$, $CF_3$], [DD120; 2, N, H, $CH_2CF_3$, $CF_3$], [DD121; 2, N, H, $CH_2CHF_2$, $CF_3$], [DD122; 2, CH, H, H, $CF_3$], [DD123; 2, CH, H, F, $CF_3$], [DD124; 2, CH, H, Cl, $CF_3$], [DD125; 2, CH, H, Br, $CF_3$], [DD126; 2, CH, H, I, $CF_3$], [DD127; 2, CH, H, $CF_3$, $CF_3$], [DD128; 2, CH, H, $CF_2H$, $CF_3$], [DD129; 2, CH, H, $C_2F_5$, $CF_3$], [DD130; 2, CH, H, $C_3F_7$, $CF_3$], [DD131; 2, CH, H, $CH_2CF_3$, $CF_3$], [DD132; 2, CH, H, $CH_2CHF_2$, $CF_3$], [DD133; N, H, H, $CHF_2$], [DD134; 0, N, F, H, $CHF_2$], [DD135; 0, N, Cl, H, $CHF_2$], [DD136; 0, N, Br, H, $CHF_2$], [DD137; 0, N, I, H, $CHF_2$], [DD138; 0, N, $CF_3$, H, $CHF_2$], [DD139; 0, N, $CF_2H$, H, $CHF_2$], [DD140; 0, N, $C_2F_5$, H, $CHF_2$], [DD141; 0, N, $C_3F_7$, H, $CHF_2$], [DD142; 0, N, $CH_2CF_3$, H, $CHF_2$], [DD143; 0, N, $CH_2CHF_2$, H, $CHF_2$], [DD144; 0, CH, H, H, $CHF_2$], [DD145; 0, CH, F, H, $CHF_2$], [DD146; 0, CH, Cl, H, $CHF_2$], [DD147; 0, CH, Br, H, $CHF_2$], [DD148; 0, CH, I, H, $CHF_2$], [DD149; 0, CH, $CF_3$, H, $CHF_2$], [DD150; 0, CH, $CF_2H$, H, $CHF_2$], [DD151; 0, CH, $C_2F_5$, H, $CHF_2$], [DD152; 0, CH, $C_3F_7$, H, $CHF_2$], [DD153; 0, CH, $CH_2CF_3$, H, $CHF_2$], [DD154; 0, CH, $CH_2CHF_2$, H, $CHF_2$], [DD155; 1, N, H, H, $CHF_2$], [DD156; 1, N, F, H, $CHF_2$], [DD157; 1, N, Cl, H, $CHF_2$], [DD158; 1, N, Br, H, $CHF_2$], [DD159; 1, N, I, H, $CHF_2$], [DD160; 1, N, $CF_3$, H, $CHF_2$], [DD161; 1, N, $CF_2H$, H, $CHF_2$], [DD162; 1, N, $C_2F_5$, H, $CHF_2$], [DD163; 1, N, $C_3F_7$, H, $CHF_2$], [DD164; 1, N, $CH_2CF_3$, H, $CHF_2$], [DD165; 1, N, $CH_2CHF_2$, H, $CHF_2$], [DD166; 1, CH, H, H, $CHF_2$], [DD167; 1, CH, F, H, $CHF_2$], [DD168; 1, CH, Cl, H, $CHF_2$], [DD169; 1, CH, Br, H, $CHF_2$], [DD170; 1, CH, I, H, $CHF_2$], [DD171; 1, CH, $CF_3$, H, $CHF_2$], [DD172; 1, CH, $CF_2H$, H, $CHF_2$], [DD173; 1, CH, $C_2F_5$, H, $CHF_2$], [DD174; 1, CH, $C_3F_7$, H, $CHF_2$], [DD175; 1, CH, $CH_2CF_3$, H, $CHF_2$], [DD176; 1, CH, $CH_2CHF_2$, H, $CHF_2$], [DD177; 2, N, H, H, $CHF_2$], [DD178; 2, N, F, H, $CHF_2$], [DD179; 2, N, Cl, H, $CHF_2$], [DD180; 2, N, Br, H, $CHF_2$], [DD181; 2, N, I, H, $CHF_2$], [DD182; 2, N, $CF_3$, H, $CHF_2$], [DD183; 2, N, $CF_2H$, H, $CHF_2$], [DD184; 2, N, $C_2F_5$, H, $CHF_2$], [DD185; 2, N, $C_3F_7$, H, $CHF_2$], [DD186; 2, N, $CH_2CF_3$, H, $CHF_2$], [DD187; 2, N, $CH_2CHF_2$, H, $CHF_2$], [DD188; 2, CH, H, H, $CHF_2$], [DD189; 2, CH, F, H, $CHF_2$], [DD190; 2, CH, Cl, H, $CHF_2$], [DD191; 2, CH, Br, H, $CHF_2$], [DD192; 2, CH, I, H, $CHF_2$], [DD193; 2, CH, $CF_3$, H, $CHF_2$], [DD194; 2, CH, $CF_2H$, H, $CHF_2$], [DD195; 2, CH, $C_2F_5$, H, $CHF_2$], [DD196; 2, CH, $C_3F_7$, H, $CHF_2$], [DD197; 2, CH, $CH_2CF_3$, H, $CHF_2$], [DD198; 2, CH, $CH_2CHF_2$, H, $CHF_2$], [DD199; 0, N, H, H, $CHF_2$], [DD200; 0, N, H, F, $CHF_2$], [DD201; 0, N, H, Cl, $CHF_2$], [DD202; 0, N, H, Br, $CHF_2$], [DD203; 0, N, H, I, $CHF_2$], [DD204; 0, N, H, $CF_3$, $CHF_2$], [DD205; 0, N, H, $CF_2H$, $CHF_2$], [DD206; 0, N, H, $C_2F_5$, $CHF_2$], [DD207; 0, N, H, $C_3F_7$, $CHF_2$], [DD208; 0, N, H, $CH_2CF_3$, $CHF_2$], [DD209; 0, N, H, $CH_2CHF_2$, $CHF_2$], [DD210; 0, CH, H, H, $CHF_2$], [DD211; 0, CH, H, F, $CHF_2$], [DD212; 0, CH, H, Cl, $CHF_2$], [DD213; 0, CH, H, Br, $CHF_2$], [DD214; 0, CH, H, I, $CHF_2$], [DD215; 0, CH, H, $CF_3$, $CHF_2$], [DD216; 0, CH, H, $CF_2H$, $CHF_2$], [DD217; 0, CH, H, $C_2F_5$, $CHF_2$], [DD218; 0, CH, H, $C_3F_7$, $CHF_2$], [DD219; 0, CH, H, $CH_2CF_3$, $CHF_2$], [DD220; 0, CH, H, $CH_2CHF_2$, $CHF_2$], [DD221; 1, N, H, H, $CHF_2$], [DD222; 1, N, H, F, $CHF_2$], [DD223; 1, N, H, Cl, $CHF_2$], [DD224; 1, N, H, Br, $CHF_2$], [DD225; 1, N, H, I, $CHF_2$], [DD226; 1, N, H, $CF_3$, $CHF_2$], [DD227; 1, N, H, $CF_2H$, $CHF_2$], [DD228; 1, N, H, $C_2F_5$, $CHF_2$], [DD229; 1, N, H, $C_3F_7$, $CHF_2$], [DD230; 1, N, H, $CH_2CF_3$, $CHF_2$], [DD231; 1, N, H, $CH_2CHF_2$, $CHF_2$], [DD232; 1, CH, H, H, $CHF_2$], [DD233; 1, CH, H, F, $CHF_2$], [DD234; 1, CH, H, Cl, $CHF_2$], [DD235; 1, CH, H, Br, $CHF_2$], [DD236; 1, CH, H, I, $CHF_2$], [DD237; 1, CH, H, $CF_3$, $CHF_2$], [DD238; 1, CH, H, $CF_2H$, $CHF_2$], [DD239; 1, CH, H, $C_2F_5$, $CHF_2$], [DD240; 1, CH, H, $C_3F_7$, $CHF_2$], [DD241; 1, CH, H, $CH_2CF_3$, $CHF_2$], [DD242; 1, CH, H, $CH_2CHF_2$, $CHF_2$], [DD243; 2, N, H, H, $CHF_2$], [DD244; 2, N, H, F, $CHF_2$], [DD245; 2, N, H, Cl, $CHF_2$], [DD246; 2, N, H, Br, $CHF_2$], [DD247; 2, N, H, I, $CHF_2$], [DD248; 2, N, H, $CF_3$, $CHF_2$], [DD249; 2, N, H, $CF_2H$, $CHF_2$], [DD250; 2, N, H, $C_2F_5$, $CHF_2$], [DD251; 2, N, H, $C_3F_7$, $CHF_2$], [DD252; 2, N, H, $CH_2CF_3$, $CHF_2$], [DD253; 2, N, H, $CH_2CHF_2$, $CHF_2$], [DD254; 2, CH, H, H, $CHF_2$], [DD255; 2, CH, H, F, $CHF_2$], [DD256; 2, CH, H, Cl, $CHF_2$], [DD257; 2, CH, H, Br, $CHF_2$], [DD258; 2, CH, H, I, $CHF_2$], [DD259; 2, CH, H, $CF_3$, $CHF_2$], [DD260; 2, CH, H, $CF_2H$, $CHF_2$], [DD261; 2, CH, H, $C_2F_5$, $CHF_2$], [DD262; 2, CH, H, $C_3F_7$, $CHF_2$], [DD263; 2, CH, H, $CH_2CF_3$, $CHF_2$], [DD264; 2, CH, H, $CH_2CHF_2$, $CHF_2$], [DD265; N, H, H, $CH_2CF_3$], [DD266; 0, N, F, H, $CH_2CF_3$], [DD267; 0, N, Cl, H, $CH_2CF_3$], [DD268; 0, N, Br, H, $CH_2CF_3$], [DD269; 0, N, I, H, $CH_2CF_3$], [DD270; 0, N, $CF_3$, H, $CH_2CF_3$], [DD271; 0, N, $CF_2H$, H, $CH_2CF_3$], [DD272; 0, N, $C_2F_5$, H, $CH_2CF_3$], [DD273; 0, N, $C_3F_7$, H, $CH_2CF_3$], [DD274; 0, N, $CH_2CF_3$, H, $CH_2CF_3$], [DD275; 0, N, $CH_2CHF_2$, H, $CH_2CF_3$], [DD276; 0, CH, H, H, $CH_2CF_3$], [DD277; 0, CH, F, H, $CH_2CF_3$], [DD278; 0, CH, Cl, H, $CH_2CF_3$], [DD279; 0, CH, Br, H, $CH_2CF_3$], [DD280; 0, CH, I, H, $CH_2CF_3$], [DD281; 0, CH, $CF_3$, H, $CH_2CF_3$], [DD282; 0, CH, $CF_2H$, H, $CH_2CF_3$], [DD283; 0, CH, $C_2F_5$, H, $CH_2CF_3$], [DD284; 0, CH, $C_3F_7$, H, $CH_2CF_3$], [DD285; 0, CH, $CH_2CF_3$, H, $CH_2CF_3$], [DD286; 0, CH, $CH_2CHF_2$, H, $CH_2CF_3$], [DD287; 1, N, H, H, $CH_2CF_3$], [DD288; 1, N, F, H, $CH_2CF_3$], [DD289; 1, N, Cl, H, $CH_2CF_3$], [DD290; 1, N, Br, H, $CH_2CF_3$], [DD291; 1, N, I, H, $CH_7CF_3$], [DD292; 1, N, $CF_3$, H, $CH_2CF_3$], [DD293; 1, N, $CF_2H$, H, $CH_2CF_3$], [DD294; 1, N, $C_2F_5$, H, $CH_2CF_3$], [DD295; 1, N, $C_3F_7$, H, $CH_2CF_3$], [DD296; 1, N, $CH_2CF_3$, H, $CH_2CF_3$], [DD297; 1, N, $CH_7CHF_2$, H, $CH_2CF_3$], [DD298; 1, CH, H, H, $CH_2CF_3$], [DD299; 1, CH, F, H, $CH_2CF_3$], [DD300; 1, CH, Cl, H, $CH_2CF_3$], [DD301; 1, CH, Br, H, $CH_2CF_3$], [DD302; 1, CH, I, H, $CH_2CF_3$], [DD303; 1, CH, $CF_3$, H, $CH_2CF_3$], [DD304; 1, CH, $CF_2H$, H, $CH_2CF_3$], [DD305; 1, CH, $C_2F_5$, H, $CH_2CF_3$], [DD306; 1, CH, $C_3F_7$, H, $CH_2CF_3$], [DD307; 1, CH, $CH_2CF_3$, H, $CH_2CF_3$], [DD308; 1, CH, $CH_2CHF_2$, H, $CH_2CF_3$], [DD309; 2, N, H, H, $CH_2CF_3$], [DD310; 2, N, F, H, $CH_2CF_3$], [DD311; 2, N, Cl, H, $CH_2CF_3$], [DD312; 2, N, Br, H, $CH_2CF_3$], [DD313; 2, N, I, H, $CH_2CF_3$], [DD314; 2, N, $CF_3$, H, $CH_2CF_3$], [DD315; 2, N, $CF_2H$, H, $CH_2CF_3$], [DD316; 2, N, $C_2F_5$, H, $CH_2CF_3$], [DD317; 2, N, $C_3F_7$, H, $CH_2CF_3$], [DD318; 2, N, $CH_2CF_3$, H, $CH_2CF_3$], [DD319; 2, N, $CH_2CHF_2$, H, $CH_2CF_3$], [DD320; 2, CH, H, H, $CH_2CF_3$], [DD321; 2, CH, F, H, $CH_2CF_3$], [DD322; 2, CH, Cl, H, $CH_2CF_3$], [DD323; 2, CH, Br, H, $CH_2CF_3$], [DD324; 2, CH, I, H, $CH_2CF_3$], [DD325; 2, CH, $CF_3$, H, $CH_2CF_3$], [DD326; 2, CH, $CF_2H$, H, $CH_2CF_3$], [DD327; 2, CH, $C_2F_5$, H, $CH_2CF_3$], [DD328; 2, CH, $C_3F_7$, H, $CH_2CF_3$], [DD329; 2, CH, $CH_2CF_3$, H, $CH_2CF_3$], [DD330; 2, CH, $CH_2CHF_2$, H, $CH_2CF_3$], [DD331; 0, N, H, H, $CH_2CF_3$], [DD332; 0, N, H, F, $CH_2CF_3$], [DD333; 0, N, H, Cl, $CH_2CF_3$], [DD334; 0, N, H, Br, $CH_2CF_3$], [DD335; 0, N, H, I, $CH_2CF_3$], [DD336; 0, N, H, $CF_3$, $CH_2CF_3$], [DD337; 0, N, H, $CF_2H$, $CH_2CF_3$], [DD338; 0, N, H, $C_2F_5$, $CH_2CF_3$], [DD339; 0, N, H, $C_3F_7$, $CH_2CF_3$], [DD340; 0, N, H, $CH_2CF_3$, $CH_2CF_3$], [DD341; 0, N, H, $CH_2CHF_2$, $CH_2CF_3$], [DD342; 0, CH, H, H, $CH_2CF_3$], [DD343; 0, CH, H, F, $CH_2CF_3$], [DD344; 0, CH, H, Cl, $CH_2CF_3$], [DD345; 0, CH, H, Br, $CH_2CF_3$], [DD346; 0, CH, H, I, $CH_2CF_3$], [DD347; 0, CH, H, $CF_3$, $CH_2CF_3$], [DD348; 0, CH, H, $CF_2H$, $CH_2CF_3$], [DD349; 0, CH, H, $C_2F_5$, $CH_2CF_3$], [DD350; 0, CH, H, $C_3F_7$, $CH_2CF_3$], [DD351; 0, CH, H, $CH_2CF_3$, $CH_2CF_3$], [DD352; 0, CH, H, $CH_2CHF_2$, $CH_2CF_3$], [DD353; 1, N, H, H, $CH_2CF_3$], [DD354; 1, N, H, F, $CH_2CF_3$], [DD355; 1, N, H, Cl, $CH_2CF_3$], [DD356; 1, N, H, Br, $CH_2CF_3$], [DD357; 1, N, H, I, $CH_2CF_3$], [DD358; 1, N, H, $CF_3$, $CH_2CF_3$], [DD359; 1, N, H, $CF_2H$, $CH_2CF_3$], [DD360; 1, N, H, $C_2F_5$, $CH_2CF_3$], [DD361; 1, N, H, $C_3F_7$, $CH_2CF_3$], [DD362; 1, N, H, $CH_2CF_3$, $CH_2CF_3$], [DD363; 1, N, H, $CH_2CHF_2$, $CH_2CF_3$], [DD364; 1, CH, H, H, $CH_2CF_3$], [DD365; 1, CH, H, F, $CH_2CF_3$], [DD366; 1, CH, H, Cl, $CH_2CF_3$], [DD367; 1, CH, H, Br, $CH_2CF_3$], [DD368; 1, CH, H, I, $CH_2CF_3$], [DD369; 1, CH, H, $CF_3$, $CH_2CF_3$], [DD370; 1, CH, H, $CF_2H$, $CH_2CF_3$], [DD371; 1, CH, H, $C_2F_5$, $CH_2CF_3$], [DD372; 1, CH, H, $C_3F_7$, $CH_2CF_3$], [DD373; 1, CH, H, $CH_2CF_3$, $CH_2CF_3$], [DD374; 1, CH, H, $CH_2CHF_2$, $CH_2CF_3$], [DD375; 2, N, H, H, $CH_2CF_3$], [DD376; 2, N, H, F, $CH_2CF_3$], [DD377; 2, N, H, Cl, $CH_2CF_3$], [DD378; 2, N, H, Br, $CH_2CF_3$], [DD379; 2, N, H, I, $CH_2CF_3$], [DD380; 2, N, H, $CF_3$, $CH_2CF_3$], [DD381; 2, N, H, $CF_2H$, $CH_2CF_3$], [DD382; 2, N, H, $C_2F_5$, $CH_2CF_3$], [DD383; 2, N, H, $C_3F_7$, $CH_2CF_3$], [DD384; 2, N, H, $CH_2CF_3$, $CH_2CF_3$], [DD385; 2, N, H, $CH_2CHF_2$, $CH_2CF_3$], [DD386; 2, CH, H, H, $CH_2CF_3$], [DD387; 2, CH, H, F, $CH_2CF_3$], [DD388; 2, CH, H, Cl, $CH_2CF_3$], [DD389; 2, CH, H, Br, $CH_2CF_3$], [DD390; 2, CH, H, I, $CH_2CF_3$], [DD391; 2, CH, H, $CF_3$, $CH_2CF_3$], [DD392; 2, CH, H, $CF_2H$, $CH_2CF_3$], [DD393; 2, CH, H, $C_2F_5$, $CH_2CF_3$], [DD394; 2, CH, H, $C_3F_7$, $CH_2CF_3$], [DD395; 2, CH, H, $CH_2CF_3$, $CH_2CF_3$], [DD396; 2, CH, H, $CH_2CHF_2$, $CH_2CF_3$], [DD397; N, H, H, $CH_2CHF_2$], [DD398; 0, N, F, H, $CH_2CHF_2$], [DD399; 0, N, Cl, H, $CH_2CHF_2$], [DD400; 0, N, Br, H, $CH_2CHF_2$], [DD401; 0, N, I, H, $CH_2CHF_2$], [DD402; 0, N, $CF_3$, H, $CH_2CHF_2$], [DD403; 0, N, $CF_2H$, H, $CH_2CHF_2$], [DD404; 0, N, $C_2F_5$, H, $CH_2CHF_2$], [DD405; 0, N, $C_3F_7$, H, $CH_2CHF_2$], [DD406; 0, N, $CH_2CF_3$, H, $CH_2CHF_2$], [DD407; 0, N, $CH_2CHF_2$, H, $CH_2CHF_2$], [DD408; 0, CH, H, H, $CH_2CHF_2$], [DD409; 0, CH, F, H, $CH_2CHF_2$], [DD410; 0, CH, Cl, H, $CH_2CHF_2$], [DD411; 0, CH, Br, H, $CH_2CHF_2$], [DD412; 0, CH, I, H, $CH_2CHF_2$], [DD413; 0, CH, $CF_3$, H, $CH_2CHF_2$], [DD414; 0, CH, $CF_2H$, H, $CH_2CHF_2$], [DD415; 0, CH, $C_2F_5$, H, $CH_2CHF_2$], [DD416; 0, CH, $C_3F_7$, H, $CH_2CHF_2$], [DD417; 0, CH, $CH_2CF_3$, H, $CH_2CHF_2$], [DD418; 0, CH, $CH_2CHF_2$, H, $CH_2CHF_2$], [DD419; 1, N, H, H, $CH_2CHF_2$], [DD420; 1, N, F, H, $CH_2CHF_2$], [DD421; 1, N, Cl, H, $CH_2CHF_2$], [DD422; 1, N, Br, H, $CH_2CHF_2$], [DD423; 1, N, I, H, $CH_2CHF_2$], [DD424; 1, N, $CF_3$, H, $CH_2CHF_2$], [DD425; 1, N, $CF_2H$, H, $CH_2CHF_2$], [DD426; 1, N, $C_2F_5$, H, $CH_2CHF_2$], [DD427; 1, N, $C_3F_7$, H, $CH_2CHF_2$], [DD428; 1, N, $CH_2CF_3$, H, $CH_2CHF_2$], [DD429; 1, N, $CH_2CHF_2$, H, $CH_2CHF_2$], [DD430; 1, CH, H, H, $CH_2CHF_2$], [DD431; 1, CH, F, H, $CH_2CHF_2$], [DD432; 1, CH, Cl, H, $CH_2CHF_2$], [DD433; 1, CH, Br, H, $CH_2CHF_2$], [DD434; 1, CH, I, H, $CH_2CHF_2$], [DD435; 1, CH, $CF_3$, H, $CH_2CHF_2$], [DD436; 1, CH, $CF_2H$, H, $CH_2CHF_2$], [DD437; 1, CH, $C_2F_5$, H, $CH_2CHF_2$], [DD438; 1, CH, $C_3F_7$, H, $CH_2CHF_2$], [DD439; 1, CH, $CH_2CF_3$, H, $CH_2CHF_2$], [DD440; 1, CH, $CH_2CHF_2$, H, $CH_2CHF_2$], [DD441; 2, N, H, H, $CH_2CHF_2$], [DD442; 2, N, F, H, $CH_2CHF_2$], [DD443; 2, N, Cl, H, $CH_2CHF_2$], [DD444; 2, N, Br, H, $CH_2CHF_2$], [DD445; 2, N, I, H, $CH_2CHF_2$], [DD446; 2, N, $CF_3$, H, $CH_2CHF_2$], [DD447; 2, N, $CF_2H$, H, $CH_2CHF_2$], [DD448; 2, N, $C_2F_5$, H, $CH_2CHF_2$], [DD449; 2, N, $C_3F_7$, H, $CH_2CHF_2$], [DD450; 2, N, $CH_2CF_3$, H, $CH_2CHF_2$], [DD451; 2, N, $CH_2CHF_2$, H, $CH_2CHF_2$], [DD452; 2, CH, H, H, $CH_2CHF_2$], [DD453; 2, CH, F, H, $CH_2CHF_2$], [DD454; 2, CH, Cl, H, $CH_2CHF_2$], [DD455; 2, CH, Br, H, $CH_2CHF_2$], [DD456; 2, CH, I, H, $CH_2CHF_2$], [DD457; 2, CH, $CF_3$, H, $CH_2CHF_2$], [DD458; 2, CH, $CF_2H$, H, $CH_2CHF_2$], [DD459; 2, CH, $C_2F_5$, H, $CH_2CHF_2$], [DD460; 2, CH, $C_3F_7$, H, $CH_2CHF_2$], [DD461; 2, CH, $CH_2CF_3$, H, $CH_2CHF_2$], [DD462; 2, CH, $CH_2CHF_2$, H, $CH_2CHF_2$], [DD463; 0, N, H, H, $CH_2CHF_2$], [DD464; 0, N, H, F, $CH_2CHF_2$], [DD465; 0, N, H, Cl, $CH_2CHF_2$], [DD466; 0, N, H, Br, $CH_2CHF_2$], [DD467; 0, N, H, I, $CH_2CHF_2$], [DD468; 0, N, H, $CF_3$, $CH_2CHF_2$], [DD469; 0, N, H, $CF_2H$, $CH_2CHF_2$], [DD470; 0, N, H, $C_2F_5$, $CH_2CHF_2$], [DD471; 0, N, H, $C_3F_7$, $CH_2CHF_2$], [DD472; 0, N, H, $CH_2CF_3$, $CH_2CHF_2$], [DD473; 0, N, H, $CH_2CHF_2$, $CH_2CHF_2$], [DD474; 0, CH, H, H, $CH_2CHF_2$], [DD475; 0, CH, H, F, $CH_2CHF_2$], [DD476; 0, CH, H, Cl, $CH_2CHF_2$], [DD477; 0, CH, H, Br, $CH_2CHF_2$], [DD478; 0, CH, H, I, $CH_2CHF_2$], [DD479; 0, CH, H, $CF_3$, $CH_2CHF_2$], [DD480; 0, CH, H, $CF_2H$, $CH_2CHF_2$], [DD481; 0, CH, H, $C_2F_5$, $CH_2CHF_2$], [DD482; 0, CH, H, $C_3F_7$, $CH_2CHF_2$], [DD483; 0, CH, H, $CH_2CF_3$, $CH_2CHF_2$], [DD484; 0, CH, H, $CH_2CHF_2$, $CH_2CHF_2$], [DD485; 1, N, H, H, $CH_2CHF_2$], [DD486; 1, N, H, F, $CH_2CHF_2$], [DD487; 1, N, H, Cl, $CH_2CHF_2$], [DD488; 1, N, H, Br, $CH_2CHF_2$], [DD489; 1, N, H, I, $CH_2CHF_2$], [DD490; 1, N, H, $CF_3$, $CH_2CHF_2$], [DD491; 1, N, H, $CF_2H$, $CH_2CHF_2$], [DD492; 1, N, H, $C_2F_5$, $CH_2CHF_2$], [DD493; 1, N, H, $C_3F_7$, $CH_2CHF_2$], [DD494; 1, N, H, $CH_2CF_3$, $CH_2CHF_2$], [DD495; 1, N, H, $CH_2CHF_2$, $CH_2CHF_2$], [DD496; 1, CH, H, H, $CH_2CHF_2$], [DD497; 1, CH, H, F, $CH_2CHF_2$], [DD498; 1, CH, H, Cl, $CH_2CHF_2$], [DD499; 1, CH, H, Br, $CH_2CHF_2$], [DD500; 1, CH, H, I, $CH_2CHF_2$], [DD501; 1, CH, H, $CF_3$, $CH_2CHF_2$], [DD502; 1, CH, H, $CF_2H$, $CH_2CHF_2$], [DD503; 1, CH, H, $C_2F_5$, $CH_2CHF_2$], [DD504; 1, CH, H, $C_3F_7$, $CH_2CHF_2$], [DD505; 1, CH, H, $CH_2CF_3$, $CH_2CHF_2$], [DD506; 1, CH, H, $CH_2CHF_2$, $CH_2CHF_2$], [DD507; 2, N, H, H, $CH_2CHF_2$], [DD508; 2, N, H, F, $CH_2CHF_2$], [DD509; 2, N, H, Cl, $CH_2CHF_2$], [DD510; 2, N, H, Br, $CH_2CHF_2$], [DD511; 2, N, H, I, $CH_2CHF_2$], [DD512; 2, N, H, $CF_3$, $CH_2CHF_2$], [DD513; 2, N, H, $CF_2H$, $CH_2CHF_2$], [DD514; 2, N, H, $C_2F_5$, $CH_2CHF_2$], [DD515; 2, N, H, $C_3F_7$, $CH_2CHF_2$], [DD516; 2, N, H, $CH_2CF_3$, $CH_2CHF_2$], [DD517; 2, N, H, $CH_2CHF_2$, $CH_2CHF_2$], [DD518; 2, CH, H, H, $CH_2CHF_2$], [DD519; 2, CH, H, F, $CH_2CHF_2$], [DD520; 2, CH, H, Cl, $CH_2CHF_2$], [DD521; 2, CH, H, Br, $CH_2CHF_2$], [DD522; 2, CH, H, I, $CH_2CHF_2$], [DD523; 2, CH, H, $CF_3$, $CH_2CHF_2$], [DD524; 2, CH, H, $CF_2H$, $CH_2CHF_2$], [DD525; 2, CH, H, $C_2F_5$, $CH_2CHF_2$], [DD526; 2, CH, H, $C_3F_7$, $CH_2CHF_2$], [DD527; 2, CH, H, $CH_2CF_3$, $CH_2CHF_2$], [DD528; 2, CH, H, $CH_2CHF_2$, $CH_2CHF_2$], [DD529; N, H, H, $SCF_3$], [DD530; 0, N, F, H, $SCF_3$], [DD531; 0, N, Cl, H, $SCF_3$], [DD532; 0, N, Br, H, $SCF_3$], [DD533; 0, N, I, H, $SCF_3$], [DD534; 0, N, $CF_3$, H, $SCF_3$], [DD535; 0, N, $CF_2H$, H, $SCF_3$], [DD536; 0, N, $C_2F_5$, H, $SCF_3$], [DD537; 0, N, $C_3F_7$, H, $SCF_3$], [DD538; 0, N, $CH_2CF_3$, H, $SCF_3$], [DD539; 0, N, $CH_2CHF_2$, H, $SCF_3$], [DD540; 0, CH, H, H, $SCF_3$], [DD541; 0, CH, F, H, $SCF_3$], [DD542; 0, CH, Cl, H, $SCF_3$], [DD543; 0, CH, Br, H, $SCF_3$], [DD544; 0, CH, I, H, $SCF_3$], [DD545; 0, CH, $CF_3$, H, $SCF_3$], [DD546; 0, CH, $CF_2H$, H, $SCF_3$], [DD547; 0, CH, $C_2F_5$, H, $SCF_3$], [DD548; 0, CH, $C_3F_7$, H, $SCF_3$], [DD549; 0, CH, $CH_2CF_3$, H, $SCF_3$], [DD550; 0, CH, $CH_2CHF_2$, H, $SCF_3$], [DD551; 1, N, H, H, $SCF_3$], [DD552; 1, N, F, H, $SCF_3$], [DD553; 1, N, Cl, H, $SCF_3$], [DD554; 1, N, Br, H, $SCF_3$], [DD555; 1, N, I, H, $SCF_3$], [DD556; 1, N, $CF_3$, H, $SCF_3$], [DD557; 1, N, $CF_2H$, H, $SCF_3$], [DD558; 1, N, $C_2F_5$, H, $SCF_3$], [DD559; 1, N, $C_3F_7$, H, $SCF_3$], [DD560; 1, N, $CH_2CF_3$, H, $SCF_3$], [DD561; 1, N, $CH_2CHF_2$, H, $SCF_3$], [DD562; 1, CH, H, H, $SCF_3$], [DD563; 1, CH, F, H, $SCF_3$], [DD564; 1, CH, Cl, H, $SCF_3$], [DD565; 1, CH, Br, H, $SCF_3$], [DD566; 1, CH, I, H, $SCF_3$], [DD567; 1, CH, $CF_3$, H, $SCF_3$], [DD568; 1, CH, $CF_2H$, H, $SCF_3$], [DD569; 1, CH, $C_2F_5$, H, $SCF_3$], [DD570; 1, CH, $C_3F_7$, H, $SCF_3$], [DD571; 1, CH, $CH_2CF_3$, H, $SCF_3$], [DD572; 1, CH, $CH_2CHF_2$, H, $SCF_3$], [DD573; 2, N, H, H, $SCF_3$], [DD574; 2, N, F, H, $SCF_3$], [DD575; 2, N, Cl, H, $SCF_3$], [DD576; 2, N, Br, H, $SCF_3$], [DD577; 2, N, I, H, $SCF_3$], [DD578; 2, N, $CF_3$, H, $SCF_3$], [DD579; 2, N, $CF_2H$, H, $SCF_3$], [DD580; 2, N, $C_2F_5$, H, $SCF_3$], [DD581; 2, N, $C_3F_7$, H, $SCF_3$], [DD582; 2, N, $CH_2CF_3$, H, $SCF_3$], [DD583; 2, N, $CH_2CHF_2$, H, $SCF_3$], [DD584; 2, CH, H, H, $SCF_3$], [DD585; 2, CH, F, H, $SCF_3$], [DD586; 2, CH, Cl, H, $SCF_3$], [DD587; 2, CH, Br, H, $SCF_3$], [DD588; 2, CH, I, H, $SCF_3$], [DD589; 2, CH, $CF_3$, H, $SCF_3$], [DD590; 2, CH, $CF_2H$, H, $SCF_3$], [DD591; 2, CH, $C_2F_5$, H, $SCF_3$], [DD592; 2, CH, $C_3F_7$, H, $SCF_3$], [DD593; 2, CH, $CH_2CF_3$, H, $SCF_3$], [DD594; 2, CH, $CH_2CHF_2$, H, $SCF_3$], [DD595; 0, N, H, H, $SCF_3$], [DD596; 0, N, H, F, $SCF_3$], [DD597; 0, N, H, Cl, $SCF_3$], [DD598; 0, N, H, Br, $SCF_3$], [DD599; 0, N, H, I, $SCF_3$], [DD600; 0, N, H, $CF_3$, $SCF_3$], [DD601; 0, N, H, $CF_2H$, $SCF_3$], [DD602; 0, N, H, $C_2F_5$, $SCF_3$], [DD603; 0, N, H, $C_3F_7$, $SCF_3$], [DD604; 0, N, H, $CH_2CF_3$, $SCF_3$], [DD605; 0, N, H, $CH_2CHF_2$, $SCF_3$], [DD606; 0, CH, H, H, $SCF_3$], [DD607; 0, CH, H, F, $SCF_3$], [DD608; 0, CH, H, Cl, $SCF_3$], [DD609; 0, CH, H, Br, $SCF_3$], [DD610; 0, CH, H, I, $SCF_3$], [DD611; 0, CH, H, $CF_3$, $SCF_3$], [DD612; 0, CH, H, $CF_2H$, $SCF_3$], [DD613; 0, CH, H, $C_2F_5$, $SCF_3$], [DD614; 0, CH, H, $C_3F_7$, $SCF_3$], [DD615; 0, CH, H, $CH_2CF_3$, $SCF_3$], [DD616; 0, CH, H, $CH_2CHF_2$, $SCF_3$], [DD617; 1, N, H, H, $SCF_3$], [DD618; 1, N, H, F, $SCF_3$], [DD619; 1, N, H, Cl, $SCF_3$], [DD620; 1, N, H, Br, $SCF_3$], [DD621; 1, N, H, I, $SCF_3$], [DD622; 1, N, H, $CF_3$, $SCF_3$], [DD623; 1, N, H, $CF_2H$, $SCF_3$], [DD624; 1, N, H, $C_2F_5$, $SCF_3$], [DD625; 1, N, H, $C_3F_7$, $SCF_3$], [DD626; 1, N, H, $CH_2CF_3$, $SCF_3$], [DD627; 1, N, H, $CH_2CHF_2$, $SCF_3$], [DD628; 1, CH, H, H, $SCF_3$], [DD629; 1, CH, H, F, $SCF_3$], [DD630; 1, CH, H, Cl, $SCF_3$], [DD631; 1, CH, H, Br, $SCF_3$], [DD632; 1, CH, H, I, $SCF_3$], [DD633; 1, CH, H, $CF_3$, $SCF_3$], [DD634; 1, CH, H, $CF_2H$, $SCF_3$], [DD635; 1, CH, H, $C_2F_5$, $SCF_3$], [DD636; 1, CH, H, $C_3F_7$, $SCF_3$], [DD637; 1, CH, H, $CH_2CF_3$, $SCF_3$], [DD638; 1, CH, H, $CH_2CHF_2$, $SCF_3$], [DD639; 2, N, H, H, $SCF_3$], [DD640; 2, N, H, F, $SCF_3$], [DD641; 2, N, H, Cl, $SCF_3$], [DD642; 2, N, H, Br, $SCF_3$], [DD643; 2, N, H, I, $SCF_3$], [DD644; 2, N, H, $CF_3$, $SCF_3$], [DD645; 2, N, H, $CF_2H$, $SCF_3$], [DD646; 2, N, H, $C_2F_5$, $SCF_3$], [DD647; 2, N, H, $C_3F_7$, $SCF_3$], [DD648; 2, N, H, $CH_2CF_3$, $SCF_3$], [DD649; 2, N, H, $CH_2CHF_2$, $SCF_3$], [DD650; 2, CH, H, H, $SCF_3$], [DD651; 2, CH, H, F, $SCF_3$], [DD652; 2, CH, H, Cl, $SCF_3$], [DD653; 2, CH, H, Br, $SCF_3$], [DD654; 2, CH, H, I, $SCF_3$], [DD655; 2, CH, H, $CF_3$, $SCF_3$], [DD656; 2, CH, H, $CF_2H$, $SCF_3$], [DD657; 2, CH, H, $C_2F_5$, $SCF_3$], [DD658; 2, CH, H, $C_3F_7$, $SCF_3$], [DD659; 2, CH, H, $CH_2CF_3$, $SCF_3$], [DD660; 2, CH, H, $CH_2CHF_2$, $SCF_3$], [DD661; N, H, H, $OCF_3$], [DD662; 0, N, F, H, $OCF_3$], [DD663; 0, N, Cl, H, $OCF_3$], [DD664; 0, N, Br, H, $OCF_3$], [DD665; 0, N, I, H, $OCF_3$], [DD666; 0, N, $CF_3$, H, $OCF_3$], [DD667; 0, N, $CF_2H$, H, $OCF_3$], [DD668; 0, N, $C_2F_5$, H, $OCF_3$], [DD669; 0, N, $C_3F_7$, H, $OCF_3$], [DD670; 0, N, $CH_2CF_3$, H, $OCF_3$], [DD671; 0, N, $CH_2CHF_2$, H, $OCF_3$], [DD672; 0, CH, H, H, $OCF_3$], [DD673; 0, CH, F, H, $OCF_3$], [DD674; 0, CH, Cl, H, $OCF_3$], [DD675; 0, CH, Br, H, $OCF_3$], [DD676; 0, CH, I, H, $OCF_3$], [DD677; 0, CH, $CF_3$, H, $OCF_3$], [DD678; 0, CH, $CF_2H$, H, $OCF_3$], [DD679; 0, CH, $C_2F_5$, H, $OCF_3$], [DD680; 0, CH, $C_3F_7$, H, $OCF_3$], [DD681; 0, CH, $CH_2CF_3$, H, $OCF_3$], [DD682; 0, CH, $CH_2CHF_2$, H, $OCF_3$], [DD683; 1, N, H, H, $OCF_3$], [DD684; 1, N, F, H, $OCF_3$], [DD685; 1, N, Cl, H, $OCF_3$], [DD686; 1, N, Br, H, $OCF_3$], [DD687; 1, N, I, H, $OCF_3$], [DD688; 1, N, $CF_3$, H, $OCF_3$], [DD689; 1, N, $CF_2H$, H, $OCF_3$], [DD690; 1, N, $C_2F_5$, H, $OCF_3$], [DD691; 1, N, $C_3F_7$, H, $OCF_3$], [DD692; 1, N, $CH_2CF_3$, H, $OCF_3$], [DD693; 1, N, $CH_7CHF_2$, H, $OCF_3$], [DD694; 1, CH, H, H, $OCF_3$], [DD695; 1, CH, F, H, $OCF_3$], [DD696; 1, CH, Cl, H, $OCF_3$], [DD697; 1, CH, Br, H, $OCF_3$], [DD698; 1, CH, I, H, $OCF_3$], [DD699; 1, CH, $CF_3$, H, $OCF_3$], [DD700; 1, CH, $CF_2H$, H, $OCF_3$], [DD701; 1, CH, $C_2F_5$, H, $OCF_3$], [DD702; 1, CH, $C_3F_7$, H, $OCF_3$], [DD703; 1, CH, $CH_2CF_3$, H, $OCF_3$],

[DD704; 1, CH, $CH_2CHF_2$, H, $OCF_3$], [DD705; 2, N, H, H, $OCF_3$], [DD706; 2, N, F, H, $OCF_3$], [DD707; 2, N, Cl, H, $OCF_3$], [DD708; 2, N, Br, H, $OCF_3$], [DD709; 2, N, I, H, $OCF_3$], [DD710; 2, N, $CF_3$, H, $OCF_3$], [DD711; 2, N, $CF_2H$, H, $OCF_3$], [DD712; 2, N, $C_2F_5$, H, $OCF_3$], [DD713; 2, N, $C_3F_7$, H, $OCF_3$], [DD714; 2, N, $CH_2CF_3$, H, $OCF_3$], [DD715; 2, N, $CH_2CHF_2$, H, $OCF_3$], [DD716; 2, CH, H, H, $OCF_3$], [DD717; 2, CH, F, H, $OCF_3$], [DD718; 2, CH, Cl, H, $OCF_3$], [DD719; 2, CH, Br, H, $OCF_3$], [DD720; 2, CH, I, H, $OCF_3$], [DD721; 2, CH, $CF_3$, H, $OCF_3$], [DD722; 2, CH, $CF_2H$, H, $OCF_3$], [DD723; 2, CH, $C_2F_5$, H, $OCF_3$], [DD724; 2, CH, $C_3F_7$, H, $OCF_3$], [DD725; 2, CH, $CH_2CF_3$, H, $OCF_3$], [DD726; 2, CH, $CH_2CHF_2$, H, $OCF_3$], [DD727; 0, N, H, H, $OCF_3$], [DD728; 0, N, H, F, $OCF_3$], [DD729; 0, N, H, Cl, $OCF_3$], [DD730; 0, N, H, Br, $OCF_3$], [DD731; 0, N, H, I, $OCF_3$], [DD732; 0, N, H, $CF_3$, $OCF_3$], [DD733; 0, N, H, $CF_2H$, $OCF_3$], [DD734; 0, N, H, $C_2F_5$, $OCF_3$], [DD735; 0, N, H, $C_3F_7$, $OCF_3$], [DD736; 0, N, H, $CH_2CF_3$, $OCF_3$], [DD737; 0, N, H, $CH_2CHF_2$, $OCF_3$], [DD738; 0, CH, H, H, $OCF_3$], [DD739; 0, CH, H, F, $OCF_3$], [DD740; 0, CH, H, Cl, $OCF_3$], [DD741; 0, CH, H, Br, $OCF_3$], [DD742; 0, CH, H, I, $OCF_3$], [DD743; 0, CH, H, $CF_3$, $OCF_3$], [DD744; 0, CH, H, $CF_2H$, $OCF_3$], [DD745; 0, CH, H, $C_2F_5$, $OCF_3$], [DD746; 0, CH, H, $C_3F_7$, $OCF_3$], [DD747; 0, CH, H, $CH_2CF_3$, $OCF_3$], [DD748; 0, CH, H, $CH_2CHF_2$, $OCF_3$], [DD749; 1, N, H, H, $OCF_3$], [DD750; 1, N, H, F, $OCF_3$], [DD751; 1, N, H, Cl, $OCF_3$], [DD752; 1, N, H, Br, $OCF_3$], [DD753; 1, N, H, I, $OCF_3$], [DD754; 1, N, H, $CF_3$, $OCF_3$], [DD755; 1, N, H, $CF_2H$, $OCF_3$], [DD756; 1, N, H, $C_2F_5$, $OCF_3$], [DD757; 1, N, H, $C_3F_7$, $OCF_3$], [DD758; 1, N, H, $CH_2CF_3$, $OCF_3$], [DD759; 1, N, H, $CH_2CHF_2$, $OCF_3$], [DD760; 1, CH, H, H, $OCF_3$], [DD761; 1, CH, H, F, $OCF_3$], [DD762; 1, CH, H, Cl, $OCF_3$], [DD763; 1, CH, H, Br, $OCF_3$], [DD764; 1, CH, H, I, $OCF_3$], [DD765; 1, CH, H, $CF_3$, $OCF_3$], [DD766; 1, CH, H, $CF_2H$, $OCF_3$], [DD767; 1, CH, H, $C_2F_5$, $OCF_3$], [DD768; 1, CH, H, $C_3F_7$, $OCF_3$], [DD769; 1, CH, H, $CH_2CF_3$, $OCF_3$], [DD770; 1, CH, H, $CH_2CHF_2$, $OCF_3$], [DD771; 2, N, H, H, $OCF_3$], [DD772; 2, N, H, F, $OCF_3$], [DD773; 2, N, H, Cl, $OCF_3$], [DD774; 2, N, H, Br, $OCF_3$], [DD775; 2, N, H, I, $OCF_3$], [DD776; 2, N, H, $CF_3$, $OCF_3$], [DD777; 2, N, H, $CF_2H$, $OCF_3$], [DD778; 2, N, H, $C_2F_5$, $OCF_3$], [DD779; 2, N, H, $C_3F_7$, $OCF_3$], [DD780; 2, N, H, $CH_2CF_3$, $OCF_3$], [DD781; 2, N, H, $CH_2CHF_2$, $OCF_3$], [DD782; 2, CH, H, H, $OCF_3$], [DD783; 2, CH, H, F, $OCF_3$], [DD784; 2, CH, H, Cl, $OCF_3$], [DD785; 2, CH, H, Br, $OCF_3$], [DD786; 2, CH, H, I, $OCF_3$], [DD787; 2, CH, H, $CF_3$, $OCF_3$], [DD788; 2, CH, H, $CF_2H$, $OCF_3$], [DD789; 2, CH, H, $C_2F_5$, $OCF_3$], [DD790; 2, CH, H, $C_3F_7$, $OCF_3$], [DD791; 2, CH, H, $CH_2CF_3$, $OCF_3$], [DD792; 2, CH, H, $CH_2CHF_2$, $OCF_3$], [DD793; N, H, H, $OCHF_2$], [DD794; 0, N, F, H, $OCHF_2$], [DD795; 0, N, Cl, H, $OCHF_2$], [DD796; 0, N, Br, H, $OCHF_2$], [DD797; 0, N, I, H, $OCHF_2$], [DD798; 0, N, $CF_3$, H, $OCHF_2$], [DD799; 0, N, $CF_2H$, H, $OCHF_2$], [DD800; 0, N, $C_2F_5$, H, $OCHF_2$], [DD801; 0, N, $C_3F_7$, H, $OCHF_2$], [DD802; 0, N, $CH_2CF_3$, H, $OCHF_2$], [DD803; 0, N, $CH_2CHF_2$, H, $OCHF_2$], [DD804; 0, CH, H, H, $OCHF_2$], [DD805; 0, CH, F, H, $OCHF_2$], [DD806; 0, CH, Cl, H, $OCHF_2$], [DD807; 0, CH, Br, H, $OCHF_2$], [DD808; 0, CH, I, H, $OCHF_2$], [DD809; 0, CH, $CF_3$, H, $OCHF_2$], [DD810; 0, CH, $CF_2H$, H, $OCHF_2$], [DD811; 0, CH, $C_2F_5$, H, $OCHF_2$], [DD812; 0, CH, $C_3F_7$, H, $OCHF_2$], [DD813; 0, CH, $CH_2CF_3$, H, $OCHF_2$], [DD814; 0, CH, $CH_2CHF_2$, H, $OCHF_2$], [DD815; 1, N, H, H, $OCHF_2$], [DD816; 1, N, F, H, $OCHF_2$], [DD817; 1, N, Cl, H, $OCHF_2$], [DD818; 1, N, Br, H, $OCHF_2$], [DD819; 1, N, I, H, $OCHF_2$], [DD820; 1, N, $CF_3$, H, $OCHF_2$], [DD821; 1, N, $CF_2H$, H, $OCHF_2$], [DD822; 1, N, $C_2F_5$, H, $OCHF_2$], [DD823; 1, N, $C_3F_7$, H, $OCHF_2$], [DD824; 1, N, $CH_2CF_3$, H, $OCHF_2$], [DD825; 1, N, $CH_2CHF_2$, H, $OCHF_2$], [DD826; 1, CH, H, H, $OCHF_2$], [DD827; 1, CH, F, H, $OCHF_2$], [DD828; 1, CH, Cl, H, $OCHF_2$], [DD829; 1, CH, Br, H, $OCHF_2$], [DD830; 1, CH, I, H, $OCHF_2$], [DD831; 1, CH, $CF_3$, H, $OCHF_2$], [DD832; 1, CH, $CF_2H$, H, $OCHF_2$], [DD833; 1, CH, $C_2F_5$, H, $OCHF_2$], [DD834; 1, CH, $C_3F_7$, H, $OCHF_2$], [DD835; 1, CH, $CH_2CF_3$, H, $OCHF_2$], [DD836; 1, CH, $CH_2CHF_2$, H, $OCHF_2$], [DD837; 2, N, H, H, $OCHF_2$], [DD838; 2, N, F, H, $OCHF_2$], [DD839; 2, N, Cl, H, $OCHF_2$], [DD840; 2, N, Br, H, $OCHF_2$], [DD841; 2, N, I, H, $OCHF_2$], [DD842; 2, N, $CF_3$, H, $OCHF_2$], [DD843; 2, N, $CF_2H$, H, $OCHF_2$], [DD844; 2, N, $C_2F_5$, H, $OCHF_2$], [DD845; 2, N, $C_3F_7$, H, $OCHF_2$], [DD846; 2, N, $CH_2CF_3$, H, $OCHF_2$], [DD847; 2, N, $CH_2CHF_2$, H, $OCHF_2$], [DD848; 2, CH, H, H, $OCHF_2$], [DD849; 2, CH, F, H, $OCHF_2$], [DD850; 2, CH, Cl, H, $OCHF_2$], [DD851; 2, CH, Br, H, $OCHF_2$], [DD852; 2, CH, I, H, $OCHF_2$], [DD853; 2, CH, $CF_3$, H, $OCHF_2$], [DD854; 2, CH, $CF_2H$, H, $OCHF_2$], [DD855; 2, CH, $C_2F_5$, H, $OCHF_2$], [DD856; 2, CH, $C_3F_7$, H, $OCHF_2$], [DD857; 2, CH, $CH_2CF_3$, H, $OCHF_2$], [DD858; 2, CH, $CH_2CHF_2$, H, $OCHF_2$], [DD859; 0, N, H, H, $OCHF_2$], [DD860; 0, N, H, F, $OCHF_2$], [DD861; 0, N, H, Cl, $OCHF_2$], [DD862; 0, N, H, Br, $OCHF_2$], [DD863; 0, N, H, I, $OCHF_2$], [DD864; 0, N, H, $CF_3$, $OCHF_2$], [DD865; 0, N, H, $CF_2H$, $OCHF_2$], [DD866; 0, N, H, $C_2F_5$, $OCHF_2$], [DD867; 0, N, H, $C_3F_7$, $OCHF_2$], [DD868; 0, N, H, $CH_2CF_3$, $OCHF_2$], [DD869; 0, N, H, $CH_2CHF_2$, $OCHF_2$], [DD870; 0, CH, H, H, $OCHF_2$], [DD871; 0, CH, H, F, $OCHF_2$], [DD872; 0, CH, H, Cl, $OCHF_2$], [DD873; 0, CH, H, Br, $OCHF_2$], [DD874; 0, CH, H, I, $OCHF_2$], [DD875; 0, CH, H, $CF_3$, $OCHF_2$], [DD876; 0, CH, H, $CF_2H$, $OCHF_2$], [DD877; 0, CH, H, $C_2F_5$, $OCHF_2$], [DD878; 0, CH, H, $C_3F_7$, $OCHF_2$], [DD879; 0, CH, H, $CH_2CF_3$, $OCHF_2$], [DD880; 0, CH, H, $CH_2CHF_2$, $OCHF_2$], [DD881; 1, N, H, H, $OCHF_2$], [DD882; 1, N, H, F, $OCHF_2$], [DD883; 1, N, H, Cl, $OCHF_2$], [DD884; 1, N, H, Br, $OCHF_2$], [DD885; 1, N, H, I, $OCHF_2$], [DD886; 1, N, H, $CF_3$, $OCHF_2$], [DD887; 1, N, H, $CF_2H$, $OCHF_2$], [DD888; 1, N, H, $C_2F_5$, $OCHF_2$], [DD889; 1, N, H, $C_3F_7$, $OCHF_2$], [DD890; 1, N, H, $CH_2CF_3$, $OCHF_2$], [DD891; 1, N, H, $CH_2CHF_2$, $OCHF_2$], [DD892; 1, CH, H, H, $OCHF_2$], [DD893; 1, CH, H, F, $OCHF_2$], [DD894; 1, CH, H, Cl, $OCHF_2$], [DD895; 1, CH, H, Br, $OCHF_2$], [DD896; 1, CH, H, I, $OCHF_2$], [DD897; 1, CH, H, $CF_3$, $OCHF_2$], [DD898; 1, CH, H, $CF_2H$, $OCHF_2$], [DD899; 1, CH, H, $C_2F_5$, $OCHF_2$], [DD900; 1, CH, H, $C_3F_7$, $OCHF_2$], [DD901; 1, CH, H, $CH_2CF_3$, $OCHF_2$], [DD902; 1, CH, H, $CH_2CHF_2$, $OCHF_2$], [DD903; 2, N, H, H, $OCHF_2$], [DD904; 2, N, H, F, $OCHF_2$], [DD905; 2, N, H, Cl, $OCHF_2$], [DD906; 2, N, H, Br, $OCHF_2$], [DD907; 2, N, H, I, $OCHF_2$], [DD908; 2, N, H, $CF_3$, $OCHF_2$], [DD909; 2, N, H, $CF_2H$, $OCHF_2$], [DD910; 2, N, H, $C_2F_5$, $OCHF_2$], [DD911; 2, N, H, $C_3F_7$, $OCHF_2$], [DD912; 2, N, H, $CH_2CF_3$, $OCHF_2$], [DD913; 2, N, H, $CH_2CHF_2$, $OCHF_2$], [DD914; 2, CH, H, H, $OCHF_2$], [DD915; 2, CH, H, F, $OCHF_2$], [DD916; 2, CH, H, Cl, $OCHF_2$], [DD917; 2, CH, H, Br, $OCHF_2$], [DD918; 2, CH, H, I, $OCHF_2$], [DD919; 2, CH, H, $CF_3$, $OCHF_2$], [DD920; 2, CH, H, $CF_2H$, $OCHF_2$], [DD921; 2, CH, H, $C_2F_5$, $OCHF_2$], [DD922; 2, CH, H, $C_3F_7$, $OCHF_2$], [DD923; 2, CH, H, $CH_2CF_3$, $OCHF_2$], [DD924; 2, CH, H, $CH_2CHF_2$, $OCHF_2$], [DD925; N, H, H, Br], [DD926; 0, N, F, H, Br], [DD927; 0, N, Cl, H, Br], [DD928; 0, N, Br, H, Br], [DD929; 0, N, I, H, Br], [DD930; 0, N, $CF_3$, H, Br], [DD931; 0, N, $CF_2H$, H, Br], [DD932; 0, N, $C_2F_5$, H, Br], [DD933; 0, N, $C_3F_7$, H, Br], [DD934; 0, N, $CH_2CF_3$, H, Br], [DD935; 0, N, $CH_2CHF_2$, H, Br], [DD936; 0, CH, H, H, Br], [DD937; 0, CH, F, H, Br], [DD938; 0, CH, Cl, H, Br], [DD939; 0, CH, Br, H, Br], [DD940; 0, CH, I, H, Br],

[DD941; 0, CH, $CF_3$, H, Br], [DD942; 0, CH, $CF_2H$, H, Br], [DD943; 0, CH, $C_2F_5$, H, Br], [DD944; 0, CH, $C_3F_7$, H, Br], [DD945; 0, CH, $CH_2CF_3$, H, Br], [DD946; 0, CH, $CH_2CHF_2$, H, Br], [DD947; 1, N, H, H, Br], [DD948; 1, N, F, H, Br], [DD949; 1, N, Cl, H, Br], [DD950; 1, N, Br, H, Br], [DD951; 1, N, I, H, Br], [DD952; 1, N, $CF_3$, H, Br], [DD953; 1, N, $CF_2H$, H, Br], [DD954; 1, N, $C_2F_5$, H, Br], [DD955; 1, N, $C_3F_7$, H, Br], [DD956; 1, N, $CH_2CF_3$, H, Br], [DD957; 1, N, $CH_2CHF_2$, H, Br], [DD958; 1, CH, H, H, Br], [DD959; 1, CH, F, H, Br], [DD960; 1, CH, Cl, H, Br], [DD961; 1, CH, Br, H, Br], [DD962; 1, CH, I, H, Br], [DD963; 1, CH, $CF_3$, H, Br], [DD964; 1, CH, $CF_2H$, H, Br], [DD965; 1, CH, $C_2F_5$, H, Br], [DD966; 1, CH, $C_3F_7$, H, Br], [DD967; 1, CH, $CH_2CF_3$, H, Br], [DD968; 1, CH, $CH_2CHF_2$, H, Br], [DD969; 2, N, H, H, Br], [DD970; 2, N, F, H, Br], [DD971; 2, N, Cl, H, Br], [DD972; 2, N, Br, H, Br], [DD973; 2, N, I, H, Br], [DD974; 2, N, $CF_3$, H, Br], [DD975; 2, N, $CF_2H$, H, Br], [DD976; 2, N, $C_2F_5$, H, Br], [DD977; 2, N, $C_3F_7$, H, Br], [DD978; 2, N, $CH_2CF_3$, H, Br], [DD979; 2, N, $CH_2CHF_2$, H, Br], [DD980; 2, CH, H, H, Br], [DD981; 2, CH, F, H, Br], [DD982; 2, CH, Cl, H, Br], [DD983; 2, CH, Br, H, Br], [DD984; 2, CH, I, H, Br], [DD985; 2, CH, $CF_3$, H, Br], [DD986; 2, CH, $CF_2H$, H, Br], [DD987; 2, CH, $C_2F$, H, Br], [DD988; 2, CH, $C_3F_7$, H, Br], [DD989; 2, CH, $CH_2CF_3$, H, Br], [DD990; 2, CH, $CH_2CHF_2$, H, Br], [DD991; 0, N, H, H, Br], [DD992; 0, N, H, F, Br], [DD993; 0, N, H, Cl, Br], [DD994; 0, N, H, Br, Br], [DD995; 0, N, H, I, Br], [DD996; 0, N, H, $CF_3$, Br], [DD997; 0, N, H, $CF_2H$, Br], [DD998; 0, N, H, $C_2F_5$, Br], [DD999; 0, N, H, $C_3F_7$, Br], [DD1000; 0, N, H, $CH_2CF_3$, Br], [DD1001; 0, N, H, $CH_2CHF_2$, Br], [DD1002; 0, CH, H, H, Br], [DD1003; 0, CH, H, F, Br], [DD1004; 0, CH, H, Cl, Br], [DD1005; 0, CH, H, Br, Br], [DD1006; 0, CH, H, I, Br], [DD1007; 0, CH, H, $CF_3$, Br], [DD1008; 0, CH, H, $CF_2H$, Br], [DD1009; 0, CH, H, $C_2F_5$, Br], [DD1010; 0, CH, H, $C_3F_7$, Br], [DD1011; 0, CH, H, $CH_2CF_3$, Br], [DD1012; 0, CH, H, $CH_2CHF_2$, Br], [DD1013; 1, N, H, H, Br], [DD1014; 1, N, H, F, Br], [DD1015; 1, N, H, Cl, Br], [DD1016; 1, N, H, Br, Br], [DD1017; 1, N, H, I, Br], [DD1018; 1, N, H, $CF_3$, Br], [DD1019; 1, N, H, $CF_2H$, Br], [DD1020; 1, N, H, $C_2F_5$, Br], [DD1021; 1, N, H, $C_3F_7$, Br], [DD1022; 1, N, H, $CH_2CF_3$, Br], [DD1023; 1, N, H, $CH_2CHF_2$, Br], [DD1024; 1, CH, H, H, Br], [DD1025; 1, CH, H, F, Br], [DD1026; 1, CH, H, Cl, Br], [DD1027; 1, CH, H, Br, Br], [DD1028; 1, CH, H, I, Br], [DD1029; 1, CH, H, $CF_3$, Br], [DD1030; 1, CH, H, $CF_2H$, Br], [DD1031; 1, CH, H, $C_2F_5$, Br], [DD1032; 1, CH, H, $C_3F_7$, Br], [DD1033; 1, CH, H, $CH_2CF_3$, Br], [DD1034; 1, CH, H, $CH_2CHF_2$, Br], [DD1035; 2, N, H, H, Br], [DD1036; 2, N, H, F, Br], [DD1037; 2, N, H, Cl, Br], [DD1038; 2, N, H, Br, Br], [DD1039; 2, N, H, I, Br], [DD1040; 2, N, H, $CF_3$, Br], [DD1041; 2, N, H, $CF_2H$, Br], [DD1042; 2, N, H, $C_2F_5$, Br], [DD1043; 2, N, H, $C_3F_7$, Br], [DD1044; 2, N, H, $CH_2CF_3$, Br], [DD1045; 2, N, H, $CH_2CHF_2$, Br], [DD1046; 2, CH, H, H, Br], [DD1047; 2, CH, H, F, Br], [DD1048; 2, CH, H, Cl, Br], [DD1049; 2, CH, H, Br, Br], [DD1050; 2, CH, H, I, Br], [DD1051; 2, CH, H, $CF_3$, Br], [DD1052; 2, CH, H, $CF_2H$, Br], [DD1053; 2, CH, H, $C_2F$, Br], [DD1054; 2, CH, H, $C_3F_7$, Br], [DD1055; 2, CH, H, $CH_2CF_3$, Br], [DD1056; 2, CH, H, $CH_2CHF_2$, Br], [DD1057; N, H, H, Cl], [DD1058; 0, N, F, H, Cl], [DD1059; 0, N, Cl, H, Cl], [DD1060; 0, N, Br, H, Cl], [DD1061; 0, N, I, H, Cl], [DD1062; 0, N, $CF_3$, H, Cl], [DD1063; 0, N, $CF_2H$, H, Cl], [DD1064; 0, N, $C_2F_5$, H, Cl], [DD1065; 0, N, $C_3F_7$, H, Cl], [DD1066; 0, N, $CH_2CF_3$, H, Cl], [DD1067; 0, N, $CH_2CHF_2$, H, Cl], [DD1068; 0, CH, H, H, Cl], [DD1069; 0, CH, F, H, Cl], [DD1070; 0, CH, Cl, H, Cl], [DD1071; 0, CH, Br, H, Cl], [DD1072; 0, CH, I, H, Cl], [DD1073; 0, CH, $CF_3$, H, Cl], [DD1074; 0, CH, $CF_2H$, H, Cl], [DD1075; 0, CH, $C_2F_5$, H, Cl], [DD1076; 0, CH, $C_3F_7$, H, Cl], [DD1077; 0, CH, $CH_2CF_3$, H, Cl], [DD1078; 0, CH, $CH_2CHF_2$, H, Cl], [DD1079; 1, N, H, H, Cl], [DD1080; 1, N, F, H, Cl], [DD1081; 1, N, Cl, H, Cl], [DD1082; 1, N, Br, H, Cl], [DD1083; 1, N, I, H, Cl], [DD1084; 1, N, $CF_3$, H, Cl], [DD1085; 1, N, $CF_2H$, H, Cl], [DD1086; 1, N, $C_2F_5$, H, Cl], [DD1087; 1, N, $C_3F_7$, H, Cl], [DD1088; 1, N, $CH_2CF_3$, H, Cl], [DD1089; 1, N, $CH_2CHF_2$, H, Cl], [DD1090; 1, CH, H, H, Cl], [DD1091; 1, CH, F, H, Cl], [DD1092; 1, CH, Cl, H, Cl], [DD1093; 1, CH, Br, H, Cl], [DD1094; 1, CH, I, H, Cl], [DD1095; 1, CH, $CF_3$, H, Cl], [DD1096; 1, CH, $CF_2H$, H, Cl], [DD1097; 1, CH, $C_2F_5$, H, Cl], [DD1098; 1, CH, $C_3F_7$, H, Cl], [DD1099; 1, CH, $CH_2CF_3$, H, Cl], [DD1100; 1, CH, $CH_2CHF_2$, H, Cl], [DD1101; 2, N, H, H, Cl], [DD1102; 2, N, F, H, Cl], [DD1103; 2, N, Cl, H, Cl], [DD1104; 2, N, Br, H, Cl], [DD1105; 2, N, I, H, Cl], [DD1106; 2, N, $CF_3$, H, Cl], [DD1107; 2, N, $CF_2H$, H, Cl], [DD1108; 2, N, $C_2F_5$, H, Cl], [DD1109; 2, N, $C_3F_7$, H, Cl], [DD1110; 2, N, $CH_2CF_3$, H, Cl], [DD1111; 2, N, $CH_2CHF_2$, H, Cl], [DD1112; 2, CH, H, H, Cl], [DD1113; 2, CH, F, H, Cl], [DD1114; 2, CH, Cl, H, Cl], [DD1115; 2, CH, Br, H, Cl], [DD1116; 2, CH, I, H, Cl], [DD1117; 2, CH, $CF_3$, H, Cl], [DD1118; 2, CH, $CF_2H$, H, Cl], [DD1119; 2, CH, $C_2F_5$, H, Cl], [DD1120; 2, CH, $C_3F_7$, H, Cl], [DD1121; 2, CH, $CH_2CF_3$, H, Cl], [DD1122; 2, CH, $CH_2CHF_2$, H, Cl], [DD1123; 0, N, H, H, Cl], [DD1124; 0, N, H, F, Cl], [DD1125; 0, N, H, Cl, Cl], [DD1126; 0, N, H, Br, Cl], [DD1127; 0, N, H, I, Cl], [DD1128; 0, N, H, $CF_3$, Cl], [DD1129; 0, N, H, $CF_2H$, Cl], [DD1130; 0, N, H, $C_2F_5$, Cl], [DD1131; 0, N, H, $C_3F_7$, Cl], [DD1132; 0, N, H, $CH_2CF_3$, Cl], [DD1133; 0, N, H, $CH_2CHF_2$, Cl], [DD1134; 0, CH, H, H, Cl], [DD1135; 0, CH, H, F, Cl], [DD1136; 0, CH, H, Cl, Cl], [DD1137; 0, CH, H, Br, Cl], [DD1138; 0, CH, H, I, Cl], [DD1139; 0, CH, H, $CF_3$, Cl], [DD1140; 0, CH, H, $CF_2H$, Cl], [DD1141; 0, CH, H, $C_2F_5$, Cl], [DD1142; 0, CH, H, $C_3F_7$, Cl], [DD1143; 0, CH, H, $CH_2CF_3$, Cl], [DD1144; 0, CH, H, $CH_2CHF_2$, Cl], [DD1145; 1, N, H, H, Cl], [DD1146; 1, N, H, F, Cl], [DD1147; 1, N, H, Cl, Cl], [DD1148; 1, N, H, Br, Cl], [DD1149; 1, N, H, I, Cl], [DD1150; 1, N, H, $CF_3$, Cl], [DD1151; 1, N, H, $CF_2H$, Cl], [DD1152; 1, N, H, $C_2F_5$, Cl], [DD1153; 1, N, H, $C_3F_7$, Cl], [DD1154; 1, N, H, $CH_2CF_3$, Cl], [DD1155; 1, N, H, $CH_2CHF_2$, Cl], [DD1156; 1, CH, H, H, Cl], [DD1157; 1, CH, H, F, Cl], [DD1158; 1, CH, H, Cl, Cl], [DD1159; 1, CH, H, Br, Cl], [DD1160; 1, CH, H, I, Cl], [DD1161; 1, CH, H, $CF_3$, Cl], [DD1162; 1, CH, H, $CF_2H$, Cl], [DD1163; 1, CH, H, $C_2F_5$, Cl], [DD1164; 1, CH, H, $C_3F_7$, Cl], [DD1165; 1, CH, H, $CH_2CF_3$, Cl], [DD1166; 1, CH, H, $CH_2CHF_2$, Cl], [DD1167; 2, N, H, H, Cl], [DD1168; 2, N, H, F, Cl], [DD1169; 2, N, H, Cl, Cl], [DD1170; 2, N, H, Br, Cl], [DD1171; 2, N, H, I, Cl], [DD1172; 2, N, H, $CF_3$, Cl], [DD1173; 2, N, H, $CF_2H$, Cl], [DD1174; 2, N, H, $C_2F_5$, Cl], [DD1175; 2, N, H, $C_3F_7$, Cl], [DD1176; 2, N, H, $CH_2CF_3$, Cl], [DD1177; 2, N, H, $CH_2CHF_2$, Cl], [DD1178; 2, CH, H, H, Cl], [DD1179; 2, CH, H, F, Cl], [DD1180; 2, CH, H, Cl, Cl], [DD1181; 2, CH, H, Br, Cl], [DD1182; 2, CH, H, I, Cl], [DD1183; 2, CH, H, $CF_3$, Cl], [DD1184; 2, CH, H, $CF_2H$, Cl], [DD1185; 2, CH, H, $C_2F_5$, Cl], [DD1186; 2, CH, H, $C_3F_7$, Cl], [DD1187; 2, CH, H, $CH_2CF_3$, Cl], [DD1188; 2, CH, H, $CH_2CHF_2$, Cl], [DD1189; N, H, H, I], [DD1190; 0, N, F, H, I], [DD1191; 0, N, Cl, H, I], [DD1192; 0, N, Br, H, I], [DD1193; 0, N, I, H, I], [DD1194; 0, N, $CF_3$, H, I], [DD1195; 0, N, $CF_2H$, H, I], [DD1196; 0, N, $C_2F_5$, H, I], [DD1197; 0, N, $C_3F_7$, H, I], [DD1198; 0, N, $CH_2CF_3$, H, I], [DD1199; 0, N, $CH_2CHF_2$, H, I], [DD1200; 0, CH, H, H, I], [DD1201; 0, CH, F, H, I], [DD1202; 0, CH, Cl, H, I],

[DD1203; 0, CH, Br, H, I], [DD1204; 0, CH, I, H, I], [DD1205; 0, CH, $CF_3$, H, I], [DD1206; 0, CH, $CF_2H$, H, I], [DD1207; 0, CH, $C_2F_5$, H, I], [DD1208; 0, CH, $C_3F_7$, H, I], [DD1209; 0, CH, $CH_2CF_3$, H, I], [DD1210; 0, CH, $CH_2CHF_2$, H, I], [DD1211; 1, N, H, H, I], [DD1212; 1, N, F, H, I], [DD1213; 1, N, Cl, H, I], [DD1214; 1, N, Br, H, I], [DD1215; 1, N, I, H, I], [DD1216; 1, N, $CF_3$, H, I], [DD1217; 1, N, $CF_2H$, H, I], [DD1218; 1, N, $C_2F_5$, H, I], [DD1219; 1, N, $C_3F_7$, H, I], [DD1220; 1, N, $CH_2CF_3$, H, I], [DD1221; 1, N, $CH_2CHF_2$, H, I], [DD1222; 1, CH, H, H, I], [DD1223; 1, CH, F, H, I], [DD1224; 1, CH, Cl, H, I], [DD1225; 1, CH, Br, H, I], [DD1226; 1, CH, I, H, I], [DD1227; 1, CH, $CF_3$, H, I], [DD1228; 1, CH, $CF_2H$, H, I], [DD1229; 1, CH, $C_2F_5$, H, I], [DD1230; 1, CH, $C_3F_7$, H, I], [DD1231; 1, CH, $CH_2CF_3$, H, I], [DD1232; 1, CH, $CH_2CHF_2$, H, I], [DD1233; 2, N, H, H, I], [DD1234; 2, N, F, H, I], [DD1235; 2, N, Cl, H, I], [DD1236; 2, N, Br, H, I], [DD1237; 2, N, I, H, I], [DD1238; 2, N, $CF_3$, H, I], [DD1239; 2, N, $CF_2H$, H, I], [DD1240; 2, N, $C_2F_5$, H, I], [DD1241; 2, N, $C_3F_7$, H, I], [DD1242; 2, N, $CH_2CF_3$, H, I], [DD1243; 2, N, $CH_2CHF_2$, H, I], [DD1244; 2, CH, H, H, I], [DD1245; 2, CH, F, H, I], [DD1246; 2, CH, Cl, H, I], [DD1247; 2, CH, Br, H, I], [DD1248; 2, CH, I, H, I], [DD1249; 2, CH, $CF_3$, H, I], [DD1250; 2, CH, $CF_2H$, H, I], [DD1251; 2, CH, $C_2F_5$, H, I], [DD1252; 2, CH, $C_3F_7$, H, I], [DD1253; 2, CH, $CH_2CF_3$, H, I], [DD1254; 2, CH, $CH_2CHF_2$, H, I], [DD1255; 0, N, H, H, I], [DD1256; 0, N, H, F, I], [DD1257; 0, N, H, Cl, I], [DD1258; 0, N, H, Br, I], [DD1259; 0, N, H, I, I], [DD1260; 0, N, H, $CF_3$, I], [DD1261; 0, N, H, $CF_2H$, I], [DD1262; 0, N, H, $C_2F_5$, I], [DD1263; 0, N, H, $C_3F_7$, I], [DD1264; 0, N, H, $CH_2CF_3$, I], [DD1265; 0, N, H, $CH_2CHF_2$, I], [DD1266; 0, CH, H, H, I], [DD1267; 0, CH, H, F, I], [DD1268; 0, CH, H, Cl, I], [DD1269; 0, CH, H, Br, I], [DD1270; 0, CH, H, I, I], [DD1271; 0, CH, H, $CF_3$, I], [DD1272; 0, CH, H, $CF_2H$, I], [DD1273; 0, CH, H, $C_2F_5$, I], [DD1274; 0, CH, H, $C_3F_7$, I], [DD1275; 0, CH, H, $CH_2CF_3$, I], [DD1276; 0, CH, H, $CH_2CHF_2$, I], [DD1277; 1, N, H, H, I], [DD1278; 1, N, H, F, I], [DD1279; 1, N, H, Cl, I], [DD1280; 1, N, H, Br, I], [DD1281; 1, N, H, I, I], [DD1282; 1, N, H, $CF_3$, I], [DD1283; 1, N, H, $CF_2H$, I], [DD1284; 1, N, H, $C_2F_5$, I], [DD1285; 1, N, H, $C_3F_7$, I], [DD1286; 1, N, H, $CH_2CF_3$, I], [DD1287; 1, N, H, $CH_2CHF_2$, I], [DD1288; 1, CH, H, H, I], [DD1289; 1, CH, H, F, I], [DD1290; 1, CH, H, Cl, I], [DD1291; 1, CH, H, Br, I], [DD1292; 1, CH, H, I, I], [DD1293; 1, CH, H, $CF_3$, I], [DD1294; 1, CH, H, $CF_2H$, I], [DD1295; 1, CH, H, $C_2F_5$, I], [DD1296; 1, CH, H, $C_3F_7$, I], [DD1297; 1, CH, H, $CH_2CF_3$, I], [DD1298; 1, CH, H, $CH_2CHF_2$, I], [DD1299; 2, N, H, H, I], [DD1300; 2, N, H, F, I], [DD1301; 2, N, H, Cl, I], [DD1302; 2, N, H, Br, I], [DD1303; 2, N, H, I, I], [DD1304; 2, N, H, $CF_3$, I], [DD1305; 2, N, H, $CF_2H$, I], [DD1306; 2, N, H, $C_2F_5$, I], [DD1307; 2, N, H, $C_3F_7$, I], [DD1308; 2, N, H, $CH_2CF_3$, I], [DD1309; 2, N, H, $CH_2CHF_2$, I], [DD1310; 2, CH, H, H, I], [DD1311; 2, CH, H, F, I], [DD1312; 2, CH, H, Cl, I], [DD1313; 2, CH, H, Br, I], [DD1314; 2, CH, H, I, I], [DD1315; 2, CH, H, $CF_3$, I], [DD1316; 2, CH, H, $CF_2H$, I], [DD1317; 2, CH, H, $C_2F_5$, I], [DD1318; 2, CH, H, $C_3F_7$, I], [DD1319; 2, CH, H, $CH_2CF_3$, I], [DD1320; 2, CH, H, $CH_2CHF_2$, I], [DD1321; N, H, H, F], [DD1322; 0, N, F, H, F], [DD1323; 0, N, Cl, H, F], [DD1324; 0, N, Br, H, F], [DD1325; 0, N, I, H, F], [DD1326; 0, N, $CF_3$, H, F], [DD1327; 0, N, $CF_2H$, H, F], [DD1328; 0, N, $C_2F_5$, H, F], [DD1329; 0, N, $C_3F_7$, H, F], [DD1330; 0, N, $CH_2CF_3$, H, F], [DD1331; 0, N, $CH_2CHF_2$, H, F], [DD1332; 0, CH, H, H, F], [DD1333; 0, CH, F, H, F], [DD1334; 0, CH, Cl, H, F], [DD1335; 0, CH, Br, H, F], [DD1336; 0, CH, I, H, F], [DD1337; 0, CH, $CF_3$, H, F], [DD1338; 0, CH, $CF_2H$, H, F], [DD1339; 0, CH, $C_2F_5$, H, F], [DD1340; 0, CH, $C_3F_7$, H, F], [DD1341; 0, CH, $CH_2CF_3$, H, F], [DD1342; 0, CH, $CH_2CHF_2$, H, F], [DD1343; 1, N, H, H, F], [DD1344; 1, N, F, H, F], [DD1345; 1, N, Cl, H, F], [DD1346; 1, N, Br, H, F], [DD1347; 1, N, I, H, F], [DD1348; 1, N, $CF_3$, H, F], [DD1349; 1, N, $CF_2H$, H, F], [DD1350; 1, N, $C_2F_5$, H, F], [DD1351; 1, N, $C_3F_7$, H, F], [DD1352; 1, N, $CH_2CF_3$, H, F], [DD1353; 1, N, $CH_2CHF_2$, H, F], [DD1354; 1, CH, H, H, F], [DD1355; 1, CH, F, H, F], [DD1356; 1, CH, Cl, H, F], [DD1357; 1, CH, Br, H, F], [DD1358; 1, CH, I, H, F], [DD1359; 1, CH, $CF_3$, H, F], [DD1360; 1, CH, $CF_2H$, H, F], [DD1361; 1, CH, $C_2F_5$, H, F], [DD1362; 1, CH, $C_3F_7$, H, F], [DD1363; 1, CH, $CH_2CF_3$, H, F], [DD1364; 1, CH, $CH_2CHF_2$, H, F], [DD1365; 2, N, H, H, F], [DD1366; 2, N, F, H, F], [DD1367; 2, N, Cl, H, F], [DD1368; 2, N, Br, H, F], [DD1369; 2, N, I, H, F], [DD1370; 2, N, $CF_3$, H, F], [DD1371; 2, N, $CF_2H$, H, F], [DD1372; 2, N, $C_2F_5$, H, F], [DD1373; 2, N, $C_3F_7$, H, F], [DD1374; 2, N, $CH_2CF_3$, H, F], [DD1375; 2, N, $CH_2CHF_2$, H, F], [DD1376; 2, CH, H, H, F], [DD1377; 2, CH, F, H, F], [DD1378; 2, CH, Cl, H, F], [DD1379; 2, CH, Br, H, F], [DD1380; 2, CH, I, H, F], [DD1381; 2, CH, $CF_3$, H, F], [DD1382; 2, CH, $CF_2H$, H, F], [DD1383; 2, CH, $C_2F_5$, H, F], [DD1384; 2, CH, $C_3F_7$, H, F], [DD1385; 2, CH, $CH_2CF_3$, H, F], [DD1386; 2, CH, $CH_2CHF_2$, H, F], [DD1387; 0, N, H, H, F], [DD1388; 0, N, H, F, F], [DD1389; 0, N, H, Cl, F], [DD1390; 0, N, H, Br, F], [DD1391; 0, N, H, I, F], [DD1392; 0, N, H, $CF_3$, F], [DD1393; 0, N, H, $CF_2H$, F], [DD1394; 0, N, H, $C_2F_5$, F], [DD1395; 0, N, H, $C_3F_7$, F], [DD1396; 0, N, H, $CH_2CF_3$, F], [DD1397; 0, N, H, $CH_2CHF_2$, F], [DD1398; 0, CH, H, H, F], [DD1399; 0, CH, H, F, F], [DD1400; 0, CH, H, Cl, F], [DD1401; 0, CH, H, Br, F], [DD1402; 0, CH, H, I, F], [DD1403; 0, CH, H, $CF_3$, F], [DD1404; 0, CH, H, $CF_2H$, F], [DD1405; 0, CH, H, $C_2F_5$, F], [DD1406; 0, CH, H, $C_3F_7$, F], [DD1407; 0, CH, H, $CH_2CF_3$, F], [DD1408; 0, CH, H, $CH_2CHF_2$, F], [DD1409; 1, N, H, H, F], [DD1410; 1, N, H, F, F], [DD1411; 1, N, H, Cl, F], [DD1412; 1, N, H, Br, F], [DD1413; 1, N, H, I, F], [DD1414; 1, N, H, $CF_3$, F], [DD1415; 1, N, H, $CF_2H$, F], [DD1416; 1, N, H, $C_2F_5$, F], [DD1417; 1, N, H, $C_3F_7$, F], [DD1418; 1, N, H, $CH_2CF_3$, F], [DD1419; 1, N, H, $CH_2CHF_2$, F], [DD1420; 1, CH, H, H, F], [DD1421; 1, CH, H, F, F], [DD1422; 1, CH, H, Cl, F], [DD1423; 1, CH, H, Br, F], [DD1424; 1, CH, H, I, F], [DD1425; 1, CH, H, $CF_3$, F], [DD1426; 1, CH, H, $CF_2H$, F], [DD1427; 1, CH, H, $C_2F_5$, F], [DD1428; 1, CH, H, $C_3F_7$, F], [DD1429; 1, CH, H, $CH_2CF_3$, F], [DD1430; 1, CH, H, $CH_2CHF_2$, F], [DD1431; 2, N, H, H, F], [DD1432; 2, N, H, F, F], [DD1433; 2, N, H, Cl, F], [DD1434; 2, N, H, Br, F], [DD1435; 2, N, H, I, F], [DD1436; 2, N, H, $CF_3$, F], [DD1437; 2, N, H, $CF_2H$, F], [DD1438; 2, N, H, $C_2F_5$, F], [DD1439; 2, N, H, $C_3F_7$, F], [DD1440; 2, N, H, $CH_2CF_3$, F], [DD1441; 2, N, H, $CH_2CHF_2$, F], [DD1442; 2, CH, H, H, F], [DD1443; 2, CH, H, F, F], [DD1444; 2, CH, H, Cl, F], [DD1445; 2, CH, H, Br, F], [DD1446; 2, CH, H, I, F], [DD1447; 2, CH, H, $CF_3$, F], [DD1448; 2, CH, H, $CF_2H$, F], [DD1449; 2, CH, H, $C_2F_5$, F], [DD1450; 2, CH, H, $C_3F_7$, F], [DD1451; 2, CH, H, $CH_2CF_3$, F], [DD1452; 2, CH, H, $CH_2CHF_2$, F]

A compound represented by formula (L-14)

(L-14)

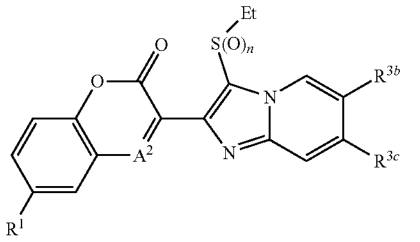

wherein the combination of the symbol n, and the substituents $A^2$, $R^{3b}$, $R^{3c}$, and $R^1$ represents any one combination indicated in the Combination DD (hereinafter referred to as "Compound group SX14").

A compound represented by formula (L-15)

(L-15)

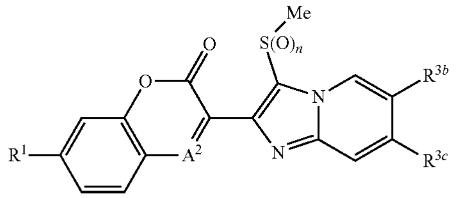

wherein the combination of the symbol n, and the substituents $A^2$, $R^{3b}$, $R^{3c}$, and $R^1$ represents any one combination indicated in the Combination DD (hereinafter referred to as "Compound group SX15").

A compound represented by formula (L-16)

(L-16)

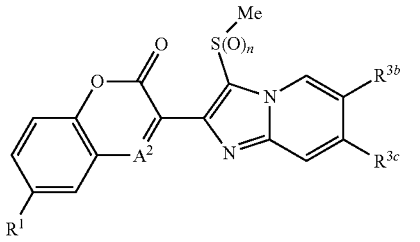

wherein the combination of the symbol n, and the substituents $A^2$, $R^{3b}$, $R^{3c}$, and $R^1$ represents any one combination indicated in the Combination DD (hereinafter referred to as "Compound group SX16").

A compound represented by formula (L-17)

(L-17)

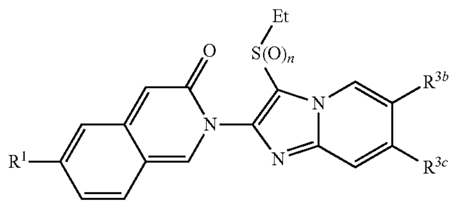

wherein the combination of the symbol n, and the substituents $R^{3b}$, $R^{3c}$, and $R^1$ represents any one combination indicated in the Combination EE (hereinafter referred to as "Compound group SX17").

The Combination EE consists of substituent numbers EE1 to EE693. The substituent numbers EE1 to EE693 represent the combinations of the symbol n, and the substituents $R^{3b}$, $R^{3c}$, and $R^1$, and hereinafter referred to as "[substituent number; n, $R^{3b}$, $R^{3c}$, $R^1$]". For example, the substituent number EE2 means a combination wherein n represents 0, $R^{3b}$ represents a fluorine atom, $R^{3c}$ represents a hydrogen atom, and $R^1$ represents $CF_3$.

Combination EE: [EE1; 0, H, H, $CF_3$], [EE2; 0, F, H, $CF_3$], [EE3; 0, Cl, H, $CF_3$], [EE4; 0, Br, H, $CF_3$], [EE5; 0, I, H, $CF_3$], [EE6; 0, $CF_3$, H, $CF_3$], [EE7; 0, $CF_2H$, H, $CF_3$], [EE8; 0, $C_2F_5$, H, $CF_3$], [EE9; 0, $C_3F_7$, H, $CF_3$], [EE10; 0, $CH_2CF_3$, H, $CF_3$], [EE11; 0, $CH_2CHF_2$, H, $CF_3$], [EE12; 1, H, H, $CF_3$], [EE13; 1, F, H, $CF_3$], [EE14; 1, Cl, H, $CF_3$], [EE15; 1, Br, H, $CF_3$], [EE16; 1, I, H, $CF_3$], [EE17; 1, $CF_3$, H, $CF_3$], [EE18; 1, $CF_2H$, H, $CF_3$], [EE19; 1, $C_2F_5$, H, $CF_3$], [EE20; 1, $C_3F_7$, H, $CF_3$], [EE21; 1, $CH_2CF_3$, H, $CF_3$], [EE22; 1, $CH_2CHF_2$, H, $CF_3$], [EE23; 2, H, H, $CF_3$], [EE24; 2, F, H, $CF_3$], [EE25; 2, Cl, H, $CF_3$], [EE26; 2, Br, H, $CF_3$], [EE27; 2, I, H, $CF_3$], [EE28; 2, $CF_3$, H, $CF_3$], [EE29; 2, $CF_2H$, H, $CF_3$], [EE30; 2, $C_2F_5$, H, $CF_3$], [EE31; 2, $C_3F_7$, H, $CF_3$], [EE32; 2, $CH_2CF_3$, H, $CF_3$], [EE33; 2, $CH_2CHF_2$, H, $CF_3$], [EE34; 0, H, F, $CF_3$], [EE35; 0, H, Cl, $CF_3$], [EE36; 0, H, Br, $CF_3$], [EE37; 0, H, I, $CF_3$], [EE38; 0, H, $CF_3$, $CF_3$], [EE39; 0, H, $CF_2H$, $CF_3$], [EE40; 0, H, $C_2F_5$, $CF_3$], [EE41; 0, H, $C_3F_7$, $CF_3$], [EE42; 0, H, $CH_2CF_3$, $CF_3$], [EE43; 0, H, $CH_2CHF_2$, $CF_3$], [EE44; 1, H, F, $CF_3$], [EE45; 1, H, Cl, $CF_3$], [EE46; 1, H, Br, $CF_3$], [EE47; 1, H, I, $CF_3$], [EE48; 1, H, $CF_3$, $CF_3$], [EE49; 1, H, $CF_2H$, $CF_3$], [EE50; 1, H, $C_2F_5$, $CF_3$], [EE51; 1, H, $C_3F_7$, $CF_3$], [EE52; 1, H, $CH_2CF_3$, $CF_3$], [EE53; 1, H, $CH_2CHF_2$, $CF_3$], [EE54; 2, H, F, $CF_3$], [EE55; 2, H, Cl, $CF_3$], [EE56; 2, H, Br, $CF_3$], [EE57; 2, H, I, $CF_3$], [EE58; 2, H, $CF_3$, $CF_3$], [EE59; 2, H, $CF_2H$, $CF_3$], [EE60; 2, H, $C_2F_5$, $CF_3$], [EE61; 2, H, $C_3F_7$, $CF_3$], [EE62; 2, H, $CH_2CF_3$, $CF_3$], [EE63; 2, H, $CH_2CHF_2$, $CF_3$], [EE64; 0, H, H, $CHF_2$], [EE65; 0, F, H, $CHF_2$], [EE66; 0, Cl, H, $CHF_2$], [EE67; 0, Br, H, $CHF_2$], [EE68; 0, I, H, $CHF_2$], [EE69; 0, $CF_3$, H, $CHF_2$], [EE70; 0, $CF_2H$, H, $CHF_2$], [EE71; 0, $C_2F_5$, H, $CHF_2$], [EE72; 0, $C_3F_7$, H, $CHF_2$], [EE73; 0, $CH_2CF_3$, H, $CHF_2$], [EE74; 0, $CH_2CHF_2$, H, $CHF_2$], [EE75; 1, H, H, $CHF_2$], [EE76; 1, F, H, $CHF_2$], [EE77; 1, Cl, H, $CHF_2$], [EE78; 1, Br, H, $CHF_2$], [EE79; 1, I, H, $CHF_2$], [EE80; 1, $CF_3$, H, $CHF_2$], [EE81; 1, $CF_2H$, H, $CHF_2$], [EE82; 1, $C_2F_5$, H, $CHF_2$], [EE83; 1, $C_3F_7$, H, $CHF_2$], [EE84; 1, $CH_2CF_3$, H, $CHF_2$], [EE85; 1, $CH_2CHF_2$, H, $CHF_2$], [EE86; 2, H, H, $CHF_2$], [EE87; 2, F, H, $CHF_2$], [EE88; 2, Cl, H, $CHF_2$], [EE89; 2, Br, H, $CHF_2$], [EE90; 2, I, H, $CHF_2$], [EE91; 2, $CF_3$, H, $CHF_2$], [EE92; 2, $CF_2H$, H, $CHF_2$], [EE93; 2, $C_2F_5$, H, $CHF_2$], [EE94; 2, $C_3F_7$, H, $CHF_7$], [EE95; 2, $CH_2CF_3$, H, $CHF_2$], [EE96; 2, $CH_2CHF_2$, H, $CHF_2$], [EE97; 0, H, F, $CHF_2$], [EE98; 0, H, Cl, $CHF_2$], [EE99; 0, H, Br, $CHF_2$], [EE100; 0, H, I, $CHF_2$], [EE101; 0, H, $CF_3$, $CHF_2$], [EE102; 0, H, $CF_2H$, $CHF_2$], [EE103; 0, H, $C_2F_5$, $CHF_2$], [EE104; 0, H, $C_3F_7$, $CHF_2$], [EE105; 0, H, $CH_2CF_3$, $CHF_2$], [EE106; 0, H, $CH_2CHF_2$, $CHF_2$], [EE107; 1, H, F, $CHF_2$], [EE108; 1, H, Cl, $CHF_2$], [EE109; 1, H, Br, $CHF_2$], [EE110; 1, H, I, $CHF_2$], [EE111; 1, H, $CF_3$, $CHF_2$], [EE112; 1, H, $CF_2H$, $CHF_2$], [EE113; 1, H, $C_2F_5$, $CHF_2$], [EE114; 1, H, $C_3F_7$, $CHF_2$], [EE115; 1, H, $CH_2CF_3$, $CHF_2$], [EE116; 1, H, $CH_2CHF_2$, $CHF_2$], [EE117; 2, H, F, $CHF_2$], [EE118; 2, H, Cl, $CHF_2$], [EE119; 2, H, Br, $CHF_2$], [EE120; 2, H, I, $CHF_2$], [EE121; 2, H, $CF_3$, $CHF_2$], [EE122; 2, H, $CF_2H$, $CHF_2$], [EE123; 2, H, $C_2F_5$, $CHF_2$], [EE124; 2, H, $C_3F_7$, $CHF_2$], [EE125; 2, H, $CH_2CF_3$, $CHF_2$], [EE126; 2, H, $CH_2CHF_2$, $CHF_2$], [EE127; 0, H, H, $CH_2CF_3$], [EE128; 0, F, H, $CH_2CF_3$], [EE129; 0, Cl, H, $CH_2CF_3$], [EE130; 0, Br, H, $CH_2CF_3$], [EE131; 0, I, H, $CH_2CF_3$], [EE132; 0, $CF_3$, H, $CH_2CF_3$], [EE133; 0, $CF_2H$, H, $CH_2CF_3$], [EE134; 0, $C_2F_5$, H, $CH_2CF_3$], [EE135; 0, $C_3F_7$, H, $CH_2CF_3$], [EE136; 0, $CH_2CF_3$, H, $CH_2CF_3$], [EE137; 0, $CH_2CHF_2$, H, $CH_2CF_3$], [EE138; 1, H, H, $CH_2CF_3$], [EE139; 1, F, H, $CH_2CF_3$], [EE140; 1, Cl, H, $CH_2CF_3$], [EE141; 1, Br, H, $CH_2CF_3$], [EE142; 1, I, H, $CH_2CF_3$], [EE143; 1, $CF_3$, H, $CH_2CF_3$], [EE144; 1, $CF_2H$, H, $CH_2CF_3$], [EE145; 1, $C_2F_5$, H, $CH_2CF_3$], [EE146; 1, $C_3F_7$, H, $CH_2CF_3$], [EE147; 1, $CH_2CF_3$, H, $CH_2CF_3$], [EE148; 1, $CH_2CHF_2$, H, $CH_2CF_3$], [EE149; 2, H, H, $CH_2CF_3$], [EE150; 2, F, H, $CH_2CF_3$], [EE151; 2, Cl, H, $CH_2CF_3$], [EE152; 2, Br, H, $CH_2CF_3$], [EE153; 2, I, H, $CH_2CF_3$], [EE154; 2, $CF_3$, H, $CH_2CF_3$], [EE155; 2, $CF_2H$, H, $CH_2CF_3$], [EE156; 2, $C_2F_5$, H, $CH_2CF_3$], [EE157; 2, $C_3F_7$, H, $CH_2CF_3$], [EE158; 2, $CH_2CF_3$, H, $CH_2CF_3$], [EE159; 2, $CH_2CHF_2$, H, $CH_2CF_3$], [EE160; 0, H, F, $CH_2CF_3$], [EE161; 0, H, Cl, $CH_2CF_3$], [EE162; 0, H, Br, $CH_2CF_3$], [EE163; 0, H, I, $CH_2CF_3$], [EE164; 0, H, $CF_3$, $CH_2CF_3$], [EE165; 0, H, $CF_2H$, $CH_2CF_3$], [EE166; 0, H, $C_2F_5$, $CH_2CF_3$], [EE167; 0, H, $C_3F_7$, $CH_2CF_3$], [EE168; 0, H, $CH_2CF_3$, $CH_2CF_3$], [EE169; 0, H, $CH_2CHF_2$, $CH_2CF_3$], [EE170; 1, H, F, $CH_2CF_3$], [EE171; 1, H, Cl, $CH_2CF_3$], [EE172; 1, H, Br, $CH_2CF_3$], [EE173; 1, H, I, $CH_2CF_3$], [EE174; 1, H, $CF_3$, $CH_2CF_3$], [EE175; 1, H, $CF_2H$, $CH_2CF_3$], [EE176; 1, H, $C_2F_5$, $CH_2CF_3$], [EE177; 1, H, $C_3F_7$, $CH_2CF_3$], [EE178; 1, H, $CH_2CF_3$, $CH_2CF_3$], [EE179; 1, H, $CH_2CHF_2$, $CH_2CF_3$], [EE180; 2, H, F, $CH_2CF_3$], [EE181; 2, H, Cl, $CH_2CF_3$], [EE182; 2, H, Br, $CH_2CF_3$], [EE183; 2, H, I, $CH_2CF_3$], [EE184; 2, H, $CF_3$, $CH_2CF_3$], [EE185; 2, H, $CF_2H$, $CH_2CF_3$], [EE186; 2, H, $C_2F_5$, $CH_2CF_3$], [EE187; 2, H, $C_3F_7$, $CH_2CF_3$], [EE188; 2, H, $CH_2CF_3$, $CH_2CF_3$], [EE189; 2, H, $CH_2CHF_2$, $CH_2CF_3$], [EE190; 0, H, H, $CH_2CHF_2$], [EE191; 0, F, H, $CH_2CHF_2$], [EE192; 0, Cl, H, $CH_2CHF_2$], [EE193; 0, Br, H, $CH_2CHF_2$], [EE194; 0, I, H, $CH_2CHF_2$], [EE195; 0, $CF_3$, H, $CH_2CHF_2$], [EE196; 0, $CF_2H$, H, $CH_2CHF_2$], [EE197; 0, $C_2F_5$, H, $CH_2CHF_2$], [EE198; 0, $C_3F_7$, H, $CH_2CHF_2$], [EE199; 0, $CH_2CF_3$, H, $CH_2CHF_2$], [EE200; 0, $CH_2CHF_2$, H, $CH_2CHF_2$], [EE201; 1, H, H, $CH_2CHF_2$], [EE202; 1, F, H, $CH_2CHF_2$], [EE203; 1, Cl, H, $CH_2CHF_2$], [EE204; 1, Br, H, $CH_2CHF_2$], [EE205; 1, I, H, $CH_2CHF_2$], [EE206; 1, $CF_3$, H, $CH_2CHF_2$], [EE207; 1, $CF_2H$, H, $CH_2CHF_2$], [EE208; 1, $C_2F_5$, H, $CH_2CHF_2$], [EE209; 1, $C_3F_7$, H, $CH_2CHF_2$], [EE210; 1, $CH_2CF_3$, H, $CH_2CHF_2$], [EE211; 1, $CH_2CHF_2$, H, $CH_2CHF_2$], [EE212; 2, H, H, $CH_2CHF_2$], [EE213; 2, F, H, $CH_2CHF_2$], [EE214; 2, Cl, H, $CH_2CHF_2$], [EE215; 2, Br, H, $CH_2CHF_2$], [EE216; 2, I, H, $CH_2CHF_2$], [EE217; 2, $CF_3$, H, $CH_2CHF_2$], [EE218; 2, $CF_2H$, H, $CH_2CHF_2$], [EE219; 2, $C_2F_5$, H, $CH_2CHF_2$], [EE220; 2, $C_3F_7$, H, $CH_2CHF_2$], [EE221; 2, $CH_2CF_3$, H, $CH_2CHF_2$], [EE222; 2, $CH_2CHF_2$, H, $CH_2CHF_2$], [EE223; 0, H, F, $CH_2CHF_2$], [EE224; 0, H, Cl, $CH_2CHF_2$], [EE225; 0, H, Br, $CH_2CHF_2$], [EE226; 0, H, I, $CH_2CHF_2$], [EE227; 0, H, $CF_3$, $CH_2CHF_2$], [EE228; 0, H, $CF_2H$, $CH_2CHF_2$], [EE229; 0, H, $C_2F_5$, $CH_2CHF_2$], [EE230; 0, H, $C_3F_7$, $CH_2CHF_2$], [EE231; 0, H, $CH_2CF_3$, $CH_2CHF_2$], [EE232; 0, H, $CH_2CHF_2$, $CH_2CHF_2$], [EE233; 1, H, F, $CH_2CHF_2$], [EE234; 1, H, Cl, $CH_2CHF_2$], [EE235; 1, H, Br, $CH_2CHF_2$], [EE236; 1, H, I, $CH_2CHF_2$], [EE237; 1, H, $CF_3$, $CH_2CHF_2$], [EE238; 1, H, $CF_2H$, $CH_2CHF_2$], [EE239; 1, H, $C_2F_5$, $CH_2CHF_2$], [EE240; 1, H, $C_3F_7$, $CH_2CHF_2$], [EE241; 1, H, $CH_2CF_3$, $CH_2CHF_2$], [EE242; 1, H, $CH_2CHF_2$, $CH_2CHF_2$], [EE243; 2, H, F, $CH_2CHF_2$], [EE244; 2, H, Cl, $CH_2CHF_2$], [EE245; 2, H, Br, $CH_2CHF_2$], [EE246; 2, H, I, $CH_2CHF_2$], [EE247; 2, H, $CF_3$, $CH_2CHF_2$], [EE248; 2, H, $CF_2H$, $CH_2CHF_2$], [EE249; 2, H, $C_2F_5$, $CH_2CHF_2$], [EE250; 2, H, $C_3F_7$, $CH_2CHF_2$], [EE251; 2, H, $CH_2CF_3$, $CH_2CHF_2$], [EE252; 2, H, $CH_2CHF_2$, $CH_2CHF_2$], [EE253; 0, H, H, $SCF_3$], [EE254; 0, F, H, $SCF_3$], [EE255; 0, Cl, H, $SCF_3$], [EE256; 0, Br, H, $SCF_3$], [EE257; 0, I, H, $SCF_3$], [EE258; 0, $CF_3$, H, $SCF_3$], [EE259; 0, $CF_2H$, H, $SCF_3$], [EE260; 0, $C_2F_5$, H, $SCF_3$], [EE261; 0, $C_3F_7$, H, $SCF_3$], [EE262; 0, $CH_2CF_3$, H, $SCF_3$], [EE263; 0, $CH_2CHF_2$, H, $SCF_3$], [EE264; 1, H, H, $SCF_3$], [EE265; 1, F, H, $SCF_3$], [EE266; 1, Cl, H, $SCF_3$], [EE267; 1, Br, H, $SCF_3$], [EE268; 1, I, H, $SCF_3$], [EE269; 1, $CF_3$, H, $SCF_3$], [EE270; 1, $CF_2H$, H, $SCF_3$], [EE271; 1, $C_2F_5$, H, $SCF_3$], [EE272; 1, $C_3F_7$, H, $SCF_3$], [EE273; 1, $CH_2CF_3$, H, $SCF_3$], [EE274; 1, $CH_2CHF_2$, H, $SCF_3$], [EE275; 2, H, H, $SCF_3$], [EE276; 2, F, H, $SCF_3$], [EE277; 2, Cl, H, $SCF_3$], [EE278; 2, Br, H, $SCF_3$], [EE279; 2, I, H, $SCF_3$], [EE280; 2, $CF_3$, H, $SCF_3$], [EE281; 2, $CF_2H$, H, $SCF_3$], [EE282; 2, $C_2F_5$, H, $SCF_3$], [EE283; 2, $C_3F_7$, H, $SCF_3$], [EE284; 2, $CH_2CF_3$, H, $SCF_3$], [EE285; 2, $CH_2CHF_2$, H, $SCF_3$], [EE286; 0, H, F, $SCF_3$], [EE287; 0, H, Cl, $SCF_3$], [EE288; 0, H, Br, $SCF_3$], [EE289; 0, H, I, $SCF_3$], [EE290; 0, H, $CF_3$, $SCF_3$], [EE291; 0, H, $CF_2H$, $SCF_3$], [EE292; 0, H, $C_2F_5$, $SCF_3$], [EE293; 0, H, $C_3F_7$, $SCF_3$], [EE294; 0, H, $CH_2CF_3$, $SCF_3$], [EE295; 0, H, $CH_2CHF_2$, $SCF_3$], [EE296; 1, H, F, $SCF_3$], [EE297; 1, H, Cl, $SCF_3$], [EE298; 1, H, Br, $SCF_3$], [EE299; 1, H, I, $SCF_3$], [EE300; 1, H, $CF_3$, $SCF_3$], [EE301; 1, H, $CF_2H$, $SCF_3$], [EE302; 1, H, $C_2F_5$, $SCF_3$], [EE303; 1, H, $C_3F_7$, $SCF_3$], [EE304; 1, H, $CH_2CF_3$, $SCF_3$], [EE305; 1, H, $CH_2CHF_2$, $SCF_3$], [EE306; 2, H, F, $SCF_3$], [EE307; 2, H, Cl, $SCF_3$], [EE308; 2, H, Br, $SCF_3$], [EE309; 2, H, I, $SCF_3$], [EE310; 2, H, $CF_3$, $SCF_3$], [EE311; 2, H, $CF_2H$, $SCF_3$], [EE312; 2, H, $C_2F_5$, $SCF_3$], [EE313; 2, H, $C_3F_7$, $SCF_3$], [EE314; 2, H, $CH_2CF_3$, $SCF_3$], [EE315; 2, H, $CH_2CHF_2$, $SCF_3$], [EE316; 0, H, H, $OCF_3$], [EE317; 0, F, H, $OCF_3$], [EE318; 0, Cl, H, $OCF_3$], [EE319; 0, Br, H, $OCF_3$], [EE320; 0, I, H, $OCF_3$], [EE321; 0, $CF_3$, H, $OCF_3$], [EE322; 0, $CF_2H$, H, $OCF_3$], [EE323; 0, $C_2F_5$, H, $OCF_3$], [EE324; 0, $C_3F_7$, H, $OCF_3$], [EE325; 0, $CH_2CF_3$, H, $OCF_3$], [EE326; 0, $CH_2CHF_2$, H, $OCF_3$], [EE327; 1, H, H, $OCF_3$], [EE328; 1, F, H, $OCF_3$], [EE329; 1, Cl, H, $OCF_3$], [EE330; 1, Br, H, $OCF_3$], [EE331; 1, I, H, $OCF_3$], [EE332; 1, $CF_3$, H, $OCF_3$], [EE333; 1, $CF_2H$, H, $OCF_3$], [EE334; 1, $C_2F_5$, H, $OCF_3$], [EE335; 1, $C_3F_7$, H, $OCF_3$], [EE336; 1, $CH_2CF_3$, H, $OCF_3$], [EE337; 1, $CH_2CHF_2$, H, $OCF_3$], [EE338; 2, H, H, $OCF_3$], [EE339; 2, F, H, $OCF_3$], [EE340; 2, Cl, H, $OCF_3$], [EE341; 2, Br, H, $OCF_3$], [EE342; 2, I, H, $OCF_3$], [EE343; 2, $CF_3$, H, $OCF_3$], [EE344; 2, $CF_2H$, H, $OCF_3$], [EE345; 2, $C_2F_5$, H, $OCF_3$], [EE346; 2, $C_3F_7$, H, $OCF_3$], [EE347; 2, $CH_2CF_3$, H, $OCF_3$], [EE348; 2, $CH_2CHF_2$, H, $OCF_3$], [EE349; 0, H, F, $OCF_3$], [EE350; 0, H, Cl, $OCF_3$], [EE351; 0, H, Br, $OCF_3$], [EE352; 0, H, I, $OCF_3$], [EE353; 0, H, $CF_3$, $OCF_3$], [EE354; 0, H, $CF_2H$, $OCF_3$], [EE355; 0, H, $C_2F_5$, $OCF_3$], [EE356; 0, H, $C_3F_7$, $OCF_3$], [EE357; 0, H, $CH_2CF_3$, $OCF_3$], [EE358; 0, H, $CH_2CHF_2$, $OCF_3$], [EE359; 1, H, F, $OCF_3$], [EE360; 1, H, Cl, $OCF_3$], [EE361; 1, H, Br, $OCF_3$], [EE362; 1, H, I, $OCF_3$], [EE363; 1, H, $CF_3$, $OCF_3$], [EE364; 1, H, $CF_2H$, $OCF_3$], [EE365; 1, H, $C_2F_5$, $OCF_3$], [EE366; 1, H, $C_3F_7$, $OCF_3$], [EE367; 1, H, $CH_2CF_3$, $OCF_3$], [EE368; 1, H, $CH_2CHF_2$, $OCF_3$], [EE369; 2, H, F, $OCF_3$], [EE370; 2, H, Cl, $OCF_3$], [EE371; 2, H, Br, $OCF_3$], [EE372; 2, H, I, $OCF_3$], [EE373; 2, H, $CF_3$, $OCF_3$], [EE374; 2, H, $CF_2H$, $OCF_3$], [EE375; 2, H, $C_2F_5$, $OCF_3$], [EE376; 2, H, $C_3F_7$, $OCF_3$], [EE377; 2, H, $CH_2CF_3$, $OCF_3$], [EE378; 2, H, $CH_2CHF_2$, $OCF_3$], [EE379; 0, H, H, $OCHF_2$], [EE380; 0, F, H, $OCHF_2$], [EE381; 0, Cl, H, $OCHF_2$], [EE382; 0, Br, H, $OCHF_2$], [EE383; 0, I, H, $OCHF_2$], [EE384; 0, $CF_3$, H, $OCHF_2$], [EE385; 0, $CF_2H$, H, $OCHF_2$], [EE386; 0, $C_2F_5$, H, $OCHF_2$], [EE387; 0, $C_3F_7$, H, $OCHF_2$], [EE388; 0, $CH_2CF_3$, H, $OCHF_2$], [EE389; 0, $CH_2CHF_2$, H, $OCHF_2$], [EE390; 1, H, H, $OCHF_2$], [EE391; 1, F, H, $OCHF_2$], [EE392; 1, Cl, H, $OCHF_2$], [EE393; 1, Br, H, $OCHF_2$], [EE394; 1, I, H, $OCHF_2$], [EE395; 1, $CF_3$, H, $OCHF_2$], [EE396; 1, $CF_2H$, H, $OCHF_2$], [EE397; 1, $C_2F_5$, H, $OCHF_2$], [EE398; 1, $C_3F_7$, H, $OCHF_2$], [EE399; 1, $CH_2CF_3$, H, $OCHF_2$], [EE400; 1, $CH_2CHF_2$, H, $OCHF_2$], [EE401; 2, H, H, $OCHF_2$], [EE402; 2, F, H, $OCHF_2$], [EE403; 2, Cl, H, $OCHF_2$], [EE404; 2, Br, H, $OCHF_2$], [EE405; 2, I, H, $OCHF_2$], [EE406; 2, $CF_3$, H, $OCHF_2$], [EE407; 2, $CF_2H$, H, $OCHF_2$], [EE408; 2, $C_2F_5$, H, $OCHF_2$], [EE409; 2, $C_3F_7$, H, $OCHF_2$], [EE410; 2, $CH_2CF_3$, H, $OCHF_2$], [EE411; 2, $CH_2CHF_2$, H, $OCHF_2$], [EE412; 0, H, F, $OCHF_2$], [EE413; 0, H, Cl, $OCHF_2$], [EE414; 0, H, Br, $OCHF_2$], [EE415; 0, H, I, $OCHF_2$], [EE416; 0, H, $CF_3$, $OCHF_2$], [EE417; 0, H, $CF_2H$, $OCHF_2$], [EE418; 0, H, $C_2F_5$, $OCHF_2$], [EE419; 0, H, $C_3F_7$, $OCHF_2$], [EE420; 0, H, $CH_2CF_3$, $OCHF_2$], [EE421; 0, H, $CH_2CHF_2$, $OCHF_2$], [EE422; 1, H, F, $OCHF_2$], [EE423; 1, H, Cl, $OCHF_2$], [EE424; 1, H, Br, $OCHF_2$], [EE425; 1, H, I, $OCHF_2$], [EE426; 1, H, $CF_3$, $OCHF_2$], [EE427; 1, H, $CF_2H$, $OCHF_2$], [EE428; 1, H, $C_2F_5$, $OCHF_2$], [EE429; 1, H, $C_3F_7$, $OCHF_2$], [EE430; 1, H, $CH_2CF_3$, $OCHF_2$], [EE431; 1, H, $CH_2CHF_2$, $OCHF_2$], [EE432; 2, H, F, $OCHF_2$], [EE433; 2, H, Cl, $OCHF_2$], [EE434; 2, H, Br, $OCHF_2$], [EE435; 2, H, I, $OCHF_2$], [EE436; 2, H, $CF_3$, $OCHF_2$], [EE437; 2, H, $CF_2H$, $OCHF_2$], [EE438; 2, H, $C_2F_5$, $OCHF_2$], [EE439; 2, H, $C_3F_7$, $OCHF_2$], [EE440; 2, H, $CH_2CF_3$, $OCHF_2$], [EE441; 2, H, $CH_2CHF_2$, $OCHF_2$], [EE442; 0, H, H, Br], [EE443; 0, F, H, Br], [EE444; 0, Cl, H, Br], [EE445; 0, Br, H, Br], [EE446; 0, I, H, Br], [EE447; 0, $CF_3$, H, Br], [EE448; 0, $CF_2H$, H, Br], [EE449; 0, $C_2F_5$, H, Br], [EE450; 0, $C_3F_7$, H, Br], [EE451; 0, $CH_2CF_3$, H, Br], [EE452; 0, $CH_2CHF_2$, H, Br], [EE453; 1, H, H, Br], [EE454; 1, F, H, Br], [EE455; 1, Cl, H, Br], [EE456; 1, Br, H, Br], [EE457; 1, I, H, Br], [EE458; 1, $CF_3$, H, Br], [EE459; 1, $CF_2H$, H, Br], [EE460; 1, $C_2F$, H, Br], [EE461; 1, $C_3F_7$, H, Br], [EE462; 1, $CH_2CF_3$, H, Br], [EE463; 1, $CH_2CHF_2$, H, Br], [EE464; 2, H, H, Br], [EE465; 2, F, H, Br], [EE466; 2, Cl, H, Br], [EE467; 2, Br, H, Br], [EE468; 2, I, H, Br], [EE469; 2, $CF_3$, H, Br], [EE470; 2, $CF_2H$, H, Br], [EE471; 2, $C_2F_5$, H, Br], [EE472; 2, $C_3F_7$, H, Br], [EE473; 2, $CH_2CF_3$, H, Br], [EE474; 2, $CH_2CHF_2$, H, Br], [EE475; 0, H, F, Br], [EE476; 0, H, Cl, Br], [EE477; 0, H, Br, Br], [EE478; 0, H, I, Br], [EE479; 0, H, $CF_3$, Br], [EE480; 0, H, $CF_2H$, Br], [EE481; 0, H, $C_2F_5$, Br], [EE482; 0, H, $C_3F_7$, Br], [EE483; 0, H, $CH_2CF_3$, Br], [EE484; 0, H, $CH_2CHF_2$, Br], [EE485; 1, H, F, Br], [EE486; 1, H, Cl, Br], [EE487; 1, H, Br, Br], [EE488; 1, H, I, Br], [EE489; 1, H, $CF_3$, Br], [EE490; 1, H, $CF_2H$, Br], [EE491; 1, H, $C_2F_5$, Br], [EE492; 1, H, $C_3F_7$, Br], [EE493; 1, H, $CH_2CF_3$, Br], [EE494; 1, H, $CH_2CHF_2$, Br], [EE495; 2, H, F, Br], [EE496; 2, H, Cl, Br], [EE497; 2, H, Br, Br], [EE498; 2, H, I, Br], [EE499; 2, H, $CF_3$, Br], [EE500; 2, H, $CF_2H$, Br], [EE501; 2, H, $C_2F_5$, Br], [EE502; 2, H, $C_3F_7$, Br], [EE503; 2, H, $CH_2CF_3$, Br], [EE504; 2, H, $CH_2CHF_2$, Br], [EE505; 0, H, H, Cl], [EE506; 0, F, H, Cl], [EE507; 0, Cl, H, Cl], [EE508; 0, Br, H, Cl], [EE509; 0, I, H, Cl], [EE510; 0, $CF_3$, H, Cl], [EE511; 0, $CF_2H$, H, Cl], [EE512; 0, $C_2F_5$, H, Cl], [EE513; 0, $C_3F_7$, H, Cl], [EE514; 0, $CH_2CF_3$, H, Cl], [EE515; 0, $CH_2CHF_2$, H, Cl], [EE516; 1, H, H, Cl], [EE517; 1, F, H, Cl], [EE518; 1, Cl, H, Cl], [EE519; 1, Br, H, Cl], [EE520; 1, I, H, Cl], [EE521; 1, $CF_3$, H, Cl], [EE522; 1, $CF_2H$, H, Cl], [EE523; 1, $C_2F_5$, H, Cl], [EE524; 1, $C_3F_7$, H, Cl], [EE525; 1, $CH_2CF_3$, H, Cl], [EE526; 1, $CH_2CHF_2$, H, Cl], [EE527; 2, H, H, Cl], [EE528; 2, F, H, Cl], [EE529; 2, Cl, H, Cl], [EE530; 2, Br, H, Cl], [EE531; 2, I, H, Cl], [EE532; 2, $CF_3$, H, Cl], [EE533; 2, $CF_2H$, H, Cl], [EE534; 2, $C_2F_5$, H, Cl], [EE535; 2, $C_3F_7$, H, Cl], [EE536; 2, $CH_2CF_3$, H, Cl], [EE537; 2, $CH_2CHF_2$, H, Cl], [EE538; 0, H, F, Cl], [EE539; 0, H, Cl, Cl], [EE540; 0, H, Br, Cl], [EE541; 0, H, I, Cl], [EE542; 0, H, $CF_3$, Cl], [EE543; 0, H, $CF_2H$, Cl], [EE544; 0, H, $C_2F_5$, Cl], [EE545; 0, H, $C_3F_7$, Cl], [EE546; 0, H, $CH_2CF_3$, Cl], [EE547; 0, H, $CH_2CHF_2$, Cl], [EE548; 1, H, F, Cl], [EE549; 1, H, Cl, Cl], [EE550; 1, H, Br, Cl], [EE551; 1, H, I, Cl], [EE552; 1, H, $CF_3$, Cl], [EE553; 1, H, $CF_2H$, Cl], [EE554; 1, H, $C_2F_5$, Cl], [EE555; 1, H, $C_3F_7$, Cl], [EE556; 1, H, $CH_2CF_3$, Cl], [EE557; 1, H, $CH_2CHF_2$, Cl], [EE558; 2, H, F, Cl], [EE559; 2, H, Cl, Cl], [EE560; 2, H, Br, Cl], [EE561; 2, H, I, Cl], [EE562; 2, H, $CF_3$, Cl], [EE563; 2, H, $CF_2H$, Cl], [EE564; 2, H, $C_2F_5$, Cl], [EE565; 2, H, $C_3F_7$, Cl], [EE566; 2, H, $CH_2CF_3$, Cl], [EE567; 2, H, $CH_2CHF_2$, Cl], [EE568; 0, H, H, I], [EE569; 0, F, H, I], [EE570; 0, Cl, H, I], [EE571; 0, Br, H, I], [EE572; 0, I, H, I], [EE573; 0, $CF_3$, H, I], [EE574; 0, $CF_2H$, H, I], [EE575; 0, $C_2F_5$, H, I], [EE576; 0, $C_3F_7$, H, I], [EE577; 0, $CH_2CF_3$, H, I], [EE578; 0, $CH_2CHF_2$, H, I], [EE579; 1, H, H, I], [EE580; 1, F, H, I], [EE581; 1, Cl, H, I], [EE582; 1, Br, H, I], [EE583; 1, I, H, I], [EE584; 1, $CF_3$, H, I], [EE585; 1, $CF_2H$, H, I], [EE586; 1, $C_2F_5$, H, I], [EE587; 1, $C_3F_7$, H, I], [EE588; 1, $CH_2CF_3$, H, I], [EE589; 1, $CH_2CHF_2$, H, I], [EE590; 2, H, H, I], [EE591; 2, F, H, I], [EE592; 2, Cl, H, I], [EE593; 2, Br, H, I], [EE594; 2, I, H, I], [EE595; 2, $CF_3$, H, I], [EE596; 2, $CF_2H$, H, I], [EE597; 2, $C_2F_5$, H, I], [EE598; 2, $C_3F_7$, H, I], [EE599; 2, $CH_2CF_3$, H, I], [EE600; 2, $CH_2CHF_2$, H, I], [EE601; 0, H, F, I], [EE602; 0, H, Cl, I], [EE603; 0, H, Br, I], [EE604; 0, H, I, I], [EE605; 0, H, $CF_3$, I], [EE606; 0, H, $CF_2H$, I], [EE607; 0, H, $C_2F_5$, I], [EE608; 0, H, $C_3F_7$, I], [EE609; 0, H, $CH_2CF_3$, I], [EE610; 0, H, $CH_2CHF_2$, I], [EE611; 1, H, F, I], [EE612; 1, H, Cl, I], [EE613; 1, H, Br, I], [EE614; 1, H, I, I], [EE615; 1, H, $CF_3$, I], [EE616; 1, H, $CF_2H$, I], [EE617; 1, H, $C_2F_5$, I], [EE618; 1, H, $C_3F_7$, I], [EE619; 1, H, $CH_2CF_3$, I], [EE620; 1, H, $CH_2CHF_2$, I], [EE621; 2, H, F, I], [EE622; 2, H, Cl, I], [EE623; 2, H, Br, I], [EE624; 2, H, I, I], [EE625; 2, H, $CF_3$, I], [EE626; 2, H, $CF_2H$, I], [EE627; 2, H, $C_2F_5$, I], [EE628; 2, H, $C_3F_7$, I], [EE629; 2, H, $CH_2CF_3$, I], [EE630; 2, H, $CH_2CHF_2$, I], [EE631; 0, H, H, F], [EE632; 0, F, H, F], [EE633; 0, Cl, H, F], [EE634; 0, Br, H, F], [EE635; 0, I, H, F], [EE636; 0, $CF_3$, H, F], [EE637; 0, $CF_2H$, H, F], [EE638; 0, $C_2F_5$, H, F], [EE639; 0, $C_3F_7$, H, F], [EE640; 0, $CH_2CF_3$, H, F], [EE641; 0, $CH_2CHF_2$, H, F], [EE642; 1, H, H, F], [EE643; 1, F, H, F], [EE644; 1, Cl, H, F], [EE645; 1, Br, H, F], [EE646; 1, I, H, F], [EE647; 1, $CF_3$, H, F], [EE648; 1, $CF_2H$, H, F], [EE649; 1, $C_2F_5$, H, F], [EE650; 1, $C_3F_7$, H, F], [EE651; 1, $CH_2CF_3$, H, F], [EE652; 1, $CH_2CHF_2$, H, F], [EE653; 2, H, H, F], [EE654; 2, F, H, F], [EE655; 2, Cl, H, F], [EE656; 2, Br, H, F], [EE657; 2, I, H, F], [EE658; 2, $CF_3$, H, F], [EE659; 2, $CF_2H$, H, F], [EE660; 2, $C_2F_5$, H, F], [EE661; 2, $C_3F_7$, H, F], [EE662; 2, $CH_2CFA$, H, F], [EE663; 2, $CH_2CHF_2$, H, F], [EE664; 0, H, F, F], [EE665; 0, H, Cl, F], [EE666; 0, H, Br, F], [EE667; 0, H, I, F], [EE668; 0, H, $CF_3$, F], [EE669; 0, H, $CF_2H$, F], [EE670; 0, H, $C_2F_5$, F], [EE671; 0, H, $C_3F_7$, F], [EE672; 0, H, $CH_2CF_3$, F], [EE673; 0, H, $CH_2CHF_2$, F], [EE674; 1, H, F, F], [EE675; 1, H, Cl, F], [EE676; 1, H, Br, F], [EE677; 1, H, I, F], [EE678; 1, H, $CF_3$, F], [EE679; 1, H, $CF_2H$, F], [EE680; 1, H, $C_2F_5$, F], [EE681; 1, H, $C_3F_7$, F], [EE682; 1, H, $CH_2CF_3$, F], [EE683; 1, H, $CH_2CHF_2$, F], [EE684; 2, H, F, F], [EE685; 2, H, Cl, F], [EE686; 2, H, Br, F], [EE687; 2, H, I, F], [EE688; 2, H, $CF_3$, F], [EE689; 2, H, $CF_2H$, F], [EE690; 2, H, $C_2F_5$, F], [EE691; 2, H, $C_3F_7$, F], [EE692; 2, H, $CH_2CF_3$, F], [EE693; 2, H, $CH_2CHF_2$, F]

A compound represented by formula (L-18)

(L-18)

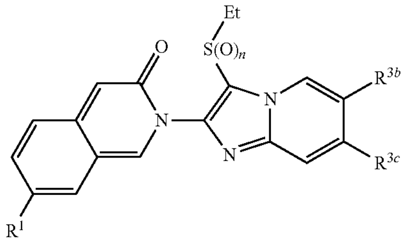

wherein the combination of the symbol n, and the substituents $R^{3b}$, $R^{3c}$, and $R^1$ represents any one combination indicated in the Combination EE (hereinafter referred to as "Compound group SX18").

A compound represented by formula (L-19)

(L-19)

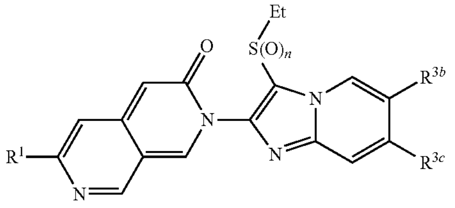

wherein the combination of the symbol n, and the substituents $R^{3b}$, $R^{3c}$, and $R^1$ represents any one combination indicated in the Combination EE (hereinafter referred to as "Compound group SX19").

A compound represented by formula (L-20)

(L-20)

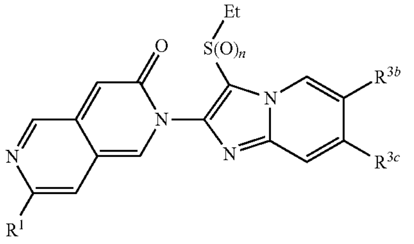

wherein the combination of the symbol n, and the substituents $R^{3b}$, $R^{3c}$, and $R^1$ represents any one combination indicated in the Combination EE (hereinafter referred to as "Compound group SX20").

A compound represented by formula (L-21)

(L-21)

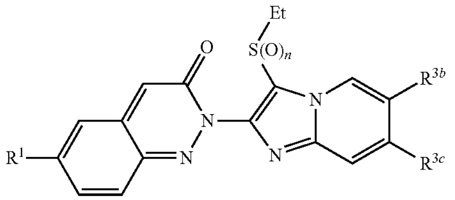

wherein the combination of the symbol n, and the substituents $R^{3b}$, $R^{3c}$, and $R^1$ represents any one combination indicated in the Combination EE (hereinafter referred to as "Compound group SX21").

A compound represented by formula (L-22)

(L-22)

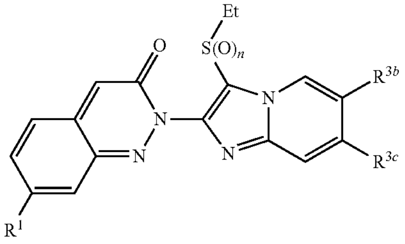

wherein the combination of the symbol n, and the substituents $R^{3b}$, $R^{3c}$, and $R^1$ represents any one combination indicated in the Combination EE (hereinafter referred to as "Compound group SX22").

A compound represented by formula (L-23)

(L-23)

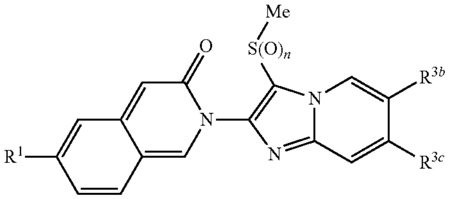

wherein the combination of the symbol n, and the substituents $R^{3b}$, $R^{3c}$, and $R^1$ represents any one combination indicated in the Combination EE (hereinafter referred to as "Compound group SX23").

A compound represented by formula (L-24)

(L-24)

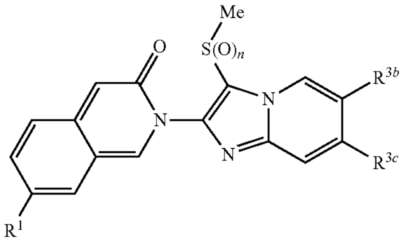

wherein the combination of the symbol n, and the substituents $R^{3b}$, $R^{3c}$, and $R^1$ represents any one combination indicated in the Combination EE (hereinafter referred to as "Compound group SX24").

A compound represented by formula (L-25)

(L-25)

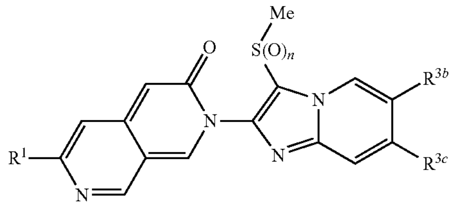

wherein the combination of the symbol n, and the substituents $R^{3b}$, $R^{3c}$, and $R^1$ represents any one combination indicated in the Combination EE (hereinafter referred to as "Compound group SX25").

A compound represented by formula (L-26)

(L-26)

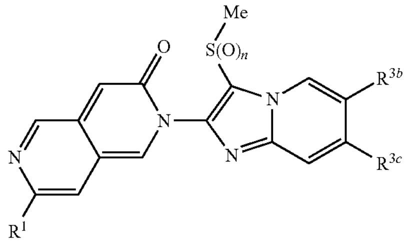

wherein the combination of the symbol n, and the substituents $R^{3b}$, $R^{3c}$, and $R^1$ represents any one combination indicated in the Combination EE (hereinafter referred to as "Compound group SX26").

A compound represented by formula (L-27)

(L-27)

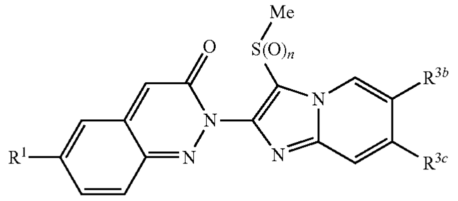

wherein the combination of the symbol n, and the substituents $R^{3b}$, $R^{3c}$, and $R^1$ represents any one combination indicated in the Combination EE (hereinafter referred to as "Compound group SX27").

A compound represented by formula (L-28)

(L-28)

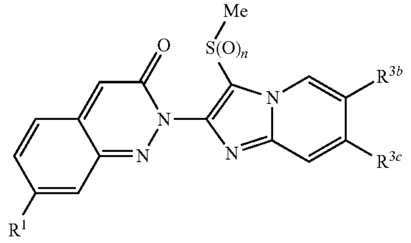

wherein the combination of the symbol n, and the substituents $R^{3b}$, $R^{3c}$, and $R^1$ represents any one combination indicated in the Combination EE (hereinafter referred to as "Compound group SX28").

Next, Formulation Examples of the Present compounds are shown below. The "part(s)" represents "part(s) by weight". Also, the expression of "Present compound S" represents the compounds described in the Compound groups SX1 to SX28.

Formulation Example 1

A mixture of polyoxyethylene alkyl ether sulfate ammonium salt and silica (weight ratio of 1:1) (35 parts), any one of the Present compound S (10 parts), and water (55 parts) are mixed, and the resulting mixture is subjected to fine grinding according to a wet grinding method to obtain each formulation.

Formulation Example 2

Any one of the Present compound S (50 parts), calcium lignin sulfonate (3 parts), sodium lauryl sulfate (2 parts), and silica (45 parts) are ground and mixed to obtain each formulation.

Formulation Example 3

Any one of the Present compound S (5 parts), polyoxyethylene styryl phenyl ether (9 parts), polyoxyethylene decyl ether (number of added ethylene-oxide: 5) (5 parts), calcium dodecylbenzene sulfonate (6 parts), and xylene (75 parts) are mixed to obtain each formulation.

Formulation Example 4

Any one of the Present compound S (2 parts), silica (1 part), calcium lignin sulfonate (2 parts), bentonite (30 parts), and kaolin clay (65 parts) are ground and mixed, an appropriate amount of water is added thereto, the resulting mixture is kneaded, subjected to granulation with a granulator, and then dried to obtain each formulation.

Formulation Example 5

Any one of the Present compound S (10 parts), and a mixture of benzyl alcohol (18 parts) and DMSO (9 parts) are mixed, GERONOL (registered trademark) TE250 (6.3 parts), Ethylan (registered trademark) NS-500LQ (2.7 parts), and solvent naphtha (54 parts) are added thereto, and the resulting mixture is mixed to obtain each formulation.

Formulation Example 6

Any one of the Present compound S (0.1 part) is mixed with kerosene (39.9 parts) and dissolved therein, the resulting solution is placed into an aerosol container, and the container is filled with liquefied petroleum gas (a mixture of propane, butane, and isobutane; saturated vapor pressure: 0.47 MPa (25° C.)) (60 parts) to obtain each formulation.

Formulation Example 7

Any one of the Present compound S (0.2 part), lees powder extracted from pyrethrum (50 parts), Tabu powder (30 parts), and wood powder (19.8 parts) are mixed, an appropriate amount of water is added thereto, the resulting mixture is kneaded, then subjected to an extruder to obtain a plate sheet, and the plate sheet is subjected to a punching machine to be converted into a spiral shape to obtain each formulation.

Next, Test Examples are used to show effects of the Present compounds on harmful arthropods. In the following Test Examples, the tests were carried out at 25° C.

Test Method 1

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all developmental stages of life) are released onto the leaves of the cucumber. After 1 day, the diluted solutions are sprayed to the seedling at a ratio of 10 mL/seedling. Further, after 5 days, the number of the surviving insects is examined and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the "untreated group" represents a group where the similar treatment procedure to that of the treated group except not using the test compound is done.

Test Example 1-1

The test was conducted by making the prescribed concentration 500 ppm and using each of the Present compounds as a test compound according to the Test Method 1. As a result of the test, the below-mentioned Present compounds showed 90% or greater as the controlling value.

Present compounds: 6, 7, 8, and 9

Test Method 2

Each test compound is made to a formulation according to a similar method to that described in the Formulation Example 5, and thereto is added water to prepare a diluted solution containing a prescribed concentration of the test compound.

Cucumber (cucumber sativus) seedling (on the developmental stage of the second true leaf) is planted in a container, and the diluted solutions are drenched to the bottom of the seedling at a ratio of 5 mL/seedling. After 7 days, approximately 30 cotton aphids (*Aphis gossypii*) (all developmental stages of life) are released onto the leaf of the seedling. After 6 days, the number of the surviving insects is examined and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the "untreated group" represents a group where the similar treatment procedure to that of the treated group except not using the test compound is done.

Test Example 2-1

The test was conducted by making the prescribed concentration 1000 ppm and using each of the below-mentioned Present compounds as a test compound according to the Test Method 2. As a result of the test, the below-mentioned Present compounds showed 90% or greater as the controlling value.

Present compounds: 6 and 9

Test Example 2-2

The test was conducted by making the prescribed concentration 250 ppm and using each of the below-mentioned Present compounds as a test compound according to the Test Method 2. As a result of the test, the below-mentioned Present compounds showed 90% or greater as the controlling value.

Present compounds: 6, 7, 8, and 9

Test Example 2-3

The test was conducted by making the prescribed concentration 200 ppm and using each of the below-mentioned Present compounds as a test compound according to the Test Method 2. As a result of the test, the below-mentioned Present compounds showed 90% or greater as the controlling value.

Present compounds: 6 and 9

Test Example 2-4

The test was conducted by making the prescribed concentration 50 ppm and using each of the below-mentioned Present compounds as a test compound according to the Test Method 2. As a result of the test, the below-mentioned Present compounds showed 90% or greater as the controlling value.

Present compounds: 6, 7, 8, and 9

Test Method 3

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Five of second-instar larvae of cotton worm (*Spodoptera litura*) are released into the container. After 5 days, the number of the surviving insects is counted, and the mortality of insects is calculated by the following equation.

$$\text{Mortality (\%)}=(1-\text{Number of surviving insects}/5)\times 100$$

Test Example 3-1

The test was conducted by making the prescribed concentration 500 ppm and using each of the below-mentioned Present compounds as a test compound according to the Test Method 3. As a result of the test, the below-mentioned Present compounds showed 80% or greater as the mortality.

Present compounds: 4, 6, 7, and 8

Test Method 4

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Five of second-instar larvae of diamondback moth (*Plutella xylostella*) are released into the container. After 5 days, the number of the surviving insects is counted, and the mortality of insects is calculated by the following equation.

$$\text{Mortality (\%)}=(1-\text{Number of surviving insects}/5)\times 100$$

Test Example 4-1

The test was conducted by making the prescribed concentration 500 ppm and using each of the Present compounds as a test compound according to the Test Method 4. As a result of the test, the below-mentioned Present compounds showed 80% or greater as the mortality.

Present compounds: 6, 7, and 8

Test Method 5

Each 1 mg of the test compounds is dissolved in 50 μL of a mixed solution consisting of 5% of polyoxyethylene sorbitan mono-cocoate and 95% of acetone by volume ratio. Thereto is added water containing 0.03% by volume of Shindain (registered trademark) to prepare a diluted solution containing a prescribed concentration of the test compound.

A young seedling of corn (*Zea mays*) is immersed into the diluted solution for 30 seconds. Thereafter, two seedlings are installed in a plastic petri dish (90 mm radius), and 10 of second-instar larvae of Western corn rootworm (*Diabrotica virgifera virgifera*) are released into the dish. After 5 days, the number of the dead insects is counted, and the mortality of insects is calculated by the following equation.

$$\text{Mortality (\%)}=(\text{Number of dead insects}/10)\times 100$$

Test Example 5-1

The test was conducted by making the prescribed concentration 200 ppm and using each of the below-mentioned Present compounds as a test compound according to the Test Method 5. As a result of the test, the below-mentioned Present compounds showed 80% or greater as the mortality.

Present compounds: 6, 7, and 8

Test Example 5-2

The test is conducted by making the prescribed concentration 50 ppm and using each of the Present compounds as a test compound according to the Test Method 5, and the effect of the test compound can be confirmed.

Test Method 6

An acetone solution which is adjusted to 800 ppm of each test compound is poured into a 50 mL glass vial, and the test compound is coated uniformly on inner face of the vial so as to 40 mg/$m^2$ of the test compound treated, and the vial is then dried.

5 German cockroach (*Blattella germanica*) male adults are released into the treated vial, and the vial is then covered with lid. After the prescribed time, the state of the German cockroach is examined, and the mortality is calculated by the following equation.

$$\text{Mortality (\%)}=(\text{Number of dead insects}/\text{Number of tested insects})\times 100$$

Test Example 6-1

The test was conducted by making the prescribed time 1 days and using each of the below-mentioned Present compounds as a test compound according to the Test Method 6. As a result of the test, the below-mentioned Present compounds showed 80% or greater as the mortality.

Present compounds: 6 and 8

Test Example 6-2

The test was conducted by making the prescribed time 3 days and using each of the below-mentioned Present compounds as a test compound according to the Test Method 6. As a result of the test, the below-mentioned Present compounds showed 80% or greater as the mortality.

Present compounds: 6, 7, and 8

Test Method 7

An acetone solution which is adjusted to 2000 ppm of each test compound is poured into a 20 mL glass vial, and the test compound is coated uniformly on inner face of the vial so as to 100 mg/$m^2$ of the test compound treated, and the vial is then dried.

5 *Haemaphysalis longicornis* nymphs are released into the treated vial, and the vial is then covered with lid. After the prescribed time, the state of the *Haemaphysalis longicornis* is examined, and the mortality is calculated by the following equation.

$$\text{Mortality (\%)}=(\text{Number of dead insects}/\text{Number of tested insects})\times 100$$

Test Method 8

An acetone solution which is adjusted to 800 ppm of each test compound is poured into a 20 mL glass vial, and the test compound is coated uniformly on inner face of the vial so as to 40 mg/$m^2$ of the test compound treated, and the vial is then dried.

5 housefly (*Musca domestica*) female adults are released into the treated vial, and the vial is then covered with lid. After the prescribed time, the state of the housefly is examined, and the mortality is calculated by the following equation.

$$\text{Mortality (\%)}=(\text{Number of dead insects}/\text{Number of tested insects})\times 100$$

Test Example 8-1

The test was conducted by making the prescribed time 1 hour and using each of the below-mentioned Present compounds as a test compound according to the Test Method 8. As a result of the test, the below-mentioned Present compounds showed 80% or greater as the mortality.

Present compounds: 6, 7, and 8

Test Method 9

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all developmental stages of life) are released onto the leaves of the cucumber. After 1 day, the diluted solutions are sprayed to the seedling at a ratio of 10 mL/seedling. Further, after 5 days, the number of the surviving insects is examined and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the "untreated group" represents a group where the similar treatment procedure to that of the treated group except not using the test compound is done.

Test Example 9-1

The test was conducted by making the prescribed concentration 200 ppm and using the below-mentioned Present compound as a test compound according to the Test Method 9. As a result of the test, the below-mentioned Present compound showed 90% or greater as the controlling value.

Present compound: 6

Test Example 9-2

The test was conducted by making the prescribed concentration 50 ppm and using each of the below-mentioned Present compounds as a test compound according to the Test Method 9. As a result of the test, the below-mentioned Present compounds showed 90% or greater as the controlling value.

Present compounds: 5, 6, 7, and 8

Test Method 10

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the third to fourth true leaf) is planted in a container, and the diluted solutions are sprayed to the seedling at a ratio of 20 mL/seedling. Thereafter, ten of third-instar larvae of cotton worm (*Spodoptera litura*) are released. After 6 days, the number of the surviving insects is counted, and the mortality of insects is calculated by the following equation.

$$\text{Mortality (\%)}=(1-\text{Number of surviving insects}/10)\times 100$$

Test Example 10-1

The test was conducted by making the prescribed concentration 200 ppm and using the below-mentioned Present compound as a test compound according to the Test Method 10. As a result of the test, the below-mentioned Present compound showed 80% or greater as the mortality.

Present compound: 6

Test Example 10-2

The test was conducted by making the prescribed concentration 50 ppm and using each of the below-mentioned Present compounds as a test compound according to the Test Method 10. As a result of the test, the below-mentioned Present compounds showed 80% or greater as the mortality.

Present compounds: 5, 6, 7, and 8

Test Method 11

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the third to fourth true leaf) is planted in a container, and the diluted solutions are sprayed to the seedling at a ratio of 20 mL/seedling. Thereafter, ten of third-instar larvae of diamondback moth (*Plutella xylostella*) are released. After 5 days, the number of the surviving insects is counted, and the mortality of insects is calculated by the following equation.

$$\text{Mortality (\%)}=(1-\text{Number of surviving insects}/10)\times 100$$

Test Example 11-1

The test was conducted by making the prescribed concentration 200 ppm and using the below-mentioned Present compound as a test compound according to the Test Method 11. As a result of the test, the below-mentioned Present compound showed 80% or greater as the mortality.

Present compound: 6

Test Example 11-2

The test was conducted by making the prescribed concentration 50 ppm and using each of the below-mentioned Present compounds as a test compound according to the Test Method 11. As a result of the test, the below-mentioned Present compounds showed 80% or greater as the mortality.

Present compounds: 5, 6, 7, and 8

Test Method 12

Each test compound is formulated to a test formulation according to a similar method to that described in the Formulation Example 1, and water is added in preparing for a diluted solution containing a prescribed concentration of the test compound.

Into the diluted solution, 30 last instar larvae of common house mosquito (*Culex pipiens pallens*) are released, and after 1 day, the state of the house mosquito larvae is examined, and the mortality is calculated by the following equation.

$$\text{Mortality (\%)}=(\text{Number of dead insects}/\text{Number of tested insects})\times 100$$

Test Example 12-1

The test was conducted by making the prescribed concentration 3.5 ppm and using each of the below-mentioned Present compounds as a test compound according to the Test Method 12. As a result of the test, the below-mentioned Present compounds showed 91% or greater as the mortality.

Present compounds: 6, 7, 8, 9, and 11

Test Method 13

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Five of second-instar larvae of diamondback moth (*Plutella xylostella*) are released into the container. After 5 days, the number of the surviving insects is counted, and the mortality of insects is calculated by the following equation.

$$\text{Mortality (\%)}=(1-\text{Number of surviving insects}/5)\times 100$$

Test Example 13-1

The test was conducted by making the prescribed concentration 500 ppm and using each of the below-mentioned Present compounds as a test compound according to the Test Method 13. As a result of the test, the below-mentioned Present compounds showed 80% or greater as the mortality.

Present compounds: 6, 7, and 8

Test Method 14

An acetone solution which is adjusted to 200 ppm of each test compound is poured into a 20 mL glass vial, and the test compound is coated uniformly on inner face of the vial so as to 10 mg/m$^2$ of the test compound treated, and the vial is then dried.

5 common house mosquito (*Culex pipiens pallens*) female adults are released into the treated vial, and the vial is then covered with lid. After the prescribed time, the state of the common house mosquito is examined, and the mortality is calculated by the following equation.

$$\text{Mortality (\%)}=(\text{Number of dead insects}/\text{Number of tested insects})\times 100$$

Test Example 14-1

The test was conducted by making the prescribed time 1 day and using each of the below-mentioned Present compounds as a test compound according to the Test Method 14. As a result of the test, the below-mentioned Present compounds showed 80% or greater as the mortality.

Present compounds: 6, 7, and 8

Test Method 15

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cucumber (cucumber *sativus*) seedling (on the developmental stage of the second leaf) is planted in a container, and the diluted solutions are sprayed into the seedling at a ratio of 10 mL/seedling. Thereafter, the first true leaf thereof is cut out and then is installed into a container, and about twenty (20) instar larvae of Western flower *thrips* (*Frankliniella occidentalis*) are released. After 7 days, the number of the surviving insects is examined, and the mortality is calculated by the following equation.

$$\text{Mortality (\%)}=\{1-\text{the number of the surviving insects}/20\}\times 100$$

Test Example 15-1

The test is conducted by making the prescribed concentration 200 ppm and using each of the Present compounds as a test compound according to the Test Method 15, and the effect of the test compound can be confirmed.

Test Example 15-2

The test is conducted by making the prescribed concentration 50 ppm and using each of the Present compounds as a test compound according to the Test Method 15, and the effect of the test compound can be confirmed.

Test Method 16

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Silverleaf whiteflies (*Bemisia tabaci*) are released on tomato (*Lycopersicon esculentum*) seedling that is planted in a container, and then spawn for about 24 hours. The seedling is stored for 8 days, and the larvae of silverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the insects shortly before the treatment in untreated group;

Cai: Number of the surviving insects at the time of the investigation in untreated group;

Tb: Number of the insects shortly before the treatment in treated group;

Tai: Number of the surviving insects at the time of the investigation in treated group;

Here the “untreated group” represents a group where the similar treatment procedure to that of the treated group except not using the test compound is done.

Test Example 16-1

The test is conducted by making the prescribed concentration 200 ppm and using each of the Present compounds as a test compound according to the Test Method 16, and the effect of the test compound can be confirmed.

Test Example 16-2

The test is conducted by making the prescribed concentration 50 ppm and using each of the Present compounds as a test compound according to the Test Method 16, and the effect of the test compound can be confirmed.

Test Method 17

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the number of the surviving insects is examined, and the mortality is calculated by the following equation.

Mortality (%)={1−the number of the surviving insects/20}×100

Test Example 17-1

The test is conducted by making the prescribed concentration 500 ppm and using each of the Present compounds as a test compound according to the Test Method 17, and the effect of the test compound can be confirmed.

Test Example 17-2

The test is conducted by making the prescribed concentration 200 ppm and using each of the Present compounds as a test compound according to the Test Method 17, and the effect of the test compound can be confirmed.

Test Example 17-3

The test is conducted by making the prescribed concentration 50 ppm and using each of the Present compounds as a test compound according to the Test Method 17, and the effect of the test compound can be confirmed.

Test Method 18

Each 1 mg of the Present compounds is dissolved in 10 μL of a mixed solution consisting of four ninths of xylene, four ninths of dimethylformamide, and one ninth of surfactant by volume ratio. Thereto is added water containing 0.02% by volume of a spreader to prepare diluted solution A containing a prescribed concentration of the Present compound.

Each 1 mg of the Present ingredients is dissolved in 10 μL of a mixed solution consisting of four ninths of xylene, four ninths of dimethylformamide, and one ninth of surfactant by volume ratio. Thereto is added water containing 0.02% by volume of a spreader to prepare diluted solution B containing a prescribed concentration of the Present ingredient.

The diluted solution A is mixed with the diluted solution B to prepare diluted solution C.

A leaf disc of cotyledon of cucumber (*Cucumis sativus*) (1.5 cm in length) is cut out and installed in each well of a 24-well microplate, and 2 apterous adults and 8 nymphs of cotton aphid (*Aphis gossypii*) are release onto the leaf disc in each well. The diluted solution C is sprayed to each leaf disc at the ratio of 20 μL/leaf disc. The procedure mentioned above represents the treated group.

Whereas, the untreated group represents a group where the similar treatment procedure to that of the treated group is done except 20 μL of water containing 0.02% by volume of a spreader is used instead of using the diluted solution C.

After the sprayed diluted solution C is dried, the microplate is covered with a film sheet. After 5 days, the number of the surviving insects in each well is examined and the controlling value is calculated by the following equation.

Controlling value (%)={1−(*Tai*)/(*Cai*)}×100 wherein the symbols in the formula represent the following descriptions.

Cai: Number of the surviving insects at the time of the investigation in untreated group;

Tai: Number of the surviving insects at the time of the investigation in treated group.

Specific diluted solutions C, which can confirm their effects according to the Test Method 18, are described in the following 1) to 5).

1) The diluted solution C comprises the combination recited in List A wherein a concentration of the Present compound is 200 ppm and a concentration of the Present ingredient is 2000 ppm. In List A, Comp X represents any one compound selected from the Present compound 1 to the Present compound 16 described in Examples.

List A:

Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Camp X+benzovindiflupyr; Camp X+boscalid; Comp X+carboxin; Comp X+penthiopyrad; Comp X+flutolanil; Comp X+captan; Comp X+thiram; Comp X+tolclofos-methyl; Camp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the Present compound is 200 ppm and a concentration of the Present ingredient is 200 ppm.

3) The diluted solution C comprises the combination recited in List A wherein a concentration of the Present compound is 500 ppm and a concentration of the Present ingredient is 50 ppm.

4) The diluted solution C comprises the combination recited in List A wherein a concentration of the Present compound is 500 ppm and a concentration of the Present ingredient is 5 ppm.

5) The diluted solution C comprises the combination recited in List A wherein a concentration of the Present compound is 500 ppm and a concentration of the Present ingredient is 0.5 ppm.

INDUSTRIAL APPLICABILITY

The Present compounds have excellent control effects on harmful arthropods.

The invention claimed is:

1. A compound represented by the following formula (I);

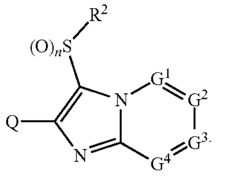

(I)

wherein:

$R^2$ represents a C1-C6 alkyl group optionally substituted with at least one halogen atom, a cyclopropyl group, or a cyclopropylmethyl group;

n represents 0, 1, or 2;

$G^1$ represents a nitrogen atom or $CR^{3a}$;

$G^2$ represents a nitrogen atom or $CR^{3b}$;

$G^3$ represents a nitrogen atom or $CR^{3c}$;

$G^4$ represents a nitrogen atom or $CR^{3d}$;

$R^{3a}$, $R^{3b}$, $R^{3c}$, and $R^{3d}$ are identical to or different from each other, and each represent a C1-C6 chain hydrocarbon group optionally substituted with at least one substituent selected from Group B, a C3-C7 cycloalkyl group optionally substituted with at least one substituent selected from Group E, a phenyl group optionally substituted with at least one substituent selected from Group H, a 5 or 6 membered aromatic heterocyclic group optionally substituted with at least one substituent selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_p R^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_mR^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with at least one halogen atom, a halogen atom, $OR^{35}$, $NR^{36}R^{37}$, or a hydrogen atom;

$R^{35}$ represents a C1-C6 chain hydrocarbon group optionally substituted with at least one halogen atom;

$R^{17}$ represents a C1-C6 chain hydrocarbon group optionally substituted with at least one halogen atom, a phenyl group optionally substituted with at least one substituent selected from Group D, or a hydrogen atom;

$R^{11}$, $R^{24}$, $R^{36}$, and $R^{37}$ are identical to or different from each other, and each represent a C1-C6 chain hydrocarbon group optionally substituted with at least one halogen atom, or a hydrogen atom;

$R^{12}$ represents a C1-C6 chain hydrocarbon group optionally substituted with at least one substituent selected from Group F, a C3-C7 cycloalkyl group optionally substituted with at least one substituent selected from Group J, a C3-C7 cycloalkenyl group optionally substituted with at least one substituent selected from Group J, a phenyl group optionally substituted with at least one substituent selected from Group D, a 6 membered aromatic heterocyclic group optionally substituted with at least one halogen atom selected from Group D, a hydrogen atom, or $S(O)_2R^{23}$;

$R^{23}$ represents a C1-C6 chain hydrocarbon group optionally substituted with at least one halogen atom, or a phenyl group optionally substituted with at least one substituent selected from Group D;

$R^{11a}$ and $R^{12a}$ are combined with the nitrogen atom to which they are attached to form a 3-7 membered nonaromatic heterocyclic group optionally substituted with at least one substituent selected from Group E;

$R^{13}$ represents a C1-C6 chain hydrocarbon group optionally substituted with at least one halogen atom, a C3-C7 cycloalkyl group optionally substituted with at least one halogen atom, a (C3-C6 cycloalkyl) C1-C3 alkyl group optionally substituted with at least one halogen atom, a phenyl group optionally substituted with at least one substituent selected from Group D, a 5 or 6 membered aromatic heterocyclic group optionally substituted with at least one substituent selected from Group D, or a hydrogen atom;

$R^{14}$ represents a C1-C6 chain hydrocarbon group optionally substituted with at least one halogen atom, a C3-C7 cycloalkyl group optionally substituted with at least one halogen atom, a (C3-C6 cycloalkyl) C1-C3 alkyl group optionally substituted with at least one halogen atom, or a phenyl C1-C3 alkyl group, wherein the phenyl moiety in said phenyl C1-C3 alkyl group is optionally substituted with at least one substituent selected from Group D;

$R^{15}$ and $R^{16}$ are identical to or different from each other, and each represent a C1-C6 alkyl group optionally substituted with at least one halogen atom;

$R^{31}$ represents a C1-C6 alkyl group optionally substituted with at least one halogen atom, or a hydrogen atom;

$R^{32}$ represents a C1-C6 chain hydrocarbon group optionally substituted with at least one substituent selected from Group F, a C3-C7 cycloalkyl group optionally substituted with at least one substituent selected from Group J, $S(O)_2R^{23}$, or a hydrogen atom;

Q represents a group represented by Q1, a group represented by Q2, a group represented by Q3, a group represented by Q4, or a group represented by Q5;

Q1

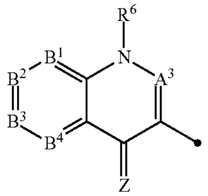

-continued

Q2

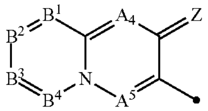

Q3

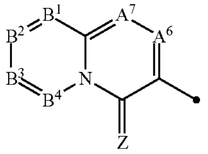

Q4

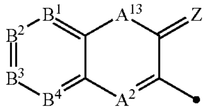

Q5

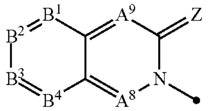

● represents the binding site to the rest of molecule;

Z represents an oxygen atom or a sulfur atom;

$A^2$ represents a nitrogen atom or $CR^{4a}$;

$A^3$ represents a nitrogen atom or $CR^{4b}$;

$A^4$ represents a nitrogen atom or $CR^{4c}$;

$A^5$ represents a nitrogen atom or $CR^{4d}$;

$A^6$ represents a nitrogen atom or $CR^{4e}$;

$A^7$ represents a nitrogen atom or $CR^{4f}$;

$A^8$ represents a nitrogen atom or $CR^{4g}$;

$A^9$ represents a nitrogen atom or $CR^{4h}$;

$A^{13}$ represents an oxygen atom, a sulfur atom, or $NR^6$;

the combination of $B^1$, $B^2$, $B^3$, and $B^4$ represents:

a combination wherein $B^1$ represents $CR^1$, $B^2$ represents a nitrogen atom or $CR^{6b}$, $B^3$ represents a nitrogen atom or $CR^{6c}$, and $B^4$ represents a nitrogen atom or $CR^{6d}$;

a combination wherein $B^1$ represents a nitrogen atom or $CR^{6a}$, $B^2$ represents $CR^1$, $B^3$ represents a nitrogen atom or $CR^{6c}$, and $B^4$ represents a nitrogen atom or $CR^{6d}$, provided that a combination wherein $B^1$, $B^2$, $B^3$, and $B^4$ all represent CH is excluded;

a combination wherein $B^1$ represents a nitrogen atom or $CR^{6a}$, $B^2$ represents a nitrogen atom or $CR^{6b}$, $B^3$ represents $CR^1$, and $B^4$ represents a nitrogen atom or $CR^6$d provided that a combination wherein $B^1$, $B^2$, $B^3$, and $B^4$ all represent CH is excluded;

a combination wherein $B^1$ represents a nitrogen atom or $CR^{6a}$, $B^2$ represents a nitrogen atom or $CR^{6b}$, $B^3$ represents $CR^{6c}$, and $B^4$ represents $CR^1$ provided that a combination wherein $B^1$, $B^2$, $B^3$, and $B^4$ all represent CH is excluded; or a combination wherein $B^1$ represents a nitrogen atom or $CR^{6a}$, $B^2$ represents $CR^{6b}$, $B^3$ represents a nitrogen atom, and $B^4$ represents $CR^1$;

$R^1$ represents a C1-C6 chain hydrocarbon group optionally substituted with at least one substituent selected from the group consisting of a cyano group and a halogen atom, a C3-C4 cycloalkyl group optionally substituted with at least one substituent selected from the group consisting of a cyano group and a halogen atom, $S(O)_kR^8$, $OR^8$, a halogen atom, $OS(O)_2R^8$, or a hydrogen atom;

$R^8$ represents a C1-C6 chain hydrocarbon group optionally substituted with at least one substituent selected from the group consisting of a cyano group and a halogen atom; or a C3-C4 cycloalkyl group optionally substituted with at least one substituent selected from the group consisting of a cyano group and a halogen atom;

k represents 0, 1, or 2;

$R^{4a}$, $R^{4b}$, $R^{4c}$, $R^{4d}$, $R^{4f}$, $R^{4g}$, and $R^{4h}$ are identical to or different from each other, and each represent a C1-C6 chain hydrocarbon group optionally substituted with at least one halogen atom, a nitro group, $OR^{18}$, $NR^{18}R^{19}$, a cyano group, an amino group, a halogen atom, or a hydrogen atom;

$R^{4e}$ represents a C1-C6 chain hydrocarbon group optionally substituted with at least one halogen atom, a nitro group, $OR^{18}$, $NR^{18}R^{19}$, a cyano group, an amino group, a halogen atom, a hydroxy group, or a hydrogen atom;

$R^{6a}$, $R^{6b}$, $R^{6c}$, and $R^{6d}$ are identical to or different from each other, and each represent a C1-C6 chain hydrocarbon group optionally substituted with at least one halogen atom, a C3-C7 cycloalkyl group optionally substituted with at least one halogen atom, a C1-C6 alkoxy group optionally substituted with at least one halogen atom, a halogen atom, or a hydrogen atom;

$R^{18}$ represents a C1-C6 chain hydrocarbon group optionally substituted with at least one halogen atom;

$R^{19}$ represents a C1-C6 chain hydrocarbon group optionally substituted with at least one halogen atom, or a hydrogen atom; and $R^6$ represents a C1-C6 chain hydrocarbon group optionally substituted with at least one substituent selected from Group F, a C3-C6 cycloalkyl group optionally substituted with at least one substituent selected from Group J, a phenyl group optionally substituted with at least one substituent selected from Group H, a 5 or 6 membered aromatic heterocyclic group optionally substituted with at least one substituent selected from Group H, or a hydrogen atom;

Group B: a group consisting of a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a C1-C6 alkylsulfanyl group optionally substituted with at least one halogen atom, a C1-C6 alkylsulfinyl group optionally substituted with at least halogen atom, a C1-C6 alkylsulfonyl group optionally substituted with at least one halogen atom, a C3-C6 cycloalkyl group optionally substituted with at least one halogen atom, a cyano group, a hydroxy group, and a halogen atom;

Group C: a group consisting of a C1-C6 chain hydrocarbon group optionally substituted with at least one halogen atom, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, and a halogen atom;

Group D: a group consisting of a C1-C6 chain hydrocarbon group optionally substituted with at least one halogen atom, a hydroxy group, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a sulfanyl group, a C1-C6 alkylsulfanyl group optionally substituted with at least one halogen atom, a C1-C6 alkylsulfinyl group optionally substituted with at least one halogen atom, a C1-C6 alkylsulfonyl group optionally substituted with at least one halogen atom, an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with at least one halogen atom;

Group E: a group consisting of a C1-C6 chain hydrocarbon group optionally substituted with at least one halogen atom, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a halogen atom, an oxo group, a hydroxy group, a cyano group, and a nitro group;

Group F: a group consisting of a CT-C6 alkoxy group optionally substituted with at least one halogen atom, a phenyl group optionally substituted with at least one substituent selected from Group D, a 5 or 6 membered aromatic heterocyclic group optionally substituted with at least one substituent selected from Group D, a C3-C7 cycloalkyl group optionally substituted with at least one halogen atom, a 3-7 membered nonaromatic heterocyclic group optionally substituted with at least one substituent selected from Group C, an amino group, $NHR^{21}$, $NR^{21}R^{22}$, a halogen atom, and a cyano group;

Group H: a group consisting of a C1-C6 alkyl group optionally substituted with at least one halogen atom, a 5 or 6 membered aromatic heterocyclic group optionally substituted with at least one substituent selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with at least one halogen atom, or a C3-C6 cycloalkyl group optionally substituted with at least one halogen atom;

$R^{10}$ represents a C1-C6 alkyl group optionally substituted with at least one halogen atom, a C3-C6 cycloalkyl group optionally substituted with at least one halogen atom, or a hydrogen atom;

Group J: a group consisting of a C1-C6 alkyl group optionally substituted with at least one halogen atom, a halogen atom, and a cyano group]

or an N-oxide thereof.

2. The compound or an N-oxide thereof according to claim 1, wherein $R^2$ represents a C1-C6 alkyl group optionally substituted with at least one halogen atom;

$G^1$ represents $CR^{3a}$;

$G^2$ represents $CR^{3b}$;

$G^3$ represents $CR^{3c}$;

$G^4$ represents $CR^{3d}$;

$R^{3a}$, $R^{3b}$, $R^{3c}$, and $R^{3d}$ are identical to or different from each other, and each represent a C1-C6 chain hydrocarbon group optionally substituted with at least one halogen atom, a C3-C7 cycloalkyl group, wherein said C3-C7 cycloalkyl group is optionally substituted with at least one substituent selected from the group consisting of a halogen atom and a cyano group, a hydrogen atom, or a halogen atom;

Q represents the group represented by Q2, the group represented by Q3, the group represented by Q4, or the group represented by Q5;

Z represents an oxygen atom;

$A^4$ represents a nitrogen atom;

$A^5$ represents CH;

$A^6$ represents CH;

$A^7$ represents a nitrogen atom;

$A^8$ represents $CR^{4g}$;

the combination of $B^1$, $B^2$, $B^3$, and $B^4$ represents:

a combination wherein $B^1$ represents a nitrogen atom or $CR^{6a}$, $B^2$ represents $CR^1$, $B^3$ represents a nitrogen atom or $CR^{6c}$, and $B^4$ represents $CR^{6d}$; or a combination wherein $B^1$ represents $CR^{6a}$, $B^2$ represents $CR^{6b}$, $B^3$ represents $CR^1$, and $B^4$ represents $CR^{6d}$;

$R^1$ represents a C1-C6 chain hydrocarbon group optionally substituted with at least one halogen atom, a C3-C4 cycloalkyl group optionally substituted with at least one halogen atom, or a halogen atom; and $R^{6a}$, $R^{6b}$, $R^{6c}$, and $R^{6d}$ each represent a hydrogen atom.

3. The compound or an N-oxide thereof according to claim 2, wherein

Q represents the group represented by Q2 or the group represented by Q3;

the combination of $B^1$, $B^2$, $B^3$, and $B^4$ represents:

a combination wherein $B^1$ represents $CR^{6a}$, $B^2$ represents $CR^1$, $B^3$ represents $CR^{6c}$, and $B^4$ represents $CR^{6d}$; or a combination wherein $B^1$ represents $CR^{6a}$, $B^2$ represents $CR^{6b}$, $B^3$ represents $CR^1$, and $B^4$ represents $CR^{6d}$; and $R^1$ represents a C1-C6 chain hydrocarbon group optionally substituted with at least one halogen atom, or a halogen atom.

4. The compound or an N-oxide thereof according to claim 2, wherein $R^{3a}$, $R^{3b}$, $R^{3c}$, and $R^{3d}$ are identical to or different from each other, and each represent a C1-C6 chain hydrocarbon group optionally substituted with at least one halogen atom, a hydrogen atom, or a halogen atom.

5. A composition for controlling a harmful arthropod comprising the compound or an N-oxide thereof of claim 1.

6. A composition comprising the compound or an N-oxide thereof of claim 1, and at least one ingredient selected from the group consisting of Group (a), Group (b), Group (c), and Group (d):

Group (a): a group consisting of insecticidal active ingredients, miticidal active ingredients, and nematicidal active ingredients;

Group (b): fungicidal active ingredients;

Group (c): plant growth regulatory ingredients; and

Group (d): repellent ingredients.

7. A method for controlling a harmful arthropod, comprising applying an effective amount of the compound or an N-oxide thereof of claim 1 to a harmful arthropod or a habitat where a harmful arthropod lives.

8. A seed or a vegetative reproductive organ comprising the compound or an N-oxide thereof claim 1.

9. A method for controlling a harmful arthropod, comprising applying an effective amount of the composition of claim 6 to a harmful arthropod or a habitat where a harmful arthropod lives.

10. A seed or a vegetative reproductive organ comprising the composition of claim 6.

* * * * *